United States Patent
Trzupek et al.

(10) Patent No.: US 10,793,579 B2
(45) Date of Patent: *Oct. 6, 2020

(54) BICYCLIC-FUSED HETEROARYL OR ARYL COMPOUNDS

(71) Applicant: Pfizer Inc., New York, NY (US)

(72) Inventors: John David Trzupek, Arlington, MA (US); Katherine Lin Lee, West Newton, MA (US); Mark Edward Bunnage, Concord, MA (US); Seungil Han, Mystic, CT (US); David Hepworth, Concord, MA (US); Frank Eldridge Lovering, Acton, MA (US); John Paul Mathias, Concord, MA (US); Nikolaos Papaioannou, Newton, MA (US); Betsy Susan Pierce, East Lyme, CT (US); Joseph Walter Strohbach, Wentzville, MO (US); Stephen Wayne Wright, Old Lyme, CT (US); Christoph Wolfgang Zapf, Marlborough, MA (US); Lori Krim Gavrin, Villanova, PA (US); Arthur Lee, San Carlos, CA (US); David Randolph Anderson, Salem, CT (US); Kevin Joseph Curran, Somerset, NJ (US); Christoph Martin Dehnhardt, Burnaby (CA); Eddine Saiah, Brookline, MA (US); Joel Adam Goldberg, New Orleans, LA (US); Xiaolun Wang, San Diego, CA (US); Horng-Chih Huang, Chesterfield, MO (US); Richard Vargas, Bedford, MA (US); Michael Dennis Lowe, White Plains, NY (US); Akshay Patny, Waltham, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,679

(22) Filed: May 14, 2019

(65) Prior Publication Data

US 2019/0270751 A1 Sep. 5, 2019

Related U.S. Application Data

(63) Continuation of application No. 15/862,691, filed on Jan. 5, 2018, now Pat. No. 10,329,302, which is a
(Continued)

(51) Int. Cl.
*C07D 401/14* (2006.01)
*A61K 31/47* (2006.01)
(Continued)

(52) U.S. Cl.
CPC .......... *C07D 491/056* (2013.01); *A61K 31/40* (2013.01); *A61K 31/4015* (2013.01); *A61K 31/47* (2013.01); *A61K 31/4709* (2013.01); *A61K 31/4725* (2013.01); *A61K 31/517* (2013.01); *A61K 31/5377* (2013.01); *A61K 31/541* (2013.01); *A61K 45/06* (2013.01); *C07C 69/94* (2013.01); *C07D 207/08* (2013.01); *C07D 207/26* (2013.01); *C07D 207/267* (2013.01); *C07D 207/273* (2013.01);
(Continued)

(58) Field of Classification Search
None
See application file for complete search history.

(56) References Cited

U.S. PATENT DOCUMENTS 3,673,238 A 6/1972 Elpern et al.
5,583,222 A 12/1996 Barbier et al.
(Continued)

FOREIGN PATENT DOCUMENTS

CN 101353307 1/2009
EP 0313943 5/1989
(Continued)

OTHER PUBLICATIONS

Hashimoto, Takashi, et al., "First Synthesis of (±)-Basidifferquinone C, an Inducer for Fruiting-Body Formation in Polyporus arcularius", Bioscience, Biotechnology, and Biochemistry, 2009, pp. 2299-2302, 73(10).
Hashimoto, Takashi, et al., "Synthetic studies on basidifferquinones: the first of (±)-basidifferquinone C", Tetrahedron Letters, Mar. 31, 2008, pp. 2258-2261, 49(14).
Hwan, Jung, et al., "Stepwise Combinatorial Evolution of Akt Bisubstrate Inhibitors", ChemBioChem, Mar. 3, 2008, pp. 507-509, 9(4).
(Continued)

*Primary Examiner* — Zinna Northington Davis
(74) *Attorney, Agent, or Firm* — James T. Wasicak

(57) ABSTRACT

Compounds, tautomers and pharmaceutically acceptable salts of the compounds are disclosed, wherein the compounds have the structure of Formula Ia,

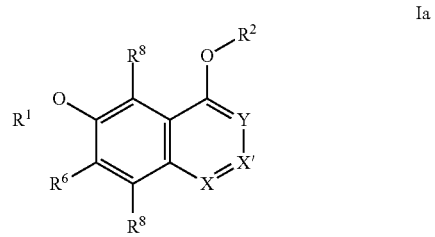

as defined in the specification. Corresponding pharmaceutical compositions, methods of treatment, methods of synthesis, and intermediates are also disclosed.

8 Claims, 2 Drawing Sheets

Related U.S. Application Data continuation of application No. 15/232,892, filed on Aug. 10, 2016, now Pat. No. 9,879,022, which is a continuation of application No. 14/678,114, filed on Apr. 3, 2015, now Pat. No. 9,458,168.

(60) Provisional application No. 61/975,473, filed on Apr. 4, 2014.

(51) Int. Cl.

| | |
|---|---|
| A61K 31/4709 | (2006.01) |
| A61K 31/4725 | (2006.01) |
| C07D 491/056 | (2006.01) |
| C07F 7/18 | (2006.01) |
| C07D 405/14 | (2006.01) |
| C07D 217/02 | (2006.01) |
| C07D 217/22 | (2006.01) |
| C07D 217/24 | (2006.01) |
| C07C 69/94 | (2006.01) |
| C07D 239/86 | (2006.01) |
| C07D 239/88 | (2006.01) |
| C07D 263/24 | (2006.01) |
| C07D 207/273 | (2006.01) |
| C07D 498/04 | (2006.01) |
| C07D 209/52 | (2006.01) |
| A61K 31/4015 | (2006.01) |
| A61K 31/517 | (2006.01) |
| A61K 31/5377 | (2006.01) |
| A61K 31/541 | (2006.01) |
| A61K 45/06 | (2006.01) |
| C07D 207/26 | (2006.01) |
| C07D 215/48 | (2006.01) |
| C07D 401/12 | (2006.01) |
| C07D 403/12 | (2006.01) |
| C07D 405/12 | (2006.01) |
| C07D 407/14 | (2006.01) |
| C07D 413/12 | (2006.01) |
| C07D 417/12 | (2006.01) |
| C07D 487/04 | (2006.01) |
| A61K 31/40 | (2006.01) |
| C07D 207/08 | (2006.01) |
| C07D 207/267 | (2006.01) |

(52) U.S. Cl.
CPC ......... C07D 209/52 (2013.01); C07D 215/48 (2013.01); C07D 217/02 (2013.01); C07D 217/22 (2013.01); C07D 217/24 (2013.01); C07D 239/86 (2013.01); C07D 239/88 (2013.01); C07D 263/24 (2013.01); C07D 401/12 (2013.01); C07D 401/14 (2013.01); C07D 403/12 (2013.01); C07D 405/12 (2013.01); C07D 405/14 (2013.01); C07D 407/14 (2013.01); C07D 413/12 (2013.01); C07D 417/12 (2013.01); C07D 487/04 (2013.01); C07D 498/04 (2013.01); C07F 7/1804 (2013.01)

(56) References Cited

U.S. PATENT DOCUMENTS

| | | | |
|---|---|---|---|
| 5,750,706 A | 5/1998 | Barbier et al. | |
| 5,830,920 A | 11/1998 | Chucholowski et al. | |
| 7,253,286 B2 | 8/2007 | Funahashi et al. | |
| 7,572,809 B2 | 8/2009 | Chen et al. | |
| 8,846,694 B2 | 9/2014 | Heinrich et al. | |
| 9,458,168 B2 | 10/2016 | Trzupek et al. | |
| 9,879,022 B2 | 1/2018 | Trzupek et al. | |
| 10,174,000 B2* | 1/2019 | Lee | C07D 401/14 |
| 2007/0179151 A1 | 8/2007 | Chen et al. | |
| 2008/0200461 A1 | 8/2008 | Anderson et al. | |
| 2011/0263561 A1 | 10/2011 | Heinrich et al. | |
| 2013/0029949 A1 | 1/2013 | Hoffmann et al. | |
| 2013/0137708 A1 | 5/2013 | Garske et al. | |
| 2018/0127432 A1 | 5/2018 | Trzupek et al. | |

FOREIGN PATENT DOCUMENTS

| | | |
|---|---|---|
| EP | 0347932 | 12/1989 |
| EP | 0492178 | 7/1992 |
| EP | 0663393 | 7/1995 |
| EP | 741128 | 11/1996 |
| EP | 1724268 | 11/2006 |
| EP | 1777218 | 4/2007 |
| JP | 05148222 | 6/1993 |
| WO | 199731006 | 8/1997 |
| WO | 200104102 | 1/2001 |
| WO | 2007008627 | 1/2007 |
| WO | 2007071348 | 6/2007 |
| WO | 2008091555 | 7/2008 |
| WO | 2009000085 | 12/2008 |
| WO | 2010003475 | 1/2010 |
| WO | 2011140228 | 11/2011 |
| WO | 2011159781 | 12/2011 |
| WO | 2013142390 | 9/2013 |
| WO | 2014039820 | 3/2014 |
| WO | 2015017610 | 2/2015 |

OTHER PUBLICATIONS

Sörgel, Sebastian, et al., "Preparation of Highly Alkoxy-Substituted Naphthaldehyde Derivatives—A Regioselective Approach to Building Blocks for the Synthesis of Rubromycins", European Journal of Organic Chemistry, Oct. 2006, pp. 4405-4418, 2006(19).
Japanese Patent JP5148222, published Jun. 15, 1993, Machine translation.
Coleman, Robert S., et al., "An efficient synthesis of the napthalene subunits of the protein kinase C inhibitor calphostin C", The Journal of Organic Chemistry, Feb. 1, 1991, pp. 1357-1359, 56(4).
CN 101245022, Yu, Xinhai, "Method for preparing 3,5-bis(2,4-diaminophenoxy)-2-naphthoic acid", Database accession No. 2008:1018912, Aug. 20, 2008, Abstract.
Database accession No. 1427393-40-5, Chemical Name: "6-lsoquinolinecarbonitrile, 1-choloro-7-methoxy—", Chemical Abstract Service, Apr. 8, 2013, Supplier: CiventiChem, XP002739597.
Tumey, L. Nathan, et al., "Identification and optimization of indolo[2,3-c]quinoline inhibitors of IRAK4", Bioorganic & Medicinal Chemistry Letters, Mar. 29, 2014, pp. 2066-2072, 24(9).
International Patent Application PCT/IB2015/052251, filed Mar. 26, 2015, International Search Report and Written Opinion, dated Jun. 3, 2015, 15 pages.
International Patent Application PCT/IB2015/052251, filed Mar. 26, 2015, International Preliminary Report on Patentability and Written Opinion, dated Oct. 4, 2016, 8 pages.
Coleman, Robert S., et al., "Atropdiastereoselective Total Synthesis of Phleichrome and the Protein Kinase C Inhibitor Calphostin A", J. Am. Chem. Soc., 1994, pp. 8795-8796, 116(19).
Coleman, Robert S., et al., "Synthesis of Helically Chiral Molecules: Stereoselective Total Synthesis of the Perylenequinones Phleichrome and Calphostin A", J. Am. Chem. Soc., 1995, pp. 10889-10904, 117(44).
Podlesny, Erin E., et al., "Divergent Approach to the Bisanthraquinone Natural Products: Total Synthesis of (S)-Bisoranjidiol and Derivatives from Binaphtho-para-quinones", The Journal of Organic Chemistry, 2013, pp. 466-476, 78(2).
He, Rongjun, et al., "Double Click Reaction for the Acquistion of a Highly Potent and Selective mPTPB Inhibitor", ChemMedChem, 2010, pp. 2015-2056, vol. 5.

* cited by examiner

Change in paw volume vs. time

BICYCLIC-FUSED HETEROARYL OR ARYL COMPOUNDS

FIELD OF THE INVENTION

This invention pertains to compounds useful for the treatment of autoimmune and inflammatory diseases associated with Interleukin-1 Receptor Associated Kinase (IRAK) and more particularly compounds that modulate the function of IRAK4.

BACKGROUND OF THE INVENTION

Protein kinases are families of enzymes that catalyze the phosphorylation of specific residues in proteins, broadly classified in tyrosine and serine/threonine kinases. Inappropriate activity arising from dysregulation of certain kinases by a variety of mechanisms is believed to underlie the causes of many diseases, including but not limited to, cancer, cardiovascular diseases, allergies, asthma, respiratory diseases, autoimmune diseases, inflammatory diseases, bone diseases, metabolic disorders, and neurological and neurodegenerative diseases. As such, potent and selective inhibitors of kinases are sought as potential treatments for a variety of human diseases.

There is considerable interest in targeting the innate immune system in the treatment of autoimmune diseases and sterile inflammation. Receptors of the innate immune system provide the first line of defense against bacterial and viral insults. These receptors recognize bacterial and viral products as well as pro-inflammatory cytokines and thereby initiate a signaling cascade that ultimately results in the up-regulation of inflammatory cytokines such as TNFα, IL6, and interferons. Recently it has become apparent that self-generated ligands such as nucleic acids and products of inflammation such as high-mobility group protein B1 (HMGB1) and Advanced Glycated End-products (AGE) are ligands for Toll-like receptors (TLRs) which are key receptors of the innate immune system (O'Neill 2003, Kanzler et al 2007, Wagner 2006). This demonstrates the role of TLRs in the initiation and perpetuation of inflammation due to autoimmunity.

Interleukin-1 receptor associated kinase 4 (IRAK4) is a ubiquitously expressed serine/threonine kinase involved in the regulation of innate immunity (Suzuki & Saito 2006). IRAK4 is responsible for initiating signaling from TLRs and members of the IL-1/18 receptor family. Kinase-inactive knock-ins and targeted deletions of IRAK4 in mice were reported to cause reductions in TLR and IL-1 induced pro-inflammatory cytokines (Kawagoe et al 2007; Fraczek et al. 2008; Kim et al. 2007). IRAK4 kinase-dead knock-in mice have also been shown to be resistant to induced joint inflammation in the antigen-induced-arthritis (AIA) and serum transfer-induced (K/BxN) arthritis models (Koziczak-Holbro 2009). Likewise, humans deficient in IRAK4 also appear to display the inability to respond to challenge by Toll ligands and IL-1 (Hernandez & Bastian 2006). However, the immunodeficient phenotype of IRAK4-null individuals is narrowly restricted to challenge by gram positive bacteria, but not gram negative bacteria, viruses or fungi. This gram positive sensitivity also lessens with age, implying redundant or compensating mechanisms for innate immunity in the absence of IRAK4 (Lavine et al 2007).

These data indicate that inhibitors of IRAK4 kinase activity should have therapeutic value in treating cytokine driven autoimmune diseases while having minimal immunosuppressive side effects. Additional recent studies suggest that targeting IRAK4 may be useful in other inflammatory pathologies such as atherosclerosis and diffuse large B-cell lymphoma (Rekhter et al 2008; Ngo et al 2011). Therefore, inhibitors of IRAK4 kinase activity are potential therapeutics for a wide variety of diseases including but not limited to autoimmunity, inflammation, cardiovascular diseases, cancer, and metabolic diseases. See the following references for additional information: N. Suzuki and T. Saito, *Trends in Immunology*, 2006, 27, 566. T. Kawagoe, S. Sato, A. Jung, M. Yamamoto, K. Matsui, H. Kato, S. Uematsu, O. Takeuchi and S. Akira, *Journal of Experimental Medicine*, 2007, 204, 1013. J. Fraczek, T. W. Kim, H. Xiao, J. Yao, Q. Wen, Y. Li, J.-L. Casanova, J. Pryjma and X. Li, *Journal of Biological Chemistry*, 2008, 283, 31697. T. W. Kim, K. Staschke, K. Bulek, J. Yao, K. Peters, K.-H. Oh, Y. Vandenburg, H. Xiao, W. Qian, T. Hamilton, B. Min, G. Sen, R. Gilmour and X. Li, *Journal of Experimental Medicine*, 2007, 204, 1025. M. Koziczak-Holbro, A. Littlewood-Evans, B. Pollinger, J. Kovarik, J. Dawson, G. Zenke, C. Burkhart, M. Muller and H. Gram, *Arthritis & Rheumatism*, 2009, 60, 1661. M. Hernandez and J. F. Bastian, *Current Allergy and Asthma Reports*, 2006, 6, 468. E. Lavine, R. Somech, J. Y. Zhang, A. Puel, X. Bossuyt, C. Picard, J. L. Casanova and C. M. Roifman, *Journal of Allergy and Clinical Immunology*, 2007, 120, 948. M. Rekhter, K. Staschke, T. Estridge, P. Rutherford, N. Jackson, D. Gifford-Moore, P. Foxworthy, C. Reidy, X.-d. Huang, M. Kalbfleisch, K. Hui, M.-S. Kuo, R. Gilmour and C. J. Vlahos, *Biochemical and Biophysical Research Communications*, 2008, 367, 642. O'Neill, L. A. (2003). "Therapeutic targeting of Toll-like receptors for inflammatory and infectious diseases." *Curr Opin Pharmacol* 3(4): 396. Kanzler, H et al. (2007) "Therapeutic targeting of innate immunity with toll-like receptor agonists and antagonists." *Nature Medicine* 13:552. Wagner, H. (2006) "Endogenous TLR ligands and autoimmunity" *Advances in Immunol* 91: 159. Ngo, V. N. et al. (2011) "Oncogenically active MyD88 mutations in human lymphoma" *Nature* 470: 115.

SUMMARY OF THE INVENTION

The invention provides for compounds of the Formula Ia,

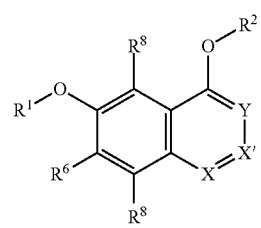

wherein

X and X' are each independently $CR^8$, N or $-N^+-O^-$; Y is independently N, $-N^+-O^-$ or $CR^{8'}$; provided that at least one of X, X' or Y is neither N nor $-N^+-O^-$ and that no more than one of X, X' or Y is $-N^+-O^-$;

$R^1$ is $C_1$-$C_6$alkyl; $C_2$-$C_6$alkenyl; $C_2$-$C_6$alkynyl; $-(CR^{3a}R^{3b})_m$-(3- to 7-membered cycloalkyl); $-(CR^{3a}R^{3b})_m$-(3- to 7-membered heterocycloalkyl) having one to three heteroatoms; $-(CR^{3a}R^{3b})_m$-(5- to 10-membered heteroaryl), having one to three heteroatoms; or $-(CR^{3a}R^{3b})_m$-$C_6$-$C_{12}$aryl; wherein said alkyl, alkenyl, alkynyl, cycloalkyl, heterocycloalkyl, heteroaryl or aryl is optionally substituted with one to five halogen, deuterium, —OR$^5$, —SR$^5$, —NR$^{11a}$R$^{11b}$, cyano, C$_1$-C$_6$alkyl, C$_3$-C$_6$cycloalkyl or —C$_1$-C$_6$alkoxy;

R$^2$ is —(CR$^{3a}$R$^{3b}$)$_m$-(3- to 10-membered cycloalkyl); —(CR$^{3a}$R$^{3b}$)$_m$-(3- to 10-membered heterocycloalkyl) having one to three heteroatoms; —(CR$^{3a}$R$^{3b}$)$_m$-(5- to 10 membered heteroaryl) having one to three heteroatoms; or —(CR$^{3a}$R$^{3b}$)$_m$—C$_6$-C$_{12}$aryl; wherein said cycloalkyl, heterocycloalkyl, heteroaryl or aryl is optionally substituted with one to five R$^4$; and wherein, if the heteroatom on said heterocycloalkyl and heteroaryl is N, said N is optionally substituted with R$^{4'}$; or R$^2$ is C$_1$-C$_6$alkyl, wherein said alkyl is optionally substituted with NH$_2$, OH or cyano;

R$^{3a}$ and R$^{3b}$ for each occurrence are independently hydrogen or C$_1$-C$_3$alkyl;

R$^4$ for each occurrence is independently a bond, deuterium, halogen, cyano, C$_1$-C$_6$alkyl, C$_2$-C$_6$alkenyl, oxo, —OR$^5$, —SR$^5$, —S(O)R$^9$, —S(O)$_2$R$^9$, —NR$^{11a}$R$^{11b}$, —C(O)R$^{10}$, —(CR$^{3a}$R$^{3b}$)$_n$-(3- to 7-membered cycloalkyl), —(CR$^{3a}$R$^{3b}$)$_n$-(4- to 10-membered heterocycloalkyl), having one to three heteroatoms, —(CR$^{3a}$R$^{3b}$)$_n$-(5- to 10 membered heteroaryl), having one to three heteroatoms, or —(CR$^{3a}$R$^{3b}$)$_n$—C$_6$-C$_{12}$aryl wherein said alkyl, cycloalkyl, heterocycloalkyl, heteroaryl or aryl is each optionally and independently substituted with one to five deuterium, halogen, OR$^5$, —SR$^5$, —NR$^{11a}$R$^{11b}$, cyano, C$_1$-C$_6$alkyl, C$_3$-C$_6$cycloalkyl or C$_1$-C$_6$alkoxy; or two R$^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, —OR$^5$, —SR$^5$, —NR$^{11a}$R$^{11b}$, cyano or C$_1$-C$_6$alkyl or C$_1$-C$_6$alkoxy, wherein the alkyl or alkoxy is optionally substituted with halogen, deuterium, —OR$^5$, —SR$^5$, —NR$^{11a}$R$^{11b}$ or cyano; and wherein, if a heteroatom on said heterocycloalkyl is N, said N is optionally substituted with R$^{4'}$;

R$^{4'}$ is independently C$_1$-C$_6$alkyl, C$_2$-C$_6$alkenyl, —C(O)R$^{10}$, —S(O)$_2$R$^9$, —(CR$^{3a}$R$^{3b}$)$_n$-(3- to 7-membered cycloalkyl), —(CR$^{3a}$R$^{3b}$)$_n$-(4- to 10-membered heterocycloalkyl) or C(O)(CH$_2$)$_t$CN; wherein said alkyl, alkenyl, cycloalkyl, or heterocycloalkyl is each optionally and independently substituted with one to five deuterium, halogen, OH, cyano or C$_1$-C$_6$alkoxy; or R$^4$ and R$^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, —OR$^5$, —SR$^5$, —NR$^{11a}$R$^{11b}$, cyano, C$_1$-C$_6$alkyl or C$_1$-C$_6$alkoxy, wherein the alkyl or alkoxy is optionally substituted with halogen, deuterium, —OR$^5$, —SR$^5$, —NR$^{11a}$R$^{11b}$, or cyano;

R$^5$ is independently hydrogen or C$_1$-C$_6$alkyl, wherein said alkyl is optionally substituted with halogen, deuterium, C$_1$-C$_6$alkoxy, C$_1$-C$_6$alkylthiolyl, —NR$^{11a}$R$^{11b}$, cyano, C$_1$-C$_6$alkyl or C$_3$-C$_6$cycloalkyl; or two R$^5$ taken together with the oxygen atoms to which they are bonded form a 5- or 6-membered heterocycloalkyl;

R$^6$ is —C(O)NHR$^7$, CO$_2$R$^7$ or cyano;

R$^7$ is hydrogen or C$_1$-C$_6$alkyl;

each R$^8$ is independently hydrogen, halogen, cyano, —OR$^5$, —SR$^5$, —NR$^{11a}$R$^{11b}$, C$_1$-C$_6$alkyl, C$_3$-C$_6$cycloalkyl, 3- to 10-membered heterocycloalkyl or 5- to 6-membered heteroaryl or aryl, wherein said alkyl, cycloalkyl, heterocycloalkyl, heteroaryl or aryl is optionally substituted with one to three halogen, —NR$^{11a}$R$^{11b}$, —OR$^5$, —SR$^5$, cyano, C$_1$-C$_3$ alkyl, —C(O)R$^{10}$ or oxo;

R$^{8'}$ is hydrogen, deuterium, halogen, cyano, —OR$^5$, —SR$^5$ or NR$^{11a}$NR$^{11b}$;

R$^9$ is —(CR$^{3a}$R$^{3b}$)$_p$—(C$_1$-C$_3$alkyl), —(CR$^{3a}$R$^{3b}$)$_p$-(4- to 6-membered cycloalkyl), —(CR$^{3a}$R$^{3b}$)$_p$-(4- to 6-membered heterocycloalkyl) or —(CR$^{3a}$R$^{3b}$)$_p$—(C$_5$-C$_9$aryl), wherein said alkyl, cycloalkyl, heterocycloalkyl or aryl is each optionally substituted with fluoro or C$_1$-C$_3$alkyl;

R$^{10}$ is C$_1$-C$_6$alkyl, wherein said alkyl is optionally substituted with deuterium, halogen, OH, C$_1$-C$_6$alkoxy or cyano;

R$^{11a}$ and R$^{11b}$ are each independently hydrogen or C$_1$-C$_6$alkyl, wherein said alkyl is optionally substituted with deuterium, C$_1$-C$_6$alkoxy or cyano; and if C$_2$-C$_6$alkyl, said alkyl is optionally substituted with deuterium, C$_1$-C$_6$alkoxy, cyano, halogen or OH;

m is independently 0, 1, 2 or 3;

n is independently 0, 1, 2 or 3;

p is independently 0 or 1; and t is 1, 2 or 3;

or a pharmaceutically acceptable salt of said compound or a tautomer of said compound or said salt.

The invention also provides for pharmaceutical compositions comprising the compounds, methods of using the compounds, combination therapies utilizing the compounds and other therapeutic agents and methods of preparing the compounds. The invention also provides for intermediates useful in the preparation of the compounds of the invention.

In particular, novel bicyclic kinase enzyme inhibitor compounds of Formula I of the present invention possess a therapeutic role of inhibiting IRAK4 useful in the area of diseases and/or disorders that include, but are not limited to, cancers, allergic diseases, autoimmune diseases, inflammatory diseases and/or disorders and/or conditions associated with inflammation and pain, proliferative diseases, hematopoietic disorders, hematological malignancies, bone disorders, renal disease, fibrosis diseases and/or disorders, metabolic disorders, muscle diseases and/or disorders, respiratory diseases, pulmonary disorders, genetic development diseases, neurological and neurodegenerative diseases and/or disorders, chronic inflammatory demyelinating neuropathies, cardiovascular, vascular or heart diseases, ophthalmic/ocular diseases, wound repair, infection and viral diseases. Therefore, inhibition of IRAK4 would have the potential for multiple therapeutic indications over a wide range of unmet needs.

DESCRIPTION OF FIGURES

FIG. 2. Delta paw volume in rat collagen-induced arthritis model using Example 26.

DETAILED DESCRIPTION OF THE INVENTION

Figure 1:
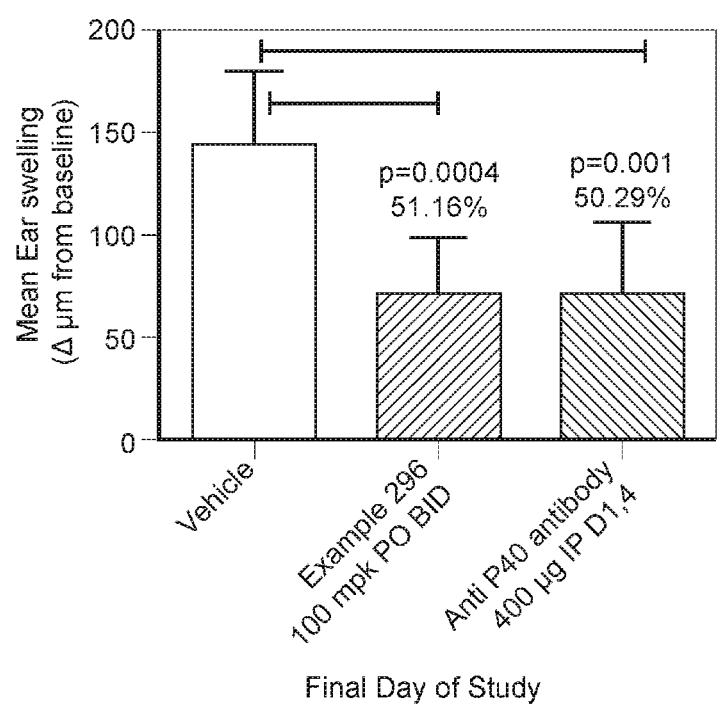
FIG. 1: Mean change in ear swelling (μm) from baseline ear measurements on day 5. Mice treated with Example 296 (PO BID daily×5 days) and P40 Ab (IP day 1, 4) had significantly reduced ear swelling on the final day compared to Vehicle (p value and %).

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

All patents, patent applications and references referred to herein are hereby incorporated by reference in their entirety.

Other features and advantages of this invention will be apparent from this specification and the appendent claims which describe the invention. There are many features of this invention that are not necessarily fully captured by the claims. It is understood, however, that all such novel subject matter is part of the invention.

Definitions

Unless otherwise defined herein, scientific and technical terms used in connection with the present invention have the meaning commonly understood by those of ordinary skill in the art. As used in the specification and the appended claims, the singular forms "a", "an", and "the" include plural referents unless the context clearly dictates otherwise.

The term "about" refers to a relative term denoting an approximation of plus or minus 10% of the nominal value it refers, in one embodiment, to plus or minus 5%, in another embodiment, to plus or minus 2%. For the field of this disclosure, this level of approximation is appropriate unless the value is specifically stated require a tighter range.

The term "alkyl" refers to a linear or branched saturated hydrocarbon moiety, consisting solely of carbon and hydrogen atoms. In one embodiment from one to six carbon atoms; and in another embodiment from one to four carbon atoms; and in another embodiment one to three carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. As appropriate, an alkyl may be optionally substituted at each carbon as defined in the claims. Typical substitution includes, but is not limited to, fluoro, chloro, OH, cyano, alkyl (optionally substituted), cycloalkyl and the like.

In some instances, the number of carbon atoms in a hydrocarbon substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$-cycloalkyl or $C_{3-6}$-cycloalkyl refers to saturated cycloalkyl containing from 3 to 6 carbon ring atoms.

Unless otherwise indicated, "alkylene," by itself or as part of another term, refers to a saturated, branched or straight chain or cyclic hydrocarbon diradical of the stated number of carbon atoms, typically 1-6 carbon atoms, and having two monovalent radical centers derived by the removal of two hydrogen atoms from the same or two different carbon atoms of a parent alkane. Typical alkylene radicals include, but are not limited to methylene (—$CH_2$—), 1,2-ethylene (—$CH_2CH_2$—), 2,2-dimethylene, 1,3-propylene (—$CH_2CH_2CH_2$—), 2-methylpropylene, 1,4-butylene (—$CH_2CH_2CH_2CH_2$—), and the like; optionally substituted, as appropriate, by 1 to 5 suitable substituents as defined above such as fluoro, chloro, deuteron, cyano, trifluoromethyl, ($C_1$-$C_6$)alkoxy, ($C_6$-$C_{10}$)aryloxy, trifluoromethoxy, difluoromethoxy or ($C_1$-$C_6$)alkyl. When the compounds of the invention contain a $C_{2-6}$alkenyl group, the compound may exist as the pure E (entgegen) form, the pure Z (zusammen) form, or any mixture thereof.

"Alkylidene" or "alkenyl" refers to a divalent group formed from an alkane by removal of two hydrogen atoms from the same carbon atom, the free valencies of which are part of a double bond, optionally substituted as described herein. The term alkylidene also includes "allenes" wherein on carbon atom has double bonds with each of its two adjacent carbon centers, such as, for example, propadiene. As appropriate, an alkenyl may be optionally substituted at each carbon as defined in the claims, optionally substituted, as appropriate, by 1 to 5 suitable substituents as defined above and herein such as fluoro, chloro, deutero, cyano, trifluoromethyl, ($C_1$-$C_6$)alkoxy, ($C_6$-$C_{10}$)aryloxy, trifluoromethoxy, difluoromethoxy or ($C_1$-$C_6$)alkyl.

"Alkynyl" refers to an aliphatic hydrocarbon having at least one carbon-carbon triple bond, including straight chain, branched chain or cyclic groups having at least one carbon-carbon triple bond, optionally substituted as described herein. Preferably, it is a lower alkynyl having 2 to 6 carbon atoms. For example, as used herein, the term "$C_{2-6}$alkynyl" is used herein to mean a straight or branched hydrocarbon chain alkynyl radical as defined above having 2 to 6 carbon atoms and one triple bond. As appropriate, an alkynyl may be optionally substituted at each carbon as defined in the claims. Typical substitution includes, but is not limited to, optionally substituted, as appropriate, by 1 to 5 suitable substituents as defined above and herein, such as fluoro, chloro, deutero, cyano, trifluoromethyl, ($C_1$-$C_6$)alkoxy, ($C_6$-$C_{10}$)aryloxy, trifluoromethoxy, difluoromethoxy or ($C_1$-$C_6$) alkyl.

The term "cycloalkyl" refers to a nonaromatic ring containing 3 to 10 carbons that is fully hydrogenated consisting of mono-, bi- or tricyclic rings. Accordingly, a cycloalkyl may be a single ring, which typically contains from 3 to 7 ring atoms. Examples include, but are not limited to, cyclopropyl, cyclobutyl, cyclopentyl, and cyclohexyl. Alternatively, 2 or 3 rings may be fused together, such as bicyclodecanyl and decalinyl. The term "cycloalkyl" also includes bridged bicycloalkyl systems such as, but not limited to, bicyclo[2.2.1]heptane and bicyclo[1.1.1]pentane. The cycloalkyl group may be optionally substituted as described herein, as appropriate, by 1 to 5 suitable substituents as defined above such as fluoro, chloro, deutero, cyano, trifluoromethyl, ($C_1$-$C_6$)alkoxy, ($C_6$-$C_{10}$)aryloxy, trifluoromethoxy, difluoromethoxy or ($C_1$-$C_6$)alkyl.

The term "heterocycloalkyl" means a monovalent saturated moiety, consisting of one to three rings, incorporating one, two, three or four heteroatoms (selected from N, O or S) and three to 10 carbon atoms. The heterocycloalkyl may be optionally substituted as defined herein. Examples of heterocycloalkyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorphilinylsulfone, dihydroquinolinyl, tetrahydroquinolinyl, tetrahydrisoquinolinyl, and the like. Heterocycloalkyls may be optionally substituted, as appropriate, by 1 to 5 suitable substituents as defined herein such as fluoro, chloro, deutero, cyano, trifluoromethyl, ($C_1$-$C_6$) alkoxy, ($C_6$-$C_{10}$)aryloxy, trifluoromethoxy, difluoromethoxy or ($C_1$-$C_6$)alkyl.

Unless otherwise indicated, the term "heteroalkyl," by itself or in combination with another term, means, unless otherwise stated, a saturated, straight or branched chain hydrocarbon radical consisting of the stated number of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom S may be placed at any position of the heteroalkyl group, including the position at which the alkyl group is attached to the remainder of the molecule. Up to two heteroatoms may be consecutive.

Unless otherwise indicated, the term "heteroalkylene" by itself or as part of another substituent means a divalent group derived from heteroalkyl (as defined above). For heteroalkylene groups, heteroatoms can also occupy either or both of the chain termini.

The term "alkoxy" and "alkyloxy", which may be used interchangeably, refers to a moiety of the formula —OR, wherein R is a straight chain saturated alkyl or branched chain saturated alkyl moiety, as defined herein, bonded through an oxygen atom. The alkoxy group may be optionally substituted as defined herein. Non-limiting examples of such alkoxy groups are methoxy, ethoxy, propoxy, isopropoxy, butoxy, isobutoxy, tertiary butoxy, pentoxy and the like.

The term "aryl" means a carbocyclic aromatic system containing one or two rings wherein such rings may be fused. If the rings are fused, one of the rings must be fully unsaturated and the fused ring(s) may be fully saturated, partially unsaturated or fully unsaturated. The term "fused" means that a second ring is present (i.e., attached or formed) by having two adjacent atoms in common (i.e., shared) with the first ring. The term "fused" is equivalent to the term "condensed". The aryl group may be optionally substituted as defined herein. The term "aryl" embraces aromatic radicals such as phenyl, naphthyl, tetrahydronaphthyl, indanyl, biphenyl, benzo[b][1,4]oxazin-3(4H)-onyl, 2,3-dihydro-1H indenyl and 1,2,3,4-tetrahydronaphthalenyl. Aryls may be optionally substituted, as appropriate, by 1 to 5 suitable substituents as defined above such as fluoro, chloro, deutero, cyano, trifluoromethyl, ($C_1$-$C_6$)alkoxy, ($C_6$-$C_{10}$)aryloxy, trifluoromethoxy, difluoromethoxy or ($C_1$-$C_6$)alkyl.

The term "heteroaryl" refers to an aromatic ring structure containing from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered ring substituents such as pyridyl, pyrazyl, pyrimidinyl, and pyridazinyl; and 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3, 4-oxadiazolyl and isothiazolyl. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring.

Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. The heteroaryl can be optionally substituted, as appropriate, by 1 to 5 suitable substituents as defined herein such as fluoro, chloro, deutero, cyano, trifluoromethyl, ($C_1$-$C_6$)alkoxy, ($C_6$-$C_{10}$)aryloxy, trifluoromethoxy, difluoromethoxy or ($C_1$-$C_6$)alkyl.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" also includes fused ring systems having one or two rings wherein such rings may be fused, wherein fused is as defined above. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "5- to 6-membered heteroaryl" refers to a heteroaryl containing from 5 to 6 atoms, including one or more heteroatoms, in the cyclic moiety of the heteroaryl. The heteroatoms for this invention are selected from nitrogen, oxygen and sulfur.

Compounds of the present invention may contain basic nitrogen atoms (e.g. alkyl amines or heterocycles such as pyridine etc.) which may be converted to N-oxides by treatment with an oxidizing agent (e.g. MCPBA and/or hydrogen peroxides) to afford other compounds of this invention. Thus, all nitrogen-containing compounds that may converted to N-oxide (N→O or —N+—O—) derivatives are part of the invention.

One skilled in the art would appreciate that metabolites may be formed as part of the natural biochemical process of degrading and eliminating the compounds. For example, some compounds of the invention may naturally form an N-oxide, as depicted below in the compound of Formula If' or in other areas of the compound of Formula Ia. Metabolites such as these or others formed as part of the natural biochemical process are within the scope of the invention.

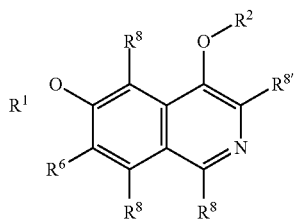

IIf

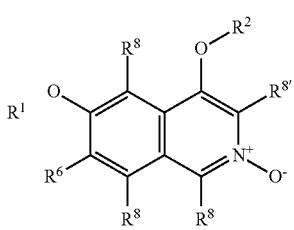

IIf'

If substituents are described as "independently" having more than one variable, each instance of a substituent is selected independent of the other from the list of variables available. Each substituent therefore may be identical to or different from the other substituent(s).

"Patient" or "subject" refers to warm-blooded animals such as, for example, guinea pigs, mice, rats→gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

As used herein, the terms "Formula I", "Formula Ia", "Formula IIa-IIg", "Formula III" and "Formula IIIa" may be hereinafter referred to as a "compound(s) of the invention," "the present invention," and collectively the "compound of Formula I." Accordingly, the term "compound of Formula I" includes the compounds of Formula Ia, IIa-IIg, III and IIIa. Such terms are also defined to include all forms of the compound of Formula I, including hydrates, solvates, isomers, crystalline and non-crystalline forms, isomorphs, polymorphs, tautomers and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention have asymmetric carbon atoms. The carbon bonds of the compounds of the invention may be depicted herein using a solid line (——————), a solid wedge ( ▬▬◼ ), or a dotted wedge ( ··········||||| ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

The compounds of the invention may exhibit the phenomenon of tautomerism. For example, the compound exemplified by 173 may exist in several tautomeric forms, including the pyrrolidin-2-one form, Example 173a, and the 5-hydroxy-3,4-dihydro-2H-pyrrol form, Example 173b. All such tautomeric forms are included within the scope of the compounds of the Formula I and the scope of the invention. One of ordinary skill in the art would appreciate and recognize that many of the Examples described herein may exhibit tautomerism and are within the scope of the compound of Formula I, Ia, IIa-IIg, III and IIIa. Tautomers exist as mixtures of a tautomeric set in solution. In solid form, usually one tautomer predominates. Even though one tautomer may be described, the present invention includes all tautomers of the compounds of the invention and salts thereof. Examples of tautomers are described by Examples 173a and 173b.

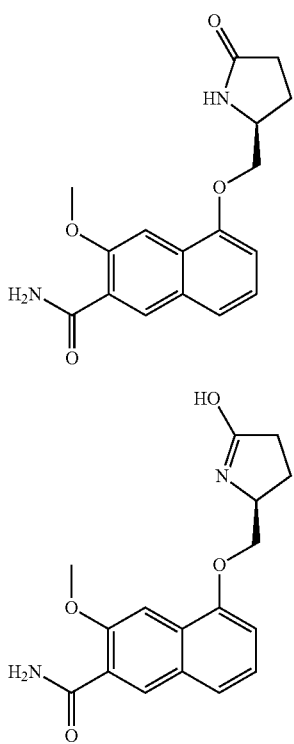

Example 173a

Example 173b

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention, which are generally prepared by reacting the free base with a suitable organic or inorganic acid.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sulfanilate, cyclohexylaminosulfonate, algenate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^{2}H$, $^{3}H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds of the invention as claimed in the claims may specifically define substitution with deutero or deuterium. The absence of the term deuteron, deuteron or deuterium, all of which are used interchangeably, in a substitution group shall not be implied to exclude deutero.

Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

All patents and publications identified herein are incorporated herein by reference in their entirety and for all purposes.

Compounds of the Invention

In one embodiment, as described above and more fully herein, the invention is directed to a compound of Formula Ia,

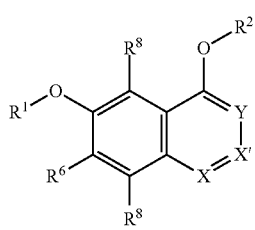

Ia wherein

X and X' are each independently $CR^8$, N or $-N^+-O^-$; Y is independently N, $-N^+-O^-$ or $CR^{8'}$; provided that at least one of X, X' or Y is neither N nor $-N^+-O^-$ and that no more than one of X, X' or Y is $-N^+-O^-$; or a pharmaceutically acceptable salt of said compound or a tautomer of said compound or said salt.

In one aspect, the invention provides for compounds of Formula Ia wherein X is N, X' is $CR^8$ and Y is $CR^{8'}$; X is N, X' is N and Y is $CR^{8'}$; X is N, X' is $CR^8$ and Y is N; X is $CR^8$, X' and Y are N; X and X' are $CR^8$ and Y is N; X is $CR^8$ and Y is $CR^{8'}$ and X' is N; X and X' are $CR^8$ and Y is $CR^{8'}$; or a pharmaceutically acceptable salt of said compound or a tautomer of said salt. In another aspect, $R^6$ is $-C(O)NHR^7$, $-CO_2R^7$ or cyano; and $R^7$ is hydrogen; or a pharmaceutically acceptable salt of said compound or a tautomer of said compound or said salt.

The invention also provides for a compound of Formula IIa, IIb, IIc, IId, IIe, IIf or IIg,

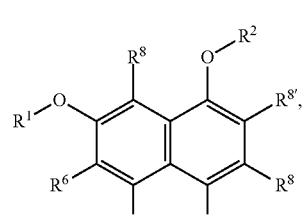

IIa

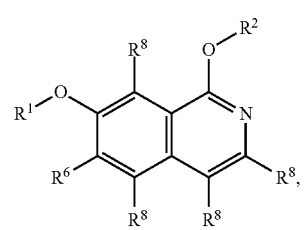

IIb

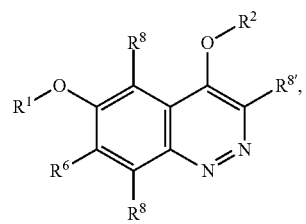

IIc

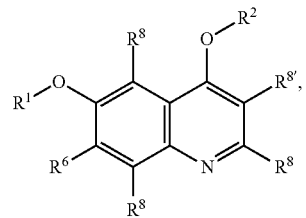

IId

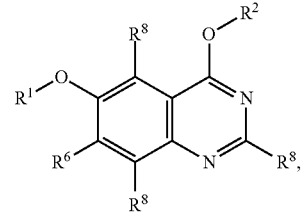

IIe

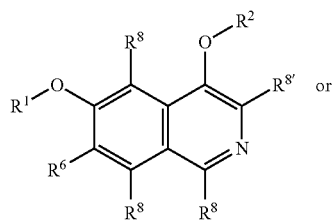

IIf or

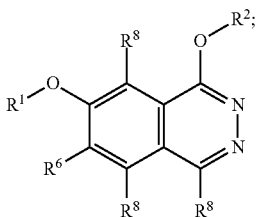

IIg wherein $R^1$ is $C_1$-$C_6$alkyl; $C_2$-$C_6$alkenyl; $C_2$-$C_6$alkynyl; —$(CR^{3a}R^{3b})_m$-(3- to 7-membered cycloalkyl); or —$(CR^{3a}R^{3b})_m$-(3- to 7-membered heterocycloalkyl) having one to three heteroatoms; wherein said alkyl, alkenyl, alkynyl, cycloalkyl or heterocycloalkyl is optionally substituted with one to five halogen, deuterium, —$OR^5$, —$SR^5$, —$NR^{11a}R^{11b}$, cyano, $C_1$-$C_6$alkyl, $C_3$-$C_6$cycloalkyl or —$C_1$-$C_6$alkoxy;

$R^2$ is —$(CR^{3a}R^{3b})_m$-(3- to 7-membered cycloalkyl), wherein said cycloalkyl is optionally substituted with one to four $R^4$; —$(CR^{3a}R^{3b})_m$-(3- to 7-membered heterocycloalkyl) having one to three heteroatoms, wherein said heterocycloalkyl is optionally substituted at a carbon atom with one to five $R^4$ and wherein, if the heteroatom is N, said N is optionally substituted with $R^{4'}$; or $R^2$ is $C_1$-$C_6$alkyl, wherein said alkyl is optionally substituted with $NH_2$, cyano or halogen $R^{3a}$ and $R^{3b}$ are each independently hydrogen or $C_1$-$C_3$alkyl;

$R^4$ for each occurrence is independently and optionally halogen, cyano, $C_1$-$C_6$alkyl, $C_2$-$C_6$alkenyl, oxo, —$OR^5$, —$SR^5$, —$S(O)R^9$, —$S(O)_2R^9$, —$C(O)R^{10}$, —$(CR^{3a}R^{3b})_n$-(3- to 7-membered cycloalkyl) or —$(CR^{3a}R^{3b})_n$-(4- to 7-membered heterocycloalkyl) wherein said alkyl, cycloalkyl or heterocycloalkyl is each optionally and independently substituted with one to five deuterium, halogen, —$OR^5$, —$SR^5$, —$NR^{11a}R^{11b}$, cyano, $C_1$-$C_6$alkyl, $C_3$-$C_6$cycloalkyl, $C_1$-$C_6$alkoxy or $NR^{11a}R^{11b}$; or two $R^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —$SR^5$, —$NR^{11a}R^{11b}$, cyano or $C_1$-$C_6$alkyl or $C_1$-$C_6$alkoxy, wherein the alkyl or alkoxy is optionally substituted with halogen, deuterium, —$OR^5$, —$NR^{11a}R^{11b}$, or cyano; and wherein, if a heteroatom on said heterocycloalkyl is N, said N is optionally substituted with $R^{4'}$;

$R^{4'}$ is independently $C_1$-$C_6$alkyl, $C_2$-$C_6$alkenyl, —$S(O)R^9$, —$S(O)_2R^9$, —$C(O)R^{10}$, $C(O)(CH_2)_tCN$; wherein said alkyl is optionally substituted with $NH_2$, cyano or halogen —$(CR^{3a}R^{3b})_n$-(3- to 7-membered cycloalkyl), or $(CR^{3a}R^{3b})_n$-(4- to 10-membered heterocycloalkyl), wherein said alkyl, alkenyl, cycloalkyl, or heterocycloalkyl is each optionally and independently substituted with one to five deuterium, halogen, OH, cyano or $C_1$-$C_6$alkoxy; or $R^4$ and $R^{4'}$ taken together with the respective atoms to which each are bonded form a 3- to 6-membered cycloalkyl or 4- to 6-membered heterocycloalkyl, wherein said cycloalkyl or heterocycloalkyl is optionally substituted with one to three halogen, deuterium, —$OR^5$, —$SR^5$, —$NR^{11a}R^{11b}$, cyano, $C_1$-$C_6$alkyl or $C_1$-$C_6$alkoxy, wherein the alkyl or alkoxy is optionally substituted with halogen, deuterium, —$OR^5$, —$SR^5$, —$NR^{11a}R^{11b}$ or cyano;

$R^5$ is hydrogen or $C_1$-$C_6$alkyl, wherein said alkyl is optionally substituted with halogen;

$R^6$ is —$C(O)NHR^7$ or cyano;

$R^7$ is hydrogen or $C_1$-$C_6$alkyl;

$R^8$ is independently hydrogen, halogen, cyano, —$NR^{11a}R^{11b}$, $C_1$-$C_6$alkyl, 5- to 6-membered heteroaryl or 5- to 6-membered aryl, wherein said alkyl or heteroaryl or aryl is optionally substituted with one to three halogen, —$NR^{11a}R^{11b}$, $C_1$-$C_3$ alkyl or oxo;

$R^{8'}$ is hydrogen, deuterium, halogen, cyano, —$OR^5$ or $NR^{11a}NR^{11b}$;

$R^9$ is —$(CR^{3a}R^{3b})_p(C_1$-$C_3$alkyl), —$(CR^{3a}R^{3b})_p$-(4- to 6-membered cycloalkyl), —$(CR^{3a}R^{3b})_p$-(4- to 6-membered heterocycloalkyl) or —$(CR^{3a}R^{3b})_p$-($C_5$-$C_9$aryl), wherein said alkyl, cycloalkyl, heterocycloalkyl or aryl is each optionally substituted with fluoro or $C_1$-$C_3$alkyl;

$R^{10}$ is $C_1$-$C_6$alkyl, wherein said alkyl is optionally substituted with fluoro or cyano;

$R^{11a}$ and $R^{11b}$ are each independently hydrogen or $C_1$-$C_6$alkyl, wherein said alkyl is optionally substituted with OH;

m is independently 0, 1 or 2;

n is independently 0 or 1;

p is independently 0 or 1; and t is 0, 1, 2 or 3;

or a pharmaceutically acceptable salt of said compound or a tautomer of said compound or said salt.

In one aspect of the invention, $R^1$ is $C_1$-$C_4$alkyl; $C_2$-$C_4$alkenyl; $C_2$-$C_4$alkynyl; —$(CR^{3a}R^{3b})_m$-(3- to 6-membered cycloalkyl); or —$(CR^{3a}R^{3b})_m$-(3- to 5-membered heterocycloalkyl) having one to three heteroatoms; wherein said alkyl, alkenyl, alkynyl, cycloalkyl or heterocycloalkyl is optionally substituted with one to three halogen, deuterium, —$OR^5$, —$SR^5$, —$NR^{11a}R^{11b}$, cyano, $C_1$-$C_6$alkyl, $C_3$-$C_6$cycloalkyl or $C_1$-$C_6$alkoxy; $R^{3a}$ and $R^{3b}$ are each independently hydrogen or $C_1$-$C_3$alkyl; $R^6$ is —$C(O)NHR^7$ or cyano; $R^7$ is hydrogen; and m is independently 0 or 1.

In another aspect, the invention provides for compounds wherein $R^1$ is fluoromethyl; difluoromethyl; trifluoromethyl; methyl, ethyl, propyl or isopropyl, each optionally substituted with one to three fluoro or deuterium; allene, propargyl, cyclopropyl, cyclobutyl, cyclopentyl, cyclopropylmethyl, oxetane or tetrahydrofuran, each of which is optionally substituted with fluoro or $C_1$-$C_3$ alkyl.

In another aspect, $R^2$ is selected from pyrrolidinyl, pyrrolidin-2-onyl, piperidinyl, piperidin-2-onyl, octahydro-1H-pyrrolo[3,4-c]pyridinyl, oxazolidinyl, oxazolidin-2-onyl, 1,3-oxazinan-2-onyl, imidazolidinyl, imidazolidin-2-onyl, morpholinyl, morpholin-3-onyl, thiazyl, isothiazyl, isothiazolidine-1,1-dioxidyl, 1,2-thiazinane 1,1-dioxidyl, hexahydrocyclopenta[b]pyrrol-2(1H)-onyl, octahydrocyclopenta[c]pyrrolyl, azetidinyl, hexahydro-1H-indol-2(3H)-onyl, octahydro-1H-isoindolyl, azepanyl, tetrahydrofuranyl, 1,3-dioxolanyl, oxetanyl, cyclopropyl, cyclobutyl, cyclopentyl, cyclohexyl, 4-azepanyl, 1,4-oxazepanyl, tetrahydro-2H-pyranyl, 6,7-dihydro-5H-pyrrolo[1,2-a]imidazolyl, cyclohex-2-enyl, or 1,2,3,4-tetrahydroisoquinolinyl; wherein said alkyl, cycloalkyl or heterocycloalkyl is optionally substituted with one to four $R^4$.

In another aspect, the cycloalkyl and heterocycloalkyl of $R^2$ is optionally substituted with one to four $R^4$; or two $R^4$ taken together with the respective carbons to which each are bonded form a 3- to 6-membered cycloalkyl or 4- to 6-membered heterocycloalkyl, wherein said cycloalkyl or heterocycloalkyl is optionally substituted with one to three F, Cl, OH, cyano, $C_1$-$C_3$alkyl (optionally substituted with OH, F or Cl), $C_1$-$C_3$fluoroalkyl or $C_1$-$C_6$alkoxy; $R^q$ is independently hydrogen, deuterium or $C_1$-$C_3$alkyl, wherein said alkyl is optionally substituted with halogen; $R^{3a}$ and $R^{3b}$ for each occurrence are independently hydrogen or $C_1$-$C_3$alkyl; $R^4$ for each occurrence is independently and optionally halogen; $C_1$-$C_3$alkyl; $C_2$-$C_4$alkenyl; oxo; —$OR^5$; —$C(O)R^{10}$; —$(CR^{3a}R^{3b})_n$-(3- to 5-membered cycloalkyl); or —$(CR^{3a}R^{3b})_n$-(4- to 7-membered heterocycloalkyl) wherein said alkyl, cycloalkyl or heterocycloalkyl is each optionally and independently substituted with one to five deuterium, halogen, OH, cyano, $C_1$-$C_6$alkoxy or —$NR^{11a}R^{11b}$; or two $R^4$ taken together with the respective carbons to which each are bonded form a cyclopropyl, cyclobutyl or cyclopentyl, wherein said cyclopropyl, cyclobutyl or cyclopentyl are optionally substituted with one to three halogen, OH, methyl, ethyl, propyl, $C_1$-$C_3$fluoroalkyl, $C_1$-$C_3$hydroxyalkyl, methoxy or ethoxy; or two $R^4$ taken together with the respective carbons to which each are bonded form a 4- to 6-membered heterocycloalkyl, wherein said heterocycloalkyl is optionally substituted with one to three fluoro, $C_1$-$C_3$alkyl, or $C_1$-$C_3$fluoroalkyl; $R^5$ is hydrogen, methyl or ethyl; $R^9$ is phenyl; $R^{10}$ is $C_1$-$C_6$alkyl, wherein said alkyl is optionally substituted with fluoro or cyano; and $R^{11a}$ and $R^{11b}$ are each independently H or $C_1$-$C_6$alkyl; or a pharmaceutically acceptable salt thereof or a tautomer of said compound or said salt.

In another aspect, $R^4$ is selected from F, Cl, OH; $C_1$-$C_3$alkyl, optionally substituted with one to five deuterium, Cl, F, OH, $C_1$-$C_3$alkyl, $C_1$-$C_3$alkoxy; or two $R^4$ taken together with the respective carbons to which each are bonded form a cyclopropyl, cyclobutyl or cyclopentyl, wherein said cyclopropyl, cyclobutyl or cyclopentyl are optionally substituted with one to three Cl, F, OH, methyl, ethyl, propyl, $C_1$-$C_3$fluoroalkyl, $C_1$-$C_3$hydroxyalkyl, methoxy or ethoxy; or two $R^4$ taken together with the respective carbons to which each are bonded form a 4- to 6-membered heterocycloalkyl, wherein said heterocycloalkyl is optionally substituted with one to three fluoro, $C_1$-$C_3$alkyl, $C_1$-$C_3$fluoroalkyl, —$C(O)(CH_2)_tCN$; or a pharmaceutically acceptable salt thereof or a tautomer of said compound or said salt.

In another embodiment, the invention is directed to a compound of Formula III

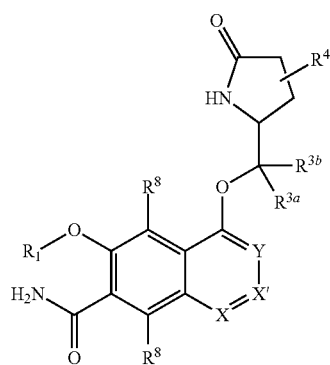

III wherein

X and X' are each independently $CR^8$ or N; Y is independently N or $CR^{8'}$; provided that at least one of X, X' or Y is not N;

$R^1$ is $C_1$-$C_6$alkyl or $C_1$-$C_6$cycloalkyl, wherein said alkyl or cycloalkyl is optionally substituted with deuterium, halogen, OH, cyano, $C_1$-$C_3$alkyl, $C_3$-$C_6$cycloalkyl, $C_1$-$C_6$alkoxy or $C_1$-$C_6$alkylthiolyl;

$R^{3a}$ and $R^{3b}$ are each independently hydrogen or $C_1$-$C_3$alkyl;

$R^4$ for each occurrence (one, two, three, four or five) is independently and optionally halogen, $C_1$-$C_6$alkyl, $C_2$-$C_6$alkenyl —$OR^5$, —$(CR^{3a}R^{3b})_n$-(3- to 6-membered cycloalkyl) or —$(CR^{3a}R^{3b})_n$-(4- to 6-membered heterocycloalkyl) wherein said alkyl, cycloalkyl or heterocycloalkyl is each optionally and independently substituted with one to five deuterium, halogen, OH, CN, —$C(O)(CH_2)_tCN$ or —$C_1$-$C_6$alkoxy; —$NR^{11a}R^{11b}$; two $R^4$ taken together with the respective carbons to which each are bonded form a cyclopropyl, cyclobutyl or cyclopentyl, wherein said cyclopropyl, cyclobutyl or cyclopentyl is optionally substituted with one to three F, Cl, OH, methyl, ethyl, propyl, $C_1$-$C_3$fluoroalkyl, $C_1$-$C_3$difluoroalkyl, $C_1$-$C_3$trifluoroalkyl, $C_1$-$C_3$hydroxyalkyl, methoxy or ethoxy;

$R^5$ is hydrogen or $C_1$-$C_6$alkyl, wherein said alkyl is optionally substituted with fluoro;

$R^8$ is independently hydrogen, halogen, cyano, —$NR^{11a}R^{11b}$, $C_1$-$C_6$alkyl, 5- to 6-membered heteroaryl or aryl, wherein said alkyl or heteroaryl or aryl is optionally substituted with one, two or three halogen, —$NR^{11a}R^{11b}$, $C_1$-$C_3$ alkyl or oxo;

$R^{8'}$ is hydrogen, deuterium, halogen or cyano;

$R^{10}$ is $C_1$-$C_6$alkyl, wherein said alkyl is optionally substituted with fluoro or cyano;

$R^{11a}$ and $R^{11b}$ are each independently hydrogen or $C_1$-$C_6$alkyl, wherein said alkyl is optionally substituted with OH;

n is independently 0 or 1; and t is 1, 2 or 3;

or a pharmaceutically acceptable salt of said compound or a tautomer of said compound or said salt.

In one aspect, the invention is directed to compounds wherein Y is N; X and X' are $CR^8$.

In another aspect, X and X' are each $CR^8$ and Y is $CR^{8'}$. In another aspect, X and Y are N and X' is $CR^8$. In another aspect, X is N, X' is $CR^8$ and Y is $CR^{8'}$.

In another aspect, $R^1$ is $C_1$-$C_3$alkyl, wherein said alkyl is optionally substituted with one to three deuterium, F, Cl or $C_1$-$C_3$alkoxy; and $R^{3a}$ and $R^{3b}$ are each independently hydrogen or methyl. In another aspect, $R^4$ for each occurrence is independently and optionally F; Cl; OH; or $C_1$-$C_3$alkyl, optionally substituted with one to five deuterium, Cl, F, OH, $C_1$-$C_3$alkyl, or $C_1$-$C_3$alkoxy; or two $R^4$ taken together with the carbons to which they are bonded form a cyclopropyl, cyclobutyl or cyclopentyl, wherein said cyclopropyl, cyclobutyl or cyclopentyl is optionally substituted with one to three Cl, F, OH, methyl, ethyl, propyl, $C_1$-$C_3$haloalkyl, $C_1$-$C_3$dihaloalkyl, $C_1$-$C_3$trihaloalkyl, $C_1$-$C_3$hydroxyalkyl, methoxy or ethoxy; or two $R^4$ taken together with the carbons to which they are bonded form a 4- to 6-membered heterocycloalkyl, wherein said heterocycloalkyl is optionally substituted with one to three fluoro, $C_1$-$C_3$alkyl, $C_1$-$C_3$fluoroalkyl or —$C(O)(CH_2)_tCN$.

In still another aspect, $R^1$ is methyl, ethyl, propyl or isopropyl wherein each of said $R^1$ moieties are optionally substituted with deuterium, fluoro or methoxy; $R^4$ is independently and optionally selected from fluoro, OH, methyl, ethyl, vinyl, propyl, wherein said methyl, ethyl, vinyl or propyl are optionally substituted with one, two or three fluoro, OH or methoxy; or two $R^4$ taken together with the carbons to which they are bonded form a cyclopropyl, cyclobutyl or cyclopentyl, wherein said cyclopropyl, cyclobutyl or cyclopentyl are optionally substituted with one to three Cl, F, OH, methyl, fluoromethyl, difluoromethyl, trifluoromethyl, ethyl, methoxymethyl, propyl, $C_1$-$C_3$haloalkyl, $C_1$-$C_3$dihaloalkyl, $C_1$-$C_3$trihaloalkyl, $C_1$-$C_3$hydroxyalkyl, methoxy, or ethoxy; and $R^8$ is independently hydrogen, halogen or $C_1$-$C_6$alkyl, wherein said alkyl is optionally substituted with fluoro.

In another embodiment, the invention is directed to a compound of Formula IIIa,

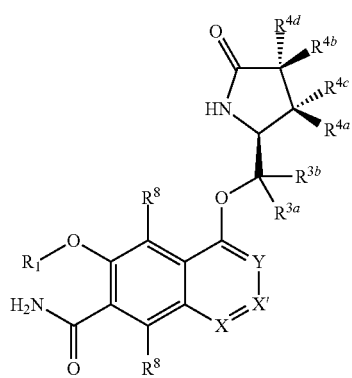

IIIa wherein

X and X' are each independently $CR^8$ or N; Y is independently N or $CR^{8'}$; provided that at least one of X, X' or Y is not N;

$R^1$ is $C_1$-$C_6$alkyl, wherein said alkyl is optionally substituted with deuterium, halogen, OH, $C_1$-$C_3$alkyl, $C_3$-$C_6$cycloalkyl or $C_1$-$C_6$alkoxy;

$R^{3a}$ and $R^{3b}$ are each independently hydrogen or $C_1$-$C_3$alkyl;

$R^{4a}$ and $R^{4b}$ are each independently hydrogen, deuterium, fluoro, OH, —$OR^5$, methyl, ethyl, vinyl, cyclopropyl or propyl, optionally substituted with one to five deuterium, fluoro, methoxy or OH;

$R^{4c}$ and $R^{4d}$ for each occurrence are independently and optionally halogen, OH, deuterium, $C_1$-$C_6$alkyl, $C_2$-$C_6$alkenyl, —$OR^5$, —$(CR^{3a}R^{3b})_n$-(3- to 6-membered cycloalkyl), or —$(CR^{3a}R^{3b})_n$-(4- to 6-membered heterocycloalkyl) wherein said alkyl, cycloalkyl and heterocycloalkyl are each optionally and independently substituted with one to five deuterium, halogen, OH, cyano, or $C_1$-$C_6$alkoxy; $NH_2$; or $R^{4c}$ and $R^{4d}$ taken together with the carbons to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl; or $R^{4a}$ and $R^{4c}$ taken together with the carbon to which they are bonded form a 4- to 7-membered heterocycloalkyl or a 3- to 7-membered cycloalkyl, wherein said heterocycloalkyl or cycloalkyl is optionally substituted with one to three fluoro, $C_1$-$C_3$alkyl or $C_1$-$C_3$fluoroalkyl;

$R^5$ is hydrogen or $C_1$-$C_6$alkyl, wherein said alkyl is optionally substituted with fluoro;

$R^8$ is hydrogen, halogen or $C_1$-$C_6$alkyl, wherein said alkyl is optionally substituted with halogen;

$R^{8'}$ is hydrogen, deuterium, halogen or cyano; and n is independently 0 or 1;

or a pharmaceutically acceptable salt of said compound or a tautomer of said compound or said salt.

In one aspect, the invention provides $R^8$ is hydrogen, methyl or fluoro; $R^1$ is methyl, ethyl, isopropyl or propyl, optionally substituted with deuterium; $R^{4a}$ is hydrogen; methyl, ethyl or propyl, optionally substituted with deuterium, fluoro, methoxy; $R^{4b}$ is hydrogen or fluoro; $R^{4c}$ is hydrogen or OH; $R^{4d}$ is hydrogen, fluoro, methoxy or OH; or methyl, optionally substituted with 1, 2 or 3 fluoro; or ethyl, optionally substituted with 1, 2 or 3 fluoro; or $R^{4c}$ and $R^{4d}$ or alternatively $R^{4a}$ and $R^{4c}$ taken together with the carbons to which they are bonded form a cyclopropyl, optionally substituted with one to three fluoro, $C_1$-$C_3$alkyl or $C_1$-$C_3$fluoroalkyl; or a pharmaceutically acceptable salt of said compound or a tautomer of said compound or said salt.

In another embodiment, the invention is directed to the compounds described in Tables 1 or 3; or a pharmaceutically acceptable salt of said compound or a tautomer of said compound or said salt.

In another embodiment, the invention is directed to the intermediate compounds described in Table 2; or a pharmaceutically acceptable salt of said compound or a tautomer of said compound or said salt In another embodiment, the invention is directed to a synthetic process and preparation of the intermediate compounds described in Table 2, as detailed in the Schemes and the preparation section described herein. In another aspect, the invention is directed to a synthetic process and preparation of the compounds of Tables 1 or 3, as detailed in the Schemes and the preparation section described herein.

IRAK4 Indications

The compounds of the invention are also useful in treating and/or preventing a disease or condition mediated by or otherwise associated with an IRAK enzyme; the method comprising administering to a subject in need thereof an effective amount of a compound of the invention.

The disease may be, but not limited to, one of the following classes: auto-immune diseases, inflammatory diseases, allergic diseases, metabolic diseases, infection-based diseases, trauma or tissue-injury based diseases, fibrotic diseases, genetic diseases, diseases driven by over-activity of IL1 pathways, cardiovascular diseases, vascular diseases, heart diseases, neurological diseases, neurodegenerative diseases, respiratory diseases, pulmonary diseases, airways diseases, renal diseases, skin and/or dermatological diseases, liver diseases, gastrointestinal diseases, oral diseases, pain and sensory diseases, hematopoietic diseases, joint diseases, muscle diseases, bone diseases, and ophthalmic and/or ocular diseases.

Specific autoimmune diseases include, but are not limited to: rheumatoid arthritis, osteoarthritis, psoriasis, allergic dermatitis, systemic lupus erythematosus (and resulting complications), Sjögren's syndrome, multiple sclerosis, asthma, glomerular nephritis, irritable bowel syndrome, inflammatory bowel disease, Crohn's disease, ankylosing spondylitis, Behçet's disease, lupus nephritis, scleroderma, systemic scleroderma, type 1 or juvenile on-set diabetes, alopecia universalis, acute disseminated encephalomyelitis, Addison's disease, antiphospholipid antibody syndrome, atrophic gastritis of pernicious anemia, autoimmune alopecia, autoimmune hemolytic anemia, autoimmune hepatitis, autoimmune encephalomyelitis, autoimmune thrombocytopenia, Bullous pemphigoid, Chagas disease, Celiac disease, chronic hepatitis, Cogan's syndrome, dermatomyositis, endometriosis, Goodpasture's syndrome, Graves' disease, Guillain-Barré syndrome, Hashimoto's disease (or Hashimoto's thyroiditis), hemolytic anemia, hidradentitis suppurativa, idiopathic thrombocytopenia purpura, interstitial cystitis, membranous glomerulopathy, morphea, mystenia gravis, narcolepsy, pemphigus, pernicous anemia, polyarteritis nodosa, polymyositis, primary biliary cirrhosis, Reiter's syndrome, schizophrenia, symphathetic opthalmia, systemic sclerosis, temporal arteritis, thyroiditis, vasculitis, vitiglio, vulvodynia, Wegner's granulomatosis, palmoplantar keratoderma, systemic-onset Juvenile Idiopathic Arthritis (SJIA), or an indication listed in a separate category herein.

Specific inflammatory diseases include, but are not limited to: chronic obstructive pulmonary diseases, airway hyper-responsiveness, cystic fibrosis, acute respiratory distress syndrome, sinusitis, rhinitis, gingivitis, atherosclerosis, chronic prostatitis, glomerular nephritis, ulcerative colitis, uveitis, periodontal disease, or an indication listed in a separate category herein.

Specific pain conditions include, but are not limited to: inflammatory pain, surgical pain, visceral pain, dental pain, premenstrual pain, central pain, pain due to burns, migraine or cluster headaches, nerve injury, interstitial cystitis, cancer pain, viral, parasitic or bacterial infection, post-traumatic injury, pain associated with irritable bowel syndrome, gout, pain associated with any of the other indications listed within this specification, or an indication listed in a separate category herein.

Specific respiratory, airway and pulmonary conditions include, but are not limited to: asthma (which may encompass chronic, late, bronchial, allergic, intrinsic, extrinsic or dust), chronic obstructive pulmonary disease, idiopathic pulmonary fibrosis, pulmonary arterial hypertension, cystic fibrosis, interstitial lung disease, acute lung injury, sarcoidosis, allergic rhinitis, chronic cough, bronchitis, recurrent airway obstruction, emphysema, or bronchospasm, or an indication listed in a separate disease category herein.

Specific gastrointestinal (GI) disorders include, but are not limited to: Irritable Bowel Syndrome (IBS), Inflammatory Bowel Disease (IBD), biliary colic and other biliary disorders, renal colic, diarrhea-dominant IBS, pain associated with GI distension, ulcerative colitis, Crohn's Disease, irritable bowel syndrome, Celiac disease, proctitis, eosinophilic gastroenteritis, mastocytosis, or an indication listed in a separate disease category herein.

Specific allergic diseases include, but are not limited to: anaphylaxis, allergic rhinitis, allergic dermatitis, allergic urticaria, angioedema, allergic asthma, allergic reactions to: food, drugs, insect bites, pollen; or an indication listed in a separate disease category herein.

Specific infection-based diseases include, but are not limited to: sepsis, septic shock, viral diseases, malaria, Lyme disease, ocular infections, conjunctivitis, Whipple Disease, or an indication listed in a separate disease category herein.

Specific trauma and tissue injury-based conditions include, but are not limited to: Renal glomerular damage, reperfusion injury (for example to heart, kidney, lung), spinal cord injury, tissue scarring, tissue adhesion, tissue repair, transplant rejection (for examples to heart, lung, bone marrow, cartilage, cornea, kidney, limb, liver, muscle, myoblast, pancreas, pancreatic islet, skin, nerve, small intestine, trachea), hypersensitivities, or an indication listed in a separate disease category herein.

Specific fibrotic diseases include, but are not limited to: Idiopathic pulmonary fibrosis, liver fibrosis, renal fibrosis, or an indication listed in a separate disease category herein.

Specific diseases considered to be driven by over-activity of IL1 pathways include, but are not limited to: Cryopyrin-associated periodic syndromes, myositis, and indications included in the following review article: C. A. Dinarello, A. Simon and J. W. M. van der Meer, Treating inflammation by blocking interleukin-1 in a broad spectrum of diseases, Nat Rev Drug Discov, 2012, 11(8), 633-652, http://dx.doi.org/10.1038/nrd3800 and supplementary information contained therein, or an indication listed in a separate disease category herein.

Specific ophthalmic/ocular diseases include, but are not limited to: uveitis, age-related macular degeneration, diabetic macular edema, keratoconjuctivitis, uveitis associated with Behçet's disease, vernal conjunctivitis, ketatitis, lens-induced uveitis, herpetic keratitis, conical keratitis, corneal epithelial dystrophy, ocular pemphigus, Mooren's ulcer, Scleritis, Graves' ophthalmopathy, Vogt-Koyanagi-Harada syndrome, keratoconjunctivitis sicca, phlyctenule, iridocyclitis, sympathetic ophthalmia, allergic conjunctivitis, ocular neovascularization, dry eye syndrome, or an indication listed in a separate disease category herein.

Specific joint, muscle and bone disorders include, but are not limited to: osteoarthritis, osteoporosis, rheumatoid arthritis, juvenile arthritis, psoriatic arthritis, erosive osteoarthritis of the hand, arthrofibrosis/traumatic knee injury, anterior cruciate knee ligament tear, relapsing polychondritis, recurrent multifocal osteomyelitis, Majeed Syndrome, ankylosing spondylitis, gout of the lumbar spine, antisynthetase syndrome, idiopathic inflammatory myopathies, articular chondrocalcinosis, systemic-onset Juvenile Idiopathic Arthritis (SJIA), gout and pyrophosphate crystal arthritis, or an indication listed in a separate disease category herein.

Specific skin/dermatological diseases include, but are not limited to: psoriasis, atopic dermatitis, cutaneous lupus, acne, dermatomyositis, eczema, pruritus, scleroderma, Sweet Syndrome/neutrophilic dermatosis, neutrophilic panniculitis, acrodermatitis (form of pustular psoriasis), or an indication listed in a separate disease category herein.

Specific renal diseases include, but are not limited to: acute kidney injury (AKI) (sepsis-AKI, coronary artery bypass graft-AKI, cardiac surgery-AKI, non-cardiac surgery-AKI, transplant surgery-AKI cisplatin-AKI, contrast/imaging agent induced-AKI), glomerulonephritis, IgA nephropathy, crescentic GN, lupus nephritis, HIV associated nephropathy, membraneous nephropathy, C3 glomerulopathy, Dense deposit disease, ANCA vasculitis, diabetic nephropathy, hemolytic-uremic syndrome, atypical Hemolytic-uremic syndrome, nephrotic syndrome, nephritic syndrome, hypertensive nephrosclerosis, ApoL1 nephropathy, focal segmental glomerulosclerosis, Alport syndrome, Fanconi, syndrome, crystal nephropathy, nephrolithiasis, nephrotic syndrome, renal transplant rejection, amyloidosis, glomerulonephritis in SJIA, or an indication listed in a separate disease category herein.

Specific genetic diseases include, but are not limited to: Familial Mediterranean fever (FMF), CAPS (FCAS, Muckle-Wells Syndrome, NOMID/CINCA), male hypoinfertility in CAPS, NLRP12 Autoinflammatory Syndrome, or an indication listed in a separate disease category herein.

Specific hematopoietic diseases include, but are not limited to: hemolytic anemia, or an indication listed in a separate disease category herein.

Specific liver diseases include, but are not limited to: liver fibrosis, liver cirrhosis, nonalcoholic steatohepatitis (NASH), or an indication listed in a separate disease category herein.

Specific oral diseases include, but are not limited to: gingivitis, periodontal disease or an indication listed in a separate disease category herein.

Specific metabolic diseases include, but are not limited to: Type 2 diabetes (and resulting complications), gout and hyperuricemia, metabolic syndrome, insulin resistance, obesity, or an indication listed in a separate disease category herein.

Compounds of the current invention are also useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, nonsmall-cell lung carcinoma, lymphomas, Hodgkins and Non-Hodgkins, a mammary carcinoma, follicular carcinoma, undifferentiated carcinoma, papillary carcinoma, seminoma, melanoma, smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, intravascular large B-cell lymphoma), or an indication listed in a separate disease category herein.

Cardiovascular conditions include, but are not limited to coronary heart disease, acute coronary syndrome, ischaemic heart disease, first or recurrent myocardial infarction, secondary myocardial infarction, non-ST segment elevation myocardial infarction, or ST segment elevation myocardial infarction, ischemic sudden death, transient ischemic attack, peripheral occlusive arterial disease, angina, atherosclerosis, hypertension, heart failure (such as congestive heart failure), diastolic dysfunction (such as left ventricular diastolic dysfunction, diastolic heart failure, and impaired diastolic filling), systolic dysfunction (such as systolic heart failure with reduced ejection fraction), vasculitis, ANCA vasculitis, post-myocardial infarction cardiac remodeling atrial fibrillation, arrhythmia (ventricular), ischemia, hypertrophic cardiomyopathy, sudden cardiac death, myocardial and vascular fibrosis, impaired arterial compliance, myocardial necrotic lesions, vascular damage, left ventricular hypertrophy, decreased ejection fraction, cardiac lesions, vascular wall hypertrophy, endothelial thickening, fibrinoid necrosis of coronary arteries, adverse remodeling, stroke, and the like, or an indication listed in a separate disease category herein. Also, included are venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty).

Cardiovascular complications of type 2 diabetes are associated with inflammation, accordingly, the compounds of the present invention may be used to treat diabetes and diabetic complications such as macrovascular disease, hyperglycemia, metabolic syndrome, impaired glucose tolerance, hyperuricemia, glucosuria, cataracts, diabetic neuropathy, diabetic nephropathy, diabetic retinopathy, obesity, dyslipidemia, hypertension, hyperinsulinemia, and insulin resistance syndrome, or an indication listed in a separate disease category herein.

Linkage of innate immunity and inflammation to disease has been demonstrated in neuroinflammatory and neurodegenerative conditions. Therefore, the compounds of the present invention are particularly indicated for use in the treatment of neuroinflammatory and neurodegenerative conditions (i.e., disorders or diseases) in mammals including humans such as multiple sclerosis, migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV associated dementia, Alzheimer's associated dementia, Huntington's associated dementia, Lewy body dementia, vascular dementia, drug related dementia, delirium, and mild cognitive impairment); mental deficiency (including Down syndrome and fragile X syndrome); sleep disorders (including hypersomnia, circadian rhythm sleep disorder, insomnia, parasomnia, and sleep deprivation) and psychiatric disorders (such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism), myotrophic lateral sclerosis, chronic fatigue syndrome, or an indication listed in a separate disease category herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous.

Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants.

Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88(10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3$^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of an IRAK inhibitor compound as provided in the compound of Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the methods of prevention and treatment described herein include use of combination agents.

The combination agents are administered to a mammal, including a human, in a therapeutically effective amount. By "therapeutically effective amount" it is meant an amount of a compound of the present invention that, when administered alone or in combination with an additional therapeutic agent to a mammal, is effective to treat the desired disease/condition e.g., inflammatory condition such as systemic lupus erythematosus. See also, T. Koutsokeras and T. Healy, Systemic lupus erythematosus and lupus nephritis, Nat Rev Drug Discov, 2014, 13(3), 173-174, for therapeutic agents useful treating lupus.

In particular, it is contemplated that the compounds of the invention may be administered with the following therapeutic agents:

Non-steroidal anti-inflammatory drugs (NSAIDs), including but not limited to, non-selective COX1/2 inhibitors such as piroxicam, naproxen, flubiprofen, fenoprofen, ketoprofen, ibuprofen, etodolac (Lodine), mefanamic acid, sulindac, apazone, pyrazolones (such as phenylbutazone), salicylates (such as aspirin); selective COX2 inhibitors such as: celecoxib, rofecoxib, etoricoxib, valdecoxib, meloxicam;

Immunomodulatory and/or anti-inflammatory agents, including but not limited to, methotrexate, leflunomide, ciclesonide chloroquine, hydroxychloroquine, d-penicillamine, auranofin, sulfasalazine, sodium aurothiomalate, cyclosporine, azathioprine, cromolyn, hydroxycarbamide, retinoids, fumarates (such as monomethyl and dimethyl fumarate), glatiramer acetate, mitoxantrone, teriflunomide, suplatast tosilate, mycophenolate mofetil and cyclophosphamide, laquinimod, voclosporin, PUR-118, AMG 357, AMG 811, BCT197;

Antimalarials, including but not limited to, hydroxychloroquine (Plaquenil) and chloroquine (Aralen), cyclophosphamide (Cytoxan), methotrexate (Rheumatrex), azathioprine (Imuran), mesalamine (Asacol) and sulfasalazine (Azulfidine):

Antibiotics, including but not limited to, Flagyl or ciprofloxacin;

Anti-TNFα agents, including but not limited to, infliximab, adalimumab, certolizumab pegol, golimumab and etanercept;

Anti-CD20 agents, including but not limited to, rituximab, ocrelizumab, ofatumumab and PF-05280586;

Antidiarrheals, such as diphenoxylate (Lomotil) and loperamide (Imodium);

Bile acid binding agents, such as cholestyramine, alosetron (Lotronex) and ubiprostone (Amitiza);

Laxatives, such as Milk of Magnesia, polyethylene glycol (MiraLax), Dulcolax, Correctol and Senokot, and anticholinergics or antispasmodics such as dicyclomine (Bentyl);

T lymphocyte activation inhibitors, including but not limited to, abatacept:

Anti-IL1 treatments, including but not limited to, anakinra, rilonacept, canakinumab, gevokizumab, MABp1 and MEDI-8968;

Glucocorticoid receptor modulators that may be dosed orally, by inhalation, by injection, topically, rectally, by ocular delivery, including but not limited to, betamethasone, prednisone, hydrocortisone, prednisolone, flunisolide, triamcinoline acetonide, beclomethasone, dipropionate, budesonide, fluticasone propionate, ciclesonide, mometasone furoate, fluocinonide, desoximetasone, methylprednisolone or PF-04171327;

Aminosalicyic acid derivatives, including but not limited to, sulfasalazine and mesalazine; Anti-α4 integrin agents, including but not limited to, natalizumab;

α1- or α2-adrenergic agonist agents including but not limited to: propylhexidrine, phenylephrine, phenylpropanolamine, pseudoephedrine or naphazoline hydrochloride, oxymetazoline hydrochloride, tetrahydrozoline hydrochloride, xylometazoline hydrochloride or ethylnorepinephrine hydrochloride;

β-adrenergic agonists, including but not limited to, metaproterenol, isoprotenerol, isoprenaline, albuterol, salbutamol, formoterol, salmeterol, terbutaline, orciprenaline, botolterol mesylate, pirbuterol;

Anticholinergic agents, including but not limited to, ipratropium bromide, tiotropium bromide, oxitropium bromide, aclindinium bromide, glycopyrrolate, pirenzipine or telenzepine;

Inhaled long acting beta-agonists, long acting muscarinic antagonists and long acting corticosteroids, including but not limited, to those included in the following reference: Y. Mushtaq, The COPD pipeline, *Nat Rev Drug Discov*, 2014, 13(4), 253-254. http://dx.doi.org/10.1038/nrd425;

Leukotriene pathway modulators, including but not limited to, 5-LO Inhibitors (such as zileuton), FLAP antagonists (such as veliflapon, fiboflapon), LTD4 antagonists (such as montelukast, zafirlukast or pranlukast;

H1 receptor antagonists, including but not limited to, cetirizine, loratidine, desloratidine, fexofenadine, astemizole, azelastine or chlorpheniramine;

PDE4 inhibitors, including but not limited to, apremilast, roflumilast or AN2728;

Vitamin D receptor modulators, including but not limited to, paricalcitol;

Nrf2 pathway activators, including but not limited to, fumarates, sulfurophane and bardoxolone methyl;

Modulators of the RAR-related orphan receptor (ROR) family, in particular RORg;

Modulator and/or antagonists of the chemokine receptors, including but not limited to, CCR2 antagonists (such as CCX140, BMS-741672, PF-4634817, CCX-872, NOX-E36), CCR2/5 antagonists (such as PF-4634817), CCR9 (such as vercirnon, CCX507), CCR1 modulators, CCR4 modulators, CCR5 modulators, CCR6 modulators, CXCR6 modulators, CXCR7 modulators) and CXCR2 modulators (such as danirixin, AZD5069);

Prostaglandins, including but not limited to, prostacyclin;

PDE5 inhibitors, including but not limited to, sildenafil, PF-489791, vardenafil and tadalafil;

Endothelin receptor antagonists, including but not limited to, bosentan, ambrisentan, sparsentan, atrasentan, zibotentan and macitentan;

Soluble guanylate cyclase activators, including but not limited to, riociguat;

Interferons, including but not limited to, interferon beta-1a interferon beta-1b;

Sphingosine 1-phosphate receptor modulators, including but not limited to, fingolimod, ponesimod;

Inhibitors of the complement pathway, including but not limited to, C5aR antagonists (such as CCX168, PMX-53, NN8210), C5 inhibitors (such as eculizumab), inhibitors of complement factors B and D, inhibitors of MASP2 (such as OMS-721) and ARC-1905;

Inhibitors of Janus kinases (one of more of JAK1, JAK2, JAK3, TYK2), including but not limited to, decernotinib, cerdulatinib, JTE-052, ruxolitinib, tofacitnib, Baricitinib, Peficitinib, GLPG-0634, INCB-47986, INCB-039110, PF-04965842, XL-019, ABT-494, R-348, GSK-2586184, AC-410, BMS-911543 and PF-06263276;

Inhibitors of other anti-inflammatory or immunomodulatory kinases, including but not limited to, spleen tyrosine kinase (SYK) inhibitors, p38 MAP kinase inhibitors (such as PF-3715455, PH-797804, AZD-7624, AKP-001, UR-13870, FX-005, semapimod, pexmetinib, ARRY-797, RV-568, dilmapimod, ralimetinib), PI3K inhibitors (such as GSK-2126458, pilaralisib, GSK-2269557), PI3Kg and/or PI3Kd inhibitors (such as CAL-101/GS-1101, duvelisib), JNK inhibitors, ERK1 and/or 2 inhibitors, IKKb inhibitors, BTK inhibitors, ITK inhibitors, ASK1 inhibitors (such as GS-4997), PKC inhibitors (such as sotrastaurin), TrkA antagonists (such as CT-327), MEK1 inhibitors (such as E6201);

Antioxidants, including but not limited to, myeloperoxidase inhibitors (such as AZD-3241), NOX4 and other NOX enzymes (such as GKT-137831) and N-acetyl cysteine;

Inhibitors of IL5, including but not limited to, mepolizumab, reslizumab and benralizumab;

Inhibitors of IL4, including but not limited to, pascolizumab, altrakincept and pitrakinra;

Inhibitors of IL13, including but not limited to, tralokinumab, anrukinzumab and lebrikizumab;

Anti-IL6 agents, including but not limited to, tocilizumab, olokizumab, siltuximab, PF-4236921 and sirukumab;

Inhibitors/Antagonists of IL17/IL17R, including but not limited to, secukinumab, RG-7624, brodalumab and ixekizumab;

Antagonists of IL12 and/or IL23, including but not limited to, tildrakizumab, guselkumab, MEDI2070 and AMG 139;

Inhibitors of IL33, including but not limited to, AMG 282;

Inhibitors of IL9, including but not limited to, MEDI-528;

Inhibitors of GM-CSF, including but not limited to, MT203;

Anti CD4 agents, including but not limited to, tregalizumab and rigerimod;

CRTH2 antagonists, including but not limited to, AZD-1981;

Inhibitors of B lymphocyte stimulator (BLYS; also known as BAFF), a protein that is often increased in patients with SLE, including but not limited to, belimumab, tabalumab, blisibimod, and atacicept;

CD22-specific monoclonal antibodies, including but not limited to, epratuzumab;

Inhibitors of interferon-α, including but not limited to, sifalimumab and rontalizumab;

Inhibitor of type I interferon receptors, including but not limited to, MEDI-546;

FcγRIIB agonists, including but not limited to, SM-101;

Modified and/or recombinant versions of Heat Shock Protein 10 (Hsp10, also known as Chaperonin 10 or EPF), including but not limited to, INV-103;

Inhibitors of the TNF superfamily receptor 12A (TWEAK receptor), including but not limited to, BIIB-023, enavatuzumab, and RG-7212;

Inhibitors of xanthine oxidase, including but not limited to, allopurinol, benzbromarone, febuxostat, topiroxostat, tisopurine and inositols;

Inhibitors of URAT1 (also known as SLC22A12), including but not limited to, lesinurad, RDEA 3170, UR1102 and levotofispam;

Additional treatments for gout and/or lowering of uric acid levels, including but not limited to, colchicines, pegloticase, benziodarone, isobrominidione, BCX4208 and arhalofenate;

Inhibitors of toll-like receptors (TLRs), including but not limited to, one or more of TLR7, TLR8, TLR9 (such as IMO-8400, IMO-3100, DV-1179), TLR2 and/or TLR 4 (such as VB-201, OPN-305);

Agonists of TLRs, including but not limited to, TLR7 (such as GSK2245035, AZD8848), TLR9 (such as AZD1419);

Activators SIRT1, including but not limited to, SRT2104;

A3 receptor agonists, including but not limited to, CF101;

Other agents of use of the treatment of psoriasis, including but not limited to, IDP-118, LAS41004, LEO 80185, LEO 90100, PH-10, WBI-1001, CNT01959, BT-061, cinzia, ustekinumab, MK-3222/SCH 900222, ACT-128800, AEB071, alitretinoin, ASP015K, Apo805K1, BMS-582949, FP187, hectoral (doxercalciferol), LEO 22811, Ly3009104 (INCB28050), calcipotriene foam (STF 115469), tofacitinib (CP-690,550), M518101 and CycloPsorb™;

Antifibrotic agents, including but not limited to: pirfenidone, inhibitors of LOXL2 (such as Simtuzumab), FT-011, modulators of epiregulin and/or TGFα (such as LY-3016859), modulators of TGFβ (such as LY-2382770, fresolimumab);

Prolyl hydroxylase inhibitors, including but not limited to, GSK1278863, FG-2216, ASP-1517/FG-4592, AKB-6548, JTZ-951, BAY-85-3934 and DS-1093;

Inhibitors of granulocyte macrophage colony-stimulating factor, including but not limited to, GSK3196165 (MOR103), PD-0360324 and mavrilimumab;

Inhibitors of MAdCAM and/or α4β7 integrin, including but not limited to, PF-00547659 and MEDI7183 (abrilumab);

Inhibitors of connective tissue growth factor (CTGF), including but not limited to, PF-06473871; Inhibitors of cathepsin C, including but not limited to, GSK2793660;

Inhibitors of soluble epoxide hydrolase, including but not limited to, GSK2269557;

Inhibitors of the TNFR1 associated death domain protein, including but not limited to, GSK2862277;

Anti-CD19 agents, including but not limited to, MEDI-551 and AMG 729;

Anti-B7RP1 agents/inhibitors of ICOS ligand, including but not limited to, MEDI15872 and AMG-557;

Inhibitors of thymic stromal lymphoprotein, including but not limited to, AMG157;

Inhibitors of IL2, including but not limited to, daclizumab;

Inhibitors of Leucine rich repeat neuronal protein 6A, including but not limited to, Anti-Lingo (Biogen);

Inhibitors of integrins, including but not limited to, alpha-V/beta-6 (STX-100) and alpha-V/beta-3 (VPI-2690B);

Anti-CD40L agents, including but not limited to, CDP-7657;

Modulators of the dopamine D3 receptor, including but not limited to, ABT-614;

Inhibitors and/or modulators of galectin-3, including but not limited to, GCS-100 and GR-MD-02;

Agents for treating diabetic nephropathy, including but not limited to, DA-9801 and ASP-8232;

Agents for treating acute kidney injury, including but not limited to, THR-184, TRC-160334, NX-001, EA-230, ABT-719, CMX-2043, BB-3 and MTP-131;

Modulators of inflammasomes, including but not limited to, inhibitors of NLRP3;

Modulators of bromodomains, including but not limited to, BRD4;

Modulators of GPR43; and

Inhibitors of TRP channels, including but not limited to, TRPA1, TRPC3, TRPC5, TRPC6 and TRPC6.

Additional therapeutic agents include anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, NO donating agents such as organonitrates, NO promoting agents such as phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid hormone receptor antagonist), anti-infective agents, anti-viral agents, anti-bacterial agents, and anti-fungal agents.

Agents used in an ICU setting are included, for example, dobutamine, dopamine, epinephrine, nitroglycerin, nitroprusside, etc.

Combination agents useful for treating vasculitis are included, for example, azathioprine, cyclophosphamide, mycophenolate, mofetil, rituximab, etc.

In another embodiment, the present invention provides a combination wherein the second agent is at least one agent selected from a factor Xa inhibitor, an anti-coagulant agent, an anti-platelet agent, a thrombin inhibiting agent, a thrombolytic agent, and a fibrinolytic agent. Exemplary factor Xa inhibitors include apixaban and rivaroxaban. Examples of suitable anti-coagulants for use in combination with the compounds of the present invention include heparins (e.g., unfractioned and low molecular weight heparins such as enoxaparin and dalteparin).

In another embodiment the second agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another embodiment, the agent is at least one anti-platelet agent. Especially preferred anti-platelet agents are aspirin and clopidogrel. The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicylic acid or ASA) and COX-2 inhibitors such as celecoxib or piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., Pletal, dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticagrelor, prasugrel, ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastrointestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase. Examples of suitable anti-arrythmic agents include: Class I agents (such as propafenone); Class II agents (such as metoprolol, atenolol, carvadiol and propranolol); Class III agents (such as sotalol, dofetilide, amiodarone, azimilide and ibutilide); Class IV agents (such as ditiazem and verapamil); K⁺ channel openers such as $I_{Ach}$ inhibitors, and $I_{Kur}$ inhibitors (e.g., compounds such as those disclosed in WO01/40231).

The compounds of the present invention may be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine and amlodipine); vasodilators (e.g., hydralazine), diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil. Examples of suitable cardiac glycosides include digitalis and ouabain.

In one embodiment, a compound of the invention may be co-administered with one or more diuretics. Examples of suitable diuretics include (a) loop diuretics such as furosemide (such as LASIX™), torsemide (such as DEMADEX™), bemetanide (such as BUMEX™), and ethacrynic acid (such as EDECRIN™); (b) thiazide-type diuretics such as chlorothiazide (such as DIURIL™, ESIDRIX™ or HYDRODIURIL™), hydrochlorothiazide (such as MICROZIDE™ or ORETIC™), benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™). In another embodiment, a compound of the invention may be co-administered with a loop diuretic. In still another embodiment, the loop diuretic is selected from furosemide and torsemide. In still another embodiment, one or more compounds of the invention may be co-administered with furosemide. In still another embodiment, one or more compounds of the invention may be co-administered with torsemide which may optionally be a controlled or modified release form of torsemide.

In another embodiment, a compound of the invention may be co-administered with a thiazide-type diuretic. In still another embodiment, the thiazide-type diuretic is selected from the group consisting of chlorothiazide and hydrochlorothiazide. In still another embodiment, one or more compounds of the invention may be co-administered with chlorothiazide. In still another embodiment, one or more compounds of the invention may be co-administered with hydrochlorothiazide. In another embodiment, one or more compounds of the invention may be co-administered with a phthalimidine-type diuretic. In still another embodiment, the phthalimidine-type diuretic is chlorthalidone.

Examples of suitable combination mineralocorticoid receptor antagonists include sprionolactone and eplerenone. Examples of suitable combination phosphodiesterase inhibitors include: PDE III inhibitors (such as cilostazol); and PDE V inhibitors (such as sildenafil).

The compounds of the present invention may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesteryl ester transfer protein inhibitors.

Anti-inflammatory agents also include sPLA2 and IpPLA2 inhibitors (such as darapladib), LO inhibitors (such as atrelueton) and IL-1 and IL-1r antagonists (such as canakinumab).

Other atherosclerotic agents include agents that modulate the action of PCSK9, for example, called bococizumab.

Cardiovascular complications of type 2 diabetes are associated with deleterious levels of MPO, accordingly, the compounds of the present invention may be used in combination with anti-diabetic agents, particularly type 2 anti-diabetic agents. Examples of suitable anti-diabetic agents include (e.g. insulins, metfomin, DPPIV inhibitors, GLP-1 agonists, analogues and mimetics, SGLT1 and SGLT2 inhibitors) Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Those skilled in the art will recognize that the compounds of this invention may also be used in conjunction with other cardiovascular or cerebrovascular treatments including PCI, stenting, drug eluting stents, stem cell therapy and medical devices such as implanted pacemakers, defibrillators, or cardiac resynchronization therapy.

The compounds of the present invention may be used in combination with neuroinflammatory and neurodegenerative agents in mammals. Examples of additional neuroinflammatory and neurodegenerative agents include antidepressants, antipsychotics, anti-pain agents, anti-Alzheimer's agents, and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, nortriptyline, protriptyline, amoxapine, desipramine and maprotiline. Examples of suitable SSRIs include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable SNRIs of use in the present invention include venlafaxine. Examples of suitable atypical anti-depressants include bupropion, lithium, trazodone and viloxazine. Examples of anti-Alzheimer's agents include NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A receptor (5-HT1A) agonists, and CRF antagonists. Suitable benzodiazepines include alprazolam, chlordiazepoxide, clonazepam, chlorazepate, diazepam, lorazepam, oxazepam, and prazepam. Suitable 5-HT1A receptor agonists include buspirone and ipsapirone. Suitable CRF antagonists include verucerfont. Suitable atypical antipsychotics include paliperidone, ziprasidone, risperidone, aripiprazole, olanzapine, and quetiapine. Suitable nicotine acetylcholine agonists include CP-601927 and varenicline. Anti-pain agents include pregabalin, gabapentin, clonidine, neostigmine, baclofen, midazolam, ketamine and ziconotide.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The present invention further comprises intermediate compounds useful in the synthesis of the compounds of the invention, including salts and/or tautomers thereof.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

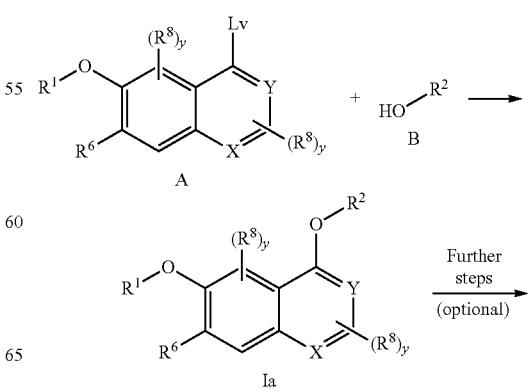

-continued

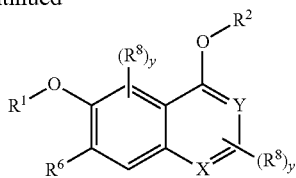

Scheme 1 illustrates a method for preparing compounds of Formula Ia. A compound of Formula A, in which Lv is a displaceable leaving group (such as chloro or fluoro, for example) is treated with a compound of Formula B (for example, see Scheme 9, or as commercially available) to furnish a product of Formula Ia. The reaction is typically carried out in the presence of a suitable base such as cesium carbonate, potassium tert-butoxide, sodium hydride or potassium hexamethyldisilazide in a suitable solvent or solvent mixture, such as THF or dimethylformamide. The compounds of Formula A may be prepared as described in the subsequent schemes. The compounds of formula $R^2$—OH may be obtained from commercial vendors, or prepared by methods reported in the chemical literature, or may be prepared as described in the subsequent schemes.

If desired, further transformations may be effected upon the compound of Formula Ia. For example, the compound of Formula Ia wherein $R^6$=CN may be subjected to a nitrile hydrolysis reaction to provide a compound of Formula Ia in which $R^6$=$CONH_2$. The reaction may be carried out in a variety of ways known to one skilled in the art, for example by the use of acids or bases, optionally in the presence of an oxidant such as hydrogen peroxide, or by using chemical or enzymatic catalysts. In other cases, the compound of Formula Ia may be further treated with reagents, such as acids, to cleave protecting groups, such as t-butoxycarbonyl groups, and/or with other reagents to derivatize functional groups such as carboxyl, amino, or hydroxyl groups.

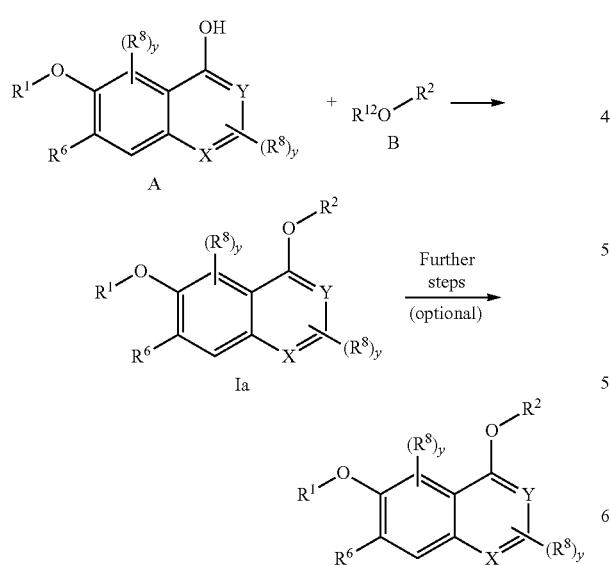

Scheme 2

Scheme 2 illustrates another method for the preparation of compounds of Formula Ia, particularly suited to those instances in which X and Y in the compound of Formula A are both carbon. This method provides for the alkylation of a compound of Formula A with a compound of Formula B (wherein the $R^{12}O$— group is either hydroxyl or a sulfonate ester such as p-toluenesulfonate or methanesulfonate; for example, see Scheme 9, or as commercially available), using methods known to those skilled in the art, to furnish a product of Formula Ia. For example, this reaction may be carried out by treating a compound of Formula A with a compound of Formula B ($R^{12}$=H) in the presence of triphenylphosphine and an azodicarboxylate ester ("Mitsunobu reaction") in a suitable solvent such as THF. Alternatively, the alkylation of a compound of Formula A may be effected using a compound of Formula B ($R^{12}O$=TsO or other sulfonate ester) in the presence of a base such as cesium carbonate, in a suitable solvent such as THF or dimethylformamide.

If desired, further transformations may be effected upon the compound of Formula Ia. For example, the compound of Formula Ia wherein $R^6$=CN may be subjected to a nitrile hydrolysis reaction to provide a compound of Formula Ia in which $R^6$=$CONH_2$. The reaction may be carried out in variety of ways known to one skilled in the art, for example by the use of acids or bases, optionally in the presence of an oxidant such as hydrogen peroxide, or by using chemical or enzymatic catalysts. In other cases, the compound of Formula Ia may be further treated with reagents, such as acids, to cleave protecting groups, such as t-butoxycarbonyl groups, and/or with other reagents to derivatize functional groups such as carboxyl, amino, or hydroxyl groups.

Scheme 3

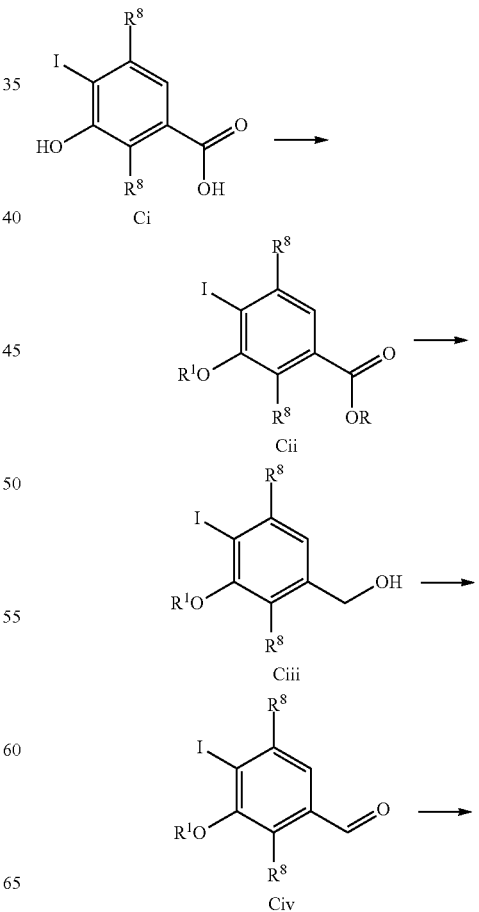

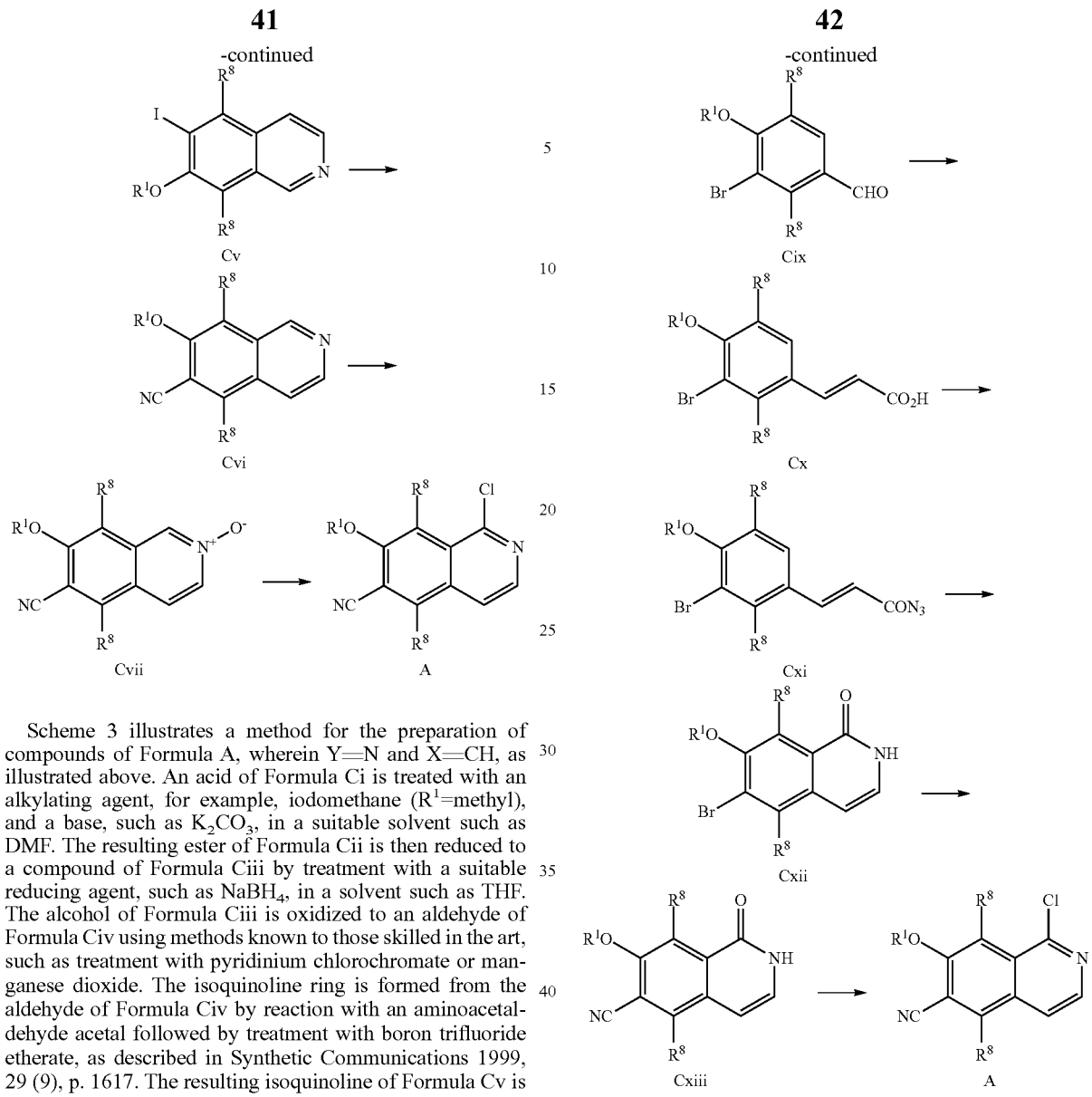

Scheme 3 illustrates a method for the preparation of compounds of Formula A, wherein Y=N and X=CH, as illustrated above. An acid of Formula Ci is treated with an alkylating agent, for example, iodomethane ($R^1$=methyl), and a base, such as $K_2CO_3$, in a suitable solvent such as DMF. The resulting ester of Formula Cii is then reduced to a compound of Formula Ciii by treatment with a suitable reducing agent, such as $NaBH_4$, in a solvent such as THF. The alcohol of Formula Ciii is oxidized to an aldehyde of Formula Civ using methods known to those skilled in the art, such as treatment with pyridinium chlorochromate or manganese dioxide. The isoquinoline ring is formed from the aldehyde of Formula Civ by reaction with an aminoacetaldehyde acetal followed by treatment with boron trifluoride etherate, as described in Synthetic Communications 1999, 29 (9), p. 1617. The resulting isoquinoline of Formula Cv is cyanated, using methods known to those skilled in the art, such as treatment with copper(I) cyanide in a solvent such as DMF or pyridine, to afford a nitrile of Formula Cvi. Oxidation with a suitable oxidizing agent, such as hydrogen peroxide or a peracid such as m-chloroperbenzoic acid or peracetic acid, yields an isoquinoline N-oxide of Formula Cvii. This may be halogenated by methods known to those skilled in the art, frequently by treatment with phosphorus oxychloride with or without an additional solvent, to afford the intermediate of Formula A (Lv=Cl)

Scheme 4

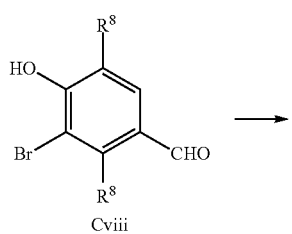

Scheme 4 illustrates a method for the preparation of compounds of Formula A wherein Y=N and X=CH. An aldehyde of Formula Cviii is treated with an alkylating agent, for example, 2-bromopropane ($R^1$=isopropyl), and a base such as $K_2CO_3$ in a suitable solvent such as DMF or DMSO. The aldehyde of Formula Cix is then subjected to Knoevenagel condensation with malonic acid, typically in the presence of pyridine and piperidine, to afford an acid of Formula Cx. The acid may be converted to an acyl azide of Formula Cxi by a variety of means known to one skilled in the art, for example by sequential treatment with a chloroformate ester followed by reaction with sodium azide. Upon exposure to heat, the acyl azide may undergo Curtius reaction to ultimately afford a compound of Formula Cxii. The Curtius reaction may be effected in a suitable solvent, for example diphenyl ether, at a temperature typically in excess of 200° C. The compound of Formula Cxii is cyanated, using methods known to those skilled in the art, such as treatment with zinc cyanide under palladium catalysis, to afford a compound of Formula Cxiii. This may be halogenated by methods known to those skilled in the art, frequently by treatment with phosphorus oxychloride with or without an additional solvent, to afford the intermediate of Formula A (Y=N, X=CH, Lv=Cl)

quinazolinone of Formula Cxvii. The resulting quinazolinone of Formula Cxvii is cyanated, using methods known to those skilled in the art, such as treatment with zinc cyanide and a palladium catalyst such as tetra(kis)triphenylphosphine palladium(0), in a solvent such as THF to afford a nitrile of Formula Cxviii. This may be halogenated by methods known to those skilled in the art, frequently by treatment with phosphorus oxychloride with or without an additional solvent, to afford the intermediate of Formula A (Lv=Cl).

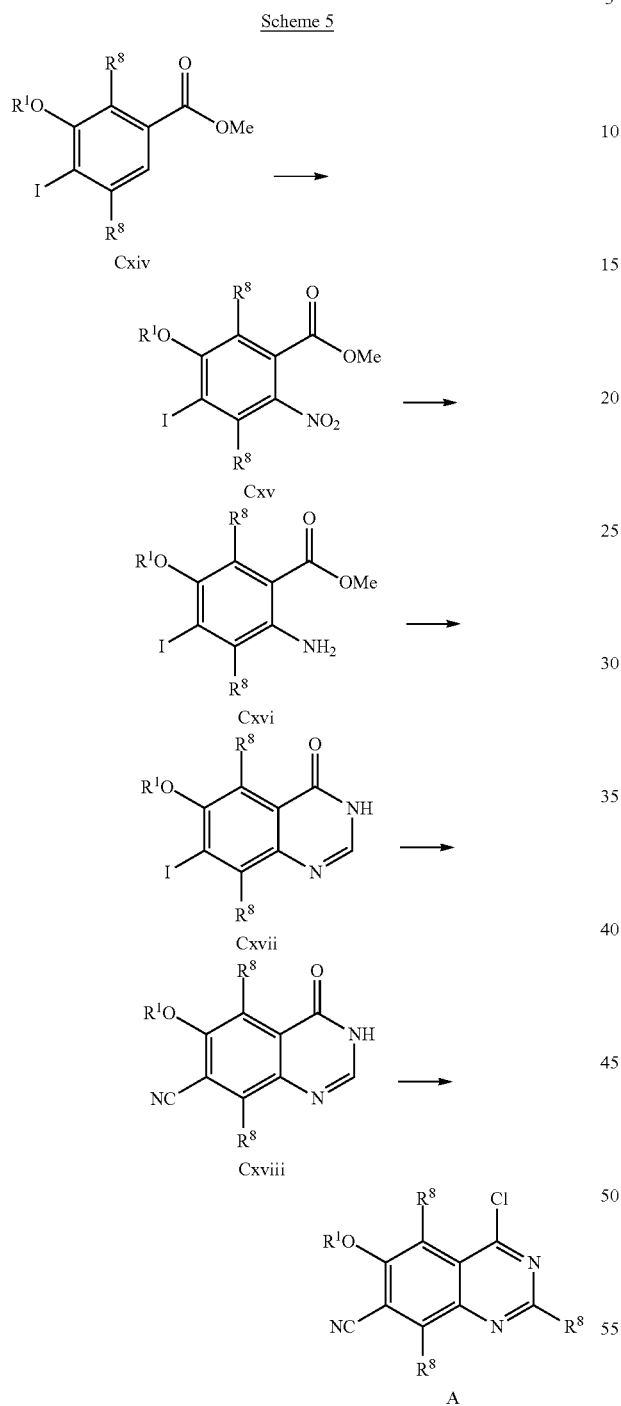

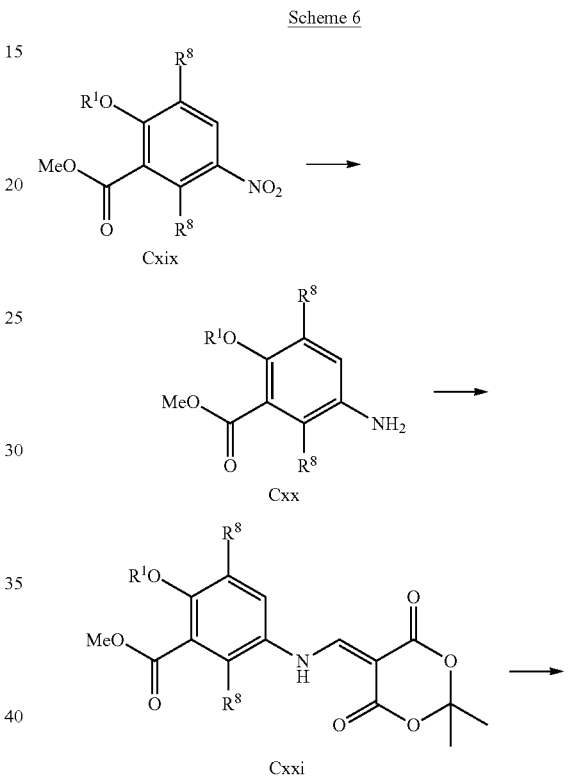

Scheme 5 illustrates a method for the preparation of compounds of Formula A wherein X and Y=N. An ester of Formula Cxiv is nitrated with nitric acid to afford a compound of Formula Cxv, which may then be reduced to an amine of Formula Cxvi by methods known to those skilled in the art, for example by treatment with tin(II) chloride in acid solution. Subsequent treatment with formamide or similar reagents may be used to effect formation of a

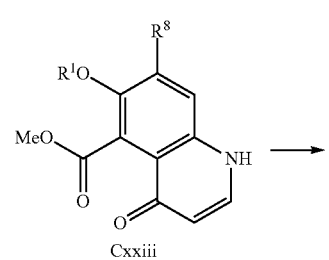

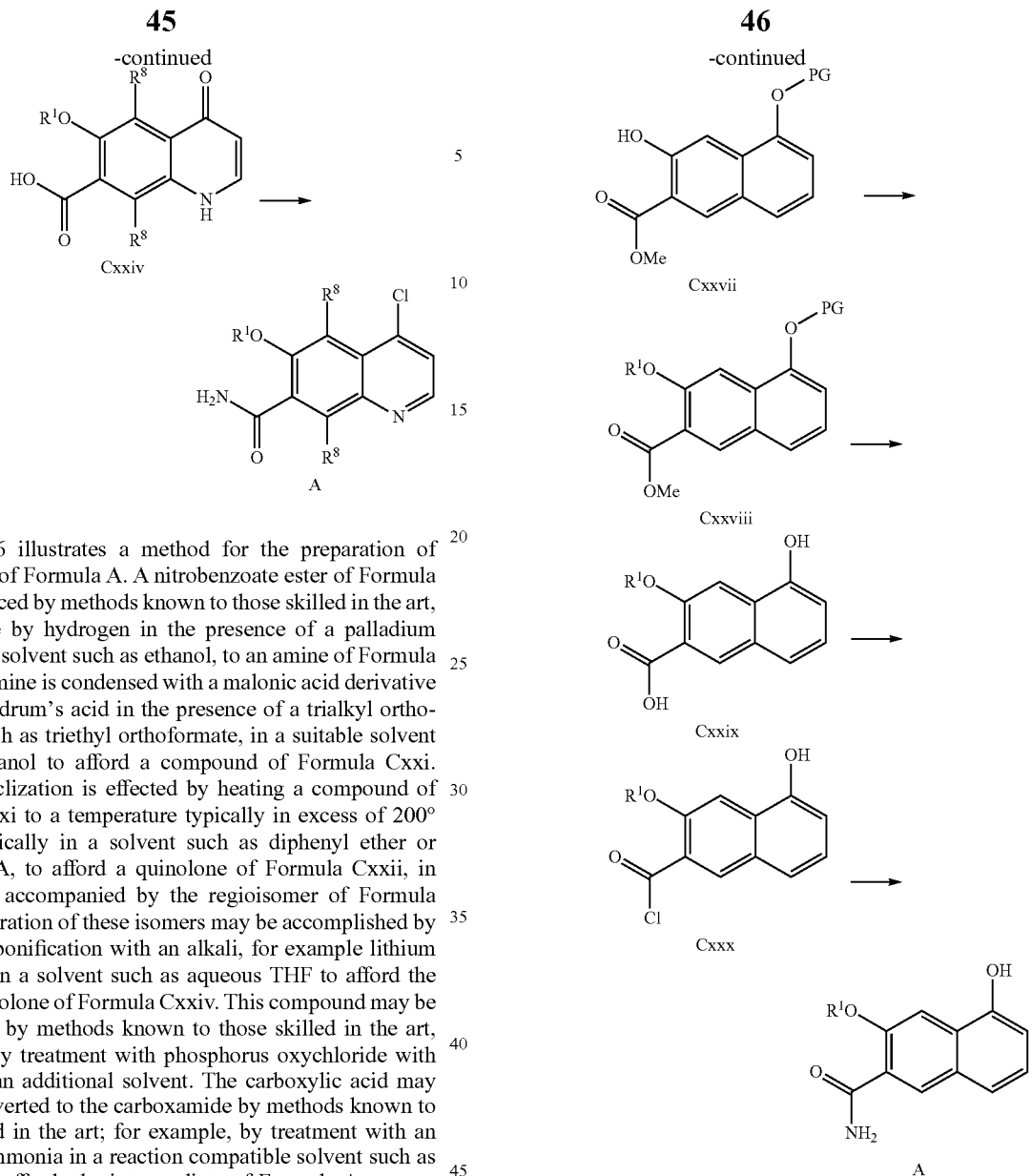

Scheme 6 illustrates a method for the preparation of compounds of Formula A. A nitrobenzoate ester of Formula Cxix is reduced by methods known to those skilled in the art, for example by hydrogen in the presence of a palladium catalyst in a solvent such as ethanol, to an amine of Formula Cxx. This amine is condensed with a malonic acid derivative such as Meldrum's acid in the presence of a trialkyl orthoformate, such as triethyl orthoformate, in a suitable solvent such as ethanol to afford a compound of Formula Cxxi. Thermal cyclization is effected by heating a compound of Formula Cxxi to a temperature typically in excess of 200° C., and typically in a solvent such as diphenyl ether or Dowtherm A, to afford a quinolone of Formula Cxxii, in some cases accompanied by the regioisomer of Formula Cxxiii. Separation of these isomers may be accomplished by selective saponification with an alkali, for example lithium hydroxide, in a solvent such as aqueous THF to afford the desired quinolone of Formula Cxxiv. This compound may be halogenated by methods known to those skilled in the art, frequently by treatment with phosphorus oxychloride with or without an additional solvent. The carboxylic acid may then be converted to the carboxamide by methods known to those skilled in the art; for example, by treatment with an excess of ammonia in a reaction compatible solvent such as 1,4-dioxane affords the intermediate of Formula A.

Scheme 7

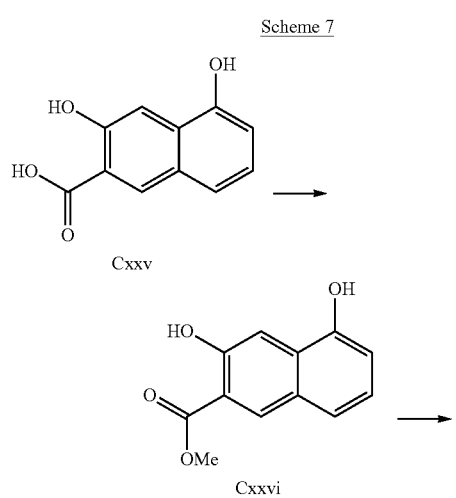

Scheme 7 illustrates a method for the preparation of compounds of Formula A wherein X and Y are both carbon. A naphthol of Formula Cxxv may be subjected to Fischer esterification to afford a compound of Formula Cxxvi. The distal hydroxyl group may be masked using a suitable protecting group (PG), for example, by forming a silyl ether using standard conditions known to one skilled in the art, for example with t-butyldiphenylsilyl chloride and imidazole, in a suitable solvent such as 1,2-dichloroethane, to provide a compound of Formula Cxxvii. Alkylation of the proximal hydroxyl group may be carried out with an alcohol $R^1$—OH in the presence of triphenylphosphine and an azodicarboxylate ester ("Mitsunobu reaction") in a suitable solvent such as THF to furnish a compound of Formula Cxxviii, which may be saponified by an alkali to afford a compound of Formula Cxxix. Conversion to the primary amide may be accomplished using standard methods known to one skilled in the art, for example by way of conversion to an acyl chloride using a reagent such as oxalyl chloride to afford a compound of Formula Cxxx, which may be converted to the primary amide of Formula A, by methods known to those skilled in the art; for example, by exposure to an excess of ammonia, typically in the presence of a suitable solvent such as THF, water, or a mixture of solvents.

Scheme 8

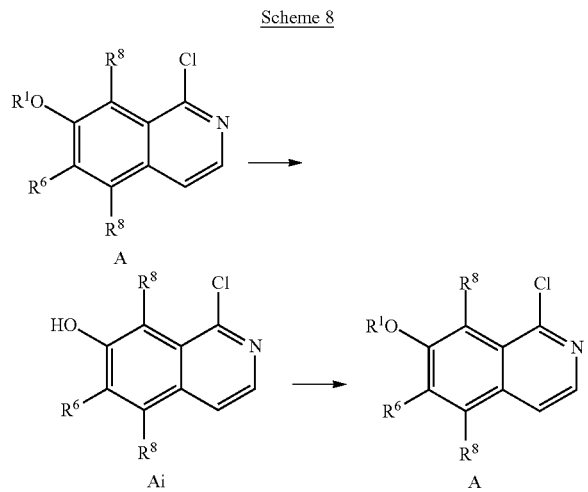

Scheme 8 illustrates a method for the preparation of additional compounds of Formula A. In this method, a compound of Formula A is dealkylated to remove the $R^1$ alkyl group to afford a compound of Formula Ai. Dealkylation may be effected by standard methods known to one skilled in the art, for example by the use of anhydrous aluminum chloride or boron tribromide in a solvent such as DCM, and may be most advantageously effected when $R^6$=CN. Subsequent alkylation of the OH group may be effected to install a new $R^1$ group to afford a new compound of Formula A, using methods known to one skilled in the art, for example by treatment with an alcohol $R^1$—OH in the presence of triphenylphosphine and an azodicarboxylate ester ("Mitsunobu reaction") in a suitable solvent such as THF, or by treatment with an alkylating agent such as an alkyl chloride, bromide, or iodide ($R^1$—Cl, $R^1$—Br, or $R^1$—I) and a base such as $K_2CO_3$ in a suitable solvent such as THF or DMF.

Scheme 9

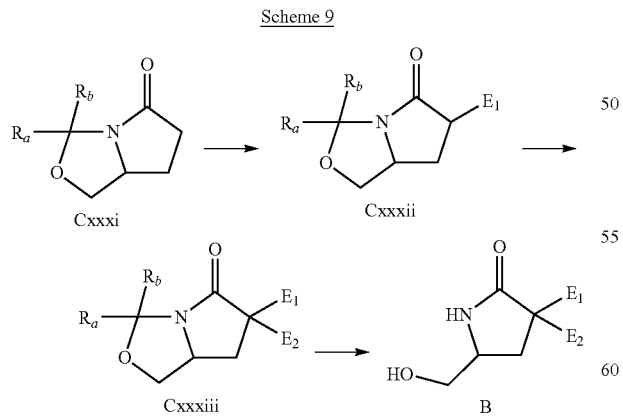

Scheme 9 illustrates a method for the preparation of certain compounds of Formula B of the type $R^2$—OH as employed in Schemes 1 and 2. Compounds of Formula Cxxxi are well known in the chemical literature, particularly those compounds in which $R_a$ and $R_b$ are both methyl, and in which $R_a$ is (substituted)phenyl and $R_b$ is H. In this method, the compound of Formula Cxxxi is treated with a suitable base, frequently lithium hexamethyldisilazide or lithium diisopropylamide, in a suitable solvent such as THF, ether, MTBE or 2-methylTHF using conditions well-established in the chemical literature. The mixture may then be treated with an electrophile to install the electrophile $E_1$ on the lactam ring. Suitable electrophiles are well known to those skilled in the art and include, but are not limited to, halogenating agents such as electrophilic halogen species, alkylating agents such as alkyl halides, carbonyl compounds such as aldehydes, ketones, or esters, oxidizing agents such as molecular oxygen or sulfonyloxaziridines, aminating agents such as sulfonyl azides, and sulfur containing electrophiles such as disulfides, thiocyanates, sulfinates, and sulfonyl halides. The resulting substituted lactam of Formula Cxxxii may be subjected to this process a second time to install another electrophile on the lactam ring, designated in the scheme by $E_2$. It will be recognized by one skilled in the art that the electrophiles $E_1$ and $E_2$ may themselves be subjected to further chemical transformations. It will also be recognized that the introduction of the electrophiles $E_1$ and $E_2$ may generate a mixture of stereoisomers, which may be separated by known methods into discrete stereoisomerically pure compounds. Finally, treatment with an acid is commonly used to remove the aminal protecting group containing $R_a$ and $R_b$ to afford the $R_2$—OH compound of Formula B. It will also be recognized that the electrophiles $E_1$ and $E_2$ will ultimately afford the substituents $R^4$ in the compound of Formula Ia.

Scheme 10

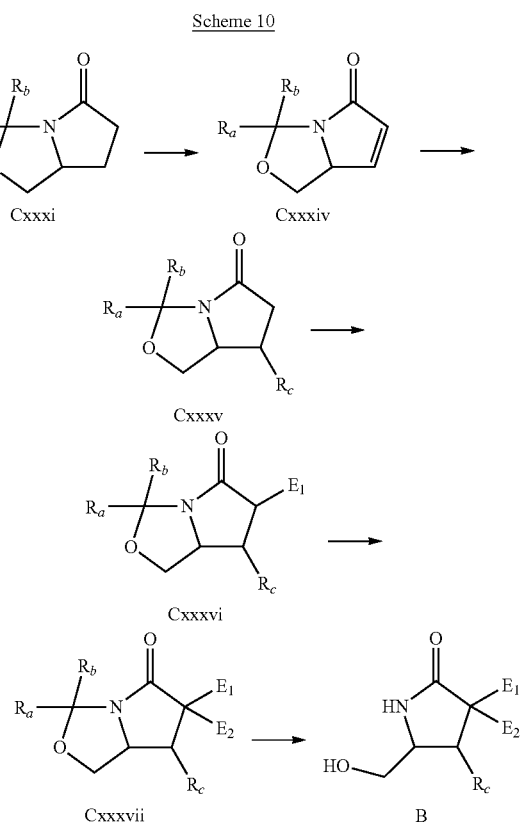

Scheme 10 illustrates a method for the preparation of certain compounds of the type $R^2$—OH as employed in Schemes 1 and 2. In this method, the compound of Formula Cxxxi is oxidized to the olefin compound of Formula Cxxxiv using methods that are known in the chemical literature. This is frequently accomplished by the elimination reaction of a sulfoxide or selenoxide, or it may be carried out by treatment with a suitable base such as lithium diisopropylamide and chlorotrimethylsilane followed by oxidation of the resulting silyl ketene aminal with a palladium salt and a carbonate ester of allyl alcohol, in a transformation known to one skilled in the art as the Saegusa-Tsuji oxidation. The olefin of Formula Cxxxiv may be converted to a compound of Formula Cxxxv using methods that are known in the chemical literature, frequently by treatment with an organometallic reagent such as methyllithium ($R_c$=methyl) or ethylmagnesium chloride ($R_c$=ethyl) in the presence of chlorotrimethylsilane and a copper compound. The compound of Formula Cxxxv may then be treated with an electrophile, designated in Scheme 10 by $E_1$, to install the electrophile $E_1$ on the lactam ring as described previously in Scheme 9. Likewise, the resulting compound of Formula Cxxxvi may be subjected to this process a second time to install another electrophile on the lactam ring, designated in Scheme 10 by $E_2$. It will be recognized by one skilled in the art that the electrophiles $E_1$ and $E_2$, and the $R_c$ group, may themselves be subjected to further chemical transformations. It will also be recognized that the introduction of the $R_c$ group and the electrophiles $E_1$ and $E_2$ may generate a mixture of stereoisomers, which may be separated into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the $R_c$ group and the electrophiles $E_1$ and $E_2$ will ultimately afford the substituents $R^4$ in the compound of Formula Ia.

methods that are known in the chemical literature, frequently by treatment with an appropriately substituted sulfonium salt and a suitable base. It will be recognized by one skilled in the art that the $R_d$ and $R_e$ groups may be subjected to further chemical transformations. It will also be recognized that the introduction of the cyclopropane ring containing the $R_d$ and $R_e$ groups may generate a mixture of stereoisomers, which may be separated by known methods into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the cyclopropane ring containing the $R_d$ and $R_e$ groups will ultimately afford the substituents $R^4$ in the compound of Formula Ia.

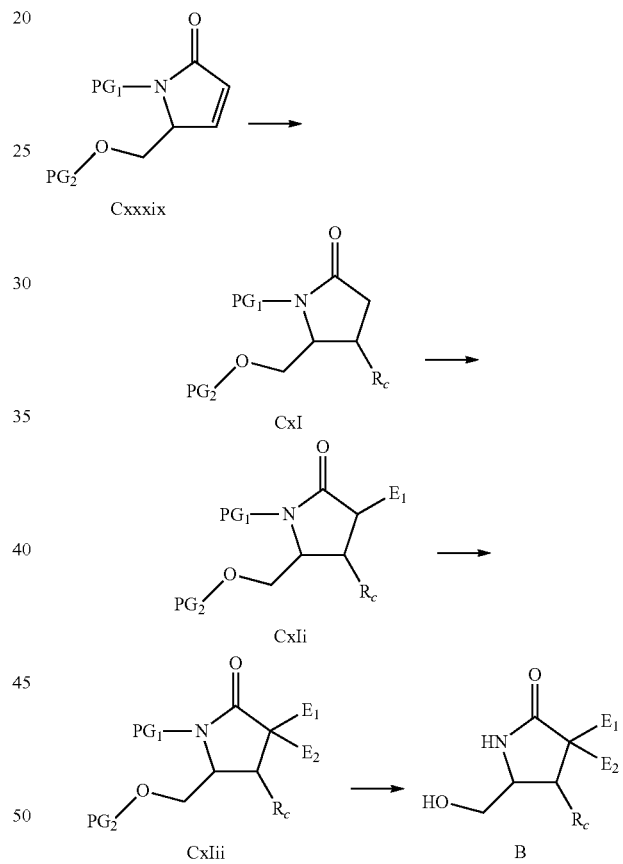

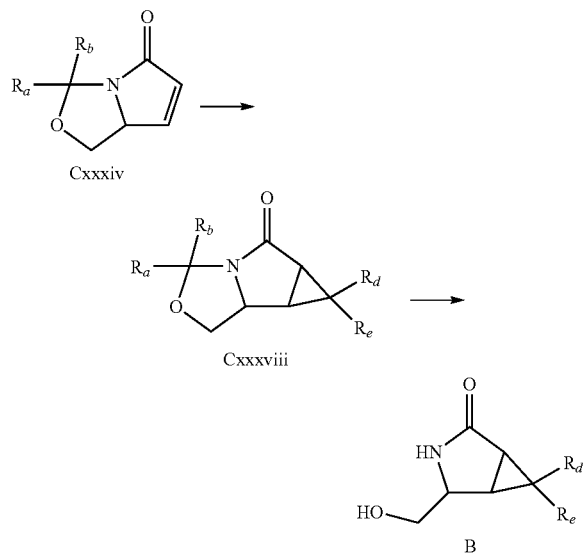

Scheme 11 illustrates a method for the preparation of certain compounds of the type $R^2$—OH as employed in Schemes 1 and 2. In this method, the olefin compound of Formula Cxxxiv is subjected to cyclopropanation using Scheme 12 illustrates a method for the preparation of certain compounds of the type $R^2$—OH as employed in Schemes 1 and 2. In this method, the olefin of Formula Cxxxix bearing suitable protecting groups $PG_1$ and $PG_2$, wherein $PG_1$ is, for example, a carbamate such as t-butyl carbamate and $PG_2$, for example, is a trialkylsilyl such as TBDMS, may be converted to a compound of Formula Cxl using methods that are known in the chemical literature. This is frequently accomplished by treatment with an organometallic reagent such as methyllithium ($R_c$=methyl) or ethylmagnesium chloride ($R_c$=ethyl) in the presence of chlorotrimethylsilane and a copper compound. The compound of Formula Cxl may then be treated with an electrophile ($E_1$), to install the electrophile $E_1$ on the lactam ring as described previously in Scheme 9. Likewise, the resulting compound of Formula Cxli may be subjected to this process a second time to install another electrophile ($E_2$). It will be recognized by one skilled in the art that the electrophiles $E_1$ and $E_2$, and the $R_c$ group, may themselves be subjected to further chemical transformations. It will also be recognized that the introduction of the $R_c$ group and the electrophiles $E_1$ and $E_2$ may generate a mixture of stereoisomers, which may be separated by known methods into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the $R_c$ group and the electrophiles $E_1$ and $E_2$ will ultimately afford the substituents $R^4$ in the compound of Formula Ia.

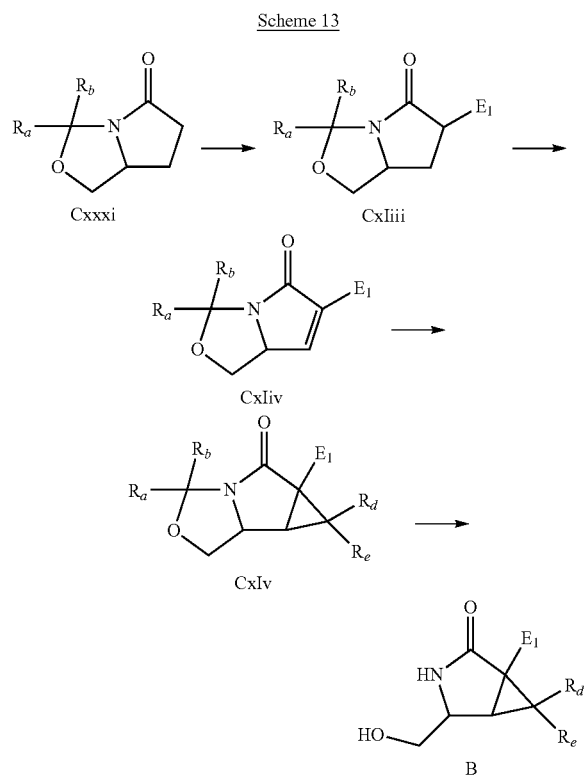

Scheme 13 illustrates a method for the preparation of certain compounds of the type $R^2$—OH as employed in Schemes 1 and 2. In this method, the compound of Formula Cxxxi is treated with a suitable base, followed by an electrophile ($E_1$), to install the electrophile $E_1$ on the lactam ring, as described previously in Scheme 9. The compound of Formula Cxliii is oxidized to an olefin compound of Formula Cxliv using methods that are known in the chemical literature, as described previously in Scheme 10. The olefin compound of Formula Cxliv is subjected to cyclopropanation, as described previously in Scheme 11. It will be recognized by one skilled in the art that the $E_1$, $R_d$ and $R_e$ groups may be subjected to further chemical transformations. It will also be recognized that the introduction of the cyclopropane ring containing the $E_1$, $R_d$ and $R_e$ groups may generate a mixture of stereoisomers, which may be separated by known methods into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the cyclopropane ring containing the $E_1$, $R_d$ and $R_e$ groups will ultimately afford the substituents $R^4$ in the compound of Formula Ia.

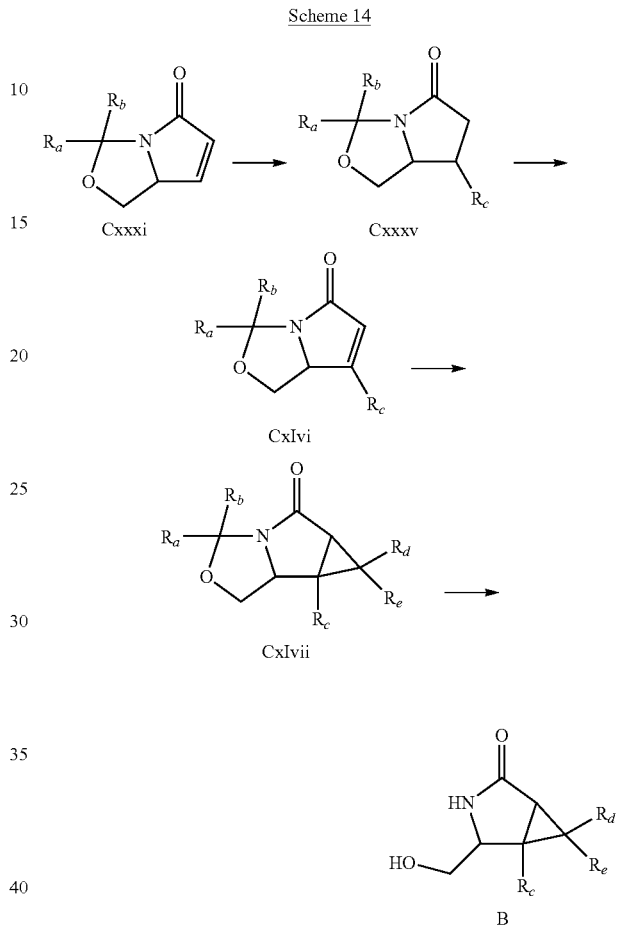

Scheme 14 illustrates a method for the preparation of certain compounds of the type $R^2$—OH as employed in Schemes 1 and 2. In this method, the olefin compound of Formula Cxxxi is converted to a compound of Formula Cxxxv using methods that are known in the chemical literature as described previously in Scheme 10. The compound of Formula Cxxxv is oxidized to an olefin compound of Formula Cxlvi using methods that are known in the chemical literature as described previously in Scheme 10. The olefin compound of Formula Cxxxv is subjected to cyclopropanation as described previously in Scheme 11. It will be recognized by one skilled in the art that the $R_c$, $R_d$ and $R_e$ groups may be subjected to further chemical transformations. It will also be recognized that the introduction of the cyclopropane ring containing the $R_c$, $R_d$ and $R_e$ groups may generate a mixture of stereoisomers, which may be separated by known methods into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the cyclopropane ring containing the $R_c$, $R_d$ and $R_e$ groups will ultimately afford the substituents $R^4$ in the compound of Formula Ia.

Scheme 15

Scheme 15 illustrates a method for the preparation of certain compounds of the type $R^2$—OH as employed in Schemes 1 and 2. In this method, the olefin of Formula Cxxxi may be converted to a compound of Formula Cxlviii using methods that are known in the chemical literature, frequently by treatment with an olefin reagent such as ethylene or propylene under irradiation by ultraviolet light in a suitable solvent such as acetone. It will be recognized by one skilled in the art that the $R_f$, $R_g$, $R_h$ and $R_i$ groups may be subjected to further chemical transformations. It will also be recognized that the introduction of the cyclobutane ring containing the $R_f$, $R_g$, $R_h$ and $R_i$ groups may generate a mixture of stereoisomers, which may be separated by known methods into discrete stereoisomerically pure compounds. As in Scheme 9, treatment with an acid is commonly used to remove the aminal protecting group containing $R_a$ and $R_b$ to afford the $R^2$—OH compound of Formula B. It will also be recognized that the cyclobutane ring containing the $R_f$, $R_g$, $R_h$ and $R_i$ groups will ultimately afford the substituents $R^4$ in the compound of Formula Ia.

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

It will be understood that the intermediate compounds of the invention depicted above are not limited to the particular enantiomer shown, but also include all stereoisomers and mixtures thereof. It will also be understood that compounds of Formula Ia can include intermediates of compounds of Formula Ia.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography and/or liquid chromatography-mass spectrometry, and subjected to work-up when appropriate. It will be recognized by one skilled in the art that purifications may vary between experiments: in general, sorbents, solvents and the solvent ratios used for eluants/gradients were chosen to provide appropriate $R_f$s or retention times. It will also be recognized by one skilled in the art that HPLC purifications may be effected in a variety of ways, including the use of normal stationary phases, reverse stationary phases, chiral stationary phases, and supercritical eluants. The appropriate choices of conditions for chromatographic and HPLC purifications will be discerned by one skilled in the art.

The following Preparations describe the preparation of certain intermediates used in the Methods and Examples that follow. The following Preparations, Methods and Examples are intended to illustrate particular embodiments of the invention and preparations thereto and are not intended to limit the specification, including the claims, in any manner. Unless noted otherwise, all reactants were obtained commercially.

Unless indicated otherwise, the following abbreviations have the indicated meanings:

APCI—atmospheric pressure chemical ionization
br.—broad peaks
° C.—degree Celsius
$CDCl_3$—deuterated chloroform
$CD_3OD$—deuterated methanol
d—doublet peak
dd—double doublet peak
$D_2O$—deuterium oxide
dmso-$d_6$—perdeuterated dimethyl sulfoxide
dt—double triplet peak
g—gram(s)
H (e.g., 1H, 2H)—hydrogen(s)
hr—hour(s)
LC—liquid chromatography
m—multiplet
M—molarity
mg—milligram(s)
MHz—megahertz
min—minute(s)
mL—milliliter(s)
mmol—millimole(s)
mp—melting point
MS—mass spectrum
NMR—nuclear magnetic resonance
pH—negative logarithm of hydronium ion concentration
psi—pounds per square inch
q—quartet peak
s—singlet peak t—triplet peak
td—triple doublet peak
μL—microliter
Unless indicated otherwise, the following chemical formulas and acronyms have the indicated meanings:
AcOH—glacial acetic acid
$BF_3$—$Et_2O$—boron trifluoride etherate
BHT—2,6-dit-t-butyl-4-methylphenol
$CHCl_3$—chloroform
DAST—(diethylamino)sulfur trifluoride
DCM—dichloromethane
DMAP—(4-dimethylamino)pyridine
DMF—dimethylformamide
DMSO—dimethylsulfoxide
EDCl—N-(3-Dimethylaminopropyl)-N'-ethylcarbodiimide hydrochloride
$Et_3N$—triethylamine
EtOAc—ethyl acetate
EtOH—ethanol
HCl—hydrochloric acid
$HNO_3$—nitric acid
$H_2SO_4$—sulfuric acid
$H_3PO_4$—phosphoric acid
LDA—lithium diisopropylamide
MeCN—acetonitrile
MeOH—methanol
$MgSO_4$—anhydrous magnesium sulfate
$K_2CO_3$—potassium carbonate
$K_3PO_4$—anhydrous tribasic potassium phosphate
KOH—potassium hydroxide
MTBE—methyl t-butyl ether
$Na_2CO_3$—sodium carbonate
$Na_2SO_4$—anhydrous sodium sulfate
$NaBH_4$—sodium borohydride
$NaHCO_3$—sodium bicarbonate
NaOH—sodium hydroxide
NFSI—N-fluoro(bisbenzenesulfonyl)imide, CAS 133745-75-2
$NH_4Cl$—ammonium chloride
$POCl_3$—phosphorus oxychloride
TFA—trifluoroacetic acid
THF—tetrahydrofuran
TMSCl—chlorotrimethylsilane

PREPARATIONS

Preparation 1:
1-chloro-7-methoxyisoquinoline-6-carbonitrile (P1)

Step 1. Synthesis of methyl
4-iodo-3-methoxybenzoate (CAS 35387-92-9, C1)

To a solution of 3-hydroxy-4-iodobenzoic acid (CAS 58123-77-6, C12) (10800 g, 40.9 moles) in DMF (65 L) was added $K_2CO_3$ (25398 g, 184 moles), followed by the slow addition of dimethyl sulfate (11352 g, 90 moles). This mixture was heated to about 50° C. for over night. The reaction mixture was cooled to about 25° C., diluted with EtOAc (50 L) and filtered through a plug of Celite®. The solid was thoroughly washed with EtOAc (10 L×3). The combined EtOAc filtrates were poured into water. After stirring for about 30 min, the EtOAc layer was separated and it was further washed sequentially with water, 1 M NaOH and brine. The EtOAc layer was separated, dried over $Na_2SO_4$, filtered and concentrated to provide the title compound C1. Yield: 11750 g (98%).

Step 2. Synthesis of
(4-iodo-3-methoxyphenyl)methanol (CAS 244257-61-2, C2)

To a solution of compound C1 (11750 g, 40.2 moles) in THF (35 L) was added $NaBH_4$ (7645 g, 201.09 moles) and refluxed. While refluxing, MeOH (25 L) was slowly added into the reaction mixture at a rate of about 1 L per hour. After completion of the reaction, it was poured into a solution of cold dilute HCl. Once the excess of $NaBH_4$ was quenched, the solution was filtered and extracted with EtOAc (2.5 L×3). The combined EtOAc extracts were washed sequentially with water, brine and dried over $Na_2SO_4$. The solvent was evaporated under reduced pressure and the resulting crude material was treated with MTBE. The resulting solid was filtered and filtrate was washed with water, brine, dried over $Na_2SO_4$, and filtered. The solvent was evaporated under reduced pressure to provide the title compound C2. Yield: 9900 g (93%).

Step 3. Synthesis of 4-iodo-3-methoxybenzaldehyde
(CAS 121404-83-9, C3)

To a solution of compound C2 (9900 g, 34.5 moles) in $CHCl_3$ (186 L), was added manganese dioxide (18000 g, 207 moles) and the resulting mixture was refluxed for about 16 h. The mixture was cooled to about 25° C. and filtered through a Celite pad, which was then washed thoroughly with $CHCl_3$. The $CHCl_3$ was evaporated under reduced pressure to provide the title compound C3. Yield: 9330 g (95%). $^1$H NMR (400 MHz, $CDCl_3$): δ 9.95 (s, 1H), 7.99 (d, 1H), 7.14 (dd, 1H), 3.95 (s, 3H).

Step 3. Synthesis of 6-iodo-7-methoxyisoquinoline
(CAS 244257-63-4, C4)

To a solution of compound C3 (9300 g, 35 moles) in toluene (60 L) was added amino acetaldehyde dimethyl acetal (5590 g, 53 moles) and the mixture was refluxed for about 4 h, while removing the liberated water by the use of a Dean-Stark water separator. The reaction mixture was cooled to about 0° C., after which trifluoroacetic anhydride (22305 g, 106 moles) followed by $BF_3$-$Et_2O$ (15080 g, 106 moles) were added, keeping internal temperature below 5° C. The reaction mixture was stirred at about 25° C. for about 16 h and quenched by pouring into a mixture of ice and ammonium hydroxide. The product was extracted with EtOAc (10 L×3), and the combined EtOAc extracts were washed sequentially with water and brine. The combined EtOAc extracts were dried over $Na_2SO_4$, filtered, and concentrated to afford a dark tan colored residue. This was treated with a mixture of MTBE and hexane (1:1 v/v, 30 L), followed by 6 M HCl (9 L), with stirring. The precipitated solid was filtered and washed with MTBE. The solid was suspended in EtOAc (5 L) and made alkaline with ammonium hydroxide. The EtOAc layer was separated, washed with brine, dried over $Na_2SO_4$, filtered, and concentrated to afford crude compound C4 as a brown solid. HPLC (230 nm) showed it to be about 83% pure.

The crude material (1000 g) was taken in AcOH (2.5 L) and stirred for about 90 min at about 25° C. The solid was filtered and washed with AcOH (500 mL). The filtrate was neutralized with saturated aqueous $Na_2CO_3$ solution. The resulting precipitated solid was filtered, washed with water (4 L), and oven dried at about 70-75° C. for about 5 h to afford about 780 g of pure C4. Similarly, the remaining crude C4 (4 kg) was purified to provide the title compound C4. Yield: 4300 g (42%). $^1$H NMR (400 MHz, CDCl$_3$): δ 9.15 (s, 1H), 8.45 (d, 1H), 8.35 (s, 1H), 7.45 (d, 1H), 7.15 (s, 1H) 4.00 (s, 3H).

Step 4. Synthesis of 7-methoxyisoquinoline-6-carbonitrile (C5)

To a solution of compound C4 (4300 g, 15 moles) in DMSO (39 L) was added copper(I) cyanide (2954 g, 33 moles) and the mixture was heated to about 120° C. for about 3 h. The reaction mixture was quenched by pouring into a mixture of ice and ammonium hydroxide (40 L) and filtered. The filtrate was extracted with EtOAc (10 L×2). While stirring, the solid residue was again treated with ammonium hydroxide solution (10 L) and EtOAc (10 L). After filtration, the precipitated material was repeatedly washed with a mixture of MeOH and CHCl$_3$ (1:9, v/v) several times and the combined extracts were washed with brine. The extracts were dried over Na$_2$SO$_4$, filtered, and concentrated under reduced pressure. The resulting crude material was triturated with hexane to provide the title compound C5. Yield: 2250 g (87%). $^1$H NMR (400 MHz, CDCl$_3$): δ 9.25 (br. s, 1H), 8.55 (br. s, 1H), 8.15 (s, 1H), 7.60 (d, 1H), 7.30 (s, 1H), 4.05 (s, 3H).

Step 5. Synthesis of 7-methoxyisoquinoline-6-carbonitrile N-oxide (C6)

To a solution of compound C5 (500 g, 2.7 moles) in DCM (5 L) was slowly added 30% peracetic acid (413 g, 5.4 moles, 2 equivalents) at about 40-45° C. over about 4 h. The resulting mixture was stirred at same temperature for about 16 h. At this stage, 50% of starting material was consumed, and for further conversion another 2 equivalents of peracetic acid was added. The reaction mixture was heated at about 40-45° C. and monitored by TLC. After approximately another 8 h, a trace of starting material still remained. An additional 0.5 equivalent of peracetic acid was added and the reaction was continued for about 5 h. The heterogeneous reaction mass was cooled to about 25° C. and filtered. The resulting solid was washed with water (2 L×3) and subsequently titrated with acetone (2 L). Upon drying, 250 g of compound C6 was obtained.

The DCM layer resulting from the filtration was washed with saturated aqueous NaHCO$_3$ solution (15 L). The resulting aqueous layer was back-extracted with DCM (1.5 L×2) and the combined DCM layers were washed with brine. Upon concentration, 150 g of compound C6 was obtained.

The acidic water layer from the original filtration was made alkaline with saturated aqueous Na$_2$CO$_3$ solution (5 L) and extracted with DCM (1 L×2). The DCM layer was dried over Na$_2$SO$_4$, filtered, and concentrated to give 30 g of compound C6. The batches of compound C6 were combined to provide the title compound C6. Yield: 430 g (80%). $^1$H NMR (400 MHz, CDCl$_3$): δ 8.85 (br. s., 1H), 8.05-8.18 (m, 2H), 7.71 (d, 1H), 7.12 (s, 1H), 4.08 (s, 3H).

Step 5. Synthesis of 1-chloro-7-methoxyisoquinoline-6-carbonitrile (P1)

To a suspension of compound C6 (700 g, 3.5 moles) in DCM (14 L) was added phosphoryl chloride (333.5 mL, 3.5 moles) dropwise over a period of about 1 h. After the addition was completed, the reaction mixture was a homogeneous solution and was stirred at about 25° C. overnight. After completion of the reaction, the mixture was poured into ice water (5 L) and the resulting solid was filtered. The solid was washed with saturated aqueous NaHCO$_3$ solution (1 L×2), followed by water. Upon drying, 360 g of compound P1 with 93% HPLC purity was obtained.

The DCM layer resulting from the filtration was separated. The aqueous layer resulting from the filtration was extracted with DCM (1 L×2). The combined DCM solutions were washed with saturated aqueous NaHCO$_3$ solution, followed sequentially by water and brine. The DCM solution was dried over Na$_2$SO$_4$, filtered, and concentrated to provide 300 g of compound P1 with 75% HPLC purity. This material was taken in a mixture of AcOH (900 mL) and EtOAc (1200 mL) mixture, then heated to about 70-75° C. for about 30 min. The solid was filtered while the mixture was still hot (about 70° C.). The solid was further washed with EtOAc (300 mL), followed by hexane (350 mL) and dried to afford 200 g of compound P1 with 95% HPLC purity. The P1 with 93% HPLC purity (360 g, 93%) was further purified by titration with a mixture of EtOAc and MTBE (1:1, v/v) and filtered. Upon drying, 300 g of compound P1 was recovered. The batches of P1 were combined to provide the title compound P1. Yield: 500 g (65%). $^1$H NMR (400 MHz, CDCl$_3$): δ 8.30 (d, 1H), 8.18 (s, 1H), 7.65 (s, 1H), 7.58 (d, 1H), 7.15 (s, 3H).

Preparation 2:
1-chloro-7-isopropoxyisoquinoline-6-carbonitrile (P2)

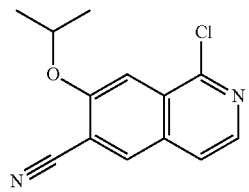 [SMILES: CC(C)Oc1cc2c(Cl)nccc2cc1C#N]

Step 1. Synthesis of 3-bromo-4-isopropoxybenzaldehyde (CAS 191602-84-3, C7)

A mixture of 3-bromo-4-hydroxybenzaldehyde (1500 g, 7.5 mol) and K$_2$CO$_3$ (1290 g, 9.3 mol) in anhydrous DMSO (15 L) was treated with 2-bromopropane (1010 g, 8.2 mol) and stirred at about 55° C. for overnight. An additional 200 g (1.6 mol) of 2-bromopropane was added and the reaction was continued for approximately an additional 4 h. The reaction was cooled to about 30° C. and EtOAc (22.5 L) and water (22.5 L) were added. The EtOAc phase was separated and the aqueous phase was back-extracted with EtOAc (2×7.5 L). The combined EtOAc phases were washed with water (2×15 L) followed by brine (15 L), dried over Na$_2$SO$_4$, filtered, and concentrated to provide the title compound C7. Yield: 1800 g (99%). $^1$H NMR (400 MHz, CDCl$_3$) δ 9.82 (s, 1H), 8.07-8.08 (d, 1H), 7.76-7.79 (d, 1H), 6.98 (d, 1H), 4.67-4.74 (m, 1H), 1.42-1.44 (d, 6H).

Step 2. Synthesis of (E)-3-(3-bromo-4-isopropoxyphenyl)acrylic acid (CAS 1344851-82-6, C8)

Compound C7 (1800 g, 7.4 mol) in anhydrous pyridine (7.56 L) was treated with malonic acid (1002 g, 9.6 mmol)

and piperidine (316 g, 3.7 mmol) and heated to reflux for about 2 h. The solvent was removed by distillation under reduced pressure. This was treated with cold water (37.8 L) and stirred for about 0.5 h, then acidified to adjust pH to about 4.0 with AcOH (about 300 mL). The suspension was vigorously stirred for about 1 hour to break up all solids and then the product was collected by filtration, washed with water (3.6 L) and dried under vacuum to provide the title compound C8. Yield: 2014 g (95%). $^1$H NMR (400 MHz, dmso-$d_6$) δ 7.94-7.95 (d, 1H) 7.64-7.67 (dd, 1H), 7.48-7.52 (d, 1H), 7.14-7.16 (d, 1H), 6.43-6.47 (d, 1H), 4.71-4.77 (m, 1H), 1.29-1.31 (d, 6H).

Step 3. Synthesis of (E)-3-(3-bromo-4-isopropoxyphenyl)acryloyl azide (C9)

To a stirred solution of compound C8 (1000 g, 3.5 mol) in acetone (17.5 L), Et$_3$N (355 g, 3.5 mol) was added and the mixture was cooled to about −5° C. Ethyl chloroformate (495 g, 4.56 mol) was added dropwise, maintaining the temperature at about −5° C. After completion of the addition, the mixture was stirred for approximately an additional 1 h at about −5° C. A solution of sodium azide (342 g, 5.3 mol) in water (1264 mL) was added slowly at about −5° C. After the addition of sodium azide solution was complete, the reaction mixture was slowly warmed to about 25° C. and stirred for about 0.5 h. The reaction mass was quenched by addition to water (50 L) and stirring for about 30 minutes at about 25° C. The precipitate was filtered, washed with water (2 L) and dried to provide the title compound C9. Yield: 978 g (90%). $^1$H NMR (300 MHz, dmso-$d_6$) δ 8.07-8.08 (d, 1H), 7.74-7.77 (dd, 1H), 7.60 (s, 1H), 7.16-7.20 (d, 1H), 6.60-6.66 (d, 1H), 4.74-4.82 (m, 1H), 1.29-1.32 (d, 6H).

Step 4. Synthesis of 6-bromo-7-isopropoxyisoquinolin-1(2H)-one (C10)

To a mixture of diphenyl ether (8 L) and tri n-butyl amine (328 g, 1.77 mol) pre-heated to about 230° C., compound C9 (550 g, 1.77 mol) dissolved in diphenyl ether (2.5 L) was added while the temperature was maintained at about 230° C. After the addition was completed, stirring and heating were continued for about 0.5 h. The reaction mixture was cooled to about 25° C. and added slowly to hexane (27.5 L). The resulting slurry was cooled to about 0° C. and stirred for about 0.5 h. The crude precipitate was filtered the precipitate was washed with cold hexane (5.5 L). The wet cake was dried under vacuum to afford 310 g of crude C10.
This reaction was repeated three more times to afford 1064 g of crude C10. This was dissolved in THF (5.3 L) at reflux and cooled to about 0° C. The slurry was stirred for about 0.5 h and then filtered and the filter cake was dried under vacuum to afford 574 g of C10. The filtrate was concentrated and purified by chromatography to afford an additional 181 g to provide the title compound C10. Yield: 755 g (46%). $^1$H NMR (300 MHz, CDCl$_3$) δ 8.24-8.26 (d, 1H), 8.16 (s, 1H), 7.65 (s, 1H), 7.55-7.56 (d, 1H), 4.85-4.91 (m, 1H), 1.51-1.52 (d, 6H).

Step 5. Synthesis of 7-isopropoxy-1-oxo-1,2-dihydroisoquinoline-6-carbonitrile (C11)

Compound C10 (490 g, 1.74 mol) and zinc cyanide (265 g, 2.25 mol) were added to dry DMF (9.8 L) and stirred well for about 5 min at 25° C. The reaction mixture was degassed with nitrogen for about 20 minutes, after which tetra(kis)triphenylphosphinepalladium (0) (120 g, 0.104 mol) was added and the reaction mixture was stirred for about 5 min at about 25° C. before being heated to about 100° C. The mixture was maintained for about 16 hours at about 100° C. The reaction mixture was cooled to about 25° C., diluted with EtOAc (4.9 L), and stirred for about 0.5 h. The mixture was filtered through celite, which was washed with EtOAc (1 L). The combined filtrate was concentrated at pressure of about 10 torr at about 75° C. Water (4.9 L) was added to the residue and the mixture was stirred for about 0.5 h. The precipitate was filtered, washed with water (1 L) and dried under vacuum at about 60° C. The precipitate was stirred for about 0.5 h with MTBE (4.9 L) and filtered. This process was repeated twice more, after which the filter cake was washed with MTBE (0.5 L) and dried under vacuum at about 60° C. to provide the title compound C11. Yield: 390 g (98%)$^1$H NMR (400 MHz, CDCl$_3$) δ 8.24-8.26 (d, 1H), 8.16 (s, 1H), 7.65 (s, 1H), 7.54-7.56 (d, 1H), 4.85-4.99 (m, 1H), 1.51-1.52 (d, 6H).

Step 6. Synthesis of 1-chloro-7-isopropoxyisoquinoline-6-carbonitrile (P2)

Compound C11 (390 g, 1.7 mol) and POCl$_3$ (10.97 kg, 71.5 mol) were stirred for about 5 min at about 25° C., then heated to about 100° C. and maintained at about 100° C. for about 0.5 h. The reaction mixture was cooled to about 25° C. and concentrated under reduced pressure at about 60° C. The residue was quenched with ice (7.8 kg), then neutralized with 25% K$_2$CO$_3$ solution (7.8 L) with stirring until the mixture was about pH=7. The solution was extracted with DCM (3×5 L), and the combined extracts were washed with 10% NaHCO$_3$ solution (2×3.9 L). The DCM was separated, dried over Na$_2$SO$_4$, filtered, and concentrated. n-Heptane (3.9 L) was added to the residue and the mixture was stirred for about 0.5 h at about 25° C. The precipitate was filtered and the filter cake was washed with n-heptane (390 mL) and dried under vacuum at about 60° C. to provide the title compound P2. Yield: 338 g (80%)$^1$H NMR (300 MHz, dmso-$d_6$) δ 8.73 (s, 1H), 8.29-8.31 (d, 1H), 7.89-7.91 (d, 1H), 7.67 (s, 1H), 5.02-5.06 (m, 1H), 1.41-1.43 (d, 6H).

Preparation 3:
4-chloro-6-methoxyquinazoline-7-carbonitrile (P3)

Step 1. Synthesis of 3-hydroxy-4-iodobenzoic acid (CAS 58123-77-6, C12)

To a stirred solution of 3-hydroxybenzoic acid (25 g, 181 mmol) in water (180 mL) were added 1 M aqueous NaOH (188 mL) and sodium iodide (28.1 g, 188 mmol), followed by slow addition aqueous sodium hypochlorite solution (0.9 M, 209 mL). The mixture was stirred at about 25° C. for about 2 h, then cooled in ice and acidified with concentrated HCl to pH=3. A sufficient quantity of 10% ascorbic acid solution was added to afford a colorless mixture. The remaining precipitate was filtered, washed with water, and dissolved in EtOAc. The EtOAc solution was washed with brine, dried over Na$_2$SO$_4$, filtered and concentrated to provide the title compound C12. Yield: 34 g (71%)$^1$H NMR (400 MHz, dmso-$d_6$) δ 12.98 (br s, 1H), 10.65 (s, 1H), 7.78 (dd, 1H), 7.32 (d, 1H), 7.11 (dd, 1H).

Step 2. Synthesis of methyl 4-iodo-3-methoxybenzoate (CAS 35387-92-9, C13)

To a stirred solution of compound C12 (84 g, 318 mmol) in DMF (300 mL) at about 0° C. was added K$_2$CO$_3$ (177 g, 1273 mmol) followed by methyl iodide (79.3 mL, 1273 mmol). The mixture was stirred at about 25° C. for about 16 h, then diluted with EtOAc (2 L) and washed with water (600 mL×2), followed by brine (100 mL×2). The EtOAc was dried over $Na_2SO_4$, filtered and concentrated to provide the title compound C13. Yield: 84 g (90%) $^1$H NMR (400 MHz, $CDCl_3$) δ 7.84 (d, 1H), 7.44 (d, 1H), 7.36 (dd, 1H), 3.93 (s, 3H), 3.91 (s, 3H).

Step 3. Synthesis of methyl 4-iodo-5-methoxy-2-nitrobenzoate (C14)

A stirred solution of compound C13 (10 g, 38 mmol) in AcOH (92 mL) was treated with 70% concentrated $HNO_3$ (11.9 mL) with cooling in an about 25° C. water bath, after which acetic anhydride (46 mL) was added. The mixture then placed in a pre-heated oil bath at about 70° C. After about 2 h, the reaction mixture was cooled to about 25° C., diluted with 1 M NaOH solution (200 mL), and extracted with EtOAc (200 mL×2). The combined extracts were washed with $NaHCO_3$, brine, dried over $Na_2SO_4$, filtered and concentrated. The residue was purified by column chromatography to provide the title compound C14. Yield: 10 g (78%) $^1$H NMR (400 MHz, dmso-$d_6$) δ 8.50 (s, 1H), 7.32 (s, 1H), 4.01 (s, 3H), 3.84 (s, 3H).

Step 4. Synthesis of methyl 2-amino-4-iodo-5-methoxybenzoate (C15)

To a stirred solution of compound C14 (19 g, 56 mmol) in MeOH (300 mL) was added a solution of stannous chloride dihydrate (40.7 g, 180 mmol) in 120 mL of 6 M HCl. The mixture was stirred at about 25° C. for about 16 h, then concentrated. The residue was stirred with a saturated aqueous solution of potassium fluoride and extracted twice with EtOAc. The combined extracts were dried over $Na_2SO_4$, filtered and concentrated. The residue was triturated with a mixture of DCM and hexane to provide the title compound C15. Yield: 14 g (81%) $^1$H NMR (400 MHz, dmso-$d_6$) δ 7.35 (s, 1H), 7.14 (s, 1H), 3.79 (s, 3H), 3.68 (s, 3H).

Step 5. Synthesis of 7-iodo-6-methoxyquinazolin-4(3H)-one (C16)

A stirred solution of compound C15 (17 g, 55 mmol) in formamide (170 mL) was heated at about 160° C. for about 18 h. The reaction mixture was cooled to about 25° C., diluted with water (170 mL), and stirred at about 10° C. for about 30 minutes. The precipitate was filtered, washed with water followed by diethyl ether, and dried under vacuum to provide the title compound C15. Yield: 12 g (71%) $^1$H NMR (400 MHz, dmso-$d_6$) δ 8.14 (s, 1H), 7.99 (s, 1H), 7.44 (s, 1H), 7.16 (br s, 1H), 3.93 (s, 3H).

Step 6. Synthesis of 6-methoxy-4-oxo-3,4-dihydro-quinazoline-7-carbonitrile (C17)

A stirred solution of compound C16 (16 g, 53 mmol) in dimethyl acetamide (80 mL) was degassed with argon for about 15 minutes, after which zinc cyanide (6.22 g, 53 mmol) was added, followed by TMEDA (2.38 mL, 16 mmol), tris(dibenzylideneacetone)dipalladium(0) (4.85 g, 5.3 mmol) and Xantphos (3.06 g, 5.3 mmol). The mixture was heated at about 80° C. for about 5 h under argon, then cooled to about 25° C., diluted with diethyl ether (1 L), and filtered. The precipitate was dissolved in a mixture of MeOH and DCM (1/4, v/v) and filtered through Celite®. The filtrate was concentrated and the residue was purified by column chromatography to provide the title compound C17. Yield: 5.4 g (50%) $^1$H NMR (400 MHz, dmso-$d_6$) δ 12.47 (br. s, 1H), 8.17 (s, 1H), 8.09 (s, 1H), 7.69 (s, 1H), 4.02 (s, 3H).

Step 7. Synthesis of 4-chloro-6-methoxyquinazoline-7-carbonitrile (P3)

A mixture of compound C17 (10 g, 49.8 mmol) and $POCl_3$ (250 mL) was heated at about 100° C. for about 16 h, then cooled to about 25° C. and concentrated. The residue was diluted with EtOAc and the ethyl acetate solution was washed with water, saturated aqueous $NaHCO_3$ solution, brine, dried over $Na_2SO_4$, filtered and concentrated. The residue was purified by column chromatography to provide the title compound P3. Yield: 2.8 g (27%) $^1$H NMR (400 MHz, dmso-$d_6$) δ 9.11 (s, 1H), 8.75 (s, 1H), 7.66 (s, 1H), 4.14 (s, 3H).

Preparation 4: 4-chloro-6-isopropoxyquinoline-7-carboxamide (P4)

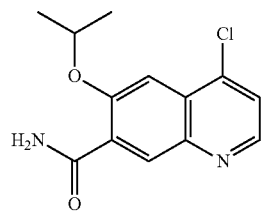 [SMILES: CC(C)Oc1cc2c(Cl)ccnc2cc1C(N)=O]

Step 1. Synthesis of methyl 2-hydroxy-5-nitrobenzoate (C18)

Concentrated $H_2SO_4$ (150 mL) was added slowly to a solution of 2-hydroxy-5-nitrobenzoic acid (1000 g, 5.4 mol) in dry MeOH (5 L). After the addition was complete, the mixture was heated to reflux for about 24 h. After completion of the reaction, the mixture was filtered and the precipitate was reserved. The filtrate was concentrated to afford a solid residue. This residue and the previous precipitate were dissolved in EtOAc and washed with water twice. The EtOAc was then washed with brine, dried over $Na_2SO_4$, filtered, and concentrated to provide the title compound C18. Yield: 900 g (84%) $^1$H NMR (300 MHz, $CDCl_3$) δ 11.42 (s, 1H), 8.80-8.79 (d, 1H), 8.31-8.35 (dd, 1H), 7.07-7.10 (d, 1H), 4.04 (s, 3H).

Step 2. Synthesis of methyl 2-isopropoxy-5-nitrobenzoate (C19)

Compound C18 (900 g, 4.56 mol), triphenylphosphine (1.33 kg, 5.02 mol) and 2-propanol (3.8 kg, 5.02 mol) were dissolved in dry THF (18 L) and cooled to about 5° C. Di-isopropyl-azodicarboxylate (1.01 kg, 5.02 mol) was added, and the reaction was allowed to warm to about 25° C. and was stirred overnight. The mixture was concentrated under reduced pressure and the residue treated with EtOAc (5 L). The undissolved solids that remained were removed by filtration, and the filtrate was evaporated. The residue was purified by column chromatography to provide the title compound C19. Yield: 760 g (70%) $^1$H NMR (300 MHz, CDCl$_3$) δ 8.60 (d, 1H), 8.29-8.34 (dd, 1H), 7.01 (d, 1H), 4.73-4.77 (m, 1H), 3.90 (s, 3H), 1.33 (d, 6H).

Step 3. Synthesis of methyl 5-amino-2-isopropoxybenzoate (C20)

A solution of compound C19 (760 g, 3.17 mol) in EtOH (12 L) was treated with palladium on carbon (76 g) and this mixture was stirred for about 1 h at about 25° C. under an atmosphere of hydrogen at about 50 psig. After completion of the reaction, the mixture was filtered through celite and filter cake was washed with additional EtOH. The filtrate was evaporated to provide the title compound C20. Yield: 600 g (60%). $^1$H NMR (400 MHz, dmso-d$_6$) δ 6.83-6.85 (d, 1H), 6.76-6.79 (dd, 1H), 4.31-4.37 (m, 1H), 3.86 (s, 3H), 2.80-3.60 (br. s, 2H), 1.29-1.31 (d, 6H).

Step 4. Synthesis of methyl 5-(((2,2-dimethyl-4,6-dioxo-1,3-dioxan-5-ylidene)methyl)amino)-2-isopropoxybenzoate (C21)

A mixture of compound C20 (600 g, 2.88 mol), Meldrum's acid (640 g, 3.44 mol), and triethyl orthoformate (560 g, 3.44 mol) in EtOH (7 L) was heated at reflux overnight. The mixture was cooled to about 20° C. and the resulting precipitate was collected by filtration to provide the title compound C21. Yield: 620 g (60%) $^1$H NMR (300 MHz, CDCl$_3$) δ 11.07-11.17 (br. d, 1H), 8.53-8.58 (d, 1H), 7.69-7.70 (d, 1H), 7.29-7.33 (dd, 1H), 7.02-7.05 (d, 1H), 4.55-4.62 (m, 1H), 2.91 (s, 3H), 1.75 (d, 6H), 1.38-1.40 (d, 6H).

Step 5. Synthesis of methyl 6-isopropoxy-4-oxo-1,4-dihydroquinoline-7-carboxylate (C22)

Compound C21 (20 g, 55 mmol) was added in portions to pre-heated Dowtherm A (480 mL) at about 240° C. Heating and stirring at that temperature were continued for approximately an additional 5 minutes after completion of the addition. The mixture was cooled to about 20° C. and purified by column chromatography to give 6.2 g of a mixture of compound C22 and methyl 6-isopropoxy-4-oxo-1,4-dihydroquinoline-5-carboxylate. This procedure was repeated 29 times more with same scale to provide a mixture of the title compound C22 and methyl 6-isopropoxy-4-oxo-1,4-dihydroquinoline-5-carboxylate. Yield: 311 g (72%)$^1$H NMR (400 MHz, dmso-d$_6$) δ 11.90 (s, 2H), 7.94-7.92 (d, 1H), 7.87-7.86 (d, 1H), 7.83 (s, 1H), 7.62-7.54 (m, 3H), 6.01-6.02 (d, 1H), 5.93-5.91 (d, 1H), 4.72-4.66 (m, 1H), 4.62-4.56 (m, 1H), 3.85 (s, 3H), 3.76 (s, 3H), 1.29-1.31 (d, 6H), 1.20-1.22 (d, 6H).

Step 6. Synthesis of 6-isopropoxy-4-oxo-1,4-dihydroquinoline-7-carboxylic acid (C23)

The mixture of compound C22 and methyl 6-isopropoxy-4-oxo-1,4-dihydroquinoline-5-carboxylate (311 g, 1.19 mol) was added to THF (1.55 L) and water (1.55 L). Lithium hydroxide monohydrate (199 g, 4760 mmol) was added and the mixture was stirred at about 25° C. overnight. The reaction mixture was diluted with water and extracted with EtOAc 4 times until the methyl 6-isopropoxy-4-oxo-1,4-dihydroquinoline-5-carboxylate was absent from the aqueous phase. The aqueous layer was adjusted to about pH=1 by the addition of 1 M HCl and the aqueous layer was extracted with EtOAc twice. The combined EtOAc extracts were dried over Na$_2$SO$_4$, filtered, and concentrated to provide the title compound C23. Yield: 129 g (44%)$^1$H NMR (400 MHz, dmso-d$_6$) δ 11.6-13.0 (br. s, 1H), 8.04-8.06 (d, 1H), 7.84 (s, 1H), 7.60 (s, 1H), 6.20-6.22 (d, 1H), 4.69-4.73 (m, 1H), 1.30-1.32 (d, 6H).

Step 7. Synthesis of 4-chloro-6-isopropoxyquinoline-7-carboxamide (P4)

A mixture of compound C23 (129 g, 520 mmol) and POCl$_3$ (2 L) was heated under reflux for about 6 h. The mixture was concentrated under reduced pressure to give a dark oil, which was immediately treated with 10 L of a saturated solution of ammonia gas in dioxane at about 0° C. The mixture was then stirred at about 25° C. overnight. The reaction mixture was filtered and the filtrate was concentrated. The residue was diluted with DCM (1 L) and washed with water. The DCM extract was concentrated to obtain a solid residue which was purified by trituration with diethyl ether to provide the title compound P4. Yield: 55 g (40%)$^1$H NMR (300 MHz, dmso-d$_6$) δ 8.90 (s, 1H), 8.71-8.72 (d, 1H), 7.80 (br. s, 1H), 7.50 (s, 1H), 4.90 (m, 1H), 1.47 (d, 6H).

Preparation 5: 5-hydroxy-3-methoxy-2-naphthamide (P5)

Step 1. Synthesis of methyl 3,5-dihydroxy-2-naphthoate (C24)

A solution of 3,5-dihydroxy-2-naphthoic acid (2.2 kg, 10.8 mol) in anhydrous MeOH (16 L) was cooled to below 25° C., after which thionyl chloride (2.56 kg, 21.5 mol) was then added over a period of about 3 h. After the addition, the mixture was stirred at about 25° C. overnight. An additional 500 g of thionyl chloride was added slowly and the mixture was stirred for approximately another 16 hours until the reaction was complete. The reaction mixture was concentrated to dryness and the residue was taken up in cold water. The resulting suspension was adjusted to about pH=8 with aqueous NaHCO$_3$. The precipitate was filtered, washed with water (0.5 L×3) and dried under vacuum to provide the title compound C24. Yield: 2.25 kg (96%)$^1$H NMR (400 MHz, dmso-d$_6$) δ 10.19 (s, 1H), 10.18 (s, 1H), 8.37 (s, 1H), 7.49 (s, 1H), 7.39-7.42 (d, 1H), 7.14-7.18 (t, 1H), 6.88-6.90 (d, 1H), 3.95 (s, 3H).

Step 2. Synthesis of methyl 5-((tert-butyldiphenylsilyl)oxy)-3-hydroxy-2-naphthoate (C25)

To a solution of compound C24 (500 g, 2.3 mol) in 1,2-dichloroethane (7.5 L) was added imidazole (233 g, 3.4 mol). After the addition, the mixture was heated to about 45° C. and stirred for about 45 minutes before t-butyldiphenylsilyl chloride (453 g, 2.7 mol) was added dropwise. The mixture was then heated to about 65° C. and held at that temperature for about two hours. Water (3 L) was added to the mixture and the dichloroethane layer was separated. The aqueous phase was extracted with DCM (1 L×2). The combined DCM extracts were washed with water (2 L×2) and brine, dried over Na$_2$SO$_4$, filtered, and concentrated under reduced pressure. Cold MeOH was added to the residue and stirred for about 10 minutes. The precipitate was filtered, washed with cold MeOH, and dried under vacuum to provide the title compound C25. Yield: 900 g (86%) This process was repeated to prepare additional compound C25. $^1$H NMR (300 MHz, dmso-d$_6$) δ 10.35 (s, 1H), 8.42 (s, 1H), 7.77 (s, 1H), 7.69-7.72 (t, 4H), 7.52 (m, 7H), 6.90-6.96 (t, 1H), 6.37-6.41 (d, 1H), 3.97 (s, 3H), 1.13 (s, 9H).

Step 3. Synthesis of methyl 5-((tert-butyldiphenyl-silyl)oxy)-3-methoxy-2-naphthoate (C26)

Triphenylphosphine (1.15 kg, 4.4 mol) was dissolved in THF (13 L) and treated with diisopropylazodicarboxylate (885 g, 4.4 mol) with stirring and cooling to maintain the temperature below about 25° C. After the addition was complete, the mixture was stirred for about 10 minutes. Methanol (876 mL, 21.9 mol) was then added into the mixture over a period of about 1 h with cooling to maintain the temperature approximately below 25° C. Compound C25 (1.0 kg, 2.2 mol) was added into the mixture in portions. The resulting solution was heated to about 80° C. for about 1 h. The mixture was then cooled to about 25° C. and concentrated to dryness. The residue was purified by column chromatography, after which it was heated under reflux with a 3/1 mixture of EtOH and petroleum ether for about 1 h to provide the title compound C26. Yield: 500 g (49%) This process was repeated to prepare additional compound C26. $^1$H NMR (300 MHz, dmso-$d_6$) δ 8.24 (s, 1H), 7.61-7.77 (m, 5H), 7.42-7.52 (m, 7H), 7.01-7.06 (t, 1H), 6.50-6.53 (d, 1H), 3.97 (s, 3H), 3.86 (s, 3H), 1.13 (s, 9H).

Step 4. Synthesis of 5-hydroxy-3-methoxy-2-naphthoic acid (C27)

Compound C26 (1.33 kg, 2.8 mol) and lithium hydroxide monohydrate (475 g, 11.3 mol) were added to a mixture of THF (3 L), MeOH (500 mL) and water (3 L). The mixture was stirred at about 25° C. overnight, after which the mixture was diluted with EtOAc (4 L) and water (2 L). The aqueous phase was separated and the EtOAc phase was extracted with water (2 L×2). The combined aqueous phases were extracted with EtOAc (2 L×2) and then acidified to about pH=3 with concentrated HCl. The precipitate was filtered, washed with water (1 L×3), and dried in vacuum to provide the title compound C27. Yield: 533 g (86%).

This process was repeated to prepare additional compound C27. $^1$H NMR (400 MHz, dmso-$d_6$) δ 12.80 (br. s, 1H), 10.16 (s, 1H), 8.12 (s, 1H), 7.50 (s, 1H), 7.37 (d, 1H), 7.15-7.24 (m, 1H), 6.92 (dd, 1H), 3.90 (s, 3H).

Step 5. Synthesis of 5-hydroxy-3-methoxy-2-naphthamide (P5)

A suspension of compound C27 (80 g, 360 mmol) in a mixture of DMF (15 mL) and dry THF (2 L) was treated with oxalyl chloride (64 mL) at about 25° C. The resulting suspension was stirred for about 1 h, then it was concentrated to dryness and the residue was suspended in 2 L of dry THF and cooled in ice. Concentrated ammonium hydroxide (220 mL) was added over a period of about five to ten minutes. The resulting mixture was then stirred at about 25° C. for approximately another twenty minutes. Saturated aqueous NaHCO$_3$ (100 mL) was added and the THF was evaporated under reduced pressure. Water (1 L) was added and the precipitate was filtered, washed with water, and dried under vacuum. The resulting solid was suspended in EtOAc and heated under reflux for about 2 h. The solid was filtered, washed with EtOAc, and dried to provide the title compound P5. Yield: 51 g (65%) By repetition of these steps a total of 1.0 kg of P5 was prepared. $^1$H NMR (400 MHz, dmso-$d_6$) δ 10.19 (s, 1H), 8.21 (s, 1H), 7.80-7.81 (br. s, 1H), 7.60-7.61 (br. s, 1H), 7.51 (s, 1H), 7.38-7.41 (d, 2H), 7.19-7.20 (t, 1H), 6.97-6.99 (d, 1H), 3.96 (s, 3H).

Synthesis of 5-hydroxy-3-isopropoxy-2-naphthamide (P6)

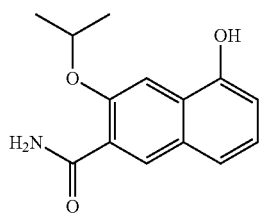 [SMILES: CC(C)Oc1cc2c(O)cccc2cc1C(N)=O]

This compound was prepared in the same manner as compound P5, substituting 2-propanol for MeOH in the reaction of compound C25 in Step 3, to provide the title compound P6. $^1$H NMR (400 MHz, dmso-$d_6$) δ 9.00-10.8 (br. s, 1H), 8.28 (s, 1H), 7.69 (s, 1H), 7.61 (s, 1H), 7.55 (s, 1H), 7.35-7.37 (d, 1H), 7.16-7.20 (t, 1H), 6.90-6.91 (d, 1H), 4.80-4.86 (m, 1H), 1.39-1.41 (d, 1H).

Preparation 6: 1-chloro-7-ethoxyisoquinoline-6-carbonitrile (P7)

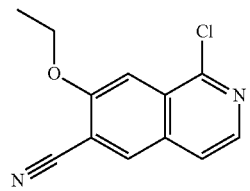 [SMILES: CCOc1cc2c(Cl)nccc2cc1C#N]

Step 1. Synthesis of 1-chloro-7-hydroxyisoquinoline-6-carbonitrile (C28)

To a stirred solution of compound P2 (10.0 g, 40.6 mmol) in 250 mL of DCM was added anhydrous aluminum chloride (16.3 g, 122 mmol). The reaction mixture was heated under reflux for about 4 h. The supernatant liquid was removed by decantation and ice was added to the residue remaining in the flask, which was broken up manually to afford a light yellow suspension. This solid was filtered and washed with water, dried, and was washed with ether to provide the title compound C28. Yield: 8.1 g (97%) $^1$H NMR (400 MHz, dmso-$d_6$) δ 11.95 (s, 1H), 8.65 (s, 1H), 8.22 (d, 1H), 7.84 (d, 1H), 7.69 (s, 1H).

Step 2. Synthesis of 1-chloro-7-ethoxyisoquinoline-6-carbonitrile (P7)

To a stirred solution of compound C28 (9.0 g, 44.1 mmol) in 190 mL of DMF was added potassium t-butoxide (6.9 g, 61.8 mmol) at 0° C. After about 15 minutes, iodoethane (8.8 mL, 110 mmol) was added. The reaction mixture was allowed to warm to about 25° C. and was stirred for about 4 h. The reaction mixture was diluted with water and the resulting precipitate was filtered and dried. The precipitate was then triturated with a mixture of MeOH and diethyl ether (9/1, v/v) to provide the title compound P7. Yield: 7.6 g (83%) $^1$H NMR (400 MHz, dmso-$d_6$) δ 8.72 (s, 1H), 8.31 (d, 1H), 7.90 (d, 1H), 7.62 (s, 1H), 7.62 (s, 1H), 4.37 (q, 2H), 1.47 (t, 3H).

Synthesis of 1-chloro-7-(prop-2-yn-1-yloxy)isoquinoline-6-carbonitrile (P8)

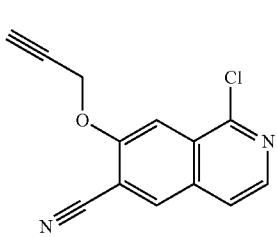 [SMILES: C#CCOc1cc2c(Cl)nccc2cc1C#N]

This compound was prepared in the same manner as compound P7, substituting 3-bromoprop-1-yne for iodoethane in the reaction of compound C28 in Step 2, to provide the title compound P8. $^1$H NMR (400 MHz, dmso-$d_6$) δ 8.78 (s, 1H), 8.34 (d, 1H), 7.93 (d, 1H), 7.84 (s, 1H), 5.25 (s, 2H), 3.79 (s, 1H).

Synthesis of 1-chloro-7-methoxy-$d_3$-isoquinoline-6-carbonitrile (P9)

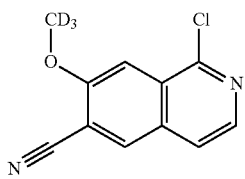 [SMILES: [2H]C([2H])([2H])Oc1cc2c(Cl)nccc2cc1C#N]

This compound was prepared in the same manner as compound P7, substituting methyl-$d_3$ 4-methylbenzenesulfonate for iodoethane in the reaction of compound C28 in Step 2, to provide the title compound P9. $^1$H NMR (400 MHz, dmso-$d_6$): δ 8.73 (s, 1H), 8.31 (d, 1H), 7.91 (d, 1H), 7.63 (s, 1H).

Synthesis of 1-chloro-7-(2-methoxyethoxy)isoquinoline-6-carbonitrile (P10)

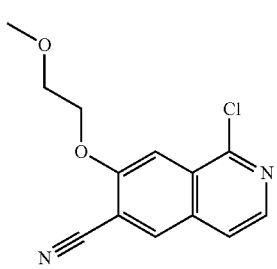 [SMILES: COCCOc1cc2c(Cl)nccc2cc1C#N]

This compound was prepared in the same manner as compound P7, substituting 1-bromo-2-methoxyethane for iodoethane in the reaction of compound C28 in Step 2, to provide the title compound P10. $^1$H NMR (400 MHz, CDCl$_3$) δ 8.28 (d, 1H), 8.16 (s, 1H), 7.70 (s, 1H), 7.56 (d, 1H), 4.40 (t, 2H), 3.90 (t, 2H), 3.51 (s, 3H).

Preparation 7; 1-chloro-7-(cyclopropylmethoxy)isoquinoline-6-carbonitrile (P11)

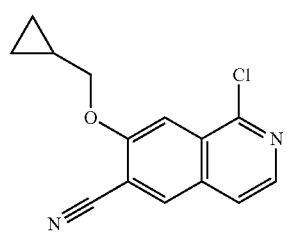 [SMILES: N#Cc1cc2ccnc(Cl)c2cc1OCC1CC1]

Step 1. Synthesis of 1-chloro-7-(cyclopropylmethoxy)isoquinoline-6-carbonitrile (P11)

A solution of triphenylphosphine (0.78 g, 3.0 mmol) in THF (8 mL) was treated with diisopropylazodicarboxylate (0.61 g, 3 mmol). After about 5 minutes, cyclopropylmethanol (0.29 g, 4.0 mmol) was added, followed by compound C28 (0.41 g, 2.0 mmol). The mixture was heated for about 1.5 h, then cooled and concentrated. The residue was triturated with MeOH and filtered to provide the title compound P11. $^1$H NMR (400 MHz, dmso-$d_6$) δ 8.75 (s, 1H), 8.31 (d, 1H), 7.91 (d, 1H), 7.64 (s, 1H), 4.20 (d, 1H), 1.35 (m, 1H), 0.65 (d, 2H), 0.46 (d, 2H).

Synthesis of 1-chloro-7-tert-butoxyisoquinoline-6-carbonitrile (P12)

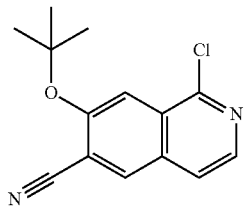 [SMILES: CC(C)(C)Oc1cc2c(Cl)nccc2cc1C#N]

This compound was prepared in the same manner as compound P11, substituting 2-methyl-2-propanol for cyclopropylmethanol in the reaction of compound C28 in Step 1, to provide the title compound P12. $^1$H NMR (400 MHz, CDCl$_3$) δ 8.29 (d, 1H), 8.17 (s, 1H), 7.97 (s, 1H), 7.58 (d, 1H), 1.63 (s, 9H)

Synthesis of 1-chloro-7-cyclobutoxyisoquinoline-6-carbonitrile (P13)

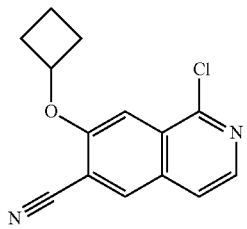 [SMILES: N#Cc1cc2ccnc(Cl)c2cc1OC1CCC1]

This compound was prepared in the same manner as compound P11, substituting cyclobutanol for cyclopropylmethanol in the reaction of compound C28 in Step 1, to provide the title compound P13. ¹H NMR (400 MHz, dmso-d₆) δ 8.75 (s, 1H), 8.31 (d, 1H), 7.91 (d, 1H), 7.50 (s, 1H), 5.10 (quin, 1H), 2.60-2.56 (m, 2H), 2.26-2.18 (m, 2H), 1.93-1.83 (m, 1H), 1.83-1.73 (m, 1H).

Synthesis of 1-chloro-7-(oxetan-3-yloxy)isoquinoline-6-carbonitrile (P14)

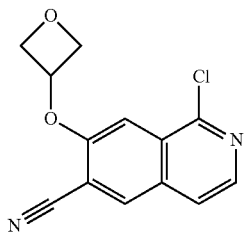 [SMILES: N#Cc1cc2ccnc(Cl)c2cc1OC1COC1]

This compound was prepared in the same manner as compound P11, substituting oxetan-3-ol for cyclopropylmethanol in the reaction of compound C28 in Step 1, to provide the title compound P14. ¹H NMR (400 MHz, dmso-d₆) δ 8.81 (s, 1H), 8.35 (d, 1H), 7.94 (d, 1H), 7.27 (s, 1H), 5.63-5.81 (m, 1H), 5.06 (t, 1H), 4.69 (m, 2H).

Preparation 8:
4-chloro-6-isopropoxyquinoline-7-carbonitrile (P15)

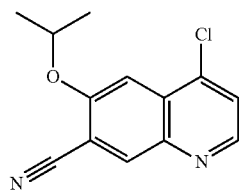 [SMILES: CC(C)Oc1cc2c(Cl)ccnc2cc1C#N]

Step 1. Synthesis of
4-chloro-6-isopropoxyquinoline-7-carbonitrile (P15)

Phosphorus oxychloride (28.2 mL, 303 mmol) was added drop wise with stirring to a solution of compound P4 (20 g, 75.8 mmol), pyridine (91 mL, 1.13 mol) and imidazole (10.3 g, 151.5 mmol) in DCM (300 mL). The mixture was stirred at about 25° C. for about 30 minutes. The reaction mixture was then cooled in ice and quenched with cold water (100 mL), added slowly enough to maintain the temperature to approximately below 5° C. Stirring was continued for approximately another 20 minutes with cooling. The mixture was then poured into 1 M HCl (500 mL) and separated. The aqueous phase was extracted with DCM. The combined DCM extracts were washed with 1 M HCl, water, Na₂CO₃ solution, brine, dried over Na₂SO₄, filtered and concentrated to provide the title compound P15. Yield: 12 g (64%) ¹H NMR: (400 MHz, CDCl₃) δ 8.70 (d, 1H), 8.41 (s, 1H), 7.54 (d, 1H), 7.52 (s, 1H), 4.85 (quin, 1H), 1.50 (d, 6H).

Preparation 9:
4-chloro-6-methoxyquinoline-7-carbonitrile (P16)

Step 1. Synthesis of
4-chloro-6-hydroxyquinoline-7-carbonitrile (C29)

To a stirred solution of compound P15 (12.0 g, 48.6 mmol) in 180 mL of DCM was added anhydrous aluminum chloride (20.6 g, 155 mmol). The reaction mixture was heated under reflux overnight. The solvent was evaporated under reduced pressure, and the residue was stirred with 0.1 M HCl (400 mL) at 25° C. for 2 h. The remaining solid was filtered, washed with water, MeOH, and dried to provide the title compound C29. Yield: 9.6 g (96%) ¹H NMR: (400 MHz, dmso-d₆) δ 11.82 (s, 1H), 8.74 (d, 1H); 8.56 (s, 1H), 7.81 (d, 1H), 7.60 (s, 1H).

Step 2. Synthesis of
4-chloro-6-methoxyquinoline-7-carbonitrile (P16)

To a stirred solution of compound C29 (9.6 g, 46.9 mmol) in DMF (190 mL) was added potassium t-butoxide (6.8 g, 61 mmol) at 0° C. After about 15 minutes, iodomethane (7.3 mL, 117 mmol) was added. The reaction mixture was allowed to warm to about 25° C. and was stirred for about 2 h. The reaction mixture was diluted with water and the resulting precipitate was filtered and dried. This solid was washed with water, hexane, and dried under vacuum to provide the title compound P15. Yield: 8.1 g (79%) ¹H NMR: (400 MHz, CDCl₃) δ 8.73 (d, 1H), 8.41 (s, 1H), 7.56 (d, 1H); 7.52 (s, 1H), 4.09 (s, 3H).

Synthesis of
4-chloro-6-ethoxyquinoline-7-carbonitrile (P17)

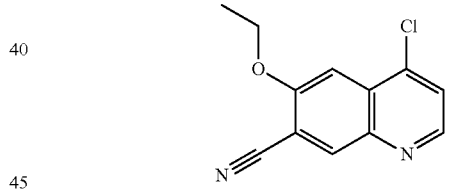

This compound was prepared in the same manner as compound P16, substituting iodoethane for iodomethane in the reaction of compound C30 in Step 3, to provide the title compound P17. ¹H NMR: (400 MHz, dmso-d₆) δ 8.72 (s, 1H), 8.31 (d, 1H), 7.89 (d, 1H), 7.62 (s, 1H), 4.38 (q, 2H), 1.46 (t, 3H).

Preparation 10: 1-chloro-7-(difluoromethoxy)isoquinoline-6-carbonitrile (P18)

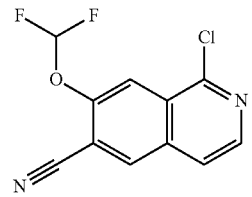 [SMILES: N#Cc1cc2ccnc(Cl)c2cc1OC(F)F]

Step 1. Synthesis of 1-chloro-7-(difluoromethoxy) isoquinoline-6-carbonitrile (P18)

A solution of compound C27 (164 mg, 0.8 mmol) in DMF (2 mL) was treated with sodium difluoroacetate (95 mg, 0.8 mmol) and cesium carbonate (285 mg, 0.9 mmol). The mixture was heated at about 60° C. for about 1 h. The mixture was diluted with 25 mL of water and 25 mL of EtOAc, and the EtOAc was separated, washed with brine, dried over $Na_2SO_4$, filtered and concentrated. The residue was purified by column chromatography to provide the title compound P18. Yield 133 mg (65%). $^1$H NMR: (400 MHz, dmso-$d_6$) δ 8.93 (s, 1H), 8.48 (d, 1H), 8.07 (d, 1H), 8.02 (dd, 1H), 7.70 (t, 1H).

Preparation 11: 6-bromo-1-chloro-7-(trifluoromethoxy)isoquinoline (P19)

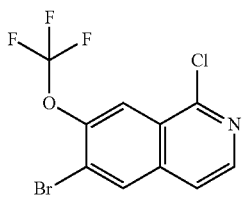 [SMILES: FC(F)(F)Oc1cc2c(Cl)nccc2cc1Br]

Step 1. Synthesis of 6-bromo-1-chloro-7-(trifluoromethoxy)isoquinoline (P19)

A suspension of 6-bromo-7-(trifluoromethoxy)isoquinolin-1(2H)-one (CAS 1445564-99-7, 410 mg, 1.3 mmol) in 6 mL of $POCl_3$ was heated under reflux for about 40 minutes. The mixture was cooled in ice and then poured into ice water with vigorous stirring. After the ice had melted, the mixture was extracted with EtOAc (100 mL). The EtOAc was separated and stirred with saturated aqueous $NaHCO_3$ solution (100 mL) until no bubbling occurred. The EtOAc was separated, washed with brine, dried over $Na_2SO_4$, filtered and concentrated. The residue was purified by silica chromatography to provide the title compound P19. Yield 130 mg (31%) $^1$H NMR (400 MHz, $CDCl_3$) δ 8.36 (d, 1H), 8.24 (d, 1H), 8.22 (s, 1H), 7.56 (d, 1H).

Preparation 12: 1-Chloro-7-cyclopropoxyisoquinoline-6-carbonitrile (P21)

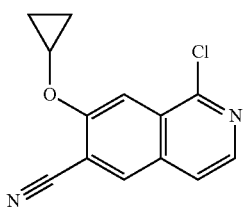 [SMILES: N#Cc1cc2ccnc(Cl)c2cc1OC1CC1]

Step 1. Synthesis of 1-chloro-7-(2-chloroethoxy) isoquinoline-6-carbonitrile (C166)

A mixture of compound C28 (2.4 g, 11.8 mmol), 2-chloroethanol-1-(4-methylbenzenesulfonate) (CAS 80-41-1, 5.5 g, 23.5 mmol), Triton-405 (6.63 g, 11.8 mmol) and cesium carbonate (4.58 g, 14.1 mmol) in 96 mL of THF was heated for about 8 h at about 65° C. The mixture was diluted with water and extracted with EtOAc. The combined EtOAc extracts were dried over $Na_2SO_4$, filtered and concentrated. The residue was purified by chromatography to provide the title compound C166. Yield: 2.0 g (64%). LCMS: $MH^+$=267.0.

Step 2. Synthesis of 1-chloro-7-(vinyloxy)isoquinoline-6-carbonitrile (C167)

A solution of compound C166 (1.4 g, 5.3 mmol) in THF (50 mL) was treated with a solution of potassium t-butoxide (1.2 g, 10.6 mmol) in 15 mL of THF at about −20° C., after which the mixture was warmed to about 25° C. and stirred for about 1 h Saturated aqueous $NH_4Cl$ was added and the mixture was extracted with EtOAc. The combined EtOAc extracts were washed with brine, dried over $Na_2SO_4$, filtered and concentrated. The residue was purified by chromatography to provide the title compound C167. Yield: 1.1 g (90%). LCMS: $MH^+$=230.9.

Step 3. Synthesis of 1-Chloro-7-cyclopropoxyisoquinoline-6-carbonitrile (P21)

A solution of compound C167 (220 mg, 0.9 mmol) in 50 mL of DCM was treated sequentially at about 0° C. with ethereal diazomethane (150 mL), followed by palladium(II) acetate (25 mg). The mixture was stirred overnight at about 25° C., then the mixture was filtered and concentrated. The residue was purified by chromatography to provide the title compound P21. Yield: 30 mg (13%). $^1$H NMR (400 MHz, dmso-$d_6$) δ 8.22-8.21 (d, 1H), 8.09 (s, 1H), 7.98 (s, 1H), 7.51-7.50 (d, 1H), 3.99-3.95 (m, 1H), 0.97-0.88 (m, 4H).

Preparation 13: 3,4-dichloro-6-methoxyquinoline-7-carbonitrile (P22)

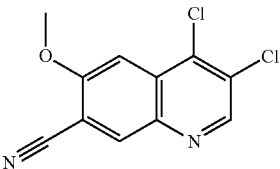 [SMILES: COc1cc2c(Cl)c(Cl)cnc2cc1C#N]

Step 1. Synthesis of 3-chloro-7-iodo-6-methoxyquinolin-4(1H)-one (C168)

A solution of 7-iodo-6-methoxyquinolin-4(1H)-one (CAS 1300031-68-8, 2.0 g, 6.6 mmol) and N-chlorosuccinimide (976 mg, 7.3 mmol) in AcOH (20 mL) was heated at about 35° C. for about 18 h. It was filtered and the precipitate was dried to provide the title compound C168. Yield: 1.4 g (63%). $^1$H NMR (400 MHz, dmso-$d_6$) δ 12.25 (br. s, 1H), 8.35 (s, 1H), 8.11 (s, 1H), 7.47 (s, 1H), 3.91 (s, 3H).

Step 2. Synthesis of 3,4-dichloro-6-methoxyquinoline-7-carbonitrile (P22)

A mixture of compound C168 (2.6 g, 7.7 mmol) and cuprous cyanide (1.31 g, 15.5 mmol) in pyridine (26 mL)

was heated at about 120° C. for about 16 h. The mixture was cooled to about 25° C., filtered, and the filtrate was concentrated. The residue was suspended in toluene and concentrated, then treated with POCl₃ (15 mL, 160 mmol) and triethylamine hydrochloride (1.47 g, 10.7 mmol). The mixture was heated at reflux for about 3 h, then cooled to about 25° C. and concentrated. The residue was stirred with aqueous NaHCO₃. The resulting precipitate was filtered, washed with n-hexane, and dried under vacuum. The dry solid was suspended in a 9/1 ratio of MeOH/DCM and solid NaHCO₃ was added. This mixture was stirred for about 5 h, filtered and the filtrate was concentrated. The residue was triturated with diethyl ether and dried under vacuum to provide the title compound P22. Yield: 1.5 g (56%). ¹H NMR (400 MHz, dmso-d₆) δ 8.98 (s, 1H), 8.71 (s, 1H), 7.60 (s, 1H), 4.11 (s, 3H).

Preparation 14: 4-bromo-1-chloro-7-isopropoxyisoquinoline-6-carbonitrile (P23)

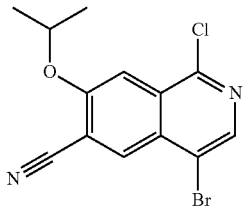 [SMILES: CC(C)Oc1cc2c(Cl)ncc(Br)c2cc1C#N]

Step 1. Synthesis of 7-isopropoxy-1-oxo-1,2-dihydroisoquinoline-6-carbonitrile (C169)

A solution of compound P2 (10.0 g, 40 mmol) and hydrogen chloride in 1,4-dioxane (4 M, 100 mL) in water (100 mL) was heated in a sealed tube at about 120° C. for about 18 h. The mixture was cooled to about 25° C. and diluted with water. The precipitate was filtered, washed with water, and dried to provide the title compound C169. Yield: 7.5 g (81%). ¹H NMR (300 MHz, dmso-d₆) δ 11.5 (br. s, 1H), 8.21 (s, 1H), 7.77 (s, 1H), 7.12-7.16 (t, 1H), 6.53-6.56 (d, 1H), 4.85-4.93 (m, 1H), 1.35-1.37 (d, 6H).

Step 2. Synthesis of 4-bromo-7-isopropoxy-1-oxo-1,2-dihydroisoquinoline-6-carbonitrile (C170)

A solution of N-bromosuccinimide (14 g, 78 mmol) in acetonitrile (150 mL) was added drop wise to a suspension of compound C169 (15 g, 65 mmol) in acetonitrile (1.38 L) at about 25° C. and stirred for about 24 h to afford a yellow suspension. The reaction mixture was concentrated to half volume. The precipitate was filtered, washed with diethyl ether and dried to provide the title compound C170. Yield: 13.0 g (65%). ¹H NMR (400 MHz, dmso-d₆) δ 11.8 (br. s, 1H), 8.08 (s, 1H), 7.84 (s, 1H), 7.52-7.53 (d, 1H), 4.92-4.98 (m, 1H), 1.36-1.38 (d, 6H).

Step 3. Synthesis of 4-bromo-1-chloro-7-isopropoxyisoquinoline-6-carbonitrile (P23)

A suspension of compound C170 (10.0 g, 32 mmol) in POCl₃ (120 mL) was heated at reflux for about 1.5 h. The mixture was concentrated and the residue was dissolved in DCM. The DCM extract was washed with K2CO3, brine, dried over Na₂SO₄, filtered and concentrated. The residue was purified by chromatography to provide the title compound P23. Yield: 9 g (85%). ¹H NMR (400 MHz, CDCl₃) δ 8.49 (s, 1H), 8.42 (s, 1H), 7.65 (s, 1H), 4.87-4.93 (m, 1H), 1.52-1.53 (d, 6H).

Preparation 15: 4-hydroxy-6-methoxyisoquinoline-7-carbonitrile (P24)

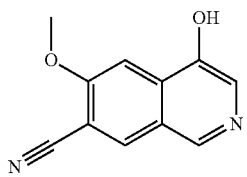

Step 1. Synthesis of ethyl 2-((3-bromo-4-methoxybenzyl)amino)acetate (C173)

To a solution of glycine ethyl ester hydrochloride (17 g, 126 mmol) and Et₃N (25.2 g, 252 mmol) in DCM (100 mL) and MeOH (100 mL) was added sodium triacetoxyborohydride (53.1 g, 252 mmol) at about 0° C. The mixture was stirred for about 30 min before 3-bromo-4-methoxybenzaldehyde (26.8 g, 126 mmol) was added, then the mixture allowed to warm up to about 25° C. for about 18 h. Water (200 mL) and saturated aqueous NH₄Cl (100 mL) were added and the mixture was extracted with DCM. The combined DCM extracts were washed with brine, dried over Na₂SO₄, filtered and concentrated. The residue was purified by chromatography to provide the title compound C173. Yield: 15 g (45%). ¹H NMR (400 MHz, dmso-d₆) δ 7.52 (d, 1H), 7.26 (dd, 1H), 7.05 (d, 1H), 4.08 (q, 2H), 3.82 (s, 3H), 3.64 (s, 2H), 3.27 (s, 2H), 2.67 (br. s., 1H), 1.19 (t, 3H).

Step 2. Synthesis of ethyl 2-(N-(3-bromo-4-methoxybenzyl)-4-methylphenylsulfonamido)acetate (C174)

To a solution of compound C173 (18 g, 60 mmol) and pyridine (24 g, 298 mmol) in THF (400 mL) was added tosyl chloride (11.4 g, 60 mmol) at 0° C. The mixture was stirred for about 16 h at about 25° C., then acidified to about pH 3 with concentrated HCl and extracted with DCM (3×300 mL). The combined DCM extracts were washed with brine, dried over Na₂SO₄, filtered and concentrated. The residue was purified by chromatography to provide the title compound C174. Yield: 17 g (63%). ¹H NMR (400 MHz, CDCl₃) δ 7.68 (d, 2H), 7.26 (d, 2H), 7.19 (s, 1H), 7.11 (dd, 1H), 6.76 (d, 1H), 4.33 (s, 2H), 3.94 (q, 2H), 3.83 (s, 2H), 3.81 (s, 3H), 2.37 (s, 3H), 1.08 (t, 3H).

Step 3. Synthesis of 2-(N-(3-bromo-4-methoxybenzyl)-4-methylphenylsulfonamido)acetic acid (C175)

To a solution of compound C174 (17 g, 37 mmol) in THF (100 mL) and MeOH (100 mL) was added a solution of lithium hydroxide (1.7 g, 74 mmol) in water (100 mL) at about 25° C. The mixture was stirred for about 4 h, then the mixture was partially concentrated to remove THF and MeOH. The remaining solution was acidified to about pH 3 with concentrated HCl and extracted with DCM (3×100 mL). The combined DCM extracts were washed with brine, dried over Na₂SO₄, filtered and concentrated to provide the title compound C175. Yield: 15 g (94%). ¹H NMR (400 MHz, CDCl₃) δ 7.75 (d, 2H), 7.33 (d, 2H), 7.27 (s, 1H), 7.17 (d, 1H), 6.83 (d, 1H), 4.38 (s, 2H), 3.93 (s, 2H), 3.88 (s, 3H), 2.43 (s, 3H).

Step 4. Synthesis of 7-bromo-6-methoxy-2-tosyl-2,3-dihydroisoquinolin-4(1H)-one (C176)

To a solution of compound C1175 (4.27 g, 10 mmol) in DCM (120 mL) were added 2 drops of DMF followed by oxalyl chloride (6.3 g, 50 mmol) at about 25° C. After about 2 h, the mixture was evaporated. The residue was dissolved in DCM (100 mL) and cooled to about −78° C. Anhydrous aluminum chloride (3.32 g, 25 mmol) was added in portions. The mixture was stirred for about 40 min at about −78° C., then stirred for about 2 h at about 0° C. Water was added, and the DCM was separated washed with brine, dried over Na₂SO₄, filtered and concentrated. The residue was triturated with a mixture of MeOH (7.5 mL) and EtOAc (7.5 mL). The precipitate was collected by filtration and dried to provide the title compound C176. Yield: 1.9 g (46%). ¹H NMR (400 MHz, CDCl₃) δ 7.63 (d, 2H), 7.47 (s, 1H), 7.31 (s, 1H), 7.27 (d, 2H), 4.43 (s, 2H), 3.99 (s, 2H), 3.89 (s, 3H), 2.39 (s, 3H).

Step 5. Synthesis of 7-bromo-6-methoxyisoquinolin-4-ol (C177)

A mixture of compound C176 (1.9 g, 4.6 mmol) and NaHCO₃ (1.54 g, 18.5 mmol) in EtOH (50 mL) was heated at reflux for about 2 h, then cooled to about 25° C. and concentrated. The residue was treated with EtOAc and water. The EtOAc was separated and the aqueous phase was extracted with additional EtOAc. The combined EtOAc extracts were dried over Na₂SO₄, filtered and concentrated. The residue was purified by chromatography to provide the title compound C177. Yield: 300 mg (26%). ¹H NMR (400 MHz, dmso-d₆) δ 10.50 (br. s., 1H), 8.67 (s, 1H), 8.39 (s, 1H), 8.03 (s, 1H), 7.47 (s, 1H), 4.01 (s, 3H).

Step 6. Synthesis of 4-hydroxy-6-methoxyisoquinoline-7-carbonitrile (P24)

A mixture of compound C177 (100 mg, 0.39 mmol), zinc cyanide (231 mg, 2 mmol) and tetrakis(triphenylphosphine) palladium (0) (45 mg, 0.04 mmol) in 5 mL of DMF was stirred for about 10 min at about 25° C., then heated at about 140° C. for about 6 h. The mixture was cooled, concentrated, the residue was treated with water, and extracted with EtOAc. The EtOAc extract was washed with brine, dried over Na₂SO₄, filtered and concentrated. The residue was purified by chromatography to provide the title compound P24. Yield: 65 mg (82%). ¹H NMR (400 MHz, dmso-d₆) δ 10.74 (s, 1H), 8.78 (s, 1H), 8.71 (s, 1H), 8.13 (s, 1H), 7.53 (s, 1H), 4.06 (s, 3H).

Preparation 16: 8-fluoro-5-hydroxy-3-methoxy-2-naphthamide (P25)

Step 1. Synthesis of methyl 5-hydroxy-3-methoxy-2-naphthoate (C178)

A solution of compound C26 (40 g, 85 mmol) in THF (150 mL) was treated with tetra-n-butylammonium fluoride (31 g, 119 mmol) and stirred for 30 min at 25° C. The reaction mixture was neutralized with AcOH before being diluted with water and EtOAc. The EtOAc extracts were dried over Na₂SO₄, filtered and concentrated. The residue was purified by chromatography to provide the title compound C178. Yield: 16.50 g (89%). ¹H NMR (400 MHz, dmso-d₆) δ 10.19 (s, 1H), 8.21 (s, 1H), 7.53 (s, 1H), 7.39-7.42 (d, 1H), 7.19-7.22 (t, 1H), 6.96 (d, 1H), 3.92 (s, 3H), 3.85 (s, 3H).

Step 2. Synthesis of methyl 8-fluoro-5-hydroxy-3-methoxy-2-naphthoate (C179)

A solution of SelectFluor (3.18 g, 8.6 mmol) in DMF (10 mL) was added slowly to a solution of compound C178 (2.00 g, 8.6 mmol) in DMF (20 mL) at about 0° C. After stirring overnight, the mixture was diluted with brine and extracted with EtOAc. The combined EtOAc extracts were dried over Na₂SO₄, filtered and concentrated. The residue was purified by chromatography to provide the title compound C179. Yield: 90 mg (4%). ¹H NMR (400 MHz, CDCl₃) δ 8.49 (s, 1H), 7.52 (d, 1H), 6.86 (dd, 1H), 6.77 (dd, 1H), 3.98 (s, 3H), 4.02 (s, 3H). ¹⁹F NMR (400 MHz, CDCl₃) δ −130.68.

Step 3. Synthesis of 8-fluoro-5-hydroxy-3-methoxy-2-naphthamide (P25)

A solution of compound C179 (90 mg, 0.36 mmol) in THF (4 mL) and water (2.5 mL) was treated with lithium hydroxide (88 mg, 3.6 mmol) at about 20° C. After stirring overnight, the mixture was acidified with 1 M HCl and concentrated to dryness. The residue was stirred in DCM (5 mL) and treated with oxalyl chloride solution (2 M, 0.27 mL) along with a catalytic amount of DMF. After about 1 h at about 20° C., the mixture was filtered and concentrated to dryness. The residue was taken up in THF (2 mL) and treated with ammonia in dioxane solution (0.5 M, 1 mL) at about 20° C. After about 1 h, the mixture was filtered and concentrated. The residue was purified by chromatography to provide the title compound P25. Yield 27 mg (32%). ¹H NMR (400 MHz, dmso-d₆) δ 10.17 (br. s., 1H), 8.32 (s, 1H), 7.81 (br. s., 1H), 7.66 (br. s., 1H), 7.53 (s, 1H), 7.00 (dd, 1H), 6.82 (dd, 1H), 3.98 (s, 3H). ¹⁹F NMR (400 MHz, dmso-d₆) δ −134.39.

Preparation 17: (S)-3,3-dimethyl-1,7a-dihydropyrrolo[12-c]oxazol-5(3H)-one (P20)

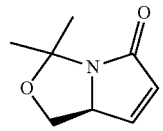

Step 1. Synthesis of (S)-3,3-dimethyl-5-(trimethylsilyloxy)-1,3,7,7a-tetrahydropyrrolo[1,2-c]oxazole (C30)

A solution of diisopropylamine (147 mL, 1.05 mol) in dry THF (875 mL) was cooled to about −25° C. and treated with n-butyllithium (2.5 M in hexanes, 387 mL, 970 mmol). The mixture was stirred at about −20° C. for about 30 minutes, then cooled to about −70° C. A solution of (S)-3,3-dimethyltetra-hydropyrrolo[1,2-c]oxazol-5(1H)-one (CAS 99208-71-6, 125 g, 806 mmol) in THF (163 mL) was added, maintaining the temperature approximately below −60° C. After the addition was completed, the mixture was stirred for approximately an additional 5 minutes before the addition of TMSCl (132 mL, 1.05 mol) at −60° C. The mixture was then allowed to warm to about −10° C. before being concentrated under reduced pressure. The residue was stirred with dry hexanes (1 L) and concentrated, then again stirred with dry hexanes (1 L) and concentrated. The residue was stirred with dry hexanes (1 L), filtered, and concentrated under reduced pressure to provide the title compound C30 which was carried on to Step 2 without further purification. $^1$H NMR (400 MHz, CDCl$_3$) δ 4.16 (m, 1H), 4.00 (dd, 1H), 3.75 (dd, 1H), 3.56 (dd, 1H), 2.54 (m, 1H), 2.31 (dd, 1H), 1.49 (s, 3H), 1.36 (s, 3H), 0.24 (s, 9H).

Step 2. Synthesis of (S)-3,3-dimethyl-1,7a-dihydropyrrolo[1,2-c]oxazol-5(3H)-one (P20)

The crude compound C30 from Step 1 was dissolved in THF (915 mL) and treated with allyl methyl carbonate (104 mL, 911 mmol) and palladium(II) acetate (9.0 g, 40 mmol). The mixture was heated to about 65 C until gas evolution ceased, and was then heated for approximately an additional 1 h after gas evolution ceased. The mixture was then cooled to about 25° C. and concentrated under reduced pressure. The residue was purified by column chromatography to provide the title compound P20. Yield: 90 g (73%) $^1$H NMR (400 MHz, CDCl$_3$) δ 7.07 (dd, 1H) 6.09 (dd, 1H) 4.60-4.71 (m, 1H) 4.13 (dd, 1H) 3.33 (dd, 1H) 1.67 (s, 3H) 1.56 (s, 3H).

Preparation 18: (5S)-5-(hydroxymethyl)-3-methyl-pyrrolidin-2-one (L1)

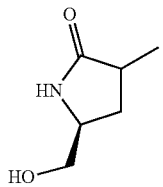

Step 1. Synthesis of (7aS)-3,3,6-trimethyltetrahydropyrrolo[1,2-c]oxazol-5(3H)-one (C31)

To a solution of (S)-3,3-dimethyltetra-hydropyrrolo[1,2-c]oxazol-5(1H)-one (CAS 99208-71-6, 3.0 g, 19 mmol) in 50 mL of THF was added LDA (2 M, 12.1 mL, 20 mmol) at about −78° C. The reaction mixture was stirred for about 30 minutes, then iodomethane (3.03 g, 21 mmol) was added. The reaction mixture was maintained for about 10 minutes at about −78° C., then allowed to warm to about 25° C. for about 1 h. The reaction was quenched by addition to EtOAc (10 mL) and water (10 mL). The EtOAc was separated and the aqueous phase was extracted with additional EtOAc (50 mL×2). The combined EtOAc extracts were washed with brine, dried over Na$_2$SO$_4$, filtered and concentrated to provide the title compound C31. Yield 3.1 g (92%). $^1$H NMR (400 MHz, CDCl$_3$) δ 4.11 (m, 2H), 3.42 (m, 1H), 2.87 (dt, 1H), 2.38 (m, 1H), 1.65 (s, 3H), 1.46 (s, 3H), 1.36 (m, 2H), 1.20 (s, 1.5H), 1.19 (s, 1.5H).

Step 2 Synthesis of (5S)-5-(hydroxymethyl)-3-methylpyrrolidin-2-one (L1)

A solution of compound C31 (58 mg, 0.34 mmol) in MeOH (1.1 mL) was treated with 4-toluenesulfonic acid (1.4 mg, 7 µmol). The resulting mixture was stirred at 60° C. for about 4 h, The mixture was concentrated under vacuum to provide the title compound L1. Yield 38 mg (86%) $^1$H NMR (400 MHz, CDCl$_3$) δ 3.70-3.83 (m, 2H), 3.39-3.49 (m, 1H), 2.51-2.64 (m, 1H), 2.30-2.42 (m, 1H), 1.34-1.46 (m, 1H), 1.23 (s, 1.5H), 1.21 (s, 1.5H).

Synthesis of (5S)-3-fluoro-5-(hydroxymethyl)pyrrolidin-2-one (L2)

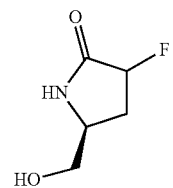

This compound was prepared in the same manner as compound L1, substituting NFSI for iodomethane in Step 1. $^1$H NMR (400 MHz, CD$_3$OD) δ 5.24-5.11 (m, 1H), 3.83-3.32 (m, 3H), 2.68-1.88 (m, 2H).

Synthesis of (3R,5R)-3-fluoro-5-(hydroxymethyl) pyrrolidin-2-one (L3)

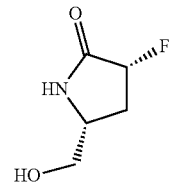

This compound was prepared in the same manner as compound L1, substituting (R)-3,3-dimethyltetra-hydropyrrolo[1,2-c]oxazol-5(1H)-one (CAS 103630-36-0, Chemical Communications, 2011, 47, 10037-10039) for (S)-3,3-dimethyltetra-hydropyrrolo[1,2-c]oxazol-5(1H)-one (CAS 99208-71-6), and NFSI for iodomethane, in Step 1, followed by separation of the diastereomeric products. $^1$H NMR (400 MHz, CDCl$_3$) δ 4.96-5.16 (m, 1H), 3.64-3.72 (m, 2H), 3.41-3.49 (m, 1H), 2.53-2.63 (m, 1H), 1.85-2.02 (m, 1H).

Synthesis of (5S)-3-ethyl-5-(hydroxymethyl) pyrrolidin-2-one (L4)

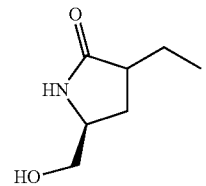

This compound was prepared in the same manner as compound L1, substituting bromoethane for iodomethane in Step 1. ¹H NMR (400 MHz, CDCl₃) δ 4.03-4.17 (m, 2H), 3.37-3.47 (m, 1H), 2.69-2.83 (m, 1H), 2.51-2.65 (m, 1H), 2.37 (s, 1H), 1.86-1.96 (m, 1H), 1.33-1.44 (m, 1H), 1.02 (t, 1H), 0.95 (t, 3H).

Synthesis of (5S)-5-(hydroxymethyl)-3-(methoxymethyl)pyrrolidin-2-one (L5)

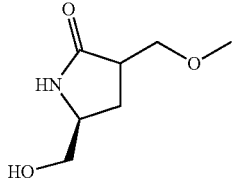

This compound was prepared in the same manner as compound L1, substituting chloro(methoxy)methane for iodomethane in Step 1. ¹H NMR (400 MHz, CDCl₃) δ 3.63-3.84 (m, 2H), 3.46-3.63 (m, 2H), 3.38 (s, 3H), 2.64-2.75 (m, 1H), 2.17-2.39 (m, 2H), 1.75-2.05 (m, 1H).

Synthesis of (3R,5S)-5-(hydroxymethyl)-3-(2-hydroxypropan-2-yl)pyrrolidin-2-one (L11)

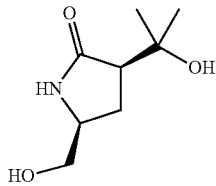

This compound was prepared in the same manner as compound L1, substituting acetone for iodomethane in Step 1. ¹H NMR (400 MHz, CDCl₃) δ 6.27-6.42 (m, 1H), 3.62-3.77 (m, 2H), 3.50-3.59 (m, 1H), 2.59-2.72 (m, 1H), 1.92-2.04 (m, 2H), 1.23 (s, 6H).

Synthesis of (5S)-3-((benzyloxy)methyl)-5-(hydroxymethyl) pyrrolidin-2-one (L12)

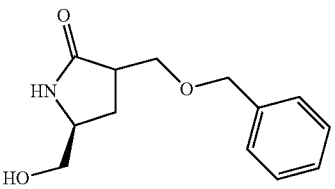 [SMILES: O=C1N[C@H](CO)CC1COCc1ccccc1]

This compound was prepared in the same manner as compound L1, substituting CAS 3587-60-8 ("benzyloxymethyl chloride") for iodomethane in Step 1. ¹H NMR (400 MHz, CDCl₃) δ 7.27-7.41 (m, 5H), 6.58 (br. s., 1H), 4.46-4.63 (m, 2H), 3.61-3.85 (m, 4H), 3.41-3.53 (m, 1H), 2.66-2.80 (m, 1H), 2.30 (m, 1H), 1.98 (s, 1H).

Synthesis of (3S,5S)-3-hydroxy-5-(hydroxymethyl) pyrrolidin-2-one (L13)

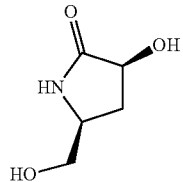

This compound was prepared in the same manner as compound L1, substituting CAS 104372-31-8 for iodomethane in Step 1. ¹H NMR (400 MHz, dmso-d₆) δ 4.41 (dd, 1H), 4.07 (dd, 1H), 3.82-3.93 (m, 1H), 3.34-3.42 (m, 1H), 2.41-2.49 (m, 1H), 1.45-1.53 (m, 1H).

Synthesis of (3R,5S)-3-hydroxy-5-(hydroxymethyl) pyrrolidin-2-one (L14)

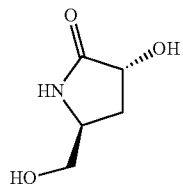

This compound was prepared in the same manner as compound L1, substituting CAS 127184-05-8 for iodomethane in Step 1. ¹H NMR (400 MHz, dmso-d₆) δ 5.79 (d, 1H), 4.22-4.32 (m, 1H), 4.16 (td, 1H), 4.01 (dd, 1H), 3.32-3.36 (m, 1H), 3.17 (d, 1H), 1.84-1.95 (m, 2H).

Synthesis of (3S,5S)-5-(hydroxymethyl)-3-(2,2,2-trifluoroethyl)pyrrolidin-2-one (L15) and (3R,5S)-5-(hydroxymethyl)-3-(2,2,2-trifluoroethyl)pyrrolidin-2-one (L16)

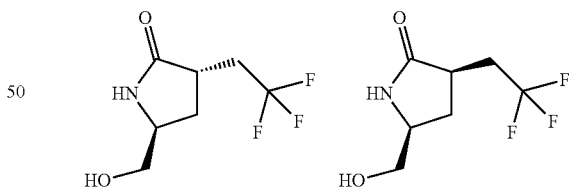

These compounds were prepared in the same manner as compound L1, substituting 1,1,1-trifluoro-2-iodoethane, added slowly, for iodomethane in Step 1, followed by separation of the diastereomeric products by silica gel chromatography prior to Step 2. Application of Step 2 to the individual diastereomers provided the title compounds L15 and L16. L15: ¹H NMR (400 MHz, CDCl₃) δ 6.48 (br. s., 1H), 3.67-3.79 (m, 2H), 3.52-3.62 (m, 1H), 2.74-2.91 (m, 2H), 2.28 (dd, 1H), 1.99-2.15 (m, 2H). L16: ¹H NMR (400 MHz, CDCl₃) δ 6.12 (br. s., 1H) 3.77-3.86 (m, 2H) 3.43-3.52 (m, 1H) 2.83-2.98 (m, 1H) 2.71-2.82 (m, 1H) 2.45-2.56 (m, 1H) 1.99-2.15 (m, 1H) 1.89 (dd, 1H) 1.51-1.58 (m, 1H).

Synthesis of (5S)-5-(hydroxymethyl)-3-(4-hydroxytetrahydro-2H-pyran-4-yl)pyrrolidin-2-one (L20)

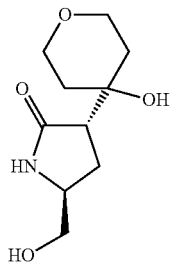

This compound was prepared in the same manner as compound L1, substituting tetrahydro-4H-pyran-4-one (CAS 29943-42-8) for iodomethane in Step 1. 1H NMR (400 MHz, CD$_3$CN) δ 4.30 (d, 1H), 3.60-3.77 (m, 4H), 3.51-3.60 (m, 1H), 3.43-3.51 (m, 1H), 3.34-3.42 (m, 1H), 2.93 (t, 1H), 2.51 (t, 1H), 1.98-2.08 (m, 1H), 1.86-1.94 (m, 2H), 1.80 (ddd, 1H), 1.58-1.69 (m, 1H), 1.41-1.52 (m, 1H), 1.24 (dd, 1H).

Synthesis of (5S)-5-(hydroxymethyl)-3-(3-hydroxyoxetan-3-yl)pyrrolidin-2-one (L22)

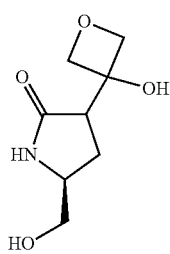

This compound was prepared in the same manner as compound L1, substituting CAS 6704-31-0 (oxetane-3-one) for iodomethane in Step 1 to provide (6S,7aS)-6-(3-hydroxyoxetan-3-yl)-3,3-dimethyltetrahydropyrrolo[1,2-c]oxazol-5(3H)-one (C81), which was used in Step 2. $^1$H NMR (400 MHz, dmso-d$_6$) δ 5.82 (d, 1H), 4.70-4.80 (m, 2H), 4.46 (d, 1H), 4.36-4.44 (m, 2H), 3.42 (dd, 1H), 3.27-3.31 (m, 1H), 2.80-2.91 (m, 1H), 1.83-1.98 (m, 2H).

Synthesis of (5S)-3-benzyl-5-(hydroxymethyl)pyrrolidin-2-one (L28)

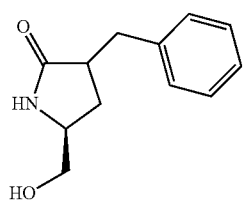 [SMILES: O=C1N[C@H](CO)CC1Cc1ccccc1]

This compound was prepared in the same manner as compound L1, substituting benzyl bromide for iodomethane in Step 1. $^1$H NMR (400 MHz, dmso-d$_6$) δ 7.64 (s, 1H), 7.31 (t, 2H), 7.24 (m, 3H), 4.74 (t, 1H), 3.16 (q, 2H), 3.02 (dd, 1H), 2.64 (m, 2H), 2.54 (s, 1H), 1.82 (m, 2H).

Synthesis of (3R,5S)-3-fluoro-5-(hydroxymethyl)-3-(tetrahydro-2H-pyran-4-yl)pyrrolidin-2-one (L31)

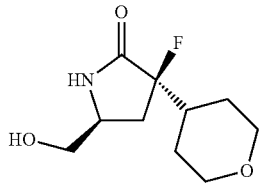 [SMILES: O=C1N[C@H](CO)C[C@@]1(F)C1CCOCC1]

This compound was prepared in the same manner as compound L1, substituting compound C49 for compound C30 and NFSI for iodomethane in Step 1. $^1$H NMR (400 MHz, CDCl$_3$) δ 4.03 (dd, 1H), 3.98 (d, 1H), 3.73 (d, 1H), 3.66-3.64 (m, 1H), 3.58-3.55 (m, 1H), 3.47-3.38 (m, 2H), 2.51-2.40 (m, 1H), 2.32-2.26 (m, 2H), 1.91 (ddd, 1H), 1.80 (d, 1H), 1.56-1.36 (m, 2H).

Preparation 19: (3S,5S)-3-ethyl-3-fluoro-5-(hydroxymethyl)pyrrolidin-2-one (L7)

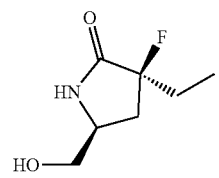

Step 1. Synthesis of (7aS)-6-ethyl-3,3-dimethyltetrahydropyrrolo[1,2-c]oxazol-5(3H)-one (C32)

To a solution of (S)-3,3-dimethyltetra-hydropyrrolo[1,2-c]oxazol-5(1H)-one (CAS 99208-71-6, 1.0 g, 6.4 mmol) in 30 mL of THF was added LDA (2 M, 4.0 mL, 8.0 mmol) at about −78° C. The reaction mixture was stirred for about 30 minutes, then bromoethane (0.80 g, 7.2 mmol) was added. The reaction mixture was maintained for about 10 minutes at about −78° C., then allowed to warm to about 25° C. for about 25 minutes. The reaction was quenched by addition to EtOAc (10 mL) and water (10 mL). The EtOAc was separated and the aqueous phase was extracted with additional EtOAc (50 mL×2). The combined EtOAc extracts were washed with brine, dried over Na$_2$SO$_4$, filtered and concentrated to provide the title compound C32. Yield 0.80 g (68%)$^1$H NMR (400 MHz, CDCl$_3$) δ 4.04-4.18 (m, 2H), 3.35-3.49 (m, 1H), 2.71-2.84 (m, 1H), 2.50-2.65 (m, 1H), 2.13-2.38 (m, 1H), 1.77-1.96 (m, 1H), 1.68 (s, 1H), 1.64 (s, 2H), 1.47 (s, 3H), 1.35-1.44 (m, 1H), 1.02 (t, 1H), 0.94 (t, 2H).

Step 2. Synthesis of (6S,7aS)-6-ethyl-6-fluoro-3,3-dimethyltetrahydropyrrolo[1,2-c]oxazol-5(3H)-one (C33) and (6R,7aS)-6-ethyl-6-fluoro-3,3-dimethyltetrahydropyrrolo[1,2-c]oxazol-5(3H)-one (C34)

To a solution of compound C32 (0.80 g, 4.4 mmol) in 5 mL of THF was added LDA (2 M, 2.8 mL, 5.6 mmol) at about −78° C. The reaction mixture was stirred for about 30 minutes, then treated with a solution of N-fluorobis(benzenesulfonyl)imide (NFSI) (1.65 g, 5.3 mmol) in 10 mL of THF. The reaction mixture was maintained for about 10 minutes at about −78° C., then allowed to warm to about 25° C. for about 1 h. The reaction was quenched by addition to EtOAc (10 mL) and water (10 mL). The EtOAc was separated and the aqueous phase was extracted with additional EtOAc (50 mL×2). The combined EtOAc extracts were washed with brine, dried over Na$_2$SO$_4$, filtered and concentrated. The residue was dissolved in DCM (20 mL) and filtered. The filtrate was concentrated and the residue was separated by column chromatography to provide the title compounds C33 (Yield: 180 mg, 20%) and C34 (Yield: 403 mg, 45%).

C33: $^1$H NMR (400 MHz, CDCl$_3$) δ 4.17 (dd, 1H), 3.84-3.95 (m, 1H), 3.47 (dd, 1H), 2.54 (ddd, 1H), 1.95-2.11 (m, 2H), 1.78-1.95 (m, 1H), 1.72 (s, 3H), 1.49 (s, 3H), 1.07 (t, 3H).

C34: $^1$H NMR (400 MHz, CDCl$_3$) δ 4.29-4.40 (m, 1H), 4.17 (dd, 1H), 3.34-3.43 (m, 1H), 2.42 (ddd, 1H), 1.98-2.11 (m, 1H), 1.76-1.83 (m, 1H), 1.71 (ddd, 1H), 1.65 (s, 3H), 1.53 (s, 3H), 1.01 (t, 3H).

Step 3: Synthesis of (3S,5S)-3-ethyl-3-fluoro-5-(hydroxymethyl)pyrrolidin-2-one (L7)

A solution of compound C33 (180 mg, 0.9 mmol) in MeOH (5 mL) was treated with 4-toluenesulfonic acid (23 mg, 135 μmol). The resulting mixture was stirred at about 70° C. for about 4 h. The mixture was concentrated under vacuum to provide the title compound L7. Yield 150 mg (100%). $^1$H NMR (400 MHz, CDCl$_3$) δ 3.75 (dd, 1H), 3.69 (dd, 1H), 3.56 (dd, 1H), 2.31-2.44 (m, 1H), 1.96-2.12 (m, 2H), 1.68-1.85 (m, 1H), 1.03 (t, 3H).

Synthesis of (S)-3,3-difluoro-5-(hydroxymethyl)pyrrolidin-2-one (L6)

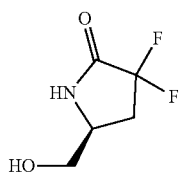

This compound was prepared in the same manner as compound L7, substituting NFSI for bromoethane in Step 1. $^1$H NMR (400 MHz, CDCl$_3$) δ 4.07-4.18 (m, 1H), 3.78-3.92 (m, 1H), 2.72-2.83 (m, 1H), 2.04-2.18 (m, 1H).

Synthesis of (3R,5S)-3-ethyl-3-fluoro-5-(hydroxymethyl)pyrrolidin-2-one (L8)

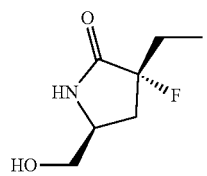

This compound was prepared in the same manner as compound L7, substituting compound C34. for compound C33 in Step 3. $^1$H NMR (400 MHz, CDCl$_3$) δ 3.90-4.01 (m, 1H), 3.81 (dd, 1H), 3.46 (dd, 1H), 2.29-2.47 (m, 1H), 2.00-2.11 (m, 1H), 1.83-2.00 (m, 1H), 1.64-1.83 (m, 1H), 1.02 (t, 3H).

Synthesis of (3R,5S)-3-fluoro-5-(hydroxymethyl)-3-methylpyrrolidin-2-one (L9) and (3S,5S)-3-fluoro-5-(hydroxymethyl)-3-methylpyrrolidin-2-one (L10)

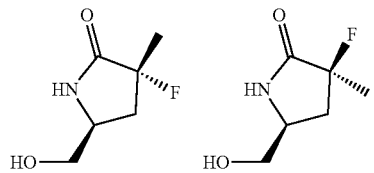

These compounds were prepared in the same manner as compounds L7 and L8, substituting iodomethane for bromoethane in Step 1, followed by separation of the diastereomeric products by chromatography prior to Step 2. L9: $^1$H NMR (400 MHz, CDCl$_3$) δ 3.77-3.83 (m, 1H), 3.69-3.77 (m, 1H), 3.53-3.62 (m, 1H), 2.42-2.60 (m, 2H), 1.53-1.64 (m, 3H).

L10: $^1$H NMR (400 MHz, CDCl$_3$) δ 3.73-3.80 (m, 1H), 3.70 (td, 1H), 3.55-3.63 (m, 1H), 2.26-2.40 (m, 1H), 2.07-2.22 (m, 1H), 1.59 (d, 3H).

Synthesis of (3S,5S)-3-((benzyloxy)methyl)-3-fluoro-5-(hydroxymethyl)pyrrolidin-2-one (L17) and (3R,5S)-3-((benzyloxy)methyl)-3-fluoro-5-(hydroxymethyl)pyrrolidin-2-one (L18)

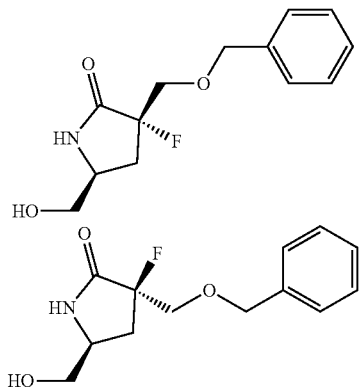

These compounds were prepared in the same manner as compounds L7 and L8, substituting NFSI for bromoethane in Step 1 and benzyloxymethyl chloride (CAS 3587-60-8) for NFSI in Step 2, followed by separation of the diastereomeric products by chromatography. The individual diastereomers were then subjected to Step 3. L17: $^1$H NMR (400 MHz, CDCl$_3$) δ 7.27-7.42 (m, 5H), 6.40-6.55 (m, 1H), 4.60 (s, 2H), 3.88-4.00 (m, 1H), 3.69-3.85 (m, 3H), 3.46 (dd, 1H), 2.35-2.56 (m, 1H), 2.16-2.33 (m, 1H). L18: $^1$H NMR (400 MHz, CDCl$_3$) δ 7.70 (br. s., 1H), 7.24-7.39 (m, 5H), 4.52-4.63 (m, 2H), 3.63-3.86 (m, 4H), 3.48 (br. s., 1H), 2.61 (d, 1H), 1.95-2.13 (m, 1H).

Synthesis of (3R,5S)-3-fluoro-5-(hydroxymethyl)-3-(2-hydroxypropan-2-yl) pyrrolidin-2-one (L19)

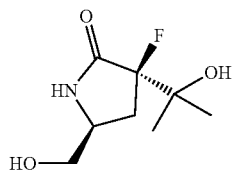

This compound was prepared in the same manner as compound L7, substituting NFSI for bromoethane in Step 1 and acetone for NFSI in Step 2, $^1$H NMR (400 MHz, CDCl$_3$) δ 3.45-3.42 (m, 1H), 3.27 (s, 1H), 2.57-2.49 (m, 1H), 1.98-1.90 (m, H), 1.86-1.83 (m, 3H), 1.32-1.31 (m, 3H).

Synthesis of (5S)-3-hydroxy-5-(hydroxymethyl)-3-(2,2,2-trifluoroethyl)pyrrolidin-2-one (L21)

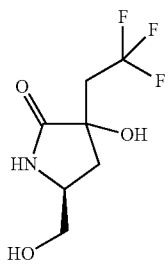 [SMILES: O=C1N[C@H](CO)CC1(O)CC(F)(F)F]

This compound was prepared in the same manner as compound L7, substituting 1,1,1-trifluoro-2-iodoethane, added slowly, for bromoethane in Step 1 and CAS 104372-31-8 for NFSI in Step 2. LCMS: R$_t$=1.128 min (213.7, MH$^+$); 1.258 (213.7, MH$^+$).

Synthesis of (5S)-3-fluoro-5-(hydroxymethyl)-3-(2,2,2-trifluoroethyl)pyrrolidin-2-one (L26)

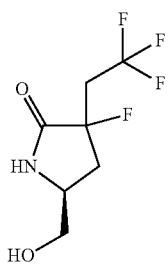 [SMILES: O=C1N[C@H](CO)CC1(F)CC(F)(F)F]

This compound was prepared in the same manner as compound L7, substituting (3R,7aS)-3-(4-methoxyphenyl)tetrahydropyrrolo[1,2-c]oxazol-5(3H)-one (CAS 170885-05-9) for (S)-3,3-dimethyltetrahydropyrrolo[1,2-c]oxazol-5(1H)-one (CAS 99208-71-6) and 1,1,1-trifluoro-2-iodoethane, added slowly, for bromoethane in Step 1. $^1$H NMR (400 MHz, CD$_3$OD) δ 3.57-3.53 (m, 1H), 3.46-3.38 (m, 2H), 2.93-2.80 (m, 1H), 2.70-2.35 (m, 2H), 2.27-2.10 (m, 1H).

Preparation 20: (3S,5S)-3-fluoro-3-(fluoromethyl)-5-(hydroxymethyl)pyrrolidin-2-one (L23)

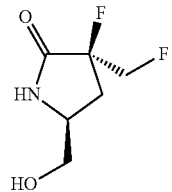 [SMILES: O=C1N[C@H](CO)C[C@@]1(F)CF]

Step 1. Synthesis of (7aS)-methyl 3,3-dimethyl-5-oxohexahydropyrrolo[1,2-c]oxazole-6-carboxylate (C35)

To a solution of (S)-3,3-dimethyltetrahydropyrrolo[1,2-c]oxazol-5(3H)-one (CAS 99208-71-6, 7.0 g, 45 mmol) in THF (70 mL) was added LDA (2.0 M, 56.4 mL, 113 mmol) dropwise at about −78° C. The reaction mixture was stirred for about 30 min before being treated with dimethyl carbonate (10.2 g, 113 mmol) in one portion. The mixture was stirred for approximately another 10 min at about −78° C. and was then warmed to about 25° C. and stirred for about 1 h. Saturated aqueous potassium dihydrogen phosphate was added and the mixture was extracted with EtOAc. The extracts were dried over Na$_2$SO$_4$ filtered and concentrated. The residue was purified by chromatography to provide the title compound C35. Yield: 6.8 g (71%). $^1$H NMR (400 MHz, CDCl$_3$) δ 4.43-4.53 (m, 1H, minor diastereomer), 4.16-4.25 (m, 1H, major diastereomer), 4.08-4.16 (m, 1H, both diastereomers), 3.85 (dd, 1H, major diastereomer), 3.81 (s, 3H, major diastereomer), 3.79 (s, 3H, minor diastereomer), 3.64 (d, 1H, minor diastereomer), 3.53-3.60 (m, 1H, major diastereomer), 3.43-3.51 (m, 1H, minor diastereomer), 2.49-2.57 (m, 1H, minor diastereomer), 2.34-2.44 (m, 1H, major diastereomer), 2.22-2.33 (m, 1H, major diastereomer), 1.98 (dt, 1 Hm minor diastereomer), 1.68 (s, 3H, minor diastereomer), 1.67 (s, 3H, major diastereomer), 1.48 (s, 3H, both diastereomers).

Step 2. Synthesis of (7aS)-methyl 6-fluoro-3,3-dimethyl-5-oxohexahydropyrrolo[1,2-c]oxazole-6-carboxylate (C36)

A solution of compound C35 (6.8 g, 32 mmol) in THF (128 mL) was treated with DBU (5.8 g, 38 mmol). The mixture was stirred for about 15 min at about 25° C., then cooled to about 0° C. and treated with NFSI (12.1 g, 38 mmol). It was kept at about 0° C. for about 15 min, then warmed to about 25° C. for about 3 h. The mixture was concentrated, and the residue was diluted with EtOAc and washed with 10% aqueous K$_2$CO$_3$. The mixture was separated and the aqueous layer was extracted with EtOAc. The combined extracts were dried over Na$_2$SO$_4$ filtered and concentrated. The residue was purified by chromatography to provide the title compound C36. Yield: 5.0 g (68%). $^1$H NMR (400 MHz, CDCl$_3$) δ 4.37-4.33 (m, 1H), 4.13-4.10 (m, 1H), 3.83 (s, 3H), 3.51-3.43 (m, 1H), 2.49-2.42 (m, 2H), 1.61 (s, 3H), 1.46 (s, 3H).

Step 3. Synthesis of (6R,7aS)-6-fluoro-6-(hydroxymethyl)-3,3-dimethyltetrahydropyrrolo[1,2-c]oxazol-5(3H)-one (C37) and (6S,7aS)-6-fluoro-6-(hydroxymethyl)-3,3-dimethyltetrahydro-pyrrolo[1,2-c]oxazol-5(3H)-one (C38)

A solution of compound C36 (6.0 g, 26 mmol) in EtOH (100 mL) at about 0° C. was treated with NaBH$_4$ (1.7 g, 44 mmol) added in one portion. The mixture was stirred at about 0° C. for about 1.5 h before being treated with 1 M HCl and then concentrated. The residue was purified by chromatography to provide the title compounds C37 (Yield: 1.8 g, 34%) and C38 (Yield: 400 mg, 8%). C37: $^1$H NMR (400 MHz, CDCl$_3$) δ 4.19 (dd, 1H), 3.80-4.06 (m, 3H), 3.46-3.54 (m, 1H), 2.79 (ddd, 1H), 2.10 (dd, 1H), 1.97-2.08 (m, 1H), 1.72 (s, 3H), 1.50 (s, 3H). C38: $^1$H NMR (400 MHz, CDCl$_3$) δ 4.36-4.45 (m, 1H), 4.19 (dd, 1H), 3.93-4.04 (m, 1H), 3.78-3.88 (m, 1H), 3.39-3.49 (m, 1H), 2.49 (dd, 1H), 2.40 (ddd, 1H), 1.97-2.14 (m, 1H), 1.67 (s, 3H), 1.54 (s, 3H).

Step 4. Synthesis of (6S,7aS)-6-fluoro-6-(fluoromethyl)-3,3-dimethyltetrahydropyrrolo[1,2-c]oxazol-5(3H)-one (C39)

A solution of compound C37 (1.5 g, 7.4 mmol) in CHCl$_3$ (30 mL) and pyridine (3.0 mL, 37 mmol) was cooled to about −78° C. and treated with DAST (2.1 mL, 16 mmol). The mixture was allowed to warm to about 25° C. and stirred for about 18 h, and then was heated at about 45° C. for about 2 h. The mixture was cooled to about −78° C. and quenched by the addition of MeOH. The mixture was allowed to warm to about 25° C., stirred for about 30 min and concentrated. The residue was purified by chromatography to provide the title compound C39. Yield: 450 mg (30%). $^1$H NMR (400 MHz, CDCl$_3$) δ 4.68-4.62 (m, 1H), 4.58-4.51 (m, 1H); 4.19 (dd, 1H), 4.03-3.95 (m, 1H), 3.49 (t, 1H), 2.84-2.79 (m, 1H), 2.14-2.03 (m, 1H), 1.70 (s, 3H), 1.52 (s, 3H).

Step 5. Synthesis of (3S,5S)-3-fluoro-3-(fluoromethyl)-5-(hydroxymethyl)pyrrolidin-2-one (L23)

To a stirred solution of compound C39 (450 mg, 2.2 mmol) in 50.4 mL of acetonitrile and 5.6 mL of water was added 4-toluenesulfonic acid (19 mg, 0.11 mmol). The reaction mixture was stirred at about 25° C. for about 16 h and then heated at about 90° C. for about 2 h. The reaction mixture was cooled to about 25° C., concentrated, and the residue was purified by chromatography to provide the title compound L23. Yield: 260 mg (72%). $^1$H NMR (400 MHz, CDCl$_3$) δ 6.47 (br s, 1H), 4.73-4.65 (m, 1H), 4.62-4.51 (m, 1H), 3.80-3.74 (m, 1H), 3.58 (br s, 1H), 2.72-2.62 (m, 1H), 2.16-2.07 (m, 1H), 2.03-2.00 (m, 1H).

Synthesis of (3R,5S)-3-fluoro-3-(fluoromethyl)-5-(hydroxymethyl)pyrrolidin-2-one (L24)

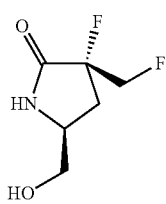 [SMILES: O=C1N[C@H](CO)C[C@]1(F)CF]

This compound was prepared in the same manner as compound L23, substituting C38 for C37 in step 4. $^1$H NMR (400 MHz, CD$_3$OD) δ 4.67 (dd, 1H), 4.63 (d, 1H), 3.82-3.90 (m, 1H), 3.62 (dd, 1H), 3.48 (dd, 1H), 2.27-2.52 (m, 2H).

Preparation 21: (5S)-5-(hydroxymethyl)-3-methoxy-pyrrolidin-2-one (L25)

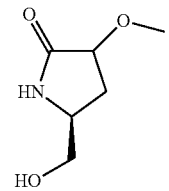

Step 1. Synthesis of (3R,7aS)-6-hydroxy-3-(4-methoxyphenyl)tetrahydropyrrolo[1,2-c]oxazol-5(3H)-one (C40)

To a solution of (3R,7aS)-3-(4-methoxyphenyl)tetrahydropyrrolo[1,2-c]oxazol-5(3H)-one (CAS 170885-05-9, 1.0 g, 4.3 mmol) in THF (20 mL) was added LDA (2.0 M, 3.0 mL) at about −78° C. The mixture was stirred at about −78° C. for about 0.5 h, then a solution of (1R)-(−)-10-camphorsulfonyl)oxaziridine (CAS 104372-31-8, 1.0 g, 4.7 mmol) in THF (10 mL) was added dropwise at about −78° C. The mixture was stirred at about −78° C. for about 10 min and then at about 25° C. for about 1.5 h. 10 mL of EtOAc and 10 mL of water were added the mixture was concentrated. The residue was diluted with water and extracted with EtOAc. The EtOAc extracts were washed with brine, dried over MgSO$_4$ filtered and concentrated. The residue was purified by chromatography to provide the title compound C40. Yield: 450 mg (42%). LCMS: m/z, 250.1 (M+1), retention time: 0.748 min

Step 2. Synthesis of (3R,7aS)-6-methoxy-3-(4-methoxyphenyl)tetrahydropyrrolo[1,2-c]oxazol-5(3H)-one (C41)

A mixture of compound C40 (468 mg, 1.8 mmol), silver (I) oxide (232 mg, 1.0 mmol) and iodomethane (710 mg, 5.0 mmol) in acetonitrile (20 mL) was stirred about 25° C. for about 6 h. Additional silver (I) oxide (464 mg, 2.0 mmol) and iodomethane (710 mg, 5.0 mmol) were added and after about 18 h, the mixture was filtered and concentrated to provide the title compound C41 which was used without further purification. Yield: 370 mg (75%). LCMS: m/z, 263.9 (M+1), retention time: 0.883 min

Step 3. Synthesis of (5S)-5-(hydroxymethyl)-3-methoxypyrrolidin-2-one (L25)

A solution of compound C41 (430 mg, 1.6 mmol) in AcOH (8 mL) and water (2 mL) was stirred at about 75° C. for about 30 min. The mixture was concentrated, MeOH was added, and the resulting mixture was again concentrated. The residue was purified by chromatography to provide the title compound L25. Yield: 204 mg (86%). $^1$H NMR (400 MHz, CD$_3$OD) δ 6.19 (br. s, 1H) 3.89-3.86 (m, 1H), 3.68-3.65 (m, 2H), 3.49-3.43 (m, 4H), 2.45-2.42 (m, 1H), 2.30-2.00 (m, 1H), 1.68-1.64 (m, 1H).

Preparation 22: (S)-6-(hydroxymethyl)-5-azaspiro[2.4]heptan-4-one (L27)

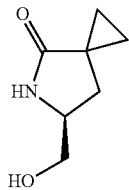

Step 1. Synthesis of (S)-3',3'-dimethyldihydro-1'H-spiro[cyclopropane-1,6'-pyrrolo[12-c]oxazol]-5'(3'H)-one (C42)

A solution of (S)-3,3-dimethyltetra-hydropyrrolo[1,2-c]oxazol-5(1H)-one (CAS 99208-71-6, 233 mg, 1.5 mmol) in THF (10 mL) was treated with LDA (2.0 M, 1.6 mL) at about −78° C. A solution of 1,3,2-dioxathiolane 2,2-dioxide (CAS 1072-53-3, 242 mg, 1.9 mmol) in THF (10 mL) was added at a rate to maintain the internal temp at about less than −65° C. The mixture was stirred at about −78° C. for about 10 min then warmed to about −20° C. The mixture was stirred for about 45 min and gradually warmed to about −3° C. before being re-cooled to about −78° C. LDA (2.0 M, 1.95 mmol) was added and the mixture was stirred for about 10 min at about −78° C., then slowly warmed to about 25° C. and kept for about 8 h. The mixture was treated with half-saturated aqueous NH$_4$Cl and extracted with EtOAc. The EtOAc extracts were washed with saturated aqueous NH$_4$Cl, dried over MgSO$_4$ filtered and concentrated. The residue was purified by chromatography to provide the title compound C42. Yield: 120 mg (44%). $^1$H NMR (400 MHz, CDCl$_3$) δ 4.29-4.21 (m, 1H), 4.08-4.05 (m, 1H), 3.43-3.38 (m, 1H), 2.04-1.99 (m, 1H), 1.94-1.90 (m, 1H), 1.61 (s, 3H), 1.45 (s, 3H), 1.19-1.14 (m, 1H), 1.25-1.17 (m, 1H), 1.16-1.14 (m, 1H), 0.95-0.94 (m, 1H), 0.93-0.90 (m, 1H).

Step 2. Synthesis of (S)-6-(hydroxymethyl)-5-azaspiro[2.4]heptan-4-one (L27)

To a stirred solution of compound C42 (120 mg, 0.66 mmol) in 4.5 mL of acetonitrile and 0.5 mL of water was added 4-toluenesulfonic acid (12 mg, 0.06 mmol). The reaction mixture was heated at about 90° C. for about 1 h. The reaction mixture was cooled to about 25° C. and concentrated to provide the title compound L27 which was used in the next step without further purification. Yield: 105 mg. $^1$H NMR (400 MHz, CD$_3$OD) δ 3.82-3.82 (m, 1H), 3.80-3.50 (m, 1H), 2.33-2.30 (m, 1H), 1.98-1.94 (m, 1H), 1.04-1.02 (m, 2H), 0.81-0.80 (m, 2H).

Preparation 23 (3R,5S)-3-fluoro-3-(2-fluoroethyl)-5-(hydroxymethyl) pyrrolidin-2-one (L29)

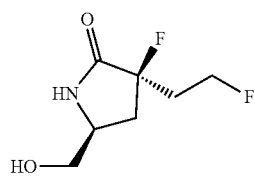 [SMILES: O=C1N[C@H](CO)C[C@@]1(F)CCF]

Step 1. Synthesis of (7aS)-6-allyl-3,3-dimethyltetra-hydropyrrolo[1,2-c]oxazol-5(3H)-one (C43)

To a stirred solution of (S)-3,3-dimethyltetra-hydropyrrolo[1,2-c]oxazol-5(1H)-one (CAS 99208-71-6, 10 g, 64.5 mmol) in THF (160 mL) at −78° C. was added LDA (2 M, 40.3 mL) and the mixture was stirred for about 0.5 h. Allyl bromide (6.2 mL, 71 mmol) was added and mixture was stirred for about 10 min at about −78° C., then allowed to warm to about 25° C. and stirred for about 1 h. It was quenched with EtOAc-water (1:1, 60 mL) and separated. The aqueous phase was extracted with EtOAc, and the combined EtOAc extracts dried over Na2SO4 filtered and concentrated. The residue was purified by chromatography to provide the title compound L29. Yield: 8.85 g (70%). $^1$H NMR (400 MHz, CDCl$_3$) δ 5.78-5.71 (m, 1H), 5.14-5.02 (m, 2H), 4.13-4.03 (m, 2H), 3.40-3.36 (m, 1H), 2.90-2.72 (m, 1H), 2.63-2.42 (m, 1H), 2.35-2.15 (m, 2H), 1.95-1.87 (m, 1H), 1.64 (s, 3H), 1.44 (s, 3H).

Step 2. Synthesis of (6S,7aS)-6-allyl-6-fluoro-3,3-dimethyltetrahydropyrrolo[1,2-c]oxazol-5(3H)-one (C44a)

To a stirred solution of L29 (5.0 g, 25.6 mmol) in THF (80 mL) at −78° C. was added LDA (2 M, 16.0 mL). After about 0.5 h, a solution of NFSI (8.89 g, 28.2 mmol) in THF (20 mL) was added and the mixture was stirred for about 10 min at about −78° C. The reaction mixture was warmed to about 25° C. for about 1 h. The mixture was quenched with EtOAc-water (1:1). The aqueous phase was extracted with EtOAc, and the combined EtOAc extracts were dried over Na$_2$SO$_4$ filtered and concentrated. The residue was purified by chromatography to provide the title compound C44a. Yield: 1.9 g (35%). There was also obtained the diastereomer C44b. Yield: 1.1 g (20%). C44a: $^1$H NMR (400 MHz, CDCl$_3$) δ 5.78-5.68 (m, 1H), 5.19-5.15 (m, 2H), 4.30-4.25 (m, 1H), 4.11 (dd, 1H), 3.33 (t, 1H), 2.72-2.65 (m, 1H), 2.55-2.47 (m, 1H), 2.37-2.27 (m, 1H), 1.85-1.70 (m, 1H), 1.59 (s, 3H), 1.48 (s, 3H). C44b: $^1$H NMR (400 MHz, CDCl$_3$) δ 5.85-5.76 (m, 1H), 5.29-5.23 (m, 2H), 4.14 (dd, 1H), 3.89-3.81 (m, 1H), 3.44 (t, 1H), 2.75-2.67 (m, 1H), 2.62-2.51 (m, 2H), 2.06-1.95 (m, 1H), 1.54 (s, 3H), 1.47 (s, 3H).

Step 3. Synthesis of (6R,7aS)-6-fluoro-6-(2-hydroxyethyl)-3,3-dimethyltetrahydropyrrolo[1,2-c]oxazol-5(3H)-one (C45)

A stream of ozonized oxygen was bubbled through a solution of compound C44a (500 mg, 1.4 mmol) in DCM (20 mL) at about −78° C. for about 15 min. A stream of argon was passed through the mixture for about 15 min, then the mixture was treated with dimethyl sulfide (5 mL) at about −78° C. and stirred for about 1 h at about −78° C. The reaction mixture was evaporated to dryness and the residue was dissolved in THF (18 mL) and water (2 mL). NaBH$_4$ (183 mg, 4.6 mmol) was added and the mixture was stirred at about 25° C. for about 2 h. The mixture was treated with saturated aqueous NH$_4$Cl solution and extracted with EtOAc. The combined EtOAc extracts were dried over Na$_2$SO$_4$ filtered and concentrated to provide the title compound C45 as a colorless liquid which was carried on without further purification. Yield: 370 mg (71%). $^1$H NMR (400 MHz, dmso-d$_6$) δ 4.61 (t, 1H), 4.11-4.08 (m, 1H), 4.00-3.94 (m, 1H), 3.62-3.52 (m, 2H), 3.47 (t, 1H), 2.74-2.69 (m, 1H), 2.05-1.91 (m, 3H), 1.56 (s, 3H), 1.36 (s, 3H).

Step 4. Synthesis of (6R,7aS)-6-fluoro-6-(2-fluoroethyl)-3,3-dimethyltetrahydropyrrolo[1,2-c]oxazol-5(3H)-one (C46)

To a solution of compound C45 (370 mg, 1.7 mmol) in $CHCl_3$ (15 mL) was added pyridine (0.69 mL, 8.5 mmol) followed by DAST (0.4 mL, 3.07 mmol) at about −78° C. The mixture was warmed to about 25° C. and stirred for about 18 h. The mixture was then cooled to about −78° C. and quenched by the slow addition of MeOH. After about 30 min at about −78° C., the mixture was warmed to about 25° C. and stirred for about 30 min before being evaporated to dryness. The residue was purified by chromatography to provide the title compound C46. Yield: 120 mg (32%). $^1H$ NMR (400 MHz, $CDCl_3$) δ 4.80-4.53 (m, 2H), 4.17-4.14 (m, 1H), 3.96-3.91 (m, 1H), 3.46 (t, 1H), 2.76-2.71 (m, 1H), 2.34-2.19 (m, 2H), 2.09-1.98 (m, 1H), 1.68 (s, 3H), 1.44 (s, 3H).

Step 5. Synthesis of (3R,5S)-3-fluoro-3-(2-fluoroethyl)-5-(hydroxymethyl)pyrrolidin-2-one (L29)

To a stirred solution of compound C46 (130 mg, 0.62 mmol) in 5 mL of acetonitrile and 0.5 mL of water was added 4-toluenesulfonic acid (11 mg, 0.06 mmol). The reaction mixture was heated at about 90° C. for about 1 h. The reaction mixture was cooled to about 25° C., concentrated, and the residue was purified by chromatography to provide the title compound L29. Yield: 170 mg (83%). $^1H$ NMR (400 MHz, $CDCl_3$) δ 6.86 (br. s., 1H), 4.52-4.96 (m, 2H), 3.72-3.90 (m, 2H), 3.55-3.72 (m, 1H), 2.53-2.73 (m, 1H), 2.31-2.51 (m, 1H), 2.05-2.31 (m, 2H).

Preparation 24: (3R,5S)-5-(hydroxymethyl)-3-(tetrahydro-2H-pyran-4-yl)pyrrolidin-2-one (L30)

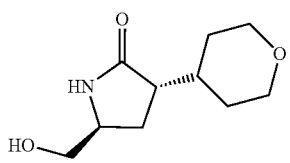 [SMILES: O=C1N[C@H](CO)C[C@H]1C1CCOCC1]

Step 1. Synthesis of (6S,7aS)-6-(4-hydroxytetrahydro-2H-pyran-4-yl)-3,3-dimethyltetrahydro-pyrrolo-[1,2-c]oxazol-5(3H)-one (C47)

A stirred solution of (S)-3,3-dimethyltetrahydropyrrolo[1,2-c]oxazol-5(3H)-one (CAS 99208-71-6, 10.0 g, 64 mmol) in THF (200 mL) was cooled to about −78° C. and LDA (2 M, 80 mL, 160 mmol) was added. The mixture was stirred at about −78° C. for about 30 min before tetrahydro-4H-pyran-4-one (CAS 29943-42-8, 15 mL, 160 mmol) in THF (50 mL) was added. The mixture was allowed to warm to about 25° C. and stirred for about 2 h before the reaction was quenched with EtOAc-water (1:1). The EtOAc was separated and the aqueous layer was extracted with EtOAc. The combined EtOAc extracts were washed with brine, dried over $Na_2SO_4$ filtered and concentrated. The residue was purified by chromatography to provide the title compound C47. Yield: 12 g (74%). $^1H$ NMR (400 MHz, dmso-$d_6$) δ 4.14 (m, 1H), 3.97-4.07 (m, 3H), 3.34-3.42 (m, 3H), 2.59-2.63 (m, 1H), 1.99-2.05 (m, 2H), 1.44-1.67 (m, 10H).

Step 2. Synthesis of (S)-6-(dihydro-2H-pyran-4(3H)-ylidene)-3,3-dimethyltetrahydropyrrolo[1,2-c]oxazol-5(3H)-one (C48)

Triethylamine (38 mL, 274 mmol) was added to a stirred solution of compound C47 (7.0 g, 27 mmol) in DCM (150 mL). The resulting mixture was cooled to about 0° C. and methanesulfonyl chloride (10.6 mL, 137 mmol) was added. The reaction mixture was warmed to about 25° C. and stirred for about 16 h before being diluted with DCM and water. The DCM was separated and the aqueous layer was extracted with DCM. The combined DCM extracts were washed with brine, dried over $Na_2SO_4$ filtered and concentrated. The residue was purified by chromatography to provide the title compound C48. Yield 1.0 g (16%). $^1H$ NMR (400 MHz, dmso-$d_6$) δ 5.61 (dd, 1H), 4.22-4.27 (m, 1H), 4.14-4.15 (m, 2H), 4.05-4.08 (dd, 1H), 3.79-3.81 (m, 2H), 3.40-3.45 (m, 1H), 3.25 (d, 1H), 2.15-2.20 (m, 2H), 2.10 (ddd, 1H), 1.92-2.04 (m, 1H), 1.65 (s, 3H), 1.45 (s, 3H).

Step 3. Synthesis of (6R,7aS)-3,3-dimethyl-6-(tetrahydro-2H-pyran-4-yl)tetrahydropyrrolo[1,2-c]oxazol-5(3H)-one (C49)

To a stirred solution of compound C48 (1.1 g, 4.6 mmol) in EtOAc (50 mL) was added platinum dioxide (105 mg, 0.46 mmol). The reaction mixture was shaken under about 50 psi of hydrogen at about 25° C. for about 4 h. The mixture was filtered and the solids were washed with EtOAc. The filtrate was concentrated and the residue was purified by chromatography to provide the title compound C49. Yield 0.75 g (68%) $^1H$ NMR (400 MHz, dmso-$d_6$) δ 4.14 (m, 1H), 4.04-4.07 (dd, 1H), 3.96-4.00 (m, 2H), 3.34-3.42 (m, 3H), 2.59-2.62 (m, 1H), 1.98-2.05 (m, 2H), 1.83-1.89 (m, 1H), 1.65-1.66 (m, 3H), 1.44-1.61 (m, 7H).

Step 4. Synthesis of (3R,5S)-5-(hydroxymethyl)-3-(tetrahydro-2H-pyran-4-yl)pyrrolidin-2-one (L30)

A solution of compound C49 (300 mg, 1.25 mmol) in acetonitrile (5 mL) and water (0.5 mL) was treated with 4-toluenesulfonic acid (11.9 mg, 0.06 mmol). The reaction mixture was heated at about 90° C. for about 2 h. The reaction mixture was cooled to about 25° C., concentrated, and the residue was purified by chromatography to provide the title compound L30. Yield 225 mg (90%). $^1H$ NMR (400 MHz, $CDCl_3$) δ 6.69 (s, 1H), 3.97 (d, 2H), 3.65 (m, 2H), 3.47-3.36 (m, 3H), 3.07 (m, 1H), 2.48-2.43 (m, 1H), 1.99-2.07 (m, 2H), 1.82-1.88 (m, 1H), 1.63-1.66 (m, 1H), 1.41-1.49 (m, 3H).

Preparation 25: (3R,5S)-3-(3-fluorooxetan-3-yl)-5-(hydroxymethyl)pyrrolidin-2-one (L32)

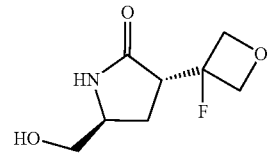 [SMILES: O=C1N[C@H](CO)C[C@H]1C1(F)COC1]

Step 1. Synthesis of (6R,7aS)-6-(3-fluorooxetan-3-yl)-3,3-dimethyltetrahydropyrrolo[1,2-c]oxazol-5(3H)-one (C50)

DAST (0.41 mL, 2.9 mmol) was added dropwise to a solution of compound C81 (0.51 g, 2.2 mmol) in DCM (20 mL) at about −78° C. After about 2 h, the reaction temperature was raised to about 0° C. and quenched with 50 mL of about pH 7 phosphate buffer and allowed to warm to about 25° C. The DCM was separated and the aqueous layer was extracted twice with DCM. The combined DCM layers were washed with NaHCO$_3$, brine, dried over Na$_2$SO$_4$ filtered and concentrated. The residue was purified by chromatography to afford a sample of compound C50 (0.47 g) which was contaminated with an olefinic by-product. To remove this olefin, the sample was dissolved in EtOH (15 mL), treated with Pearlman's catalyst (170 mg), and hydrogenated at 40 psi for about 2 h. The mixture was filtered and concentrated. The residue was purified by chromatography to provide the title compound C50. Yield 0.14 g (36%) $^1$H NMR (400 MHz, CDCl$_3$) δ 4.93-5.09 (m, 2H) 4.74-4.87 (m, 1H) 4.53-4.65 (m, 1H) 4.16-4.25 (m, 1H) 4.10-4.15 (m, 1H) 3.52-3.67 (m, 1H) 3.47 (t, 1H) 2.32 (ddd, 1H) 1.75 (td, 1H) 1.65 (s, 3H) 1.48 (s, 3H). There was also obtained in Step 1 (6S,7aS)-3,3-dimethyl-6-(oxetan-3-yl)tetrahydropyrrolo[1,2-c]oxazol-5(3H)-one (C51). $^1$H NMR (400 MHz, CDCl$_3$) δ 4.93 (dd, 1H), 4.79 (dd, 1H), 4.60-4.68 (m, 1H), 4.40 (t, 1H), 4.13-4.22 (m, 1H), 4.06-4.13 (m, 3H), 3.39-3.47 (m, 1H), 3.16-3.35 (m, 2H), 2.37 (ddd, 1H), 1.60 (s, 3H), 1.46-1.56 (m, 1H), 1.44 (s, 3H).

Step 2. Synthesis of (3R,5S)-3-(3-fluorooxetan-3-yl)-5-(hydroxymethyl)pyrrolidin-2-one (L32)

Compound C50 (130 mg, 0.56 mmol) was dissolved in 18 mL of acetonitrile and 2 mL of water and treated with 4-toluenesulfonic acid (5 mg, 0.03 mmol). The resulting mixture was stirred at about 25° C. for about 18 h, with additional stirring at about 95° C. for about 2 h. The reaction mixture was cooled to about 25° C., concentrated, and the residue was purified by chromatography to provide the title compound L32. Yield 68 mg (64%). This was used without further characterization.

Preparation 26: (3R,5S)-3-fluoro-5-(hydroxymethyl)-3-(methoxymethyl)pyrrolidin-2-one (L33)

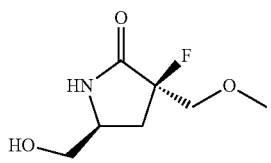

Step 1. Synthesis of (6R,7aS)-6-fluoro-6-(methoxymethyl)-3,3-dimethyltetrahydropyrrolo[1,2-c]oxazol-5(3H)-one (C52)

Lithium hexamethyldisilazide (1 M, 1.3 mL) was added to a solution of compound C37 (180 mg, 0.89 mmol) in THF (6 mL) at about 0° C. After about 0 minutes, iodomethane (0.55 mL, 8.8 mmol) was added. The mixture was allowed to warm to about 25° C. and was stirred for about 12 h. Additional lithium hexamethyldisilazide and iodomethane were added, and the mixture was stirred for approximately another 12 h. The reaction was then treated with water and EtOAc. The EtOAc was separated, and the aqueous phase was extracted with EtOAc. The combined EtOAc extracts were dried over Na$_2$SO$_4$ filtered and concentrated. The residue was purified by chromatography to provide the title compound C52. Yield: 116 mg (60%). $^1$H NMR (400 MHz, CDCl$_3$) δ 4.17 (dd, 1H), 3.99 (dd, 1H), 3.64-3.78 (m, 2H), 3.40-3.52 (m, 4H), 2.78 (ddd, 1H), 1.94-2.11 (m, 1H), 1.72 (s, 3H), 1.49 (s, 3H).

Step 2. Synthesis of (3R,5S)-3-fluoro-5-(hydroxymethyl)-3-(methoxymethyl)pyrrolidin-2-one (L33)

Compound C52 (116 mg, 0.53 mmol) was dissolved in 18 mL of acetonitrile and 2 mL of water and treated with 4-toluenesulfonic acid (5 mg, 0.03 mmol). The resulting mixture was stirred at about 25° C. for about 18 h, with additional stirring at about 95° C. for about 2 h. The reaction mixture was cooled to about 25° C., concentrated, and the residue was purified by chromatography to provide the title compound L33. Yield: 89 mg (94%). This was used without further characterization.

Preparation 27: (3R,5S)-5-(hydroxymethyl)-3-(oxetan-3-yl)pyrrolidin-2-one (L34)

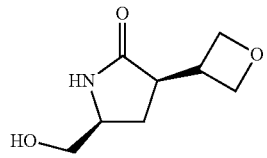 [SMILES: O=C1N[C@H](CO)C[C@@H]1C1COC1]

Step 1. Synthesis of (3R,5S)-5-(hydroxymethyl)-3-(oxetan-3-yl)pyrrolidin-2-one (L34)

To a stirred solution of compound C51 (130 mg, 0.62 mmol) in 8 mL of acetonitrile and 0.5 mL of water was added 4-toluenesulfonic acid (6 mg, 0.03 mmol). The reaction mixture was heated at about 90° C. for about 6 h. The reaction mixture was cooled to about 25° C., concentrated, and the residue was purified by chromatography to provide the title compound L34. Yield: 35 mg (33%). $^1$H NMR (400 MHz, CDCl$_3$) δ 6.04 (bs, 1H), 4.91 (t, 1H), 4.80 (t, 1H), 4.69 (t, 1H), 4.46 (t, 1H), 3.75-3.80 (m, 2H), 3.42-3.47 (m, 1H), 3.20-3.26 (m, 1H), 2.89-2.96 (m, 1H), 2.33-2.40 (m, 2H).

Preparation 28: (4R,5S)-5-(hydroxymethyl)-4-methylpyrrolidin-2-one (L36)

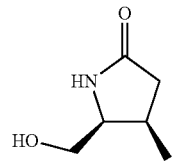

Step 1. Synthesis of (7R,7aS)-3,3,7-trimethyltetrahydropyrrolo[1,2-c]oxazol-5(3H)-one (C53)

A suspension of cuprous bromide-dimethyl sulfide complex (11.9 g, 57 mmol) in ether (100 mL) was cooled to about −10° C. and a solution of methyllithium (1.6 M, 71.4 mL, 114 mmol) was added slowly. The mixture was then cooled to about −73° C. and TMSCl (7.18 mL, 57 mmol) was added slowly. After the addition was complete, the mixture was maintained for about 15 min before compound P20 (3.50 g, 23 mmol) in THF (10 mL) was added slowly. The mixture was maintained for approximately another additional 75 min at about −78° C. before being allowed to warm to about 0° C. The mixture was maintained at about 0° C. for about 45 min before being treated with a mixture of saturated aqueous NH₄Cl and ammonium hydroxide. The ethereal layer was separated and the aqueous phase was extracted twice with EtOAc. The combined extracts were dried over MgSO₄ filtered and concentrated. The residue was purified by chromatography to provide the title compound C53. Yield: 2.27 g (59%). ¹H NMR (400 MHz, CDCl₃) δ 4.32 (dt, 1H), 3.89 (dd, 1H), 3.66-3.77 (m, 1H), 2.99 (dd, 1H), 2.42-2.56 (m, 1H), 2.13 (dd, 1H), 1.65 (s, 3H), 1.47 (s, 3H), 1.02 (d, 3H).

Step 2. Synthesis of (4R,5S)-5-(hydroxymethyl)-4-methylpyrrolidin-2-one (L36)

To a stirred solution of compound C53 (1.00 g, 5.9 mmol) in 18 mL of acetonitrile and 2 mL of water was added 4-toluenesulfonic acid (8 mg, 0.04 mmol). The reaction mixture was heated at about 95° C. for about 2 h. The reaction mixture was cooled to about 25° C., concentrated, and the residue was purified by chromatography to provide the title compound L36. Yield: 0.67 g (88%). ¹H NMR (400 MHz, CD₃OD) δ 3.53-3.71 (m, 3H), 2.57-2.74 (m, 1H), 2.36 (dd, 1H), 2.10 (dd, 1H), 1.11 (d, 3H).

Synthesis of (4S,5S)-5-(hydroxymethyl)-4-methylpyrrolidin-2-one (L35)

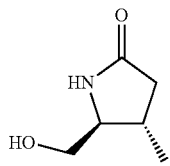

This compound was prepared in the same manner as compound L36, substituting (S)-tert-butyl 2-(((tert-butyldimethylsilyl)oxy)methyl)-5-oxo-2,5-dihydro-1H-pyrrole-1-carboxylate (CAS 81658-27-7) for P20 in Step 1 to afford (2S,3S)-tert-butyl 2-(((tert-butyldimethylsilyl)oxy)methyl)-3-methyl-5-oxopyrrolidine-1-carboxylate (C78), which was used in Step 2. ¹H NMR (400 MHz, CD₃OD) δ 3.60 (dd, 1H), 3.48 (dd, 1H), 3.27 (d, 1H), 2.55 (dd, 1H), 2.32-2.22 (m, 1H), 1.95 (dd, 1H), 1.15 (d, 3H).

Synthesis of (4S,5S)-4-ethyl-5-(hydroxymethyl) pyrrolidin-2-one (L46)

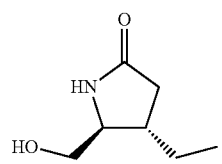

This compound was prepared in the same manner as compound L36, substituting CAS 170885-07-1 for P20, and ethylmagnesium bromide for methyllithium, in Step 1, to afford (3R,7S,7aS)-7-ethyl-3-(4-methoxyphenyl)tetrahydropyrrolo[1,2-c]oxazol-5(3H)-one (C63), which was used in step 2. ¹H NMR (400 MHz, CDCl₃) δ 3.66-3.64 (m, 1H), 3.42-3.35 (m, 2H), 2.49-2.42 (m, 1H), 2.01-1.92 (m, 2H), 1.54-1.47 (m, 1H), 1.39-1.32 (m, 1H), 0.88-0.84 (m, 3H).

Synthesis of (4R,5S)-4-ethyl-5-(hydroxymethyl) pyrrolidin-2-one (L47)

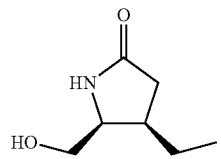

This compound was prepared in the same manner as compound L36, substituting ethylmagnesium bromide for methyllithium in Step 1, to afford (7R,7aS)-7-ethyl-3,3-dimethyltetrahydropyrrolo[1,2-c]oxazol-5(3H)-one (C54), which was used in Step 2. ¹H NMR (400 MHz, CDCl₃) δ 4.34 (dt, 1H), 3.90 (dd, 1H), 3.72 (dd, 1H), 2.91 (dd, 1H), 2.31 (dd, 1H), 2.25 (m, 1H), 1.65 (s, 3H), 1.52 (d, 1H), 1.48 (s, 3H), 1.27-1.38 (m, 1H), 0.92 (t, 3H).

Synthesis of (4S,5S)-5-(hydroxymethyl)-4-vinylpyrrolidin-2-one (L50)

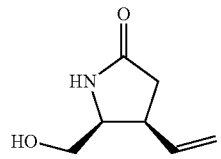

This compound was prepared in the same manner as compound L36, substituting vinylmagnesium bromide for methyllithium in Step 1, to afford (7S,7aS)-3,3-dimethyl-7-vinyltetrahydropyrrolo[1,2-c]oxazol-5(3H)-one (C55), which was used in Step 2. ¹H NMR (400 MHz, CDCl₃) δ 6.84 (br. s., 1H), 5.88 (ddd, 1H), 5.18 (d, 1H), 5.15 (d, 1H), 3.75 (td, 1H), 3.63-3.71 (m, 1H), 3.54-3.63 (m, 1H), 3.16-3.29 (m, 2H), 2.33-2.48 (m, 2H).

Synthesis of (4R,5S)-5-(hydroxymethyl)-4-vinylpyrrolidin-2-one (L51)

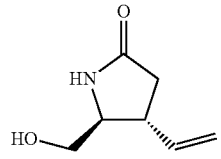

This compound was prepared in the same manner as compound L36, substituting CAS 170885-07-1 for P20, and vinylmagnesium bromide for methyllithium, in Step 1. ¹H NMR (400 MHz, CDCl$_3$) δ 6.61 (br. s., 1H), 5.74-5.91 (m, 1H), 5.06-5.20 (m, 2H), 3.80 (d, 1H), 3.46-3.62 (m, 2H), 2.70-2.87 (m, 1H), 2.56 (dd, 1H), 2.30 (dd, 2H).

Synthesis of (4S,5S)-4-cyclopropyl-5-(hydroxymethyl)pyrrolidin-2-one (L58)

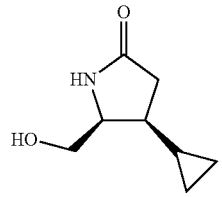 [SMILES: O=C1C[C@@H](C2CC2)[C@@H](CO)N1]

This compound was prepared in the same manner as compound L36, substituting cyclopropylmagnesium bromide for methyllithium in Step 1, to afford (7S,7aS)-7-cyclopropyl-3,3-dimethyltetrahydropyrrolo[1,2-c]oxazol-5 (3H)-one (C56), which was used in Step 2. $^1$H NMR (400 MHz, CD$_3$OD) δ 3.80 (d, 2H), 3.64 (dt, 1H), 2.23-2.42 (m, 2H), 1.69-1.87 (m, 1H), 0.89 (dtd, 1H), 0.52 (dd, 2H), 0.04-0.23 (m, 2H).

Synthesis of (4R,5S)-5-(hydroxymethyl)-4-propylpyrrolidin-2-one (L59)

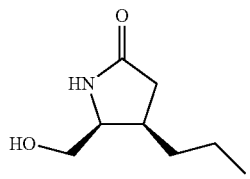

This compound was prepared in the same manner as compound L36, substituting propylmagnesium bromide for methyllithium in Step 1, to afford (7R,7aS)-3,3-dimethyl-7-propyltetrahydropyrrolo[1,2-c]oxazol-5(3H)-one (C57), which was used in Step 2. $^1$H NMR (400 MHz, dmso-d$_6$) δ 7.46 (br. s, 1H), 4.63 (t, 1H), 3.44-3.36 (m, 3H), 2.37-2.31 (m, 1H), 2.07-2.01 (dd, 1H), 1.95-1.89 (dd, 1H), 1.48-1.41 (m, 1H), 1.39-1.20 (m, 3H), 0.86 (t, H).

Preparation 29: (3R,4S,5S)-3-fluoro-5-(hydroxymethyl)-4-methylpyrrolidin-2-one (L37)

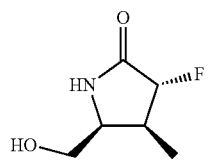

Step 1. Synthesis of (6R,7S,7aS)-6-fluoro-3,3,7-trimethyltetrahydropyrrolo[1,2-c]oxazol-5(3H)-one (C58)

A solution of compound C53 (0.93 g, 5.5 mmol) in THF (22 mL) was cooled to about −78° C. and treated with LDA (2.0 M, 3.44 mL, 6.88 mmol). The mixture was maintained at about −78° C. for about 25 min before being treated with NFSI (2.23 g, 6.8 mmol) in THF (8 mL). After stirring at about −78° C. for another approximate 5 min, the mixture was warmed to about 25° C. for about 1 h. Ethyl acetate and water were added, and the mixture was concentrated under reduced pressure to remove the THF present. The mixture was extracted twice with EtOAc, and the combined extracts were dried over Na$_2$SO$_4$ filtered and concentrated. The residue was purified by chromatography to provide the title compound C58. Yield: 0.56 g (55%). $^1$H NMR (400 MHz, CDCl$_3$) δ 4.58-4.77 (m, 1H), 4.54 (dtd, 1H), 3.96 (dd, 1H), 3.68 (dd, 1H), 2.53-2.73 (m, 1H), 1.66 (s, 3H), 1.53 (s, 3H), 1.05 (d, 3H). $^{19}$F NMR (376 MHz, CDCl$_3$) δ −184.92. There was also obtained (6S,7S,7aS)-6-fluoro-3,3,7-trimethyltetrahydropyrrolo[1,2-c]oxazol-5(3H)-one (C59). Yield: 0.11 g (11%). $^1$H NMR (400 MHz, CDCl$_3$) δ 5.25 (dd, 1H), 3.95-4.10 (m, 2H), 3.71-3.82 (m, 1H), 2.86-3.03 (m, 1H), 1.68 (s, 3H), 1.49 (s, 3H), 1.01 (dd, 3H). $^{19}$F NMR (376 MHz, CDCl$_3$) δ −202.08.

Step 2. Synthesis of (3R,4S,5S)-3-fluoro-5-(hydroxymethyl)-4-methylpyrrolidin-2-one (L37)

To a stirred solution of compound C58 (590 mg, 3.1 mmol) in 18 mL of acetonitrile and 2 mL of water was added 4-toluenesulfonic acid (27 mg, 0.16 mmol). The reaction mixture was heated at about 90° C. for about 2 h. The reaction mixture was cooled to about 25° C., concentrated, and the residue was purified by chromatography to provide the title compound L37. Yield: 451 mg (97%). $^1$H NMR (400 MHz, CDCl$_3$) δ 6.94 (br. s., 1H), 4.94 (dd, 1H), 3.66-3.77 (m, 2H), 3.60-3.66 (m, 1H), 2.93 (t, 1H), 2.61-2.81 (m, 1H), 1.29 (d, 3H). $^{19}$F NMR (376 MHz, CDCl$_3$) δ −194.85.

Synthesis of (3S,4S,5S)-3-fluoro-5-(hydroxymethyl)-4-methylpyrrolidin-2-one (L38)

This compound was prepared in the same manner as compound L37, substituting compound C59 for compound C58 in Step 2. $^1$H NMR (400 MHz, CDCl$_3$) δ 6.63 (br. s., 1H), 4.86 (dd, 1H), 3.72-3.83 (m, 2H), 3.60-3.68 (m, 1H), 2.67-2.80 (m, 1H), 1.96 (br. s., 1H), 1.10 (dd, 3H).
$^{19}$F NMR (376 MHz, CDCl$_3$) δ −201.74.

Synthesis of (4R,5S)-5-(hydroxymethyl)-3,4-dimethylpyrrolidin-2-one (L48)

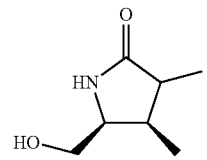

This compound was prepared in the same manner as compound L37, substituting iodomethane for NFSI in Step 1, to afford (7R,7aS)-3,3,6,7-tetramethyltetrahydropyrrolo[1,2-c]oxazol-5(3H)-one (C60), which was used in Step 2. $^1$H NMR (400 MHz, CD$_3$OD) δ 3.75-3.50 (m, 3H), 2.70-2.58 (m, 1H), 2.29-2.15 (m, 1H), 1.21-1.05 (overlapping d, 6H).

Synthesis of (3S,4S,5S)-4-ethyl-3-fluoro-5-(hydroxymethyl)pyrrolidin-2-one (L54)

This compound was prepared in the same manner as compound L37, substituting compound C54 for compound C53 in Step 1, to afford (6S,7S,7aS)-7-ethyl-6-fluoro-3,3-dimethyltetrahydropyrrolo[1,2-c]oxazol-5(3H)-one (C61), which was used in Step 2. $^1$H NMR (400 MHz, CDCl$_3$) δ 7.59 (br. s., 1H), 4.80 (dd, 1H), 3.69-3.83 (m, 2H), 3.52-3.64 (m, 1H), 3.48 (br. s, 1H), 2.27-2.52 (m, 1H), 1.57-1.73 (m, 1H), 1.49 (dt, 1H), 1.04 (t, 3H). $^{19}$F NMR (376 MHz, CDCl$_3$) δ −198.72. There was also obtained in Step 1 (6R,7S,7aS)-7-ethyl-6-fluoro-3,3-dimethyltetrahydro-pyrrolo[1,2-c]oxazol-5(3H)-one (C62). $^1$H NMR (400 MHz, CD$_3$CN) δ 4.78 (dd, 1H), 4.40 (dt, 1H), 3.93 (dd, 1H), 3.56 (dd, 1H), 2.30-2.46 (m, 1H), 1.56 (s, 3H), 1.52 (ddd, 1H), 1.42 (s, 3H), 1.35-1.48 (m, 1H), 0.97 (t, 3H).

Synthesis of (3R,4S,5S)-4-ethyl-3-fluoro-5-(hydroxymethyl)pyrrolidin-2-one (L55)

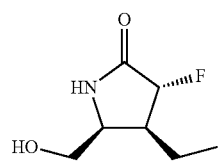

This compound was prepared in the same manner as compound L37, substituting compound C62 for compound C58 in Step 2. $^1$H NMR (400 MHz, dmso-d$_6$) δ 8.05 (br. s, 1H), 4.88 (dd, 1H), 3.48-3.46 (m, 1H), 3.41-3.38 (m, 2H), 2.32-2.23 (m, 1H), 1.62-1.55 (m, 2H), 0.95 (t, 3H). $^{19}$F NMR (376 MHz, CDCl$_3$) δ −189.64.

Synthesis of (3R,4R,5S)-4-ethyl-3-fluoro-5-(hydroxymethyl)pyrrolidin-2-one (L57)

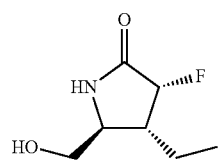

This compound was prepared in the same manner as compound L37, substituting compound C63 for compound C53 in Step 1, to afford (3R,6R,7R,7aS)-7-ethyl-6-fluoro-3-(4-methoxy-phenyl)tetrahydropyrrolo[1,2-c]oxazol-5(3H)-one (C64), which was used in Step 2. $^1$H NMR (400 MHz, CDCl$_3$) δ 4.92 (dd, 1H), 3.83-3.80 (m, 1H), 3.56-3.48 m, 2H), 2.17-2.10 (m, 1H), 1.76-1.70 (m, 1H), 1.52-1.46 (m, 1H), 0.99 (t, 1H).

Synthesis of (3S,4R,5S)-3-fluoro-5-(hydroxymethyl)-4-methylpyrrolidin-2-one (L90)

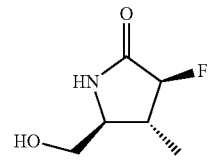

This compound was prepared in the same manner as compound L37, substituting compound C78 for compound C53 in Step 1. $^1$H NMR (400 MHz, CDCl$_3$) δ 6.82 (br. s., 1H), 4.73 (dd, 1H), 3.87 (dd, 1H), 3.56 (dd, 1H), 3.28-3.37 (m, 1H), 2.24-2.37 (m, 1H), 1.21 (d, 3H).

Synthesis of (3S,4S,5S)-4-cyclopropyl-3-fluoro-5-(hydroxymethyl)pyrrolidin-2-one (L119)

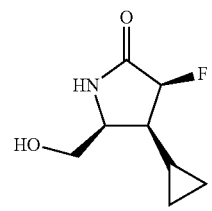 [SMILES: O=C1N[C@H](CO)[C@H](C2CC2)[C@@H]1F]

This compound was prepared in the same manner as compound L37, substituting compound C56 for compound C53 in Step 1, to afford (6S,7S,7aS)-7-cyclopropyl-6-fluoro-3,3-dimethyltetrahydropyrrolo[1,2-c]oxazol-5(3H)-one (C162), which was used in Step 2. $^1$H NMR (400 MHz, CD$_3$OD) δ 4.85 (dd, 1H), 3.94 (dd, 1H), 3.70-3.79 (m, 1H), 3.60-3.70 (m, 1H), 1.74-1.94 (m, 1H), 0.78-0.94 (m, 1H), 0.53-0.70 (m, 2H), 0.23-0.37 (m, 2H). There was also obtained in Step 1 (6R,7S,7aS)-7-cyclopropyl-6-fluoro-3,3-dimethyltetrahydro-pyrrolo[1,2-c]oxazol-5(3H)-one (C163). $^1$H NMR (400 MHz, CDCl$_3$) δ 4.91 (d, 1H), 4.44-4.57 (m, 1H), 3.94-4.09 (m, 2H), 1.70-1.76 (m, 1H), 1.67 (s, 3H), 1.54 (s, 3H), 0.55-0.73 (m, 3H), 0.29-0.38 (m, 1H), 0.17-0.27 (m, 1H)

Synthesis of (3R,4S,5S)-4-cyclopropyl-3-fluoro-5-(hydroxymethyl) pyrrolidin-2-one (L120)

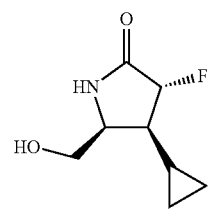

This compound was prepared in the same manner as compound L37, substituting compound C163 for compound C58 in Step 2. $^1$H NMR (400 MHz, CD30D) δ 5.13 (dd, 1H), 3.86 (dd, 1H), 3.58-3.72 (m, 2H), 1.71-1.92 (m, 1H), 1.08 (dtd, 1H), 0.51-0.70 (m, 2H), 0.37 (dq, 1H), 0.14-0.26 (m, 1H).

Preparation 30: (4S,5S)-4-ethyl-3,3-difluoro-5-(hydroxymethyl)pyrrolidin-2-one (L40)

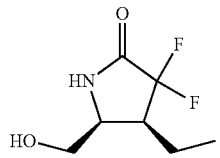

Step 1. Synthesis of (7S,7aS)-7-ethyl-6,6-difluoro-3,3-dimethyltetrahydropyrrolo[1,2-c]oxazol-5(3H)-one (C65)

A solution of compound C62 (0.80 g, 4.0 mmol) in THF (30 mL) was treated with LDA (2 M, 4.97 mL, 9.94 mmol) slowly at about −78° C. The mixture was kept at about −78° C. for about 45 min before the addition of a solution of NFSI (1.63 g, 5.17 mmol) in THF (10 mL). The mixture was maintained at about −78° C. for about 15 min after the completion of the addition, then was warmed to about 25° C. for about 2 h. Water and EtOAc were added and the EtOAc was separated. The aqueous phase was extracted with EtOAc, and the combined EtOAc extracts were washed with water, brine, dried over Na$_2$SO$_4$ filtered and concentrated. The residue was purified by chromatography to provide the title compound C65. Yield: 350 mg (40%). $^1$H NMR (400 MHz, dmso-d$_6$) δ 4.24 (dd, 1H), 4.09 (dd, 1H), 3.57 (m, 1H), 2.80-2.76 (m, 1H), 1.56 (s, 3H), 1.53-1.38 (m, 2H), 1.42 (s, 3H), 0.92 (t, 3H).

Step 2. Synthesis of (4S,5S)-4-ethyl-3,3-difluoro-5-(hydroxymethyl)pyrrolidin-2-one (L40)

To a stirred solution of compound C65 (350 mg, 1.91 mmol) in 14 mL of acetonitrile and 1.6 mL of water was added 4-toluenesulfonic acid (18 mg, 0.09 mmol). The reaction mixture was heated at about 90° C. for about 2 h. The reaction mixture was cooled to about 25° C., concentrated, and the residue was purified by chromatography to provide the title compound L40. Yield: 260 mg (76%). $^1$H NMR (400 MHz, CDCl$_3$) δ 6.59 (br. s, 1H), 3.78-3.75 (m, 2H), 3.53-3.51 (m, 1H), 2.65-2.52 (m 1H), 1.89 (br. s, 1H), 1.79-1.69 (m, 1H), 1.52-1.45 (m, 1H), 1.08 (t, 3H).

Synthesis of (4S,5S)-3,3-difluoro-5-(hydroxymethyl)-4-methylpyrrolidin-2-one (L39)

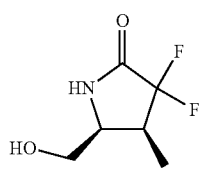

This compound was prepared in the same manner as compound L40, substituting compound C58 for compound C62 in Step 1. $^1$H NMR (400 MHz, CDCl$_3$) δ 3.76-3.48 (m, 2H), 3.29-2.71 (m, 1H), 2.69-2.60 (m, 1H), 1.18-1.06 (d, 3H).

Synthesis of (3R,4S,5S)-3-((benzyloxy)methyl)-3-fluoro-5-(hydroxymethyl)-4-methylpyrrolidin-2-one (L41)

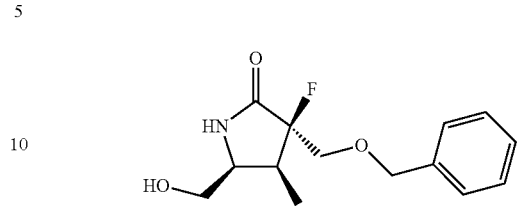

This compound was prepared in the same manner as compound L40, substituting compound C58 for compound C62, and benzyloxymethyl chloride (CAS 3587-60-8) for NFSI, in Step 1 to afford a (6R,7S,7aS)-6-((benzyloxy)methyl)-6-fluoro-3,3,7-trimethyltetrahydro-pyrrolo[1,2-c]oxazol-5(3H)-one (C66), which was used in Step 2. $^1$H NMR (400 MHz, CDCl$_3$) δ 7.21-7.41 (m, 5H), 4.57 (d, 2H), 3.47-3.86 (m, 5H), 2.71-2.93 (m, 1H), 1.04 (d, 3H). There was also obtained in Step 1 (6S,7S,7aS)-6-((benzyloxy)methyl)-6-fluoro-3,3,7-trimethyltetrahydropyrrolo[1,2-c]oxazol-5(3H)-one (C67). $^1$H NMR (400 MHz, CDCl$_3$) δ 7.28-7.40 (m, 5H), 4.68 (d, 1H), 4.53 (d, 1H), 4.45-4.51 (m, 1H), 3.95 (dd, 1H), 3.88 (dd, 1H), 3.59-3.74 (m, 2H), 2.72-2.85 (m, 1H), 1.61 (s, 3H), 1.51 (s, 3H), 0.99 (d, 3H)

Synthesis of (3S,4S,5S)-3-((benzyloxy)methyl)-3-fluoro-5-(hydroxymethyl)-4-methylpyrrolidin-2-one (L42)

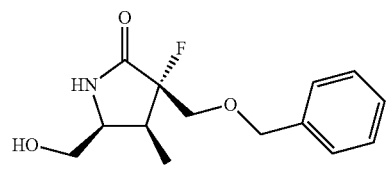 [SMILES: C[C@H]1[C@@H](CO)NC(=O)[C@@]1(F)COCc1ccccc1]

This compound was prepared in the same manner as compound L40, substituting compound C67 for compound C65 in Step 2. $^1$H NMR (400 MHz, CDCl$_3$) δ 7.28-7.45 (m, 5H), 6.85 (br. s., 1H), 4.60 (s, 2H), 3.87-3.99 (m, 1H), 3.65-3.86 (m, 3H), 3.44 (dd, 1H), 2.32-2.55 (m, 1H), 2.20-2.33 (m, 1H).

Synthesis of (3R,4S,5S)-3-fluoro-5-(hydroxymethyl)-3,4-dimethylpyrrolidin-2-one (L44)

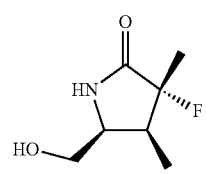

This compound was prepared in the same manner as compound L40, substituting compound C60 for compound C62 in Step 1, to afford (6R,7S,7aS)-6-fluoro-3,3,6,7-tetramethyltetrahydropyrrolo[1,2-c]oxazol-5(3H)-one (C68), which was used in Step 2. $^1$H NMR (400 MHz, CD$_3$OD) δ 4.90-4.78 (m, 2H), 3.74-3.59 (m, 1H), 2.81-2.66 (m, 1H), 1.42 (dd, 3H), (1.04 (d, 3H). There was also obtained in Step 1 (6S,7S,7aS)-6-fluoro-3,3,6,7-tetramethyltetrahydro-pyrrolo[1,2-c]oxazol-5(3H)-one (C69).

Synthesis of (3S,4S,5S)-3-fluoro-5-(hydroxymethyl)-3,4-dimethylpyrrolidin-2-one (L45)

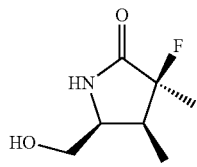

This compound was prepared in the same manner as compound L40, substituting compound C69 for compound C65 in Step 2. $^1$H NMR (400 MHz, CD$_3$OD) δ 3.59-3.56 (m, 2H), 3.46-3.44 (m, 1H), 2.41-2.22 (m, 1H), 1.48-1.39 (m, 3H), 1.10-1.01 (m, 3H).

Preparation 31

(4S,5S)-4-((benzyloxy)methyl)-5-(hydroxymethyl)pyrrolidin-2-one (L43)

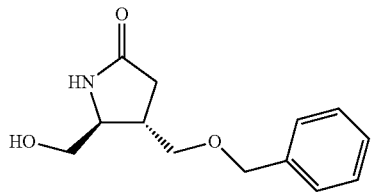 [SMILES: O=C1C[C@H](COCc2ccccc2)[C@@H](CO)N1]

Step 1. Synthesis of (3R,7R,7aS)-3-(4-methoxyphenyl)-7-(2-methylprop-1-en-1-yl)tetrahydropyrrolo[1,2-c]oxazol-5(3H)-one (C70)

To a solution of cuprous bromide dimethyl sulfide (6.24 g, 30.2 mmol) in THF (120 mL) was slowly added 2-methyl-1-propenylmagnesium bromide (0.5 M, 121 60.5 mmol) at about −15° C. After about 15 min, the mixture was cooled to about −78° C. A solution of CAS 170885-07-1 (1.4 g, 6.0 mmol) and TMSCl (1.3 g, 12.1 mmol) in THF (25 mL) was added over about 15 min. After about 1 h, aqueous NH$_4$Cl was added to the mixture and it was allowed to warm to about 25° C. Ethyl acetate was added and the EtOAc was separated, dried over Na$_2$SO$_4$ filtered and concentrated. The residue was purified by chromatography to provide the title compound C70. Yield: 1.1 g (64.0%). $^1$H NMR (400 MHz, dmso-d$_6$) δ 7.30 (d, 2H), 6.92 (d, 2H), 6.05 (s, 1H), 5.27 (dt, 1H), 4.13 (dd, 1H), 3.87-3.94 (m, 1H), 3.74 (s, 3H), 3.59-3.65 (m, 1H), 3.15-3.25 (m, 1H), 2.55-2.65 (m, 1H), 2.46-2.52 (s, 1H), 1.67 (d, 3H), 1.61 (d, 3H).

Step 2. Synthesis of (3R,7S,7aS)-7-(hydroxymethyl)-3-(4-methoxyphenyl)tetrahydropyrrolo[1,2-c]oxazol-5(3H)-one (C71)

A solution of compound C70 (1.1 g, 3.8 mmol) in DCM (20 mL) was treated with ozone at about −78° C. Once excess ozone was present, methyl sulfide (5 mL) was added slowly. The mixture was stirred at about −78° C. for about 1 hour before being evaporated to dryness. The residue was dissolved in 9 mL of THF and 1 mL of water and treated with NaBH$_4$ (307 mg, 7.6 mmol). The mixture was stirred for about 2 h at about 25° C. before being treated with aqueous NH$_4$Cl and EtOAc. The EtOAc extracts were dried over Na$_2$SO$_4$ filtered and concentrated. The residue was purified by chromatography to provide the title compound C71. Yield: 460 mg (46%). $^1$H NMR (400 MHz, dmso-d$_6$) δ 7.29 (d, 2H), 6.93 (d, 2H), 6.03 (s, 1H), 4.87 (t, 1H), 4.15 (dd, 1H), 3.89-3.97 (m, 1H), 3.75 (s, 3H), 3.40-3.55 (m, 3H), 2.39-2.55 (m, 3H).

Step 3. Synthesis of (4S,5S)-4-((benzyloxy)methyl)-5-(hydroxymethyl)pyrrolidin-2-one (L43)

A solution of compound C71 (220 mg, 0.84 mmol) in DMF (4.2 mL) was cooled to about 0° C. and treated with sodium hydride (60%, 40 mg, 1.0 mmol) followed by (bromomethyl)benzene (0.11 mL, 0.92 mmol). The mixture was kept for about 1 h at about 0° C. before being diluted with water. The mixture was extracted with EtOAc. The extracts were dried over Na$_2$SO$_4$ filtered and concentrated. The residue was subjected to treatment with 4-toluenesulfonic acid in acetonitrile and water to provide the title compound L43. Yield: 100 mg (51%). $^1$H NMR (400 MHz, dmso-d$_6$) δ 7.52 (s, 1H), 7.26-7.39 (m, 5H), 4.77 (t, 1H), 4.48 (s, 2H), 3.35-3.46 (m, 3H), 3.26-3.35 (m, 2H), 2.33-2.42 (m, 1H), 2.24-2.33 (m, 1H), 1.85-1.95 (m, 1H).

Preparation 32: (4S,5S)-4-(fluoromethyl)-5-(hydroxymethyl)pyrrolidin-2-one (L49)

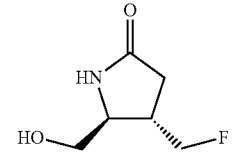

Step 1. Synthesis of (3R,7S,7aS)-7-(fluoromethyl)-3-(4-methoxyphenyl)tetrahydropyrrolo[1,2-c]oxazol-5(3H)-one (C72)

A solution of compound C71 (460 mg, 1.75 mmol) and 2,6-lutidine (468 mg, 4.37 mmol) in DCM at about 0° C. was treated with DAST (563 mg, 3.5 mmol). The mixture was stirred at about 25° C. for about 5 h before being quenched with saturated aqueous NaHCO$_3$ and extracted with DCM. The combined DCM extracts dried over Na$_2$SO$_4$, filtered and concentrated. The residue was purified by chromatography to provide the title compound C72. Yield: 410 mg (88%). LCMS: m/z, 265.3 (M+1), retention time: 1.602 min.

Step 2. Synthesis of (4S,5S)-4-(fluoromethyl)-5-(hydroxymethyl)pyrrolidin-2-one (L49)

To a stirred solution of compound C71 (100 mg, 0.38 mmol) in 9 mL of acetonitrile and 1 mL of water was added 4-toluenesulfonic acid (3 mg, 0.02 mmol). The reaction mixture was heated at about 90° C. until the solvent was evaporated. Additional acetonitrile and water were added and the operation was repeated several more times. The reaction mixture was cooled to about 25° C., concentrated, and the residue was purified by chromatography to provide the title compound L49. Yield: 50 mg (90%). $^1$H NMR (400 MHz, CD$_3$OD) δ 4.53-4.51 (m, 1H), 4.41-4.40 (m, 1H), 3.66-3.53 (m, 3H), 2.65-2.54 (m, 2H), 2.21-2.16 (m, 1H).

Preparation 33: (3S,4S,5S)-4-(fluoromethyl)-5-(hydroxy-methylpyrrolidin-2-one (L52)

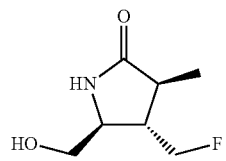

Step 1. Synthesis of (3R,7S,7aS)-7-(fluoromethyl)-3-(4-methoxyphenyl)-6-methyltetrahydropyrrolo[1,2-c]oxazol-5(3H)-one (C73)

To a solution of compound C73 (160 mg, 0.61 mmol) in THF (3 mL) at about −78° C. was added LDA (2 M, 0.38 mL). The mixture was stirred for about 0.5 h before iodomethane (107 mg, 0.76 mmol) was added. The mixture was maintained for about 10 min at about −78° C. before it was warmed to about 25° C. and stirred for about 1 h. EtOAc and water were added and the mixture was extracted with EtOAc. The combined EtOAc extracts were dried over Na$_2$SO$_4$, filtered and concentrated. The residue was purified by chromatography to provide the title compound C73. Yield: 140 mg (82%). LCMS: m/z, 279 (M+1), retention time: 1.244 min Step 2. Synthesis of (3S,4S,5S)-4-(fluoromethyl)-5-(hydroxymethyl)-3-methylpyrrolidin-2-one (L52)

A solution of compound C73 (140 mg, 0.5 mmol) in 6.5 mL of AcOH and 3.5 mL of water was heated to about 90° C. for about 40 min before being evaporated to dryness. The residue was dissolved in 25 mL of MeOH and concentrated. The residue was purified by chromatography to provide the title compound L52. Yield: 70 mg (87%). $^1$H NMR (400 MHz, CD$_3$OD) δ 4.62-4.51 (d, 2H), 3.71-3.68 (m, 1H), 3.54 (m, 2H), 2.41-2.39 (m, 1H), 2.23-2.10 (m, 1H), 1.25 (s, 3H).

Preparation 34: (3R,4R,5R)-3-fluoro-5-(hydroxymethyl)-4-methylpyrrolidin-2-one (L53)

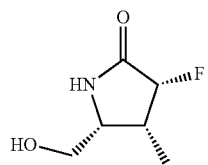

Step 1. Synthesis of (7aR)-3,3-dimethyl-6-(phenylselanyl)tetrahydropyrrolo[1,2-c]oxazol-5(3H)-one (C74)

LDA (2 M, 41.9 mL) was added to a solution of (R)-3,3-dimethyltetra-hydropyrrolo[1,2-c]oxazol-5(1H)-one (CAS 103630-36-0, 10 g, 64.4 mmol) in THF (130 mL) at about −78° C. After about 30 min, diphenyl diselenide (24.13 g, 77.3 mmol) in THF (125 mL) was added. The mixture was kept at about −78° C. for about 30 min before being warmed to about 25° C. for about 1 h. Ethyl acetate and water were added, and the mixture was partially concentrated before being extracted with EtOAc. The combined EtOAc extracts were dried over Na$_2$SO$_4$, filtered and concentrated. The residue was purified by chromatography to provide the title compound C74. Yield: 12.0 g (60%). $^1$H NMR (400 MHz, CDCl$_3$) δ 7.72-7.64 (m, 2H), 7.38-7.27 (m, 3H), 4.27 (dd, 1H), 4.12-4.07 (m, 1H), 3.98-3.92 (m, 2H), 3.72-3.64 (m, 1H), 3.31 (t, 1H), 3.13 (t, 1H), 2.59-2.53 (m, 1H), 2.33 (dd, 2H), 1.84-1.75 (m, 1H), 1.62 and 1.56 (s, 3H), 1.59 (s, 3H), 1.44 and 1.28 (s, 3H).

Step 2. Synthesis of (R)-3,3-dimethyl-1,7a-dihydropyrrolo[1,2-c]oxazol-5(3H)-one (C75)

A solution of compound C74 (12.0 g, 38.7 mmol) in DCM (150 mL) and pyridine (6.8 mL) at about 0° C. was treated with 30% hydrogen peroxide solution (17.86 mL, 128 mmol). The mixture was kept at about 0° C. for about 30 min before being warmed slowly to about 25° C. After about 3 h, the mixture was diluted with DCM (100 mL) and washed with saturated aqueous NaHCO$_3$ solution. The DCM extracts were washed with brine, dried over Na$_2$SO$_4$, filtered and concentrated. The residue was purified by chromatography to provide the title compound C75. Yield: 4.0 g (68%). $^1$H NMR (400 MHz, CDCl$_3$) δ 7.06 (dd, 1H), 6.09 (dd, 1H), 4.66-4.62 (m, 1H), 4.12 (dd, 1H), 3.33 (dd, 1H), 1.67 (s, 3H), 1.55 (s, 3H).

Step 3. Synthesis of (7S,7aR)-3,3,7-trimethyltetrahydropyrrolo[1,2-c]oxazol-5(3H)-one (C76)

Methyllithium (1.6 M, 34.7 mL) was added to a suspension of cuprous bromide-dimethylsulfide complex (5.7 g, 27.8 mmol) in diethyl ether (40 mL) at about −10° C. After the addition was complete, the solution was cooled to about −78° C. After about 10 min, TMSCl (3.5 mL, 27.7 mmol) was added, followed by a solution of compound C75 (1.7 g, 11.1 mmol) in THF (28 mL). The mixture was stirred at about −78° C. for about 2 h. then was allowed to warm to about 20° C. for about 1 h. A mixture of aqueous NH$_4$Cl and ammonium hydroxide was added with stirring, after which the mixture was diluted with EtOAc. The EtOAc was separated and the aqueous phase was extracted with EtOAc. The combined EtOAc extracts were washed with water, brine, dried over Na$_2$SO$_4$, filtered and concentrated. The residue was purified by chromatography to provide the title compound C76. Yield: 1.75 g (93%). $^1$H NMR (400 MHz, CDCl$_3$) δ 4.33-4.28 (m, 1H), 3.86 (dd, 1H), 3.71 (t, 1H), 2.97 (dd, 1H), 2.50-2.43 (m, 1H), 2.11 (d, 1H), 1.63 (s, 3H), 1.45 (s, 3H), 1.01 (d, 3H).

Step 4. Synthesis of (6R,7R,7aR)-6-fluoro-3,3,7-trimethyltetrahydropyrrolo[1,2-c]oxazol-5(3H)-one (C77)

LDA (1.8 M, 7.03 mL) was added to a −78° C. solution of compound C76 (1.427 g, 8.4 mmol) in THF (27 mL). After about 1 h, a solution of NFSI (3.43 g, 10.5 mmol) in THF (8 mL) was added. After about 5 min, the mixture was allowed to warm to about 25° C. After about 3 h, EtOAc and water were added, and the mixture was partially concentrated before being extracted with EtOAc. The combined EtOAc extracts were dried over MgSO4, filtered, and concentrated. The residue was dissolved in DCM and filtered. The filtrate was concentrated and the residue was purified by chromatography to provide the title compound C77. Yield: 282 mg (18%). $^1$H NMR (400 MHz, CD$_3$CN) δ 5.27 (dd, 1H), 3.99-4.08 (m, 1H), 3.95 (dd, 1H), 3.72 (t, 1H), 2.94 (quind, 1H), 1.58 (s, 3H), 1.39 (s, 3H), 0.90 (dd, 3H).

Step 5. Synthesis (3R,4R,5R)-3-fluoro-5-(hydroxymethyl)-4-methylpyrrolidin-2-one (L53)

To a stirred solution of compound C77 (280 mg, 1.5 mmol) in 9 mL of acetonitrile and 1 mL of water was added 4-toluenesulfonic acid (15 mg 0.07 mmol). The reaction mixture was heated at about 90° C. for about 1.5 h. The reaction mixture was cooled to about 25° C., concentrated, and the residue was purified by chromatography to provide the title compound L53. Yield: 169 mg (77%). $^1$H NMR (400 MHz, CD$_3$CN) 6.56 (br. s, 1H), 4.83 (dd, 1H), 3.52-3.67 (m, 2H), 3.37-3.50 (m, 1H), 2.83-2.94 (m, 1H), 2.63-2.80 (m, 1H), 0.98 (dd, 3H).

Preparation 35: (3S,4S,5S)-4-ethyl-d$_5$-3-fluoro-5-(hydroxymethyl) pyrrolidin-2-one (L56)

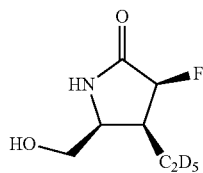

Step 1. Synthesis of (7R,7aS)-7-ethyl-d$_5$-3,3-dimethyltetrahydropyrrolo[1,2-c]oxazol-5(3H)-one (C79)

A solution of perdeuteroethylmagnesium bromide was prepared from 11.06 g (97 mmol) of ethyl-d5 bromide and magnesium metal (2.73 g, 112 mmol) in 80 mL of THF. A portion of this solution (43.5 mL) was added to a suspension of cuprous bromide-dimethyl sulfide complex (6.78 g, 32.6 mmol) complex in THF (40 mL) at about −10° C. The mixture was stirred at about −10° C. for about 10 min before being cooled to about −78° C. Chlorotrimethylsilane (3.55 g, 32.6 mmol) was added. After about 15 min, compound P20 (2.0 g, 13.1 mmol) in THF (20 mL) was added. The mixture was kept at about −78° C. for about 30 min before being warmed to about 25° C. for about 18 h. A mixture of aqueous NH$_4$Cl and ammonium hydroxide was added with stirring, after which the mixture was diluted with EtOAc and filtered. The EtOAc was separated and the aqueous phase was extracted with EtOAc. The combined EtOAc extracts were washed with NaHCO$_3$, brine, dried over Na$_2$SO$_4$, filtered and concentrated. The residue was purified by chromatography to provide the title compound C79. Yield: 850 mg (35%). $^1$H NMR (400 MHz, CDCl$_3$) δ 4.34 (dt, 1H), 3.90 (dd, 1H), 3.68-3.75 (m, 1H), 2.91 (dd, 1H), 2.31 (dd, 1H), 2.24 (t, 1H), 1.65 (s, 3H), 1.48 (s, 3H).

Step 2. Synthesis of (6S,7S,7aS)-7-ethyl-6-fluoro-3,3-dimethyltetrahydropyrrolo[1,2-c]oxazol-5(3H)-one (C80)

A solution of compound C79 (512 mg, 2.7 mmol) in 2-methylTHF (12.5 mL) was treated at about −78° C. with lithium hexamethyldisilazide (1 M, 3.0 mL) and the mixture was kept for about 45 min at about −78° C. before being added into an approximate −78° C. solution of NSFI (1.12 g, 3.54 mmol) in 2-methylTHF (12.5 mL). The mixture was kept at about −78° C. for about 30 min, then water (10 mL) and EtOAc (10 mL) were added. The EtOAc was separated and the aqueous phase was extracted with EtOAc (10 mL). The combined EtOAc extracts were washed with sodium iodide solution, sodium thiosulfate solution, NaOH solution, brine, dried over Na$_2$SO$_4$, filtered and concentrated. The residue was purified by chromatography to provide the title compound C80. Yield: 94 mg (17%). $^1$H NMR (400 MHz, CD$_3$CN) δ 5.26 (dd, 1H), 3.95-4.08 (m, 2H), 3.61-3.71 (m, 1H), 2.62-2.75 (m, 1H), 1.58 (s, 3H), 1.40 (s, 3H).

Step 3. Synthesis of (3S,4S,5S)-4-ethyl-d$_5$-3-fluoro-5-(hydroxymethyl)pyrrolidin-2-one (L56)

To a stirred solution of compound C80 (94 mg, 0.46 mmol) in 18 mL of acetonitrile and 2 mL of water was added 4-toluenesulfonic acid (4 mg, 0.02 mmol). The reaction mixture was heated at about 90° C. for about 4 h. The reaction mixture was cooled to about 25° C., concentrated, and the residue was purified by chromatography to provide the title compound L56. Yield: 51 mg (67%). $^1$H NMR (400 MHz, CD$_3$CN) δ 6.76 (br. s., 1H), 4.73 (dd, 1H), 3.57-3.67 (m, 2H), 3.32-3.42 (m, 1H), 2.85 (t, 1H), 2.40 (dt, 1H).

Preparation 36: (4R,5S)-5-(hydroxymethyl)-4-(methoxymethyl)pyrrolidin-2-one (L60)

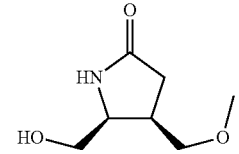

Step 1. Synthesis of (7R,7aS)-7-(hydroxymethyl)-3,3-dimethyltetrahydropyrrolo[1,2-c]oxazol-5(3H)-one (C82)

A stream of ozonized oxygen was bubbled through a solution of compound C55 (1.95 g, 10.8 mmol) in DCM (49 mL) and MeOH (16 mL) at about −78° C. for about 2 h. Dimethyl sulfide (10 mL) was added at about −78° C., followed NaBH$_4$ (2.44 g, 64.6 mmol) at the same temperature. After about 30 min, the reaction was warmed to about 0° C. and stirred for about 2 h. Ethyl acetate was added, and the mixture was washed with water, then brine. The combined EtOAc extracts were dried over Na$_2$SO$_4$, filtered and concentrated. The residue was purified by chromatography to provide the title compound C82. Yield: 1.2 g (60%). $^1$H NMR (400 MHz, CDCl$_3$) δ 4.40-4.34 (m, 1H), 3.97 (dd, 1H), 3.86 (dd, 1H), 3.72-3.62 (m, 2H), 2.94 (dd, 1H), 2.58-2.53 (m, 1H), 2.25 (d, 1H), 1.64 (s, 3H), 1.45 (s, 3H).

Step 2. Synthesis of (7R,7aS)-7-(methoxymethyl)-3,3-dimethyltetrahydropyrrolo[1,2-c]oxazol-5(3H)-one (C83)

To a stirred solution of compound C55 (1.4 g, 7.5 mmol) in THF (40 mL) was added freshly prepared silver(I) oxide (17.48 g, 75.7 mmol), followed by iodomethane (5.37 g, 37.8 mmol). The mixture was heated at about 70° C. for about 16 h. The mixture was then cooled to about 25° C., filtered and concentrated. The residue was purified by chromatography to provide the title compound C83. Yield: 1.1 g (73%). $^1$H NMR (400 MHz, CDCl$_3$) δ 4.36-4.30 (m, 1H), 3.92 (dd, 1H), 3.68 (dd, 1H), 3.39-3.25 (m, 2H), 3.30 (s, 3H), 2.93 (dd, 1H), 2.61-2.53 (m, 1H), 2.22 (dd, 1H), 1.62 (s, 3H), 1.46 (s, 3H).

Step 3. Synthesis of (4R,5S)-5-(hydroxymethyl)-4-(methoxymethyl)pyrrolidin-2-one (L60)

To a stirred solution of compound C83 (200 mg, 1.0 mmol) in 18.8 mL of acetonitrile and 2.1 mL of water was added 4-toluenesulfonic acid (9 mg, 0.05 mmol). The reaction mixture was heated to reflux for about 2 h. The reaction mixture was cooled to about 25° C., concentrated, and the residue was purified by chromatography to provide the title compound L60. Yield: 150 mg (93%). $^1$H NMR (400 MHz, dmso-d$_6$) δ 3.49-3.34 (m, 5H), 3.32 (s, 3H), 3.23 (s, 3H), 2.73-2.60 (m, 1H), 2.09-1.95 (m, 2H).

Preparation 37: (4R,5S)-3-fluoro-5-(hydroxymethyl)-4-(methoxymethyl)pyrrolidin-2-one (L61)

Step 1. Synthesis of (7R,7aS)-6-fluoro-7-(methoxymethyl)-3,3-dimethyltetrahydropyrrolo[1,2-c]oxazol-5(3H)-one (C84)

A solution of compound C83 (250 mg, 1.3 mmol) in THF (10 mL) was treated with lithium hexamethyldisilazide (1 M, 2.13 mL) at −78° C. and kept for about 30 min before the addition of a solution of NFSI (436 mg, 1.4 mmol) in THF (10 mL). The mixture was maintained for about 30 min at about −78° C. and then was allowed to warm to about 25° C. for about 1 h. Water and EtOAc were added and the phases were separated. The EtOAc extract EtOAc extracts were washed with sodium iodide solution, sodium thiosulfate solution, NaOH solution, brine, dried over Na$_2$SO$_4$, filtered and concentrated. The residue was purified by chromatography to provide the title compound C84. Yield: 90 mg (33%). $^1$H NMR (400 MHz, CDCl$_3$) δ 4.88 (d, 1H), 4.51-4.46 (m, 1H), 3.96 (dd, 1H), 3.70 (dd, 1H), 3.49-3.44 (m, 2H), 3.31 (s, 3H), 2.74-2.63 (m, 1H), 1.63 (s, 3H), 1.46 (s, 3H). There was also obtained (7R,7aS)-6,6-difluoro-7-(methoxymethyl)-3,3-dimethyltetrahydro-pyrrolo[1,2-c]oxazol-5(3H)-one (C85). Yield 45 mg (15%). $^1$H NMR (400 MHz, CDCl$_3$) δ 4.24-4.19 (m, 1H), 4.08 (dd, 1H), 3.79 (dd, 1H), 3.55 (dd, 1H), 3.48 (dd, 1H), 3.30 (s, 3H), 2.94-2.85 (m, 1H), 1.65 (s, 3H), 1.53 (s, 3H).

Step 2. Synthesis of (7R,7aS)-6-fluoro-7-(methoxymethyl)-3,3-dimethyltetrahydropyrrolo[1,2-c]oxazol-5(3H)-one (C86)

A solution of compound C84 (125 mg, 0.575 mmol) in THF (10 mL) was treated with potassium hexamethyldisilazide (1 M, 0.115 mL) at about 0° C. After about 5 min, the mixture was allowed to warm to about 25° C. for about 2 h. Aqueous sodium dihydrogen phosphate was added and the mixture was extracted with EtOAc. The combined EtOAc extracts were washed with water, brine, dried over Na$_2$SO$_4$, filtered and concentrated to provide the title compound C86. Yield: 115 mg (92%). $^1$H NMR (400 MHz, CDCl$_3$) δ 5.28 (dd, 1H, diastereomer 1), 4.89 (d, 1H, diastereomer 2), 4.51-4.47 (m, 1H, diastereomer 2), 4.07-4.01 (m, 2H, diastereomer 1), 3.96 (dd, 1H, diastereomer 2), 3.83-3.78 (m, 1H, diastereomer 1), 3.70 (dd, 1H, diastereomer 2), 3.57-3.53 (m, 1H, diastereomer 1), 3.49-3.44 (m, 2H, diastereomer 2), 3.47-3.43 (m, 1H, diastereomer 1), 3.31 (s, 3H, diastereomer 2), 3.30 (s, 3H, diastereomer 1), 3.04-3.00 (m, 1H, diastereomer 1), 2.74-2.63 (m, 1H, diastereomer 2), 1.67 (s, 3H, diastereomer 1), 1.63 (s, 3H, diastereomer 2), 1.49 (s, 3H, diastereomer 1), 1.46 (s, 3H, diastereomer 2).

Step 3. Synthesis of (4R,5S)-3-fluoro-5-(hydroxymethyl)-4-(methoxymethyl)pyrrolidin-2-one (L61)

To a stirred solution of compound C86 (130 mg, 0.6 mmol) in 10 mL of acetonitrile and 0.6 mL of water was added 4-toluenesulfonic acid (6 mg, 0.03 mmol). The reaction mixture was heated at about 90° C. for about 2 h. The reaction mixture was cooled to about 25° C., concentrated, and the residue was purified by chromatography to provide the title compound L61. Yield: 80 mg (76%). $^1$H NMR (400 MHz, CDCl$_3$) δ 5.12 (dd, 1H, diastereomer 1), 4.94 (dd, 1H, diastereomer 2), 3.85-3.54 (m, 10H, diastereomers 1 and 2), 3.42 (s, 3H, diastereomer 1), 3.37 (s, 3H, diastereomer 2), 2.95-2.84 (m, 2H, diastereomers 1 and 2).

Synthesis of (4R,5S)-3,3-difluoro-5-(hydroxymethyl)-4-(methoxymethyl)pyrrolidin-2-one (L63)

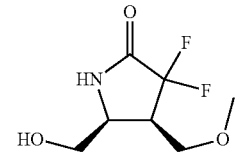

This compound was prepared in the same manner as compound L61, substituting compound C85 for compound C86 in Step 3. $^1$H NMR (400 MHz, CDCl$_3$) δ 3.88-3.81 (m, 2H), 3.75-3.71 (m, 1H), 3.66-3.61 (m, 2H), 3.39 (s, 3H), 3.05-2.95 (m, 1H).

Preparation 38: (3S,4S,5S)-4-ethyl-5-(hydroxymethyl)-3-methoxypyrrolidin-2-one (L66)

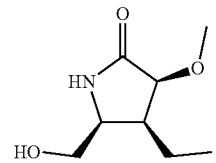

Step 1. Synthesis of (7S,7aS)-7-ethyl-6-hydroxy-3,3-dimethyltetrahydropyrrolo[1,2-c]oxazol-5(3H)-one (C87)

A solution of compound C54 (1.0 g, 5.5 mmol) in THF (25 mL) was treated with LDA (3.4 mL, 6.8 mmol) at about −78° C. The mixture was kept for about 20 min and then treated with a solution of (1R)-(−)-(10-camphorsulfonyl)oxaziridine (CAS 104372-31-8, 1.50 g, 6.5 mmol) in THF (5 mL). After about 30 min, the mixture was allowed to warm to about 25° C. for about 30 min. Methanol (2 mL) was added and the mixture was concentrated. The residue was purified by chromatography to provide the title compound C87. Yield: 800 mg (73%). This was used in the next step without further characterization.

Step 2. Synthesis of (6S,7S,7aS)-7-ethyl-6-methoxy-3,3-dimethyltetrahydropyrrolo[1,2-c]oxazol-5(3H)-one (C88)

To a stirred solution of compound C87 (800 mg, 4.0 mmol) in THF (50 mL) was added freshly prepared silver(I) oxide (9.3 g, 40.2 mmol), followed by iodomethane (1.25 ml, 20.1 mmol). The mixture was heated at about 75° C. for about 16 h. The mixture was then cooled to about 25° C., filtered and concentrated. The residue was purified by chromatography to provide the title compound C88. Yield: 180 mg (21%). $^1$H NMR (400 MHz, CDCl$_3$) δ 4.09 (d, 1H), 4.04-3.96 (m, 2H), 3.70-3.66 (m, 1H), 3.55 (s, 3H), 2.52-2.50 (m, 1H), 1.69-1.64 (m, 1H), 1.62 (s, 3H), 1.48-1.41 (m, 1H), 1.47 (s, 3H), 0.90 (t, 3H). There was also obtained (6R,7S,7aS)-7-ethyl-6-methoxy-3,3-dimethyltetrahydropyrrolo[1,2-c]oxazol-5(3H)-one (C89). Yield: 375 mg (44%). $^1$H NMR (400 MHz, CDCl$_3$) δ 4.44-4.40 (m, 1H), 3.92-3.89 (m, 1H), 3.66 (s, 1H), 3.64-3.59 (m, 1H), 3.53 (s, 3H), 2.17-2.12 (m, 1H), 1.62 (s, 3H), 1.50-1.41 (m, 1H), 1.48 (s, 3H), 1.38-1.30 (m, 1H), 0.97 (t, 3H).

Step 3. Synthesis of (3S,4S,5S)-4-ethyl-5-(hydroxymethyl)-3-methoxypyrrolidin-2-one (L66)

To a stirred solution of compound C88 (180 mg, 0.8 mmol) in 9 mL of acetonitrile and 1 mL of water was added 4-toluenesulfonic acid (7 mg, 0.04 mmol). The reaction mixture was heated at about 90° C. for about 2 h. The reaction mixture was cooled to about 25° C., concentrated, and the residue was purified by chromatography to provide the title compound L66. Yield: 75 mg (51%). $^1$H NMR (400 MHz, CDCl$_3$) δ 6.09 (br, 1H), 3.68-3.64 (m, 2H), 3.61 (s, 3H), 3.57 (d, 1H), 3.48 (br. s, 1H), 2.84 (br. s, 1H), 2.42-2.30 (m, 1H), 1.64-1.58 (m, 1H), 1.47-1.33 (m, 1H), 0.97 (t, 3H).

Synthesis of (3R,4S,5S)-4-ethyl-5-(hydroxymethyl)-3-methoxypyrrolidin-2-one (L67)

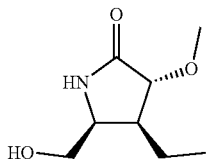

This compound was prepared in the same manner as compound L66, substituting compound C89 for compound C88 in Step 3. $^1$H NMR (400 MHz, CDCl$_3$) δ 6.10 (br. s, 1H), 3.75-3.70 (m, 2H), 3.63 (s, 3H), 3.62-3.60 (m, 2H), 2.35-2.27 (m, 1H), 2.12 (br. s, 1H), 1.73-1.64 (m, 1H), 1.61-1.52 (m, 1H), 1.00 (t, 3H).

Synthesis of (3S,4S,5S)-5-(hydroxymethyl)-3-methoxy-4-methylpyrrolidin-2-one (L64)

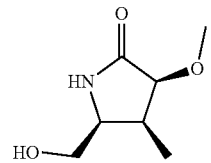

This compound was prepared in the same manner as compound L66, substituting compound C53 for compound C54 in Step 1 to afford (7S,7aS)-6-hydroxy-3,3,7-trimethyltetrahydro-pyrrolo[1,2-c]oxazol-5(3H)-one (C90). Application of Step 2 to compound C90 afforded (6S,7S,7aS)-6-methoxy-3,3,7-trimethyltetrahydropyrrolo[1,2-c]oxazol-5 (3H)-one (C91) and (6R,7S,7aS)-6-methoxy-3,3,7-trimethyltetrahydropyrrolo[1,2-c]oxazol-5(3H)-one (C92). Application of Step 3 to compound C91 afforded the title compound L64. $^1$H NMR (400 MHz, CDCl$_3$) δ 3.65-3.62 (m, 4H), 3.59 (s, 3H), 3.48 (br. s, 1H), 2.69-2.64 (m, 1H), 1.01 (d, 3H).

Synthesis of (3R,4S,5S)-5-(hydroxymethyl)-3-methoxy-4-methylpyrrolidin-2-one (L65)

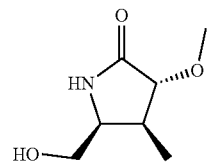

This compound was prepared in the same manner as compound L64, substituting compound C92 for compound C91 in Step 3. $^1$H NMR (400 MHz, CDCl$_3$) δ 6.37 (br. s, 1H), 3.74-3.64 (m, 3H), 3.63 (s, 3H), 3.58-3.55 (m, 1H), 2.53-2.47 (m, 1H), 2.45 (br. s, 1H), 1.20 (d, 3H).

Synthesis of (4S,5S)-3-(benzyloxy)-4-ethyl-5-(hydroxymethyl)pyrrolidin-2-one (L68)

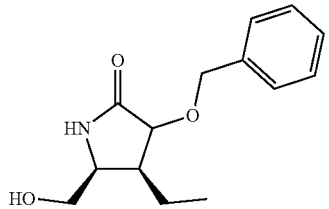 [SMILES: CC[C@@H]1C(OCc2ccccc2)C(=O)N[C@@H]1CO]

This compound was prepared in the same manner as compound L66, substituting (bromomethyl)benzene for iodomethane in Step 2 and using the resulting mixture of diastereomers in Step 3. $^1$H NMR (400 MHz, CDCl$_3$) δ 7.39-7.26 (m, 5H, both diastereomers), 6.27 (br. s, 1H, both diastereomers), 5.15 (d, 1H, diastereomer 1), 5.01 (d, 1H, diastereomer 2), 4.71 (d, 1H, both diastereomers), 3.93 (d, 1H, diastereomer 1), 3.78 (d, 1H, diastereomer 2), 3.69-3.60 (m, 3H, both diastereomers), 2.40-2.32 (m, 1H, both diastereomers), 1.69-1.63 (m, 1H, both diastereomers), 1.54-1.40 (m, 1H, both diastereomers), 0.98 (t, 3H, diastereomer 1), 0.92 (t, 3H, diastereomer 2).

Preparation 39: tert-butyl ((4S,5S)-4-ethyl-5-(hydroxymethyl)-2-oxopyrrolidin-3-yl)carbamate (L70)

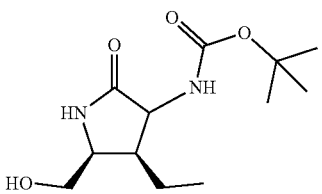 [SMILES: CC[C@@H]1C(NC(=O)OC(C)(C)C)C(=O)N[C@@H]1CO]

Step 1. Synthesis of (7S,7aS)-6-azido-7-ethyl-3,3-dimethyltetrahydropyrrolo[1,2-c]oxazol-5(3H)-one (C93)

LDA (2.0 M, 1.7 mL) was added to a solution of compound C54 (500 mg, 2.7 mmol) in THF (20 mL) at about −78° C. After about 30 minutes at about −78° C., a 10% solution 2,4,6-triisopropylbenzenesulfonyl azide (CAS 36982-84-0, 2.0 mL, 0.66 mmol) was added. After stirring at about −78° C. for about 10 min, the solution was allowed to warm to about 25° C. for about 1 h. Aqueous NH$_4$Cl solution was added and the mixture was extracted with EtOAc. The EtOAc extracts were dried over Na$_2$SO$_4$, filtered and concentrated. The residue was purified by chromatography to provide the title compound C93. Yield: 500 mg (82%). $^1$H NMR (400 MHz, CDCl$_3$) δ 4.43 (d, 1H), 4.13-4.08 (m, 1H), 4.00-3.97 (m, 1H), 3.70-3.65 (m 1H), 2.49-2.47 (m, 1H), 1.65 (s, 3H), 1.75-1.42 (m, 2H), 1.47 (s, 3H), 0.90 (t, 3H).

Step 2. Synthesis of (7R,7aS)-6-amino-7-ethyl-3,3-dimethyltetrahydropyrrolo[1,2-c]oxazol-5(3H)-one (C94)

To a solution of compound C93 (500 mg, 2.2 mmol) in MeOH (30 mL) was added palladium on carbon (100 mg) and the mixture was stirred under a hydrogen atmosphere (1 atm) for about 16 h. The mixture was filtered and the filtrate was concentrated to provide the title compound C94. Yield: 380 mg (86%). This was used in the next step without further characterization.

Step 3. Synthesis of (4R,5S)-3-amino-4-ethyl-5-(hydroxymethyl)pyrrolidin-2-one (C95)

To a stirred solution of compound C94 (380 mg, 1.9 mmol) in 27 mL of acetonitrile and 3 mL of water was added 4-toluenesulfonic acid (0.40 g, 2.3 mmol). The reaction mixture was heated at about 90° C. for about 2 h. The reaction mixture was cooled to about 25° C. and concentrated to provide the title compound C95. Yield: 300 mg (47%). $^1$H NMR (400 MHz, dmso-d$_6$) δ 7.47 (d, 2H), 7.11 (d, 2H), 4.13-4.10 (m, 1H), 3.71-3.56 (m, 2H), 3.46-3.43 (m, 1H), 2.07 (s, 3H), 2.06-1.91 (m, 1H), 1.50-1.47 (m, 1H), 1.39-1.35 (m, 1H), 0.92 (t, 3H).

Step 4. Synthesis of tert-butyl ((4S,5S)-4-ethyl-5-(hydroxymethyl)-2-oxopyrrolidin-3-yl)carbamate (L70)

To a solution of compound C95 (300 mg, 1.9 mmol) and Et$_3$N (0.78 mL, 5.7 mmol) in THF (10 mL) and water (10 mL) was added di-t-butyl dicarbonate (0.83 mL, 3.8 mmol). The mixture was kept at about 25° C. for about 16 h. The reaction mixture was concentrated and the residue was purified by chromatography to provide the title compound L70. Yield: 280 mg (ca. 100%). $^1$H NMR (400 MHz, dmso-d$_6$) δ 7.76 (br. s, 1H), 6.37 (d, 1H), 5.44 (t, 1H), 4.07-3.93 (m, 1H), 3.48-3.43 (m, 2H), 3.37 (br. m, 1H), 2.36-2.33 (m, 1H), 1.55-1.45 (m, 1H), 1.37 (s, 9H), 1.33-1.28 (m, 1H), 0.83 (t, 3H).

Preparation 40: (1R,4S,5S,6S)-4-(hydroxymethyl)-6-methyl-3-azabicyclo[3.1.0]hexan-2-one (L74)

Step 1. Synthesis of (3R,5aR,6S,6aS,6bS)-3-(4-methoxyphenyl)-6-methyltetrahydro-1H-cyclopropa[3,4]pyrrolo[1,2-c]oxazol-5(3H)-one (C96)

To a stirred suspension of ethyldiphenylsulfonium tetrafluoroborate (CAS 893-69-6, 31.36 g, 104 mmol) in THF (200 mL) was added LDA (2 M, 65 mL, 130 mmol) slowly at about −78° C. The reaction mixture was kept at about −78° C. for about 1.5 h, at which point a solution of (3R,7aS)-3-(4-methoxyphenyl)-1,7a-dihydropyrrolo[1,2-c]oxazol-5(3H)-one (CAS 170885-07-1, 12.0 g, 51.9 mmol) in THF (90 mL) was added slowly. The reaction mixture was maintained at about −78° C. for about 1.5 h and then allowed to warm to about 25° C. It was stirred for about 1.5 h at about 25° C. before being quenched with EtOAc and NaHCO$_3$ solution. The EtOAc was separated, and the aqueous phase was back extracted with EtOAc. The combined EtOAc extracts were dried over Na$_2$SO$_4$ filtered and concentrated. The residue was purified by chromatography to provide the title compound C96. Yield 6.5 g (48%). $^1$H NMR (400 MHz, CDCl$_3$): δ 7.27 (d, 2H), 6.84 (d, 2H), 6.23 (s, 1H), 4.14 (dd, 1H), 3.88 (dd, 1H), 3.78 (s, 3H), 3.38 (dd, 1H), 1.88-1.86 (m, 1H), 1.79-1.77 (m, 1H), 1.51-1.47 (m, 1H), 1.14 (d, 3H). There was also obtained (3R,5aR,6R,6aS,6bS)-3-(4-methoxyphenyl)-6-methyltetrahydro-1H-cyclopropa[3,4]pyrrolo[1,2-c]oxazol-5(3H)-one (C97). Yield: 1.5 g (11%). $^1$H NMR (400 MHz, CDCl$_3$): δ 7.29 (d, 2H), 6.85 (d, 2H), 6.26 (s, 1H), 4.20 (t, 1H), 3.78 (s, 3H), 3.70 (t, 1H), 3.53 (dd, 1H), 2.12-2.06 (m, 2H), 1.61-1.55 (m, 1H), 1.26 (d, 3H).

Step 2. Synthesis of (1R,4S,5S,6S)-4-(hydroxymethyl)-6-methyl-3-azabicyclo[3.1.0]hexan-2-one (L74)

To a stirred solution of compound C96 (1.7 g, 6.6 mmol) in 45 mL of acetonitrile and 5 mL of water was added 4-toluenesulfonic acid (64 mg, 0.33 mmol). The reaction mixture was heated at about 90° C. for about 45 min. The reaction mixture was cooled to about 25° C., concentrated, and the residue was purified by chromatography to provide the title compound L74. Yield: 0.83 g (90%). $^1$H NMR (400 MHz, CD$_3$OD) δ 3.40-3.59 (m, 3H), 1.71 (dd, 1H), 1.57 (dt, 1H), 1.13 (d, 3H), 1.02 (dd, 1H).

Synthesis of (1R,4S,5S,6R)-4-(hydroxymethyl)-6-methyl-3-azabicyclo[3.1.0]hexan-2-one (L75)

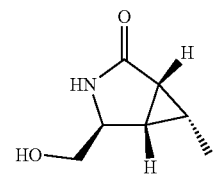

This compound was prepared in the same manner as compound L74, substituting compound C97 for compound C96 in Step 2. $^1$H NMR (400 MHz, CD$_3$CN) δ 6.12 (br. s., 1H), 3.45-3.54 (m, 2H), 3.35 (br. s, 1H), 3.26-3.33 (m, 1H), 1.69-1.80 (m, 2H), 1.23-1.39 (m, 1H), 1.02 (d, 3H).

Synthesis of (1R,4S,5S)-4-(hydroxymethyl)-3-azabicyclo[3.1.0]hexan-2-one (L72)

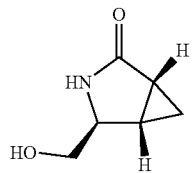

This compound was prepared in the same manner as compound L74, substituting (3R,5aR,6aS,6bS)-3-(4-methoxyphenyl)tetrahydro-1H-cyclopropa[3,4]pyrrolo[1,2-c]oxazol-5(3H)-one (CAS 187742-05-8) for compound C96 in Step 2. $^1$H NMR (400 MHz, CD$_3$OD) δ 3.47-3.61 (m, 3H), 1.97 (ddd, 1H), 1.75-1.86 (m, 1H), 1.19 (td, 1H), 0.59-0.68 (m, 1H).

Synthesis of (1S,4S,5R)-4-(hydroxymethyl)-6,6-dimethyl-3-azabicyclo[3.1.0]hexan-2-one (L73)

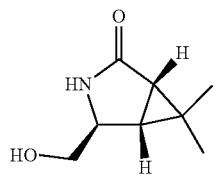

This compound was prepared in the same manner as compound L74, substituting (1-methyl)ethyldiphenylsulfonium tetrafluoroborate (CAS 40447-58-3) for CAS 893-69-6 in Step 1. $^1$H NMR (400 MHz, CDCl$_3$) δ 7.04 (br. s., 1H), 3.88 (br. s., 1H), 3.61-3.70 (m, 1H), 3.48-3.61 (m, 1H), 3.44 (d, 1H), 1.70 (d, 1H), 1.51 (d, 1H), 1.10 (s, 3H), 1.10 (s, 3H).

Synthesis of (1R,4S,5S,6S)-6-ethyl-4-(hydroxymethyl)-3-azabicyclo[3.1.0]hexan-2-one (L76)

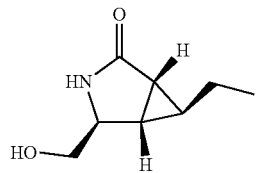

This compound was prepared in the same manner as compound L74, substituting propyldiphenylsulfonium tetrafluoroborate (CAS 14264-05-2) for CAS 893-69-6 in Step 1 to afford (3R,5aR,6S,6aS,6bS)-6-ethyl-3-(4-methoxyphenyl)tetrahydro-1H-cyclopropa[3,4]pyrrolo-[1,2-c]oxazol-5(3H)-one (C98), which was used in Step 2. $^1$H NMR (400 MHz, CDCl$_3$) δ 6.56 (br. s., 1H), 3.63-3.69 (m, 1H), 3.62 (d, 1H), 3.49-3.56 (m, 1H), 3.48 (br. s, 1H), 1.63 (ddd, 1H), 1.55 (ddd, 1H), 1.29-1.39 (m, 2H), 0.99 (t, 3H), 0.95-1.05 (m, 1H). There was also obtained in Step 1 (3R,5aR,6R,6aS,6bS)-6-ethyl-3-(4-methoxyphenyl)-tetrahydro-1H-cyclopropa[3,4]pyrrolo[1,2-c]oxazol-5(3H)-one (C99). $^1$H NMR (400 MHz, CDCl$_3$) δ 7.30 (d, 2H), 6.88 (d, 2H), 6.28 (s, 1H), 4.22 (dd, 1H), 3.81 (s, 3H), 3.73 (dd, 1H), 3.53 (dd, 1H), 2.14 (d, 2H), 1.57-1.67 (m, 2H), 1.51 (dd, 1H), 1.08 (t, 3H).

Synthesis of (1R,4S,5S,6R)-6-ethyl-4-(hydroxymethyl)-3-azabicyclo[3.1.0]hexan-2-one (L77)

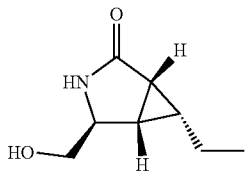

This compound was prepared in the same manner as compound L74, substituting compound C99 for compound C96 in Step 2. $^1$H NMR (400 MHz, CDCl$_3$) δ 6.99 (br. s, 1H), 4.41 (br. s., 1H), 3.68 (dd, 1H), 3.57 (dd, 1H), 3.40-3.48 (m, 1H), 1.95 (ddt, 1H), 1.71-1.77 (m, 1H), 1.34-1.43 (m, 2H), 1.19-1.29 (m, 1H), 1.02 (t, 3H).

Preparation 41: (1S,4S,5R,6S)-6-(fluoromethyl)-4-(hydroxymethyl)-3-azabicyclo[3.1.0]hexan-2-one (L79)

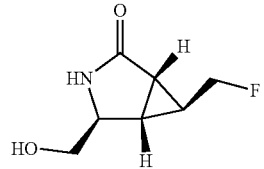 [SMILES: O=C1N[C@H](CO)[C@H]2[C@H](CF)[C@@H]12]

Step 1. Synthesis of (3R,5aS,6S,6aR,6bS)-ethyl 3-(4-methoxyphenyl)-5-oxohexahydro-1H-cyclopropa[3,4]pyrrolo[1,2-c]oxazole-6-carboxylate (C100)

(Carbethoxymethyl)dimethyl-sulfonium bromide (CAS 5187-82-6, 15 g, 64.9 mmol) was dissolved in CHCl$_3$ (130 mL). A saturated aqueous K$_2$CO$_3$ solution (61 mL) was added slowly with vigorous stirring, followed by aqueous NaOH solution (50%, 5.7 mL). Stirring was continued for about 30 min. The CHCl$_3$ layer was separated and the aqueous phase was extracted with additional CHCl$_3$. The combined CHCl$_3$ extracts were dried over K$_2$CO$_3$, filtered and concentrated to afford a clear yellow colored liquid (9.58 g). This was dissolved in DMSO (100 mL). A solution of CAS 170885-07-1 (6.17 g, 26.7 mmol) in DMSO (33 mL) was added. The mixture was kept for 3 days at about 25° C. Ethyl acetate (500 mL) was added and the mixture was washed with brine (3×200 mL). The combined brine washes were extracted with EtOAc and the combined EtOAc extracts were dried over MgSO$_4$, filtered and concentrated. The residue was purified by chromatography to provide the title compound C100. Yield: 4.0 g (47%). $^1$H NMR (400

MHz, CDCl₃) δ 7.27 (d, 2H), 6.86 (d, 2H), 6.24 (s, 1H), 4.19-4.24 (m, 1H), 4.13-4.19 (m, 2H), 3.96 (dd, 1H), 3.79 (s, 3H), 3.46 (dd, 1H), 2.61 (dd, 1H), 2.50 (ddd, 1H), 2.24 (t, 1H), 1.27 (t, 3H). There was also obtained (3R,5aS,6R,6aR,6bS)-ethyl 3-(4-methoxyphenyl)-5-oxohexahydro-1H-cyclopropa[3,4]pyrrolo[1,2-c]oxazole-6-carboxylate (C101). Yield: 4.33 g (51%). ¹H NMR (400 MHz, CDCl₃) δ 7.25 (d, 2H), 6.84 (d, 2H), 6.26 (s, 1H), 4.20 (dd, 1H), 4.08-4.15 (m, 1H), 4.08 (q, 2H), 3.78 (s, 3H), 3.46 (dd, 1H), 2.37-2.45 (m, 3H), 1.10 (t, 3H).

Step 2. Synthesis of (3R,5aS,6S,6aS,6bS)-6-(hydroxymethyl)-3-(4-methoxyphenyl)tetrahydro-1H-cyclopropa[3,4]pyrrolo[1,2-c]oxazol-5(3H)-one (C102)

Lithium triethylborohydride (1 M, 22.1 mL) was slowly added to a solution of compound C100 (1.80 g, 5.7 mmol) in THF (5.3 mL) at −78° C. The mixture was kept at about −78° C. for an additional about 1 h before the slow addition of saturated aqueous NaHCO₃ solution (4.0 mL). The mixture was allowed to warm to about 0° C., after which aqueous hydrogen peroxide solution (30%, 3.0 mL) was added dropwise to control the ensuing exothermic reaction. The mixture was then kept for about 20 min at about 0° C. The THF was evaporated under educed pressure and water (10 mL) was added. The mixture was extracted with DCM and the combined DCM extracts were dried over Na₂SO₄, filtered and concentrated. The residue was purified by chromatography to provide the title compound C102. Yield: 900 mg (58%). ¹H NMR (400 MHz, CDCl₃) δ 7.28 (d, 1H), 6.86 (d, 2H), 6.24 (s, 1H), 4.17 (dd, 1H), 3.92 (dd, 1H), 3.79 (s, 3H), 3.61 (d, 2H), 3.42 (dd, 1H), 2.36 (br. s., 1H), 2.14 (dd, 1H), 2.00-2.06 (m, 1H), 1.73-1.81 (m, 1H). There was also obtained 400 mg (25%) of the aldehyde. C108. In a similar manner, treatment of compound C101 with lithium triethylborohydride afforded C104. ¹H NMR (400 MHz, CDCl₃) δ 7.29 (d, 2H), 6.87 (d, 2H), 6.27 (s, 1H), 4.24 (dd, 1H), 3.97 (dd, 1H), 3.81-3.88 (m, 2H), 3.80 (s, 3H), 3.53 (dd, 1H), 2.21-2.32 (m, 2H), 1.81-1.94 (m, 2H).

Step 3. Synthesis of (3R,5aS,6S,6aR,6bS)-6-(fluoromethyl)-3-(4-methoxyphenyl)tetrahydro-1H-cyclopropa[3,4]pyrrolo[1,2-c]oxazol-5(3H)-one (C103)

A solution of compound C102 (200 mg 0.73 mmol) in DCM (3.6 mL) was treated with Et₃N (1.1 mL 7.3 mmol) followed by XtalFluor-E (249 mg 1.1 mmol) and triethylamine trihydrofluoride (0.24 mL 1.4 mmol) in a polyethylene vial at about 25° C. The mixture was kept for 3 days at about 25° C. Three additional experiments were prepared similarly. Aqueous NaHCO₃ (4 mL) was added to each vial with stirring. After about 20 min, the experiments were poured into aqueous NaHCO₃ and extracted with DCM. The combined DCM extracts were dried over Na₂SO₄, filtered and concentrated. The residue was purified by chromatography to provide the title compound C103. Yield: 421 mg (52%). ¹H NMR (400 MHz, CD₃CN) δ 7.27 (d, 2H), 6.90 (d, 2H), 6.06 (s, 1H), 4.39 (ddd, 1H), 4.20-4.34 (m, 1H), 4.17 (dd, 1H), 3.97 (dd, 1H), 3.77 (s, 3H), 3.38 (dd, 1H), 2.25-2.32 (m, 1H), 1.99-2.04 (m, 1H), 1.90 (dt, 1H).

Step 4. Synthesis of (1S,4S,5R,6S)-6-(fluoromethyl)-4-(hydroxymethyl)-3-azabicyclo[3.1.0]hexan-2-one (L79)

To a stirred solution of compound C103 (421 mg, 1.5 mmol) in 18 mL of acetonitrile and 2 mL of water was added 4-toluenesulfonic acid (15 mg, 0.08 mmol). The reaction mixture was heated at about 85° C. for about 1.5 h. The reaction mixture was cooled to about 25° C., concentrated, and the residue was purified by chromatography to provide the title compound L79. Yield: 209 mg (87%). ¹H NMR (400 MHz, CD₃OD) δ 4.43 (ddd, 1H), 4.31 (ddd, 1H), 3.51-3.66 (m, 3H), 2.04 (ddd, 1H), 1.93 (m, 1H), 1.49 (qt, 1H).

Synthesis of (1S,4S,5R,6R)-6-(fluoromethyl)-4-(hydroxymethyl)-3-azabicyclo[3.1.0]hexan-2-one (L78)

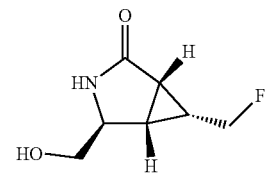 [SMILES: O=C1N[C@H](CO)[C@H]2[C@@H](CF)[C@@H]12]

This compound was prepared in the same manner as compound L79, substituting compound C101 for compound C100 in Step 2. ¹H NMR (400 MHz, CDCl₃) δ 4.40 (ddd, 1H), 4.28 (ddd, 1H), 3.69 (s, 2H), 3.53-3.61 (m, 1H), 1.89 (m, 2H), 1.45-1.55 (m, 1H).

Preparation 42: (1R,4S,5S)-6-(2-fluoroethyl)-4-(hydroxymethyl)-3-azabicyclo[3.1.0]hexan-2-one (L80)

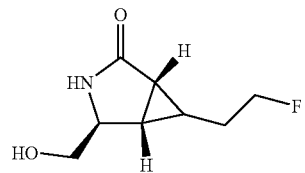 [SMILES: O=C1N[C@H](CO)[C@H]2C(CCF)[C@@H]12]

Step 1. Synthesis of (3-fluoropropyl)diphenylsulfonium tetrafluoroborate (C105)

A mixture of 1-iodo-3-fluoropropane (CAS 462-40-8, 8.80 g, 46.8 mmol), diphenyl sulfide (23.5 mL, 140 mmol) and silver(I) tetrafluoroborate (9.11 g, 46.8 mmol) in DCM (100 mL) was heated at about 38° C. for about 19 h. The mixture was diluted with DCM (100 mL), filtered, and the filtrate was concentrated to about 50 mL volume. After filtration, the filtrate was diluted with ethyl ether (100 mL). The white precipitate was separated from the liquid by decantation, and the precipitate was washed with two additional portions of DCM-ethyl ether, then dried under reduced pressure to provide the title compound C105. Yield: 10.0 g (53%). ¹H NMR (400 MHz, CDCl₃) δ 7.92-8.00 (m, 4H), 7.64-7.78 (m, 6H), 4.66 (dt, 2H), 4.31 (t, 2H), 2.21 (dtt, 2H).

Step 2. Synthesis of (3R,5aR,6aS,6bS)-6-(2-fluoroethyl)-3-(4-methoxyphenyl)tetrahydro-1H-cyclopropa[3,4]pyrrolo[1,2-c]oxazol-5(3H)-one (C106)

A solution of compound C105 (578 mg, 1.7 mmol) in THF (15 mL) was treated with tert-butyllithium solution (1.7 M, 1.32 mL) at about −78° C. The mixture was kept for about 30 min at about −78° C., then a solution of CAS 170885-07-1 (200 mg, 0.87 mmol) in THF (5 mL) was added. After about 3 h at about −78° C., aqueous NH₄Cl solution was added and the mixture was extracted with EtOAc. The combined EtOAc extracts were dried over Na₂SO₄, filtered and concentrated. The residue was purified by chromatography to provide the title compound C106. Yield: 170 mg (67%). ¹H NMR (400 MHz, CD₃CN) δ 7.27 (d, 2H, diastereomer 1), 7.26 (d, 2H, diastereomer 2), 6.90 (d, 2H, diastereomer 1), 6.89 (d, 2H, diastereomer 2), 6.07 (s, 1H, diastereomer 1), 6.06 (s, 1H, diastereomer 2), 4.60 (q, 2H, diastereomer 1), 4.48 (q, 2H, diastereomer 2), 4.24 (dd, 1H, diastereomer 2), 4.20 (dd, 1H, diastereomer 1), 4.13 (dd, 1H, diastereomer 2), 3.92 (dd, 1H, diastereomer 1), 3.78 (s, 3H, diastereomer 1), 3.77 (s, 3H, diastereomer 2), 3.48 (dd, 1H, diastereomer 1), 3.34 (dd, 1H, diastereomer 2).

Step 3. Synthesis of (1R,4S,5S)-6-(2-fluoroethyl)-4-(hydroxymethyl)-3-azabicyclo[3.1.0]hexan-2-one (L80)

To a stirred solution of compound C106 (250 mg, 0.86 mmol) in 6 mL of acetonitrile and 1 mL of water was added 4-toluenesulfonic acid (8 mg, 0.04 mmol). The reaction mixture was heated at about 90° C. for about 1 h. The reaction mixture was cooled to about 25° C., concentrated, and the residue was purified by chromatography to provide the title compound L80. Yield: 140 mg (94%). ¹H NMR (400 MHz, CD₃CN) δ 4.39-4.64 (m, 2H), 3.31-3.56 (m, 2H), 3.07-3.30 (m, 1H), 2.21-2.35 (m, 2H), 0.96-1.89 (m, 3H).

Preparation 43: (1S,4S,5S,6S)-4-(hydroxymethyl)-6-(methoxymethyl)-3-azabicyclo[3.1.0]hexan-2-one (L81)

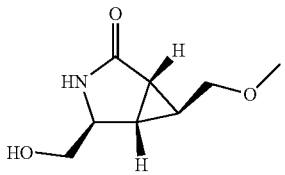

Step 1. Synthesis of (3R,5aS,6S,6aS,6bS)-6-(methoxymethyl)-3-(4-methoxyphenyl)tetrahydro-1H-cyclopropa[3,4]pyrrolo[1,2-c]oxazol-5(3H)-one (C107)

To a stirred solution of compound C102 (400 mg, 1.46 mmol) in THF (10 mL) was added freshly prepared silver(I) oxide (1.68 g, 7.27 mmol), followed by iodomethane (0.46 ml, 7.27 mmol). The mixture was heated at about 60° C. for about 16 h. The mixture was then cooled to about 25° C., filtered and concentrated. The residue was purified by chromatography to provide the title compound C107. Yield: 180 mg (43%). ¹H NMR (400 MHz, CDCl₃) δ 7.26 (d, 2H), 6.84 (d, 2H), 4.15 (dd, 1H), 3.92 (dd, 1H), 3.78 (s, 3H), 3.48 (dd, 1H), 3.40 (dd, 1H), 3.33 (s, 3H), 3.21 (dd, 1H), 2.13-2.11 (m, 1H), 1.99-1.97 (m, 1H), 1.78-1.75 (m, 1H).

Step 2. Synthesis of (1S,4S,5S,6S)-4-(hydroxymethyl)-6-(methoxymethyl)-3-azabicyclo[3.1.0]-hexan-2-one (L81)

To a stirred solution of compound C107 (100 mg, 0.35 mmol) in 3.6 mL of acetonitrile and 0.4 mL of water was added 4-toluenesulfonic acid (3 mg, 0.02 mmol). The reaction mixture was heated at about 90° C. for about 2 h. The reaction mixture was cooled to about 25° C., concentrated, and the residue was purified by chromatography to provide the title compound L81. Yield: 45 mg (76%). ¹H NMR (400 MHz, CDCl₃) δ 6.16 (br. s, 1H), 3.68 (m, 2H), 3.56 (m, 1H), 3.48 (m, 1H), 3.33 (s, 3H), 3.17 (m, 1H), 1.82 (m, 2H), 1.37 (m, 1H).

Synthesis of (1S,4S,5S,6R)-4-(hydroxymethyl)-6-(methoxymethyl)-3-azabicyclo[3.1.0]hexan-2-one (L82)

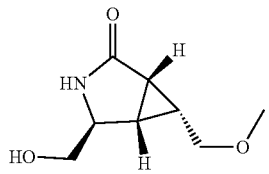

This compound was prepared in the same manner as compound L81, substituting compound C104 for compound C102 in Step 1. ¹H NMR (400 MHz, CDCl₃) δ 6.42 (br. s, 1H), 3.73-3.68 (m, 1H), 3.61-3.57 (m, 3H), 3.42-3.38 (m, 1H), 3.35 (s, 3H), 3.18 (br. m, 1H), 2.08-2.04 (m, 1H), 1.92-1.88 (m, 1H), 1.68-1.62 (m, 1H).

Synthesis of (1S,4S,5S,6S)-6-((benzyloxy)methyl)-4-(hydroxymethyl)-3-azabicyclo[3.1.0]hexan-2-one (L85)

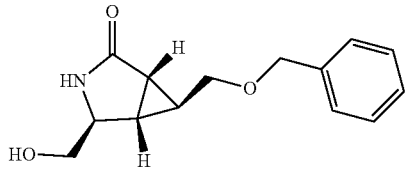 [SMILES: O=C1N[C@H](CO)[C@H]2[C@H](COCc3ccccc3)[C@@H]12]

This compound was prepared in the same manner as compound L81, substituting (bromomethyl)benzene for iodomethane in Step 1. ¹H NMR (400 MHz, CDCl₃) δ 7.36-7.27 (m, 5H), 5.67 (br. s, 1H), 4.49 (dd, 2H), 3.67-3.54 (m 4H), 3.30-3.24 (m, 1H), 1.85-1.76 (br. m, 2H), 1.37-1.32 (br. m, 1H).

Synthesis of (1S,4S,5S,6R)-6-((benzyloxy)methyl)-4-(hydroxymethyl)-3-azabicyclo[3.1.0]hexan-2-one (L86)

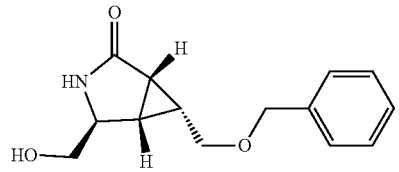 [SMILES: O=C1N[C@H](CO)[C@H]2[C@@H](COCc3ccccc3)[C@@H]12]

This compound was prepared in the same manner as compound L81, substituting compound C104 for compound C102, and (bromomethyl)benzene for iodomethane, in Step 1. $^1$H NMR (400 MHz, CDCl$_3$) δ 7.35-7.27 (m, 5H), 5.96 (br. s, 1H), 4.56 (d, 1H), 4.48 (d, 1H), 3.73-3.64 (m, 2H), 3.60-3.55 (m, 2H), 3.47-3.43 (m, 1H), 2.06-2.00 (m, 1H), 1.96-1.88 (m, 1H), 1.72-1.64 (m, 1H).

Preparation 44: (1S,4S,5R,6S)-6-(difluoromethyl)-4-(hydroxymethyl)-3-azabicyclo[3.1.0]hexan-2-one (L84)

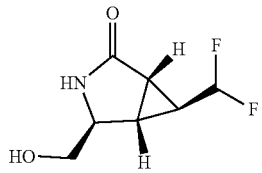 [SMILES: O=C1N[C@H](CO)[C@@H]2[C@H]1[C@H]2C(F)F]

Step 1. Synthesis of (3R,5aS,6S,6aS,6bS)-3-(4-methoxyphenyl)-5-oxohexahydro-1H-cyclopropa-[3,4]pyrrolo[1,2-c]oxazole-6-carbaldehyde (C108)

A solution of compound C102 (9.20 g, 33 mmol) in DCM (167 mL) and water (1 mL) was treated with Dess Martin periodinane (28.3 g, 67 mmol) and stirred at about 25° C. for about 2 h. at which time saturated aqueous NaHCO$_3$ solution (200 mL) was added and stirring continued for about 30 min. The DCM was separated and the aqueous phase was extracted with additional DCM. The combined DCM extracts were dried over MgSO$_4$, filtered and concentrated. The residue was purified by chromatography to provide the title compound C108. Yield: 5.50 g (60%). $^1$H NMR (400 MHz, CD$_3$OD) δ 9.40 (d, 1H), 7.32 (d, 2H), 6.93 (d, 2H), 6.17 (s, 1H), 4.29 (dd, 1H), 4.12 (dd, 1H), 3.83 (s, 3H), 3.53 (dd, 1H), 2.89 (dd, 1H), 2.64 (ddd, 1H), 2.59 (q, 1H).

Step 2. Synthesis of (3R,5aS,6S,6aR,6bS)-6-(difluoromethyl)-3-(4-methoxyphenyl)tetrahydro-1H-cyclopropa[3,4]pyrrolo[1,2-c]oxazol-5(3H)-one (C109)

A solution of compound C108 (4.0 g, 14.6 mmol) in 1,2-dichloroethane (16.3 mL) and pyridine (24.1 mL), and a solution of DAST (7.7 mL, 58 mmol) in 1,2-dichloroethane (33 mL) were prepared. A VaporTec Flow Reactor fitted with 10 mL loops was used for the experiment. A 10 mL portion of the solution of compound C108 was added to first loop. A 10 mL portion of the solution of DAST was added to the second loop. Both loops were co-injected into the heating coils at a rate 0.2 mL/minute at about 90° C. Upon exiting the reactor coil, the eluate was passed through a calcium carbonate plug. Upon completion of the passage, the eluate was diluted with 50 mL of DCM and washed with saturated aqueous NaHCO$_3$. The DCM was separated and the aqueous phase was extracted with additional DCM. The combined DCM extracts were dried over MgSO$_4$, filtered and concentrated. The experiment was repeated three additional times and the combined residues were purified by chromatography to provide the title compound C109. Yield: 2.39 g (55%). $^1$H NMR (400 MHz, CDCl$_3$) δ 7.29 (d, 2H), 6.87 (d, 2H), 6.27 (s, 1H), 5.87 (td, 1H), 4.25 (dd, 1H), 3.98 (dd, 1H), 3.81 (s, 3H), 3.47 (dd, 1H), 2.42 (dd, 1H), 2.30 (dd, 1H), 1.92-2.02 (m, 1H). $^{19}$F NMR (376 MHz, CDCl$_3$) δ -117.50, -120.09.

Step 3. Synthesis of (1S,4S,5R,6S)-6-(difluoromethyl)-4-(hydroxymethyl)-3-azabicyclo[3.1.0]hexan-2-one (L84)

To a stirred solution of compound C109 (2.39 g, 8.0 mmol) in 87 mL of acetonitrile and 14 mL of water was added 4-toluenesulfonic acid (80 mg, 0.4 mmol). The reaction mixture was heated at about 85° C. for about 1 h. The reaction mixture was cooled to about 25° C., concentrated, and the residue was purified by chromatography to provide the title compound L84. Yield: 1.41 g (99%). $^1$H NMR (400 MHz, CDCl$_3$) δ 6.74 (br. s., 1H), 5.83 (td, 1H), 3.67-3.76 (m, 2H), 3.55-3.63 (m, 1H), 2.03-2.14 (m, 2H), 1.50-1.61 (m, 1H). $^{19}$F NMR (376 MHz, CDCl$_3$) δ -116.67, -118.70.

Preparation 45: (1R,4S,5S,6S)-6-fluoro-4-(hydroxymethyl)-3-azabicyclo[3.1.0]hexan-2-one (L83)

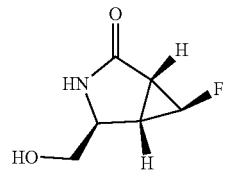

Step 1. Synthesis of (3R,5aR,6S,6aS,6bS)-6-fluoro-3-(4-methoxyphenyl)tetrahydro-1H-cyclopropa[3,4]pyrrolo[1,2-c]oxazol-5(3H)-one (C110)

A solution of CAS 170885-07-1 (242 mg, 1.0 mmol) and N-[(fluoromethyl)oxidophenyl-λ$^4$-sulfanylidene]-4-methylbenzenesulfonamide (CAS 1097193-08-2, 513 mg, 1.6 mmol) in THF (10 mL) was treated with lithium hexamethyldisilazide (1 M, 1.3 mL) at about -78° C. The mixture was stirred at about -78° C. for about 10 min, then was allowed to warm to about 25° C. for about 3 h. Aqueous NH$_4$Cl solution was added and the mixture was extracted twice with EtOAc. The combined EtOAc extracts were washed with brine, dried over MgSO$_4$, filtered and concentrated. The residue was purified by chromatography to provide the title compound C110. Yield: 192 mg (70%). $^1$H NMR (400 MHz, CD$_3$CN) δ 7.22-7.32 (m, 2H), 6.85-6.95 (m, 2H), 6.05 (s, 1H), 4.88 (dd, 1H), 4.17 (dd, 1H), 3.94 (dd, 1H), 3.77 (s, 3H), 3.40 (dd, 1H), 2.61 (ddd, 1H), 2.38 (dd, 1H). $^{19}$F NMR (376 MHz, CD$_3$CN) δ -201.68.

Step 2. Synthesis of (1R,4S,5S,6S)-6-fluoro-4-(hydroxymethyl)-3-azabicyclo[3.1.0]hexan-2-one (L83)

To a stirred solution of compound C110 (1.10 g, 4.2 mmol) in 54 mL of acetonitrile and 6 mL of water was added 4-toluenesulfonic acid (40 mg, 0.21 mmol). The reaction mixture was stirred for about 6 h, then concentrated. The residue was purified by chromatography to provide the title compound L83. Yield: 534 g (88%). $^1$H NMR (400 MHz, CDCl$_3$) δ 5.72 (br. s., 1H), 4.41-4.63 (m, 1H), 3.67-3.76 (m, 2H), 3.55-3.65 (m, 1H), 2.33 (dd, 1H), 2.18 (dd, 1H). $^{19}$F NMR (376 MHz, CDCl$_3$) δ -205.65.

Preparation 46: (1R,4S,5S,6R)-6-fluoro-4-(hydroxymethyl)-3-azabicyclo[3.1.0]hexan-2-one (L87)

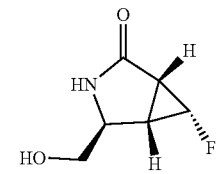

Step 1. Synthesis of 4-methyl-N—[(S)-(fluoromethyl)oxidophenyl-λ⁴-sulfanylidene]benzenesulfonamide (C111)

A solution of CAS 170885-07-1 (330 mg, 1.4 mmol) and 4-methyl-N—[(R)-methyloxidophenyl-λ⁴-sulfanylidene]benzenesulfonamide (CAS 49620-56-6, 701 mg, 2.1 mmol) in THF (15 mL) was treated with lithium hexamethyldisilazide (1 M, 1.9 mL) at about −78° C. The mixture was stirred at about −78° C. for about 10 min, then was allowed to warm to about 25° C. for about 3 h. Aqueous $NH_4Cl$ solution was added and the mixture was extracted twice with EtOAc. The combined EtOAc extracts were washed with brine, dried over $MgSO_4$, filtered and concentrated. The residue was purified by chromatography to provide the title compound C111. Yield: 60 mg (16%). This was used in the next step without further characterization.

Step 2. Synthesis of (1R,4S,5S,6R)-6-fluoro-4-(hydroxymethyl)-3-azabicyclo[3.1.0]hexan-2-one (L87)

To a stirred solution of compound C111 (60 mg, 0.23 mmol) in 9 mL of acetonitrile and 1 mL of water was added 4-toluenesulfonic acid (6 mg, 0.03 mmol). The reaction mixture was heated at about 90° C. for about 2 h. The reaction mixture was cooled to about 25° C., concentrated, and the residue was purified by chromatography to provide the title compound L87. Yield: 25 mg (75%). This was used in the next step without further characterization.

Preparation 47

(1R,4S,5S,6S)-6-fluoro-4-(hydroxymethyl)-6-methyl-3-azabicyclo[3.1.0]hexan-2-one (L88)

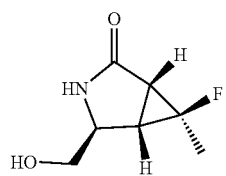

Step 1. Synthesis of (3R,5aR,6S,6aS,6bS)-6-fluoro-3-(4-methoxyphenyl)-6-methyltetrahydro-1H-cyclopropa[3,4]pyrrolo[1,2-c]oxazol-5(3H)-one (C112)

A solution of CAS 170885-07-1 (430 mg, 1.9 mmol) and 4-methyl-N—[(R)-[(1S)-1-fluoroethyl]-oxidophenyl-λ⁴-sulfanylidene]benzenesulfonamide (CAS 1422176-84-8, 952 mg, 2.8 mmol) in THF (19 mL) was treated with lithium hexamethyldisilazide (1 M, 2.4 mL) at −78° C. The mixture was stirred at about −78° C. for about 10 min, then was allowed to warm to about 25° C. for about 3 h. Aqueous $NH_4Cl$ solution was added and the mixture was extracted twice with EtOAc. The combined EtOAc extracts were washed with brine, dried over $MgSO_4$, filtered and concentrated. The residue was purified by chromatography to provide the title compound C112. Yield: 200 mg (39%). ¹H NMR (400 MHz, $CDCl_3$) δ 7.26 (d, 2H), 6.88 (d, 2H), 6.24 (s, 1H), 4.25 (dd, 1H), 3.81 (s, 3H), 3.76-3.84 (m, 1H), 3.50-3.57 (m, 1H), 2.39-2.54 (m, 2H), 1.56 (s, 3H). ¹⁹F NMR (376 MHz, $CDCl_3$) δ −157.20. There was also obtained (3R,5aR,6R,6aS,6bS)-6-fluoro-3-(4-methoxyphenyl)-6-methyltetra-hydro-1H-cyclopropa[3,4]pyrrolo[1,2-c]oxazol-5(3H)-one (C113). It was used in the next step without further characterization.

Step 2. Synthesis of (1R,4S,5S,6S)-6-fluoro-4-(hydroxymethyl)-6-methyl-3-azabicyclo[3.1.0]hexan-2-one (L88)

To a stirred solution of compound C112 (211 mg, 0.76 mmol) in 9 mL of acetonitrile and 1 mL of water was added 4-toluenesulfonic acid (7 mg, 0.04 mmol). The reaction mixture was heated at about 90° C. for about 2 h. The reaction mixture was cooled to about 25° C., concentrated, and the residue was purified by chromatography to provide the title compound L88. Yield: 110 mg (91%). ¹H NMR (400 MHz, $CDCl_3$) δ 6.20 (br. s., 1H), 3.69-3.78 (m, 1H), 3.54-3.68 (m, 2H), 2.68 (s, 1H), 2.32 (dd, 1H), 2.11 (dd, 1H), 1.67 (s, 3H). ¹⁹F NMR (376 MHz, $CDCl_3$) δ −161.43.

Synthesis of (1R,4S,5S,6R)-6-fluoro-4-(hydroxymethyl)-6-methyl-3-azabicyclo[3.1.0]hexan-2-one (L89)

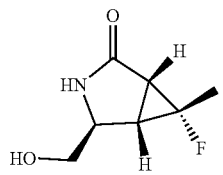

This compound was prepared in the same manner as compound L88, substituting compound C113 for compound C112 in Step 2. It was used in the next step without further characterization.

Preparation 48: (1R,4S,5S)-4-(hydroxymethyl)-1-methyl-3-azabicyclo[3.1.0]hexan-2-one (L91)

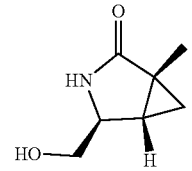

Step 1. Synthesis of (3R,5aR,6aS,6bS)-3-(4-methoxyphenyl)-5a-methyltetrahydro-1H-cyclopropa[3,4]-pyrrolo[1,2-c]oxazol-5(3H)-one (C114)

LDA (2 M, 0.31 mL) was added very slowly to a solution of (3R,5aR,6aS,6bS)-3-(4-methoxyphenyl)tetrahydro-1H-cyclopropa[3,4]pyrrolo[1,2-c]oxazol-5(3H)-one (CAS 187742-05-8, 150 mg, 0.61 mmol) and iodomethane (0.20 mL, 3 mmol) in THF (3 mL) at about −78° C. After about 1 h, an additional 0.31 mL of LDA and 0.2 mL of iodomethane were added. The mixture was warmed to about −20° C. over about 45 min, and allowed to warm to about 25° C. for about 1.5 h. The mixture was poured into $NaHCO_3$ solution and was extracted twice with EtOAc. The combined EtOAc extracts were dried over $MgSO_4$, filtered and concentrated.

The residue was purified by chromatography to provide the title compound C114. Yield: 31 mg (20%). $^1$H NMR (400 MHz, CD$_3$CN) δ 7.27 (d, 2H), 6.89 (d, 2H), 6.07 (s, 1H), 4.13 (dd, 1H), 3.81 (dd, 1H), 3.77 (s, 3H), 3.31 (dd, 1H), 2.06 (dd, 1H), 1.30 (s, 3H), 1.08-1.18 (m, 2H).

Step 2. Synthesis of (1R,4S,5S)-4-(hydroxymethyl)-1-methyl-3-azabicyclo[3.1.0]hexan-2-one (L91)

To a stirred solution of compound C114 (41 mg, 0.16 mmol) in 2 mL of acetonitrile and 0.2 mL of water was added 4-toluenesulfonic acid (2 mg, 0.008 mmol). The reaction mixture was heated at about 90° C. for about 45 min. The reaction mixture was cooled to about 25° C., concentrated, and the residue was purified by chromatography to provide the title compound L91. Yield: 21 mg (93%). $^1$H NMR (400 MHz, CD$_3$OD) δ 3.46-3.55 (m, 2H), 3.43 (q, 1H), 1.75 (dd, 1H), 1.28 (s, 3H), 0.98 (dd, 1H), 0.68 (t, 1H).

Preparation 49

(1S,4S,5R,6S)-1-fluoro-4-(hydroxymethyl)-6-methyl-3-azabicyclo[3.1.0]hexan-2-one (L92)

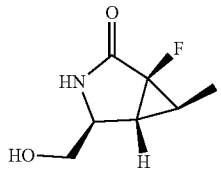

Step 1. Synthesis of (3R,7aS)-6-fluoro-3-(4-methoxyphenyl)tetrahydropyrrolo[1,2-c]oxazol-5(3H)-one (C115)

To a solution of (3R,7aS)-3-(4-methoxyphenyl)tetrahydropyrrolo[1,2-c]oxazol-5(3H)-one (CAS 170885-05-9, 16.0 g, 68.59 mmol) in THF (160 mL) was added LDA (2 M, 48 mL) at about −78° C., and stirred for about 30 min. A solution of NFSI (22.68 g, 72 mmol) in THF (80 mL) was added at about −78° C. After about 30 min at about −78° C., the mixture was allowed to warm to about 25° C. for about 30 min. EtOAc and water were added and the phases separated. The aqueous phase was extracted with EtOAc. The combined EtOAc extracts were washed with brine, dried over Na$_2$SO$_4$, filtered and concentrated. The residue was purified by chromatography to provide the title compound C115. Yield: 12.4 g (72%). $^1$H NMR (400 MHz, CDCl$_3$) δ 7.36 (d, 2H), 6.88 (d, 2H), 6.22 (s, 1H), 5.14 (dd, 1H), 4.40-4.29 (m, 2H), 3.79 (s, 1H), 3.46 (dd, 1H), 2.62-2.51 (m 1H), 2.23-2.07 (m 1H).

Step 2. Synthesis of (3R,7aS)-6-fluoro-3-(4-methoxyphenyl)-6-(phenylselanyl)tetrahydropyrrolo[1,2-c]oxazol-5(3H)-one (C116)

To a stirred solution of compound C115 (12.4 g, 49 mmol) in THF (130 mL) was added LDA (2 M, 35 mL) at about −78° C. and stirred for about 30 min before a solution of diphenyl diselenide (16.96 g, 54 mmol) in THF (70 mL) was added. The mixture was kept at about −78° C. for about 30 min, then allowed to warm to about 25° C. for about 30 min. EtOAc and water were added and the phases separated. The aqueous phase was extracted with EtOAc. The combined EtOAc extracts were washed with brine, dried over Na$_2$SO$_4$, filtered and concentrated. The residue was purified by chromatography to provide the title compound C116. Yield: 13 g (65%). This was used in the next step without further characterization.

Step 3. Synthesis of (3R,7aS)-6-fluoro-3-(4-methoxyphenyl)-1,7a-dihydropyrrolo[1,2-c]oxazol-5(3H)-one (C117)

A solution of compound C116 (13.0 g, 32 mmol) in DCM (260 mL) and pyridine (5.7 mL, 70 mmol) was treated with hydrogen peroxide (30%, 11.9 mL, 106 mmol) at about 0° C. The mixture was kept at about 0° C. for about 30 min, and allowed to warm to about 25° C. for about 2 h before being diluted with DCM and water. The DCM was separated and the aqueous phase was extracted with DCM. The combined DCM extracts were washed with water, brine, dried over Na$_2$SO$_4$, filtered and concentrated. The residue was purified by chromatography to provide the title compound C117. Yield: 4.6 g (58%). $^1$H NMR (400 MHz, CD$_3$CN) δ 7.43 (d, 2H), 6.96 (d, 2H), 6.72 (dd, 1H), 5.91 (s, 1H), 4.59 (m, 1H), 4.36 (dd, 1H), 3.80 (s, 3H), 3.29-3.36 (m, 1H). $^{19}$F NMR (376 MHz, CD$_3$CN) δ −137.11.

Step 4. Synthesis of (3R,5aS,6S,6aR,6bS)-5a-fluoro-3-(4-methoxyphenyl)-6-methyltetrahydro-1H-cyclopropa[3,4]pyrrolo[1,2-c]oxazol-5(3H)-one (C118)

To a stirred suspension of ethyldiphenylsulfonium tetrafluoroborate (CAS 893-69-6, 5.31 g, 17 mmol) in DME (62 mL) was added LDA (2 M, 8.0 mL, 16 mmol) slowly at about −55° C. The reaction mixture was kept at about −55° C. for about 45 min, at which point it was warmed to about −35° C. and a solution of compound C117 (1.99 g, 8.0 mmol) in DME (20 mL) was added. The reaction mixture was maintained at about −30° C. for about 1.5 h, then aqueous NaHCO$_3$ and EtOAc were added. The EtOAc was separated and the aqueous phase was extracted with EtOAc. The combined EtOAc extracts were dried over MgSO$_4$, filtered and concentrated. The residue was purified by chromatography to provide the title compound C118. Yield: 362 mg (16%). $^1$H NMR (400 MHz, CD$_3$CN) δ 7.28 (d, 2H), 6.90 (d, 2H), 6.12 (s, 1H), 4.17 (dd, 1H), 3.78 (s, 3H), 3.66-3.75 (m, 1H), 3.45 (dd, 1H), 2.33 (dd, 1H), 1.64 (d, 1H), 1.25 (dd, 3H). There was also obtained (3R,5aS,6R,6aR,6bS)-5a-fluoro-3-(4-methoxyphenyl)-6-methyltetrahydro-1H-cyclopropa[3,4]pyrrolo[1,2-c]oxazol-5(3H)-one (C119). Yield: 816 mg (37%). $^1$H NMR (400 MHz, CD$_3$CN) δ 7.30 (d, 2H), 6.92 (d, 2H), 6.15 (s, 1H), 4.20-4.24 (m, 1H), 3.78 (s, 3H), 3.57-3.62 (m, 2H), 2.72 (dd, 1H), 2.13-2.23 (m, 1H), 1.15 (dd, 3H).

Step 5. Synthesis of (1S,4S,5R,6S)-1-fluoro-4-(hydroxymethyl)-6-methyl-3-azabicyclo[3.1.0]-hexan-2-one (L92)

To a stirred solution of compound C118 (400 mg, 1.4 mmol) in 18 mL of acetonitrile and 2 mL of water was added 4-toluenesulfonic acid (14 mg, 0.07 mmol). The reaction mixture was kept at about 25° C. for about 12 h, then concentrated and the residue was purified by chromatography to provide the title compound L92. Yield: 181 mg (79%). $^1$H NMR (400 MHz, CDCl$_3$) δ 6.07 (br. s., 1H), 3.66-3.81 (m, 1H), 3.54-3.67 (m, 1H), 3.36-3.50 (m, 1H), 1.77-1.87 (m, 2H), 1.29 (d, 3H).

Synthesis of (1S,4S,5R,6R)-1-fluoro-4-(hydroxymethyl)-6-methyl-3-azabicyclo[3.1.0]hexan-2-one (L93)

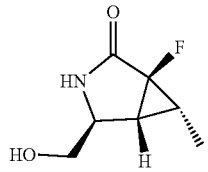

This compound was prepared in the same manner as compound L92, substituting compound C119 for compound C118 in Step 5. $^1$H NMR (400 MHz, CD$_3$OD) δ 3.63 (dd, 2H), 3.28 (dt, 1H), 2.38 (dd, 1H), 1.95-2.07 (m, 1H), 1.07 (dd, 3H).

Preparation 50: (1R,4S,5S)-4-(hydroxymethyl)-5-methyl-3-azabicyclo[3.1.0]hexan-2-one (L94)

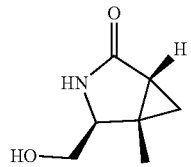

Step 1. Synthesis of (3R,7S,7aS)-3-(4-methoxyphenyl)-7-methyltetrahydropyrrolo[1,2-c]oxazol-5(3H)-one (C120)

A suspension cuprous bromide-dimethyl sulfide complex (2.24 g, 10.8 mmol) in ether (30 mL) was cooled to about −10° C. and a solution of methyllithium (1.6 M, 13.5 mL) was added slowly. The mixture was then cooled to about −78° C. and TMSCl (1.36 mL, 10.8 mmol) was added slowly. After the addition was complete, the mixture was kept for about 15 min before (3R,7aS)-3-(4-methoxyphenyl)-1,7a-dihydropyrrolo[1,2-c]oxazol-5(3H)-one (CAS 170885-07-1, 1.00 g, 4.3 mmol) in THF (20 mL) was added slowly. The mixture was kept an additional about 2 h at about −78° C. before being allowed to warm to about 25° C. The mixture was kept at about 25° C. for about 1 h before being treated with a mixture of saturated aqueous NH$_4$Cl and ammonium hydroxide. The ethereal layer was separated and the aqueous phase was extracted twice with EtOAc. The combined extracts were dried over MgSO$_4$ filtered and concentrated. The residue was purified by chromatography to provide the title compound C120. Yield: 457 mg (43%). $^1$H NMR (400 MHz, CDCl$_3$) δ 7.36 (d, 2H), 6.89 (d, 2H), 6.31 (s, 1H), 4.20 (dd, 1H), 3.81 (s, 3H), 3.77 (q, 1H), 3.59 (dd, 1H), 2.61-2.72 (m, 1H), 2.44-2.55 (m, 1H), 2.29-2.42 (m, 1H), 1.23 (d, 3H).

Step 2. Synthesis of (3R,7R,7aS)-3-(4-methoxyphenyl)-7-methyl-6-(phenylselanyl)tetrahydropyrrolo[1,2-c]oxazol-5(3H)-one (C121)

To a stirred solution of compound C120 (450 mg, 1.8 mmol) in THF (10 mL) was added LDA (2 M, 1.18 mL) at about −78° C. and stirred for about 30 min before a solution of phenylselenenyl chloride (462 mg, 2.4 mmol) in THF (5 mL) was added. The mixture was kept at about −78° C. for about 30 min, then allowed to warm to about 25° C. for about 2 h. EtOAc and water were added and the phases separated. The aqueous phase was extracted with EtOAc. The combined EtOAc extracts were washed with brine, dried over Na$_2$SO$_4$, filtered and concentrated. The residue was purified by chromatography to provide the title compound C121. Yield: 343 mg (47%). This was used in the next step without further characterization.

Step 3. Synthesis of (3R,7aS)-3-(4-methoxyphenyl)-7-methyl-1,7a-dihydropyrrolo[1,2-c]oxazol-5(3H)-one (C122)

A solution of compound C121 (343 mg, 0.85 mmol) in DCM (15 mL) and pyridine (0.15 mL) at about 0° C. was treated with 30% hydrogen peroxide solution (0.17 mL, 2.8 mmol). The mixture was kept at about 0° C. for about 30 min before being warmed slowly to about 25° C. After about 3 h, the mixture was diluted with DCM (10 mL) and washed with saturated aqueous NaHCO$_3$ solution. The DCM extracts were washed with brine, dried over Na$_2$SO$_4$, filtered and concentrated. The residue was purified by chromatography to provide the title compound C122. Yield: 143 mg (68%). $^1$H NMR (400 MHz, CDCl$_3$) δ 7.44 (d, 2H), 6.91 (d, 2H), 6.18 (s, 1H), 5.82 (s, 1H), 4.39-4.49 (m, 1H), 4.21 (s, 1H), 3.82 (s, 3H), 3.47 (s, 1H), 2.09 (d, 3H).

Step 4. Synthesis of (3R,5aR,6aS,6bS)-3-(4-methoxyphenyl)-6a-methyltetrahydro-1H-cyclopropa[3,4]pyrrolo[1,2-c]oxazol-5(3H)-one (C123)

Sodium hexamethyldisilazide (1 M, 0.57 mL) was added to a suspension of trimethylsulfoxonium iodide (128 mg, 0.57 mmol) in DMSO (2 mL) at about 25° C. The mixture was kept at about 25° C. for about 30 min then heated to about 55° C. for about 30 min. The mixture was cooled to about 25° C., then a solution of compound C122 (100 mg, 0.41 mmol) in THF (1 mL) was added. After about 18 h, aqueous NH$_4$Cl was added and the mixture was extensively extracted with ethyl ether. The combined ether extracts were washed with water, brine, dried over MgSO$_4$, filtered and concentrated. The residue was purified by chromatography to provide the title compound C123. Yield: 55 mg (52%). $^1$H NMR (400 MHz, CD$_3$CN) δ 7.24-7.29 (m, 2H) 6.86-6.92 (m, 2H) 6.06 (s, 1H) 4.11-4.16 (m, 1H) 3.92 (ddd, 1H) 3.77 (s, 3H) 3.50 (dd, 1H) 1.72-1.77 (m, 1H) 1.30 (s, 3H) 1.19 (s, 1H) 1.17 (d, 1H).

Step 5. Synthesis of (1R,4S,5S)-4-(hydroxymethyl)-5-methyl-3-azabicyclo[3.1.0]hexan-2-one (L94)

To a stirred solution of compound C123 (200 mg, 0.77 mmol) in 18 mL of acetonitrile and 2 mL of water was added 4-toluenesulfonic acid (7 mg, 0.04 mmol). The reaction mixture was heated at about 95° C. for about 1 h. The reaction mixture was cooled to about 25° C., concentrated, and the residue was purified by chromatography to provide the title compound L94. Yield: 95 mg (87%). $^1$H NMR (400 MHz, CDCl$_3$) δ 6.04 (br. s., 1H) 3.81 (dd, 1H) 3.62-3.68 (m, 1H) 3.57-3.61 (m, 1H) 2.12 (br. s., 1H) 1.62-1.68 (m, 1H) 1.30 (s, 3H) 0.99 (dd, 1H) 0.85-0.89 (m, 1H).

Synthesis of (1R,4S,5S)-5-ethyl-4-(hydroxymethyl)-3-azabicyclo[3.1.0]hexan-2-one (L95)

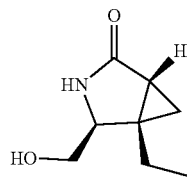

This compound was prepared in the same manner as compound L94, substituting ethylmagnesium chloride for methyllithium in Step 1. It was used in the next step without further characterization.

Preparation 51; (1S,4S,5R)-1-fluoro-4-(hydroxymethyl)-3-azabicyclo[3.1.0]hexan-2-one (L96)

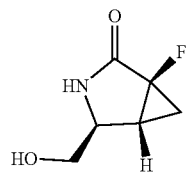

Step 1. Synthesis of (3R,7R,7aS)-3-phenyl-7-vinyltetrahydropyrrolo[1,2-c]oxazol-5(3H)-one (C124)

A suspension cuprous bromide-dimethyl sulfide complex (10.4 g, 50 mmol) in ether (70 mL) was cooled to about −10° C. and a solution of vinylmagnesium bromide (1 M, 100 mL) was added slowly. The mixture was stirred at about −10° C. for about 30 min. The mixture was then cooled to about −78° C. and TMSCl (9.2 mL, 73 mmol) was added slowly. After the addition was complete, the mixture was kept for about 15 min before (3R,7aS)-3-phenyl-1,7a-dihydropyrrolo[1,2-c]oxazol-5(3H)-one (CAS 134107-65-6, 6.70 g, 33 mmol) in THF (70 mL) was added slowly. The mixture was kept an additional about 4 h at about −78° C. before being treated with a mixture of saturated aqueous NH$_4$Cl and ammonium hydroxide. The ethereal layer was separated and the aqueous phase was extracted twice with EtOAc. The combined extracts were dried over MgSO$_4$ filtered and concentrated. The residue was purified by chromatography to provide the title compound C124. Yield: 5.53 g (72%). $^1$H NMR (400 MHz, CDCl$_3$) δ 7.42-7.47 (m, 2H), 7.31-7.40 (m, 3H), 6.39 (s, 1H), 5.88 (ddd, 1H), 5.12-5.20 (m, 2H), 4.19 (dd, 1H), 3.96 (q, 1H), 3.71 (dd, 1H), 2.95 (dq, 1H), 2.63-2.81 (m, 2H).

Step 2. Synthesis of (3R,7R,7aS)-6-fluoro-3-phenyl-7-vinyltetrahydropyrrolo[1,2-c]oxazol-5(3H)-one (C125)

A solution of LDA was generated from n-butyllithium (2.5 M, 1.1 mL) and diisopropylamine (0.73 mL, 5.2 mmol) in THF at about 0° C. for about 1 h. A solution of compound C124 (1.00 g, 4.4 mmol) in THF (40 mL) was treated with the LDA solution at about −78° C. After about 30 min, a solution of NFSI (1.70 g, 5.2 mmol) in THF (5 mL) was added. The mixture was allowed to warm to about 25° C. for about 16 h. Saturated aqueous NH$_4$Cl solution was added and the mixture was extracted with EtOAc (50 mL). The EtOAc extract was washed with brine, dried over MgSO$_4$, filtered and concentrated. The residue was purified by chromatography to provide the title compound C125. Yield: 441 mg (41%). $^1$H NMR (400 MHz, CDCl$_3$) δ 7.33-7.50 (m, 5H), 6.48 (s, 1H), 5.95 (ddd, 1H), 5.31-5.38 (m, 2H), 5.22 (dd, 1H), 4.22-4.33 (m, 1H), 3.75-3.86 (m, 2H), 2.93-3.08 (m, 1H). $^{19}$F NMR (376 MHz, CDCl$_3$) δ −194.19, −198.01.

Step 3. Synthesis of (3R,7S,7aS)-6-fluoro-7-(hydroxymethyl)-3-phenyltetrahydropyrrolo[1,2-c]oxazol-5(3H)-one (C126)

A stream of ozonized oxygen was bubbled through a solution of compound C125 (440 mg, 1.8 mmol) in DCM (6 mL) and MeOH (2 mL) at about −78° C. After a blue color persisted in the mixture, the mixture was treated with dimethyl sulfide (3 mL). NaBH$_4$ (202 mg, 5.3 mmol) was added and the mixture was stirred at about −78° C. for about 30 min before being allowed to warm to about 0° C. for about 30 min. The mixture was treated with saturated aqueous NH$_4$Cl solution and extracted with EtOAc. The EtOAc extract was washed with brine, dried over MgSO$_4$, filtered and concentrated. The residue was purified by chromatography to provide the title compound C126. Yield: 207 mg (46%). $^1$H NMR (400 MHz, CDCl$_3$) δ 7.31-7.50 (m, 5H), 6.44 (s, 1H), 5.31 (dd, 1H), 4.36 (dd, 1H), 4.04 (dt, 1H), 3.87-3.97 (m, 2H), 3.76 (dd, 1H), 2.49-2.69 (m, 1H), 1.69 (t, 1H). $^{19}$F NMR (376 MHz, CDCl$_3$) δ −193.64.

Step 4. Synthesis of (3R,7R,7aS)-7-(bromomethyl)-6-fluoro-3-phenyltetrahydropyrrolo[1,2-c]oxazol-5(3H)-one (C127)

A solution of compound C126 (202 mg, 0.8 mL) in DCM was treated with pyridine (0.13 mL, 1.6 mmol) and carbon tetrabromide (323 mg, 1.0 mmol). Triphenylphosphine (258 mg, 1.0 mmol) was slowly added to the mixture. The mixture was kept about 2 h at about 25° C., then saturated aqueous NaHCO$_3$ was added and the mixture was extracted with EtOAc. The combined EtOAc extracts were washed with water, brine, dried over MgSO$_4$, filtered and concentrated. The residue was purified by chromatography to provide the title compound C127. Yield: 185 mg (73%). $^1$H NMR (400 MHz, CDCl$_3$) δ 7.34-7.47 (m, 5H), 6.45 (s, 1H), 5.21 (dd, 1H), 4.41-4.49 (m, 1H), 3.82-3.89 (m, 2H), 3.76-3.81 (m, 1H), 3.56 (dd, 1H), 2.74-2.88 (m, 1H). $^{19}$F NMR (376 MHz, CDCl$_3$) δ −193.19.

Step 5. Synthesis of (3R,5aS,6aR,6bS)-5a-fluoro-3-phenyltetrahydro-1H-cyclopropa[3,4]pyrrolo-[1,2-c]oxazol-5(3H)-one (C128)

A solution of compound C127 (185 mg, 0.59 mmol) in THF (10 mL) was treated with lithium hexamethyldisilazide (1 M, 0.62 mL) at about −78° C. After about 15 min at about −78° C., the mixture was allowed to warm to about 0° C. for about 30 min, then an additional portion of lithium hexamethyldisilazide (1 M, 0.31 mL) was added. After approximately another 30 min at about 0° C., The mixture was treated with saturated aqueous NH$_4$Cl solution and extracted with EtOAc. The combined EtOAc extracts were washed with water, brine, dried over MgSO$_4$, filtered and concentrated. The residue was purified by chromatography to provide the title compound C128. Yield: 110 mg (80%). $^1$H NMR (400 MHz, CDCl$_3$) δ 7.29-7.44 (m, 5H), 6.40 (s, 1H), 4.26 (dd, 1H), 3.61-3.69 (m, 1H), 3.53-3.60 (m, 1H), 2.60 (td, 1H), 1.90 (ddd, 1H), 1.44 (dt, 1H). $^{19}$F NMR (376 MHz, CDCl$_3$) −208.58.

Step 6. Synthesis of (1S,4S,5R)-1-fluoro-4-(hydroxymethyl)-3-azabicyclo[3.1.0]hexan-2-one (L96)

To a stirred solution of compound C128 (110 mg, 0.47 mmol) in 18 mL of acetonitrile and 2 mL of water was added 4-toluenesulfonic acid (5 mg, 0.02 mmol). The reaction mixture was kept at about 25° C. for about 6 h, then heated at about 60° C. for about 6 h. The reaction mixture was cooled to about 25° C., concentrated, and the residue was purified by chromatography to provide the title compound L96. Yield 53 mg (77%). It was used in the next step without further characterization.

Preparation 52: (1R,4S,5S)-4-(hydroxymethyl)-3-azabicyclo[3.2.0]heptan-2-one (L97)

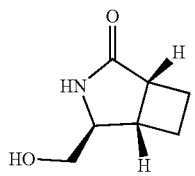

Step 1. Synthesis of (1S,2S,5R)-tert-butyl 2-(((tert-butyldimethylsilyl)oxy)methyl)-4-oxo-3-azabicyclo[3.2.0]heptane-3-carboxylate (C129)

A solution of (S)-tert-butyl 2-(((tert-butyldimethylsilyl)oxy)methyl)-5-oxo-2,5-dihydro-1H-pyrrole-1-carboxylate (CAS 81658-27-7, 1.00 g, 3.1 mmol) in acetone (330 mL) was saturated with ethylene gas and irradiated with ultraviolet light at about −20° C. for about 6 h. A steady flow of ethylene gas was maintained throughout the irradiation. The mixture was then concentrated and the residue was purified by chromatography to provide the title compound C129. Yield: 250 mg (23%). $^1$H NMR (400 MHz, CDCl$_3$) δ 3.89 (s, 1H), 3.81 (dd, 1H), 3.59 (d, 1H), 3.03 (t, 1H), 2.88 (q, 1H), 2.49-2.44 (m, 1H), 2.29-2.25 (m, 1H), 2.11-1.99 (m, 2H), 1.54 (s, 9H), 0.84 (s, 9H), 0.06 (m, 6H).

Step 2. Synthesis of (1S,2S,5R)-tert-butyl 2-(hydroxymethyl)-4-oxo-3-azabicyclo[3.2.0]heptane-3-carboxylate (C130)

A solution of compound C129 (568 mg, 1.6 mmol) in THF (8 mL) was treated with a solution off tetrabutylammonium fluoride (1 M, 3.2 mL) at about 25° C. After about about 4 h, the mixture was poured into water and extracted with EtOAc. The combined EtOAc extracts were dried over MgSO$_4$, filtered and concentrated. The residue was purified by chromatography to provide the title compound C130. Yield: 357 mg (93%). $^1$H NMR (400 MHz, CDCl$_3$) δ 6.66 (br. s., 1H), 3.90-4.01 (m, 1H), 3.79-3.86 (m, 1H), 3.61 (t, 1H), 2.91-2.99 (m, 1H), 2.78-2.88 (m, 1H), 2.41-2.52 (m, 1H), 2.30-2.41 (m, 1H), 2.01-2.16 (m, 2H), 1.46 (s, 9H).

Step 3. Synthesis of (1R,4S,5S)-4-(hydroxymethyl)-3-azabicyclo[3.2.0]heptan-2-one (L97)

Compound C130 (357 mg, 1.5 mmol) was dissolved in DCM (1 mL) at about 25° C. A mixture of DCM (1 mL) and TFA (1 mL) was added and the mixture was kept at about 25° C. for about 2 h. It was then concentrated to dryness to provide the title compound L97. Yield: 211 mg (100%). $^1$H NMR (400 MHz, CDCl$_3$) δ 5.55 (br. s., 2H), 4.34 (dd, 1H), 4.17 (dd, 1H), 3.82 (t, 1H), 3.02-3.18 (m, 1H), 2.82-2.99 (m, 1H), 2.48-2.64 (m, 1H), 2.36-2.48 (m, 1H), 2.02-2.26 (m, 2H).

Preparation 53: (1S,4S,5R)-1-fluoro-4-(hydroxymethyl)-3-azabicyclo[3.2.0]heptan-2-one (L98)

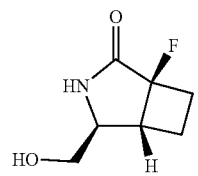

Step 1. Synthesis of (3R,5aS,7aR,7bS)-5a-fluoro-3-(4-methoxyphenyl)hexahydrocyclo-buta[3,4]pyrrolo[1,2-c]oxazol-5(3H)-one (C131)

A solution of compound C117 (300 mg, 1.2 mmol) in acetone (450 mL) was saturated with ethylene gas and irradiated with ultraviolet light at about −20° C. for about 6 h. A steady flow of ethylene gas was maintained throughout the irradiation. The mixture was then concentrated and the residue was purified by chromatography to provide the title compound C131. Yield: 170 mg (51%). $^1$H NMR (400 MHz, CDCl$_3$) δ 7.38 (d, 2H), 6.90 (d, 2H), 6.37 (s, 1H), 4.21 (dd, 1H), 3.81 (s, 3H), 3.78-3.74 (m, 1H), 3.32 (dd, 1H), 3.06-3.01 (m, 1H), 2.65-2.56 (m, 2H), 2.49-2.42 (m, 1H), 1.67-1.62 (m, 1H).

Step 2. Synthesis of (1S,4S,5R)-1-fluoro-4-(hydroxymethyl)-3-azabicyclo[3.2.0]heptan-2-one (L98)

To a stirred solution of compound C131 (200 mg, 0.72 mmol) in 9 mL of acetonitrile and 1 mL of water was added 4-toluenesulfonic acid (7 mg, 0.04 mmol). The reaction mixture was heated at about 70° C. for about 1 h. The reaction mixture was cooled to about 25° C., concentrated, and the residue was purified by chromatography to provide the title compound L98. Yield: 115 (100%). $^1$H NMR (400 MHz, CDCl$_3$) δ 7.84 (br. s., 1H), 3.55-3.71 (m, 2H), 3.39-3.55 (m, 1H), 2.81-3.00 (m, 1H), 2.41-2.60 (m, 2H), 2.18-2.34 (m, 1H), 1.36-1.53 (m, 1H).

Preparation 54: (±)-(1S,5S)-5-(hydroxymethyl)-3-azabicyclo[3.1.0]hexan-2-one (L100)

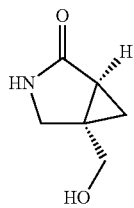

Step 1. Synthesis of tert-butyl 1-((benzoyloxy)methyl)-3-azabicyclo[3.1.0]hexane-3-carboxylate (C132)

A solution of tert-butyl 1-(hydroxymethyl)-3-azabicyclo[3.1.0]hexane-3-carboxylate (CAS 161152-76-7, 427 mg, 2 mmol) in DCM (6.4 mL) was treated with benzoic acid (368 mg, 3 mmol), EDCl hydrochloride (581 mg, 3 mmol), and DMAP (49 mg, 0.4 mmol), and heated to about 40° C. for about 12 h. The mixture was cooled to about 25° C., diluted with DCM, washed with 1 M HCl and 10% aqueous Na$_2$CO$_3$. The DCM solution was concentrated, and the residue was purified by chromatography to provide the title compound C132, which was used in the next step without further characterization. Yield: 0.57 g (90%).

Step 2. Synthesis of tert-butyl 1-((benzoyloxy)methyl)-4-oxo-3-azabicyclo[3.1.0]hexane-3-carboxylate (C133)

A solution of compound C132 (0.57 g, 1.8 mmol) in EtOAc (20 mL) was treated with a solution of sodium periodate (1.5 g, 7.2 mmol) in water (20 mL) and ruthenium trichloride (21 mg (50%), 0.054 mmol). The mixture was stirred at about 20° C. for about 6 h, then treated with 2-propanol (20 mL) and stirred for about 0.5 h. It was then diluted with water and extracted twice with EtOAc. The combined EtOAc extracts were dried over Na$_2$SO$_4$ filtered and concentrated. The residue was purified by chromatography to provide the title compound C133, which was used in the next step without further characterization. Yield: 0.40 g (60%).

Step 3. Synthesis of (4-oxo-3-azabicyclo[3.1.0]hexan-1-yl)methyl benzoate (C134)

A solution of compound C133 (0.40 g, 0.5 mmol) in DCM (2 mL) was treated with TFA (0.5 mL) and stirred at about 25° C. for about 15 minutes. The mixture was concentrated and the residue was redissolved in toluene and again concentrated to provide the title compound C134, which was used in the next step without further characterization.

Step 4. Synthesis of (5-(hydroxymethyl)-3-azabicyclo[3.1.0]hexan-2-one (L100)

Compound C134 (presumed 0.4 mmol) in THF (2 mL) was treated with NaOH (0.3 mL of a 2 M aqueous solution, 0.6 mmol) and stirred at about 25° C. for about 1 h. This solution of compound L100 was used in the next step without further characterization.

Preparation 55: (±)-3-(hydroxymethyl)octahydro-1H-isoindol-1-one (L101)

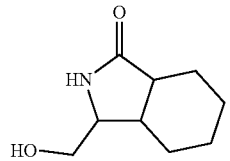 [SMILES: O=C1NC(CO)C2CCCCC12]

Step 1. Synthesis of (±)-3-(hydroxymethyl)octahydro-1H-isoindol-1-one (L101)

Ethyl 3-oxooctahydro-1H-isoindole-1-carboxylate (CAS 84385-29-5, 400 mg, 1.9 mmol) was dissolved in THF (9.5 mL) to which lithium borohydride (59 mg, 2.65 mmol) was added. The reaction was stirred at about 25° C. overnight. The mixture was cooled to about 0° C. and 2 M HCl was added dropwise until gas evolution ceased. The solution was neutralized with K$_2$CO$_3$ and filtered. The filtrate was concentrated The residue was purified by chromatography to provide the title compound L101. Yield: 0.26 g (81%). $^1$H NMR (400 MHz, dmso-d$_6$) δ 4.63 (t, 1H), 3.42-3.50 (m, 1H), 3.38-3.42 (m, 2H), 2.35-2.40 (m, 1H), 2.23-2.30 (m, 1H), 1.90-1.98 (m, 1H), 1.40-1.63 (m, 3H), 1.27-1.40 (m, 1H), 0.84-1.11 (m, 3H).

Preparation 56: (S)-5-(hydroxymethyl)-5-methylpyrrolidin-2-one (L102)

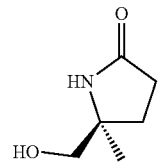

Step 1. Synthesis of (S)-methyl 2-methyl-5-oxopyrrolidine-2-carboxylate (C135)

A solution (S)-1-tert-butyl 2-methyl 2-methyl-5-oxopyrrolidine-1,2-dicarboxylate (CAS 1109790-91-1, 1.2 g, 4.7 mmol) in DCM was treated with TFA (0.36 mL, 4.7 mmol) for about 2 h at about 25° C. The mixture was concentrated to provide the title compound C135. Yield: 1.2 g (100%). $^1$H NMR (400 MHz, CDCl$_3$) δ 7.78 (br. s., 1H), 3.80 (s, 3H), 2.48-2.66 (m, 3H), 2.02-2.15 (m, 1H), 1.58 (s, 3H).

Step 2. Synthesis of (S)-5-(hydroxymethyl)-5-methylpyrrolidin-2-one (L102)

A solution of compound C135 (1.2 g, 4.7 mmol) in THF (76 mL) was treated with lithium borohydride (218 mg, 9.9 mmol). The reaction was allowed to proceed overnight, after which the solution was cooled to about 0° C. and 2 M HCl was added dropwise until gas evolution ceased. The solution was neutralized with K$_2$CO$_3$ and filtered. The filtrate was concentrated. The residue was purified by chromatography to provide the title compound C136 an oil which crystallized. This was triturated with ether and filtered to provide the title compound L102. Yield: 0.30 g (49%). $^{1}$H NMR (400 MHz, dmso-d$_{6}$) δ 7.43 (br. s., 1H), 4.83-4.87 (m, 1H), 3.16-3.24 (m, 2H), 2.06-2.21 (m, 2H), 1.96 (ddd, 1H), 1.59 (ddd, 1H), 1.09 (s, 3H).

Preparation 57: 5-(hydroxymethyl)-4-(trifluoromethyl)pyrrolidin-2-one (L104)

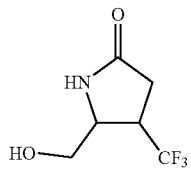

Step 1. Synthesis of Diethyl 2-((diphenylmethylene)amino)-3-(trifluoromethyl)pentanedioate (C136)

A mixture of ethyl 2-((diphenylmethylene)amino)acetate (CAS 69555-14-2, 1.9 g, 7 mmol), benzyltriethyl NH$_{4}$Cl (0.3 g, 1.3 mmol), 10% aqueous NaOH (10 mL) and DCM (10 mL) was stirred at about 0° C. for about 15 min. Following the addition of (E)-ethyl 4,4,4-trifluorobut-2-enoate (CAS 25597-16-4, 1 mL, 7 mmol) the mixture was stirred vigorously for about 90 min at about 0° C. The DCM was separated and the aqueous phase was extracted with DCM. The combined DCM extracts were washed with brine, dried over MgSO$_{4}$, filtered and concentrated to provide the title compound C136. Yield: 2.6 g (85%). $^{1}$H NMR (400 MHz, CDCl$_{3}$) δ 7.62-7.67 (m, 2H), 7.43-7.50 (m, 4H), 7.31-7.38 (m, 2H), 7.14-7.20 (m, 2H), 4.43 (d, 1H), 4.13-4.25 (overlapping q, 4H), 3.62-3.74 (m, 1H), 3.12 (dd, 1H), 2.81 (dd, 1H), 1.27 (overlapping t, 6H).

Step 2. Synthesis of Ethyl 5-oxo-3-(trifluoromethyl)pyrrolidine-2-carboxylate (C137)

A mixture of compound C136 (2.6 g, 6.0 mmol), 10% aqueous citric acid (24 mL, 212 mmol) and THF (17 mL) was stirred at about 25° C. for 2 days. The reaction was extracted with EtOAc and the combined EtOAc extracts were washed with brine, dried over MgSO$_{4}$, filtered and concentrated. The residue was purified by chromatography to provide the title compound C137. Yield: 1.1 g (85%). $^{1}$H NMR (400 MHz, CDCl$_{3}$) δ 6.72 (br. s., 1H), 4.28 (q, 2H), 3.40 (m, 1H), 2.70 (dd, 1H), 2.52 (dd, 1H), 1.33 (t, 3H).

Step 3. Synthesis of 5-(Hydroxymethyl)-4-(trifluoromethyl)pyrrolidin-2-one (L104)

To a solution of compound C137 (1.1 g, 5.1 mmol) in THF (25 mL) was added lithium borohydride (0.16 g, 7.1 mmol). The mixture was stirred at about 25° C. overnight. The mixture was cooled to about 0° C. and 2 M HCl was added until gas evolution ceased. The mixture was neutralized with K$_{2}$CO$_{3}$ and filtered. The filtrate was concentrated and the residue was purified by chromatography to provide the title compound L104. Yield: 0.44 g (47%). $^{1}$H NMR (400 MHz, dmso-d$_{6}$) δ 7.92 (br. s., 1H, diastereomer 1), 6.89 (d, 1H, diastereomer 2), 5.35 (m, 1H, diastereomer 2), 5.07 (t, 1H, diastereomer 1), 3.84 (m, 1H, diastereomer 2), 3.58 (m, 1H, diastereomer 1), 3.30-3.46 (m, 3H, mixture of 1H diastereomer 1 and 2H diastereomer 2), 3.12 (m, 1H, diastereomer 1), 2.74 (dd, 1H, diastereomer 2), 2.59 (dd, 1H, diastereomer 1), 2.42 (dd, 1H, diastereomer 2), 2.17 (dd, 1H, diastereomer 1).

Preparation 58: (±)-((1R,6S)-3-benzyl-3-azabicyclo[4.1.0]heptan-1-yl)methanol (L105)

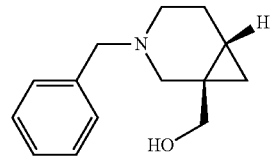 [SMILES: OC[C@]12C[C@H]1CCN(Cc1ccccc1)C2]

Step 1. Synthesis of (±)-((1R,6S)-3-benzyl-3-azabicyclo[4.1.0]heptan-1-yl)methanol (L105)

To obtain the desired target material, (1-benzyl-1,2,5,6-tetrahydropyridin-3-yl)methanol (CAS 244267-39-8, 545 mg, 2.7 mmol)) was cyclopropanated as described in Tetrahedron 2003, 59, 6363 to provide the title compound L105. Yield: 252 mg (43%). $^{1}$H NMR (400 MHz, dmso-d$_{6}$) δ 7.13-7.41 (m, 5H), 4.42 (t, 1H), 3.32-3.49 (m, 2H), 3.28 (dd, 1H), 3.08 (dd, 1H), 2.74 (d, 1H), 2.21-2.39 (m, 2H), 1.77-1.98 (m, 2H), 1.49-1.70 (m, 1H), 0.69-0.85 (m, 1H), 0.39-0.53 (m, 2H).

Preparation 59: (S)-4-(hydroxymethyl)-1-methylimidazolidin-2-one (L106)

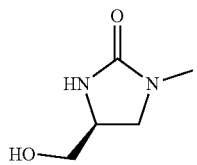

Step 1. Synthesis of (S)-1-Benzyl 5-methyl 2-oxoimidazolidine-1,5-dicarboxylate (C138)

To a suspension of (S)-3-((benzyloxy)carbonyl)-2-oxoimidazolidine-4-carboxylic acid (CAS 59760-01-9, 3.0 g, 11.4 mmol) in MeOH (40 mL) was added thionyl chloride (0.4 mL, 5.7 mmol) slowly at about 25° C. The mixture was stirred at about 25° C. overnight before the volatiles where removed under reduced pressure. The residue was dissolved in DCM and the DCM was washed with saturated aqueous NaHCO$_{3}$. The DCM was dried over MgSO$_{4}$, filtered and concentrated to provide the title compound C138. Yield: 2.9 g (93%). $^{1}$H NMR (400 MHz, dmso-d$_{6}$) δ 7.26-7.45 (m, 5H), 5.19 (q, 2H), 4.78 (dd, Hz, 1H), 3.66 (s, 3H), 3.63-3.71 (m, 1H), 3.37 (dd, 1H), 2.71 (s, 3H).

Step 2. Synthesis of (S)-1-Benzyl 5-methyl 3-methyl-2-oxoimidazolidine-1,5-dicarboxylate (C139)

To a solution of compound C138 (0.96 g, 3.5 mmol) in DME (17 mL) was added K$_{2}$CO$_{3}$ (0.96 g, 6.9 mmol)

followed by iodomethane (0.87 mL, 13.9 mmol). The mixture was heated at about 50° C. for about 19 h. The mixture was then allowed to cool to about 25° C. and diluted with water. The layers were separated and the aqueous phase was extracted three times with EtOAc. The combined DME and EtOAc extracts were washed with half-saturated aqueous NH$_4$Cl, brine, dried over Na$_2$SO$_4$, filtered and concentrated. The residue was purified by chromatography to provide the title compound C139. Yield: 0.75 g (74%). $^1$H NMR (400 MHz, dmso-d$_6$) δ 7.31-7.44 (m, 5H), 5.19 (dd, 2H), 4.78 (dd, 1H), 3.67-3.74 (m, 1H), 3.37 (dd, 1H), 3.31 (s, 2H), 2.71 (s, 3H).

Step 3. Synthesis of (S)-Benzyl 5-(hydroxymethyl)-3-methyl-2-oxoimidazolidine-1-carboxylate (C140)

NaBH$_4$ (119 mg, 3.1 mmol) was added slowly to solution of compound C139 (0.75 g, 2.6 mmol) in EtOH (7 mL) at about 0° C. The mixture was stirred at about 0° C. for about 2.5 h, at which time after which an additional 119 mg of NaBH$_4$ was added. Stirring was continued at about 0° C. for approximately an additional 1.5 h. Hydrochloric acid (10%) was added dropwise to the cooled mixture until the evolution of gas ceased. The mixture was concentrated under reduced pressure and the residue was taken up in EtOAc. The EtOAc extract was washed with saturated aqueous NaHCO$_3$, water, brine, dried over Na$_2$SO$_4$, filtered and concentrated to provide the title compound C140. Yield: 200 mg (30%). $^1$H NMR (400 MHz, dmso-d$_6$) δ 7.24-7.49 (m, 5H), 5.10-5.28 (m, 2H), 5.02 (t, 1H), 4.04-4.19 (m, 1H), 3.42-3.60 (m, 2H), 3.25 (dd, 1H), 2.71 (s, 3H).

Step 4. Synthesis of (S)-4-(Hydroxymethyl)-1-methylimidazolidin-2-one

To a solution of compound C140 (200 mg, 0.74 mmol) in MeOH (19 mL) was added palladium on carbon (25 mg) and the mixture was stirred under a hydrogen atmosphere (1 atm) for about 6 h. The mixture was filtered and the filtrate was concentrated. The residue was purified by chromatography to provide the title compound L106. Yield: 61 mg (64%). $^1$H NMR (400 MHz, dmso-d$_6$) δ 3.46-3.55 (m, 1H), 3.31-3.38 (m, 2H), 3.24-3.31 (m, 1H), 3.05 (dd, 1H), 2.59 (s, 3H).

Preparation 60: 1-benzyl-6-hydroxy-1-azaspiro[4.4]nonan-2-one (L107)

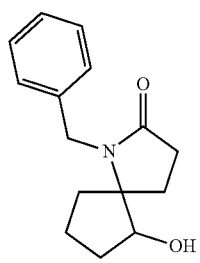 [SMILES: O=C1CCC2(CCCC2O)N1Cc1ccccc1]

Step 1. Synthesis of 1-benzyl-1H-pyrrol-2(5H)-one (C141)

A mixture of 2,5-dimethoxy-2,5-dihydrofuran (12.2 mL, 100 mmol), N-benzylamine (10.9 mL, 100 mmol), conc. HCl (12.5 mL, 150 mmol) and H$_2$O (400 mL) was stirred for about 5 h at about 25° C. The mixture was neutralized with solid NaHCO$_3$ and extracted with EtOAc. The EtOAc extracts were dried over Na$_2$SO$_4$, filtered and concentrated. The residue was purified by chromatography to provide the title compound C141. Yield: 5.0 g (29%). $^1$H NMR (400 MHz, CDCl$_3$) δ 7.26-7.38 (m, 5H), 6.33-6.36 (m, 1H), 5.29-5.32 (m, 1H), 4.65 (s, 2H), 3.14-3.15 (m, 2H).

Step 2. Synthesis of 1-benzyl-2-((tert-butyldimethylsilyl)oxy)-1H-pyrrole (C142)

To a solution of compound C141 (2.0 g, 12 mmol) and Et$_3$N (3.3 mL, 23 mmol) in anhydrous DCM (20 mL) was added t-butyldimethylsilyl triflate (2.4 mL, 12 mmol) at about 25° C. After about 5 h the reaction mixture was diluted with EtOAc and H$_2$O. The aqueous phase was separated and extracted with EtOAc. The combined EtOAc extracts were washed with saturated aqueous NaHCO$_3$ and concentrated. The residue was purified by chromatography to provide the title compound C142. Yield: 2.0 g (61%). $^1$H NMR (400 MHz, CDCl$_3$) δ 7.10-7.15 (m, 4H), 6.90-6.93 (m, 1H), 6.03-6.04 (m, 1H), 5.78-5.80 (m, 1H), 5.07-5.09 (m, 1H), 4.76 (s, 2H), 0.073 (s, 9H), 0.00 (s, 6H).

Step 3. Synthesis of 1-benzyl-5-(1-hydroxycyclobutyl)-1H-pyrrol-2(5H)-one (C143)

To a solution of compound C142 (500 mg, 1.7 mmol) in DCM (12 mL) at 25° C. was added 3 A molecular sieves and cyclobutanone (0.21 mL, 2.8 mmol). The resulting mixture was stirred for about 15 min at about 25° C. and was then cooled to about −78° C. BF$_3$-Et$_2$O (0.32 mL, 370 mg, 2.6 mmol) was added dropwise. The mixture was stirred at about −78° C. for about 2 h then warmed to about 0° C. and quenched with H$_2$O. The DCM was separated, washed with saturated aqueous NaHCO$_3$, and the aqueous phase was extracted with DCM. The DCM extracts were washed with satd. NaHCO$_3$, dried over Na$_2$SO$_4$, filtered and concentrated. The residue was purified by chromatography to provide the title compound C143. Yield: 300 mg (71%). $^1$H NMR (300 MHz, CDCl$_3$) δ 7.09-7.24 (m, 5H), 6.90-6.92 (m, 1H), 6.23-6.25 (m, 1H), 5.00 (d, 1H), 4.27 (d, 1H), 4.05-4.06 (m, 1H), 2.21-2.23 (m, 1H), 1.95-2.04 (m, 2H), 1.82-1.86 (m, 2H), 1.81 (s, 1H), 1.42-1.49 (m, 1H).

Step 4. Synthesis of 1-benzyl-1-azaspiro[4.4]nonane-2,6-dione (C144)

To a solution of compound C143 (300 mg, 1.2 mmol) in DCM (20 mL) at 0° C. was added concentrated HCl (0.2 mL, 2.2 mmol). The mixture was stirred at about 0° C. for about 5 h and concentrated to afford compound C144 which was used without purification. $^1$H NMR (400 MHz, CDCl$_3$) δ 7.06-7.30 (m, 5H), 4.75 (d, 1H), 3.90 (d, 1H), 2.37-2.59 (m, 2H), 2.21-2.37 (m, 1H), 1.99-2.10 (m, 1H), 1.83-1.99 (m, 3H), 1.58-1.83 (m, 3H).

Step 5. Synthesis of 1-benzyl-6-hydroxy-1-azaspiro[4.4]nonan-2-one (L107)

NaBH$_4$ (38 mg, 0.93 mmol) was added to a solution of compound C144 (150 mg, 0.62 mmol) in MeOH (4 mL). The mixture was stirred at about 25° C. for about 20 min before being diluted with H$_2$O and extracted with EtOAc. The combined EtOAc extracts were washed with water, brine, dried over MgSO$_4$, filtered and concentrated. The residue was purified by chromatography to provide the title compound L107 as a mixture of diastereomers. Yield: 105 mg (70%). It was used in the next step without further characterization.

Preparation 61:
(S)-4-(hydroxymethyl)imidazolidin-2-one (L108)

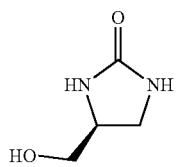

Step 1. Synthesis of methyl
(4S)-2-oxoimidazolidine-4-carboxylate (C145)

A suspension of 1-benzyl 5-methyl (5S)-2-oxoimidazolidine-1,5-dicarboxylate (CAS 168399-08-4, 325 mg, 1.2 mmol) and 10% Pd/C (33 mg) in MeOH (4.7 mL) was shaken under a hydrogen atmosphere at about 25° C. for about 5.5 h. The mixture was filtered and concentrated to afford the title compound C145. Yield: 163 mg (97%). $^1$H NMR (400 MHz, dmso-$d_6$) δ 6.73 (s, 1H), 6.34 (s, 1H), 4.25 (ddd, 1H), 3.52-3.65 (m, 2H), 3.32 (2, 3H).

Step 2. Synthesis of
(4S)-4-(hydroxymethyl)imidazolidin-2-one (L108)

Sodium borohydride (56 mg, 1.4 mmol) was added to a solution of compound C145 (160 mg, 1.1 mmol) at about 0° C. The mixture was stirred at about 0° C. for about 3 h, and then 10% HCl solution was added dropwise until gas evolution ceased. The mixture was concentrated and the residue was diluted with EtOAc. The EtOAc was washed with saturated aqueous NaHCO$_3$, brine, dried over Na$_2$SO$_4$, filtered and concentrated to provide the title compound L108. Yield: 360 mg (a mixture of desired product and salts). This was used in the next step without purification. $^1$H NMR (400 MHz, dmso-$d_6$) δ 3.53-3.61 (m, 1H), 3.30-3.36 (m, 2H), 3.23-3.30 (m, 1H), 3.04 (dd, 1H).

Preparation 62: (3S,3aR,6aS)-5-benzyl-3-(hydroxymethyl)hexahydropyrrolo[3,4-c]pyrrol-1(2H)-one (L109)

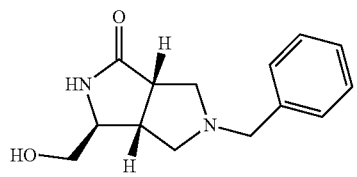 [SMILES: O=C1N[C@H](CO)[C@H]2CN(Cc3ccccc3)C[C@@H]12]

Step 1. Synthesis of (5aS,8aR,8bS)-7-benzyl-3,3-dimethylhexahydro-1H-pyrrolo[3',4':3,4]-pyrrolo[1,2-c]oxazol-5(3H)-one (C146)

A solution of compound P20 (100 mg, 0.65 mmol) in DCM (5 mL) and N-(methoxymethyl)-N-[(trimethylsilyl)methyl]-benzenemethanamine (CAS 93102-05-7, 232 mg, 0.98 mmol) was treated with TFA (0.01 mL, 0.13 mmol) at 0° C. The mixture was kept at about 25° C. for about 16 h, then heated at about 40° C. for about 4 h, before an additional 232 mg of CAS 93102-05-7 was added. Heating was continued for about 16 h. The reaction mixture was cooled to about 25° C., neutralized with Et$_3$N (18 μL, 0.13 mmol), and concentrated. The residue was purified by chromatography to provide the title compound C146. Yield: 110 mg (59%). $^1$H NMR (400 MHz, dmso-$d_6$) δ 7.16-7.41 (m, 5H), 3.98 (dd, 1H), 3.78-3.87 (m, 1H), 3.59-3.68 (m, 1H), 3.48-3.58 (m, 1H), 3.35 (dd, 1H), 3.10 (t, 1H), 2.95 (d, 1H), 2.79 (d, 1H), 2.56-2.66 (m, 1H), 2.24 (t, 1H), 2.18 (dd, 1H), 1.53 (s, 3H), 1.33 (s, 3H).

Step 2. Synthesis of (3S,3aR,6aS)-5-benzyl-3-(hydroxymethyl)hexahydropyrrolo[3,4-c]pyrrol-1(2H)-one (L109)

To a stirred solution of compound C5146 (110 mg, 0.38 mmol) in 6 mL of acetonitrile and 0.6 mL of water was added TFA (36 μL, 0.46 mmol). The reaction mixture was heated at about 60° C. for about 2 h. The reaction mixture was cooled to about 25° C., concentrated, and the residue was purified by chromatography to provide the title compound L109. Yield: 60 mg (64%). $^1$H NMR (400 MHz, CD$_3$OD) δ 7.20-7.37 (m, 5H), 3.61 (s, 2H), 3.46-3.55 (m, 2H), 3.39-3.45 (m, 1H), 2.92-3.02 (m, 2H), 2.66-2.78 (m, 2H), 2.57 (dd, 1H), 2.45-2.53 (m, 1H).

Preparation 63: 2-((5S)-5-(hydroxymethyl)-2-oxopyrrolidin-3-yl)acetonitrile (L110)

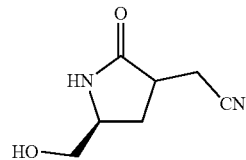 [SMILES: N#CCC1C[C@@H](CO)NC1=O]

Step 1: Synthesis of (5S)-tert-butyl 5-(((tert-butoxycarbonyl)oxy)methyl)-3-(cyanomethyl)-2-oxopyrrolidine-1-carboxylate (C147)

LDA solution (2 M, 2.4 mL) was added to a solution of (S)-tert-butyl 2-(((tert-butoxycarbonyl)-oxy)methyl)-5-oxopyrrolidine-1-carboxylate (CAS 360782-62-3, 1.0 g, 3.2 mmol) in THF (20 mL) at about −78° C. After about 30 min, bromoacetonitrile (0.22 mL, 3.2 mmol) was added. The mixture was stirred at about −78° C. for about 20 min, and then saturated aqueous NaHCO$_3$ (2 mL) was added. The mixture was diluted with H$_2$O and extracted with EtOAc. The combined EtOAc extracts were washed with H$_2$O, brine, dried over MgSO$_4$, filtered and concentrated. The residue was purified by chromatography to provide the title compound C147. Yield: 0.86 g (77%). $^1$H NMR (400 MHz, CDCl$_3$) δ 4.50 (dd, 1H), 4.36-4.44 (m, 1H), 4.10-4.19 (m, 1H), 3.08-3.22 (m, 1H), 2.88 (dd, 1H), 2.60 (dd, 1H), 2.41 (dd, 1H), 2.06-2.20 (m, 1H), 1.53-1.62 (m, 18H).

Step 2. Synthesis of 2-((5S)-5-(hydroxymethyl)-2-oxopyrrolidin-3-yl)acetonitrile (L110)

Concentrated HCl (2 mL) was added to a solution of compound C147 (500 mg, 1.4 mmol) in MeOH (5 mL) and DCM (5 mL). The mixture was stirred at about 25° C. overnight, then concentrated provide the title compound L110. ¹H NMR (400 MHz, CD₃OD) δ 3.76-3.67 (m, 1H), 3.56-3.48 (m, 2H), 2.90-2.87 (m, 1H), 2.73-2.65 (m, 2H), 2.27-2.24 (m, 1H), 2.12-2.05 (m, 1H).

Preparation 64: (1S,3aS,6aR)-di-tert-butyl 1-(hydroxymethyl)-3-oxotetrahydropyrrolo[3,4-c]pyrrole-2,5(1H,3H)-dicarboxylate (L111)

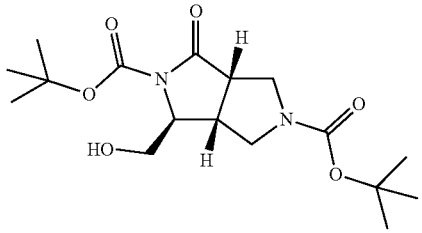 [SMILES: CC(C)(C)OC(=O)N1C[C@@H]2[C@@H](CO)N(C(=O)OC(C)(C)C)C(=O)[C@@H]2C1]

Step 1. Synthesis of (1S,3aS,6aR)-tert-butyl 5-benzyl-1-(((tert-butyldimethylsilyl)oxy)methyl)-3-oxo-hexahydropyrrolo[3,4-c]pyrrole-2(1H)-carboxylate (C148)

A solution of (S)-tert-butyl 2-(((tert-butyldimethylsilyl)oxy)methyl)-5-oxo-2,5-dihydro-1H-pyrrole-1-carboxylate (CAS 81658-27-7, 3.0 g, 9.2 mmol) and N-(methoxymethyl)-N-[(trimethylsilyl)methyl]-benzenemethanamine (CAS 93102-05-7, 3.27 g, 13.8) in DCM (80 mL) was treated with TFA (208 mg, 1.84 mmol) at about 25° C. and kept for about 18 h. Triethylamine (0.26 mL, 1.84 mmol) was added and mixture was concentrated. The residue was purified by chromatography to provide the title compound C148. Yield: 2.6 g (61%). ¹H NMR (400 MHz, dmso-d₆) δ 7.27-7.34 (m, 2H), 7.19-7.27 (m, 3H), 3.87-3.91 (m, 1H), 3.84 (dd, 1H), 3.65 (d, 1H), 3.53 (s, 2H), 2.90-2.97 (m, 1H), 2.82-2.89 (m, 1H), 2.65-2.73 (m, 2H), 2.54-2.63 (m, 2H), 1.45 (s, 9H), 0.82 (s, 9H), 0.01 (s, 3H), −0.02 (s, 3H)

Step 2: Synthesis of (1S,3aS,6aR)-di-tert-butyl 1-(((tert-butyldimethylsilyl)oxy)methyl)-3-oxotetrahydropyrrolo[3,4-c]pyrrole-2,5(1H,3H)-dicarboxylate (C149)

To a solution of compound C148 (2.2 g, 4.8 mmol) and di-t-butyl dicarbonate (3.1 g, 14.4 mmol) in MeOH (150 mL) was added palladium on carbon (200 mg) and the mixture was stirred under a hydrogen atmosphere (1 atm) for about 18 h. The mixture was filtered and the filtrate was concentrated. The residue was purified by chromatography to provide the title compound C149. Yield: 1.12 g (49%). ¹H NMR (400 MHz, CD₃OD) δ 3.99-4.10 (m, 2H), 3.68-3.88 (m, 4H), 3.45-3.55 (m, 1H), 3.11 (dd, 1H), 2.87-2.99 (m, 1H), 1.54 (s, 9H), 1.45 (s, 9H), 0.89 (s, 9H), 0.08 (s, 3H), 0.06 (s, 3H).

Step 3. Synthesis of (1S,3aS,6aR)-di-tert-butyl 1-(hydroxymethyl)-3-oxotetrahydropyrrolo[3,4-c] pyrrole-2,5(1H,3H)-dicarboxylate (L111)

A solution of compound C149 (1.22 g, 2.6 mmol) in THF (100 mL) was treated with tetrabutylammonium fluoride (1 M, 3.9 mL) at about 25° C. After about 2 h, the mixture was concentrated. The residue was purified by chromatography to provide the title compound L111. Yield: 600 mg (65%). ¹H NMR (400 MHz, CD₃OD) δ 4.18 (dd, 1H), 4.05 (dd, 1H), 3.69-3.82 (m, 2H), 3.56-3.69 (m, 1H), 3.47 (dd, 1H), 3.21 (dd, 1H), 3.08-3.17 (m, 1H), 2.87-2.99 (m, 1H), 1.46 (s, 9H), 1.46 (s, 9H)

Preparation 65: (4R,5S)-4-(hydroxymethyl)-5-methyloxazolidin-2-one (L112)

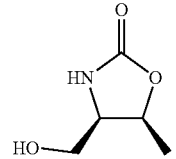

Step 1. Synthesis of (4R,5S)-4-(hydroxymethyl)-5-methyloxazolidin-2-one (L112)

To a mixture of (4S,5S)-methyl 5-methyl-2-oxooxazolidine-4-carboxylate (CAS 182267-22-7, 165 mg, 1.0 mmol) in EtOH (6 mL) at about 0° C. was added NaBH₄ (43 mg, 1.1 mmol). After gas evolution ceased, the mixture was stirred at about 25° C. for about 4 h. The mixture was re-cooled to about 0° C. and additional NaBH₄ (35 mg, 0.9 mmol) was added. The mixture was warmed to about 25° C. and after about 2 h, saturated aqueous NH₄Cl was added and the mixture was stirred overnight. The mixture was filtered and the solids were washed with EtOH. The filtrate was concentrated and the residue was purified by chromatography to provide the title compound L112. Yield: 97 mg (72%). ¹H NMR (400 MHz, CDCl₃) δ 6.72 (s, 1H), 4.72-4.88 (m, 1H), 3.99 (br. s., 1H), 3.74-3.86 (m, 1H), 3.54-3.73 (m, 2H), 1.38 (d, 3H).

Preparation 66: (1S,4S,5R)-4-(hydroxymethyl)-3-azabicyclo[3.1.0]hexan-2-one (L113)

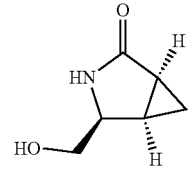

Step 1. Synthesis of (5aS,6aR,6bS)-3,3-dimethyltetrahydro-1H-cyclopropa[3,4]pyrrolo[1,2-c]oxazol-5(3H)-one (C150)

A solution of compound P20 (1.0 g, 6.5 mmol) in DCM (40 mL) was cooled to 0° C. and a solution of diazomethane (prepared from 6.7 g of N-methyl-N-nitrosurea in 65 mL of diethyl ether) was added. Palladium acetate (72 mg, 0.32 mmol) was added in portions at about 0° C. The mixture was allowed to warm to about 25° C. for about 16 h. The mixture was filtered and a second portion of diazomethane and palladium acetate were added and stirred over night. The addition of diazomethane and palladium acetate were repeated twice more. The mixture was filtered and the filtrate was concentrated. The residue was purified by HPLC to the title compound C150. Yield: 100 mg (9%). $^1$H NMR (400 MHz, CD$_3$OD) δ 3.47-3.57 (m, 3H), 1.90-1.98 (m, 1H), 1.75-1.81 (m, 1H), 1.12-1.19 (m, 1H), 0.58-0.63 (m, 1H).

Step 2. Synthesis of (1S,4S,5R)-4-(hydroxymethyl)-3-azabicyclo[3.1.0]hexan-2-one (L113)

To a stirred solution of compound C150 (95 mg, 0.57 mmol) in 5 mL of acetonitrile and 1 mL of water was added 4-toluenesulfonic acid (5 mg, 0.03 mmol). The reaction mixture was heated at about 90° C. for about 1 h. The reaction mixture was cooled to about 25° C., concentrated, and the residue was purified by chromatography to provide the title compound L113. Yield: 35 mg (33%). $^1$H NMR (400 MHz, CD$_3$OD) δ 4.61 (br. s, 1H), 3.95 (d, 1H), 3.65 (dd, 1H), 3.51 (dd, 1H), 3.34 (dt, 1H), 2.01-2.10 (m, 1H), 0.98-1.05 (m, 1H), 0.78-0.83 (m, 1H).

Preparation 67: (1S,2S,5R)-tert-butyl 6,6-dichloro-2-(hydroxymethyl)-4-oxo-3-azabicyclo[3.1.0]hexane-3-carboxylate (L114)

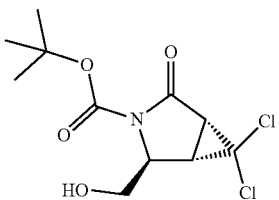 [SMILES: CC(C)(C)OC(=O)N1C(=O)[C@H]2[C@@H]([C@H]1CO)C2(Cl)Cl]

Step 1. Synthesis of (1S,2S,5R)-tert-butyl 2-(((tert-butyldimethylsilyl)oxy)methyl)-6,6-dichloro-3-azabicyclo[3.1.0]hexane-3-carboxylate (C151)

To a stirred solution of (S)-tert-butyl 2-(((tert-butyldimethylsilyl)oxy)methyl)-2,5-dihydro-1H-pyrrole-1-carboxylate (CAS 247200-49-3, 5.0 g, 16 mmol) and benzyltriethyl NH$_4$Cl (0.73 g, 3.2 mmol) in CHCl$_3$ (100 mL) was added 50% NaOH solution (100 mL). The mixture was stirred at about 25° C. for about 16 h, then diluted with DCM and separated. The aqueous phase was extracted twice with additional DCM. The combined DCM extracts were washed with water, brine, dried over Na$_2$SO$_4$, filtered and concentrated. The residue was purified by chromatography to provide the title compound C151. Yield: 3.6 g (57%) as colorless liquid. $^1$H NMR (400 MHz, CDCl$_3$) δ 3.90-4.09 (m, 1H), 3.81-3.89 (m, 1H), 3.73-3.81 (m, 1H), 3.61-3.73 (m, 1H), 3.57 (dd, 1H), 2.28-2.39 (m, 1H), 2.22-2.29 (m, 1H), 1.43 (d, 9H), 0.90 (d, 9H), 0.03-0.10 (m, 6H)

Step 2. Synthesis of (1S,2S,5R)-tert-butyl 2-(((tert-butyldimethylsilyl)oxy)methyl)-6,6-dichloro-4-oxo-3-azabicyclo[3.1.0]hexane-3-carboxylate (C152)

Sodium periodate (654 mg, 3.0 mmol) was dissolved in water (6.5 mL) and a catalytic amount of hydrated ruthenium dioxide was added. After stirring for 5 min, a solution of compound C151 (400 mg, 1.0 mmol) in EtOAc (6.5 mL) was added. The resulting mixture was stirred vigorously overnight. The phases were separated and the EtOAc phase was washed with sodium bisulfate solution, brine, dried over Na$_2$SO$_4$, filtered and concentrated. The residue was purified by chromatography to provide the title compound C152. Yield: 290 mg (70%). $^1$H NMR (400 MHz, CDCl$_3$) δ 4.16-4.21 (m, 1H), 3.92-3.98 (m, 1H), 3.85-3.91 (m, 1H), 2.82 (dd, 1H), 2.56 (d, 1H), 1.51 (s, 9H), 0.89 (s, 9H), 0.08 (s, 3H), 0.06 (s, 3H).

Step 3. Synthesis of (1S,2S,5R)-tert-butyl 6,6-dichloro-2-(hydroxymethyl)-4-oxo-3-azabicyclo[3.1.0]hexane-3-carboxylate (L114)

Compound C152 (290 mg, 0.7 mmol) in THF (8 mL) was treated with tetrabutylammonium fluoride (1 M, 1.4 mL) at about 25° C. The mixture was stirred at about 25° C. for about 4 h, then water was added and the mixture was extracted twice with EtOAc (15 mL each). The combined EtOAc extracts were washed with brine, dried over MgSO$_4$, filtered and concentrated. The residue was purified by chromatography to provide the title compound L114. Yield: 124 mg (59%). $^1$H NMR (400 MHz, CDCl$_3$) δ 5.57 (br. s., 1H), 4.19-4.27 (m, 1H), 4.08-4.15 (m, 1H), 3.90 (t, 1H), 2.81 (d, 1H), 2.55 (d, 1H), 1.51 (s, 9H).

Preparation 68: (S)-5-((S)-1-hydroxyethyl)pyrrolidin-2-one (L115)

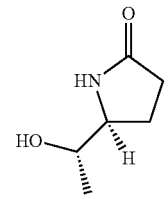

Step 1. Synthesis of (S)-5-((S)-1-hydroxyethyl)pyrrolidin-2-one (L115)

A mixture of (S)-5-((S)-1-hydroxyethyl)-1-(9-phenyl-9H-fluoren-9-yl)pyrrolidin-2-one (CAS 191406-21-0, 750 mg, 2.0 mmol) and palladium on carbon (350 mg) in MeOH (36 mL) and EtOAc (36 mL) was hydrogenated at about 40 psi for about 30 h at about 25° C. The mixture was filtered and the filtrate was concentrated. The residue was purified by chromatography to provide the title compound L115. Yield: 220 mg (84%). $^1$H NMR (400 MHz, dmso-d$_6$) δ 7.51 (br. s, 1H), 4.66 (d, 1H), 3.41-3.45 (m, 1H), 3.31-3.36 (m, 1H), 2.08-2.13 (m, 2H), 1.93-2.05 (m, 1H), 1.62-1.70 (m, 1H), 0.98 (d, 3H).

Preparation 69: (4S,5S)-4-(2-fluoroethyl)-5-(hydroxymethyl)pyrrolidin-2-one (L116)

Step 1. Synthesis of (7R,7aS)-7-(2-hydroxyethyl)-3,3-dimethyltetrahydropyrrolo[1,2-c]oxazol-5(3H)-one (C153)

Cyclohexene (4.3 mL, 42 mmol) was added to a solution of borane in THF (1 M, 21.1 mL) at about 0° C. After 30 min, the mixture was warmed to about 25° C. and stirred approximately 30 min longer. After cooling to about 0° C., a solution of compound C55 (2.55 g, 14.1 mmol) in DCM (70 mL) was added dropwise over about 15 min. After about 90 minutes at 0° C., water (40 mL) was added and the mixture was stirred for approximately 30 min at about 0° C.

The mixture was partially concentrated to remove about 50 mL of DCM and THF (20 mL) was added. Sodium perborate tetrahydrate (8.93 g, 56 mmol) was added and the mixture was stirred overnight while being allowed to warm to about 20° C. The phases were separated and the aqueous phase was extracted 5 times with DCM and 3 times with MTBE. The combined DCM and MTBE extracts were dried over $Na_2SO_4$, filtered and concentrated. The residue was purified by chromatography to provide the title compound C153. Yield: 2.04 g (73%). $^1$H NMR (400 MHz, $CDCl_3$) δ 4.38 (dt, 1H), 3.91 (dd, 1H), 3.68-3.77 (m, 2H), 3.60-3.68 (m, 1H), 2.94 (dd, 1H), 2.53-2.65 (m, 1H), 2.34 (dd, 1H), 1.71-1.82 (m, 1H), 1.65 (s, 3H), 1.51-1.62 (m, 2H), 1.48 (s, 3H).

Step 2. Synthesis of (7S,7aS)-7-(2-fluoroethyl)-3,3-dimethyltetrahydropyrrolo[1,2-c]oxazol-5(3H)-one (C154)

To a solution of compound C153 (1.43 g, 7.2 mmol) in DCM (36 mL) at about 0° C. were added 2,6-lutidine (2.09 mL, 17.9 mmol), DAST (1.75 mL, 14.4 mmol), and triethylamine trihydrofluoride (1.16 mL, 7.2 mmol). The mixture was stirred overnight while warming to about 20° C., then was added dropwise into saturated aqueous $NaHCO_3$. The mixture was extracted 4 times with DCM. The combined DCM extracts were dried over $Na_2SO_4$, filtered and concentrated. The residue was purified by chromatography to provide the title compound C154. Yield: 1.06 g (73%). $^1$H NMR (400 MHz, $CD_3OD$) δ 4.55-4.52 (m, 1H), 4.47-4.40 (m, 2H), 3.92 (dd, 1H), 3.78-3.73 (m, 1H), 2.99 (dd, 1H), 2.66-2.58 (m, 1H), 2.36 (dd, 1H), 2.01-1.86 (m, 1H), 1.74-1.61 (m, 1H), 1.60 (s, 3H), 1.44 (s, 3H). $^{19}$F NMR (376 MHz, $CD_3OD$) δ −221.50.

Step 3. Synthesis of 4S,5S)-4-(2-fluoroethyl)-5-(hydroxymethyl)pyrrolidin-2-one (L116)

To a stirred solution of compound C154 (130 mg, 0.65 mmol) in 6.5 mL of acetonitrile and 1.3 mL of water was added TFA (5 uL, 0.07 mmol). The reaction mixture was heated at about 90° C. for about 1 h. The reaction mixture was cooled to about 25° C., concentrated, then twice redissolved in acetonitrile and water and concentrated to provide the title compound L116. Yield: 90 mg (86%). $^1$H NMR (400 MHz, $CD_3OD$) δ 4.63-4.51 (m, 1H), 4.51-4.37 (m, 1H), 3.70-3.57 (m, 3H), 2.72 (m, 1H), 2.38-2.18 (m, 2H), 2.14-1.95 (m, 1H), 1.95-1.73 (m, 1H). $^{19}$F NMR (376 MHz, $CD_3OD$) δ −220.91.

Preparation 70: (4R,5S)-4-(fluoromethyl)-5-(hydroxymethyl)pyrrolidin-2-one (L117)

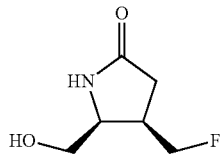

Step 1. Synthesis of (7R,7aS)-7-(1,2-dihydroxyethyl)-3,3-dimethyltetrahydropyrrolo[1,2-c]oxazol-5 (3H)-one (C155)

To a solution of compound C55 (1.50 g, 8.3 mmol) in acetone (30 mL) and $H_2O$ (3 mL) was added N-methylmorpholine-N-oxide (1.38 g, 11.8 mmol) followed by osmium tetroxide (31 mg, 0.12 mmol) at about 25° C. The mixture was stirred at about 25° C. for about 3 h, then concentrated. The residue was purified by chromatography to provide the title compound C155 as a mixture of two diastereomers. Yield: 1.47 g (82%).

Step 2. Synthesis of (7R,7aS)-7-(hydroxymethyl)-3,3-dimethyltetrahydropyrrolo[1,2-c]oxazol-5(3H)-one (C156)

To a solution of compound C155 (2.00 g, 9.3 mmol) in MeCN (50 mL) was added water (5 mL) followed by sodium periodate (2.19 g, 10.2 mmol) at about 25° C. The mixture was stirred at about 25° C. for 1 h, then cooled to about 0° C. and treated with $NaBH_4$ (538 mg, 13.9 mmol) and stirred for about 1 h. The mixture was filtered, concentrated, and the residue was taken up in DCM and filtered. The filtrate was concentrated to provide the title compound C156. Yield: 1.69 g (98%). $^1$H NMR (400 MHz, $CD_3OD$) δ 4.43 (td, 1H), 3.98-3.84 (m, 2H), 3.63-3.48 (m, 2H), 2.98 (dd, 1H), 2.59-2.49 (m, 1H), 2.27 (dd, 1H), 1.59 (s, 3H), 1.43 (s, 3H).

Step 3. Synthesis of (7R,7aS)-7-(fluoromethyl)-3,3-dimethyltetrahydropyrrolo[1,2-c]oxazol-5(3H)-one (C157)

To a solution of compound C156 (1.70 g, 9.3 mmol) in DCM (20 mL) at about 0° C. were added 2,6-lutidine (2.7 mL, 23 mmol), DAST (2.3 mL, 18.6 mmol), and triethylamine trihydrofluoride (1.5 mL, 9.3 mmol). The mixture was stirred at about 25° C. for about 18 h. The reaction was quenched with saturated aqueous $NaHCO_3$ and extracted with DCM. The combined DCM extracts were dried over $Na_2SO_4$, filtered and concentrated. The residue was purified by chromatography to provide the title compound C157. Yield: 800 mg (46%). $^1$H NMR (400 MHz, $CDCl_3$) δ 4.34-4.63 (m, 3H), 4.01 (dd, 1H), 3.79-3.87 (m, 1H), 3.03 (ddd, 1H), 2.72-2.85 (m, 1H), 2.26 (dd, 1H), 1.67 (s, 3H), 1.51 (s, 3H). $^{19}$F NMR (376 MHz, $CDCl_3$) δ −218.27.

Step 4. Synthesis of (4R,5S)-4-(fluoromethyl)-5-(hydroxymethyl)pyrrolidin-2-one (L117)

To a stirred solution of compound C157 (87 mg, 0.46 mmol) in 4 mL of acetonitrile and 1 mL of water was added TFA (0.1 mL, 1.4 mmol). The reaction mixture was heated at about 90° C. for about 1 h. The reaction mixture was cooled to about 25° C., filtered, concentrated, then redissolved in MeOH and toluene and concentrated. The residue was dissolved in MeOH and toluene and concentrated several more times to provide the title compound L117. Yield: 57 mg (83%). $^1$H NMR (400 MHz, $CD_3OD$) δ 4.47-4.75 (m, 2H), 3.73-3.82 (m, 1H), 3.58-3.73 (m, 2H), 2.96 (td, 1H), 2.31 (qd, 2H). $^{19}$F NMR (376 MHz, $CD_3OD$) δ −222.48.

Preparation 71: (3S,4R,5S)-3-fluoro-4-(fluoromethyl)-5-(hydroxymethyl)pyrrolidin-2-one (L118)

Step 1. Synthesis of (6S,7R,7aS)-6-fluoro-7-(fluoromethyl)-3,3-dimethyltetrahydropyrrolo[1,2-c]oxazol-5(3H)-one (C158)

A solution of compound C157 (730 mg, 3.9 mmol) in THF (20 mL) was slowly treated with LDA (2 M, 2.9 mL) at −78° C. After 30 min at −78° C., a pre-cooled (−78° C.)

solution of NFSI (1.97 g, 6.2 mmol) in THF (20 mL) was added via cannula. Immediately after the complete addition of NFSI, the reaction was quenched with water at −78° C. and allowed to warm to 25° C. The solution was diluted with additional water (15 mL) and extracted with MTBE (50 mL). The aqueous phase was again extracted with MTBE (50 mL) and the combined MTBE extracts were dried over Na$_2$SO$_4$, filtered and concentrated. The residue was purified by chromatography to provide the title compound C158. Yield: 120 mg (15%). $^1$H NMR (400 MHz, CDCl$_3$) δ 5.36 (dd, 1H), 4.78-4.65 (m, 1H), 4.65-4.53 (m, 1H), 4.17-4.04 (m, 2H), 3.96-3.86 (m, 1H), 3.28-3.08 (m, 1H), 1.69 (s, 3H), 1.50 (s, 3H). $^{19}$F NMR (376 MHz, CDCl$_3$) δ −202.40, −228.51. There was also obtained (6R,7R,7aS)-6-fluoro-7-(fluoromethyl)-3,3-dimethyltetrahydropyrrolo-[1,2-c]oxazol-5(3H)-one (C159). Yield: 540 mg (68%). $^1$H NMR (400 MHz, CDCl$_3$) δ 4.95 (dd, 1H), 4.65 (d, 1H), 4.50-4.58 (m, 2H), 4.04 (ddd, 1H), 3.75 (ddd, 1H), 2.76-2.96 (m, 1H), 1.65 (s, 3H), 1.54 (s, 3H). $^{19}$F NMR (376 MHz, CDCl$_3$) δ −187.58, −223.88.

Step 2. Epimerization of (6R,7R,7aS)-6-fluoro-7-(fluoromethyl)-3,3-dimethyltetrahydropyrrolo-[1,2-c]oxazol-5(3H)-one (C159)

LDA (2 M, 0.89 mL) was added to a solution of compound C159 (240 mg, 1.2 mmol) in toluene (3 mL) at −78° C. The mixture was stirred for 30 min, after which a −78° C. solution of BHT (517 mg, 2.3 mmol) in toluene (6 mL) was added. Immediately after the addition of BHT, water (2 mL) was added and the mixture was allowed to warm to 20° C. EtOAc was added and the aqueous phase was extracted again with EtOAc. The combined EtOAc extracts were dried over Na$_2$SO$_4$, filtered and concentrated. The residue was purified by chromatography to provide compound C158. Yield: 113 mg (47%).

Step 3. Synthesis of (3S,4R,5S)-3-fluoro-4-(fluoromethyl)-5-(hydroxymethyl)pyrrolidin-2-one (L118)

To a stirred solution of compound C158 (370 mg, 1.8 mmol) in 12 mL of acetonitrile and 3 mL of water was added silica bound 4-toluenesulfonic acid (132 mg, 0.09 mmol). The reaction mixture was heated at 80° C. for 2 h. The reaction mixture was cooled to 25° C. and concentrated to provide the title compound L118. Yield: 250 mg (84%). $^1$H NMR (400 MHz, CD$_3$OD) δ 5.03 (dd, 1H), 4.81-4.74 (m, 1H), 4.74-4.61 (m, 1H), 3.86-3.77 (m, 1H), 3.69 (dd, 1H), 3.61 (dd, 1H), 3.15-2.94 (m, 1H). $^{19}$F NMR (376 MHz, CD$_3$OD) δ −203.74, −227.31.

Preparation 72: (3S,4S,5S)-3-fluoro-4-(2-fluoroethyl)-5-(hydroxymethyl)pyrrolidin-2-one (L121)

Step 1. Synthesis of (6S,7S,7aS)-6-fluoro-7-(2-fluoroethyl)-3,3-dimethyltetrahydropyrrolo[1,2-c]oxazol-5(3H)-one (C160)

A solution of compound C154 (1.01 g, 5.0 mmol) in THF (25 mL) was slowly treated with LDA (2 M, 3.8 mL) at −78° C. After 30 min at −78° C., a pre-cooled (−78° C.) solution of NFSI (2.58 g, 8.0 mmol) in THF (25 mL) was added via cannula. After 20 min, the reaction was quenched with water (4 mL) at −78° C. and allowed to warm to 25° C. The solution was diluted with additional water (25 mL) and extracted with MTBE (25 mL). The aqueous phase was extracted 3 times with MTBE (20 mL each) and the combined MTBE extracts were dried over Na$_2$SO$_4$, filtered and concentrated. The residue was purified by chromatography to provide the title compound C160. Yield: 350 mg (32%). 1H NMR (400 MHz, CDCl$_3$) δ 5.29 (dd, 1H), 4.48-4.66 (m, 1H), 4.51 (ddd, 1H), 4.11 (dt, 1H), 3.99-4.06 (m, 1H), 3.71-3.79 (m, 1H), 2.98-3.08 (m, 1H), 1.75-2.07 (m, 2H), 1.68 (s, 3H), 1.49 (s, 3H). $^{19}$F NMR (376 MHz, CDCl$_3$) δ −198.87, −219.80. There was also obtained (6R,7S,7aS)-6-fluoro-7-(2-fluoroethyl)-3,3-dimethyltetrahydropyrrolo-[1,2-c]oxazol-5(3H)-one (C161). Yield: 516 mg (47%). $^1$H NMR (400 MHz, CDCl$_3$) δ 4.83 (dd, 1H), 4.58-4.64 (m, 1H), 4.44-4.53 (m, 2H), 3.99 (dd, 1H), 3.57 (dd, 1H), 2.64-2.79 (m, 1H), 1.72-2.01 (m, 2H), 1.65 (s, 3H), 1.51 (s, 3H). $^{19}$F NMR (376 MHz, CDCl$_3$) δ −185.95, −219.45.

Step 2. Epimerization of (6R,7S,7aS)-6-fluoro-7-(2-fluoroethyl)-3,3-dimethyltetrahydropyrrolo-[1,2-c]oxazol-5(3H)-one (C161)

LDA (2 M, 0.34 mL) was added to a solution of compound C161 (100 mg, 0.46 mmol) in toluene (2 mL) at about −78° C. The mixture was stirred for 30 min, after which a about −78° C. solution of BHT (201 mg, 0.91 mmol) in toluene (4 mL) was added. Immediately after the addition of BHT, water (4 mL) was added and the mixture was allowed to warm to about 20° C. MTBE was added and the phases were separated. The MTBE extract was dried over MgSO$_4$, filtered and concentrated. The residue was purified by chromatography to provide compound C160. Yield: 36 mg (36%).

Step 3. Synthesis of (3S,4S,5S)-3-fluoro-4-(2-fluoroethyl)-5-(hydroxymethyl)pyrrolidin-2-one (L121)

To a stirred solution of compound C160 (460 mg, 0.39 mmol) in 21 mL of acetonitrile and 5 mL of water was added TFA (8 uL, 0.1 mmol). The reaction mixture was heated at 90° C. for 1 h. The reaction mixture was cooled to 25° C., concentrated, then twice redissolved in acetonitrile and water and concentrated. The residue was triturated with CHCl$_3$ to provide the title compound L121. Yield: 270 mg (72%). $^1$H NMR (400 MHz, CD$_3$OD) δ 4.86 (dd, 1H), 4.62-4.70 (m, 1H), 4.50-4.58 (m, 1H), 3.71-3.82 (m, 2H), 3.50-3.57 (m, 1H), 2.78 (m, 1H), 1.95-2.10 (m, 2H). $^{19}$F NMR (376 MHz, CD$_3$OD) δ −194.88, −217.30.

Preparation 73: (±)-(3R,4R)-tert-butyl 3-(hydroxymethyl)-4-(trifluoromethyl)pyrrolidine-1-carboxylate (L122)

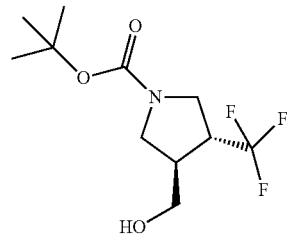 [SMILES: CC(C)(C)OC(=O)N1C[C@H](CO)[C@@H](C(F)(F)F)C1]

Step 1. Synthesis of (±)-(3R,4R)-ethyl 1-benzyl-4-(trifluoromethyl)pyrrolidine-3-carboxylate (C164)

To a solution of ethyl (E)-4,4,4-trifluorocrotonate (CAS 25597-16-4, 6.0 g, 36 mmol) and TFA (0.55 mL, 7 mmol) in DCM (60 mL) at about 0° C. was added N-(methoxymethyl)-N-[(trimethylsilyl)methyl]-benzenemethanamine (CAS 93102-05-7, 16.85 g, 71 mmol) over a period of about 20 minutes. The reaction mixture was then heated at reflux for 16 h. It was diluted with DCM (100 mL), washed with saturated aqueous $NaHCO_3$ solution (2×100 mL), water (100 mL), and brine (50 mL). The DCM extracts were dried over $Na_2SO_4$, filtered and concentrated. The residue was purified by chromatography to provide the title compound C164. Yield: 10.5 g (99%). $^1$H NMR (400 MHz, dmso-$d_6$) δ 7.23-7.34 (m, 5H), 4.07-4.15 (m, 2H), 3.64 (d, 1H), 3.54 (d, 1H), 3.35-3.41 (m, 1H), 3.12 (q, 1H), 2.81 (t, 2H), 2.69-2.73 (m, 1H), 2.55-2.59 (m, 1H), 1.17 (t, 3H).

Step 2. Synthesis of (±)-(3R,4R)-1-tert-butyl 3-ethyl 4-(trifluoromethyl)pyrrolidine-1,3-dicarboxylate (C165)

To a solution of compound C164 (2.0 g, 6.6 mmol) and di-t-butyl dicarbonate (2.3 mL, 9.97 mmol) in EtOH (30 mL) was added palladium hydroxide on carbon (600 mg) and the mixture was stirred under a hydrogen atmosphere (1 atm) for about 16 h. The mixture was filtered and the filtrate was concentrated. The residue was purified by chromatography to provide the title compound C165. Yield: 1.8 g (87%). $^1$H NMR (400 MHz, dmso-$d_6$) δ 4.13 (q, 2H), 3.60-3.68 (m, 2H), 3.43-3.59 (m, 2H), 3.25-3.39 (m, 2H), 1.39 (s, 9H), 1.19 (t, 1H).

Step 3. Synthesis of (±)-(3R,4R)-tert-butyl 3-(hydroxymethyl)-4-(trifluoromethyl)pyrrolidine-1-carboxylate (L122)

A solution of compound C165 (1.8 g, 5.8 mmol) in THF (20 mL) was cooled to about 0° C. and lithium borohydride (630 mg, 29 mmol) was added in portions. The mixture was heated under reflux for about 16 hours. It was then cooled to about 25° C. and diluted with EtOAc (50 mL). The EtOAc extract was washed with water, brine, dried over $Na_2SO_4$, filtered and concentrated. The residue was purified by chromatography to provide the title compound L122. Yield: 1.3 g (83%). $^1$H NMR (400 MHz, dmso-$d_6$) δ 4.95 (t, 1H), 3.55 (br. s, 1H), 3.33-3.46 (m, 4H), 3.14-3.19 (m, 1H), 3.02 (br. s, 1H), 2.44 (br. s, 1H), 1.39 (s, 9H).

Preparation 74: (3S,4S,5S)-3,4-$d_2$-4-ethyl-3-fluoro-5-(hydroxymethyl) pyrrolidin-2-one (L123)

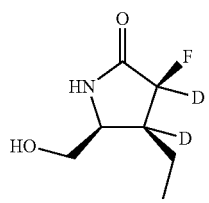

Step 1. Synthesis of (S)-7-ethyl-6-fluoro-3,3-dimethyl-1,7a-dihydropyrrolo[1,2-c]oxazol-5(3H)-one (C172)

A solution of compound C62 (2.00 g, 9.9 mmol) and diphenyl diselenide (3.32 g, 10.4 mmol) in THF (40 mL) was treated with lithium hexamethyldisilazide (1 M, 10.4 mL) at about 0° C. The mixture was kept at about 0° C. for about 30 min, then was warmed to about 25° C. for about 3 h. Water and EtOAc were added and the phases were separated. The aqueous phase was extracted with EtOAc, and the combined EtOAc extracts were dried over $Na_2SO_4$, filtered and concentrated. The residue was dissolved in DCM (100 mL) and pyridine (5.1 mL, 63 mmol) and was treated with hydrogen peroxide (30%, 4.8 mL, 47 mmol) at about 0° C. The mixture was stirred at about 0° C. for about 30 min, then allowed to warm to about 25° C. for about 2 h. The mixture was washed with saturated aqueous $NaHCO_3$, 1 M NaOH (twice), water, and brine. The DCM extract was dried over $MgSO_4$, filtered and concentrated. The residue was purified by chromatography to provide the title compound C172. Yield: 1.56 g (55%). $^1$H NMR (400 MHz, $CDCl_3$) δ 4.36 (dt, 1H), 4.21 (dd, 1H), 3.27-3.37 (m, 1H), 2.31-2.50 (m, 2H), 1.67 (s, 3H), 1.57 (s, 3H), 1.16 (t, 3H).

Step 2. Synthesis of (3S,4S,5S)-3,4-$d_2$-4-ethyl-3-fluoro-5-(hydroxymethyl) pyrrolidin-2-one (L123)

A solution of compound C172 (1.20 g, 6.0 mmol) in ethanol-$d_1$ (50 mL) was treated with a rhodium on carbon catalyst (5 mg) and stirred under a deuterium atmosphere at a pressure of 1 atmosphere and a temperature of about 20° C. for about 2 h. The mixture was filtered and concentrated. The residue was purified by chromatography to provide the title compound L123. Yield: 250 mg (25%). $^1$H NMR (400 MHz, $CDCl_3$) δ 7.02 (br. s., 1H), 3.72-3.82 (m, 2H), 3.55-3.66 (m, 1H), 2.61 (t, 1H), 1.59-1.71 (m, 1H), 1.44-1.57 (m, 1H), 1.06 (t, 3H).

Preparation 75: (3R,4R,5S)-3-fluoro-4-(fluoromethyl)-5-(hydroxymethyl)pyrrolidin-2-one (L124)

Step 1. Synthesis of (3R,4R,5S)-3-fluoro-4-(fluoromethyl)-5-(hydroxymethyl)pyrrolidin-2-one (L124)

To a stirred solution of compound C159 (70 mg, 0.34 mmol) in 4 mL of acetonitrile and 1 mL of water was added TFA (3 uL, 0.03 mmol). The reaction mixture was heated at 90° C. for 1 h. The reaction mixture was cooled to 25° C. and concentrated to provide the title compound L124. Yield: 69 mg (100%). $^1$H NMR (400 MHz, $CD_3OD$) δ 5.07 (dd, 1H) 4.89-4.80 (m, 3H), 4.79-4.67 (m, 1H), 3.76 (td, 1H), 3.67-3.58 (m, 2H), 3.13-2.92 (m, 1H). $^{19}$F NMR (400 MHz, $CD_3OD$) δ −193.07, −226.18.

Preparation 76: 4-(hydroxymethyl)-5-azaspiro[2.4]heptan-6-one (L125)

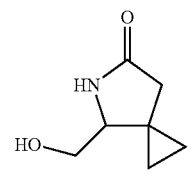

Step 1. Synthesis of ethyl 2-cyclopropylideneacetate (C180)

To a stirred solution of 1-ethoxy-1-[(trimethylsilyl)oxy]-cyclopropane (CAS 27374-25-0, 10 g, 57 mmol) in toluene (50 mL) was added (carbethoxymethylene)triphenylphosphorane (CAS 1099-45-2, 26 g, 74 mmol) followed by benzoic acid (0.91 g, 7.5 mmol) at about 25° C. The mixture was heated overnight at about 90° C., then cooled and concentrated. The residue was purified by chromatography to provide the title compound C180. Yield: 3.2 g (44%). $^1$H NMR (400 MHz, CDCl$_3$) δ 6.22 (s, 1H), 4.14 (q, 2H), 1.40-1.46 (m, 2H), 1.27 (t, 3H), 1.20-1.24 (m, 2H).

Step 2. Synthesis of ethyl 2-(1-(nitromethyl)cyclopropyl)acetate (C181)

A solution of compound C180 (2.3 g, 18 mmol), nitromethane (4.90 mL, 91 mmol) and DBU (2.73 mL, 18 mmol) in MeCN (50 mL) was heated overnight at about 60° C. The mixture was cooled, diluted with EtOAc, and washed with saturated aqueous NH$_4$Cl solution. The EtOAc was separated and the aqueous phase was extracted with EtOAc. The combined EtOAc extracts were dried over Na$_2$SO$_4$, filtered and concentrated. The residue was purified by chromatography to provide the title compound C181. Yield: 1.7 g (50%). $^1$H NMR (400 MHz, CDCl$_3$) δ 4.41 (s, 2H), 4.15 (q, 2H), 2.48 (s, 2H), 1.26 (t, 3H), 0.80-0.83 (m, 2H), 0.70-0.74 (m, 2H).

Step 3. Synthesis of ethyl 2-(1-(2-hydroxy-1-nitroethyl)cyclopropyl)acetate (C182)

A solution of compound C181 (2.5 g, 13 mmol), paraformaldehyde (0.802 g, 26 mmol) and potassium fluoride (78 mg, 1.3 mmol) in 2-propanol (30 mL) was stirred for about 36 h at about 25° C. and then concentrated. The residue was purified by chromatography to provide the title compound C182. Yield 1.1 g (38%). $^1$H NMR (400 MHz, CDCl$_3$) δ 4.14 (q, 2H), 4.03-4.10 (m, 2H), 3.92-3.96 (m, 1H), 3.16-3.20 (m, 1H), 2.86 (d, 1H), 2.23 (d, 1H), 1.27 (t, 3H), 0.90-0.99 (m, 2H), 0.79-0.83 (m, 1H), 0.64-0.68 (m, 1H).

Step 4. Synthesis of 4-(hydroxymethyl)-5-azaspiro[2.4]heptan-6-one (L125)

To a solution of compound C182 (600 mg, 2.7 mmol) in EtOH (10 mL) was added platinum dioxide (60 mg) and the mixture was stirred under a hydrogen atmosphere (1 atm) for about 20 h at about 25° C. The mixture was filtered and the filtrate was heated at about 80° C. for about 24 h, then concentrated. The residue was purified by chromatography to provide the title compound L125. Yield: 220 mg (56%). $^1$H NMR (400 MHz, dmso-d$_6$) δ 7.70 (br. s., 1H), 4.66 (t, 1H), 3.25-3.39 (m, 2H), 3.08 (t, 1H), 2.39 (d, 1H), 1.89 (d, 1H), 0.73-0.86 (m, 1H), 0.40-0.61 (m, 3H).

Preparation 76: 1-{[(2R,3R,4S)-3-ethyl-4-fluoro-3-hydroxy-5-oxopyrrolidin-2-yl]methoxy}-7-methoxy-isoquinoline-6-carboxamide

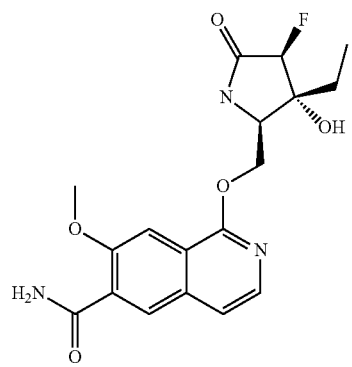 [SMILES: CC[C@]1(O)[C@H](F)C(=O)N[C@@H]1COc1nccc2cc(C(N)=O)c(OC)cc12]

Step 1

Sterile medium was prepared using deionized water containing dextrose (10 g/L), glycerol (20 g/L), Difco Yeast Extract (5 g/L), Nutrisoy flour (5 g/L), NaCl (5 g/L), K$_2$HPO$_4$ (5 g/L), P2000 (1 ml/L), pH adjusted to 7.0 prior to autoclaving to sterilize.

Step 2

*Streptomyces spectabilis* ATCC 27465 was grown in 25 mL of this medium which had been added to each of three sterile Nalgene flasks (250 mL, baffled, vented closures) on a 2" throw rotary shaker at 30° C., 210 rpm, for two days. The contents of each flask were aseptically transferred to each of three sterile 2L Nalgene flasks (baffled, vented closures) containing 400 mL of the same sterile medium then incubated as above. After two days, 16 mL of a solution of 1-{[(2S,3S,4S)-3-ethyl-4-fluoro-5-oxopyrrolidin-2-yl]methoxy}-7-methoxyisoquinoline-6-carboxamide in DMSO (5 mg/mL) was added to each flask. Incubation continued as above; flasks were aseptically sampled every 24 hours. After three days, contents of the flasks were combined and extracted twice with an equal volume of ethyl acetate. The organic phases were combined, dried with anhydrous sodium sulfate then concentrated under vacuum to yield 3.7 g of brown oil.

Step 3

High performance liquid preparative chromatography using a 0.1% trifluoroacetic acid in water with acetonitrile gradient on a Phenomenex Luna phenyl-hexyl column was utilized to isolate compounds from the above preparation. Time based fraction collection was used to collect all peaks of interest. Each sample was dried and tested by LCMS to confirm retention time identification and the parent ion of m/z=378 daltons. 1-{[(2R,3R,4S)-3-ethyl-4-fluoro-3-hydroxy-5-oxopyrrolidin-2-yl]methoxy}-7-methoxyisoquinoline-6-carboxamide (Example 196): $^1$H NMR (600 MHz, dmso-d$_6$) δ 8.85 (s, 1H), 8.17 (s, 1H), 7.91 (d, 1H), 7.85 (br. s, 1H), 7.71 (s, 2H), 7.45 (d, 1H), 4.58 (dd, 1H), 4.48 (d, 1H), 4.30 (dd, 1H), 3.98 (s, 3H), 3.87 (dd, 1H), 1.72 (q, 2H), 1.01 (t, 3H).

The following two examples were also prepared:

1-{[(3S,4S)-3-ethyl-4-fluoro-2-hydroxy-5-oxopyrrolidin-2-yl]methoxy}-7-methoxyisoquinoline-6-carboxamide (Example 197), as a mixture of diastereomers: Major diastereomer: $^1$H NMR (600 MHz, dmso-d$_6$) δ 9.25 (s, 1H), 8.18 (s, 1H), 7.92 (d, 1H), 7.6 (s, 1H), 7.72 (s, 1H), 7.6 (s, 1H), 7.54 (s, 1H), 4.96 (dd, 1H), 4.5 (dd, 2H), 3.98 (s, 3H), 2.47 (m, 1H), 1.67 (m, 1H), 0.99 (t, 3H). Minor diastereomer $^1$H NMR (600 MHz, dmso-d$_6$) δ 9.18 (s, 1H), 8.16 (s, 1H), 7.91 (d, 1H), 7.83 (s, 1H), 7.71 (s, 1H), 7.69 (s, 1H), 7.44 (s, 1H), 5.14 (dd, 1H), 4.5 (dd, 2H), 3.92 (s, 3H), 2.39 (m, 1H), 1.58 (m, 1H), 0.99 (t, 3H).

1-{[(2S,3R,4S)-4-fluoro-3-(1-hydroxyethyl)-5-oxopyrrolidin-2-yl]methoxy}-7-methoxyisoquinoline-6-carboxamide (Example 198): $^1$H NMR (600 MHz, dmso-d$_6$) δ 9.0 (s, 1H), 8.17 (s, 1H), 7.91 (d, J 1H), 7.86 (br s, 1H), 7.76 (s, 1H), 7.71 (bs, 1H), 7.44 (d, 1H), 4.94 (d, 1H), 4.83 (dd, 1H), 4.60 (dd, 1H), 4.26 (dd, 1H), 4.07 (m, 1H), 3.99 (m, 1H), 3.916 (m, 1H), 2.56 (m, 1H), 1.23 (d, 3H).

Methods

The Methods set forth hereinbelow are intended only to exemplify various aspects and embodiments of the invention, and are not intended to limit the scope of the claimed invention in any way. It will be apparent to one skilled in the art that the Methods described below may be modified in various ways, for example by changing reaction solvents or volumes, by substituting similar reagents to those described, or by substituting similar catalysts to those described.

Method 1

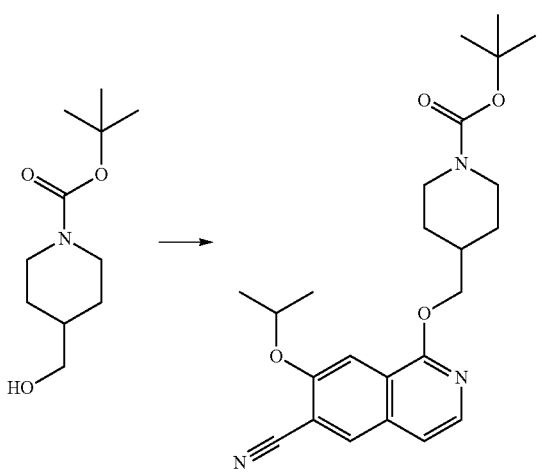 [SMILES: CC(C)(C)OC(=O)N1CCC(CO)CC1 ; CC(C)Oc1cc2c(OCC3CCN(C(=O)OC(C)(C)C)CC3)nccc2cc1C#N]

A reactant B such as tert-butyl 4-(hydroxymethyl)piperidine-1-carboxylate (CAS 123855-51-6, commercially available, 28 mg, 0.13 mmol) was dissolved in 0.5 mL of DMSO and a reactant A such as 1-chloro-7-isopropoxyisoquinoline-6-carbonitrile (P2) (0.2 M in DMSO, 0.5 mL, 0.10 mmol) was added. The mixture was then treated with potassium tert-butoxide (1 M in THF, 0.13 mL, 0.13 mmol). The reaction mixture was heated at about 50° C. to about 100° C. for about 2 to 16 hours until the reaction was judged to be complete. The mixture was then cooled to about 25° C. and filtered and the filtrate was concentrated. The residue may be used directly for subsequent work, or it may be purified by chromatography or HPLC.

Method 2

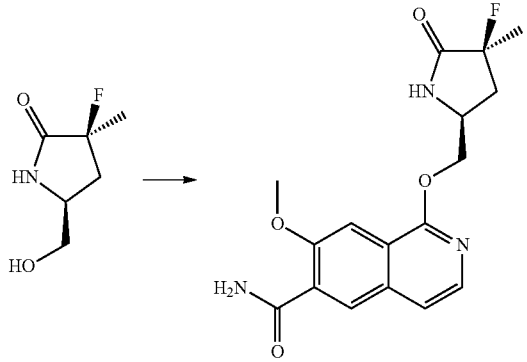

To a solution of a reactant B such as (3S,5S)-3-fluoro-5-(hydroxymethyl)-3-methyl-pyrrolidin-2-one (L10) (314 mg, 2.1 mmol) in 15 mL of DMF was added sodium hydride (60% in mineral oil, 342 mg, 8.6 mmol) at about 25° C. and the mixture was stirred for about 15 minutes. A reactant A such as 1-chloro-7-methoxyisoquinoline-6-carbonitrile (P1) (513 mg, 2.3 mmol) was added and stirring was continued for about 16 h. The reaction was quenched with EtOAc and water at about 0° C. The mixture was extracted with EtOAc and the EtOAc was separated, washed with brine, dried over Na$_2$SO$_4$, filtered and concentrated. The residue may be used directly for subsequent work, or it may be purified by chromatography or HPLC.

Method 3

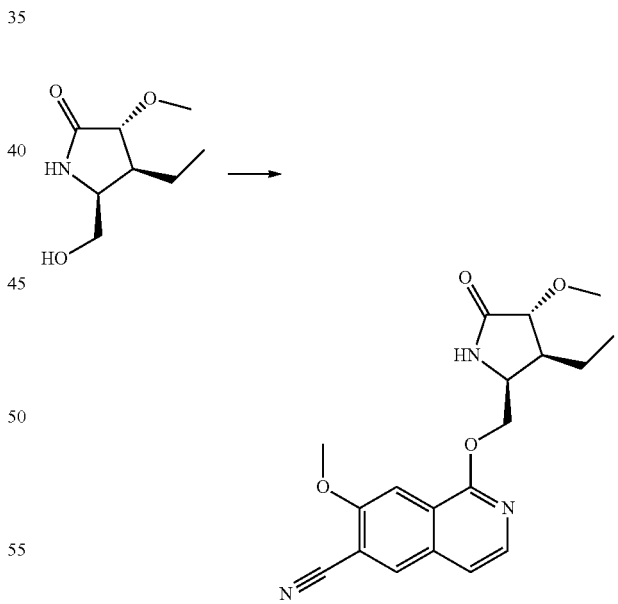

A reactant B such as (3R,4S,5S)-5-(hydroxymethyl)-3-methoxy-4-methylpyrrolidin-2-one (L65) (105 mg, 0.66 mmol) and a reactant A such as 1-chloro-7-methoxyisoquinoline-6-carbonitrile (P1) (120 mg, 0.55 mmol) were stirred in DMF (15 mL) at about 25° C. A solution of potassium hexamethyldisilazide (1 M in THF, 1.37 mL) was added dropwise to the reaction mixture. After the addition of potassium hexamethyldisilazide was complete, the reaction was stirred for approximately an additional 50 minutes. The Method 4

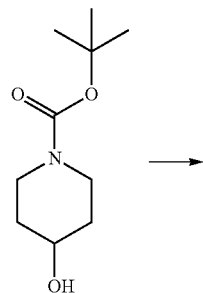

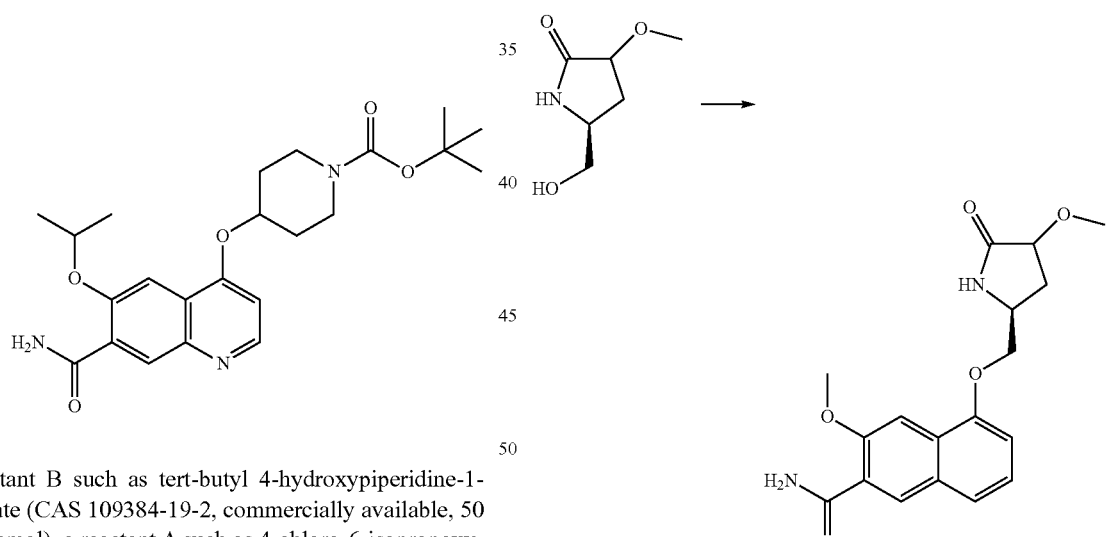

A reactant B such as tert-butyl 4-hydroxypiperidine-1-carboxylate (CAS 109384-19-2, commercially available, 50 mg, 0.2 mmol), a reactant A such as 4-chloro-6-isopropoxy-quinoline-7-carboxamide (P4) (30 mg, 0.1 mmol), and cesium carbonate (300 mg, 0.9 mmol) were combined in a small microwave vessel and diluted with 1 mL of DMSO. The vessel was capped and heated in a microwave reactor at about 150° C. for about 15 minutes. The reaction mixture was then diluted with EtOAc and water and the phases were separated. The aqueous phase was extracted three times with EtOAc and the combined EtOAc extracts were dried and concentrated. The residue may be used directly for subsequent work, or it may be purified by chromatography or HPLC. Potassium carbonate may be used in place of cesium carbonate in some instances.

Method 5

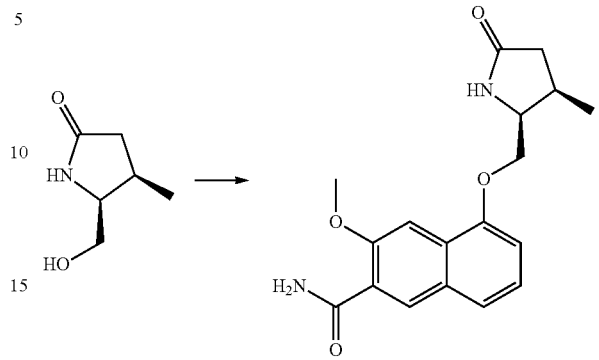

Triphenylphosphine (1.59 g, 5.9 mmol) was added to a suspension of a reactant B such as (4R,5S)-5-(hydroxymethyl)-4-methylpyrrolidin-2-one (L36) (393 mg, 2 mmol) and a reactant A such as 5-hydroxy-3-methoxy-2-naphthamide (P5) (430 mg, 2 mmol) in 10 mL of THF. Diisopropyl azodicarboxylate (0.84 g, 3.9 mmol) was added dropwise. The mixture was stirred at about 20° C. for 6 days and then concentrated. The residue may be used directly for subsequent work, or it may be purified by chromatography or HPLC.

Method 6

A solution of a reactant B such as (5S)-5-(hydroxymethyl)-3-methoxypyrrolidin-2-one (L25) (264 mg, 2 mmol) in 15 mL of DCM was treated with p-toluenesulfonyl chloride (760 mg, 4 mmol) and DMAP (512 mg, 4 mmol). The reaction mixture was stirred for about 12 h at about 25° C. The mixture was washed with water (15 mL). The DCM was dried over Na$_2$SO$_4$, filtered and concentrated. The residue was purified by silica gel chromatography to give 312 mg (52%) of the intermediate p-toluenesulfonate ester of L25.

To a solution of the intermediate p-toluenesulfonate ester of L25 prepared above (166 mg, 0.55 mmol) in dry DMF (5 mL) was added cesium carbonate (357 mg, 1.1 mmol) and a reactant A such as 5-hydroxy-3-methoxy-2-naphthamide (P5) (132 mg, 0.6 mmol). The mixture was stirred for about 2 h at about 65° C. The DMF was evaporated, and the residue was stirred with EtOAc and the mixture was filtered. The filter cake was washed with water (5 mL×2). The filter cake was dried under vacuum, treated with EtOAc and filtered. The residue may be used directly for subsequent work, or it may be purified by chromatography or HPLC.

Method 7

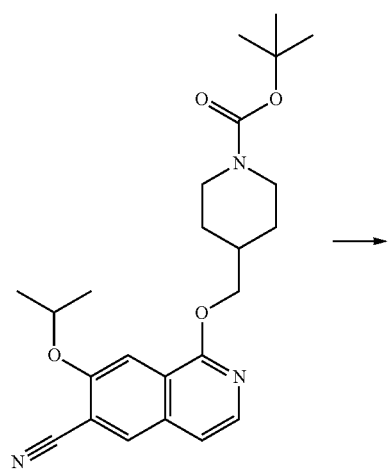

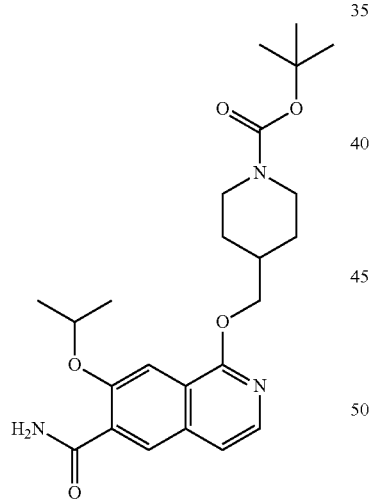

A solution of a reactant such as tert-butyl 4-(((6-cyano-7-isopropoxyisoquinolin-1-yl)oxy)methyl)-piperidine-1-carboxylate (42 mg, 0.10 mmol) in DMSO (1 mL) was treated with powdered K₂CO₃ (41 mg, 0.30 mmol) followed by 30% hydrogen peroxide solution (0.2 mL, 1.8 mmol). The mixture was heated at about 40° C. to 60° C. for about 15 minutes to 16 hours until the reaction was judged to be complete. The mixture was then cooled to about 25° C. and filtered and the filtrate was concentrated. The residue may be used directly for subsequent work, or it may be purified by chromatography or HPLC. Sodium hydroxide or potassium hydroxide may be substituted for K₂CO₃ in some cases.

Method 8

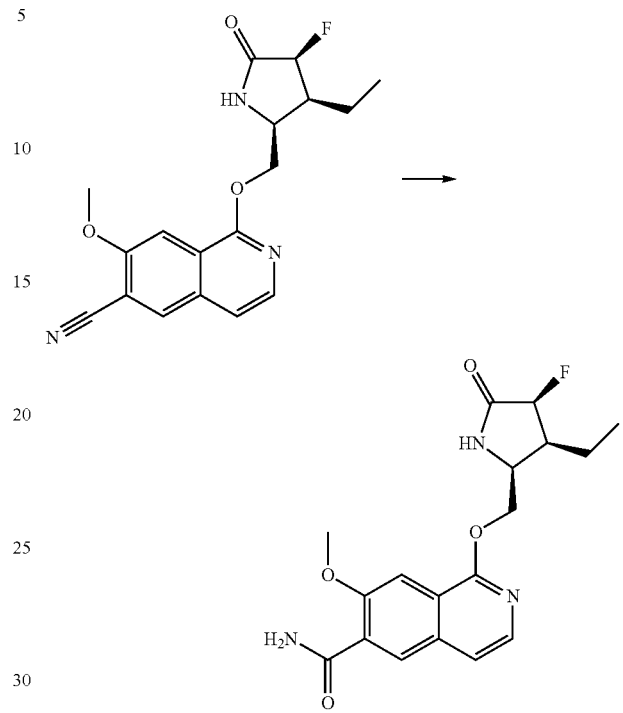

A solution of a reactant such as 1-(((2S,3S,4S)-3-ethyl-4-fluoro-5-oxopyrrolidin-2-yl)methoxy)-7-methoxyisoquinoline-6-carbonitrile (200 mg, 0.5 mmol) in concentrated H₂SO₄ (1.5 mL) was warmed to about 55° C. for about two hours, then cooled to about 20° C. The reaction mixture was added dropwise with vigorous stirring to 7.3 mL of ice cold concentrated ammonium hydroxide with cooling in ice. The precipitated solid was filtered and washed with water, heptane, ether, and dried under vacuum. The residue may be used directly for subsequent work, or it may be purified by chromatography or HPLC.

Method 9

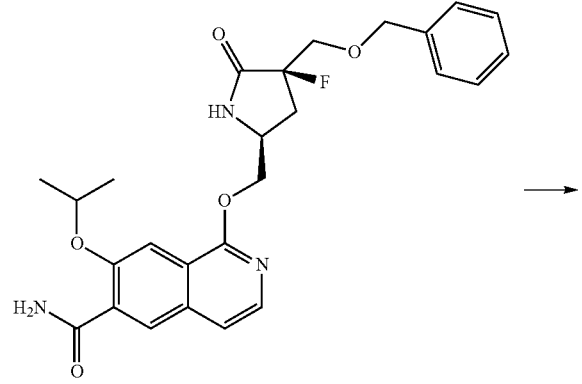

-continued

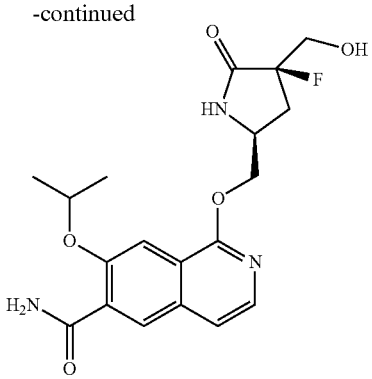

A solution of a reactant such as 1-(((2S,4R)-4-((benzyloxy)methyl)-4-fluoro-5-oxopyrrolidin-2-yl)methoxy)-7-isopropoxyisoquinoline-6-carboxamide (20 mg, 0.44 mmol) in MeOH (0.46 mL) was treated with a palladium on carbon catalyst (5 mg) and stirred under a hydrogen atmosphere at a pressure of about 1 to 5 atmospheres and a temperature of about 20° C. to 65° C. The mixture was then cooled to about 20° C. and filtered and the filtrate was concentrated. The residue may be used directly for subsequent work, or it may be purified by chromatography or HPLC.

Method 10

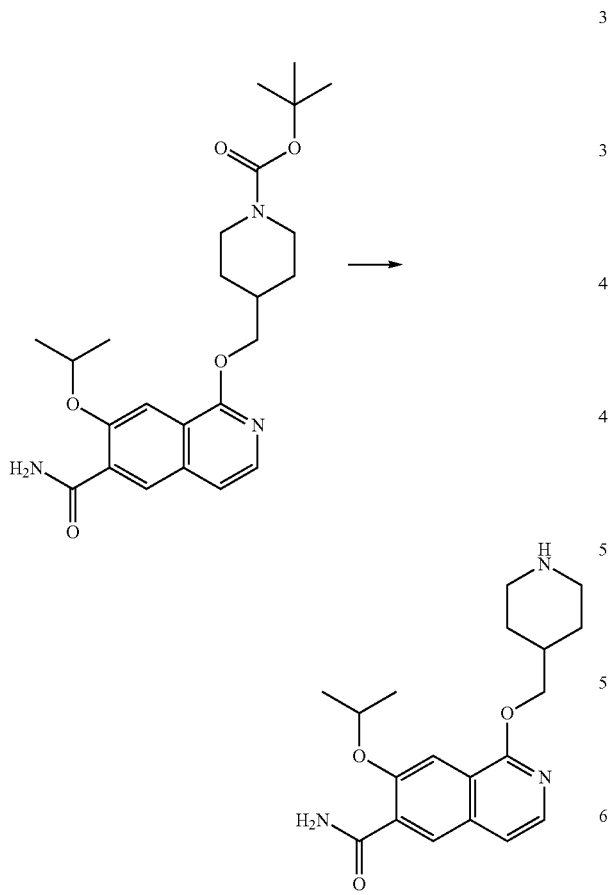

A solution of a reactant such as tert-butyl 4-(((6-carbamoyl-7-isopropoxyisoquinolin-1-yl)oxy)methyl)piperidine-1-carboxylate (44 mg, 0.1 mmol) in 1.0 to 2.0 mL of a suitable solvent such as DCM was treated with either TFA (0.10 mL) or hydrogen chloride (4 M in dioxane, 0.4 mL). The reaction mixture was heated at about 30° C. to 40° C. for about 1 to 4 hours until the reaction was judged to be complete. The mixture was then cooled to about 25° C. and concentrated under vacuum and purified using by chromatography or HPLC.

Method 11

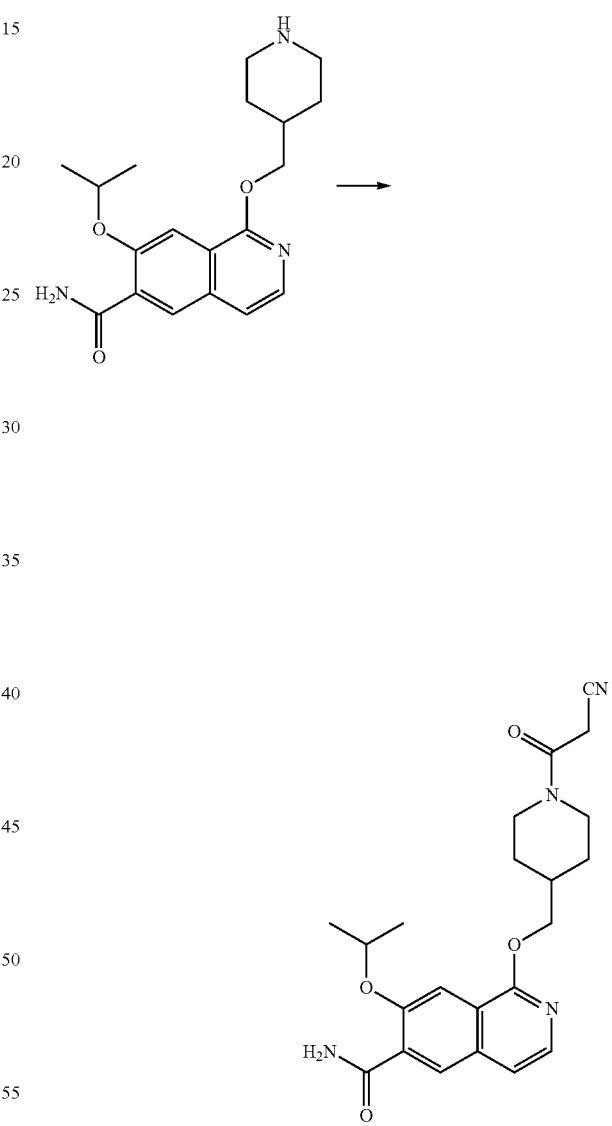

A solution of a reactant such as 7-isopropoxy-1-(piperidin-4-ylmethoxy)isoquinoline-6-carboxamide (41 mg, 0.12 mmol) in DMF (1.0 mL) was treated with cyanoacetic acid (11 mg, 0.12 mmol), followed by HATU (47 mg, 0.12 mmol) and Et₃N (35 µL, 0.25 mmol). The reaction mixture was heated at about 30° C. to 50° C. for about 4 to 16 hours until the reaction was judged to be complete. The mixture was then cooled to about 25° C. and concentrated under vacuum and purified by chromatography or HPLC.

Method 12

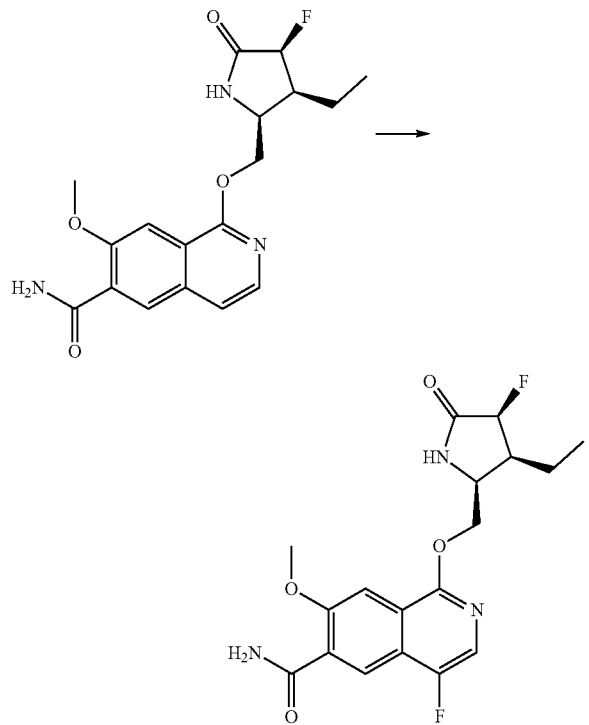 [SMILES: CC[C@@H]1[C@H](F)C(=O)N[C@@H]1COc1nccc2cc(C(N)=O)c(OC)cc12 ; CC[C@@H]1[C@H](F)C(=O)N[C@@H]1COc1ncc(F)c2cc(C(N)=O)c(OC)cc12]

A solution of a reactant such as 1-(((2S,3S,4S)-3-ethyl-4-fluoro-5-oxopyrrolidin-2-yl)methoxy)-7-methoxyisoquinoline-6-carboxamide (500 mg, 1.4 mmol) in DMF (15 mL) was treated with SelectFluor® (511 mg, 1.4 mmol) and heated at about 55° C. for about 24 h. The mixture was concentrated, xylene was added, and the mixture was concentrated again. The concentration with xylene was repeated twice more, and the residue was stirred with EtOAc. The precipitated solid was filtered and washed with EtOAc, and the EtOAc filtrates were combined, concentrated, and treated with EtOAc and water. The EtOAc was separated, concentrated under vacuum and purified by chromatography or HPLC.

Method 13

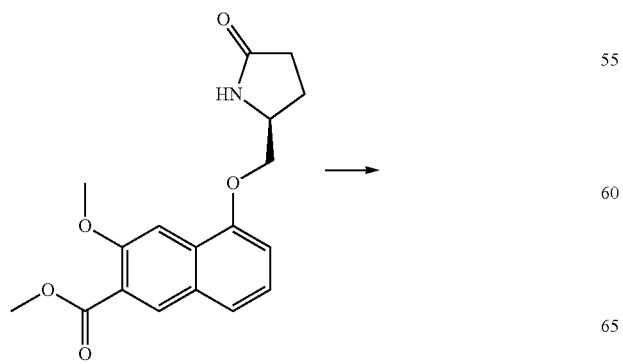

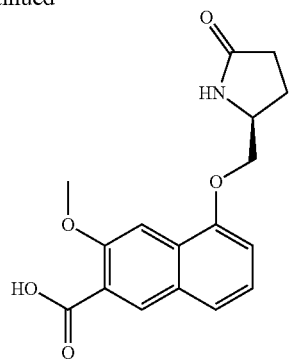

A solution of a reactant such as (S)-methyl 3-methoxy-5-((5-oxopyrrolidin-2-yl)methoxy)-2-naphthoate (366 mg, 1.1 mmol) in THF (25 mL) and water (25 mL) was treated with lithium hydroxide (272 mg, 11.1 mmol). The resulting mixture was stirred at about 25° C. for about 1 hour, then the mixture was partially concentrated under vacuum to remove the THF. The remaining solution was acidified with 10% aqueous citric acid, and the resulting precipitate was collected by filtration, washed with water and dried. The residue may be used directly for subsequent work, or it may be purified by chromatography or HPLC.

Method 14

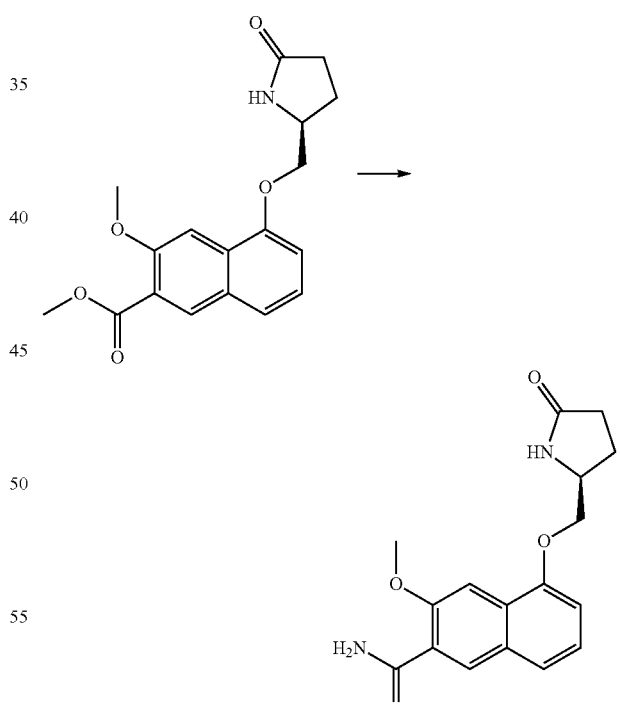

A solution of a reactant such as (S)-methyl 3-methoxy-5-((5-oxopyrrolidin-2-yl)methoxy)-2-naphthoate (385 mg, 1.2 mmol) in THF (25 mL) was treated with Et₃N (0.26 mL, 1.8 mmol) and heated under reflux. The mixture was cooled to about 25° C., then BOP reagent (CAS 56602-33-6, 709 mg, 1.6 mmol) was added. The mixture was stirred for about 25 min until almost all of the BOP reagent had dissolved, Method 15

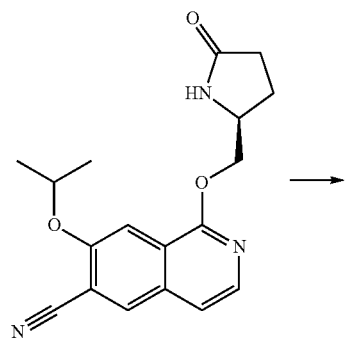

A solution of a reactant such as (S)-7-isopropoxy-1-((5-oxopyrrolidin-2-yl)methoxy)-isoquinoline-6-carbonitrile (100 mg, 0.3 mmol) in acetonitrile (6.1 mL) was with N-bromosuccinimide (55 mg, 0.3 mmol) was heated at about 60° C. for about 1.5 h. An additional portion of N-bromosuccinimide (30 mg 0.14 mmol) was added. After about 30 min, the mixture was cooled to about 25° C. and diluted with 10 mL of EtOAc. The EtOAc extract was washed with saturated aqueous sodium thiosulfate (10 mL). The aqueous phase was back-extracted with EtOAc (10 mL), and the combined EtOAc extracts were washed with saturated aqueous sodium thiosulfate (15 mL), brine (15 mL), dried over $Na_2SO_4$, filtered and concentrated. The residue may be used directly for subsequent work, or it may be purified by chromatography or HPLC.

Method 16

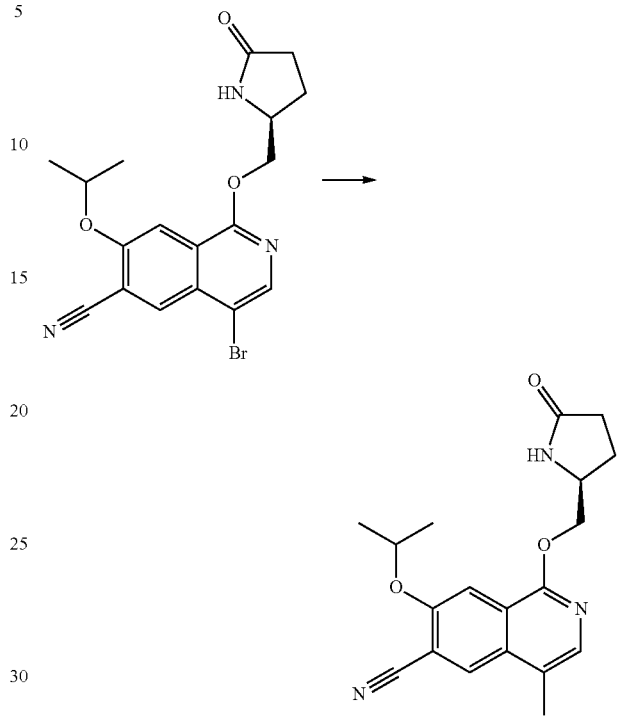

A solution of a reactant such as (S)-4-bromo-7-isopropoxy-1-((5-oxopyrrolidin-2-yl)methoxy)isoquinoline-6-carbonitrile (54 mg, 0.1 mmol), palladium bis(triphenylphosphine)-dichloride (19 mg, 0.03 mmol), potassium methyltrifluoroborate (25 mg, 0.2 mmol), and $K_2CO_3$ (55 mg, 0.4 mmol) in acetonitrile (0.75 mL) and water (0.5 mL) was heated in a microwave reactor at about 125° C. for about 30 min. The mixture was diluted with EtOAc (10 mL) and washed brine. The aqueous phase was back-extracted with EtOAc (10 mL) and the combined EtOAc extracts were dried over $Na_2SO_4$, filtered and concentrated. The residue may be used directly for subsequent work, or it may be purified by chromatography or HPLC.

Method 17

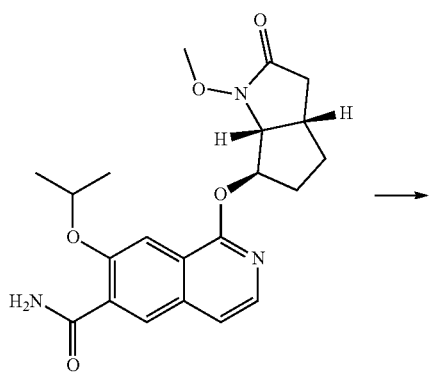

-continued

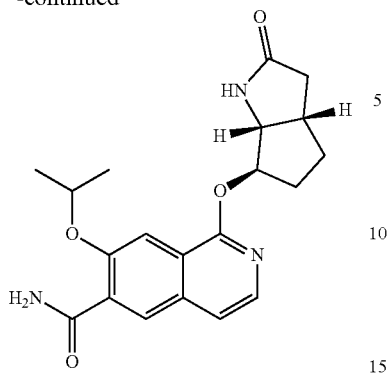

A solution of a reactant such as 7-isopropoxy-1-(((3aS, 6R,6aR)-1-methoxy-2-oxooctahydrocyclopenta[b]pyrrol-6-yl)oxy)isoquinoline-6-carboxamide (42 mg, 0.1 mmol) in 3.25 mL of acetonitrile and 0.25 mL of water was treated with molybdenum hexacarbonyl (34 mg, 0.13 mmol). The reaction was heated at reflux for about 18 h. The mixture cooled to about 25° C., diluted with MeOH, filtered and concentrated. The residue may be used directly for subsequent work, or it may be purified by chromatography or HPLC.

Method 18

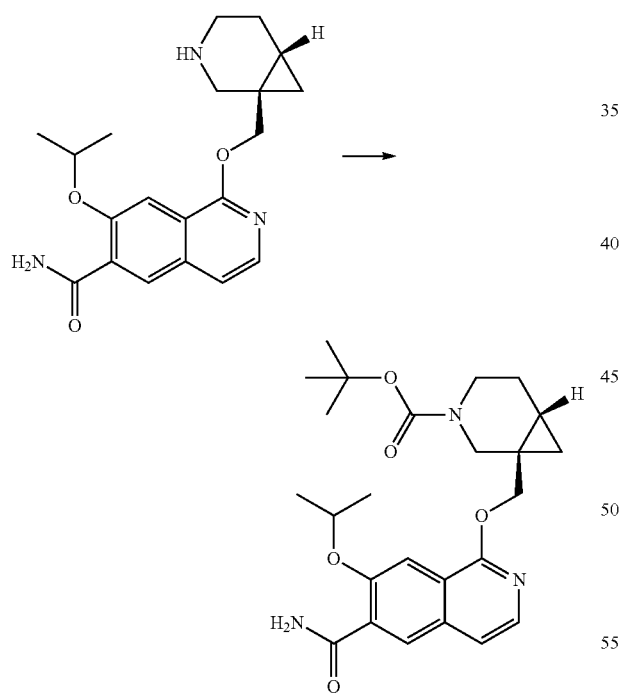

A solution of a reactant such as (±)-1-((1R,6S)-3-azabicyclo[4.1.0]heptan-1-ylmethoxy)-7-isopropoxyisoquinoline-6-carboxamide (54 mg, 0.15 mmol) and di-t-butyl dicarbonate (37 mg, 0.17 mmol) in THF (2 mL) and water (2 mL) was stirred for about 45 min at about 25° C., then diluted with EtOAc and water. The EtOAc was separated, washed with brine, dried over Na₂SO₄, filtered and concentrated. The residue may be used directly for subsequent work, or it may be purified by chromatography or HPLC.

Method 19

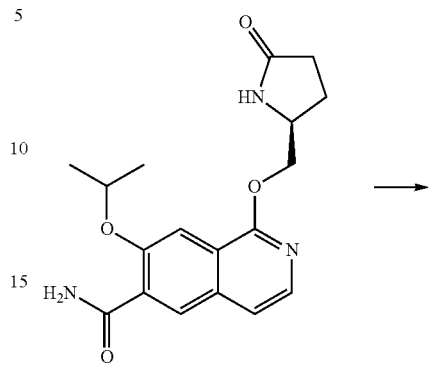

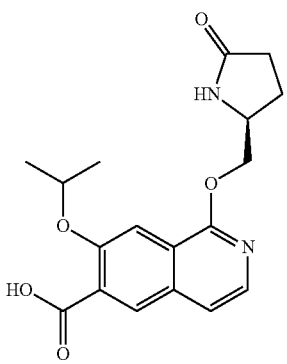

A solution of a reactant such as (S)-7-isopropoxy-1-((5-oxopyrrolidin-2-yl)methoxy)-isoquinoline-6-carboxamide (272 mg, 0.80 mmol) in 1,4-dioxane (20 mL) was treated with 5 mL of cold 50% H₂SO₄. The mixture was heated at about 55° C. for about 24 h, then cooled to about 25° C. and allowed to remain for about 18 h. The dioxane was separated and the aqueous phase was neutralized to about pH 5 with K2CO3, then extracted repeatedly with EtOAc. The combined dioxane and EtOAc extracts were dried over Na₂SO₄, filtered and concentrated. The residue may be used directly for subsequent work, or it may be purified by chromatography or HPLC.

Method 20

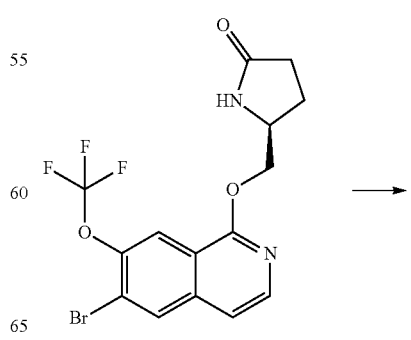

-continued

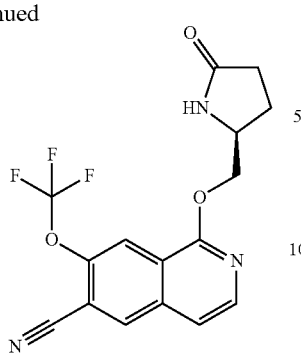

A solution of a reactant such as (S)-5-((((6-bromo-7-(trifluoromethoxy)isoquinolin-1-yl)oxy)methyl)pyrrolidin-2-one (78 mg, 0.19 mmol) and zinc cyanide (46 mg, 0.38 mmol) in DMF (2.5 mL) was treated with tetrakis(triphenylphosphine)palladium (0) (45 mg, 0.04 mmol). The mixture was heated for about 20 min at about 150° C., then diluted with ice water (35 mL) and filtered. The precipitate was dissolved in DCM, washed with brine, dried over Na₂SO₄, filtered and concentrated. The residue may be used directly for subsequent work, or it may be purified by chromatography or HPLC.

Method 21

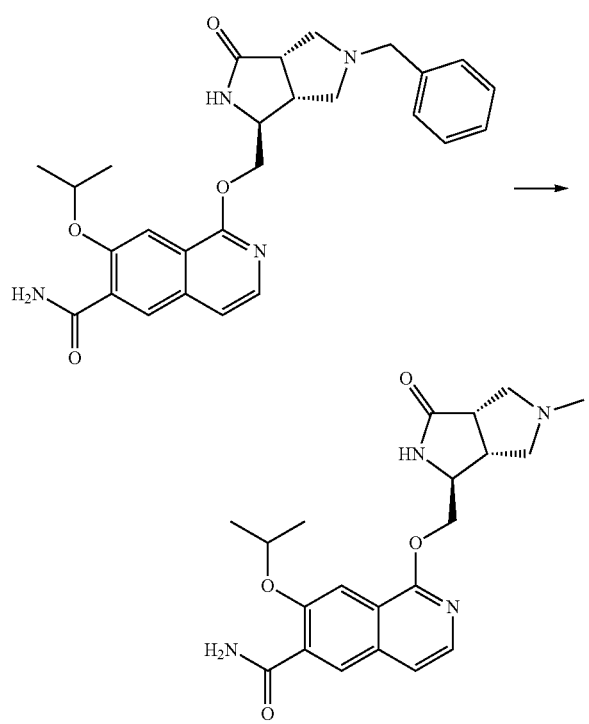

A solution of a reactant such as 1-(((1S,3aS,6aR)-5-benzyl-3-oxooctahydropyrrolo[3,4-c]pyrrol-1-yl)methoxy)-7-isopropoxyisoquinoline-6-carboxamide (50 mg, 0.10 mmol), aqueous formaldehyde solution (37%, 6 mL) in MeOH (50 mL) was treated with a palladium on carbon catalyst (5 mg) and stirred under a hydrogen atmosphere at a pressure of 1 atmosphere and a temperature of about 20° C. for about 2 h. The mixture was filtered and concentrated. The residue may be used directly for subsequent work, or it may be purified by chromatography or HPLC.

Method 22

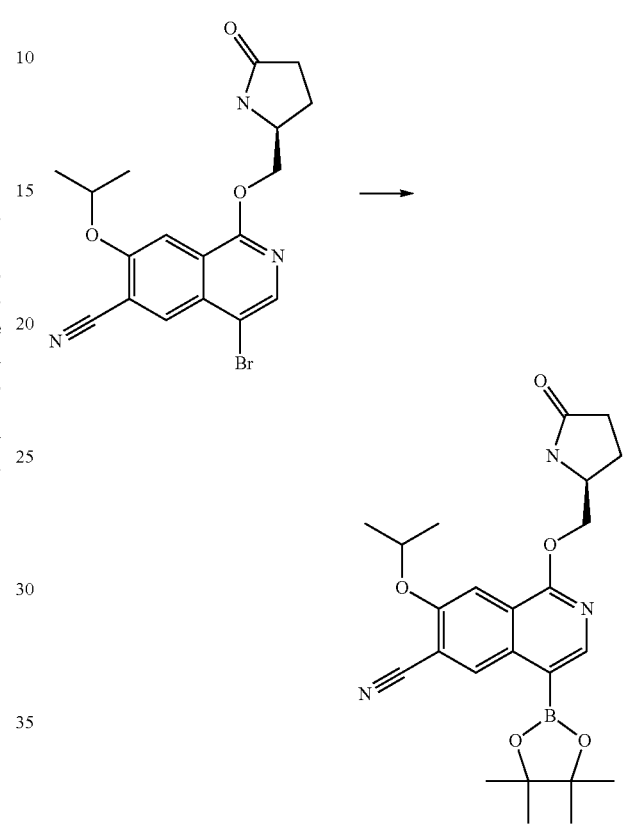

A solution of a reactant such as (S)-4-bromo-7-isopropoxy-1-((5-oxopyrrolidin-2-yl)methoxy)isoquinoline-6-carbonitrile (1.0 g, 2.4 mmol) in 1,4-dioxane (20 mL) was treated with freshly dried potassium acetate (729 mg, 7.4 mmol), bis(pinacolato diboron) (880 mg, 3.5 mmol), and tetrakis(triphenylphosphine)palladium (0) (143 mg, 0.12 mmol). The mixture was heated at about 100° C. for about 16 h. The mixture was cooled to about 25° C., filtered, and concentrated. The residue may be used directly for subsequent work, or it may be purified by chromatography or HPLC.

EXAMPLES

1-{((2S,3S,4S)-3-ethyl-4-fluoro-5-oxopyrrolidin-2-yl methoxy}-7-methoxyisoquinoline-6-carboxamide Step 1. Synthesis of (7R,7aS)-7-ethyl-3,3-dimethyl-tetrahydropyrrolo[1,2-c]oxazol-5(3H)-one (C54)

A suspension of copper bromide dimethyl sulfide complex (833 g, 4.05 mol) in diethyl ether (6 L) was cooled to about −20 to −30° C., and ethylmagnesium bromide solution (2 M in THF, 4.05 L, 8 moles) was added over about 1 hour allowing the temperature to rise to about −3° C. After stirring for about 10 min the slurry was cooled to about −70° C., and TMSCl (382 mL, 3.04 mol) was added drop wise over about 1 h. After about 50 min, compound P20 (310 g, 2.02 mol) in 500 mL of MTBE was added to the mixture drop wise over about 2 hours. The temperature was maintained at about −72 to −68° C. during the addition. The reaction mixture was stirred at about −72° C. for about 4 hours, after which time it was warmed up to about −40° C. over about 16 hours. The reaction mixture was quenched with half-saturated aqueous NH$_4$Cl (4 L). After a phase separation, the solvent phase was washed with water, dried over Na$_2$SO$_4$, filtered, and concentrated. The reaction was performed six times in total and the combined crude products were purified by silica chromatography to provide the title compound C54. Yield 1.4 kg (63%, based on 12.1 mol of P20). $^1$H NMR (400 MHz, CDCl$_3$) δ 4.34 (dt, 1H), 3.90 (dd, 1H), 3.72 (dd, 1H), 2.91 (dd, 1H), 2.31 (dd, 1H), 2.25 (m, 1H), 1.65 (s, 3H), 1.52 (d, 1H), 1.48 (s, 3H), 1.27-1.38 (m, 1H), 0.92 (t, 3H).

Step 2. Synthesis of (6S,7S,7aS)-7-ethyl-6-fluoro-3,3-dimethyltetrahydropyrrolo[1,2-c]oxazol-5(3H)-one (C61)

A solution of diisopropylamine (184 mL, 1.31 mol) in THF (1.65 L) was cooled to about −20 to −30° C. and treated with n-butyllithium solution (2.5 M in hexanes, 491 mL, 1.23 mol) over about 10 minutes, allowing the temperature to rise to about −20° C. After stirring for about 10 minutes, the solution was cooled to about −70° C., and a solution of compound C54 (235 g, 1.17 mol) in THF (588 mL) was added drop wise over about 30 minutes. The temperature was maintained at about −70 to −60° C. during the addition, and after stirring for about 30 minutes at this temperature, a solution of NFSI (387 g, 1.23 mol) in 1.2 L THF was added over about 80 minutes at about −70 to −72° C. After stirring for about 1 h at about −70 to −60° C., the reaction was allowed to warm to about 20° C. overnight. The precipitated solids were filtered and washed with THF (1 L). The filtrate was concentrated to an oily residue. This entire reaction was conducted three times at this scale and once using 500 g of compound C61. The combined crude products were purified by silica chromatography to provide the title compound C61. Yield: 350 g (27% based on 6.6 mol of C54). $^1$H NMR (400 MHz, CDCl$_3$) δ 5.23 (dd, 1H), 3.97-4.11 (m, 2H), 3.68-3.77 (m, 1H), 2.62-2.76 (m, 1H), 1.69-1.79 (m, 1H), 1.68 (s, 3H), 1.45-1.52 (m, 3H), 1.28-1.42 (m, 1H), 0.97 (t, 3H). $^{19}$F NMR (376 MHz, CDCl$_3$) δ −199.61. There was also obtained (6R,7S,7aS)-7-ethyl-6-fluoro-3,3-dimethyltetrahydropyrrolo[1,2-c]oxazol-5(3H)-one C62. Yield: 700 g (54% from 6.6 mol of C54). $^1$H NMR (400 MHz, CD$_3$CN) δ 4.78 (dd, 1H), 4.40 (dt, 1H), 3.93 (dd, 1H), 3.56 (dd, 1H), 2.30-2.46 (m, 1H), 1.56 (s, 3H), 1.52 (ddd, 1H), 1.42 (s, 3H), 1.35-1.48 (m, 1H), 0.97 (t, 3H). $^{19}$F NMR (376 MHz, CD$_3$CN) δ −185.41.

Step 3. Epimerization of (6R,7S,7aS)-7-ethyl-6-fluoro-3,3-dimethyltetrahydropyrrolo[1,2-c]oxazol-5(3H)-one (C62)

To a solution of diisopropylamine (310 g, 3.07 mol) in toluene (4 L) was added n-butyllithium (2.5 M, 1.22 L, 3.05 mol) dropwise at −30° C. The mixture was maintained at −30° C. for an additional 30 min, then was added dropwise to a solution of compound C62 (556 g, 2.77 mol) in toluene (2 L) at −78° C. After the addition was complete, the mixture was kept at −78° C. for 30 min more before a solution of BHT (1.26 kg, 5.73 mol) in toluene (5 L) was added dropwise over 3 h, keeping the internal temperature below −65° C. After the addition was complete, the mixture was kept at −78° C. for 30 min. The mixture was warmed to 25° C., water was added, and the toluene was separated. The aqueous layer was extracted with DCM twice, the combined toluene and DCM extracts were dried over Na$_2$SO$_4$, filtered and concentrated. The residue was purified by chromatography to provide compound C61. Yield: 250 g (45%). There was also recovered compound C62. Yield: 150 g (27%).

Step 4. Synthesis of (3S,4S,5S)-4-ethyl-3-fluoro-5-(hydroxymethyl)pyrrolidin-2-one (L54)

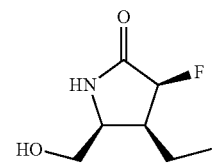

A solution of compound C61 (90 g, 0.45 mol) in acetonitrile (450 mL) and water (45 mL) was treated with TFA (6.8 mL, 90 mmol). The mixture was warmed to about 65° C. over about 1 h, and held at that temperature for about 3 h. The mixture was then cooled and about 350 mL of solvent was distilled by rotary evaporation. The residue was diluted with acetonitrile (400 mL) and evaporated to dryness. Isopropyl acetate (250 mL) was added to the residue and the mixture was concentrated again. The residue was diluted with heptane (200 mL) and crystallization was induced by seeding. The precipitate was filtered in two crops to provide the title compound L54. Yield: 46 g (64%). $^1$H NMR (400 MHz, CDCl$_3$) δ 7.59 (br. s., 1H), 4.80 (dd, 1H), 3.69-3.83 (m, 2H), 3.52-3.64 (m, 1H), 3.48 (br. s, 1H), 2.27-2.52 (m, 1H), 1.57-1.73 (m, 1H), 1.49 (dt, 1H), 1.04 (t, 3H). $^{19}$F NMR (376 MHz, CDCl$_3$) δ −198.72.

Step 5. Synthesis of 1-(((2S,3S,4S)-3-ethyl-4-fluoro-5-oxopyrrolidin-2-yl) methoxy)-7-methoxy-isoquinoline-6-carbonitrile (C171)

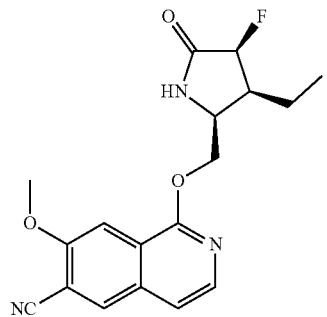 [SMILES: CC[C@@H]1[C@H](F)C(=O)N[C@@H]1COc1nccc2cc(C#N)c(OC)cc12]

A mixture of compound L54 (8.00 g, 49.6 mmol) and compound P1 (9.87 g, 45.1 mmol) were stirred in DMF (83 mL) and cooled to about −10° C. A solution of potassium hexamethyldisilazide (1 M in THF, 99 mL, 99 mmol) was added to the reaction mixture over about 45 minutes, maintaining the internal reaction temperature at about −10° C. After the addition of potassium hexamethyldisilazide was complete, the reaction was stirred at about −10° C. for approximately an additional 30 minutes. A solution of 24.9 g of sodium dihydrogen phosphate in 250 mL of water was prepared. The reaction mixture was then poured into 220 mL of this aqueous sodium dihydrogen phosphate solution and 250 mL of EtOAc with vigorous stirring. The reaction flask was rinsed with the remaining 30 mL of the aqueous sodium dihydrogen phosphate solution and the rinse was added to the EtOAc mixture. The EtOAc was separated. The aqueous mixture was extracted three times with EtOAc. The combined EtOAc extracts were dried over MgSO$_4$, filtered and concentrated. Xylene was added to the residue and the mixture was concentrated. Addition of xylene and subsequent evaporation was carried out two more times to provide the title compound C171. Yield: 15.37 g (90%). $^1$H NMR (400 MHz, dmso-d$_6$) δ 8.89 (s, 1H), 8.50 (s, 1H), 7.98 (d, 1H), 7.80 (s, 1H), 7.41 (d, 1H), 4.90 (dd, 1H), 4.56 (dd, 1H), 4.24 (dd, 1H), 4.09 (dt, 1H), 4.03 (s, 3H), 2.62 (m, 1H), 1.58 (m, 2H), 1.02 (t, 3H). $^{19}$F NMR (376 MHz, dmso-d$_6$) δ −199.18.

Step 6. Synthesis of 1-{[(2S,3S,4S)-3-ethyl-4-fluoro-5-oxopyrrolidin-2-yl]methoxy}-7-methoxy-isoquinoline-6-carboxamide (Example 296)

A mixture of compound C171 (15.37 g, 44.7 mmol) and methanesulfonic acid (218 mL, 3.36 mol) was heated at about 60° C. with stirring for about 26 hours. The mixture was then cooled to about 25° C. and slowly added to 1 kg of crushed ice with stirring. During the addition, 150 g of additional ice was added so as to ensure that, at the conclusion of the addition, there was still ice remaining in the mixture. Ethyl acetate (1 L) was added. Ammonium hydroxide (274 mL) was then added slowly to the stirring biphasic mixture, along with another 750 g of ice, until the pH of the mixture rose to about 8. The mixture was then warmed to about 30° C. to dissolve all of the solids present. The EtOAc was separated and the aqueous phase was extracted with EtOAc (4×100 mL). The combined EtOAc extracts were washed with brine, dried over MgSO$_4$, filtered and concentrated to provide the title compound. Yield 14.72 g (91%). Recrystallization from EtOH afforded an analytically pure sample, mp 286° C. $^1$H NMR (400 MHz, dmso-d$_6$) δ 8.86 (s, 1H), 8.16 (s, 1H), 7.90 (d, 1H), 7.84 (br. s., 1H), 7.74 (s, 1H), 7.69 (br. s., 1H), 7.43 (d, 1H), 4.91 (dd, 1H), 4.54 (dd, 1H), 4.26 (dd, 1H), 4.09 (br. s., 1H), 3.97 (s, 3H), 2.63 (m, 1H), 1.60 (m, 2H), 1.02 (t, 3H). $^{19}$F NMR (H decoupled, 376 MHz, dmso-d$_6$) δ −199.26.

The following compounds of the invention were prepared similarly using the methods described above. The reactants A were prepared as described in this specification. The reactants B were either known compounds that were commercially available, or known compounds that were prepared as described in the cited references, or compounds prepared as described in this specification. For those examples characterized by HPLC retention time, the following HPLC conditions were used:

| Method PF-AB01 | Method PF-AB10 | Method PF-CD05 |
|---|---|---|
| Column Xbridge C18 2.1 × 50 mm 5 μm Temperature 50° C. Mobile Phase A 0.0375% TFA in water Mobile Phase B 0.01875% TFA in acetonitrile Gradient - Initial 1% B Time 0.00 mins 1% B Time 0.60 mins 5% B Time 4.00 mins 100% B Time 4.30 mins 1% B Time 4.70 mins 1% B Flow rate 0.8 ml/min Injection volume 2 μl Agilent 1200 HPLC/ 1956 MSD/SEDEX 75 ELSD Ionization Mode API-ES Polarity - Positive | Column Xbridge C18 2.1 × 50 mm 5 μm Temperature 50° C. Mobile Phase A 0.0375% TFA in water Mobile Phase B 0.01875% TFA in acetonitrile Gradient - Initial 10% B Time 0.00 mins 10% B Time 0.50 mins 10% B Time 4.00 mins 100% B Time 4.30 mins 10% B Time 4.70 mins 10% B Flow rate 0.8 ml/min Injection volume 2 μl Agilent 1200 HPLC/ 1956 MSD/SEDEX 75 ELSD Ionization Mode API-ES Polarity - Positive | Column Xbridge C18 2.1 × 50 mm 5 μm Temperature 50° C. Mobile Phase A 0.05% NH$_4$OH in water Mobile Phase B 100% acetonitrile Gradient - Initial 5% B Time 0.00 mins 5% B Time 0.50 mins 5% B Time 3.40 mins 100% B Time 4.20 mins 100% B Time 4.21 mins 5% B Time 4.70 mins 5% B Flow rate 0.8 ml/min Injection volume 2 μl Agilent 1200 HPLC/ 1956 MSD/SEDEX 75 ELSD Ionization Mode API-ES Polarity - Positive |

TABLE 1

| Ex. | Structure | Reactant A | Reactant B | Source | Methods | MH$^+$ | Characterization |
|---|---|---|---|---|---|---|---|
| 1 | 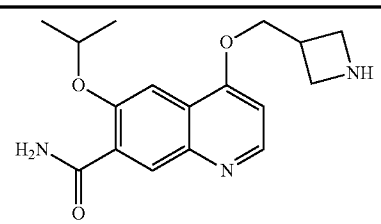 | P4 | 95849-02-8 | commercial | 1 | 316 | Rt = 1.752 min; method PF-AB01 |
| 2 | Chiral | P4 | 140695-84-7 | commercial | 4, 10 | 344 | $^1$H NMR (400 MHz, CD$_3$OD) δ 8.95 (d, 1 H), 8.53 (s, 1 H), 7.81 (s, 1 H), 7.52 (d, 1 H), 5.08 (dt, 1 H), 4.55-4.64 (m, 1 H), 4.43-4.55 (m, 1 H), 3.65-3.77 (m, 1 H), 3.46 (d, 1 H), 2.95-3.10 (m, 2 H), 2.64 (td, 1 H), 2.00-2.20 (m, 2 H), 1.82-2.00 (m, 1 H), 1.54-1.69 (m, 1 H), 1.51 (d, 6 H) |

TABLE 1-continued

| Ex. | Structure | Reactant A | Reactant B | Source | Methods | MH+ | Characterization |
|---|---|---|---|---|---|---|---|
| 3 | (Chiral) | P4 | 140695-85-8 | commercial | 4, 10 | 344 | ¹H NMR (400 MHz, CD₃OD) δ 8.59 (d, 1 H), 8.49 (s, 1 H), 7.89 (s, 1 H), 7.65 (s, 1 H), 7.01 (d, 1 H), 4.91 (dt, 1 H), 4.18-4.26 (m, 1 H), 4.09-4.18 (m, 1 H), 3.32-3.39 (m, 1 H), 3.03-3.13 (m, 1 H), 2.56-2.72 (m, 2 H), 2.18-2.33 (m, 1 H), 1.97-2.08 (m, 1 H), 1.77-1.87 (m, 1 H), 1.59-1.72 (m, 1 H), 1.50 (d, 6 H), 1.36-1.47 (m, 1 H) |
| 4 | 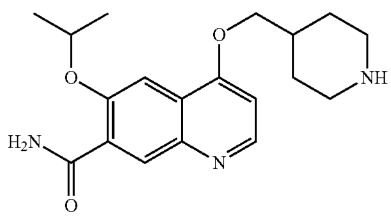 [SMILES: CC(C)Oc1cc2c(OCC3CCNCC3)ccnc2cc1C(N)=O] | P4 | 123855-51-6 | commercial | 4, 10 | 344 | ¹H NMR (600 MHz, dmso-d₆) δ 8.59-8.60 (d, 1 H), 8.26-8.32 (m, 1 H), 7.72 (br. s., 1 H), 7.68 (br. s., 1 H), 6.98-6.99 (d, 1 H), 4.81-4.85 (dt, 1 H), 4.55 (br. s., 1 H), 3.53-3.55 (d, 2 H), 3.41 (br. t., 2 H), 2.78-2.82 (t, 2 H), 1.88-1.90 (d, 2 H), 1.65 (br. s., 1 H), 1.48-1.55 (m, 2 H), 1.45-1.46 (d, 6 H) |
| 5 | 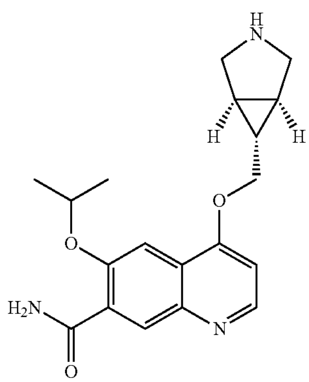 [SMILES: CC(C)Oc1cc2c(OC[C@H]3[C@@H]4CNC[C@@H]43)ccnc2cc1C(N)=O] | P4 | 419572-18-2 | Ref. 1 | 1, 10 | 342 | ¹H NMR (400 MHz, dmso-d₆) δ 8.60 (d, 1 H), 8.21 (s, 1 H), 7.71 (d, 2 H), 7.52 (s, 1 H), 6.99 (d, 1 H), 4.80 (quin, 1 H), 4.20 (d, 2 H), 2.87 (d, 2 H), 2.67 (d, 2 H), 1.50 (m, 2 H), 1.40 (d, 6 H), 1.30 (m, 1 H) |
| 6 | 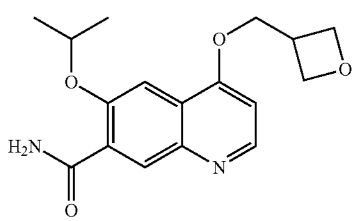 [SMILES: CC(C)Oc1cc2c(OCC3COC3)ccnc2cc1C(N)=O] | P4 | 6246-06-6 | commercial | 1 | 317 | Rt = 2.039 min; method PF-AB01 |
| 7 | 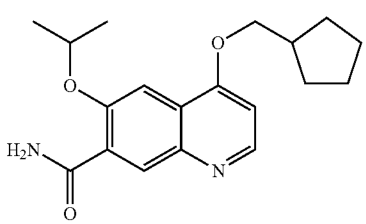 [SMILES: CC(C)Oc1cc2c(OCC3CCCC3)ccnc2cc1C(N)=O] | P4 | 3637-61-4 | commercial | 1 | 329 | Rt = 2.528 min; method PF-AB10 |

TABLE 1-continued

| Ex. | Structure | Reactant A | Reactant B | Source | Methods | MH+ | Characterization |
|---|---|---|---|---|---|---|---|
| 8 | 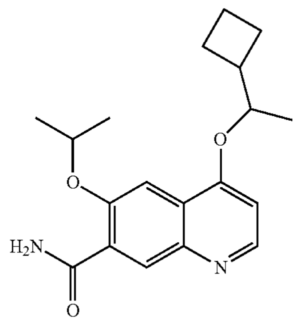 [SMILES: CC(C)Oc1cc2c(OC(C)C3CCC3)ccnc2cc1C(N)=O] | P4 | 7515-29-9 | commercial | 1 | 329 | Rt = 2.488 min; method PF-AB10 |
| 9 | 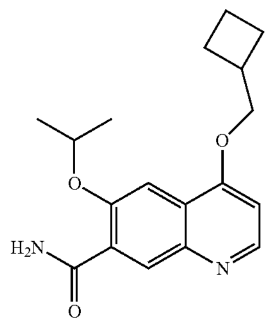 [SMILES: CC(C)Oc1cc2c(OCC3CCC3)ccnc2cc1C(N)=O] | P4 | 4415-82-1 | commercial | 1 | 315 | Rt = 2.384 min; method PF-AB10 |
| 10 | 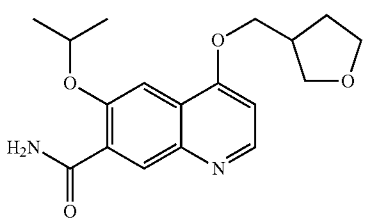 [SMILES: CC(C)Oc1cc2c(OCC3CCOC3)ccnc2cc1C(N)=O] | P4 | 15833-61-1 | commercial | 1 | 331 | Rt = 2.179 min, method PF-AB01 |
| 11 | 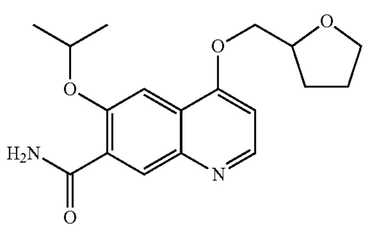 [SMILES: CC(C)Oc1cc2c(OCC3CCCO3)ccnc2cc1C(N)=O] | P4 | 97-99-4 | commercial | 1 | 331 | Rt = 2.210 min, method PF-AB01 |
| 12 | 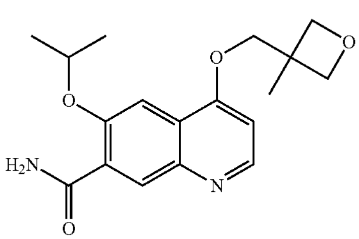 [SMILES: CC(C)Oc1cc2c(OCC3(C)COC3)ccnc2cc1C(N)=O] | P4 | 3143-02-0 | commercial | 1 | 331 | Rt = 2.175 min, method PF-AB01 |

TABLE 1-continued

| Ex. | Structure | Reactant A | Reactant B | Source | Methods | MH+ | Characterization |
|---|---|---|---|---|---|---|---|
| 13 | 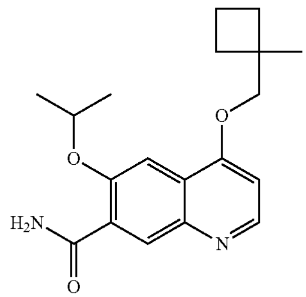 [SMILES: CC(C)Oc1cc2c(OCC3(C)CCC3)ccnc2cc1C(N)=O] | P4 | 38401-41-1 | commercial | 1 | 329 | Rt = 2.533 min; method PF-AB10 |
| 14 | 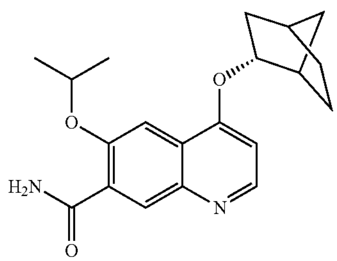 [SMILES: CC(C)Oc1cc2c(O[C@@H]3CC4CCC3C4)ccnc2cc1C(N)=O] | P4 | 497-36-9 | commercial | 1 | 341 | Rt = 2.501 min; method PF-AB10 |
| 15 | Chiral | P4 | 22415-59-4 | commercial | 1 | 331 | Rt = 2.213 min; method PF-AB01 |
| 16 | 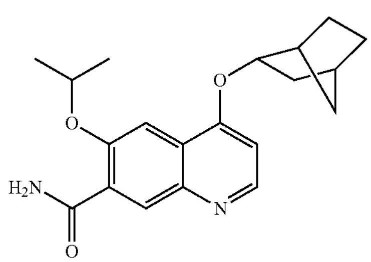 [SMILES: CC(C)Oc1cc2c(OC3CC4CCC3C4)ccnc2cc1C(N)=O] | P4 | 1632-68-4 | commercial | 1 | 341 | Rt = 2.496 min; method PF-AB10 |
| 17 | 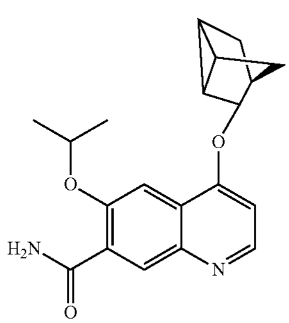 | P4 | 695-04-5 | Ref. 2 | 1 | 339 | Rt = 2.404 min; method PF-AB10 |

TABLE 1-continued

| Ex. | Structure | Reactant A | Reactant B | Source | Methods | MH+ | Characterization |
|---|---|---|---|---|---|---|---|
| 18 | 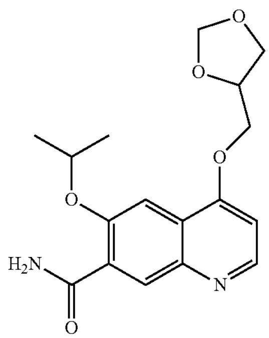 [SMILES: CC(C)Oc1cc2c(OCC3COCO3)ccnc2cc1C(N)=O] | P4 | 5464-28-8 | commercial | 1 | 333 | Rt = 2.097 min; method PF-AB01 |
| 19 | 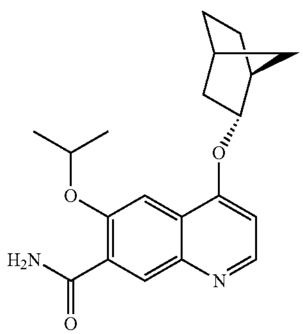 [SMILES: CC(C)Oc1cc2c(O[C@@H]3CC4CC[C@H]3C4)ccnc2cc1C(N)=O] | P4 | 61277-90-5 | commercial | 1 | 341 | Rt = 2.507 min; method PF-AB10 |
| 20 | 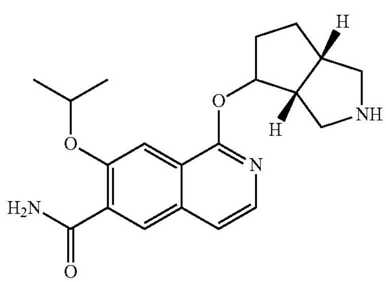 [SMILES: CC(C)Oc1cc2c(OC3CC[C@@H]4CNC[C@H]34)nccc2cc1C(N)=O] | P2 | 130658-13-8 | Ref. 3 | 1, 7, 10 | 356 | 1H NMR (400 MHz, dmso-d6) δ 9.07 (br. s., 2 H), 8.21 (s, 1 H), 7.90 (d, 1 H), 7.73 (br. s., 2 H), 7.57 (s, 1 H), 7.43 (d, 1 H), 5.55 (m, 1 H), 4.92 (dt, 2 H), 3.50 (d, 1 H), 3.22 (m, 3 H), 2.90 (m, 2 H), 2.15 (m, 1 H), 2.07 (d, 1 H), 1.87 (m, 1 H), 1.67 (br. s., 1 H), 1.39 (m, 4 H) |
| 21 | 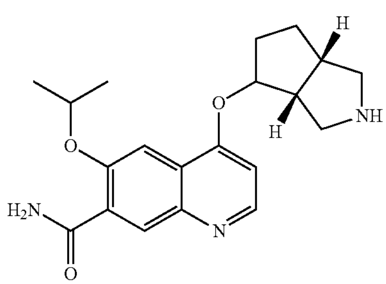 [SMILES: CC(C)Oc1cc2c(OC3CC[C@@H]4CNC[C@H]34)ccnc2cc1C(N)=O] | P4 | 130658-13-8 | Ref. 3 | 1, 10 | 356 | Rt = 2.363 min; method PF-CD05 |

TABLE 1-continued
| Ex. | Structure | Reactant A | Reactant B | Source | Methods | MH+ | Characterization |
|---|---|---|---|---|---|---|---|
| 22 | 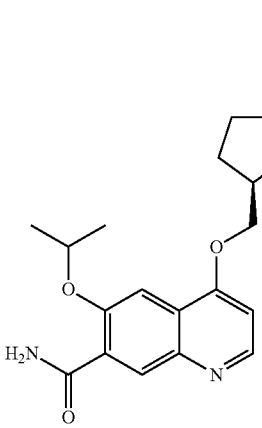<br>Chiral | P4 | 199174-24-8 | commercial | 1, 10, 11 | 397 | $^1$H NMR (400 MHz, dmso-d$_6$) δ 8.67 (d, 1 H), 8.23 (s, 1 H), 7.72 (br. s, 2 H), 7.51 (d, 1 H), 7.02 (s, 1 H), 4.88 (quin, 1 H), 4.23- 4.32 (m, 2 H), 3.95 (d, 2 H), 3.38-3.78 (m, 4 H), 2.79-2.93 (m, 1 H), 2.12-2.23 (m, 1 H), 1.80-2.11 (m 1 H), 1.41 (d, 6 H) |
| 23 | 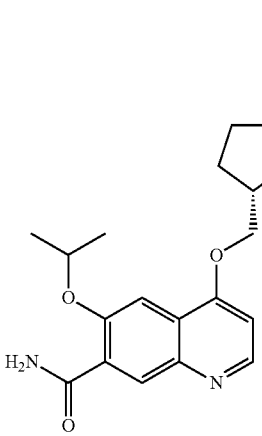<br>Chiral | P4 | 138108-72-2 | commercial | 1, 10, 11 | 397 | $^1$H NMR (400 MHz, dmso-d$_6$) δ 8.67 (d, 1 H), 8.23 (s, 1 H), 7.72 (br. s, 2 H), 7.51 (d, 1 H), 7.02 (s, 1 H), 4.88 (quin, 1 H), 4.23-4.32 (m, 2 H), 3.95 (d, 2 H), 3.38-3.78 (m, 4 H), 2.79-2.93 (m, 1 H), 2.12-2.23 (m, 1 H), 1.80-2.11 (m 1 H), 1.41 (d, 6 H) |
| 24 | 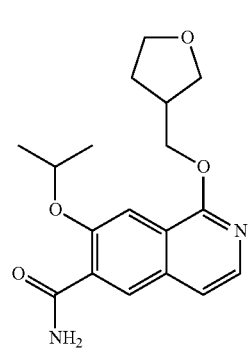 [SMILES: CC(C)Oc1cc2c(OCC3CCOC3)nccc2cc1C(N)=O] | P2 | 15833-61-1 | commercial | 1, 7 | 331 | Rt = 2.767 min; method PF-AB01 |

TABLE 1-continued

| Ex. | Structure | Reactant A | Reactant B | Source | Methods | MH+ | Characterization |
|---|---|---|---|---|---|---|---|
| 25 | 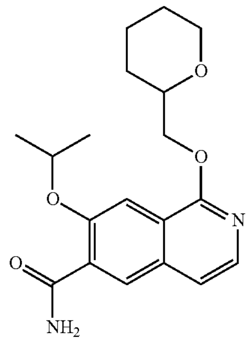 [SMILES: CC(C)Oc1cc2c(OCC3CCCCO3)nccc2cc1C(N)=O] | P2 | 100-72-1 | commercial | 1, 7 | 345 | Rt = 3.053 min; method PF-AB01 |
| 26 | 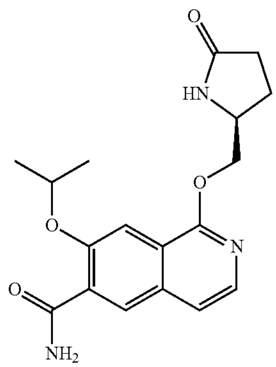 [SMILES: CC(C)Oc1cc2c(OC[C@@H]3CCC(=O)N3)nccc2cc1C(N)=O] | P2 | 17342-08-4 | commercial | 1, 7 | 344 | ¹H NMR (400 MHz, dmso-d₆) δ 8.19 (s, 1 H), 8.11 (s, 1 H), 7.88 (d, 1 H), 7.72 (br. d, 2 H), 7.64 (s, 1 H), 7.42 (d, 1 H), 4.91 (m, 1 H), 4.47 (dd, 1 H), 4.31 (dd, 1 H), 4.02 (br. s., 1 H), 2.30 (m, 3 H), 1.91 (m, 1 H), 1.39 (d, 6 H) |
| 27 | 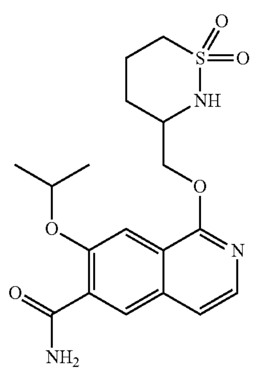 [SMILES: CC(C)Oc1cc2c(OCC3CCCS(=O)(=O)N3)nccc2cc1C(N)=O] | P2 | 849599-08-2 | Ref. 4 | 1, 7 | 394 | Rt = 2.598 min; method PF-AB01 |
| 28 | 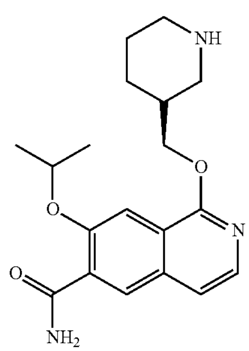 | P2 | 140695-84-7 | commercial | 1, 7, 10 | 344 | ¹H NMR (400 MHz, dmso-d₆) δ 8.18 (s, 1 H), 7.88 (d, 1 H), 7.72 (br. s, 2 H), 7.55 (s, 1 H), 7.38 (d, 1 H), 4.82 (m, 1 H), 4.31 (m, 2 H), 3.32 (br. s., 1 H), 3.07 (m, 1 H), 2.85 (d, 1 H), 2.41 (m, 2 H), 2.19 (m, 1 H), 2.01 (m, 1 H), 1.85 (m, 1 H), 1.58 (br. s., 1 H), 1.40 (d, 6 H), 1.25 (m, 1 H) |

TABLE 1-continued
| Ex. | Structure | Reactant A | Reactant B | Source | Methods | MH+ | Characterization |
|---|---|---|---|---|---|---|---|
| 29 | 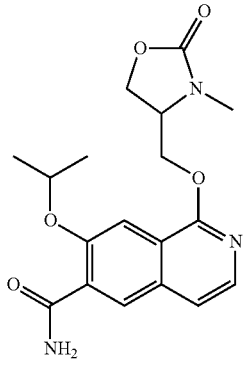 [SMILES: CC(C)Oc1cc2c(OCC3COC(=O)N3C)nccc2cc1C(N)=O] | P2 | 1217272-20-2 | Ref. 5 | 1, 7 | 360 | Rt = 2.458 min; method PF-AB01 |
| 30 | 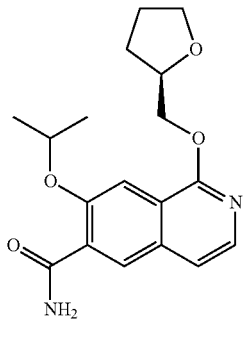 [SMILES: CC(C)Oc1cc2c(OC[C@H]3CCCO3)nccc2cc1C(N)=O]  Chiral | P2 | 22415-59-4 | commercial | 1, 7 | 331 | Rt = 2.809 min; method PF-AB01 |
| 31 | 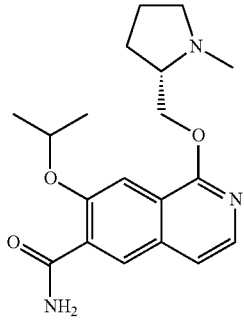 [SMILES: CC(C)Oc1cc2c(OC[C@@H]3CCCN3C)nccc2cc1C(N)=O]  Chiral | P2 | 34381-71-0 | commercial | 1, 7 | 344 | Rt = 2.184 min; method PF-AB01 |
| 32 | 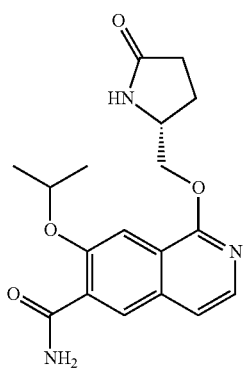 [SMILES: CC(C)Oc1cc2c(OC[C@H]3CCC(=O)N3)nccc2cc1C(N)=O]  Chiral | P2 | 66673-40-3 | commercial | 1, 7 | 344 | $^1$H NMR (500 MHz, dmso-d$_6$) δ 8.18 (s, 1 H), 8.10 (br. s, 1 H), 7.87 (d, 1 H), 7.76 (br. s., 1 H), 7.70 (br. s., 1 H), 7.63 (s, 1 H), 7.41 (d, 1 H), 4.90 (dt, 1 H), 4.46 (dd, 1 H), 4.31 (dd, 1 H), 3.98-4.08 (m, 1 H), 2.15-2.36 (m, 3 H), 1.86-1.95 (m, 1 H), 1.40 (d, 3 H), 1.38 (d, 3 H) |

TABLE 1-continued

| Ex. | Structure | Reactant A | Reactant B | Source | Methods | MH+ | Characterization |
|---|---|---|---|---|---|---|---|
| 33 | 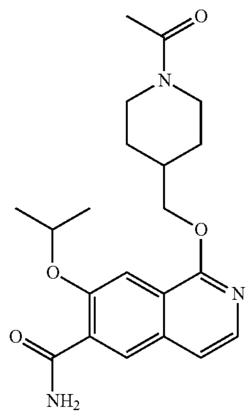 [SMILES: CC(=O)N1CCC(COc2nccc3cc(C(N)=O)c(OC(C)C)cc23)CC1] | P2 | 846057-27-0 | commercial | 1, 7 | 386 | Rt = 2.626 min; method PF-AB01 |
| 34 | 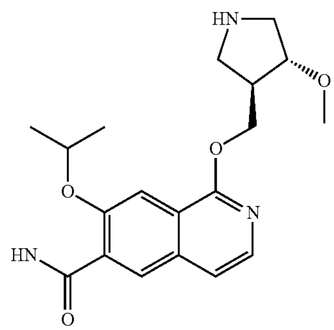 [SMILES: CO[C@H]1CNC[C@@H]1COc1nccc2cc(C(N)=O)c(OC(C)C)cc12] | P2 | 1428775-91-0 | Ref. 6 | 1, 7, 10 | 360 | Rt = 2.208 min; method PF-AB01 |
| 35 | 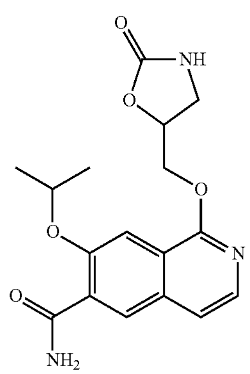 [SMILES: CC(C)Oc1cc2c(OCC3CNC(=O)O3)nccc2cc1C(N)=O] | P2 | 7517-99-9 | commercial | 1, 7 | 346 | Rt = 2.319 min; method PF-AB01 |
| 36 | 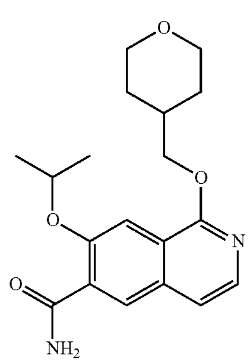 [SMILES: CC(C)Oc1cc2c(OCC3CCOCC3)nccc2cc1C(N)=O] | P2 | 14774-37-9 | commercial | 1, 7 | 345 | Rt = 2.874 min; method PF-AB01 |

TABLE 1-continued

| Ex. | Structure | Reactant A | Reactant B | Source | Methods | MH+ | Characterization |
|---|---|---|---|---|---|---|---|
| 37 | (Chiral) | P2 | 135065-76-8 | commercial | 1, 7, 10 | 346 | Rt = 2.149 min; method PF-AB01 |
| 38 | 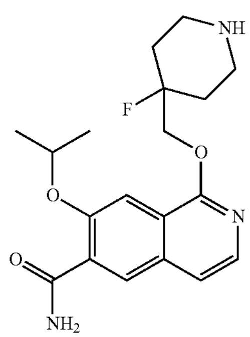 [SMILES: CC(C)Oc1cc2c(OCC3(F)CCNCC3)nccc2cc1C(N)=O] | P2 | 614730-97-1 | commercial | 1, 7, 10 | 362 | Rt = 2.258 min; method PF-AB01 |
| 39 | 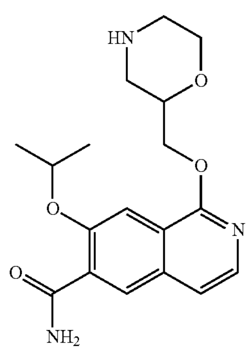 [SMILES: CC(C)Oc1cc2c(OCC3CNCCO3)nccc2cc1C(N)=O] | P2 | 135065-69-9 | commercial | 1, 7, 10 | 346 | Rt = 2.145 min; method PF-AB01 |
| 40 | 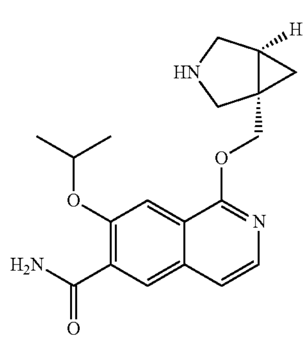 [SMILES: CC(C)Oc1cc2c(OC[C@]34CNC[C@H]3C4)nccc2cc1C(N)=O] | P2 | 161152-76-7 | Ref. 7 | 1, 7, 10 | 342 | $^1$H NMR (400 MHz, dmso-d$_6$) δ 8.18 (s, 1 H), 7.87 (d, 1 H), 7.72 (br. s., 2 H), 7.55 (s, 1 H), 7.38 (d, 1 H), 4.81 (dt, 1 H), 4.62 (d, 2 H), 2.95 (d, 1 H), 2.70-2.85 (m, 3 H), 1.40 (d, 6 H), 0.68 (d, 2 H), 0.02 (d, 1 H); |

TABLE 1-continued

| Ex. | Structure | Reactant A | Reactant B | Source | Methods | MH+ | Characterization |
|---|---|---|---|---|---|---|---|
| 41 | (structure) Chiral | P2 | 83435-58-9 | commercial | 1, 7, 10 | 330 | Rt = 2.132 min; method PF-AB01 |
| 42 | (structure) | P2 | 419572-18-2 | Ref. 8 | 1, 7, 10 | 342 | Rt = 2.211 min; method PF-AB01 |
| 43 | (structure) | P2 | 157634-00-9 | commercial | 1, 7, 10 | 344 | Rt = 2.227 min; method PF-AB01 |
| 44 | (structure) | P2 | 40987-46-0 | Ref. 9 | 1, 7 | 360 | Rt = 2.156 min; method PF-AB01 |

TABLE 1-continued

| Ex. | Structure | Reactant A | Reactant B | Source | Methods | MH+ | Characterization |
|---|---|---|---|---|---|---|---|
| 45 | 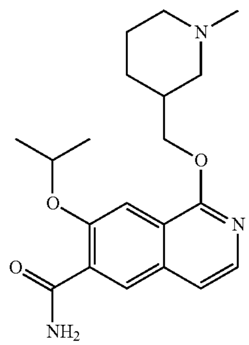 [SMILES: CC(C)Oc1cc2c(OCC3CCCN(C)C3)nccc2cc1C(N)=O] | P2 | 7583-53-1 | commercial | 1, 7 | 358 | Rt = 2.259 min; method PF-AB01 |
| 46 | 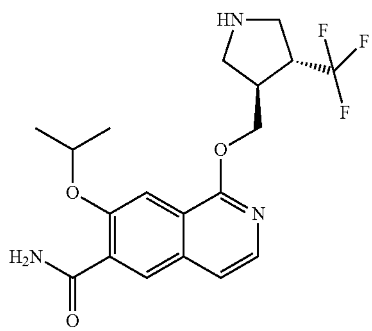 [SMILES: CC(C)Oc1cc2c(OC[C@H]3CNC[C@@H]3C(F)(F)F)nccc2cc1C(N)=O] | P2 | L122 | | 1, 7, 10 | 398 | Rt = 2.349 min; method PF-AB01 |
| 47 | Chiral | P2 | 135065-71-3 | commercial | 1, 7, 10 | 346 | Rt = 2.088 min; method PF-AB01 |
| 48 | Chiral | P2 | 140695-85-8 | commercial | 1, 7, 10 | 344 | Rt = 2.216 min; method PF-AB01 |

TABLE 1-continued

| Ex. | Structure | Reactant A | Reactant B | Source | Methods | MH+ | Characterization |
|---|---|---|---|---|---|---|---|
| 49 | Chiral | P2 | 199174-24-8 | commercial | 1, 7, 10 | 330 | Rt = 2.127 min; method PF-AB01 |
| 50 | Chiral | P4 | 199174-24-8 | commercial | 1, 10 | 330 | Rt = 1.824 min; method PF-AB01 |
| 51 | Chiral | P4 | 135065-76-8 | Commercial | 1, 10 | 346 | Rt = 1.805 min; method PF-AB01 |
| 52 | 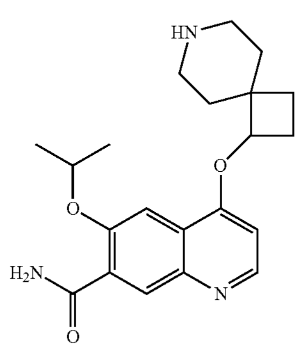 [SMILES: CC(C)Oc1cc2c(OC3CCC34CCNCC4)ccnc2cc1C(N)=O] | P4 | 1338247-76-9 | commercial | 1, 10 | 370 | Rt = 1.963 min; method PF-AB01 |

TABLE 1-continued

| Ex. | Structure | Reactant A | Reactant B | Source | Methods | MH+ | Characterization |
|---|---|---|---|---|---|---|---|
| 53 | Chiral | P4 | 135065-71-3 | commercial | 1, 10 | 346 | Rt = 1.812 min; method PF-AB01 |
| 54 | 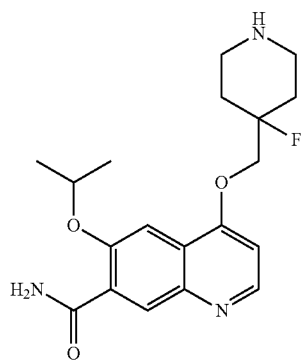 [SMILES: CC(C)Oc1cc2c(OCC3(F)CCNCC3)ccnc2cc1C(N)=O] | P4 | 614730-97-1 | commercial | 1, 10 | 362 | Rt = 1.887 min; method PF-AB01 |
| 55 | 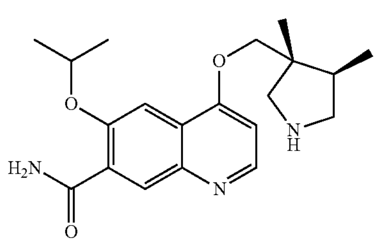 [SMILES: CC(C)Oc1cc2c(OC[C@@]3(C)CNC[C@@H]3C)ccnc2cc1C(N)=O] | P4 | 1239999-37-1 | Ref. 10 | 1, 10 | 358 | Rt = 1.963 min; method PF-AB01 |
| 56 | 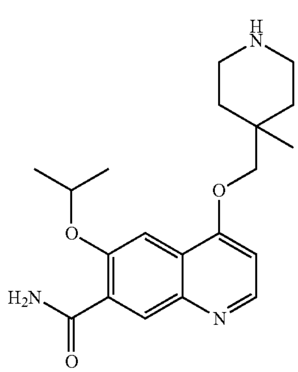 [SMILES: CC(C)Oc1cc2c(OCC3(C)CCNCC3)ccnc2cc1C(N)=O] | P4 | 236406-21-6 | commercial | 1, 10 | 358 | Rt = 2.454 min; method PF-CD05 |

TABLE 1-continued

| Ex. | Structure | Reactant A | Reactant B | Source | Methods | MH+ | Characterization |
|---|---|---|---|---|---|---|---|
| 57 | (Chiral) | P4 | 97859-49-9 | Ref. 11 | 1, 10 | 346 | Rt = 1.887 min; method PF-AB01 |
| 58 | 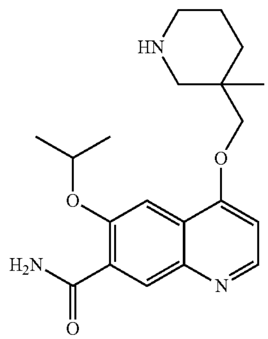 [SMILES: CC(C)Oc1cc2c(OCC3(C)CCCNC3)ccnc2cc1C(N)=O] | P4 | 221298-00-6 | commercial | 1, 10 | 358 | Rt = 1.964 min; method PF-AB01 |
| 59 | 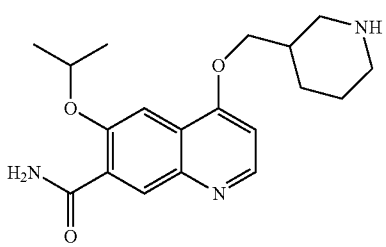 [SMILES: CC(C)Oc1cc2c(OCC3CCCNC3)ccnc2cc1C(N)=O] | P4 | 4606-65-9 | commercial | 1 | 344 | Rt = 2.349 min; method PF-CD05 |
| 60 | 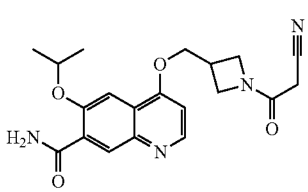 [SMILES: CC(C)Oc1cc2c(OCC3CN(C(=O)CC#N)C3)ccnc2cc1C(N)=O] | P4 | 142253-56-3 | commercial | 1, 10, 11 | 383 | ¹H NMR (400 MHz, dmso-d₆) δ 8.66 (d, 1 H), 8.25 (s, 1 H), 7.73 (br. s., 2 H), 7.49 (s, 1 H), 7.07 (d, 1 H), 4.81 (dt, 1 H), 4.37-4.47 (m, 2 H), 4.29-4.37 (m, 1 H), 4.16 (dd, 1 H), 4.09 (t, 1 H), 3.93 (dd, 1 H), 3.80 (d, 2 H), 3.19 (td, 1 H), 1.40 (d, 2 H), 1.37 (d, 3 H) |
| 61 | (Chiral) | P2 | 83435-58-9 | commercial | 1, 7, 10, 11 | 397 | Rt = 2.637 min; method PF-AB01 |

TABLE 1-continued
| Ex. | Structure | Reactant A | Reactant B | Source | Methods | MH+ | Characterization |
|---|---|---|---|---|---|---|---|
| 62 | 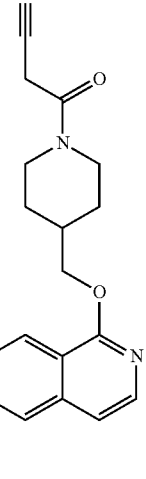 | P2 | 123855-51-6 | commercial | 1, 7, 10, 11 | 411 | Rt = 2.666 min; method PF-AB01 |
| 63 | 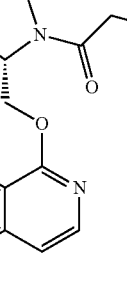  Chiral | P2 | 69610-40-8 | commercial | 1, 7, 10, 11 | 397 | Rt = 2.638 min; method PF-AB01 |
| 64 | 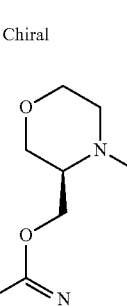  Chiral | P2 | 714971-28-5 | commercial | 1, 7, 10, 11 | 413 | Rt = 2.522 min; method PF-AB01 |

TABLE 1-continued

| Ex. | Structure | Reactant A | Reactant B | Source | Methods | MH+ | Characterization |
|---|---|---|---|---|---|---|---|
| 65 | 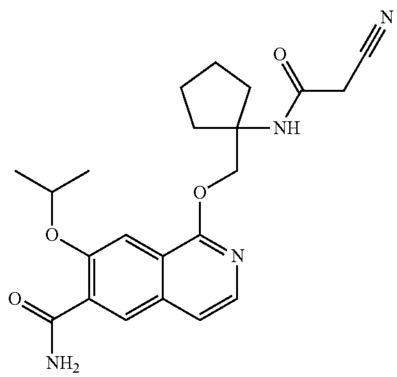 [SMILES: CC(C)Oc1cc2c(OCC3(NC(=O)CC#N)CCCC3)nccc2cc1C(N)=O] | P2 | 168540-07-6 | commercial | 1, 7, 10, 11 | 411 | Rt = 2.876 min; method PF-AB01 |
| 66 | Chiral | P2 | 199174-24-8 | commercial | 1, 7, 10, 11 | 397 | Rt = 2.576 min; method PF-AB01 |
| 67 | Chiral | P2 | 140695-85-8 | commercial | 1, 7, 10, 11 | 411 | Rt = 2.755 min; method PF-AB01 |

TABLE 1-continued

| Ex. | Structure | Reactant A | Reactant B | Source | Methods | MH+ | Characterization |
|---|---|---|---|---|---|---|---|
| 68 | (Chiral structure) | P2 | 1244772-37-9 | Ref. 12 | 1, 7, 10, 11, chiral HPLC | 423 | Rt = 2.83 min; method PF-AB01 |
| 69 | (structure) | P2 | 142253-56-3 | commercial | 1, 7, 10, 11 | 383 | Rt = 2.458 min; method PF-AB01 |
| 70 | (Chiral structure) | P2 | 138108-72-2 | commercial | 1, 7, 10, 11 | 397 | Rt = 2.577 min; method PF-AB01 |
| 71 | (structure) | P4 | 130658-13-8 | Ref. 13 | 1, 10, 11 | 423 | $^1$H NMR (400 MHz, dmso-d$_6$) δ 8.71 (d, 2 H), 8.27 (s, 0.5 H, diastereomer 1), 8.25 (s, 0.5 H, diastereomer 2), 7.75 (br. s., 2 H), 7.44 (s, 0.5 H, diastereomer 1), 7.32 (s, 0.5 H, diastereomer, 1), 7.18 (m, 1 H), 5.10-5.25 (m, 1 H), 4.87 (quin, 0.5 H, diastereomer 1), 4.77 (quin, 0.5 H, diastereomer 2), 4.00 (d, 2 H), 3.82 (m, 1 H), 3.65 (m, 1 H), 3.35 (m, 1 H), 3.07-3.26 (m, 1 H), 2.80-2.97 (m, 1 H), 1.83-2.31 (m, 3 H), 1.53-1.70 (m, 1 H), 1.33-1.44 (m, 6 H) |

TABLE 1-continued

| Ex. | Structure | Reactant A | Reactant B | Source | Methods | MH+ | Characterization |
|---|---|---|---|---|---|---|---|
| 72 | 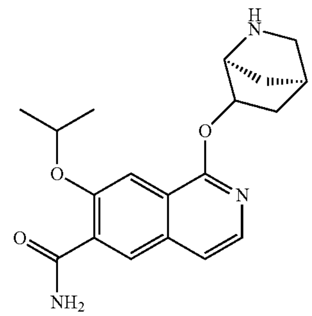 [SMILES: CC(C)Oc1cc2c(OC3C[C@@H]4CN[C@H]3C4)nccc2cc1C(N)=O] | P2 | 1279569-31-1 | Ref. 14 | 1, 7, 10 | 342 | ¹H NMR (400 MHz, dmso-d₆) δ 8.21 (s, 1 H), 7.91 (d, 1 H), 7.73 (br. s, 2 H), 7.57 (s, 1 H), 7.47 (d, 1 H), 5.49 (d, 1 H), 4.90 (dt, 1 H), 3.01-3.12 (m, 1 H), 2.92 (dd, 1 H), 2.73-2.80 (m, 1 H), 2.64-2.70 (m, 1 H), 2.53-2.59 (m, 1 H), 2.14-2.23 (m, 1 H), 2.00-2.10 (m, 1 H), 1.77-1.86 (m, 1 H), 1.70-1.77 (m, 1 H), 1.38 (d, 6 H) |
| 73 | Chiral | P2 | 161511-85-9 | commercial | 1, 7, 10, 11 | 383 | Rt = 2.518 min; method PF-AB01 |
| 74 | Chiral | P2 | 198835-07-3 | Ref. 15 | 1, 7, 10, 11 | 409 | Rt = 2.615 min; method PF-AB01 |
| 75 | Chiral | P2 | 135065-76-8 | commercial | 1, 7, 10, 11 | 413 | Rt = 2.541 min; method PF-AB01 |

TABLE 1-continued

| Ex. | Structure | Reactant A | Reactant B | Source | Methods | MH+ | Characterization |
|---|---|---|---|---|---|---|---|
| 76 | 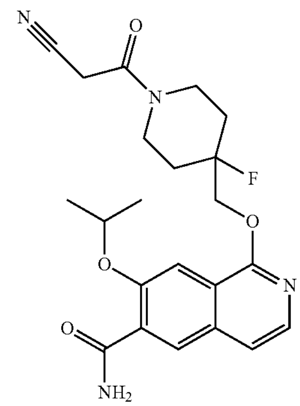 [SMILES: CC(C)Oc1cc2c(OCC3(F)CCN(C(=O)CC#N)CC3)nccc2cc1C(N)=O] | P2 | 614730-97-1 | commercial | 1, 7, 10, 11 | 429 | Rt = 2.726 min; method PF-AB01 |
| 77 | 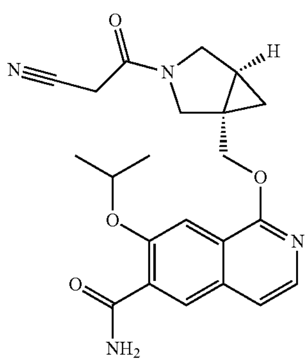 [SMILES: CC(C)Oc1cc2c(OC[C@@]34C[C@@H]3CN(C(=O)CC#N)C4)nccc2cc1C(N)=O] | P2 | 161152-76-7 | Ref. 7 | 1, 7, 10, 11 | 409 | Rt = 2.68 min; method PF-AB01 |
| 78 | Chiral | P2 | 135065-71-3 | commercial | 1, 7, 10, 11 | 413 | Rt = 2.542 min; method PF-AB01 |

| Ex. | Structure | Reactant A | Reactant B | Source | Methods | MH+ | Characterization |
|---|---|---|---|---|---|---|---|
| 79 | *(Chiral structure with isoquinoline carboxamide, isopropoxy, and bicyclic pyrrolidine-cyclopentane with cyanoacetyl group)* | P2 | 130658-13-8 | Ref. 13 | 1, 7, 10, 11 | 423 | Rt = 2.754 min; method PF-AB01 |
| 80 | *(Structure with isoquinoline carboxamide, isopropoxy, and ethyl-pyrrolidine with cyanoacetyl group)* | P2 | 1441392-37-5 | Ref. 16 | 1, 7, 10, 11 | 425 | Rt = 2.874 min; method PF-AB01 |
| 81 | *(Chiral structure with isoquinoline carboxamide, isopropoxy, and azabicyclic group with cyanoacetyl)* | P2 | 1244772-37-9 | Ref. 12 | 1, 7, 10, 11, chiral HPLC | 423 | Rt = 2.827 min; method PF-AB01 |

TABLE 1-continued

| Ex. | Structure | Reactant A | Reactant B | Source | Methods | MH+ | Characterization |
|---|---|---|---|---|---|---|---|
| 82 | 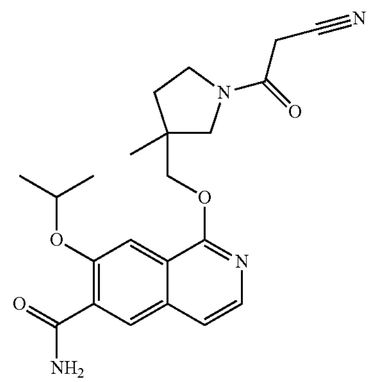 [SMILES: CC(C)Oc1cc2c(OCC3(C)CCN(C(=O)CC#N)C3)nccc2cc1C(N)=O] | P2 | 1263506-20-2 | commercial | 1, 7, 10, 11 | 411 | Rt = 2.709 min; method PF-AB01 |
| 83 | 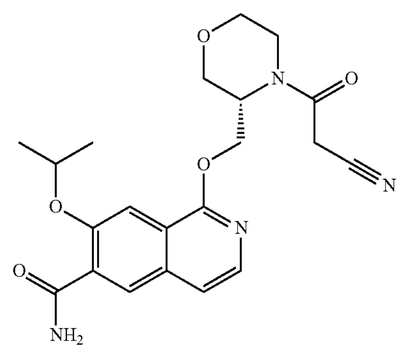 [SMILES: CC(C)Oc1cc2c(OC[C@@H]3COCCN3C(=O)CC#N)nccc2cc1C(N)=O] | P2 | 215917-99-0 | commercial | 1, 7, 10, 11 | 413 | Rt = 2.521 min; method PF-AB01 |
| 84 | Chiral | P2 | 1428775-91-0 | Ref. 6 | 1, 7, 10, 11 | 427 | Rt = 2.58 min; method PF-AB01 |

TABLE 1-continued

| Ex. | Structure | Reactant A | Reactant B | Source | Methods | MH+ | Characterization |
|---|---|---|---|---|---|---|---|
| 85 | 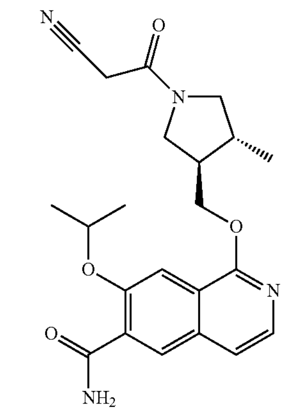 [SMILES: CC(C)Oc1cc2c(OC[C@H]3CN(C(=O)CC#N)C[C@@H]3C)nccc2cc1C(N)=O] | P2 | 1349715-96-3 | commercial | 1, 7, 10, 11 | 411 | Rt = 2.728 min; method PF-AB01 |
| 86 | 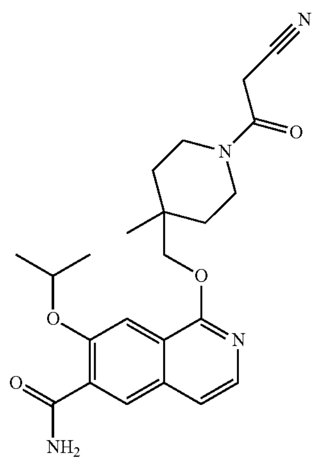 [SMILES: CC(C)Oc1cc2c(OCC3(C)CCN(C(=O)CC#N)CC3)nccc2cc1C(N)=O] | P2 | 236406-21-6 | commercial | 1, 7, 10, 11 | 425 | Rt = 2.861 min; method PF-AB01 |
| 87 | 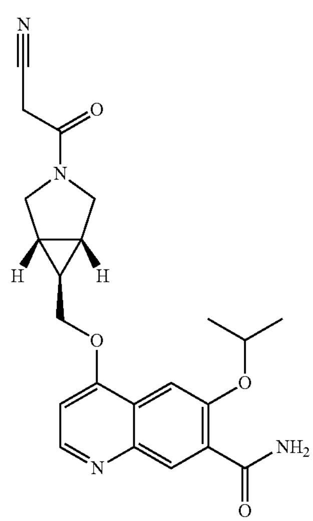 [SMILES: CC(C)Oc1cc2c(OC[C@@H]3[C@H]4CN(C(=O)CC#N)C[C@@H]34)ccnc2cc1C(N)=O] | P4 | 419572-18-2 | Ref. 1 | 1, 10, 11 | 409 | Rt = 2.114 min; method PF-AB01 |

TABLE 1-continued

| Ex. | Structure | Reactant A | Reactant B | Source | Methods | MH+ | Characterization |
|---|---|---|---|---|---|---|---|
| 88 | 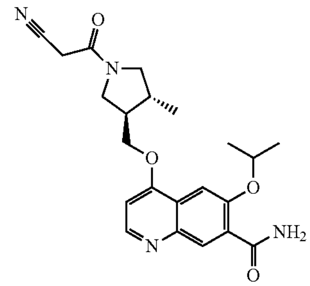 [SMILES: CC(C)Oc1cc2c(OC[C@H]3CN(C(=O)CC#N)C[C@@H]3C)ccnc2cc1C(N)=O] | P4 | 1349715-96-3 | commercial | 1, 10, 11 | 411 | Rt = 2.197 min; method PF-AB01 |
| 89 | Chiral | P4 | 1244772-37-9 | Ref. 12 | 1, 10, 11, chiral HPLC | 423 | Rt = 2.235 min; method PF-CD05 |
| 90 | Chiral | P4 | 161152-76-7 | Ref. 7 | 1, 10, 11, chiral HPLC | 409 | Rt = 2.149 min; method PF-AB01 |
| 91 | 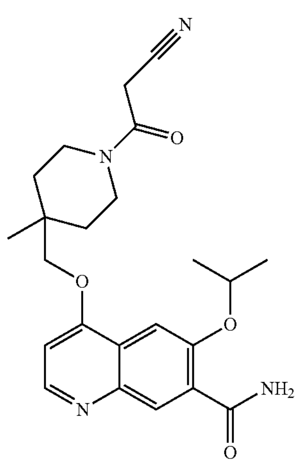 [SMILES: CC(C)Oc1cc2c(OCC3(C)CCN(C(=O)CC#N)CC3)ccnc2cc1C(N)=O] | P4 | 236406-21-6 | commercial | 1, 10, 11 | 425 | Rt = 2.254 min; method PF-AB01 |

TABLE 1-continued

| Ex. | Structure | Reactant A | Reactant B | Source | Methods | MH+ | Characterization |
|---|---|---|---|---|---|---|---|
| 92 | Chiral | P4 | 1244772-37-9 | Ref. 12 | 1, 10, 11 | 423 | Rt = 2.21 min; method PF-AB01 |
| 93 | Chiral | P4 | 140695-84-7 | commercial | 1, 10, 11 | 411 | Rt = 2.221 min; method PF-AB01 |
| 94 | 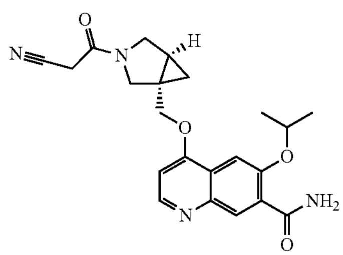 [SMILES: CC(C)Oc1cc2c(OC[C@@]34C[C@@H]3CN(C(=O)CC#N)C4)ccnc2cc1C(N)=O] | P4 | 161152-76-7 | Ref. 7 | 1, 10, 11 | 409 | Rt = 2.136 min; method PF-AB01 |
| 95 | 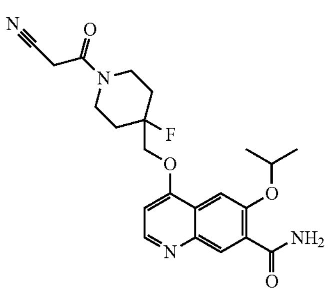 [SMILES: CC(C)Oc1cc2c(OCC3(F)CCN(C(=O)CC#N)CC3)ccnc2cc1C(N)=O] | P4 | 614730-97-1 | commercial | 1,10, 11 | 429 | Rt = 2.211 min; method PF-AB01 |

TABLE 1-continued

| Ex. | Structure | Reactant A | Reactant B | Source | Methods | MH+ | Characterization |
|---|---|---|---|---|---|---|---|
| 96 | 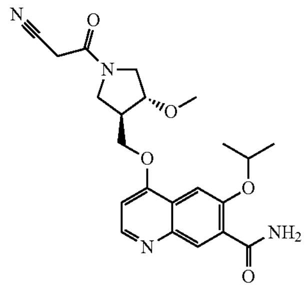 [SMILES: CO[C@H]1CN(C(=O)CC#N)C[C@@H]1COc1ccnc2cc(C(N)=O)c(OC(C)C)cc12] | P4 | 1428775-91-0 | Ref. 6 | 1, 10, 11 | 427 | Rt = 2.119 min; method PF-AB01 |
| 97 | Chiral | P4 | 140695-85-8 | commercial | 1, 10, 11 | 411 | Rt = 2.212 min; method PF-AB01 |
| 98 | Chiral | P4 | 135065-76-8 | commercial | 1, 10, 11 | 413 | Rt = 2.059 min; method PF-AB01 |
| 99 | 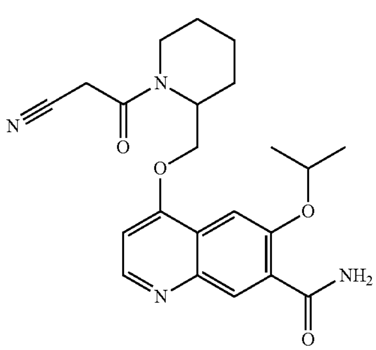 [SMILES: CC(C)Oc1cc2c(OCC3CCCCN3C(=O)CC#N)ccnc2cc1C(N)=O] | P4 | 157634-00-9 | commercial | 1, 10, 11 | 411 | Rt = 2.163 min; method PF-AB01 |

TABLE 1-continued

| Ex. | Structure | Reactant A | Reactant B | Source | Methods | MH+ | Characterization |
|---|---|---|---|---|---|---|---|
| 100 | 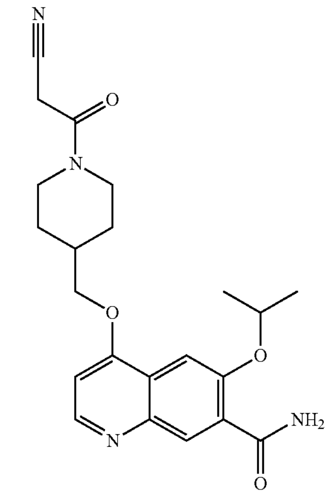 [SMILES: CC(C)Oc1cc2c(OCC3CCN(C(=O)CC#N)CC3)ccnc2cc1C(N)=O] | P4 | 123855-51-6 | commercial | 1, 10, 11 | 411 | Rt = 2.159 min; method PF-AB01 |
| 101 | Chiral | P P2 | 198835-07-3 | Ref. 15 | 1, 7, 10 | 342 | $^1$H NMR (400 MHz, dmso-d$_6$) δ 8.18 (s, 1 H), 7.83-7.93 (m, 1 H), 7.72 (br. s., 2 H), 7.60 (s, 1 H), 7.38 (d, 1 H), 5.35-5.48 (m, 1 H), 4.86 (dt, 1 H), 3.39 (br. s., 1 H), 3.25 (d, 1 H), 2.82 (br. s., 1 H), 2.68-2.80 (m, 1 H), 2.12-2.24 (m, 1 H), 1.58-1.67 (m, 1 H), 1.50-1.58 (m, 1 H), 1.40 (d, 6 H), 1.26-1.37 (m, 1 H) |
| 102 | Chiral | P2 | 198835-07-3 | Ref. 14 | 1, 7, 10 | 342 | $^1$H NMR (400 MHz, dmso-d$_6$) δ 8.19 (s, 1 H), 7.88 (d, 1 H), 7.73 (br. s., 2 H), 7.62 (s, 1 H), 7.38 (d, 1 H), 5.42 (s, 1 H), 4.77-4.93 (m, 1 H), 3.24 (d, 1 H), 2.81 (br. s., 1 H), 2.69 (dd, 1 H), 2.18 (ddd, 1 H), 1.49-1.68 (m, 2 H), 1.41 (d, 6 H), 1.29-1.39 (m, 1 H) |
| 103 | Chiral | P2 | 17342-08-4 | commercial | 1 | 326 | $^1$H NMR (500 MHz, CDCl$_3$) δ 8.07 (s, 1 H), 7.93 (d, 1 H), 7.54 (s, 1 H), 7.22 (d, 1 H), 6.12 (br. s., 1 H), 4.83 (dt, 1 H), 4.68 (dd, 1 H), 4.43 (dd, 1 H), 4.22 (dd, 1 H), 2.34-2.55 (m, 3 H), 1.95-2.09 (m, 1 H), 1.49 (dd, 6 H) |

TABLE 1-continued

| Ex. | Structure | Reactant A | Reactant B | Source | Methods | MH+ | Characterization |
|---|---|---|---|---|---|---|---|
| 104 | Chiral | P2 | 132682-23-6 | Ref. 17 | 1, 7 | 346 | $^1$H NMR (500 MHz, dmso-d$_6$) δ 8.15 (s, 1 H), 7.95 (br. s, 1 H), 7.84 (d, 1 H), 7.69 (br. s., 1 H), 7.67 (br. s., 1 H), 7.59 (s, 1 H), 7.39 (d, 1 H), 4.84 (quin, 1 H), 4.44-4.47 (m, 1 H), 4.43 (d, 1 H), 4.35 (dd, 1 H), 4.28 (dd, 1 H), 4.21 (dq, 1 H), 1.36 (d, 3 H), 1.34 (d, 3 H) |
| 105 | Chiral | P2 | 17342-08-4 | commercial | 1, 15, 16, 7 | 358 | $^1$H NMR (500 MHz, dmso-d$_6$) δ 8.21 (s, 1 H), 8.09 (br. s, 1 H), 7.76 (br. s., 2 H), 7.71 (s, 1 H), 7.67 (s, 1 H), 4.92 (dt, 1 H), 4.42 (dd, 1 H), 4.28 (dd, 1 H), 3.98-4.05 (m, 1 H), 2.44 (s, 3H), 2.15-2.35 (m, 3 H), 1.87-1.94 (m, 1 H), 1.40 (d, 3 H), 1.38 (d, 3 H) |
| 106 | Chiral | P2 | 128726-47-6 | commercial | 1, 7 | 358 | $^1$H NMR (500 MHz, dmso-d$_6$) δ 8.19 (s, 1 H), 7.88 (dd, 1 H), 7.74 (br. s., 1 H), 7.70 (br. s., 2 H), 7.66 (s, 1 H), 7.41 (d, 1 H), 4.89 (dt, 1 H), 4.40 (d, 2 H), 3.78-3.86 (m, 1 H), 2.12-2.23 (m, 3 H), 1.91-2.00 (m, 1 H), 1.81-1.90 (m, 2 H), 1.61-1.73 (m, 3 H), 1.40 (d, 3 H), 1.38 (d, 3 H) |
| 107 | 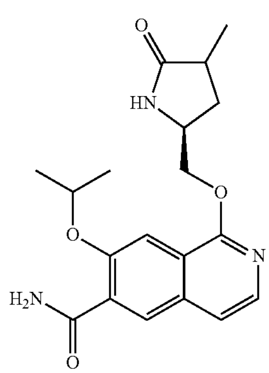 [SMILES: CC(C)Oc1cc2c(OC[C@@H]3CC(C)C(=O)N3)nccc2cc1C(N)=O] | P2 | L1 | | 1, 7 | 358 | $^1$H NMR (400 MHz, dmso-d$_6$) δ 8.21 (s, 1 H), 7.88 (d, 1 H), 7.74 (br. s, 1 H), 7.71 (br. s, 1 H), 7.69 (s, 1 H), 7.42 (d, 1 H), 4.85-5.00 (m, 1 H), 4.50-4.61 (m, 1 H), 4.16-4.28 (m, 1 H), 3.89-4.04 (m, 1 H), 2.30-2.48 (m, 3 H), 1.36-1.44 (m, 6 H), 1.09-1.13 (m, 3 H) |

TABLE 1-continued

| Ex. | Structure | Reactant A | Reactant B | Source | Methods | MH+ | Characterization |
|---|---|---|---|---|---|---|---|
| 108 | 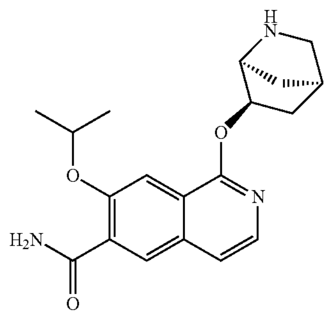 [SMILES: CC(C)Oc1cc2c(O[C@@H]3C[C@@H]4CN[C@H]3C4)nccc2cc1C(N)=O] | P2 | 207405-59-2 | commercial | 1, 7, 10, chiral HPLC | 342 | ¹H NMR (400 MHz, dmso-d₆) δ 8.18 (s, 1 H), 7.88 (d, 1 H), 7.71 (br. s, 2 H), 7.53 (s, 1 H), 7.39 (d, 1 H), 5.13-5.19 (m, 1 H), 4.85 (dt, 1 H), 3.60 (br. s, 1 H), 2.73-2.79 (m, 1 H), 2.51-2.55 (m, 2 H), 1.99 (ddd, 1 H), 1.73-1.79 (m, 1 H), 1.60-1.68 (m, 1 H), 1.45-1.51 (m, 1 H), 1.38 (dd, 6 H) |
| 109 | 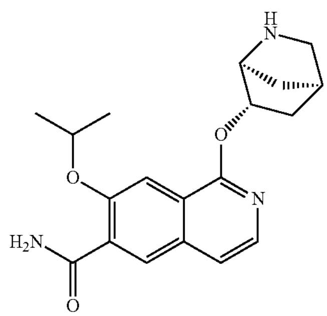 [SMILES: CC(C)Oc1cc2c(O[C@H]3C[C@@H]4CN[C@H]3C4)nccc2cc1C(N)=O] | P2 | 207405-59-2 | commercial | 1, 7, 10, chiral HPLC | 342 | ¹H NMR (400 MHz, dmso-d₆) δ 8.18 (s, 1 H), 7.88 (d, 1 H), 7.71 (br. s., 2 H), 7.52 (s, 1 H), 7.37 (d, 1 H), 5.07-5.11 (m, 1 H), 4.85 (dt, 1 H), 3.45 (br. s, 1 H), 2.66-2.73 (m, 1 H), 2.42-2.46 (m, 2 H), 1.95 (ddd, 1 H), 1.67-1.73 (m, 1 H), 1.57-1.64 (m, 1 H), 1.40-1.45 (m, 1 H), 1.38 (dd, 6 H) |
| 110 | Chiral | P2 | 156088-46-9 | Ref. 18 | 1, 7 | 372 | ¹H NMR (500 MHz, dmso-d₆) δ 8.18 (s, 1 H), 8.13 (s, 1 H), 7.88 (d, 1 H), 7.74 (br. s., 1 H), 7.71 (br. s., 1 H), 7.69 (s, 1 H), 7.41 (d, 1 H), 4.92 (dt, 1 H), 4.57 (dd, 1 H), 4.21 (dd, 1 H), 3.91-4.06 (m, 1 H), 2.10 (dd, 1 H), 1.74 (dd, 1 H), 1.39 (t, 6 H), 1.11 (s, 3 H), 1.09 (s, 3 H) |
| 111 | 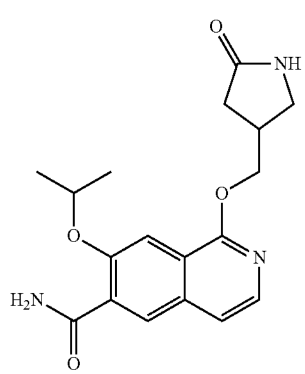 [SMILES: CC(C)Oc1cc2c(OCC3CNC(=O)C3)nccc2cc1C(N)=O] | P2 | 64320-89-4 | commercial | 1, 7 | 344 | ¹H NMR (400 MHz, dmso-d₆) δ 8.19 (s, 1 H), 7.88 (d, 1 H), 7.72 (br. s., 2 H), 7.59 (s, 1 H), 7.55 (s, 1 H), 7.40 (d, 1 H), 4.87 (dt, 1 H), 4.49 (dd, 1 H), 4.41 (dd, 1 H), 3.50 (dd, 1 H), 3.19 (dd, 1 H), 2.88-3.01 (m, 1 H), 2.42 (dd, 1 H), 2.13 (dd, 1 H), 1.39 (d, 3 H), 1.38 (d, 3 H) |

TABLE 1-continued

| Ex. | Structure | Reactant A | Reactant B | Source | Methods | MH+ | Characterization |
|---|---|---|---|---|---|---|---|
| 112 | 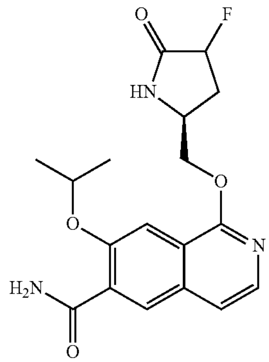 [SMILES: CC(C)Oc1cc2c(OC[C@@H]3CC(F)C(=O)N3)nccc2cc1C(N)=O] | P2 | L2 | | 1, 7 | 362 | ¹H NMR (500 MHz, dmso-d₆) δ 8.74 (br. s, 1 H), 8.19 (s, 1 H), 7.88 (d, 1 H), 7.74 (br. s., 1 H), 7.71 (br. s., 1 H), 7.57 (s, 1 H), 7.43 (d, 1 H), 5.28 (dt, 1 H), 4.91 (dt, 1 H), 4.47 (dd, 1 H), 4.34 (dd, 1 H), 4.08-4.19 (m, 1 H), 2.30-2.48 (m, 2 H), 1.41 (d, 3 H), 1.38 (d, 3 H) |
| 113 | 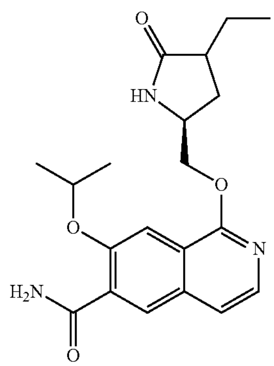 [SMILES: CCC1C[C@@H](COc2nccc3cc(C(N)=O)c(OC(C)C)cc23)NC1=O] | P2 | L4 | | 1, 7 | 372 | ¹H NMR (500 MHz, dmso-d₆) δ 8.19 (d, 1 H), 8.16 (s, 1 H, diastereomer 1), 8.07 (s, 1 H, diastereomer 2), 7.88 (d, 1 H), 7.74 (br. s., 1 H), 7.71 (br. s., 1 H), 7.68 (s, 1 H, diastereomer 1), 7.61 (s, 1 H, diastereomer 2), 7.41 (d, 1 H), 4.90 (dt, 1 H), 4.57 (dd, 1 H, diastereomer 1), 4.46 (dd, 1 H, diastereomer 2), 4.32 (dd, 1 H, diastereomer 1), 4.20 (dd, 1 H, diastereomer 2), 3.97 (td, 1 H), 1.88-2.48 (m, 2 H), 1.66-1.80 (m, 1 H), 1.39 (td, 6 H), 1.24-1.37 (m, 2 H), 0.92 (td, 3 H) |
| 114 | Chiral | P6 | 17342-08-4 | commercial | 5 | 343 | ¹H NMR (500 MHz, dmso-d₆) δ 8.32 (s, 1 H), 8.02 (s, 1 H), 7.71 (br. s., 1 H), 7.63 (br. s., 1 H), 7.60 (s, 1 H), 7.51 (d, 1 H), 7.29 (t, 1 H), 6.99 (d, 1 H), 4.91 (quin, 1 H), 4.10 (t, 2 H), 4.04 (dd, 1 H), 2.17-2.43 (m, 3 H), 1.97 (br. s., 1 H), 1.41 (d, 3 H), 1.39 (d, 3 H) |
| 115 | Chiral | P6 | 138108-72-2 | commercial | 5 | 329 | ¹H NMR (500 MHz, dmso-d₆) δ 8.33 (s, 1 H), 7.70 (br. s., 1 H), 7.65 (br. s., 1 H), 7.55 (s, 1 H), 7.53 (d, 1 H), 7.31 (t, 1 H), 7.02 (d, 1 H), 4.86 (dt, 1 H), 4.19-4.28 (m, 1 H), 4.10-4.19 (m, 1 H), 3.21-3.54 (m, 4 H), 3.13 (dd, 1 H), 2.90 (dt, 1 H), 2.14-2.27 (m, 1 H), 1.80-1.93 (m, 1 H), 1.41 (d, 6 H) |

TABLE 1-continued

| Ex. | Structure | Reactant A | Reactant B | Source | Methods | MH+ | Characterization |
|---|---|---|---|---|---|---|---|
| 116 | 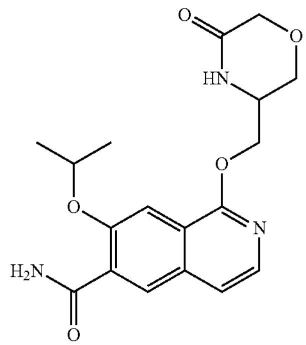 [SMILES: CC(C)Oc1cc2c(OCC3COCC(=O)N3)nccc2cc1C(N)=O] | P2 | 1073338-64-3 | Ref. 19 | 1, 7 | 360 | $^1$H NMR (500 MHz, dmso-d$_6$) δ 8.44 (d, 1 H), 8.19 (s, 1 H), 7.88 (d, 1 H), 7.74 (br. s., 1 H), 7.70 (br. s., 1 H), 7.67 (s, 1 H), 7.42 (d, 1 H), 4.93 (dt, 1 H), 4.48- 4.56 (m, 1 H), 4.39-4.48 (m, 1 H), 4.04 (s, 2 H), 3.86-3.96 (m, 3 H), 1.38 (t, 6 H) |
| 117 | Chiral | P2 | 138108-72-2 | commercial | 1, 7, 10 | 330 | $^1$H NMR (500 MHz, dmso-d$_6$) δ 8.20 (s, 1 H), 7.89 (d, 1 H), 7.73 (br. s., 1 H), 7.71 (br. s., 1 H), 7.56 (s, 1 H), 7.42 (d, 1 H), 4.87 (quin, 1 H), 4.48-4.57 (m, 1 H), 4.39-4.48 (m, 1 H), 3.35-3.52 (m, 2 H), 3.31 (br. s., 1 H), 3.19- 3.27 (m, 1 H), 3.07-3.17 (m, 1 H), 2.89 (dt, 1 H), 2.11-2.23 (m 1 H), 1.78-1.90 (m, 1 H), 1.39 (d, 6 H) |
| 118 | 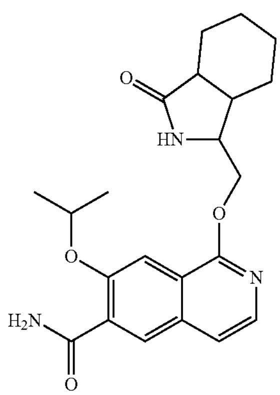 [SMILES: CC(C)Oc1cc2c(OCC3NC(=O)C4CCCCC34)nccc2cc1C(N)=O] | P2 | L101 | Ref. 20 | 1, 7 | 398 | $^1$H NMR (500 MHz, dmso-d$_6$) δ 8.20 (s, 1 H), 8.03 (br. s, 1 H), 7.90 (d, 1 H), 7.74 (br. s., 1 H), 7.71 (br. s., 1 H), 7.69 (s, 1 H), 7.42 (d, 1 H), 4.93 (dt, 1 H), 4.60 (dd, 1 H), 4.40 (dd, 1 H), 3.92-4.06 (m, 1 H), 1.98 (d, 1 H), 1.62 (br. s., 2 H), 1.51 (d, 1 H), 1.40 (t, 6 H), 1.22 (d, 2 H), 1.10 (d, 2 H), 1.01 (br. s., 2 H) |
| 119 | Chiral | P2 | 161511-85-9 | commercial | 1, 7, 10 | 316 | $^1$H NMR (400 MHz, dmso-d$_6$) δ 8.93 (br. s, 1 H), 8.22 (s, 1 H), 7.93 (d, 1 H), 7.70 (br. s, 2 H), 7.65 (s, 1 H), 7.48 (d, 1 H), 4.80-4.92 (m, 2 H), 4.68-4.79 (m, 2 H), 4.13-3.57 (m, 1 H), 3.82-3.95 (m, 1 H), 1.36-1.45 (m, 6 H), 1.23-1.30 (m, 2 H) |

TABLE 1-continued

| Ex. | Structure | Reactant A | Reactant B | Source | Methods | MH+ | Characterization |
|---|---|---|---|---|---|---|---|
| 120 | Chiral | P13 | 17342-08-4 | commercial | 1, 7 | 356 | ¹H NMR (500 MHz, dmso-d₆) δ 8.16 (s, 1 H), 8.03 (s, 1 H), 7.88 (d, 1 H), 7.77 (br. s., 1 H), 7.70 (br. s., 1 H), 7.38-7.45 (m, 2 H), 4.93 (quin, 1 H), 4.42 (dd, 1 H), 4.37 (dd, 1 H), 3.97-4.07 (m, 1 H), 2.08-2.38 (m, 6 H), 1.90-1.98 (m, 2 H), 1.85 (q, 1 H), 1.67-1.80 (m, 1 H) |
| 121 | Chiral | P1 | 17342-08-4 | commercial | 1, 7 | 316 | ¹H NMR (500 MHz, dmso-d₆) δ 8.16 (s, 1 H), 8.13 (br. s, 1 H), 7.89 (d, 1 H), 7.84 (br. s., 1 H), 7.69 (br. s., 1 H), 7.63 (s, 1 H), 7.42 (d, 1 H), 4.49 (dd, 1 H), 4.29 (dd, 1 H), 4.01-4.08 (m, 1 H), 3.99 (s, 3 H), 2.14-2.37 (m, 3 H), 1.84-1.96 (m, 1 H) |
| 122 | Chiral | P7 | 17342-08-4 | commercial | 1, 7 | 330 | ¹H NMR (500 MHz, dmso-d₆) δ 8.17 (s, 1 H), 8.12 (s, 1 H), 7.88 (d, 1 H), 7.79 (br. s., 1 H), 7.70 (br. s., 1 H), 7.62 (s, 1 H), 7.41 (d, 1 H), 4.48 (dd, 1 H), 4.26-4.35 (m, 2 H), 4.18-4.25 (m, 1 H), 4.03 (br. s., 1 H), 2.12-2.38 (m, 3 H), 1.84-1.94 (m, 1 H), 1.44 (t, 3 H) |
| 123 | 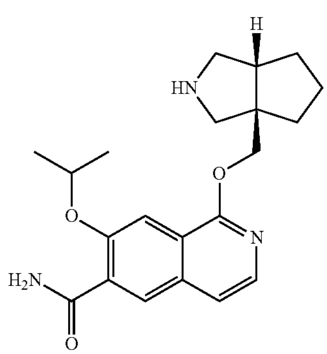 [SMILES: CC(C)Oc1cc2c(OC[C@]34CCC[C@H]3CNC4)nccc2cc1C(N)=O] | P2 | 1445951-44-9 | Ref. 21 | 1, 7, 10 | 370 | ¹H NMR (500 MHz, dmso-d₆) δ 8.21 (s, 1 H), 7.88 (d, 1 H), 7.73 (br. s, 2 H), 7.52 (s, 1 H), 7.43 (d, 1 H), 4.84 (dt, 1 H), 4.38-4.50 (m, 2 H), 3.34-3.49 (m, 2 H), 3.18 (d, 1 H), 3.02 (dd, 1 H), 2.62-2.72 (m, 1 H), 1.75-1.95 (m, 4 H), 1.66-1.75 (m, 1 H), 1.55-1.64 (m, 1 H), 1.40 (d, 6 H) |

TABLE 1-continued

| Ex. | Structure | Reactant A | Reactant B | Source | Methods | MH+ | Characterization |
|---|---|---|---|---|---|---|---|
| 124 | Chiral | P2 | L1 | | 1, 7, chiral HPLC | 358 | ¹H NMR (500 MHz, dmso-d₆) δ 8.19 (s, 1 H), 8.07 (br. s, 1 H), 7.88 (d, 1 H), 7.73 (br. s., 1 H), 7.71 (br. s., 1 H), 7.61 (s, 1 H), 7.41 (d, 1 H), 4.89 (quin, 1 H), 4.45 (dd, 1 H), 4.33 (dd, 1 H), 3.91-4.00 (m, 1 H), 2.54-2.59 (m, 1 H), 2.15-2.27 (m, 1 H), 1.88 (dt, 1 H), 1.39 (t, 6 H), 1.09 (d, 3 H) |
| 125 | Chiral | P2 | L1 | | 1, 7, chiral HPLC | 358 | ¹H NMR (500 MHz, dmso-d₆) δ 8.16 (s, 1 H), 8.12 (br. s, 1 H), 7.85 (d, 1 H), 7.71 (br. s., 1 H), 7.68 (br. s., 1 H), 7.65 (s, 1 H), 7.38 (d, 1 H), 4.88 (quin, 1 H), 4.53 (dd, 1 H), 4.18 (dd, 1 H), 3.88-3.99 (m, 1 H), 2.32-2.49 (m, 2 H), 1.39-1.49 (m, 1 H), 1.31-1.39 (m, 6 H), 1.08 (d, 3 H) |
| 126 | Chiral | P2 | L102 | Ref. 22 | 1, 7 | 358 | ¹H NMR (500 MHz, dmso-d₆) δ 8.21 (s, 1 H), 7.55-8.12 (m, 5 H), 7.42 (d, 1 H), 4.91 (dt, 1 H), 4.24-4.42 (m, 2 H), 2.35-2.47 (m, 1 H), 2.23-2.35 (m, 1 H), 2.10-2.23 (m, 1 H), 1.83-1.97 (m, 1 H) |

TABLE 1-continued

| Ex. | Structure | Reactant A | Reactant B | Source | Methods | MH+ | Characterization |
|---|---|---|---|---|---|---|---|
| 127 | 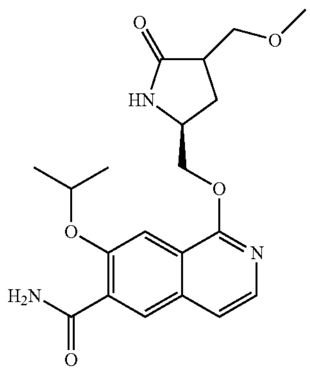 [SMILES: COCC1C[C@@H](COc2nccc3cc(C(N)=O)c(OC(C)C)cc23)NC1=O] | P2 | L5 | | 1, 7 | 388 | See Ref. 36. |
| 128 | Chiral | P2 | L6 | | 1, 7 | 380 | ¹H NMR (400 MHz, dmso-d₆) δ 9.28 (br. s., 1 H), 8.19 (s, 1 H), 7.89 (d, 1 H), 7.72 (br. s., 1 H), 7.70 (br. s., 1 H), 7.62 (s, 1 H), 7.44 (d, 1 H), 4.83 (dt, 1 H), 4.57 (dd, 1 H), 4.35 (dd, 1 H), 4.15-4.26 (m, 1 H), 2.76-2.96 (m, 1 H), 2.54-2.71 (m, 1 H), 1.39 (t, 6 H) |
| 129 | Chiral | P18 | 17342-08-4 | commercial | 1, 7 | 352 | ¹H NMR (400 MHz, dmso-d₆) δ 8.10 (s, 1 H), 8.07 (br. s, 1 H), 8.04 (d, 1 H), 7.96 (s, 2 H), 7.75 (br. s., 1 H), 7.50 (d, 1 H), 7.31 (t, 1 H), 4.52 (dd, 1 H), 4.30 (dd, 1 H), 4.00-4.08 (m, 1 H), 2.14-2.34 (m, 3 H), 1.85-1.96 (m, 1 H) |
| 130 | 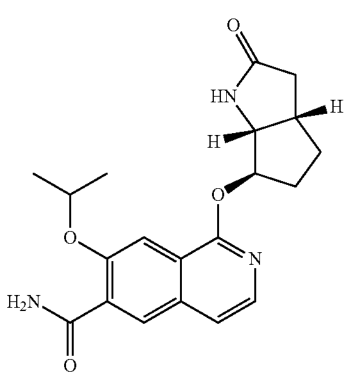 [SMILES: CC(C)Oc1cc2c(O[C@@H]3CC[C@H]4CC(=O)N[C@H]43)nccc2cc1C(N)=O] | P2 | 1192180-58-7 | Ref. 23 | 1, 7, 17 | 370 | ¹H NMR (500 MHz, dmso-d₆) δ 8.19 (s, 1 H), 7.81-7.98 (m, 2 H), 7.72 (d, 2 H), 7.41 (d, 1 H), 5.34 (br. s., 1 H), 4.85 (dt, 1 H), 4.05 (d, 1 H), 2.95-3.09 (m, 1 H), 2.43-2.53 (m, 1 H), 2.01-2.25 (m, 2 H), 1.82-2.03 (m, 2 H), 1.49-1.68 (m, 1 H), 1.39 (d, 6 H) |

TABLE 1-continued
| Ex. | Structure | Reactant A | Reactant B | Source | Methods | MH+ | Characterization |
|---|---|---|---|---|---|---|---|
| 131 | 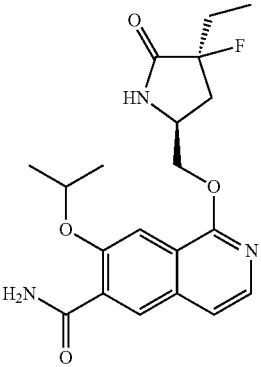 [SMILES: CC[C@]1(F)C[C@@H](COc2nccc3cc(C(N)=O)c(OC(C)C)cc23)NC1=O]<br>Chiral | P2 | L7 | | 1, 7 | 390 | ¹H NMR (400 MHz, dmso-d$_6$) δ 8.77 (s, 1 H), 8.19 (s, 1 H), 7.88 (d, 1 H), 7.64-7.79 (m, 3 H), 4.89 (dt, 1 H), 4.58 (dd, 1 H), 4.26 (dd, 1 H), 3.93-4.05 (m, 1 H), 2.10-2.26 (m, 1 H), 1.82-1.99 (m, 1 H), 1.61-1.80 (m, 1 H), 1.32-1.44 (m, 6 H), 0.89-1.01 (m, 3 H) |
| 132 | 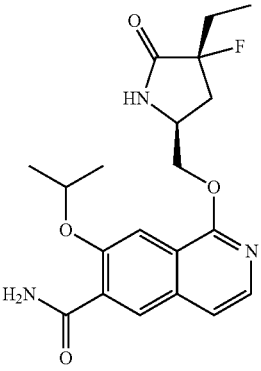 [SMILES: CC[C@@]1(F)C[C@@H](COc2nccc3cc(C(N)=O)c(OC(C)C)cc23)NC1=O]<br>Chiral | P2 | L8 | | 1, 7 | 390 | ¹H NMR (400 MHz, dmso-d$_6$) δ 8.87 (s, 1 H), 8.19 (s, 1 H), 7.89 (d, 1 H), 7.72 (d, 2 H), 7.66 (s, 1 H), 7.43 (d, 1 H), 4.81-5.02 (m, 1 H), 4.59 (dd, 1 H), 4.26 (dd, 1 H), 4.10-4.21 (m, 1 H), 2.31-2.54 (m, 1 H), 2.05-2.27 (m, 1 H), 1.86-2.03 (m, 1 H), 1.58-1.83 (m, 1 H), 1.24-1.44 (m, 6 H), 0.96 (s, 3 H) |
| 133 | 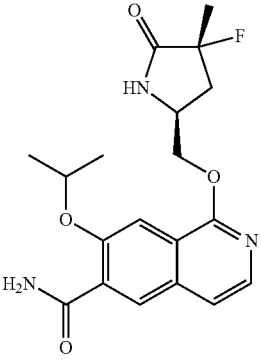 [SMILES: CC(C)Oc1cc2c(OC[C@@H]3C[C@@](C)(F)C(=O)N3)nccc2cc1C(N)=O]<br>Chiral | P2 | L9 | | 1, 7 | 376 | ¹H NMR (500 MHz, dmso-d$_6$) δ 8.85 (s, 1 H), 8.20 (s, 1 H), 7.58-7.81 (m, 3 H), 7.43 (d, 1 H), 4.92 (quin, 1 H), 4.57 (dd, 1 H), 4.29 (dd, 1 H), 4.15 (dd, 1 H), 2.38-2.68 (m, 1 H), 1.96-2.28 (m, 1 H), 1.54 (s, 3 H), 1.39 (d, 6 H) |

TABLE 1-continued

| Ex. | Structure | Reactant A | Reactant B | Source | Methods | MH+ | Characterization |
|---|---|---|---|---|---|---|---|
| 134 | Chiral | P2 | L10 | | 1, 7 | 376 | ¹H NMR (500 MHz, dmso-d₆) δ 8.75 (s, 1 H), 8.20 (s, 1 H), 7.61-7.82 (m, 3 H), 7.43 (d, 1 H), 4.90 (dt, 1 H), 4.57 (dd, 1 H), 4.28 (dd, 1 H), 3.95-4.09 (m, 1H), 2.47-2.55 (m, 1 H), 2.19-2.37 (m, 1 H), 1.44-1.56 (m, 3 H), 1.39 (t, 6 H) |
| 135 | Chiral | P2 | L4 | | 1, 7, chiral HPLC | 372 | ¹H NMR (400 MHz, dmso-d₆) δ 8.19 (s, 1 H), 8.08 (s, 1 H), 7.88 (d, 1 H), 7.72 (d, 2 H), 7.61 (s, 1 H), 7.42 (d, 1 H), 4.80-5.00 (m, 1 H), 4.46 (dd, 1 H), 4.32 (dd, 1 H), 3.82-4.03 (m, 1 H), 2.33-2.56 (m, 2 H), 1.96-2.21 (m, 1 H), 1.94 (d, 1 H), 1.19-1.35 (m, 1 H), 1.38-1.41 (m, 3 H), 1.51-1.82 (m, 1 H), 1.38-1.41 (m, 6 H), 0.91 (t, 3 H) |
| 136 | Chiral | P2 | L4 | | 1, 7, chiral HPLC | 372 | ¹H NMR (400 MHz, dmso-d₆) δ 8.12-8.28 (m, 2 H), 7.89 (d, 1 H), 7.63-7.80 (m, 3 H), 7.42 (d, 1 H), 4.91 (dt, 1 H), 4.58 (dd, 1 H), 4.20 (dd, 1 H), 3.98 (dd, 1 H), 2.26-2.46 (m, 2 H), 1.75 (ddd, 1 H), 1.47-1.60 (m, 1 H), 1.19-1.35 (m, 1 H), 1.38-1.41 (m, 6 H), 0.87-0.99 (m, 3 H) |

| Ex. | Structure | Reactant A | Reactant B | Source | Methods | MH+ | Characterization |
|---|---|---|---|---|---|---|---|
| 137 | Chiral | P2 | L11 | | 1, 7 | 402 | ¹H NMR (400 MHz, dmso-d₆) δ 8.24 (s, 1 H), 8.20 (s, 1 H), 7.89 (d, 1 H), 7.73 (d, 2 H), 7.61 (s, 1 H), 7.42 (d, 1 H), 4.84-4.97 (m, 1 H), 4.41-4.54 (m, 1 H), 4.32 (dd, 1 H), 3.90-4.01 (m, 1 H), 2.18-2.30 (m, 1 H), 1.92-2.10 (m, 1 H), 1.32-1.48 (m, 6 H), 1.23 (s, 3 H), 1.13 (s, 3 H) |
| 138 | 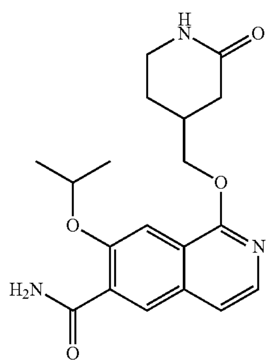 [SMILES: CC(C)Oc1cc2c(OCC3CCNC(=O)C3)nccc2cc1C(N)=O] | P2 | 53611-47-5 | commercial | 1, 7 | 358 | ¹H NMR (500 MHz, dmso-d₆) δ 8.20 (s, 1 H), 7.73 (d, 2 H), 7.52 (br. s., 1 H), 7.41 (d, 1 H), 4.87 (dt, 1 H), 4.40 (d, 2 H), 3.14-3.30 (m, 2 H), 2.34-2.48 (m, 2 H), 2.07-2.20 (m, 1 H), 1.92-2.03 (m, 1 H), 1.51-1.65 (m, 1 H), 1.31-1.45 (m, 6 H) |
| 139 | 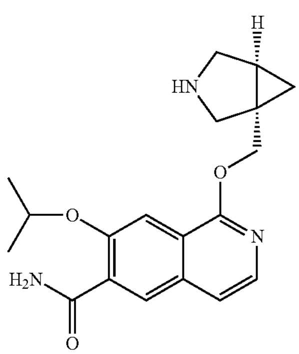 [SMILES: CC(C)Oc1cc2c(OC[C@]34CNC[C@H]3C4)nccc2cc1C(N)=O] | P2 | 161152-76-7 | Ref. 7 | 1, 7, 10 | 342 | ¹H NMR (500 MHz, dmso-d₆) δ 8.20 (s, 1 H), 7.88 (d, 1 H), 7.74 (d, 2 H), 7.58 (s, 1 H), 7.42 (d, 1 H), 4.79-4.95 (m, 1 H), 4.52-4.76 (m, 2 H), 3.56 (br. s., 1 H), 3.20-3.38 (m, 2 H), 2.51 (s, 1 H), 1.75-1.94 (m, 1 H), 1.40 (d, 6 H), 1.04 (dd, 1 H), 0.86 (t, 1 H) |
| 140 | 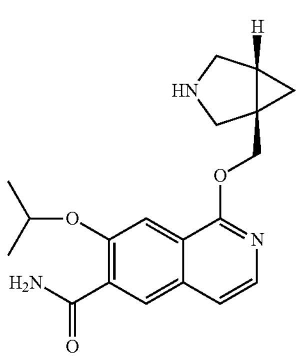 [SMILES: CC(C)Oc1cc2c(OC[C@@]34CNC[C@@H]3C4)nccc2cc1C(N)=O] | P2 | 161152-76-7 | Ref. 7 | 1, 7, 10 | 342 | ¹H NMR (500 MHz, dmso-d₆) δ 8.20 (s, 1 H), 7.88 (d, 1 H), 7.74 (d, 2 H), 7.58 (s, 1 H), 7.42 (d, 1 H), 4.79-4.92 (m, 1 H), 4.55-4.74 (m, 2 H), 3.56 (br. s., 2 H), 3.23-3.36 (m, 2 H), 2.48-2.53 (m, 1 H), 1.79-1.91 (m, 1 H), 1.40 (d, 6 H), 1.03 (dd, 1 H), 0.86 (t, 1 H) |

TABLE 1-continued

| Ex. | Structure | Reactant A | Reactant B | Source | Methods | MH+ | Characterization |
|---|---|---|---|---|---|---|---|
| 141 | (structure shown) Chiral | P2 | L35 | | 1, 7 | 358 | ¹H NMR (500 MHz, dmso-d$_6$) δ 8.20 (s, 1 H), 8.07 (s, 1 H), 7.90 (s, 1 H), 7.73 (d, 2 H), 7.65 (s, 1 H), 7.42 (d, 1 H), 4.91 (dt, 1 H), 4.50 (dd, 1 H), 4.36 (dd, 1 H), 3.53-3.66 (m, 1 H), 2.47-2.52 (m, 1 H), 2.26-2.37 (m, 1 H), 1.88 (dd, 1 H), 1.31-1.48 (m, 6 H), 1.17 (s, 3 H) |
| 142 | (structure shown) | P2 | 146059-77-0 | commercial | 1, 7 | 358 | ¹H NMR (500 MHz, dmso-d$_6$) δ 8.20 (s, 1 H), 7.90 (d, 1 H), 7.72 (d, 2 H), 7.57 (s, 1 H), 7.48 (br. s., 1 H), 7.41 (d, 1 H), 4.87 (dt, 1 H), 4.45-4.55 (m, 1 H), 4.40 (dd, 1 H), 3.11 (t, 1 H), 2.51 (d, 1 H), 2.37 (br. s., 1 H), 2.25 (dd, 2 H), 1.84-2.04 (m, 1 H), 1.57-1.73 (m, 1 H), 1.40 (d, 6 H) |
| 143 | (structure shown) | P2 | 67838-56-6 | Ref. 24 | 1, 7 | 380 | ¹H NMR (500 MHz, dmso-d$_6$) δ 8.21 (s, 1 H), 7.89 (d, 1 H), 7.74 (br. s., 1 H), 7.73 (s, 1 H), 7.71 (br. s., 1 H), 7.34-7.50 (m, 2 H), 4.92 (dt, 1 H), 4.46 (dd, 1 H), 4.39 (dd, 1 H), 4.00-4.09 (m, 1 H), 3.28 (ddd, 1 H), 3.10 (dt, 1 H), 2.50-2.59 (m, 1 H), 2.17-2.27 (m, 1 H), 1.40 (t, 6 H) |
| 144 | (structure shown) Chiral | P2 | L2 | 1, 7, chiral HPLC | 1, 7 | 362 | ¹H NMR (500 MHz, dmso-d$_6$) δ 8.74 (s, 1 H), 8.21 (s, 1 H), 7.89 (d, 1 H), 7.73 (d, 2 H), 7.59 (s, 1 H), 7.44 (d, 1 H), 5.15-5.43 (m, 1 H), 4.92 (dt, 1 H), 4.49 (dd, 1 H), 4.35 (dd, 1 H), 4.15 (d, 1 H), 2.48-2.64 (m, 1 H), 2.23-2.46 (m, 1 H), 1.30-1.58 (m, 6 H) |

TABLE 1-continued

| Ex. | Structure | Reactant A | Reactant B | Source | Methods | MH+ | Characterization |
|---|---|---|---|---|---|---|---|
| 145 | Chiral | P2 | L2 | 1, 7, chiral HPLC | 1, 7 | 362 | $^1$H NMR (500 MHz, dmso-d$_6$) δ 8.71 (s, 1 H), 8.20 (s, 1 H), 7.89 (d, 1 H), 7.74 (br. s., 3 H), 7.43 (d, 1 H), 5.01-5.27 (m, 1 H), 4.88 (dt, 1 H), 4.59 (dd, 1 H), 4.29 (dd, 1 H), 4.04 (br. s., 1 H), 2.62-2.84 (m, 1 H), 1.97-2.21 (m, 1 H), 1.39 (t, 6 H) |
| 146 | Chiral | P1 | L6 | Ref. 25 | 2, 7 | 352 | $^1$H NMR (500 MHz, dmso-d$_6$) δ 9.29 (br. s., 1 H), 8.12 (s, 1 H), 7.85 (d, 1 H), 7.82 (br. s., 1 H), 7.60-7.71 (m, 1 H), 7.56 (s, 1 H), 7.39 (d, 1 H), 4.55 (dd, 1 H), 4.29 (dd, 1 H), 4.10-4.22 (m, 1 H), 3.91 (s, 3 H), 2.75-2.95 (m, 1 H), 2.51-2.66 (m, 1 H) |
| 147 | 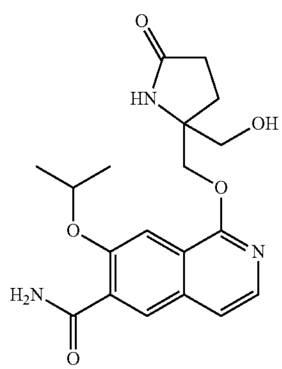 [SMILES: CC(C)Oc1cc2c(OCC3(CO)CCC(=O)N3)nccc2cc1C(N)=O] | P2 | 89531-65-7 | Ref. 26 | 1, 7 | 374 | $^1$H NMR (400 MHz, dmso-d$_6$) δ 8.19 (s, 1 H), 7.97 (s, 1 H), 7.88 (d, 1 H), 7.72 (d, 2 H), 7.64 (s, 1 H), 7.41 (d, 1 H), 5.03 (t, 1 H), 4.91 (dt, 1 H), 4.38-4.49 (m, 1 H), 4.28-4.38 (m, 1 H), 3.54-3.66 (m, 1 H), 3.43-3.53 (m, 1 H), 2.21-2.38 (m, 2 H), 1.85-2.12 (m, 2 H), 1.33-1.50 (m, 6 H) |
| 148 | 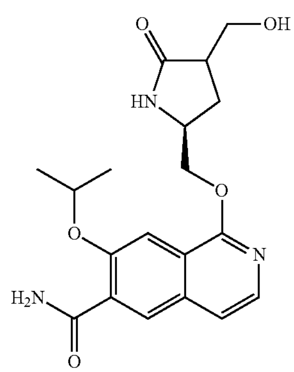 [SMILES: CC(C)Oc1cc2c(OC[C@@H]3CC(CO)C(=O)N3)nccc2cc1C(N)=O] | P2 | L12 | 2, 7, 9 | | 374 | $^1$H NMR (500 MHz, dmso-d$_6$) δ 8.18 (s, 1 H), 8.10 (br. s, 1 H), 7.87 (d, 1 H), 7.75 (br. s., 1 H), 7.70 (s, 1 H), 7.61 (br. s, 1 H), 7.40 (d, 1 H), 4.90-4.98 (m, 1 H), 4.43-4.48 (m, 2 H), 4.29-4.36 (m, 1 H), 4.23 (dd, 1 H), 3.96-4.02 (m, 1 H), 2.52-2.63 (m, 1 H), 2.15-2.29 (m, 1 H), 1.95-2.08 (m, 1 H), 1.39 (t, 6 H) |

| Ex. | Structure | Reactant A | Reactant B | Source | Methods | MH+ | Characterization |
|---|---|---|---|---|---|---|---|
| 149 | Chiral | P2 | 203982-57-4 | Ref. 27 | 2, 7, 9 | 359 | $^1$H NMR (500 MHz, dmso-d$_6$) δ 8.20 (s, 1 H), 8.05 (s, 1 H), 7.89 (d, 1 H), 7.74 (br. s., 1 H), 7.72 (br. s., 1 H), 7.65 (s, 1 H), 7.42 (d, 1 H), 4.92 (dt, 1 H), 4.58 (dd, 1 H), 4.32 (dd, 1 H), 3.58-3.65 (m, 1 H), 3.44-3.50 (m, 1 H), 1.97 (dd, 1 H), 1.36-1.44 (m, 7 H) |
| 150 | Chiral | P2 | L13 |  | 1, 7 | 360 | $^1$H NMR (400 MHz, dmso-d$_6$) δ 8.28 (s, 1 H), 8.12-8.24 (m, 1 H), 7.88 (d, 1 H), 7.64-7.82 (m, 3 H), 7.41 (d, 1 H), 5.55 (d, 1 H), 4.95 (quin, 1 H), 4.56 (dd, 1 H), 4.22 (dd, 1 H), 4.13 (td, 1 H), 3.90 (qd, 1 H), 2.52-2.57 (m, 1 H), 1.67 (dt, 1 H), 1.29-1.47 (m, 6 H) |
| 151 | Chiral | P2 | L15 |  | 2, 7, HPLC | 426 | $^1$H NMR (400 MHz, dmso-d$_6$) δ 8.30 (s, 1 H), 8.11 (s, 1 H), 7.80-7.82 (d, 2 H), 7.47 (s, 1 H), 7.34-7.36 (d, 1 H), 4.74-4.77 (m, 1 H), 4.39-4.40 (m, 1 H), 4.32-4.34 (m, 1 H), 3.93-3.98 (m, 1 H), 2.59-2.75 (m, 3 H), 2.18-2.31 (m, 3 H), 1.29-1.33 (m, 6 H). |

TABLE 1-continued

| Ex. | Structure | Reactant A | Reactant B | Source | Methods | MH+ | Characterization |
|---|---|---|---|---|---|---|---|
| 152 | Chiral | P2 | L16 | | 2, 7, HPLC | 426 | ¹H NMR (400 MHz, dmso-d₆) δ 8.44 (s, 1 H), 8.11 (s, 1 H), 7.80-7.81 (d, 1 H), 7.61-7.66 (m, 3 H), 7.33-7.35 (d, 1 H), 4.83- 4.86 (m, 1 H), 4.49-4.52 (m, 1 H), 4.14-4.18 (m, 1 H), 3.96 (s, 1 H), 2.59-2.66 (m, 3 H), 2.25-2.28 (m, 1 H), 1.61-1.64 (m, 1 H), 1.29-1.33 (m, 6 H). |
| 153 | Chiral | P2 | 89531-65-7 | Ref. 26 | 1, 7, HPLC | 374 | ¹H NMR (500 MHz, dmso-d₆) δ 8.19 (s, 1 H), 7.97 (s, 1 H), 7.88 (d, 1 H), 7.68-7.79 (m, 2 H), 7.63 (s, 1 H), 7.41 (d, 1 H), 5.11 (t, 1 H), 4.91 (dt, 1 H), 4.40-4.49 (m, 1 H), 4.30-4.39 (m, 1 H), 3.49-3.62 (m, 2 H), 2.23-2.39 (m, 2 H), 2.01-2.13 (m, 1 H), 1.90-2.01 (m, 1 H), 1.33-1.44 (m, 6 H) |
| 154 | Chiral | P2 | 89531-65-7 | Ref. 26 | 1, 7, HPLC | 374 | ¹H NMR (500 MHz, dmso-d₆) δ 8.19 (s, 1 H), 7.97 (s, 1 H), 7.88 (d, 1 H), 7.70-7.80 (m, 2 H), 7.41 (d, 1 H), 5.11 (t, 1 H), 4.91 (dt, 1 H), 4.40-4.47 (m, 1 H), 4.32-4.40 (m, 1 H), 3.49-3.63 (m, 2 H), 2.24-2.41 (m, 2 H), 2.02-2.13 (m, 1 H), 1.90-2.02 (m, 1 H), 1.32-1.44 (m, 6 H) |

TABLE 1-continued

| Ex. | Structure | Reactant A | Reactant B | Source | Methods | MH+ | Characterization |
|---|---|---|---|---|---|---|---|
| 155 | Chiral | P2 | L104 | | 1, 7, HPLC | 412 | ¹H NMR (500 MHz, dmso-d₆) δ 8.40 (s, 1 H), 8.21 (s, 1 H), 7.90 (d, 1 H), 7.73 (d, 2 H), 7.61 (s, 1 H), 7.45 (d, 1 H), 4.87 (dt, 1 H), 4.48 (dd, 2 H), 4.07-4.20 (m, 2 H), 2.79 (dd, 1 H), 2.34 (dd, 1 H), 1.42 (d, 6 H) |
| 156 | Chiral | P2 | 1315057-77-2 | Ref. 28 | 1, 7, HPLC | 358 | ¹H NMR (500 MHz, dmso-d₆) δ 8.08-8.24 (m, 2 H), 7.88 (d, 1 H), 7.64-7.78 (m, 2 H), 7.55 (s, 1 H), 7.39 (d, 1 H), 5.29 (dd, 1 H), 4.83 (dt, 1 H), 4.14 (t, 1 H), 3.73-3.93 (m, 1 H), 1.95-2.30 (m, 3 H), 1.74-1.93 (m, 1 H), 1.31-1.46 (m, 9 H) |
| 157 | Chiral | P2 | 1315057-77-2 | Ref. 28 | 1, 7, HPLC | 358 | ¹H NMR (500 MHz, dmso-d₆) δ 8.18 (s, 1 H), 7.93-8.03 (m, 1 H), 7.89 (d, 1 H), 7.60 (s, 1 H), 7.39 (d, 1 H), 5.38 (dd, 1 H), 4.90 (dt, 1 H), 3.81-3.95 (m, 1 H), 3.42-3.54 (m, 1 H), 2.04-2.38 (m, 4 H), 1.30-1.48 (m, 9 H) |
| 158 | Chiral | P2 | 714971-28-5 | commercial | | 346 | Rt = min 2.159; method PF-AB01 |

TABLE 1-continued

| Ex. | Structure | Reactant A | Reactant B | Source | Methods | MH+ | Characterization |
|---|---|---|---|---|---|---|---|
| 159 | 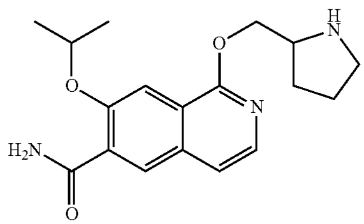 [SMILES: CC(C)Oc1cc2c(OCC3CCCN3)nccc2cc1C(N)=O] | P2 | 170491-63-1 | commercial | | 330 | Rt = min 2.200; method PF-AB01 |
| 160 | Chiral | P2 | 215917-99-0 | commercial | | 346 | Rt = min 2.160; method PF-AB01 |
| 161 | Chiral | P2 | L105 | | 1, 7, 9, 18, HPLC, 10 | 356 | $^1$H NMR (500 MHz, dmso-d$_6$) δ 8.20 (s, 1 H), 7.87 (d, 1 H), 7.74 (br. s., 1 H), 7.72 (br. s., 1 H), 7.61 (s, 1 H), 7.41 (d, 1 H), 4.88 (dt, 1 H), 4.48 (d, 1 H), 4.23 (d, 1 H), 3.64 (d, 1 H), 3.31 (d, 1 H), 2.90-3.00 (m, 1 H), 2.73-2.86 (m, 1 H), 2.12-2.22 (m, 1 H), 1.79-1.90 (m, 1 H), 1.40 (d, 6 H), 1.30-1.38 (m, 2 H), 0.99 (dd, 1 H), 0.86 (t, 1 H) |
| 162 | Chiral | P2 | L105 | | 1, 7, 9, 18, HPLC, 10 | 356 | $^1$H NMR (500 MHz, dmso-d$_6$) δ 8.54 (br. s, 1 H), 8.20 (s, 1 H), 7.87 (d, 1 H), 7.74 (br. s., 1 H), 7.72 (br. s., 1 H), 7.61 (s, 1 H), 7.41 (d, 1 H), 4.88 (dt, 1 H), 4.49 (d, 1 H), 4.23 (d, 1 H), 3.64 (d, 1 H), 3.31 (d, 1 H), 2.90-3.03 (m, 1 H), 2.72-2.85 (m, 1 H), 2.07-2.25 (m, 1 H), 1.78-1.93 (m, 1 H), 1.40 (d, 6 H), 1.30-1.38 (m, 1 H), 0.99 (dd, 1 H), 0.85 (t, 1 H) |

TABLE 1-continued
| Ex. | Structure | Reactant A | Reactant B | Source | Methods | MH+ | Characterization |
|---|---|---|---|---|---|---|---|
| 163 | 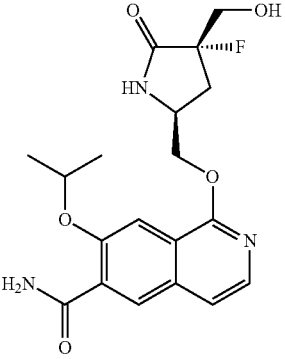 [SMILES: CC(C)Oc1cc2c(OC[C@@H]3C[C@](F)(CO)C(=O)N3)nccc2cc1C(N)=O]<br>Chiral | P2 | L17 | | 2, 7, 9 | 392 | $^1$H NMR (500 MHz, dmso-d$_6$) δ 8.90 (s, 1 H), 8.20 (s, 1 H), 7.89 (d, 1 H), 7.59-7.80 (m, 3 H), 7.43 (d, 1 H), 4.95 (dt, 1 H), 4.57 (dd, 1 H), 4.27 (dd, 1 H), 4.07-4.22 (m, 1 H), 3.69-3.72 (m, 1 H), 3.35 (d, 1 H), 2.29-2.54 (m, 3 H), 1.26-1.48 (m, 6 H) |
| 164 | 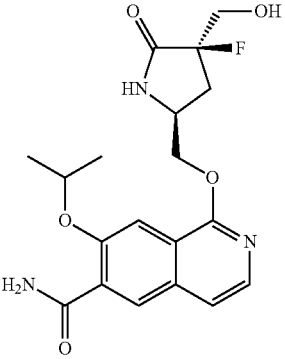 [SMILES: CC(C)Oc1cc2c(OC[C@@H]3C[C@@](F)(CO)C(=O)N3)nccc2cc1C(N)=O]<br>Chiral | P2 | L18 | | 2, 7, 9 | 392 | $^1$H NMR (500 MHz, dmso-d$_6$) δ 8.75 (s, 1 H), 8.20 (s, 1 H), 7.89 (d, 1 H), 7.74 (br. s., 3 H), 7.43 (d, 1 H), 4.88 (dt, 1 H), 4.59 (dd, 1 H), 4.29 (dd, 1 H), 4.00 (br. s., 1 H), 3.57-3.73 (m, 2 H), 2.77 (ddd, 1 H), 2.05-2.31 (m, 1 H), 1.39 (t, 6 H) |
| 165 | 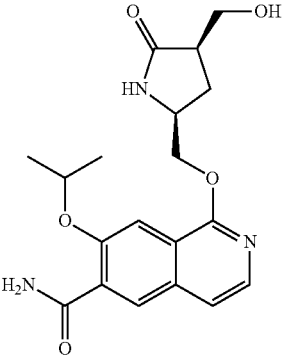 [SMILES: CC(C)Oc1cc2c(OC[C@@H]3C[C@H](CO)C(=O)N3)nccc2cc1C(N)=O]<br>Chiral | P2 | L12 | | 2, 7, 9, HPLC | 374 | $^1$H NMR (400 MHz, dmso-d$_6$) δ 8.22 (s, 1 H), 8.19 (s, 1 H), 7.88 (d, 1 H), 7.73 (br. s., 1 H), 7.71 (s, 1 H), 7.70 (br. s., 1 H), 7.41 (d, 1 H), 4.95 (dt, 1 H), 4.71 (t, 1 H), 4.54 (dd, 1 H), 4.23 (dd, 1 H), 3.95-4.04 (m, 1 H), 3.55-3.63 (m, 2 H), 2.27-2.38 (m, 1 H), 1.78-1.89 (m, 1 H), 1.39 (dd, 6 H) |

TABLE 1-continued

| Ex. | Structure | Reactant A | Reactant B | Source | Methods | MH+ | Characterization |
|---|---|---|---|---|---|---|---|
| 166 | Chiral | P2 | L12 | | 2, 7, 9, HPLC | 374 | ¹H NMR (400 MHz, dmso-d₆) δ 8.19 (s, 1 H), 8.11 (s, 1 H), 7.88 (d, 1 H), 7.73 (br. s., 1 H), 7.71 (br. s., 1 H), 7.62 (s, 1 H), 7.42 (d, 1 H), 4.90 (dt, 1 H), 4.70 (t, 1 H), 4.46 (dd, 1 H), 4.32 (dd, 1 H), 3.91-4.01 (m, 1 H), 3.59 (t, 2 H), 2.24 (dt, 1 H), 1.96-2.10 (m, 1 H), 1.39 (t, 6 H) |
| 167 | Chiral | P2 | 254441-91-3 | Ref. 29 | 1, 7 | 416 | ¹H NMR (500 MHz, dmso-d₆) δ 8.30 (s, 1 H), 7.90 (d, 1 H), 7.73 (d, 2 H), 7.39-7.59 (m, 2 H), 4.88 (dt, 1 H), 4.80 (d, 1 H), 4.68 (d, 1 H), 4.50-4.59 (m, 1 H), 4.37-4.50 (m, 1 H), 4.00 (t, 1 H), 1.24-1.51 (m, 12 H) |
| 168 | Chiral | special case | 17342-08-4 | commercial | 1, 7, 12, HPLC | 362 | ¹H NMR (500 MHz, dmso-d₆) δ 8.21 (s, 1 H), 8.11 (s, 1 H), 7.75-7.92 (m, 3 H), 7.63-7.72 (m, 1 H), 4.96 (dt, 1 H), 4.46 (dd, 1 H), 4.28 (dd, 1 H), 3.96-4.12 (m, 1 H), 2.14-2.36 (m, 3 H), 1.85-1.97 (m, 1 H,), 1.34-1.47 (m, 6 H) |

TABLE 1-continued

| Ex. | Structure | Reactant A | Reactant B | Source | Methods | MH+ | Characterization |
|---|---|---|---|---|---|---|---|
| 169 | Chiral | P2 | 17342-08-4 | commercial | 1, 7, 19, HPLC | 345 | ¹H NMR (400 MHz, dmso-$d_6$) δ 13.10 (br. s, 1 H), 8.00-8.21 (m, 2 H), 7.89 (d, 1 H), 7.65 (s, 1 H), 7.40 (d, 1 H), 4.85 (dt, 1 H), 4.47 (dd, 1 H), 4.30 (dd, 1 H), 3.89-4.14 (m, 1 H), 2.11-2.37 (m, 3 H), 1.79-2.01 m, 1 H), 1.20-1.47 (m, 6 H) |
| 170 | Chiral | P2 | L37 | | 2, 7, HPLC | 376 | ¹H NMR (500 MHz, dmso-$d_6$) δ 8.60 (br. s, 1 H), 8.21 (s, 1 H), 7.91 (d, 1 H), 7.73 (d, 2 H), 7.39-7.53 (m, 2 H), 4.93-5.14 (m, 1 H), 4.79-4.92 (m, 1 H), 4.41-4.57 (m, 2 H), 4.00 (br. s, 1 H), 2.68-2.86 (m, 1 H), 1.41 (dd, 6 H), 1.21 (d, 3 H) |
| 171 | Chiral | P2 | L19 | | 1, 7, HPLC | 420 | ¹H NMR (400 MHz, dmso-$d_6$) δ 8.70 (br. s., 1 H), 8.17 (s, 1 H), 7.88 (d, 1 H), 7.72 (m, 3 H), 7.41 (d, 1 H), 4.98 (s, 1 H), 4.87-4.91 (m, 1 H), 4.55 (d, 1 H), 4.23 (dd, 1 H), 3.92-3.95 (m, 1 H), 2.82-2.93 (m, 1 H), 1.88-2.05 (m, 1 H), 1.38 (m, 6 H), 1.02 (s, 3 H), 0.93 (s, 3 H) |

TABLE 1-continued

| Ex. | Structure | Reactant A | Reactant B | Source | Methods | MH+ | Characterization |
|---|---|---|---|---|---|---|---|
| 173 | Chiral | P5 | 17342-08-4 | commercial | 5, 13, 14 | 315 | ¹H NMR (500 MHz, dmso-d$_6$) δ 8.29 (s, 1 H), 8.07 (s, 1 H), 7.80 (br. s, 1 H), 7.57-7.70 (m, 2 H), 7.53 (d, 1 H), 7.32 (t, 1 H), 7.01 (d, 1 H), 4.02-4.20 (m, 2 H), 4.00 (s, 3 H), 3.92-4.02 (m, 1 H), 2.12-2.46 (m, 3 H,), 1.86-2.06 (m, 1 H) |
| 174 | Chiral | P2 | L72 | | 3, 7 | 356 | ¹H NMR (400 MHz, dmso-d$_6$) δ 8.21 (s, 1 H), 7.90 (d, 1 H), 7.73 (d, 2 H), 7.65 (s, 1 H), 7.59 (s, 1 H), 7.43 (d, 1 H), 4.92 (dt, 1 H), 4.45-4.60 (m, 1 H), 4.33-4.45 (m, 1 H), 3.88 (t, 1 H), 1.92-2.12 (m, 1 H), 1.76 (br. s, 1 H), 1.42 (t, 6 H), 1.10 (td, 1 H), 0.60 (q, 1 H) |
| 175 | 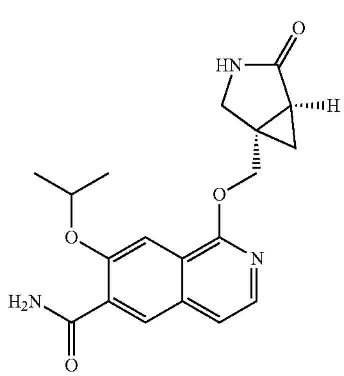 [SMILES: CC(C)Oc1cc2c(OC[C@]34CNC(=O)[C@H]3C4)nccc2cc1C(N)=O] | P2 | L100 | Ref. 7 | 1, 7 | 356 | ¹H NMR (400 MHz, dmso-d$_6$) δ 8.19 (s, 1 H), 7.88 (d, 1 H), 7.72 (br. s., 1 H), 7.70 (br. s., 1 H), 7.56 (s, 1 H), 7.41 (d, 1 H), 7.20 (br. s, 1 H), 4.84 (dt, 1 H), 4.67 (d, 1 H), 4.60 (d, 1 H), 3.54 (d, 1 H), 3.39 (d, 1 H), 1.77-1.89 (m, 1 H), 1.40 (d, 6 H), 1.36 (dd, 1 H), 0.84 (t, 1 H) |

TABLE 1-continued

| Ex. | Structure | Reactant A | Reactant B | Source | Methods | MH+ | Characterization |
|---|---|---|---|---|---|---|---|
| 176 | Chiral | P2 | 17342-08-4 | commercial | 1, 7, 12, HPLC | 362 | $^1$H NMR (500 MHz, dmso-d$_6$) δ 7.98 (d, 1 H), 7.81-7.93 (m, 2 H), 7.77 (s, 2 H), 7.47 (dd, 1 H), 4.32-4.56 (m, 3 H), 3.90-4.08 (m, 1 H), 2.09-2.44 (m, 3 H), 1.91-2.05 (m, 1 H), 1.30 (dd, 6 H) |
| 177 | Chiral | P1 | L10 | | 2, 7 | 348 | $^1$H NMR (400 MHz, dmso-d$_6$) δ 9.00 (s, 1 H), 8.35 (s, 1 H), 8.04-8.10 (m, 3 H), 7.89 (s, 2 H), 7.62-7.63 (d, 1 H), 4.76-4.790 (m, 1 H), 4.43-4.47 (m, 1 H), 4.18-4.26 (m, 1 H), 4.17 (s, 3 H), 2.64-2.75 (m, 1 H), 2.42-2.52 (m, 1 H), 1.65-1.71 (m, 3 H) |
| 178 | Chiral | P19 | 17342-08-4 | commercial | 1, 20, 7 | 370 | $^1$H NMR (500 MHz, dmso-d$_6$) δ 8.24 (s, 1 H), 8.16-8.21 (m, 2 H), 8.12 (d, 2 H), 7.79 (s, 1 H), 7.55 (d, 1 H), 4.54 (dd, 1 H), 4.30 (dd, 1 H), 3.94-4.12 (m, 1 H), 2.13-2.34 (m, 3 H), 1.81-1.99 (m, 1 H) |

TABLE 1-continued

| Ex. | Structure | Reactant A | Reactant B | Source | Methods | MH+ | Characterization |
|---|---|---|---|---|---|---|---|
| 179 | Chiral | P2 | L14 | | 1, 7, HPLC | 360 | ¹H NMR (500 MHz, dmso-d₆) δ 8.21 (br. s, 1 H), 8.19 (s, 1 H), 7.88 (d, 1 H), 7.73 (br. s., 1 H), 7.70 (br. s., 1 H), 7.60 (s, 1 H), 7.41 (d, 1 H), 4.89 (dt, 1 H), 4.45 (dd, 1 H), 4.31 (dd, 1 H), 4.27 (t, 1 H), 3.94-4.04 (m, 1 H), 2.30 (ddd, 1 H), 2.04 (dt, 1 H), 1.40 (dd, 7 H) |
| 180 | Chiral | P2 | 122663-19-8 | Ref. 30 | 1, 7 | 358 | ¹H NMR (500 MHz, dmso-d₆) δ 8.20 (s, 1 H), 7.90 (d, 1 H), 7.72 (br. s, 2 H), 7.46 (s, 1 H), 7.43 (d, 1 H), 4.80 (dt, 1 H), 4.72 (dd, 1 H), 4.49 (dd, 1 H), 3.88-4.14 (m, 1 H), 2.81 (s, 3 H), 2.35-2.47 (m, 1 H), 2.18-2.35 (m, 2 H), 1.86-2.10 (m, 1 H), 1.41 (d, 6 H) |
| 181 | 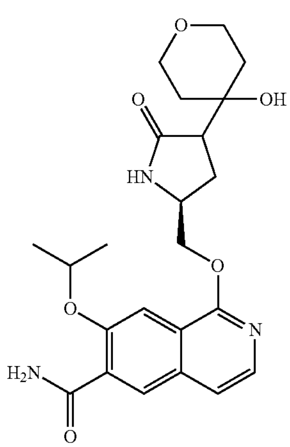 [SMILES: CC(C)Oc1cc2c(OC[C@@H]3CC(C4(O)CCOCC4)C(=O)N3)nccc2cc1C(N)=O] | P2 | L20 | | 1, 7 | 444 | ¹H NMR (400 400 MHz, dmso-d₆) δ 8.13-8.25 (m, 2 H), 7.83-7.97 (m, 1 H), 7.67-7.77 (m, 2 H), 7.56-7.68 (m, 1 H), 7.42 (dd, 1 H), 4.78-5.02 (m, 1 H), 4.40-4.52 (m, 1 H), 4.26-4.40 (m, 1 H), 3.94 (d, 1 H), 3.65 (d, 3 H), 2.53-2.64 (m, 1 H), 2.10-2.42 (m, 2 H), 1.84-2.10 (m, 2 H), 1.58-1.83 (m, 2 H), 1.33-1.46 (m, 6 H), 1.17-1.33 (m, 1 H) |

TABLE 1-continued
| Ex. | Structure | Reactant A | Reactant B | Source | Methods | MH+ | Characterization |
|---|---|---|---|---|---|---|---|
| 182 | 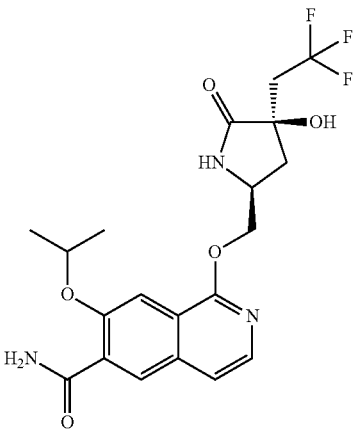 [SMILES: CC(C)Oc1cc2c(OC[C@@H]3C[C@@](O)(CC(F)(F)F)C(=O)N3)nccc2cc1C(N)=O] Chiral | P2 | L21 | | 2, 7, HPLC | 442 | ¹H NMR (400 MHz, CD₃OD) δ 8.35 (s, 1 H), 7.86-7.88 (m, 2 H), 7.34-7.35 (d, 1 H), 5.00-5.06 (m, 1 H), 4.63-4.67 (m, 1 H), 4.46-4.50 (m, 1 H), 4.12-4.16 (m, 1 H), 3.66-3.67 (m, 1 H), 2.69-2.78 (m, 2 H), 2.57-2.63 (m, 1 H), 2.22-2.27 (m, 1 H), 1.41-1.50 (m, 6 H) |
| 183 | 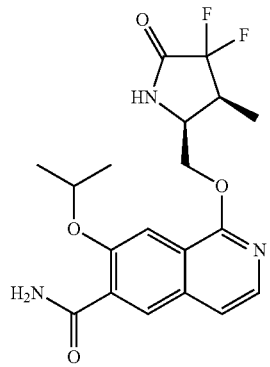 [SMILES: CC(C)Oc1cc2c(OC[C@H]3NC(=O)C(F)(F)[C@H]3C)nccc2cc1C(N)=O] Chiral | P2 | L39 | | 2, 7 | 394 | ¹H NMR (400 MHz, dmso-d₆) δ 9.32 (s, 1 H), 8.24 (s, 1 H), 7.95-7.94 (d, 1 H), 7.77 (s, 2 H), 7.66 (s, 1 H), 7.50-7.48 (d, 1 H), 4.87-4.85 (m, 1 H), 4.61-4.58 (m, 1 H), 4.42-4.41 (m, 1 H), 4.20 (s, 1 H), 3.09-3.04 (m, 1 H), 1.44-1.43 (d, 6 H), 1.23-1.21 (d, 3 H). |
| 184 | 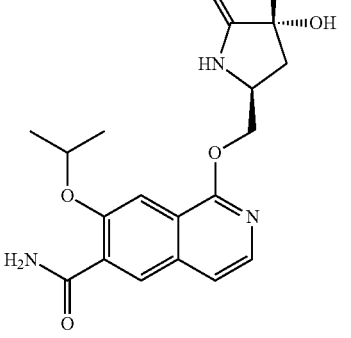 Chiral | P2 | L21 | | 2, 7, HPLC | 442 | ¹H NMR (400 MHz, CD₃OD) δ 8.24 (s, 1 H), 7.78-7.80 (d, 1 H), 7.67 (s, 1H), 7.24-7.26 (d, 1 H), 4.86-4.91 (m, 1 H), 4.57-4.6 (m, 1 H), 4.29-4.33 (m, 2 H), 2.67-2.73 (m, 1 H), 2.33-2.47 (m, 2 H), 2.13-2.19 (m, 1 H), 1.37-1.39 (m, 6 H). |

TABLE 1-continued

| Ex. | Structure | Reactant A | Reactant B | Source | Methods | MH+ | Characterization |
|---|---|---|---|---|---|---|---|
| 185 | Chiral | P2 | L106 | | 7, 2 | 359 | ¹H NMR (500 MHz, dmso-d₆) δ 8.18 (s, 1 H), 7.87 (d, 1 H), 7.76 (br. s, 1 H), 7.68 (br. s, 1 H), 7.62 (s, 1 H), 7.41 (d, 1 H), 4.91 (dt, 1 H), 4.45 (dd, 1 H), 4.32 (dd, 1 H), 4.03 (dd, 1 H), 3.47-3.58 (m, 1 H), 3.28 (dd, 1 H), 2.68 (s, 3 H), 1.31-1.45 (m, 6 H) |
| 186 | 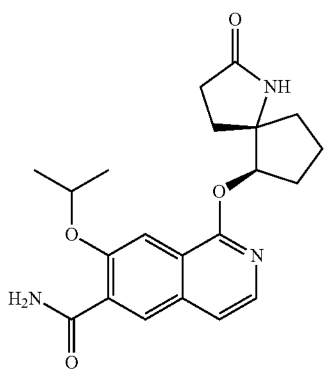 [SMILES: CC(C)Oc1cc2c(O[C@@H]3CCC[C@]34CCC(=O)N4)nccc2cc1C(N)=O] | P2 | L107 | | 7, 2, 9 | 384 | ¹H NMR (500 MHz, dmso-d₆) δ 8.19 (s, 1 H), 7.86-7.91 (m, 2 H), 7.71 (br. s., 2 H), 7.49 (s, 1 H), 7.40 (d, 1 H), 5.29 (t, 1 H), 4.80 (quin, 1 H), 2.52-2.60 (m, 1 H), 2.22-2.38 (m, 3 H), 1.79-1.96 (m, 3 H), 1.70-1.79 (m, 2 H), 1.60-1.71 (m, 1 H), 1.40 (dd, 6 H) |
| 187 | Chiral | P2 | L38 | | 2, 7 | 376 | ¹H NMR (400 MHz, dmso-d₆) δ 8.72 (s, 1 H), 8.18 (s, 1 H), 7.84-8.01 (m, 1 H), 7.63-7.84 (m, 3 H), 7.42 (d, 1 H), 4.80-5.10 (m, 2 H), 4.55 (dd, 1 H), 4.30 (dd, 1 H), 4.04 (m, 1 H), 1.31-1.44 (m, 6 H), 1.09 (d, 3 H) |

TABLE 1-continued

| Ex. | Structure | Reactant A | Reactant B | Source | Methods | MH+ | Characterization |
|---|---|---|---|---|---|---|---|
| 188 | Chiral | P1 | L37 | | 2, 7 | 348 | $^1$H NMR (400 MHz, dmso-d$_6$) δ 8.65 (s, 1 H), 8.12-8.23 (m, 1 H), 7.92 (d, 1 H), 7.84 (s, 1 H), 7.71 (br. s, 1 H), 7.29-7.53 (m, 2 H), 4.91-5.21 (m, 1 H), 4.47 (s, 2 H), 3.89-4.11 (m, 4 H), 2.65-2.86 (m, 1 H), 1.03-1.28 (m, 3 H) |
| 189 | Chiral | P1 | L38 | | 3, 7 | 348 | $^1$H NMR (400 MHz, dmso-d$_6$) δ 8.78 (s, 1 H), 8.61-8.90 (m, 1 H), 8.12-8.13 (m, 1 H), 7.92 (d, 1 H), 7.85 (br. s., 1 H), 7.71 (br. s., 2 H), 7.45 (d, 1 H), 4.78-5.13 (m, 1 H), 4.58 (dd, 1 H), 4.30 (dd, 1 H), 4.03-4.11 (m, 1 H), 3.99 (s, 3 H), 2.75-3.03 (m, 1 H), 1.11 (dd, 3 H) |
| 190 | Chiral | P2 | 17342-08-4 | commercial | 1, 7, 15, 20 | 369 | $^1$H NMR (500 MHz, dmso-d$_6$) δ 8.56 (s, 1 H), 8.13-8.25 (m, 2 H), 7.80-7.98 (m, 2 H), 7.76 (s, 1 H), 4.99 (dt, 1 H), 4.59 (dd, 1 H), 4.41 (dd, 1 H), 4.07 (d, 1 H), 2.14-2.39 (m, 4 H), 1.79-2.00 (m, 1 H), 1.42 (dd, 6 H) |

TABLE 1-continued
| Ex. | Structure | Reactant A | Reactant B | Source | Methods | MH+ | Characterization |
|---|---|---|---|---|---|---|---|
| 191 | 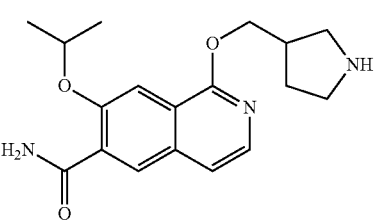 [SMILES: CC(C)Oc1cc2c(OCC3CCNC3)nccc2cc1C(N)=O] | P2 | 644971-22-2 | commercial | 1, 7, 10 | 330 | Rt = 2.175 min; method PF-AB01 |
| 192 | 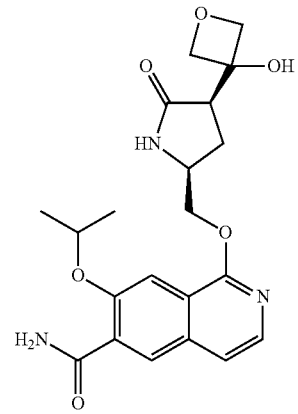 [SMILES: CC(C)Oc1cc2c(OC[C@@H]3C[C@H](C4(O)COC4)C(=O)N3)nccc2cc1C(N)=O]  Chiral | P2 | L22 | | 2, 7 | 416 | $^1$H NMR (500 MHz, dmso-d$_6$) δ 8.31 (s, 1 H), 8.14-8.22 (m, 1 H), 7.88 (d, 1 H), 7.66-7.79 (m, 3 H), 7.41 (d, 1 H), 5.96 (s, 1 H), 4.98 (dt, 1 H), 4.84 (d, 1 H), 4.40-4.62 (m, 4 H), 4.25 (dd, 1 H), 4.00 (dd, 1 H), 2.96-3.11 (m, 1 H), 2.29-2.43 (m, 1 H), 1.65-1.83 (m, 1 H), 1.31-1.46 (m, 6 H) |
| 193 | 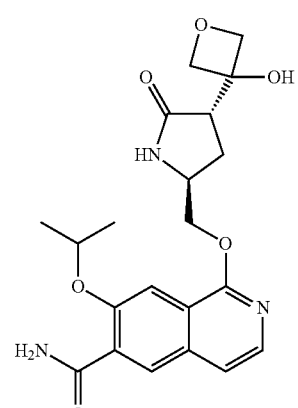  Chiral | P2 | L22 | | 2, 7 | 416 | $^1$H NMR (500 MHz, dmso-d$_6$) δ 8.21 (s, 1 H), 8.15 (s, 1 H), 7.90 (d, 1 H), 7.73 (d, 2 H), 7.65 (s, 1 H), 7.43 (d, 1 H), 5.96 (s, 1 H), 4.93 (dt, 1 H), 4.83 (d, 1 H), 4.54 (d, 1 H), 4.40-4.52 (m, 3 H), 4.32 (dd, 1 H), 3.96 (d, 1 H), 3.11 (t, 1 H), 2.01-2.24 (m, 2 H), 1.40 (dd, 6 H) |

TABLE 1-continued

| Ex. | Structure | Reactant A | Reactant B | Source | Methods | MH+ | Characterization |
|---|---|---|---|---|---|---|---|
| 194 | Chiral | P5 | L10 | | 5, 13, 1, 4 | 347 | ¹H NMR (500 MHz, dmso-d₆) δ 8.75 (s, 1 H), 8.29 (s, 1 H), 7.79 (br. s., 1 H), 7.69 (s, 1 H), 7.62 (br. s., 1 H), 7.54 (d, 1 H), 7.31 (t, 1 H), 7.01 (d, 1 H), 4.16-4.31 (m, 1 H), 3.93-4.09 (m, 5 H), 2.23-2.40 (m, 1 H), 1.36-1.59 (m, 3 H) |
| 195 | Chiral | P2 | 17342-08-4 | commercial | 1, 7, 15, 20, 9 | 373 | ¹H NMR (500 MHz, dmso-d₆) δ 8.35 (s, 1 H), 8.11 (s, 1 H), 7.92 (s, 1 H), 7.63-7.83 (m, 3 H), 4.93 (dt, 1 H), 4.48 (dd, 1 H), 4.33 (dd, 1 H), 4.22 (br. s., 2 H), 4.04 (br. s., 2 H), 2.17-2.35 (m, 3 H), 1.85-1.99 (m, 1 H), 1.33-1.48 (m, 6 H) |
| 196 | Chiral | | | | | 378 | ¹H NMR (600 MHz, dmso-d₆) δ 8.85 (s, 1H), 8.17 (s, 1H), 7.91 (d, 1H), 7.85 (br. s, 1H), 7.71 (s, 2H), 7.45 (d, 1H), 4.58 (dd, 1H), 4.48 (d, 1H), 4.30 (dd, 1H), 3.98 (s, 3H), 3.87 (dd, 1H), 1.72 (q, 2H), 1.01 (t, 3H). |

TABLE 1-continued

| Ex. | Structure | Reactant A | Reactant B | Source | Methods | MH+ | Characterization |
|---|---|---|---|---|---|---|---|
| 197 | 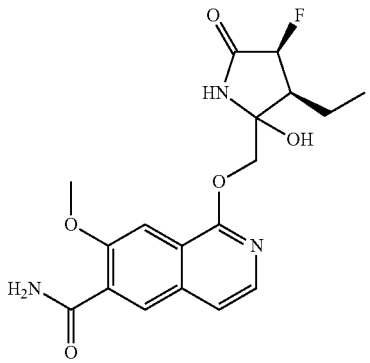 [SMILES: CC[C@@H]1[C@H](F)C(=O)NC1(O)COc1nccc2cc(C(N)=O)c(OC)cc12] Chiral | | | | | 378 | Major Diastereomer: ¹H NMR (600 MHz, dmso-d₆) δ 9.25 (s, 1H), 8.18 (s, 1H), 7.92 (d, 1H), 7.6 (s, 1H), 7.72 (s, 1H), 7.6 (s, 1H), 7.54 (s, 1H), 4.96 (dd, 1H), 4.5 (dd, 2H), 3.98 (s, 3H), 2.47 (m, 1H), 1.67 (m, 1H), 0.99 (t, 3H). Minor Diastereomer: ¹H NMR (600 MHz, dmso-d₆) δ 9.18 (s, 1H), 8.16 (s, 1H), 7.91 (d, 1H), 7.83 (s, 1H), 7.71 (s, 1H), 7.69 (s, 1H), 7.44 (s, 1H), 5.14 (dd, 1H), 4.5 (dd, 2H), 3.92 (s, 3H), 2.39 (m, 1H), 1.58 (m, 1H), 0.99 (t, 3H). |
| 198 | 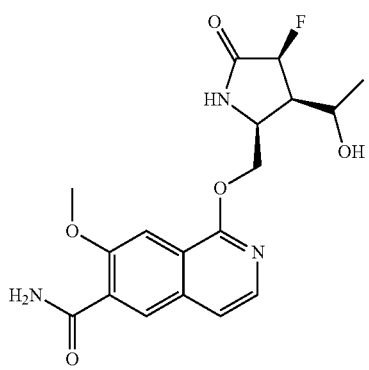 [SMILES: COc1cc2c(OC[C@H]3NC(=O)[C@@H](F)[C@H]3C(C)O)nccc2cc1C(N)=O] Chiral | | | | | 378 | ¹H NMR (600 MHz, dmso-d₆) δ 9.0 (s, 1H), 8.17 (s, 1H), 7.91 (d, J 1H), 7.86 (br s, 1H), 7.76 (s, 1H), 7.71 (bs, 1H), 7.44 (d, 1H), 4.94 (d, 1H), 4.83 (dd, 1H), 4.60 (dd, 1H), 4.26 (dd, 1H), 4.07 (m, 1H), 3.99 (m, 1H), 3.916 (m, 1H), 2.56 (m, 1H), 1.23 (d, 3H). |
| 199 | 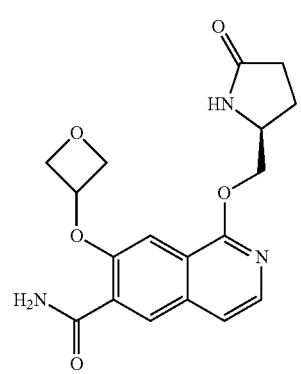 [SMILES: NC(=O)c1cc2ccnc(OC[C@@H]3CCC(=O)N3)c2cc1OC1COC1] Chiral | P14 | 17342-08-4 | commercial | 1, 7 | 358 | ¹H NMR (500 MHz, dmso-d₆) δ 8.01-8.25 (m, 2 H), 7.92 (d, 1 H), 7.86 (br. s., 1 H), 7.74 (br. s., 1 H), 7.44 (d, 1 H), 7.14 (s, 1 H), 5.52 (quin, 1 H), 4.91-5.18 (m, 2 H), 4.72 (dd, 1 H), 4.65 (dd, 1 H), 4.38-4.48 (m, 1 H), 4.34 (dd, 1 H), 3.94-4.13 (m, 1 H), 2.10-2.41 (m, 3 H), 1.84-2.00 (m, 1 H) |

TABLE 1-continued
| Ex. | Structure | Reactant A | Reactant B | Source | Methods | MH+ | Characterization |
|---|---|---|---|---|---|---|---|
| 200 | 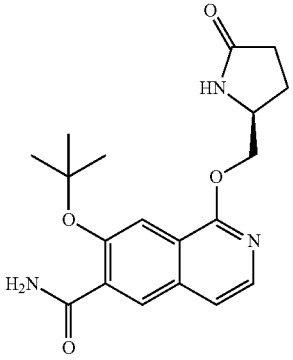 [SMILES: CC(C)(C)Oc1cc2c(OC[C@@H]3CCC(=O)N3)nccc2cc1C(N)=O]<br>Chiral | P12 | 17342-08-4 | commercial | 1, 7 | 358 | ¹H NMR (500 MHz, dmso-d$_6$) δ 8.15 (s, 1 H), 8.01 (s, 1 H), 7.93 (d, 1 H), 7.79 (s, 1 H), 7.71 (br. s., 2 H), 7.44 (d, 1 H), 4.32-4.47 (m, 2 H), 3.95-4.10 (m, 1 H), 2.11-2.39 (m, 3 H), 1.89-2.05 (m, 1 H), 1.44 (s, 9 H) |
| 201 | 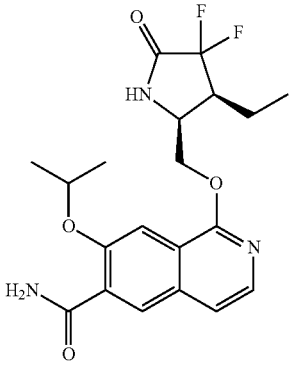 [SMILES: CC[C@H]1[C@@H](COc2nccc3cc(C(N)=O)c(OC(C)C)cc23)NC(=O)C1(F)F]<br>Chiral | P2 | L40 | | 2, 7 | 408 | ¹H NMR (400 MHz, dmso-d$_6$) δ 9.32 (s, 1 H), 8.24 (s, 1 H), 7.94-7.96 (d, 1 H), 7.77 (s, 2 H), 7.66 (s, 1 H), 7.49-7.50 (d, 1 H), 4.85-4.87 (m, 1 H), 4.59-4.61 (m, 1 H), 4.40-4.43 (m, 1 H), 4.20 (s, 1 H), 3.04-3.09 (m, 1 H), 1.43-1.44 (d, 6 H), 1.22-1.23 (m, 3 H) |
| 202 | 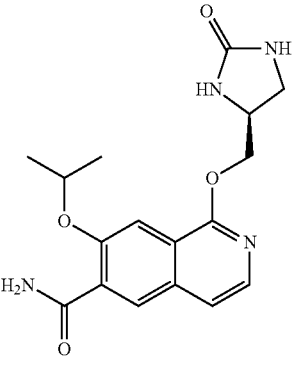<br>Chiral | P2 | L108 | | 7, 1 | 345 | ¹H NMR (500 MHz, dmso-d$_6$) δ 8.20 (s, 1 H), 7.88 (d, 1 H), 7.63-7.82 (m, 3 H), 7.41 (d, 1 H), 6.76 (s, 1 H), 6.26 (s, 1 H), 4.95 (dt, 1 H), 4.45 (dd, 1 H), 4.33 (dd, 1 H), 4.11 (dq, 1 H), 3.56 (t, 1 H), 3.25 (dd, 1 H), 1.32-1.44 (m, 6 H) |

TABLE 1-continued
| Ex. | Structure | Reactant A | Reactant B | Source | Methods | MH+ | Characterization |
|---|---|---|---|---|---|---|---|
| 203 | 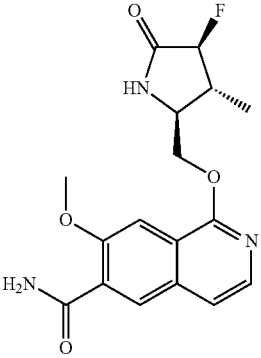 [SMILES: COc1cc2c(OC[C@H]3NC(=O)[C@@H](F)[C@@H]3C)nccc2cc1C(N)=O] Chiral | P1 | L90 | | 2, 7 | 348 | $^1$H NMR (400 MHz, dmso-d$_6$) δ 8.71 (s, 1 H), 8.17 (s, 1 H), 7.91 (d, 1 H), 7.85 (br. s., 1 H), 7.70 (br. s., 1 H), 7.65 (s, 1 H), 7.45 (d, 1 H), 4.75-4.99 (m, 1 H), 4.66 (dd, 1 H), 4.35 (dd, 1 H), 3.97 (s, 3 H), 3.62 (dt, 1 H), 2.27-2.46 (m, 1 H), 1.28 (d, 3 H) |
| 204 | 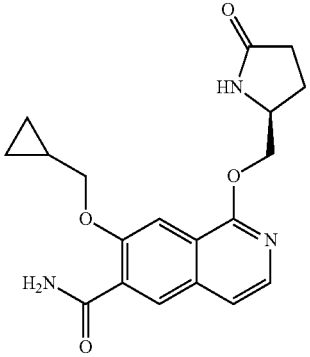 [SMILES: NC(=O)c1cc2ccnc(OC[C@@H]3CCC(=O)N3)c2cc1OCC1CC1] Chiral | P11 | 17342-08-4 | commercial | 1, 7 | 356 | $^1$H NMR (500 MHz, dmso-d$_6$) δ 8.08-8.29 (m, 2 H), 7.80-7.95 (m, 2 H), 7.77 (br. s., 1 H), 7.62 (s, 1 H), 7.43 (d, 1 H), 4.49 (dd, 1 H), 4.28 (dd, 1 H), 4.09-4.21 (m, 1 H), 3.92-4.09 (m, 2 H), 2.10-2.40 (m, 3 H), 1.81-1.97 (m, 1 H), 1.27-1.45 (m, 1 H), 0.58-0.70 (m, 2 H), 0.34-0.49 (m, 2 H) |
| 205 | 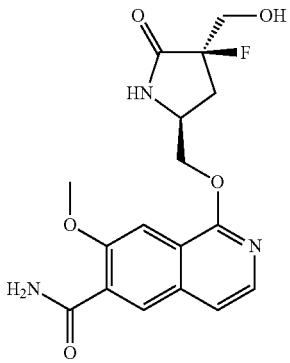 [SMILES: COc1cc2c(OC[C@@H]3C[C@@](F)(CO)C(=O)N3)nccc2cc1C(N)=O] Chiral | P1 | L18 | | 3, 7, 9 | 364 | $^1$H NMR (400 MHz, dmso-d$_6$) δ 8.79 (br. s, 1 H), 8.16 (s, 1 H), 7.90 (d, 1 H), 7.84 (br. s., 1 H), 7.70 (s, 2 H), 7.44 (d, 1 H), 5.31 (t, 1 H), 4.60 (dd, 1 H), 4.27 (dd, 1 H), 3.98-4.10 (m, 1 H), 3.97 (s, 3 H), 3.56-3.72 (m, 1 H), 2.69-2.85 (m, 1 H), 2.06-2.21 (m, 1 H) |

TABLE 1-continued
| Ex. | Structure | Reactant A | Reactant B | Source | Methods | MH+ | Characterization |
|---|---|---|---|---|---|---|---|
| 206 | 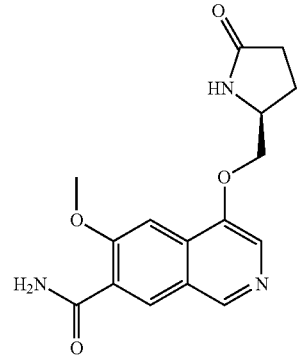 [SMILES: COc1cc2c(OC[C@@H]3CCC(=O)N3)cncc2cc1C(N)=O] Chiral | P24 | 17342-08-4 | commercial | 6, 7 | 316 | $^1$H NMR (400 MHz, dmso-d$_6$) δ 8.91 (s, 1 H), 8.41 (s, 1 H), 8.14 (br. s., 2 H), 7.83 (br. s., 1 H), 7.70 (br. s., 1 H), 7.53 (s, 1 H), 4.21-4.24 (m, 1 H), 4.11-4.15 (m, 1 H), 4.04-4.06 (m 1 H), 4.02 (s, 3 H), 2.20-2.35 (m, 3 H), 1.0-1.93 (m, 1 H) |
| 207 | 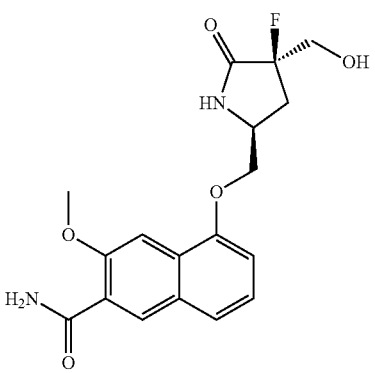 [SMILES: COc1cc2c(OC[C@@H]3C[C@@](F)(CO)C(=O)N3)cccc2cc1C(N)=O] Chiral | P5 | L18 | | 5, 9 | 363 | $^1$H NMR (400 MHz, dmso-d$_6$) δ 8.75 (br. s, 1 H), 8.48 (br. s, 1 H), 8.28 (s, 1 H), 7.78 (br. s, 1 H), 7.68 (s, 1 H), 7.62 (br. s., 1 H), 7.54 (d, 1 H), 7.32 (t, 1 H), 7.02 (d, 1 H), 4.23 (dd, 1 H), 3.99-4.11 (m, 2 H), 3.97 (s, 3 H), 3.59-3.71 (m, 2 H), 2.72-2.88 (m, 1 H), 2.07-2.28 (m, 1H) |
| 208 | 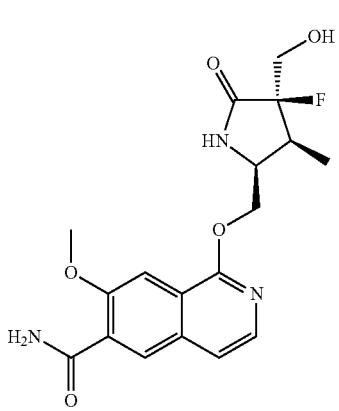 [SMILES: COc1cc2c(OC[C@H]3NC(=O)[C@](F)(CO)[C@H]3C)nccc2cc1C(N)=O] Chiral | P1 | L41 | | 2, 7, 9 | 378 | $^1$H NMR (400 MHz, dmso-d$_6$) δ 8.85 (s, 1 H), 8.15 (s, 1 H), 7.79-7.97 (m, 1 H), 7.61-7.77 (m, 2 H), 7.43 (d, 1 H), 5.25 (br. s., 1 H), 4.57 (dd, 1 H), 4.27 (dd, 1 H), 3.97 (s, 3 H), 3.49-3.80 (m, 2 H), 2.80-3.04 (m, 1 H), 1.13 (s, 3 H) |

TABLE 1-continued
| Ex. | Structure | Reactant A | Reactant B | Source | Methods | MH+ | Characterization |
|---|---|---|---|---|---|---|---|
| 209 | 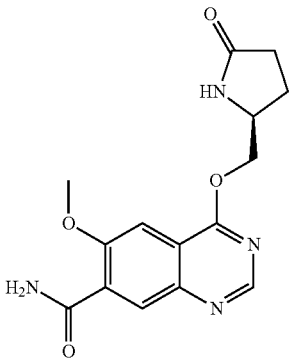 [SMILES: COc1cc2c(OC[C@@H]3CCC(=O)N3)ncnc2cc1C(N)=O]<br>Chiral | P3 | 17342-08-4 | commercial | 2, 7 | 317 | $^1$H NMR (400 MHz, dmso-d$_6$) δ 8.71 (s, 1 H), 8.22 (br. s, 1 H), 8.03 (s, 1 H), 7.91 (br. s., 1 H), 7.76 (br. s., 1 H), 7.62 (s, 1 H), 4.62 (dd, 1 H), 4.31-4.42 (m, 1 H), 4.03-4.12 (m, 1 H), 4.00 (s, 3 H), 2.14-2.37 (m, 3 H), 1.85-1.94 (m, 1 H) |
| 210 | 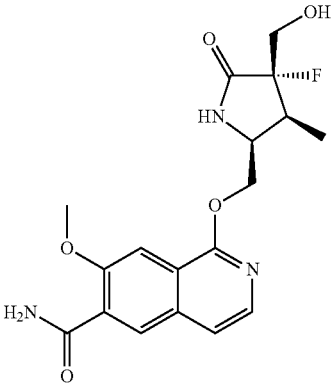 [SMILES: COc1cc2c(OC[C@H]3NC(=O)[C@@](F)(CO)[C@H]3C)nccc2cc1C(N)=O]<br>Chiral | P1 | L42 | | 2, 7, 9 | 378 | $^1$H NMR (400 MHz, dmso-d$_6$) δ 9.01 (s, 1 H), 8.16 (s, 1 H), 7.90 (d, 1 H), 7.85 (br. s., 1 H), 7.70 (br. s., 1 H), 7.71 (s, 2 H), 7.43 (d, 1 H), 5.36 (br. s., 1 H), 4.63 (dd, 1 H), 4.34-4.50 (m, 1 H), 4.07-4.24 (m, 1 H), 4.02 (s, 3 H), 3.68 (d, 2 H), 2.77-3.04 (m, 1 H), 1.21 (d, 3 H) |
| 211 | 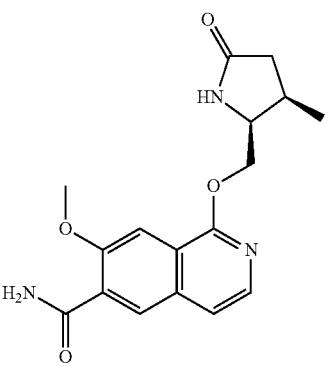<br>Chiral | P1 | L36 | | 2, 7 | 330 | $^1$H NMR (400 MHz, dmso-d$_6$) δ 8.15 (s, 1 H), 8.03 (s, 1 H), 7.90-7.94 (m, 1 H), 7.85 (s, 1 H), 7.71 (s, 1 H), 7.57 (s, 1 H), 7.42-7.44 (m, 1 H), 4.40-4.49 (m, 2 H), 3.97 (s, 3 H), 3.91-3.94 (m, 1 H), 2.66-2.72 (m, 1 H), 2.28-2.34 (m, 1 H), 2.06-2.12 (m, 1 H), 1.07-1.08 (m, 3 H). |

TABLE 1-continued

| Ex. | Structure | Reactant A | Reactant B | Source | Methods | MH+ | Characterization |
|---|---|---|---|---|---|---|---|
| 212 | Chiral | P2 | L43 | | 1, 7, 9 | 374 | ¹H NMR (500 MHz, dmso-d₆) δ 8.14-8.31 (m, 1 H), 8.06 (s, 1 H), 7.83-7.98 (m, 1 H), 7.63-7.82 (m, 3 H), 7.42 (d, 1 H), 4.83-5.02 (m, 1 H), 4.50 (dd, 1 H), 4.34 (dd, 1 H), 3.82 (br. s., 1 H), 3.47 (br. s., 2 H), 2.32-2.47 (m, 2 H), 2.03 (dd, 1 H), 1.35-1.46 (m, 6 H) |
| 213 | Chiral | P2 | L109 | | 1, 7, 9, 21 | 399 | ¹H NMR (400 MHz, dmso-d₆) δ 9.73 (s, 1H), 8.18-8.19 (d, 1 H), 8.13 (s, 1 H), 7.87-7.90 (m, 2 H), 7.57-7.59 (d, 1 H), 7.41-7.44 (m, 1 H), 4.85-4.90 (m, 1 H), 4.37-4.47 (m, 2 H), 3.80-3.91 (m, 1 H), 3.49-3.52 (m, 1 H), 3.03-3.16 (m, 3 H), 2.73-2.87 (m, 2 H), 2.32-2.49 (m, 3 H), 1.37-1.41 (m, 6 H) |
| 214 | Chiral | P1 | L43 | | 1, 7, 9 | 346 | ¹H NMR (500 MHz, dmso-d₆) δ 8.17 (s, 1 H), 8.10 (s, 1 H), 7.83-7.98 (m, 2 H), 7.60-7.76 (m, 2 H), 7.43 (d, 1 H), 4.52 (dd, 1 H), 4.33 (dd, 1 H), 4.00 (s, 3 H), 3.78-3.87 (m, 1 H), 3.48 (d, 2 H), 2.30-2.49 (m, 2 H), 2.02 (dd, 1 H) |

TABLE 1-continued
| Ex. | Structure | Reactant A | Reactant B | Source | Methods | MH+ | Characterization |
|---|---|---|---|---|---|---|---|
| 215 | 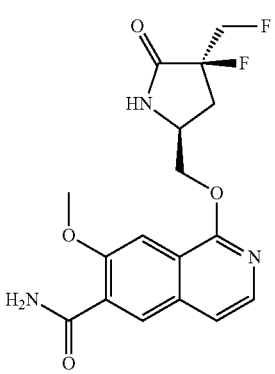 [SMILES: COc1cc2c(OC[C@@H]3C[C@@](F)(CF)C(=O)N3)nccc2cc1C(N)=O]<br>Chiral | P1 | L23 | | 2, 7 | 366 | $^1$H NMR (400 MHz, CD$_3$OD) δ 8.35 (s, 1 H), 7.91-7.92 (d, 1 H), 7.82 (s, 1 H), 7.37-7.39 (d, 1 H), 4.63-4.86 (m, 3 H), 4.44-4.48 (m, 1 H), 4.22-4.24 (m, 1 H), 4.08 (s, 3 H), 2.89-3.00 (m, 1 H), 2.40-2.58 (m, 1 H). |
| 216 | 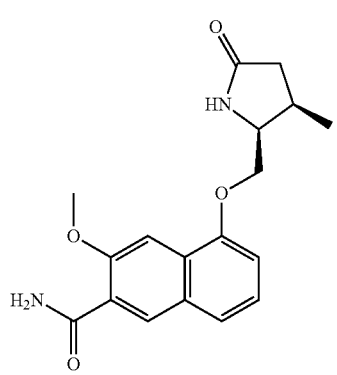<br>Chiral | P5 | L36 | | 5 | 329 | $^1$H NMR (400 MHz, CDCl$_3$) δ 8.61 (s, 1 H), 7.38-7.51 (m, 2 H), 7.23 (t, 3 H), 6.82 (d, 1 H), 4.16-4.26 (m, 1 H), 4.04 (dd, 4 H), 2.73-2.94 (m, 1 H), 2.51 (dd, 1 H), 2.27 (dd, 1 H), 1.08-1.16 (m, 3 H) |
| 218 | 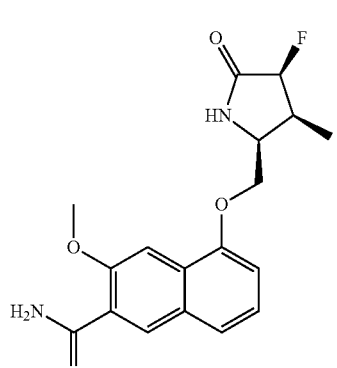<br>Chiral | P5 | L38 | | 5 | 347 | $^1$H NMR (500 MHz, dmso-d$_6$) δ 8.56 (s, 1 H), 8.30 (s, 1 H), 7.79 (br. s., 1 H), 7.63 (br. s., 1 H), 7.56 (d, 1 H), 7.43 (s, 1 H), 7.33 (t, 1 H), 7.07 (d, 1 H), 5.01-5.23 (m, 1 H), 4.30 (dd, 1 H), 4.01 (d, 4 H), 2.68-2.88 (m, 1 H), 1.22 (d, 3 H) |

TABLE 1-continued
| Ex. | Structure | Reactant A | Reactant B | Source | Methods | MH+ | Characterization |
|---|---|---|---|---|---|---|---|
| 219 | 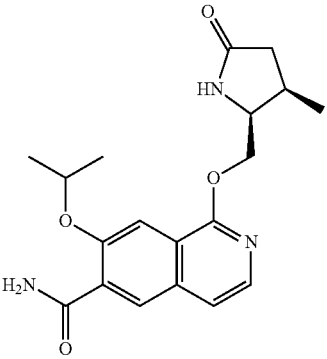 [SMILES: CC(C)Oc1cc2c(OC[C@H]3NC(=O)C[C@H]3C)nccc2cc1C(N)=O] Chiral | P2 | L36 | | 1, 7 | 358 | ¹H NMR (500 MHz, dmso-d$_6$) δ 8.20 (s, 1 H), 7.97 (s, 1 H), 7.90 (d, 1 H), 7.73 (d, 2 H), 7.58 (s, 1 H), 7.43 (d, 1 H), 4.87 (dt, 1 H), 4.44-4.55 (m, 2 H), 3.80-3.99 (m, 1 H), 2.66-2.80 (m, 1 H), 2.33 (dd, 1 H), 2.09 (dd, 1 H), 1.31-1.47 (m, 6 H), 1.09 (d, 3 H) |
| 220 | 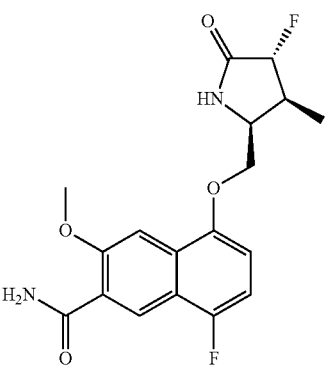 Chiral | P25 | L37 | | 5 | 365 | ¹H NMR (400 MHz, dmso-d$_6$) δ 8.57 (s, 1 H), 8.35 (s, 1 H), 7.84 (br. s., 1 H), 7.72 (br. s., 1 H), 7.44 (s, 1 H), 7.13 (dd, 1 H), 7.01 (dd, 1 H), 5.08 (dd, 1 H), 4.28 (dd, 1 H), 3.99 (s, 3 H), 3.92-4.08 (m, 2 H), 2.66-2.83 (m, 1 H), 1.21 (d, 3 H) |
| 221 | 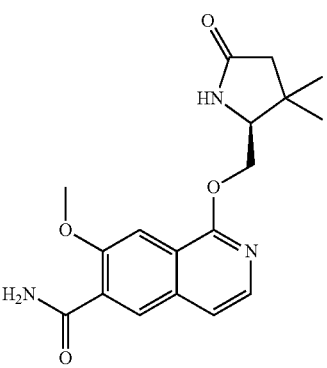 [SMILES: COc1cc2c(OC[C@H]3NC(=O)CC3(C)C)nccc2cc1C(N)=O] Chiral | P1 | 194421-58-4 | Ref. 31 | 1, 7, HPLC | 344 | ¹H NMR (500 MHz, dmso-d$_6$) δ 8.17 (s, 1 H), 8.06 (s, 1 H), 7.92 (d, 1 H), 7.85 (br. s., 1 H), 7.70 (br. s., 1 H), 7.61 (s, 1 H), 7.44 (d, 1 H), 4.47-4.55 (m, 1 H), 4.42 (dd, 1 H), 3.61 (t, 1 H), 2.27 (d, 1 H), 2.04 (d, 1 H), 1.22 (s, 3 H), 1.12 (s, 3 H) |

TABLE 1-continued

| Ex. | Structure | Reactant A | Reactant B | Source | Methods | MH+ | Characterization |
|---|---|---|---|---|---|---|---|
| 222 | Chiral | P1 | 194421-58-4 | Ref. 31 | 1, 7, HPLC | 344 | ¹H NMR (500 MHz, dmso-d₆) δ 8.17 (s, 1 H), 8.06 (s, 1 H), 7.92 (d, 1 H), 7.85 (br. s., 1 H), 7.70 (br. s., 1 H), 7.61 (s, 1 H), 7.44 (d, 1 H), 4.47-4.55 (m, 1 H), 4.42 (dd, 1 H), 3.61 (t, 1 H), 2.27 (d, 1 H), 2.04 (d, 1 H), 1.22 (s, 3 H), 1.12 (s, 3 H) |
| 223 | Chiral | P2 | 194421-58-4 | Ref. 31 | 1, 7, HPLC | 372 | ¹H NMR (500 MHz, dmso-d₆) δ 8.19 (s, 1 H), 7.99 (s, 1 H), 7.89 (d, 1 H), 7.70 (s, 1 H), 7.73 (s, 1 H), 7.60 (s, 1 H), 7.41 (d, 1 H), 4.77-4.94 (m, 1 H), 4.34-4.54 (m, 2 H), 3.52-3.64 (m, 1 H), 2.24 (d, 1 H), 2.03 (d, 1 H), 1.38 (d, 3 H), 1.40 (d, 3 H), 1.21 (s, 3 H), 1.10 (s, 3 H) |
| 224 | Chiral | P1 | L110 |  | 7, 2, HPLC | 355 | ¹H NMR (500 MHz, dmso-d₆) δ 8.50 (s, 1 H), 8.17 (s, 1 H), 7.91 (d, 1 H), 7.85 (br. s., 1 H), 7.70 (br. s., 1 H), 7.67 (s, 1 H), 7.44 (d, 1 H), 4.63 (dd, 1 H), 4.24 (dd, 1 H), 4.05 (m, 1 H), 3.99 (s, 3 H), 2.67-2.84 (m, 3 H), 1.66-1.74 (m, 1 H) |

TABLE 1-continued
| Ex. | Structure | Reactant A | Reactant B | Source | Methods | MH+ | Characterization |
|---|---|---|---|---|---|---|---|
| 225 | 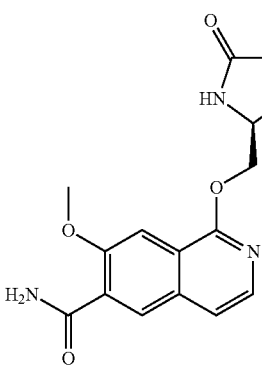 Chiral | P1 | L110 | | 7, 2, HPLC | 355 | $^1$H NMR (500 MHz, dmso-d$_6$) δ 7.91 (d, 1 H), 7.85 (br. s., 1 H), 7.70 (br. s., 1 H), 7.60 (s, 1 H), 7.44 (d, 1 H), 4.49 (dd, 1 H), 4.37 (dd, 1 H), 4.05 (m, 1 H), 3.99 (s, 3 H), 2.96 (m, 1 H), 2.73-2.80 (m, 2 H), 2.29 (m, 1 H), 2.12 (m, 1 H) |
| 226 | 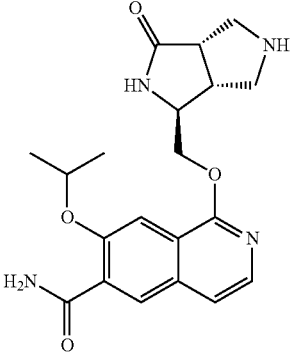 [SMILES: CC(C)Oc1cc2c(OC[C@H]3NC(=O)[C@@H]4CNC[C@H]34)nccc2cc1C(N)=O] Chiral | P2 | L111 | | 2, 7, 10 | 385 | $^1$H NMR (400 MHz, dmso-d$_6$) δ 9.51 (s, 1 H), 69.24 (s, 1 H), δ 8.44 (s, 1 H), δ 8.20 (s, 1 H), 7.90-7.88 (d, 1 H), 7.72 (s, 2 H), δ 7.57 (s, 1 H), 7.44-7.43 (d, 1 H), 4.91-4.81 (m, 1 H), 4.48-4.47 (m, 2 H), 3.98-3.92 (m, 1 H), 3.55-3.47 (m, 1 H), 3.37-3.25 (m, 3 H), 3.20-3.16 (m, 1 H), 3.08-3.02 (m, 1 H), 1.41-1.35 (m, 6 H) |
| 227 | 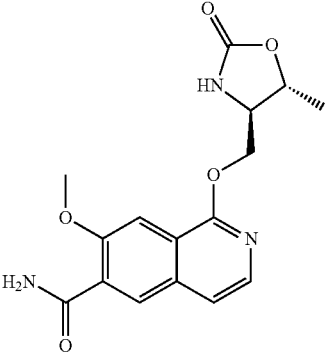 [SMILES: COc1cc2c(OC[C@H]3NC(=O)O[C@@H]3C)cccc2cc1C(N)=O] Chiral | P1 | 127913-30-8 | Ref. 32 | 2, 7 | 332 | $^1$H NMR (400 MHz, dmso-d$_6$) δ 8.07 (s, 1 H), 7.93 (s, 1 H), 7.77-7.81 (m, 2 H), 7.61 (s, 1 H), 7.51 (s, 1 H), 7.34-7.35 (d, 1 H), 4.49-4.52 (m, 1 H), 4.38-4.41 (m, 1 H), 4.30-4.34 (m, 1 H), 3.87 (s, 3 H), 3.74-3.75 (m, 1 H), 1.29-1.30 (d, 3 H) |

TABLE 1-continued

| Ex. | Structure | Reactant A | Reactant B | Source | Methods | MH+ | Characterization |
|---|---|---|---|---|---|---|---|
| 228 | Chiral | P5 | 127913-30-8 | Ref. 32 | 6 | 331 | $^1$H NMR (400 MHz, dmso-d$_6$) δ 8.29 (s, 1 H), 7.99 (s, 1 H), 7.79 (br. s, 1 H), 7.64 (br. s, 1 H), 7.61 (s, 1 H), 7.54 (d, 1 H), 7.32 (t, 1 H), 7.01 (d, 1 H), 4.63 (quin, 1 H), 4.19 (d, 2 H), 3.85 (m, 1 H), 1.43 (d, 1 H) |
| 229 | Chiral | P1 | 15546-08-4 | Ref. 17 | 2, 7 | 318 | $^1$H NMR (400 MHz, dmso-d$_6$) δ 8.18 (m, 1 H), 8.08 (m, 1 H), 7.87-7.92 (m, 2 H), 7.73 (m, 1 H), 7.63 (m, 1 H), 7.45-7.46 (m, 2 H), 4.49-4.52 (m, 2 H), 4.38-4.417 (m, 1 H), 4.28-4.32 (m, 2 H), 3.98 1 (s, 3 H) |
| 230 | Chiral | P1 | 15546-08-4 | Ref. 17 | 6 | 318 | $^1$H NMR (400 MHz, dmso-d$_6$) δ 8.18 (m, 1 H), 8.08 (m, 1 H), 7.87-7.92 (m, 2 H), 7.73 (m, 1 H), 7.63 (m, 1 H), 7.45-7.46 (m, 2 H), 4.49-4.52 (m, 2 H), 4.38-4.417 (m, 1 H), 4.28-4.32 (m, 2 H), 3.98 1 (s, 3 H) |

TABLE 1-continued
| Ex. | Structure | Reactant A | Reactant B | Source | Methods | MH+ | Characterization |
|---|---|---|---|---|---|---|---|
| 231 | 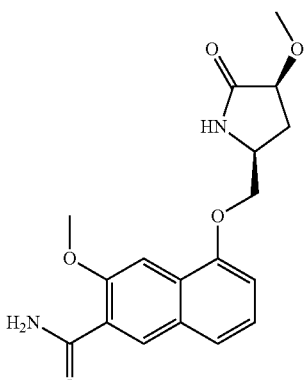 Chiral | P5 | L25 | | 6, HPLC | 345 | ¹H NMR (400 MHz, dmso-d₆) δ 8.44 (s, 1 H), 68.28 (s, 1 H), 7.80 (s, 1 H), 7.67-7.65 (m, 2 H), 7.54-7.52 (m, 1 H), 7.33-7.29 (m, 1 H), 7.01-7.00 (m, 1 H), 4.20-4.19 (m, 1 H), 4.03-3.94 (m, 6 H), 3.44 (s, 3 H), 2.61-2.58 (m, 1 H), 1.85-1.84 (m, 1 H) |
| 232 | 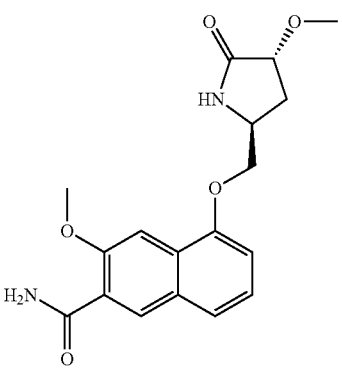 [SMILES: COc1cc2c(OC[C@@H]3C[C@@H](OC)C(=O)N3)cccc2cc1C(N)=O] Chiral | P5 | L25 | | 6, HPLC | 345 | ¹H NMR (400 MHz, dmso-d₆) δ 8.35 (s, 1 H), 68.29 (s, 1 H), 7.80 (s, 1 H), 7.65 (s, 1 H), 7.55-7.54 (m, 2 H), 7.34-7.30 (m, 1 H), 7.02-7.00 (m, 1 H), 4.19-4.15 (m, 1 H), 4.12-4.10 (m, 2 H), 4.01 (s, 3 H), 3.46 (s, 3 H), 2.41-2.33 (m, 1 H), 2.17-2.13 (m, 1 H) |
| 233 | 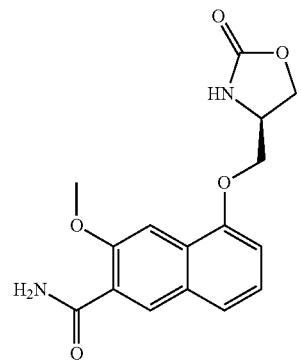 Chiral | P5 | 15546-08-4 | Ref. 17 | 6 | 317 | ¹H NMR (400 MHz, dmso-d₆) δ 8.29 (m, 1 H), 8.01 (m, 1 H), 7.80 (m, 1 H), 7.62-7.65 (m, 2 H), 7.53-7.55 (m, 1 H), 7.00-7.02 (m, 1 H), 4.50-4.52 (s, 1 H), 4.36-4.37 (s, 1 H), 4.34 (m, 1 H), 4.17-4.18 (m, 2 H), 3.98 (s, 3 H) |

TABLE 1-continued
| Ex. | Structure | Reactant A | Reactant B | Source | Methods | MH+ | Characterization |
|---|---|---|---|---|---|---|---|
| 234 | 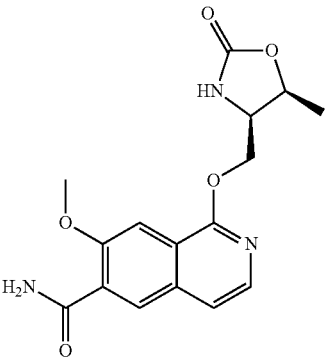 [SMILES: COc1cc2c(OC[C@H]3NC(=O)O[C@H]3C)nccc2cc1C(N)=O] Chiral | P5 | L112 | | 5 | 331 | $^1$H NMR (400 MHz, CD$_3$OD) δ 8.45 (s, 1 H), 7.72 (s, 1 H), 7.49 (d, 1 H), 7.32 (t, 1 H), 7.00 (d, 1 H), 4.97-5.07 (m, 1 H), 4.32 (dd, 1 H), 4.23 (dd, 1 H), 4.14-4.20 (m, 1 H), 4.08 (s, 3 H), 1.51 (d, 3 H) |
| 235 | 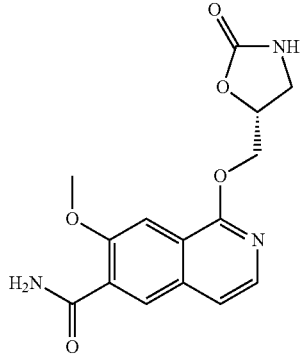 [SMILES: COc1cc2c(OC[C@H]3CNC(=O)O3)nccc2cc1C(N)=O] Chiral | P1 | 97859-49-9 | Ref. 11 | 3, 7 | 318 | $^1$H NMR (400 MHz, dmso-d$_6$) δ 8.17 (s, 1 H), 7.91 (d, 1 H), 7.84 (bs, 1 H), 7.70 (bs, 1 H), 7.67 (bs, 1 H), 7.53 (s, 1 H), 7.46 (d, 1 H), 5.06 (m, 1 H), 4.62 (m, 2 H), 3.96 (s, 3 H), 3.70 (m, 1 H), 3.45 (m, 1 H) |
| 236 | 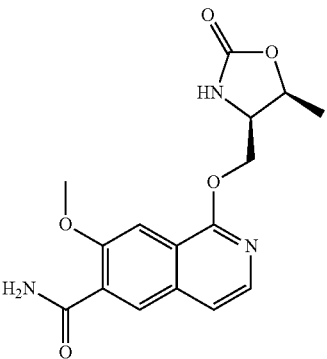 Chiral | P1 | L112 | | 3, 7 | 332 | $^1$H NMR (400 MHz, dmso-d$_6$) δ 8.16 (s, 1 H), 7.91 (d, 1 H), 7.89 (s, 1 H), 7.84 (br. s., 1 H), 7.70 (br. s., 1 H), 7.62 (s, 1 H), 7.44 (d, 1 H), 4.87 (quin, 1 H), 4.42-4.53 (m, 2 H), 4.10-4.18 (m, 1 H), 3.97 (s, 3 H), 1.37 (d, 3 H) |

TABLE 1-continued
| Ex. | Structure | Reactant A | Reactant B | Source | Methods | MH+ | Characterization |
|---|---|---|---|---|---|---|---|
| 237 | 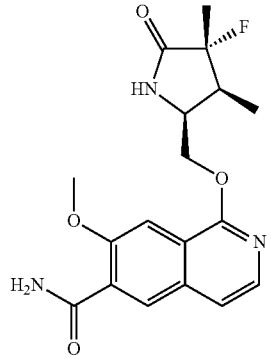 [SMILES: COc1cc2c(OC[C@H]3NC(=O)[C@](C)(F)[C@H]3C)nccc2cc1C(N)=O] Chiral | P1 | L44 | | 4, 7 | 362 | ¹H NMR (400 MHz, dmso-d$_6$) δ 8.83 (s, 1 H), 8.17 (s, 1 H), 7.85-7.93 (m, 2 H), 7.63-7.70 (m, 2 H), 7.45-7.46 (m, 1 H), 4.55-4.59 (m, 1 H), 4.32-4.37 (m, 1 H), 4.01-4.16 (m, 1 H), 4.00 (s, 3 H), 2.51 (m, 1 H), 1.40-1.46 (m, 3 H), 1.09-1.11 (m, 3 H) |
| 238 | 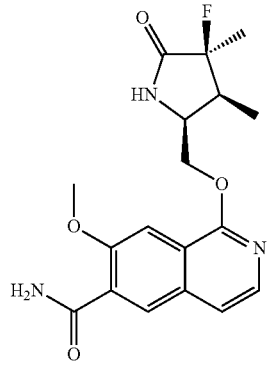 [SMILES: COc1cc2c(OC[C@H]3NC(=O)[C@@](C)(F)[C@H]3C)nccc2cc1C(N)=O] Chiral | P1 | L45 | | 4, 7 | 362 | ¹H NMR (400 MHz, dmso-d$_6$) δ 8.95 (s, 1 H), 8.16 (s, 1 H), 7.85-7.92 (m, 2 H), 7.69-7.74 (m, 2 H), 7.43-7.44 (m, 1 H), 4.56-4.59 (m, 1 H), 4.24-4.28 (m, 1 H), 4.00-4.06 (m, 1 H), 3.99 (s, 3 H), 2.51 (m, 1 H), 1.40-1.46 (m, 3 H), 1.13-1.15 (m, 3 H) |
| 239 | 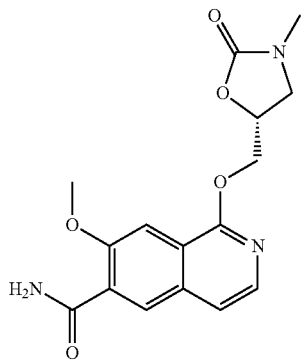 [SMILES: COc1cc2c(OC[C@H]3CN(C)C(=O)O3)nccc2cc1C(N)=O] Chiral | P1 | 1315020-11-1 | commercial | 2, 7 | 332 | ¹H NMR (400 MHz, dmso-d$_6$) δ 8.19 (m, 1 H), 7.87-7.93 (m, 2 H), 7.73 (s, 1 H), 7.46-7.48 (m, 2 H), 5.00-5.02 (m, 1 H), 4.58-4.68 (m, 2 H), 4.00 (s, 3 H), 3.77-3.81 (m, 1 H), 3.52-3.54 (m, 1 H), 2.83 (s, 3 H) |

TABLE 1-continued
| Ex. | Structure | Reactant A | Reactant B | Source | Methods | MH+ | Characterization |
|---|---|---|---|---|---|---|---|
| 240 | 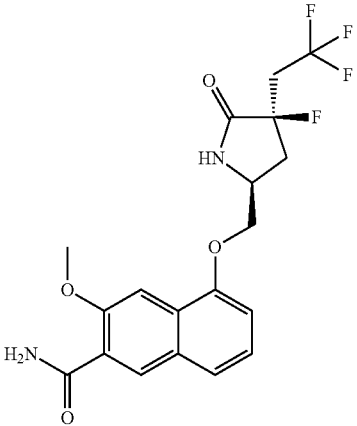 [SMILES: COc1cc2c(OC[C@@H]3C[C@@](F)(CC(F)(F)F)C(=O)N3)cccc2cc1C(N)=O] Chiral | P5 | L26 | | 6 | 415 | $^1$H NMR (400 MHz, CDCl$_3$) δ 8.62 (s, 1 H), 7.81-7.82 (m, 1 H), 7.44-7.50 (m, 2 H), 7.22-7.24 (m, 1 H), 6.78-6.80 (m, 1 H), 6.55 (s, 1 H), 5.87 (s, 1 H), 4.03-4.22 (m, 3 H), 4.00 (s, 3 H), 2.70-3.07 (m, 2 H), 2.41-2.63 (m, 2 H) |
| 241 | 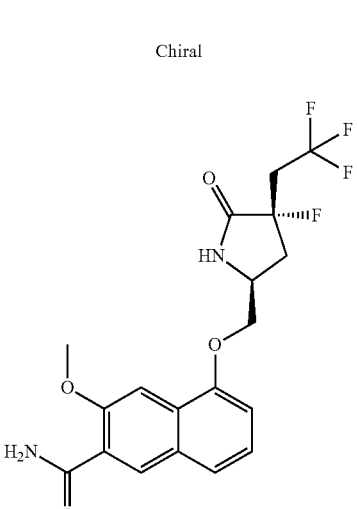 Chiral | P5 | L26 | | 6 | 415 | $^1$H NMR (400 MHz, CD$_3$OD) δ 8.34 (s, 1 H), 7.61 (s, 1 H), 7.40-7.42 (m, 1 H), 7.21-7.25 (m, 1 H), 6.93-6.95 (m, 1 H), 4.09-4.21 (m, 3 H), 3.97 (s, 3 H), 2.23-3.03 (m, 4 H) |
| 242 | 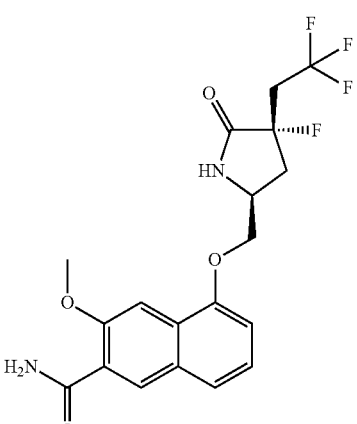 Chiral | P1 | L1 | | 2, 7, HPLC | 330 | $^1$H NMR (400 MHz, dmso-d$_6$) δ 8.17-8.21 (m, 2 H) 7.90-7.91 (m, 2 H), 7.68-7.72 (m, 2 H), 7.43-7.44 (m, 1 H), 4.58-4.60 (m, 1 H), 4.18-4.22 (m, 1 H), 4.00 (s, 4 H), 2.68 (m, 1 H), 2.34 (m, 1 H), 1.47-1.48 (m, 1 H), 1.11-1.13 (d, 3 H) |

TABLE 1-continued
| Ex. | Structure | Reactant A | Reactant B | Source | Methods | MH+ | Characterization |
|---|---|---|---|---|---|---|---|
| 243 | 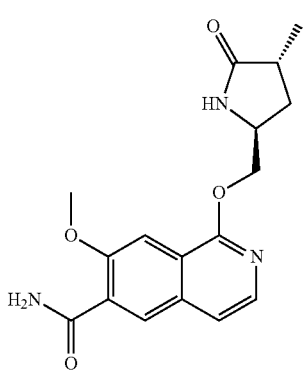<br>Chiral | P1 | L1 | | 2, 7, HPLC | 330 | $^1$H NMR (400 MHz, CD$_3$OD) δ 8.23 (m, 2 H), 7.78-7.80 (m, 1 H), 7.61 (m, 1 H), 7.25-7.26 (m, 1 H), 4.39-4.47 (m, 2 H), 4.04-4.05 (m, 1 H), 3.98 (s, 3 H), 2.63-2.65 (m, 1 H), 2.27 (m, 1 H), 1.94-1.98 (m, 1 H), 1.12-1.14 (d, 3 H) |
| 244 | 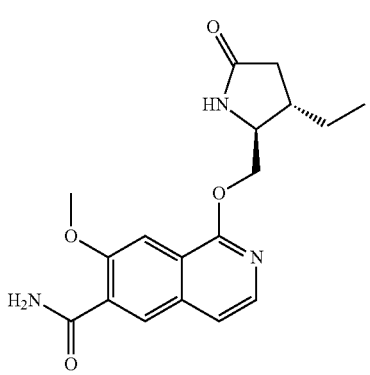 [SMILES: CC[C@H]1CC(=O)N[C@@H]1COc1nccc2cc(C(N)=O)c(OC)cc12]<br>Chiral | P1 | L46 | | 2, 7 | 344 | $^1$H NMR (400 MHz, dmso-d$_6$) δ 8.04 (s, 1 H), 8.01 (s, 1 H), 7.75-7.79 (m, 2 H), 7.60 (s, 1 H), 7.52 (s, 1 H), 7.31-7.32 (m, 1 H), 4.37-4.48 (m, 1 H), 4.17-4.22 (m, 1 H), 3.87 (s, 3 H), 3.55-3.58 (m, 1 H), 2.52-2.55 (m, 1 H), 1.97-2.03 (m, 1 H), 1.77-1.82 (m, 1 H), 1.46-1.50 (m, 1 H), 1.34-1.35 (m, 1 H), 0.79-0.83 (m, 3 H) |
| 245 | 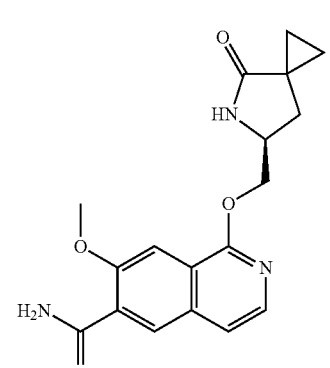<br>Chiral | P1 | L27 | | 2, 7 | 342 | $^1$H NMR (400 MHz, dmso-d$_6$) δ 8.22 (s, 1 H), 8.15 (s, 1 H), 7.90 (d, 1 H), 7.85 (br. s, 1 H), 7.70 (br. s, 1 H), 7.65 (s, 1 H), 7.42 (d, 1 H), 4.52-4.55 (m, 1 H), 4.29-4.33 (m, 1 H), 4.12 (m, 1 H), 3.99 (s, 3 H), 2.38-2.41 (m, 1 H), 1.97-2.01 (m, 1 H), 0.86 (m, 2 H), 0.75 (m, 2 H) |

TABLE 1-continued
| Ex. | Structure | Reactant A | Reactant B | Source | Methods | MH+ | Characterization |
|---|---|---|---|---|---|---|---|
| 246 | 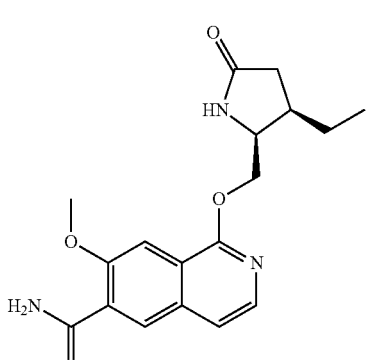<br>Chiral | P1 | L47 | | 3, 7 | 344 | $^1$H NMR (400 MHz, dmso-d$_6$) δ 8.17 (s, 1 H), 8.06 (s, 1 H), 7.86-7.92 (m, 2 H), 7.73 (s, 1 H), 7.57 (s, 1 H), 7.43-7.45 (m, 1 H), 4.45 (d, 2 H), 3.99 (s, 3 H), 3.96-3.98 (m, 1 H), 2.34-2.12 (m, 3 H), 1.55-1.64 (m, 1 H), 1.35-1.45 (m, 1 H), 0.92-0.95 (m, 3 H) |
| 247 | 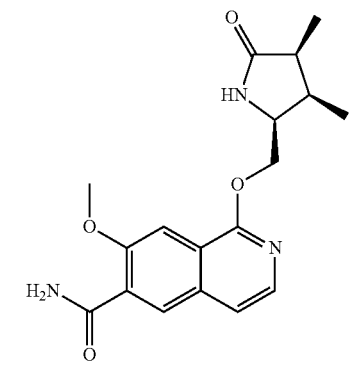<br>Chiral | P1 | L48 | | 2, 7, HPLC | 344 | $^1$H NMR (400 MHz, CD$_3$OD) δ 8.22 (s, 1 H), 7.79-7.80 (m, 1 H), 7.64 (s, 1 H), 7.24-7.25 (m, 1 H), 4.53-4.54 (m, 1 H), 4.39-4.41 (m, 1 H), 4.09-4.11 (m, 1 H), 3.99 (s, 3 H), 2.59-2.78 (m, 2 H), 1.05-1.07 (m, 3 H), 0.93-0.95 (m, 3 H) |
| 248 | 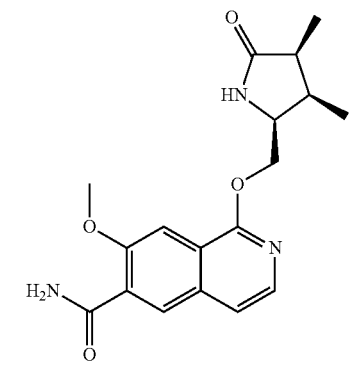<br>Chiral | P1 | L48 | | 2, 7, HPLC | 344 | $^1$H NMR (400 MHz, CD$_3$OD) δ 8.24 (s, 1 H), 7.79-7.81 (m, 1 H), 7.53 (s, 1 H), 7.25-7.27 (m, 1 H), 4.46-4.53 (m, 2 H), 3.96 (s, 3 H), 3.89-3.91 (m, 1 H), 2.29-2.33 (m, 2 H), 1.10-1.13 (m, 6 H) |

TABLE 1-continued
| Ex. | Structure | Reactant A | Reactant B | Source | Methods | MH+ | Characterization |
|---|---|---|---|---|---|---|---|
| 249 | 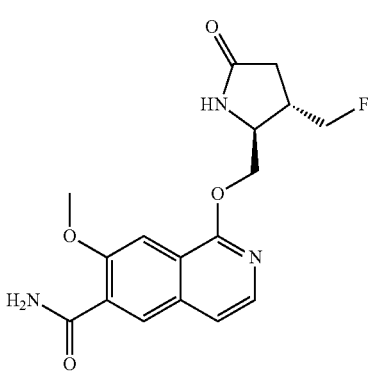 [SMILES: COc1cc2c(OC[C@H]3NC(=O)C[C@@H]3CF)nccc2cc1C(N)=O]<br>Chiral | P1 | L49 | | 2, 7 | 348 | ¹H NMR (400 MHz, CD₃OD) δ 8.38 (s, 1 H), 7.91 (d, 1 H), 7.78 (s, 1 H), 7.48 (d, 1 H), 4.62-4.66 (m, 3 H), 4.51-4.55 (m, 1 H), 4.13-4.15 (m, 1 H), 4.11 (s, 3 H), 2.83-2.96 (m, 1 H), 2.68-2.78 (m, 1 H), 2.27-2.32 (m, 1 H). |
| 250 | 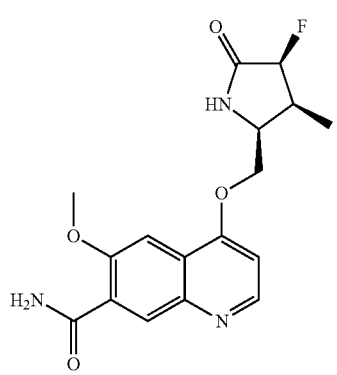 [SMILES: COc1cc2c(OC[C@H]3NC(=O)[C@@H](F)[C@H]3C)ccnc2cc1C(N)=O]<br>Chiral | P16 | L38 | | 3, 7 | 348 | ¹H NMR (400 MHz, dmso-d₆) δ 10.18 (s, 1 H), 8.76 (s, 1 H), 8.63 (d, 1 H), 7.81 (br. s., 1 H), 7.60-7.71 (m, 2 H), 7.09 (d, 1 H), 4.99 (d, 1 H), 4.86 (d, 1 H), 4.30 (dd, 1 H), 4.02-4.19 (m, 2 H), 3.96 (s, 3 H), 2.76-2.99 (m, 1 H), 1.09 (d, 3 H) |
| 251 | 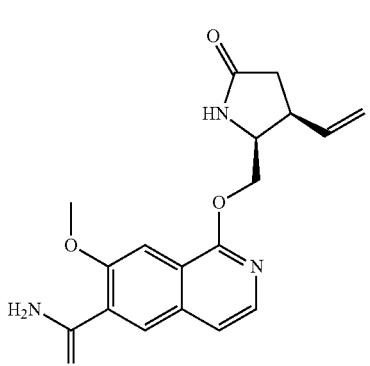<br>Chiral | P1 | L50 | | 3, 7 | 342 | ¹H NMR (600 MHz, dmso-d₆) δ 8.16 (s, 1 H) 8.13 (s, 1 H) 7.90 (d, 1 H) 7.83 (br. s., 1 H) 7.67-7.71 (m, 1 H) 7.58 (s, 1 H) 7.42 (d, 1 H) 5.94 (ddd, 1 H) 5.20 (d, 1 H) 5.11 (d, 1 H) 4.40-4.46 (m, 1 H) 4.30-4.38 (m, 1 H) 4.01-4.09 (m, 1 H) 3.32-3.41 (m, 1 H) 2.37-2.47 (m, 1 H) 2.27-2.36 (m, 1 H) |

TABLE 1-continued
| Ex. | Structure | Reactant A | Reactant B | Source | Methods | MH+ | Characterization |
|---|---|---|---|---|---|---|---|
| 252 | 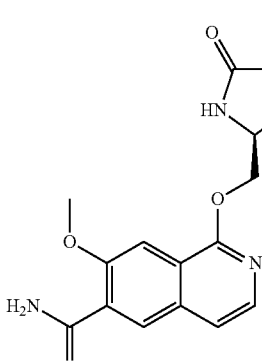 Chiral | P1 | L2 | | 2, 7, HPLC | 334 | $^1$H NMR (400 MHz, dmso-d$_6$) δ 8.90 (s, 1 H), 8.35 (s, 1 H), 8.09 (d, 1 H), 8.05 (br, s, 1 H), 7.90 (br. s, 1 H), 7.81 (s, 1 H), 7.63 (d, 1 H), 5.25-5.42 (m, 1 H), 4.77 (dd, 1 H), 4.43-4.48 (m, 1 H), 4.23 (m, 1 H), 4.16 (s, 3 H), 2.85-3.00 (m, 1 H), 2.19-2.32 (m, 1 H) |
| 253 | 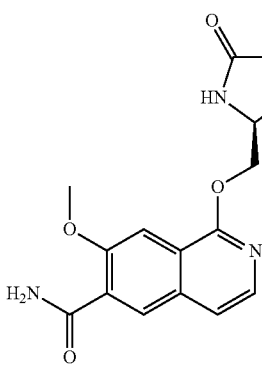 Chiral | P1 | L2 | | 2, 7, HPLC | 334 | $^1$H NMR (400 MHz, dmso-d$_6$) δ 9.01 (s, 1 H), 8.36-8.38 (m, 1 H), 8.06-8.12 (m, 2 H), 7.92 (br. s, 1 H), 7.77-7.79 (m, 1 H), 7.65-7.66 (m, 1 H), 5.42-5.57 (m, 1 H), 4.69-4.71 (m, 1 H), 4.50-4.55 (m, 1 H), 4.35 (m, 1 H), 4.18-4.20 (m, 3 H), 2.53-2.62 (m, 2 H) |
| 254 | 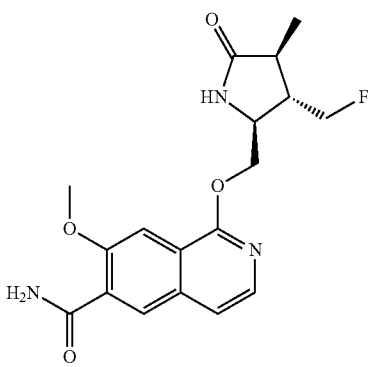 [SMILES: COc1cc2c(OC[C@H]3NC(=O)[C@@H](C)[C@@H]3CF)nccc2cc1C(N)=O] Chiral | P1 | L52 | | 2, 7, HPLC | 362 | $^1$H NMR (400 MHz, CD$_3$OD) δ 8.32 (s, 1 H), 7.89 (d, 1 H), 7.73 (s, 1 H), 7.36 (d, 1 H), 4.66-4.73 (m, 2 H), 4.58-4.62 (m, 1 H), 4.45-4.49 (m, 1 H), 4.08 (s, 3 H), 4.01-4.07 (m, 1 H), 2.43-2.49 (m, 1 H), 2.32-2.40 (m, 1 H), 1.29 (d, 3 H) |

| Ex. | Structure | Reactant A | Reactant B | Source | Methods | MH+ | Characterization |
|---|---|---|---|---|---|---|---|
| 255 | (Chiral structure) | P1 | 66673-40-3 | commercial | 3, 7 | 316 | ¹H NMR (400 MHz, CD₃OD) δ 8.36 (s, 1 H), 7.92 (d, 1 H), 7.74 (s, 1 H), 7.38 (d, 1 H), 4.55-4.66 (m, 1 H), 4.49 (dd, 1 H), 4.20-4.31 (m, 1 H), 4.11 (s, 3 H), 2.36-2.63 (m, 3 H), 2.05-2.19 (m, 1 H) |
| 256 | (Chiral structure) | P1 | L8 | | 3, 7 | 362 | ¹H NMR (400 MHz, dmso-d₆) δ 8.92 (s, 1 H), 8.18 (s, 1 H), 7.92 (d, 1 H), 7.87 (br. s., 1 H), 7.73 (br. s., 1 H), 7.66 (s, 1 H), 7.46 (d, 1 H), 4.63 (dd, 1 H), 4.22-4.30 (m, 1 H), 4.12-4.22 (m, 1 H), 2.39-2.50 (m, 1 H), 2.09-2.26 (m, 1 H), 1.95 (ddd, 1 H), 1.62-1.82 (m, 1 H), 0.98 (t, 3 H) |
| 257 | (Chiral structure) | P1 | L7 | | 3, 7 | 362 | ¹H NMR (400 MHz, dmso-d₆) δ 8.82 (s, 1 H), 8.18 (s, 1 H), 7.92 (d, 1 H), 7.86 (br. s., 1 H), 7.72 (s, 2 H), 7.45 (d, 1 H), 4.60 (dd, 1 H), 4.27 (dd, 1 H), 3.90-4.09 (m, 4 H), 2.59 (td, 1 H), 2.12-2.27 (m, 1 H), 1.92 (td, 1 H), 1.66-1.81 (m, 1 H), 0.97 (t, 3 H) |
| 258 | (structure) | P1 | L28 | | 3, 7 | 406 | ¹H NMR (600 MHz, dmso-d₆) δ 8.11-8.22 (m, 2 H), 7.87 (d, 1 H), 7.81 (br. s., 1 H), 7.65 (br. s., 1 H), 7.58 (s, 1 H), 7.41 (d, 1 H), 7.16-7.32 (m, 5 H), 4.46 (dd, 1 H), 4.28 (dd, 1 H), 3.93-4.01 (m, 3 H), 3.86-3.93 (m, 1 H), 3.07 (dd, 1 H), 2.83 (dd, 1 H), 2.61 (dd, 1 H), 1.99 (dd, 2 H) |

TABLE 1-continued
| Ex. | Structure | Reactant A | Reactant B | Source | Methods | MH+ | Characterization |
|---|---|---|---|---|---|---|---|
| 259 | 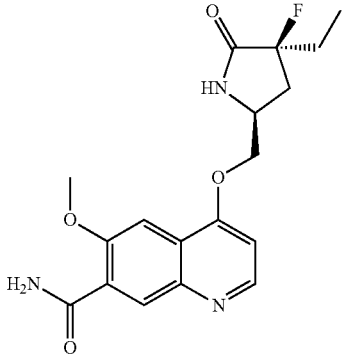 [SMILES: CC[C@]1(F)C[C@@H](COc2ccnc3cc(C(N)=O)c(OC)cc23)NC1=O] Chiral | P16 | L7 | | 3, 7 | 362 | ¹H NMR (500 MHz, CD₃OD) δ 8.63 (d, 1 H), 8.50 (s, 1 H), 7.80 (s, 1 H), 7.05 (d, 1 H), 4.42 (dd, 1 H), 4.28 (dd, 1 H), 4.19 (dt, 1 H), 4.08 (s, 3 H), 2.68-2.82 (m, 1 H), 2.37-2.50 (m, 1 H), 2.00-2.14 (m, 1 H), 1.80-1.96 (m, 1 H), 1.09 (t, 3 H) |
| 260 |  Chiral | P16 | L8 | | 3, 7 | 362 | ¹H NMR (500 MHz, CD₃OD) δ 8.62 (d, 1 H), 8.48 (s, 1 H), 7.68 (s, 1 H), 7.06 (d, 1 H), 4.32-4.46 (m, 2 H), 4.24 (dd, 1 H), 4.08 (s, 3 H), 2.53-2.68 (m, 1 H), 2.21-2.36 (m, 1 H), 2.09 (ddd, 1 H), 1.74-1.90 (m, 1 H), 1.07 (t, 3 H) |
| 261 | 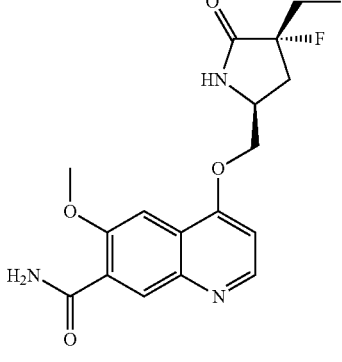 Chiral | P1 | L24 | | 3, 7 | 366 | ¹H NMR (400 MHz, dmso-d₆) δ 9.16 (s, 1 H), 8.19 (s, 1 H), 7.92 (d, 1 H), 7.86 (br. s., 1 H), 7.71 (br. s., 1 H), 7.66 (s, 1 H), 7.46 (d, 1 H), 4.78-4.90 (m, 1 H), 4.61-4.77 (m, 2 H), 4.20-4.36 (m, 2 H), 4.00 (s, 3 H), 2.55-2.67 (m, 1 H), 2.35-2.49 (m, 1 H) |

TABLE 1-continued

| Ex. | Structure | Reactant A | Reactant B | Source | Methods | MH+ | Characterization |
|---|---|---|---|---|---|---|---|
| 262 | Chiral | P16 | 17342-08-4 | commercial | 3, 7 | 316 | ¹H NMR (500 MHz, dmso-d₆) δ 8.64 (d, 1 H), 8.20 (s, 1 H), 8.16 (s, 1 H), 7.84 (br. s., 1 H), 7.68 (br. s., 1 H), 7.58 (s, 1 H), 7.04 (d, 1 H), 4.26 (dd, 1 H), 4.15 (dd, 1 H), 4.05-4.12 (m, 1 H), 4.00 (s, 3 H), 2.17-2.40 (m, 3 H), 1.89-1.97 (m, 1 H) |
| 263 | Chiral | P1 | L73 | | 3, 7 | 356 | ¹H NMR (500 MHz, CD₃OD) δ 8.35 (s, 1 H), 7.91 (d, 1 H), 7.76 (s, 1 H), 7.37 (d, 1 H), 4.61 (dd, 1 H), 4.55 (dd, 1 H), 4.11 (s, 3 H), 3.94 (s, 1 H), 2.68 (s, 1 H), 1.91 (d, 1 H), 1.86 (dd, 1 H), 1.24 (s, 3 H), 1.21 (s, 3 H) |
| 264 | Chiral | P1 | L72 | | 3, 7 | 328 | ¹H NMR (400 MHz, dmso-d₆) δ 8.18 (s, 1 H), 7.92 (d, 1 H), 7.86 (br. s., 1 H), 7.71 (br. s., 1 H), 7.64 (s, 2 H), 7.45 (d, 1 H), 4.49 (dd, 1 H), 4.41 (dd, 1 H), 4.01 (s, 3 H), 3.90 (t, 1 H), 1.92-2.05 (m, 1 H), 1.78 (br. s., 1 H), 1.10 (td, 1 H), 0.60 (q, 1 H) |

TABLE 1-continued

| Ex. | Structure | Reactant A | Reactant B | Source | Methods | MH+ | Characterization |
|---|---|---|---|---|---|---|---|
| 265 | (structure) | P1 | 1004-59- | Ref. 33 | 1, 7 | 346 | Rt = 2.037 min; method PF-AB01 |
| 266 | (structure) | P1 | 29-8-2 | Ref. 34 | 1, 7 | 332 | Rt = 2.043 min; method PF-AB01 |
| 267 | (structure) Chiral | P1 | L15 | | 3, 7 | 398 | $^1$H NMR (400 MHz, dmso-d$_6$) δ 8.50 (br. s., 1 H), 8.23 (s, 1 H), 7.97 (d, 1 H), 7.90 (br. s., 1 H), 7.76 (br. s., 1 H), 7.63 (s, 1 H), 7.50 (d, 1 H), 4.60 (d, 1 H), 4.45 (d, 1 H), 4.08 (br. s., 1 H), 4.03 (s, 3 H), 2.93 (d, 1 H), 2.75 (br. s., 1 H), 2.37 (d, 2 H), 2.25 (br. s., 1 H) |
| 268 | (structure) Chiral | P16 | L10 | | 3, 7 | 348 | $^1$H NMR (400 MHz, dmso-d$_6$) δ 8.83 (s, 1 H), 8.65 (d, 1 H), 8.20 (s, 1 H), 7.85 (br. s., 1 H), 7.69 (br. s., 1 H), 7.67 (s, 1 H), 7.05 (d, 1 H), 4.35 (dd, 1 H), 4.03-4.17 (m, 2 H), 3.99 (s, 3 H), 2.54-2.63 (m, 1 H), 2.23-2.38 (m, 1 H), 1.52 (d, 3H) |

TABLE 1-continued
| Ex. | Structure | Reactant A | Reactant B | Source | Methods | MH+ | Characterization |
|---|---|---|---|---|---|---|---|
| 269 | 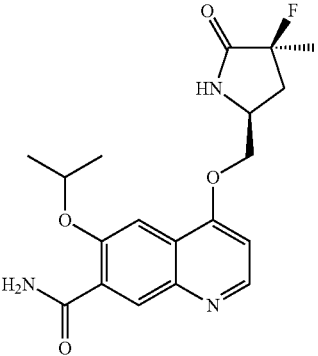 [SMILES: CC(C)Oc1cc2c(OC[C@@H]3C[C@](C)(F)C(=O)N3)ccnc2cc1C(N)=O] Chiral | P15 | L10 | | 3, 7 | 376 | 1H NMR (400 MHz, dmso-d6) δ 8.78 (s, 1 H), 8.64 (d, 1 H), 8.24 (s, 1 H), 7.63-7.79 (m, 3 H), 7.04 (d, 1 H), 4.90 (dt, 1 H), 4.34 (dd, 1 H), 3.99-4.20 (m, 3 H), 3.18 (d, 1 H), 2.54-2.62 (m, 1 H), 2.23-2.38 (m, 1 H), 1.52 (d, 1 H), 1.39 (d, 3 H), 1.41 (d, 3 H) |
| 270 | 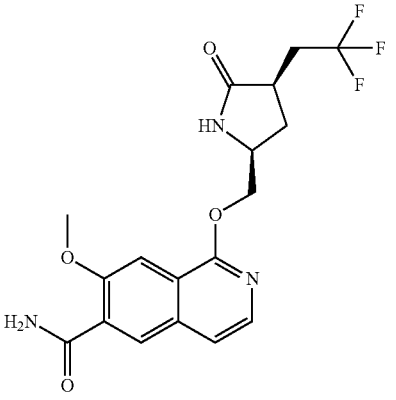 [SMILES: COc1cc2c(OC[C@@H]3C[C@H](CC(F)(F)F)C(=O)N3)nccc2cc1C(N)=O] Chiral | P1 | L16 | | 3, 7 | 398 | 1H NMR (400 MHz, CDCl3) δ 8.68 (s, 1 H), 7.93 (d, 1 H), 7.80 (br. s., 1 H), 7.56 (s, 1 H), 7.33 (d, 1 H), 6.39 (br. s., 1 H), 5.94 (br. s., 1 H), 4.78 (dd, 1 H), 4.39 (dd, 1 H), 4.20 (d, 1 H), 4.11 (s, 3 H), 2.76-3.01 (m, 2 H), 2.66-2.76 (m, 1 H), 2.10 (dt, 1 H), 1.69-1.82 (m, 1 H) |
| 271 | 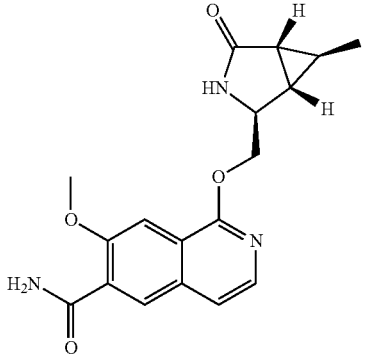 [SMILES: COc1cc2c(OC[C@H]3NC(=O)[C@@H]4[C@@H](C)[C@@H]43)nccc2cc1C(N)=O] Chiral | P1 | L74 | | 3, 7 | 342 | 1H NMR (400 MHz, dmso-d6) δ 8.18 (s, 1 H), 7.92 (d, 1 H), 7.86 (br. s., 1 H), 7.71 (s, 1 H), 7.64 (s, 1 H), 7.62 (s, 1 H), 7.45 (d, 1 H), 4.47 (dd, 1 H), 4.36 (dd, 1 H), 4.01 (s, 3 H), 3.87-3.94 (m, 1 H), 1.73-1.82 (m, 1 H), 1.59 (d, 1 H), 1.10 (d, 3 H), 0.98-1.06 (m, 1 H) |

US 10,793,579 B2
TABLE 1-continued
| Ex. | Structure | Reactant A | Reactant B | Source | Methods | MH+ | Characterization |
|---|---|---|---|---|---|---|---|
| 272 | 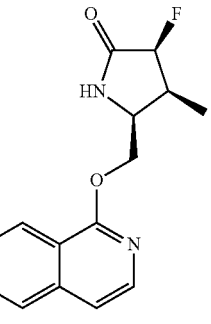 Chiral | P1 | L38 | | 3 | 330 | ¹H NMR (600 MHz, dmso-d₆) δ 8.72 (s, 1 H), 8.49 (s, 1 H), 7.98 (d, 1 H), 7.78 (s, 1 H), 7.41 (d, 1 H), 4.92 (dd, 1 H), 4.58 (dd, 1 H), 4.28 (dd, 1 H), 3.99-4.08 (m, 4 H), 2.79-2.92 (m, 1 H), 1.08 (dd, 3 H) |
| 273 | 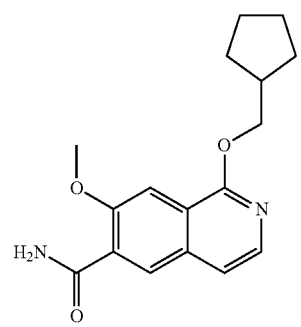 [SMILES: COc1cc2c(OCC3CCCC3)nccc2cc1C(N)=O] | P1 | 3637-61-4 | commercial | 3, 7 | 301 | ¹H NMR (400 MHz, dmso-d₆) δ 8.16 (s, 1 H), 7.89 (d, 1 H), 7.82 (br. s., 1 H), 7.68 (br. s., 1 H), 7.53 (s, 1 H), 7.39 (d, 1 H), 4.37 (d, 2 H), 3.97 (s, 3 H), 2.42-2.50 (m, 1 H), 1.80-1.85 (m, 2 H), 1.58-1.66 (m, 4 H), 1.40-1.46 (m, 2 H) |
| 274 | 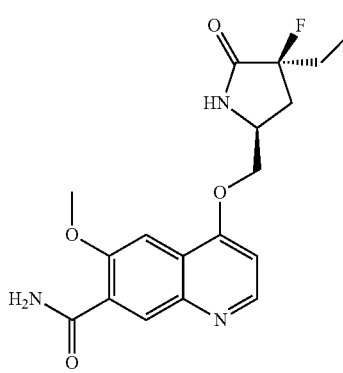 Chiral | P16 | L29 | | 3, 7 | 380 | ¹H NMR (600 MHz, dmso-d₆) δ 8.88 (s, 1 H), 8.59-8.65 (m, 1 H), 8.17-8.22 (m, 1 H), 7.79 (br. s., 1 H), 7.65 (s, 1 H), 7.61 (br. s., 1 H), 7.00-7.05 (m, 1 H), 4.60-4.76 (m, 2 H), 4.30-4.39 (m, 1 H), 4.04-4.20 (m, 3 H), 3.94-4.00 (m, 3 H), 2.61-2.73 (m, 1 H), 2.13-2.36 (m, 3 H) |
| 275 | 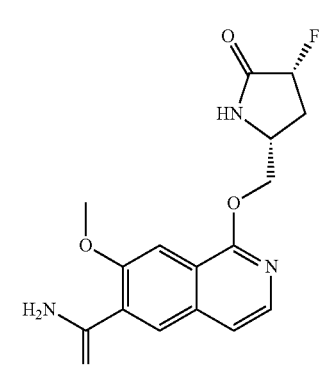 Chiral | P1 | L3 | | 3, 7 | 334 | ¹H NMR (400 MHz, dmso-d₆) δ 8.77 (s, 1 H), 8.18 (s, 1 H), 7.92 (d, 1 H), 7.86 (br. s., 1 H), 7.70 (s, 2 H), 7.45 (d, 1 H), 5.16 (ddd, 1 H), 4.61 (dd, 1 H), 4.28 (dd, 1 H), 4.04 (br. s., 1 H), 3.98 (s, 3 H), 2.65-2.84 (m, 1 H), 1.98-2.18 (m, 1 H) |

TABLE 1-continued
| Ex. | Structure | Reactant A | Reactant B | Source | Methods | MH+ | Characterization |
|---|---|---|---|---|---|---|---|
| 276 | 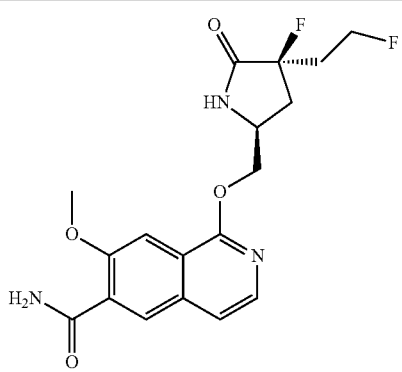 [SMILES: COc1cc2c(OC[C@@H]3C[C@@](F)(CCF)C(=O)N3)nccc2cc1C(N)=O] Chiral | P1 | L29 | | 3, 7 | 380 | $^1$H NMR (400 MHz, dmso-d$_6$) δ 8.95 (s, 1 H), 8.18 (s, 1 H), 7.92 (d, 1 H), 7.86 (br. s., 1 H), 7.72 (s, 2 H), 7.45 (d, 1 H), 4.70-4.85 (m, 1 H), 4.54-4.70 (m, 2 H), 4.28 (dd, 1 H), 4.02-4.13 (m, 1 H), 3.99 (s, 3 H), 2.58-2.75 (m, 1 H), 2.12-2.41 (m, 3 H) |
| 277 | 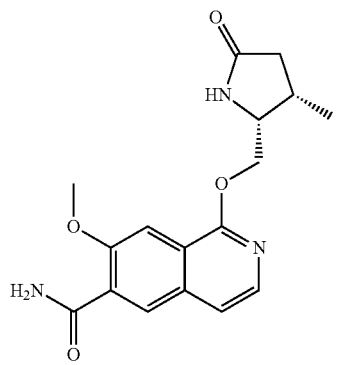 [SMILES: COc1cc2c(OC[C@@H]3NC(=O)C[C@@H]3C)nccc2cc1C(N)=O] Chiral | P1 | L35 | | 3, 7 | 330 | $^1$H NMR (400 MHz, dmso-d$_6$) δ 8.18 (s, 1 H), 8.03 (s, 1 H), 7.93 (d, 1 H), 7.85 (br. s., 1 H), 7.71 (br. s., 1 H), 7.60 (s, 1 H), 7.45 (d, 1 H), 4.39-4.55 (m, 2 H), 3.99 (s, 3 H), 3.91-3.97 (m, 1 H), 2.65-2.78 (m, 1 H), 2.34 (dd, 1 H), 2.11 (dd, 1 H), 1.10 (d, 3 H) |
| 278 | 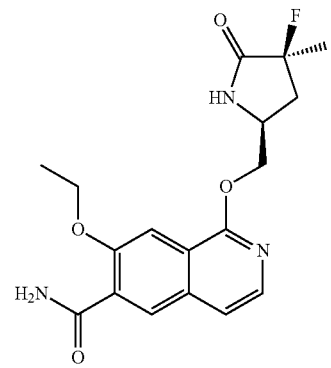 [SMILES: CCOc1cc2c(OC[C@@H]3C[C@](C)(F)C(=O)N3)nccc2cc1C(N)=O] Chiral | P7 | L10 | | 3, 7 | 362 | $^1$H NMR (400 MHz, dmso-d$_6$) δ 8.79 (s, 1 H), 8.17 (s, 1 H), 7.89 (d, 1 H), 7.78 (br. s., 1 H), 7.69 (s, 2 H), 7.43 (d, 1 H), 4.60 (dd, 1 H), 4.21-4.31 (m, 3 H), 3.99-4.00 (m, 1 H), 2.21-2.33 (m, 2 H), 1.43-1.52 (m, 6 H) |

TABLE 1-continued
| Ex. | Structure | Reactant A | Reactant B | Source | Methods | MH+ | Characterization |
|---|---|---|---|---|---|---|---|
| 279 | 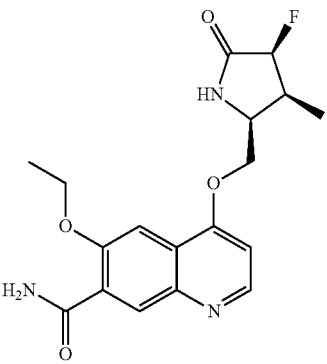 Chiral | P17 | L38 | | 3, 7 | 362 | $^1$H NMR (600 MHz, dmso-$d_6$) δ 8.96 (d, 1 H) 8.78 (s, 1 H) 8.30 (s, 1 H) 7.84 (br. s., 1 H) 7.82 (br. s., 1 H) 7.76 (s, 1 H) 7.48 (d, 1 H) 4.92 (dd, 1 H) 4.51 (dd, 1 H) 4.29-4.36 (m, 2 H) 4.23-4.29 (m, 1 H) 4.10-4.15 (m, 1 H) 2.85-2.95 (m, 1 H) 1.45 (t, 3 H) 1.10 (dd, 3 H) |
| 280 | 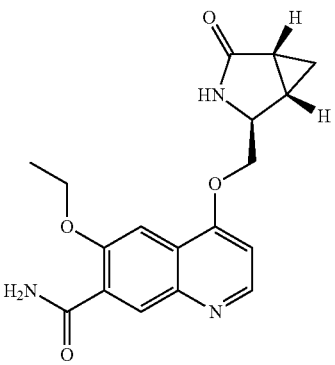 [SMILES: CCOc1cc2c(OC[C@H]3NC(=O)[C@@H]4C[C@H]34)ccnc2cc1C(N)=O] Chiral | P17 | L72 | | 3, 7, HPLC | 342 | $^1$H NMR (600 MHz, dmso-$d_6$) δ 8.98 (br. s., 1 H), 8.47 (d, 1 H), 8.32 (s, 1 H), 8.16 (s, 1 H), 6.79 (d, 1 H), 5.08 (br. s., 2 H), 4.37 (q, 2 H), 4.10 (br. s., 1 H), 3.83 (dd, 1 H), 3.69 (dd, 1 H), 1.80-1.88 (m, 1 H), 1.74-1.79 (m, 1 H), 1.48 (t, 3 H), 1.26 (td, 1 H), 1.05-1.11 (m, 1 H) |
| 281 | 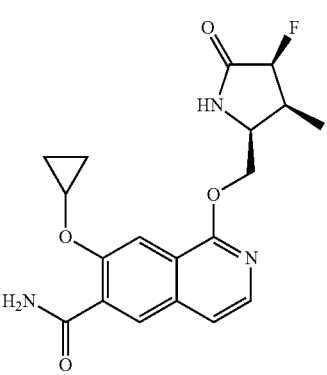 [SMILES: C[C@@H]1[C@H](F)C(=O)N[C@@H]1COc1nccc2cc(C(N)=O)c(OC3CC3)cc12] Chiral | P21 | L38 | | 3, 7 | 374 | $^1$H NMR (400 MHz, dmso-$d_6$) δ 8.67 (s, 1 H), 8.12 (s, 1 H), 8.06 (s, 1 H), 7.93 (d, 1 H), 7.66 (br. s., 2 H), 7.44 (d, 1 H), 4.99 (dd, 1 H), 4.50 (dd, 1 H), 4.42 (dd, 1 H), 3.96-4.12 (m, 2 H), 2.78-2.98 (m, 1 H), 1.11 (dd, 3 H), 0.89-1.02 (m, 2 H), 0.80-0.89 (m, 1 H), 0.69-0.80 (m, 1 H) |

TABLE 1-continued

| Ex. | Structure | Reactant A | Reactant B | Source | Methods | MH+ | Characterization |
|---|---|---|---|---|---|---|---|
| 282 | Chiral | P7 | L72 | | 3, 7 | 342 | ¹H NMR (400 MHz, dmso-d₆) δ 8.19 (s, 1 H), 7.91 (d, 1 H), 7.80 (br. s., 1 H), 7.73 (br. s., 1 H), 7.63 (s, 2 H), 7.44 (d, 1 H), 4.49 (dd, 1 H), 4.39 (dd, 1 H), 4.18-4.35 (m, 2 H), 3.89 (t, 1 H), 1.94-2.05 (m, 1 H), 1.77 (br. s., 1 H), 1.47 (t, 3 H), 1.10 (td, 1 H), 0.60 (q, 1 H) |
| 283 | Chiral | P7 | L38 | | 3, 7 | 361 | ¹H NMR (400 MHz, dmso-d₆) δ 8.77 (s, 1 H), 8.18 (s, 1 H), 7.91 (d, 1 H), 7.79 (br. s., 1 H), 7.72 (s, 2 H), 7.44 (d, 1 H), 4.95 (dd, 1 H), 4.58 (dd, 1 H), 4.18-4.37 (m, 3 H), 4.05 (br. s., 1 H), 2.78-2.98 (m, 1 H), 1.46 (t, 3 H), 1.05-1.16 (m, 3 H) |
| 284 | Chiral | P1 | L31 | | 3, 7 | 417 | ¹H NMR (400 MHz, dmso-d₆) δ 8.88 (s, 1 H), 8.16 (s, 1 H), 7.90 (d, 1 H), 7.84 (br. s., 1 H), 7.70 (s, 2 H), 7.43 (d, 1 H), 4.57 (dd, 1 H), 4.25 (dd, 1 H), 3.87-3.96 (m, 6 H), 2.62-2.68 (m, 1 H), 2.07-2.19 (m, 2 H), 1.70 (d, 1 H), 1.33-1.43 (m, 3 H) |

TABLE 1-continued

| Ex. | Structure | Reactant A | Reactant B | Source | Methods | MH+ | Characterization |
|---|---|---|---|---|---|---|---|
| 285 | Chiral | P1 | L75 | | 3, 7 | 341 | ¹H NMR (400 MHz, dmso-d₆) δ 8.18 (s, 1 H), 7.92 (d, 1 H), 7.86 (br. s., 1 H), 7.83 (s, 1 H), 7.71 (br. s., 1 H), 7.66 (s, 1 H), 7.45 (d, 1 H), 4.56 (dd, 1 H), 4.40 (dd, 1 H), 4.01 (s, 3 H), 3.74 (br. s., 1 H), 1.83-1.98 (m, 2 H), 1.31-1.42 (m, 1 H), 1.06 (d, 3 H) |
| 286 | Chiral | P1 | L30 | | 3, 7 | 399 | ¹H NMR (400 MHz, dmso-d₆) δ 8.19 (s, 1 H), 8.16 (s, 1 H), 7.89 (d, 1 H), 7.85 (br. s., 1 H), 7.70 (br. s., 1 H), 7.62 (s, 1 H), 7.42 (d, 1 H), 4.47 (dd, 1 H), 4.28 (dd, 1 H), 3.95-3.99 (m, 4 H), 3.85 (dd, 2 H) 3.24-3.29 (m, 2 H), 2.02-2.14 (m, 1 H) 1.93-2.02 (m, 1 H), 1.82-1.93 (m, 1 H), 1.72 (d, 1 H), 1.45 (dq, 1 H), 1.20-1.38 (m, 3 H) |
| 287 | Chiral | P17 | L10 | | 3, 7 | 361 | ¹H NMR (400 MHz, dmso-d₆) δ 8.82 (s, 1 H), 8.63 (d, 1 H), 8.20 (s, 1 H), 7.78 (br. s., 1 H), 7.70 (br. s., 1 H), 7.64 (s, 1 H), 7.03 (d, 1 H), 4.29-4.19 (m, 3 H), 4.11-4.05 (m, 2 H), 2.59-2.50 (m, 1 H), 2.29-2.22 (m, 1 H), 1.53-1.43 (m, 6 H) |

TABLE 1-continued
| Ex. | Structure | Reactant A | Reactant B | Source | Methods | MH+ | Characterization |
|---|---|---|---|---|---|---|---|
| 288 | 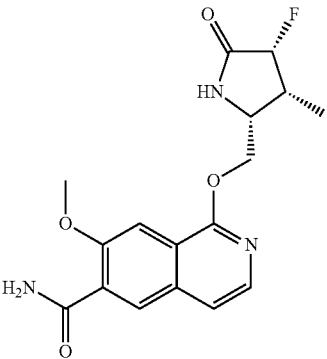 [SMILES: COc1cc2c(OC[C@@H]3NC(=O)[C@H](F)[C@@H]3C)nccc2cc1C(N)=O]<br>Chiral | P1 | L53 | | 3, 7 | 347 | ¹H NMR (400 MHz, dmso-d₆) δ 8.78 (s, 1 H), 8.17 (s, 1 H), 7.92 (d, 1 H), 7.85 (br. s., 1 H), 7.73 (s, 1 H), 7.71 (br. s., 1 H), 7.45 (d, 1 H), 4.95 (dd, 1 H), 4.58 (dd, 1 H), 4.30 (dd, 1 H), 4.03-4.11 (m, 1 H), 3.99 (s, 3 H), 2.79-2.98 (m, 1 H), 1.10 (d, 3 H) |
| 289 | 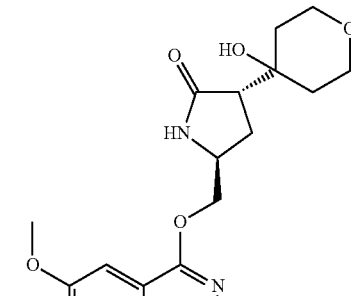<br>Chiral | P1 | L20 | | 3, 7 | 415 | ¹H NMR (400 MHz, dmso-d₆) δ 8.26 (s, 1 H), 8.18 (s, 1 H), 7.92 (d, 1 H), 7.86 (br. s., 1 H), 7.72 (br. s., 1 H), 7.63 (s, 1 H), 7.45 (d, 1 H), 4.66 (s, 1 H), 4.48 (dd, 1 H), 4.32 (dd, 1 H), 4.01 (s, 3 H), 3.97 (br. s., 1 H), 3.59-3.69 (m, 4 H), 2.61 (t, 1 H), 2.33 (dt, 1 H), 1.93-2.04 (m, 2 H), 1.71- 1.78 (m, 1 H), 1.56- 1.68 (m, 1 H), 1.29 (d, 1 H) |
| 290 | 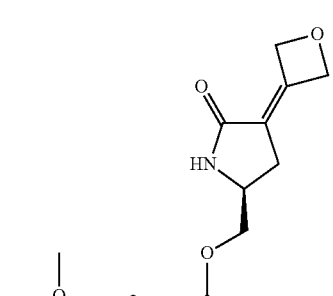<br>Chiral | P1 | L32 | | 3, 7 | 369 | ¹H NMR (400 MHz, dmso-d₆) δ 8.54 (s, 1 H), 8.18 (s, 1 H), 7.91 (d, 1 H), 7.86 (br. s., 1 H), 7.71 (s, 1 H), 7.64 (s, 1 H), 7.45 (d, 1 H), 5.31-5.46 (m, 2 H), 5.15-5.27 (m, 2 H), 4.54 (dd, 1 H), 4.27 (dd, 1 H), 4.15 (d, 1 H), 4.02 (s, 3 H), 2.77-2.91 (m, 1 H) |

TABLE 1-continued

| Ex. | Structure | Reactant A | Reactant B | Source | Methods | MH+ | Characterization |
|---|---|---|---|---|---|---|---|
| 291 | Chiral | P17 | 17342-08-4 | commercial | 3, 7 | 329 | ¹H NMR (400 MHz, dmso-d₆) δ 8.63 (d, 1 H), 8.20 (s, 1 H), 8.15 (s, 1 H), 7.77 (br. s., 1 H), 7.70 (br. s., 1 H), 7.57 (s, 1 H), 7.02 (d, 1 H), 4.28-4.37 (m, 1 H), 4.18-4.28 (m, 2 H), 4.10-4.17 (m, 1 H), 4.03-4.10 (m, 1 H), 2.17-2.40 (m, 3 H), 1.87-1.97 (m, 1 H), 1.45 (t, 3 H) |
| 292 | Chiral | P1 | L33 | | 3, 7 | 377 | ¹H NMR (600 MHz, dmso-d₆) δ 8.80 (s, 1 H), 8.17 (s, 1 H), 7.90 (d, 1 H), 7.80 (br. s., 1 H), 7.69 (s, 1 H), 7.63 (br. s., 1 H), 7.43 (d, 1 H), 4.59 (dd, 1 H), 4.29 (dd, 1 H), 4.03 (d, 1 H), 3.97 (s, 3 H), 3.63 (s, 1 H), 3.61 (d, 1 H), 3.35 (s, 3 H), 2.68-2.77 (m, 1 H), 2.14-2.25 (m, 1 H) |
| 293 | Chiral | P17 | L23 | | 3, 7 | 379 | ¹H NMR (400 MHz, dmso-d₆) δ 9.04 (s, 1 H), 8.64 (d, 1 H), 8.20 (s, 1 H), 7.77 (s, 1 H), 7.70 (s, 1 H), 7.63 (s, 1 H), 7.04 (d, 1 H), 4.63-4.82 (m, 2 H), 4.35-4.37 (m, 1 H), 4.14-4.27 (m, 4 H), 2.72-2.85 (m, 1 H), 2.20-2.35 (m, 1 H), 1.44 (t, 3 H) |

TABLE 1-continued
| Ex. | Structure | Reactant A | Reactant B | Source | Methods | MH+ | Characterization |
|---|---|---|---|---|---|---|---|
| 294 | 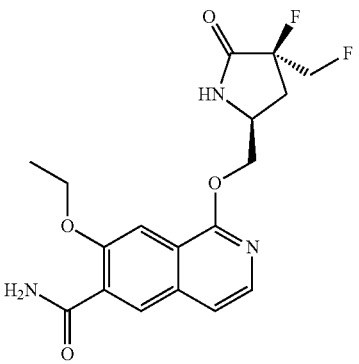 [SMILES: CCOc1cc2c(OC[C@@H]3C[C@@](F)(CF)C(=O)N3)nccc2cc1C(N)=O] Chiral | P7 | L23 | | 3, 7 | 379 | $^1$H NMR (400 MHz, dmso-d$_6$) δ 9.02 (s, 1 H), 8.17 (s, 1 H), 7.90 (d, 1 H), 7.78 (br. s., 1 H), 7.71 (br. s., 1 H), 7.68 (s, 1 H), 7.44 (d, 1 H), 4.69-4.80 (m, 2 H), 4.59-4.65 (m, 2 H), 4.19-4.31 (m, 3 H), 4.10 (br. s., 1 H), 2.70-2.81 (m, 1 H), 2.21-2.28 (m, 1 H), 1.44 (t, 3 H) |
| 295 | 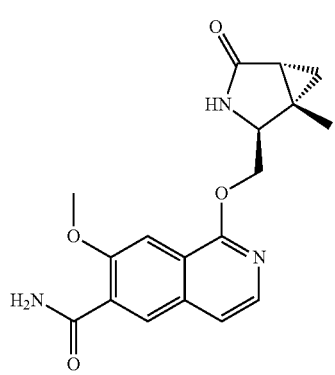 Chiral | P1 | L94 | | 3, 7 | 341 | $^1$H NMR (400 MHz, dmso-d$_6$) δ 8.23 (s, 1 H), 7.98 (d, 1 H), 7.90 (br. s., 1 H), 7.75 (br. s., 1 H), 7.66 (s, 1 H), 7.47-7.54 (m, 2 H), 4.56 (dd, 2 H), 4.05 (s, 3 H), 3.93 (br. s., 1 H), 1.69 (dd, 1 H), 1.35 (s, 3 H), 1.05 (dd, 1 H), 0.84 (t, 1 H) |
| 296 | 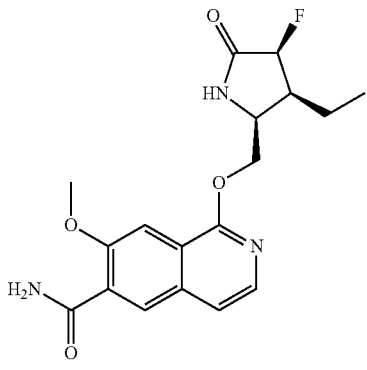 [SMILES: CC[C@@H]1[C@H](F)C(=O)N[C@@H]1COc1nccc2cc(C(N)=O)c(OC)cc12] Chiral | P1 | L54 | | 3, 8 | 361 | $^1$H NMR (400 MHz, dmso-d$_6$) δ 8.87 (s, 1 H), 8.17 (s, 1 H), 7.91 (d, 1 H), 7.85 (br. s., 1 H), 7.75 (s, 1 H), 7.70 (br. s., 1 H), 7.44 (d, 1 H), 4.92 (dd, 1 H), 4.55 (dd, 1 H), 4.27 (dd, 1 H), 4.10 (br. s., 1 H), 3.98 (s, 3 H), 2.55- 2.73 (m, 1 H), 1.52-1.72 (m, 2 H), 1.03 (t, 3 H) |

TABLE 1-continued
| Ex. | Structure | Reactant A | Reactant B | Source | Methods | MH+ | Characterization |
|---|---|---|---|---|---|---|---|
| 297 | 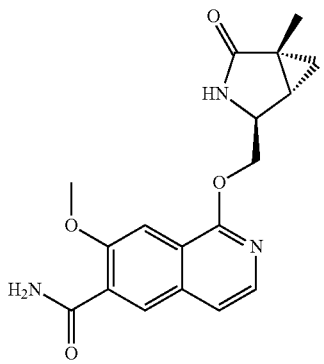 [SMILES: COc1cc2c(OC[C@H]3NC(=O)[C@]4(C)C[C@H]34)nccc2cc1C(N)=O] Chiral | P1 | L91 | | 3, 7 | 341 | ¹H NMR (600 MHz, dmso-d$_6$) δ 8.17 (s, 1 H), 7.90 (d, 1 H), 7.81 (br. s., 1 H), 7.64 (br. s., 1 H), 7.61 (s, 1 H), 7.55 (s, 1 H), 7.42 (d, 1 H), 4.43 (d, 2 H), 3.99 (s, 3 H), 3.79 (t, 1 H), 1.82 (dd, 1 H), 1.23 (s, 3 H), 0.94 (dd, 1 H), 0.66 (t, 1 H) |
| 298 | 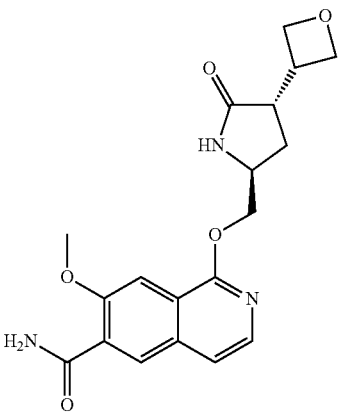 [SMILES: COc1cc2c(OC[C@@H]3C[C@@H](C4COC4)C(=O)N3)nccc2cc1C(N)=O] Chiral | P1 | L34 | | 3, 7 | 371 | Mixture of rotamers (major/minor): ¹H NMR (400 MHz, 27° C., dmso-d$_6$) δ 8.30/8.24 (s, 1 H), 8.16/8.17 (s, 1 H), 7.90 (d, 1 H), 7.85 (br. s., 1 H), 7.70 (br. s., 1 H), 7.66/7.63 (s, 1 H), 7.43 (d, 1 H), 4.30-4.73 (m, 6 H), 4.21 (dd, 1 H), 3.95-4.07 (m, 4 H), 3.09-3.20 (m, 1 H), 2.95-3.05 (m, 1 H), 2.82-2.92 (m, 1 H), 2.45 (~1 H), 2.29-3.35 (m, <1 H), 2.17-2.25 (m, <1 H), 1.93-2.03 (m, <1 H), 1.02-1.13 (m, 1 H). |
| 299 | 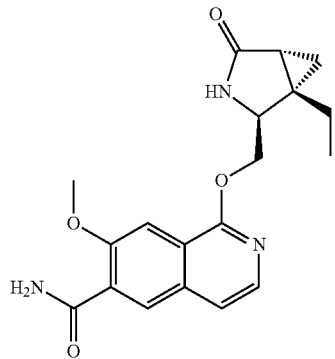 [SMILES: CC[C@]12C[C@H]1C(=O)N[C@@H]2COc1nccc2cc(C(N)=O)c(OC)cc12] Chiral | P1 | L95 | | 3, 7 | 355 | ¹H NMR (400 MHz, dmso-d$_6$) δ 8.18 (s, 1 H), 7.93 (d, 1 H), 7.85 (br. s., 1 H), 7.71 (br. s., 1 H), 7.60 (s, 1 H), 7.49 (s, 1 H), 7.45 (d, 1 H), 4.46-4.59 (m, 2 H), 4.00 (s, 3 H), 3.95 (d, 1 H), 1.97 (dd, 1 H), 1.70 (d, 1 H), 1.15-1.28 (m, 1 H), 0.94-1.05 (m, 4 H), 0.72 (br. s., 1 H) |

TABLE 1-continued
| Ex. | Structure | Reactant A | Reactant B | Source | Methods | MH+ | Characterization |
|---|---|---|---|---|---|---|---|
| 300 | 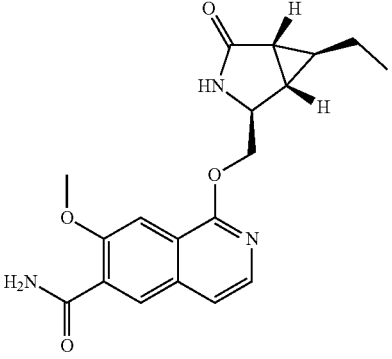 [SMILES: CC[C@@H]1[C@H]2C(=O)N[C@H](COc3nccc4cc(C(N)=O)c(OC)cc34)[C@@H]12] Chiral | P1 | L76 | | 3, 7 | 355 | $^1$H NMR (400 MHz, CDCl$_3$) δ 8.66 (s, 1 H), 7.93 (d, 1 H), 7.82 (br. s., 1 H), 7.60 (s, 1 H), 7.31 (d, 1 H), 5.96 (br. s., 1 H), 5.54 (br. s., 1 H), 4.62 (dd, 1 H), 4.50 (dd, 1 H), 4.12 (s, 3 H), 4.09 (d, 1 H), 1.69-1.78 (m, 2 H), 1.40 (dd, 2 H), 1.22 (t, 1 H), 1.05 (t, 3 H) |
| 301 | 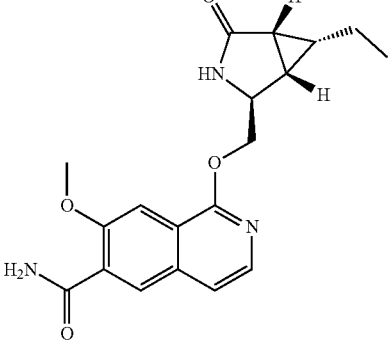 Chiral | P1 | L77 | | 3, 7 | 355 | $^1$H NMR (400 MHz, CDCl$_3$) δ 8.65 (s, 1 H), 7.94 (d, 1 H), 7.80 (br. s., 1 H), 7.62 (s, 1 H), 7.32 (d, 1 H), 6.20 (s, 1 H), 6.12 (br. s., 1 H), 4.69 (dd, 1 H), 4.55 (dd, 1 H), 4.12 (s, 3 H), 3.96 (d, 1 H), 2.04-2.11 (m, 1 H), 1.95-2.02 (m, 1 H), 1.49-1.60 (m, 2 H), 1.33-1.43 (m, 1 H), 1.13 (t, 3 H) |
| 302 | 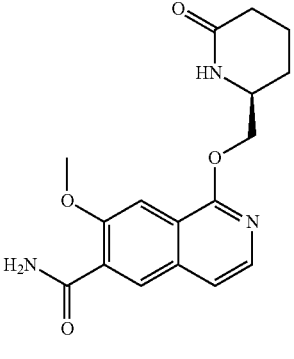 [SMILES: COc1cc2c(OC[C@@H]3CCCC(=O)N3)nccc2cc1C(N)=O] Chiral | P1 | 128726-47-6 | commercial | 3, 7 | 329 | $^1$H NMR (400 MHz, dmso-d$_6$) δ 8.17 (s, 1 H), 7.90 (d, 1 H), 7.84 (br. s., 1 H), 7.66-7.75 (m, 2 H), 7.64 (s, 1 H), 7.43 (d, 1 H), 4.41 (d, 2 H), 3.99 (s, 3 H), 3.79-3.89 (m, 1 H), 2.19 (t, 2 H), 1.81-2.04 (m, 2 H), 1.61-1.76 (m, 2 H) |

TABLE 1-continued

| Ex. | Structure | Reactant A | Reactant B | Source | Methods | MH+ | Characterization |
|---|---|---|---|---|---|---|---|
| 303 | Chiral | P1 | L78 | | 3, 7 | 359 | ¹H NMR (400 MHz, dmso-d₆) δ 8.19 (s, 1 H), 7.92 (d, 1 H), 7.86 (br. s., 1 H), 7.78 (s, 1 H), 7.72 (br. s., 1 H), 7.62 (s, 1 H), 7.45 (d, 1 H), 4.38-4.52 (m, 3 H), 4.31 (ddd, 1 H), 4.01 (s, 3 H), 3.97 (br. s., 1 H), 2.10 (br. s., 1 H), 1.95 (d, 1 H), 1.49 (d, 1 H) |
| 304 | Chiral | P1 | L79 | | 3, 7 | 359 | ¹H NMR (400 MHz, dmso-d₆) δ 8.19 (s, 1 H), 7.92 (d, 1 H), 7.85 (br. s., 1 H), 7.77 (s, 1 H), 7.71 (br. s., 1 H), 7.62 (s, 1 H), 7.45 (d, 1 H), 4.38-4.53 (m, 3 H), 4.31 (ddd, 1 H), 4.01 (s, 3 H), 3.94-3.99 (m, 1 H), 2.08-2.12 (m, 1 H), 1.92-1.97 (m, 1 H), 1.50 (td, 1 H) |
| 305 | Chiral | P1 | L58 | | 3, 7 | 355 | ¹H NMR (400 MHz, dmso-d₆) δ 8.14 (s, 1 H), 8.04 (s, 1 H), 7.89 (d, 1 H), 7.82 (br. s., 1 H), 7.68 (br. s., 1 H), 7.59 (s, 1 H), 7.41 (d, 1 H), 4.52-4.64 (m, 2 H), 3.94-3.99 (m, 4 H), 2.19-2.34 (m, 2 H), 1.85-1.97 (m, 1 H), 0.70-0.83 (m, 1 H), 0.36-0.50 (m, 2 H), 0.09-0.25 (m, 2 H) |
| 306 | 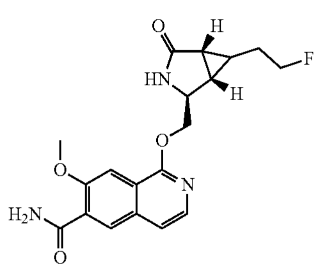 [SMILES: COc1cc2c(OC[C@H]3NC(=O)[C@@H]4C(CCF)[C@@H]43)nccc2cc1C(N)=O] | P1 | L80 | | 3, 7 | 373 | ¹H NMR (400 MHz, dmso-d₆) δ 8.10 (s, 1 H), 7.84 (d, 1 H), 7.81 (s, 1 H), 7.78 (br. s., 1 H), 7.63 (br. s., 1 H), 7.57 (s, 1 H), 7.37 (d, 1 H), 4.52-4.58 (m, 1 H), 4.48 (dd, 1 H), 4.40-4.45 (m, 1 H), 4.32 (dd, 1 H), 3.93 (s, 3 H), 3.72 (t, 2 H), 1.87-1.97 (m, 2 H), 1.54-1.81 (m, 2 H), 1.27-1.39 (m, 1 H) |

TABLE 1-continued
| Ex. | Structure | Reactant A | Reactant B | Source | Methods | MH+ | Characterization |
|---|---|---|---|---|---|---|---|
| 307 | 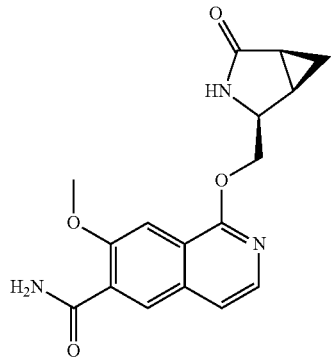 [SMILES: COc1cc2c(OC[C@H]3NC(=O)[C@H]4C[C@H]43)nccc2cc1C(N)=O] Chiral | P1 | L113 | | 3, 7 | 327 | $^1$H NMR (400 MHz, dmso-d$_6$) δ 8.17 (s, 1 H), 7.92 (d, 1 H), 7.86 (br. s., 1 H), 7.79 (s, 1 H), 7.71 (s, 2 H), 7.44 (d, 1 H), 4.63-4.72 (m, 1 H), 4.18-4.29 (m, 2 H), 4.02 (s, 3 H), 2.08-2.15 (m, 1 H), 1.75-1.82 (m, 1 H), 0.97 (td, 1 H), 0.85-0.90 (m, 1 H) |
| 308 | 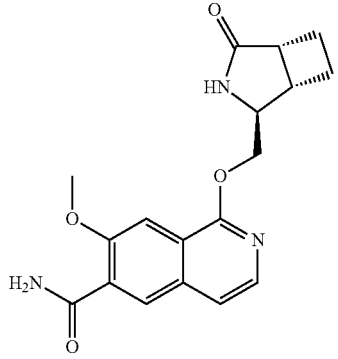 [SMILES: COc1cc2c(OC[C@H]3NC(=O)[C@@H]4CC[C@H]34)nccc2cc1C(N)=O] Chiral | P1 | L97 | | 3, 7 | 341 | $^1$H NMR (400 MHz, dmso-d$_6$) δ 8.18 (s, 2 H), 7.90 (d, 1 H), 7.84 (br. s., 1 H), 7.70 (br. s., 1 H), 7.55 (s, 1 H), 7.43 (d, 1 H), 4.36 (dd, 1 H), 4.29 (dd, 1 H), 3.99 (s, 3 H), 3.78 (t, 1 H), 2.94-3.02 (m, 1 H), 2.87-2.94 (m, 1 H), 2.27-2.46 (m, 2 H), 2.00-2.11 (m, 1 H), 1.87-1.97 (m, 1 H) |
| 309 | 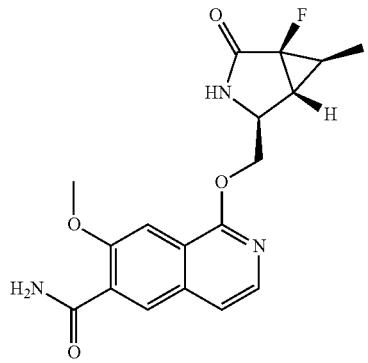 [SMILES: COc1cc2c(OC[C@H]3NC(=O)[C@@]4(F)[C@@H]3[C@@H]4C)nccc2cc1C(N)=O] Chiral | P1 | L92 | | 3, 7 | 359 | $^1$H NMR (400 MHz, dmso-d$_6$) δ 8.18 (s, 1 H), 8.01 (br. s., 1 H), 7.92 (d, 1 H), 7.84 (br. s., 1 H), 7.70 (br. s., 1 H), 7.61 (s, 1 H), 7.45 (d, 1 H), 4.53 (dd, 1 H), 4.40 (dd, 1 H), 3.98 (s, 3 H), 3.73-3.82 (m, 1 H), 2.19-2.28 (m, 1 H), 1.27-1.35 (m, 1 H), 1.21-1.26 (m, 3 H) |

TABLE 1-continued
| Ex. | Structure | Reactant A | Reactant B | Source | Methods | MH+ | Characterization |
|---|---|---|---|---|---|---|---|
| 310 | 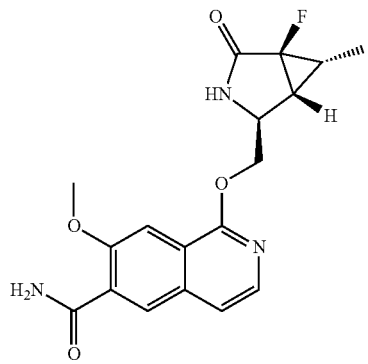 [SMILES: COc1cc2c(OC[C@H]3NC(=O)[C@@]4(F)[C@@H]3[C@H]4C)nccc2cc1C(N)=O] Chiral | P1 | L93 | | 3, 7 | 359 | ¹H NMR (600 MHz, dmso-d₆) δ 8.17 (s, 1 H), 8.15 (br. s., 1 H), 7.91 (d, 1 H), 7.80 (br. s., 1 H), 7.64 (br. s., 1 H), 7.61 (s, 1 H), 7.43 (d, 1 H), 4.62 (dd, 1 H), 4.42 (dd, 1 H), 3.95 (s, 3 H), 3.64 (dd, 1 H), 2.53-2.59 (m, 1 H), 1.98-2.09 (m, 1 H), 1.01 (dd, 3 H) |
| 311 | 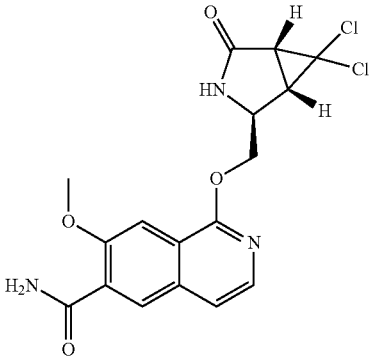 [SMILES: COc1cc2c(OC[C@H]3NC(=O)[C@H]4[C@@H]3C4(Cl)Cl)nccc2cc1C(N)=O] Chiral | P1 | L114 | | 3, 7 | 396 | ¹H NMR (400 MHz, dmso-d₆) δ 8.49 (s, 1 H), 8.19 (s, 1 H), 7.93 (d, 1 H), 7.85 (br. s., 1 H), 7.68-7.74 (br. s., 1 H), 7.62 (s, 1 H), 7.47 (d, 1 H), 4.65 (dd, 1 H), 4.49 (dd, 1 H), 4.02-4.08 (m, 1 H), 4.01 (s, 3 H), 3.01-3.11 (m, 2 H) |
| 312 | 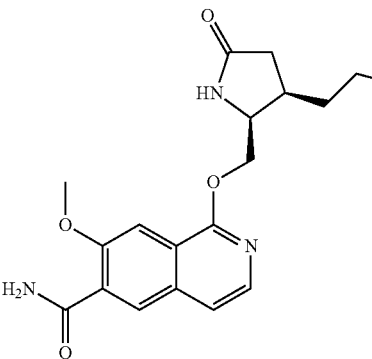 Chiral | P1 | L59 | | 3, 7 | 358 | ¹H NMR (400 MHz, dmso-d₆) δ 8.16 (s, 1 H), 8.03 (br. s., 1 H), 7.91 (d, 1 H), 7.84 (br. s., 1 H), 7.70 (br. s., 1 H), 7.59 (s, 1 H), 7.43 (d, 1 H), 4.44 (d, 2 H), 3.93-3.98 (m, 4 H), 2.56-2.65 (m, 1 H), 2.27 (dd, 1 H), 2.15 (dd, 1 H), 1.48-1.58 (m, 1 H), 1.27-1.44 (m, 3 H), 0.88 (t, 3 H) |

TABLE 1-continued

| Ex. | Structure | Reactant A | Reactant B | Source | Methods | MH+ | Characterization |
|---|---|---|---|---|---|---|---|
| 313 | Chiral | P1 | L81 | | 3, 7 | 372 | ¹H NMR (400 MHz, dmso-d₆) δ 8.17 (s, 1 H), 7.90 (d, 1 H), 7.84 (br. s., 1 H), 7.64-7.73 (m, 2 H), 7.61 (s, 1 H), 7.43 (d, 1 H), 4.46 (dd, 1 H), 4.38 (dd, 1 H), 3.99 (s, 3 H), 3.89-3.95 (m, 1 H), 3.25 (s, 3 H), 1.90-1.96 (m, 1 H), 1.85 (s, 1 H), 1.73-1.78 (m, 1 H), 1.21-1.31 (m, 2 H) |
| 314 | Chiral | P1 | L82 | | 3, 7 | 372 | ¹H NMR (400 MHz, dmso-d₆) δ 8.17 (s, 1 H), 7.91 (d, 2 H), 7.85 (br. s., 1 H), 7.71 (br. s., 1 H), 7.63 (s, 1 H), 7.44 (d, 1 H), 4.53 (dd, 1 H), 4.37 (dd, 1 H), 3.99 (s, 3 H), 3.77-3.85 (m, 1 H), 3.44 (d, 2 H), 3.27 (s, 3 H), 2.05-2.11 (m, 1 H), 1.97-2.04 (m, 1 H), 1.58 (quin, H) |
| 315 | Chiral | P1 | L83 | | 3, 7 | 346 | ¹H NMR (400 MHz, dmso-d₆) δ 8.19 (s, 1 H), 7.94 (br. s., 1 H), 7.92 (d, 1 H), 7.85 (br. s., 1 H), 7.71 (br. s., 1 H), 7.63 (s, 1 H), 7.46 (d, 1 H), 4.81 (d, 1 H), 4.38-4.51 (m, 2 H), 3.99-4.06 (m, 4 H), 2.34-2.50 (m, 2 H) |
| 316 | Chiral | P16 | L54 | | 3, 7 | 362 | ¹H NMR (400 MHz, dmso-d₆) δ 8.87 (s, 1 H), 8.62 (d, 1 H), 8.18 (s, 1 H), 7.83 (br. s., 1 H), 7.69 (s, 1 H), 7.67 (br. s., 1 H), 7.08 (d, 1 H), 4.92 (dd, 1 H), 4.22-4.32 (m, 1 H), 4.06-4.16 (m, 2 H), 3.96 (s, 3 H), 2.55-2.74 (m, 1 H), 1.52-1.69 (m, 2 H), 1.01 (t, 3 H) |

TABLE 1-continued

| Ex. | Structure | Reactant A | Reactant B | Source | Methods | MH+ | Characterization |
|---|---|---|---|---|---|---|---|
| 317 | Chiral | P1 | L96 | | 3, 7 | 346 | ¹H NMR (400 MHz, dmso-d₆) δ 8.17 (s, 1 H), 8.00 (br. s., 1 H), 7.91 (d, 1 H), 7.83 (br. s., 1 H), 7.68 (br. s., 1 H), 7.59 (s, 1 H), 7.44 (d, 1 H), 4.54 (dd, 1 H), 4.42 (dd, 1 H), 3.95 (s, 3 H), 3.66-3.77 (m, 1 H), 2.56-2.70 (m, 1 H), 1.68-1.86 (m, 1 H), 0.98-1.12 (m, 1 H) |
| 318 | Chiral | P8 | 17342-08-4 | commercial | 3, 7 | 340 | ¹H NMR (400 MHz, dmso-d₆) δ 8.14 (s, 1 H), 8.06 (br. s, 1 H), 7.92 (d, 1 H), 7.83 (br. s., 1 H), 7.76 (s, 1 H), 7.73 (br. s., 1 H), 7.44 (d, 1 H), 5.05 (s, 2 H), 4.50 (dd, 1 H), 4.28 (dd, 1 H), 3.96-4.07 (m, 1 H), 3.67 (s, 1 H), 2.34 (s, 1 H), 2.10-2.29 (m, 2 H), 1.90-1.99 (m, 1 H) |
| 319 | Chiral | P8 | 17342-08-4 | commercial | 3, 7 | 340 | ¹H NMR (400 MHz, dmso-d₆) δ 8.15 (s, 1 H), 8.06 (s, 1 H), 7.95 (d, 1 H), 7.88 (s, 1 H), 7.84 (br. s., 1 H), 7.70 (br. s., 1 H), 7.45 (d, 1 H), 7.39 (t, 1 H), 5.68 (dd, 2 H), 4.49 (dd, 1 H), 4.29 (dd, 1 H), 4.00-4.07 (m, 1 H), 2.15-2.34 (m, 3 H), 1.88-1.94 (m, 1 H) |

TABLE 1-continued
| Ex. | Structure | Reactant A | Reactant B | Source | Methods | MH+ | Characterization |
|---|---|---|---|---|---|---|---|
| 320 | 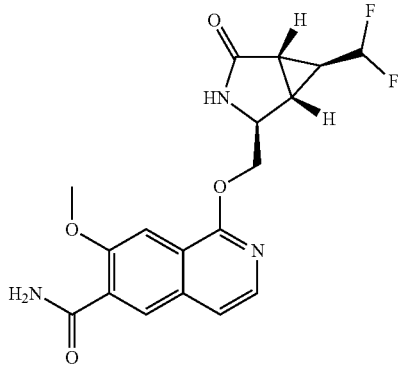 [SMILES: COc1cc2c(OC[C@H]3NC(=O)[C@@H]4[C@@H](C(F)F)[C@@H]43)nccc2cc1C(N)=O] Chiral | P1 | L84 | | 3, 7 | 378 | ¹H NMR (400 MHz, dmso-d₆) δ 8.17 (s, 1 H), 7.91 (d, 1 H), 7.88 (s, 1 H), 7.84 (br. s., 1 H), 7.70 (br. s., 1 H), 7.59 (s, 1 H), 7.44 (d, 1 H), 5.90 (td, 1 H), 4.47-4.58 (m, 1 H), 4.38-4.48 (m, 1 H), 4.02-4.10 (m, 1 H), 3.99 (s, 3 H), 2.25-2.33 (m, 1 H), 2.09-2.17 (m, 1 H), 1.62-1.74 (m, 1 H) |
| 321 | 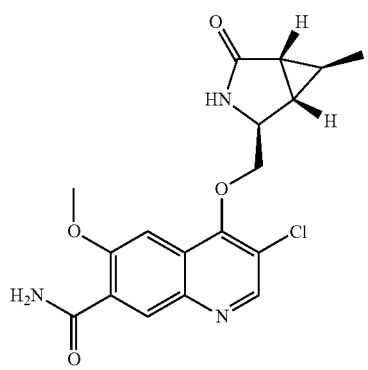 [SMILES: COc1cc2c(OC[C@H]3NC(=O)[C@@H]4[C@@H](C)[C@@H]43)c(Cl)cnc2cc1C(N)=O] Chiral | P22 | L74 | | 4, 7 | 376 | ¹H NMR (600 MHz, dmso-d₆) δ 8.84 (s, 1 H), 8.22 (s, 1 H), 7.86 (br. s., 1 H), 7.69 (br. s., 1 H), 7.58 (s, 1 H), 5.10 (br. s., 1 H), 4.05-4.13 (m, 1 H), 3.97-4.05 (m, 1 H), 3.93 (s, 3 H), 3.39-3.53 (m, 2 H), 1.94 (d, 1 H), 1.47-1.59 (m, 1 H), 1.18 (d, 3 H) |
| 322 | 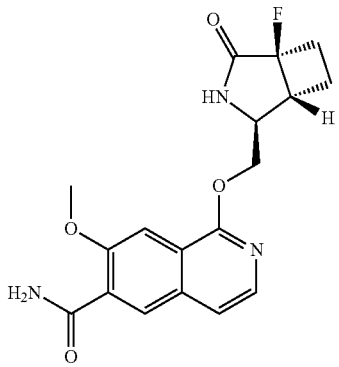 [SMILES: COc1cc2c(OC[C@H]3NC(=O)[C@]4(F)CC[C@H]34)nccc2cc1C(N)=O] Chiral | P1 | L98 | | 3, 7 | 360 | ¹H NMR (400 MHz, dmso-d₆) δ 8.61 (br. s, 1 H), 8.15 (s, 1 H), 7.89 (d, 1 H), 7.81 (br. s., 1 H), 7.67 (br. s, 2 H), 7.42 (d, 1 H), 4.46 (dd, 1 H), 4.29 (dd, 1 H), 3.91 (s, 3 H), 3.71-3.87 (m, 1 H), 3.14-3.27 (m, 1 H), 2.36-2.50 (m, 1 H), 2.19-2.36 (m, 2 H), 1.29-1.49 (m, 1 H) |

TABLE 1-continued
| Ex. | Structure | Reactant A | Reactant B | Source | Methods | MH+ | Characterization |
|---|---|---|---|---|---|---|---|
| 323 | 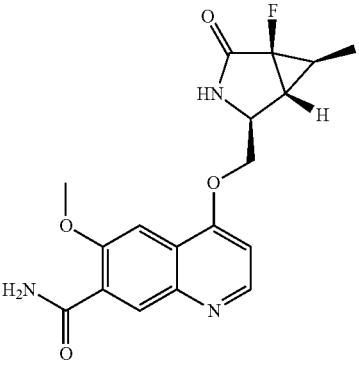 [SMILES: COc1cc2c(OC[C@H]3NC(=O)[C@@]4(F)[C@@H]3[C@@H]4C)ccnc2cc1C(N)=O]<br>Chiral | P16 | L92 | | 3, 7 | 360 | $^1$H NMR (400 MHz, dmso-d$_6$) δ 8.64 (d, 1 H), 8.19 (s, 1 H), 7.99 (br. s., 1 H), 7.82 (br. s., 1 H), 7.66 (br. s., 1 H), 7.53 (s, 1 H), 7.03 (d, 1 H), 4.27 (d, 2 H), 3.96 (s, 3 H), 3.79 (d, 1 H), 2.22 (m, 1 H), 1.27-1.36 (m, 1 H), 1.23 (s, 3 H) |
| 324 | 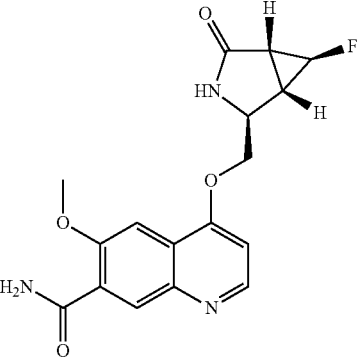 [SMILES: COc1cc2c(OC[C@H]3NC(=O)[C@@H]4[C@@H](F)[C@@H]43)ccnc2cc1C(N)=O]<br>Chiral | P16 | L83 | | 3, 7 | 346 | $^1$H NMR (400 MHz, dmso-d$_6$) δ 8.64 (d, 1 H), 8.20 (s, 1 H), 7.92 (br. s., 1 H), 7.83 (br. s., 1 H), 7.67 (br. s., 1 H), 7.54 (s, 1 H), 7.03 (d, 1 H), 4.82 (d, 1 H), 4.25 (d, 2 H), 4.05 (t, 1 H), 4.00 (s, 3 H), 2.37-2.48 (m, 2 H) |
| 325 | 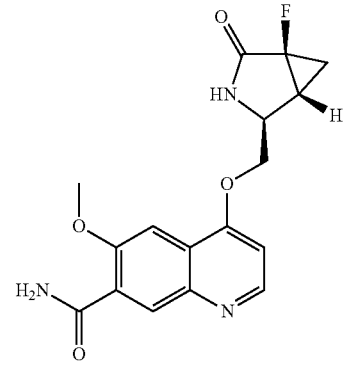 [SMILES: COc1cc2c(OC[C@H]3NC(=O)[C@]4(F)C[C@H]34)ccnc2cc1C(N)=O]<br>Chiral | P16 | L96 | | 3, 7 | 346 | 1H NMR (400 MHz, dmso-d$_6$) δ 8.65 (d, 1 H), 8.19 (s, 1 H), 8.01 (br. s., 1 H), 7.82 (br. s., 1 H), 7.66 (br. s., 1 H), 7.53 (s, 1 H), 7.04 (d, 1 H), 4.30 (d, 2 H), 3.95 (s, 3 H), 3.76 (d, 1 H), 2.56-2.65 (m, 1 H), 1.80 (ddd, 1 H), 1.09 (dt, 1 H) |

TABLE 1-continued

| Ex. | Structure | Reactant A | Reactant B | Source | Methods | MH+ | Characterization |
|---|---|---|---|---|---|---|---|
| 326 | (Chiral structure) | P16 | L72 | | 3, 7 | 328 | ¹H NMR (400 MHz, dmso-d₆) δ 8.64 (d, 1 H), 8.19 (s, 1 H), 7.83 (br. s., 1 H), 7.67 (br. s., 1 H), 7.61 (s, 1 H), 7.57 (s, 1 H), 7.05 (d, 1 H), 4.25-4.33 (m, 1 H), 4.16-4.24 (m, 1 H), 4.00 (s, 3 H), 3.88-3.95 (m, 1 H), 1.91- 2.04 (m, 1 H), 1.72-1.86 (m, 1 H), 1.11 (td, 1 H), 0.62 (q, 1 H) |
| 327 | (Chiral structure) | P1 | L85 | | 3, 7, 9 | 358 | ¹H NMR (400 MHz, CD₃OD) δ 8.33 (s, 1 H), 7.89 (d, 1 H), 7.72 (s, 1 H), 7.35 (d, 1 H), 4.47-4.63 (m, 2 H), 4.10 (s, 3 H), 4.04-4.08 (m, 1 H), 3.54 (d, 1 H), 3.44-3.50 (m, 1 H), 3.12 (d, 1 H), 2.04-2.10 (m, 1 H), 1.93 (br. s., 1 H), 1.33-1.41 (m, 1 H) |
| 328 | (Chiral structure) | P1 | L86 | | 3, 7, 9 | 358 | ¹H NMR (400 MHz, CD₃OD) δ 8.33 (s, 1 H), 7.90 (d, 1 H), 7.74 (s, 1 H), 7.36 (d, 1 H), 4.52-4.66 (m, 2 H), 4.09 (s, 3 H), 3.99-4.08 (m, 1 H), 3.82 (dd, 1 H), 3.61 (dd, 1 H), 2.20-2.30 (m, 1 H), 2.18 (d, 1 H), 1.66-1.78 (m, 1 H) |
| 329 | (Chiral structure) | P1 | L51 | | 3, 7 | 342 | 1H NMR (400 MHz, dmso-d₆) δ 8.21 (s, 1 H), 8.16 (s, 1 H), 7.90 (d, 1 H), 7.84 (br. s., 1 H), 7.69 (br. s., 1 H), 7.64 (s, 1 H), 7.43 (d, 1 H), 5.98 (ddd, 1 H), 5.19 (d, 1 H), 5.08 (d, 1 H), 4.55 (dd, 1 H), 4.35 (dd, 1 H), 3.99 (s, 3 H), 3.80 (td, 1 H), 2.93 (dt, 1 H), 2.47 (d, 1 H), 2.18 (dd, 1 H) |

TABLE 1-continued
| Ex. | Structure | Reactant A | Reactant B | Source | Methods | MH+ | Characterization |
|---|---|---|---|---|---|---|---|
| 330 | 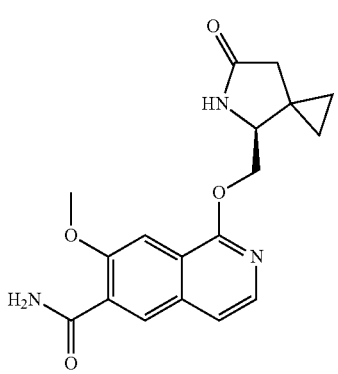 [SMILES: COc1cc2c(OC[C@H]3NC(=O)CC34CC4)nccc2cc1C(N)=O] Chiral | P1 | L125 | | 3, 7 | 342 | $^1$H NMR (400 MHz, dmso-d$_6$) δ 8.24 (br. s., 1 H), 8.17 (s, 1 H), 7.90 (d, 1 H), 7.83 (br. s., 1 H), 7.69 (br. s., 1 H), 7.59 (s, 1 H), 7.42 (d, 1 H), 4.33-4.43 (m, 2 H), 3.98 (s, 3 H), 3.58 (t, 1 H), 2.65 (d, 1 H), 2.03 (d, 1 H), 0.79-0.90 (m, 1 H), 0.70-0.79 (m, 1 H), 0.54-0.70 (m, 2 H) |
| 333 | 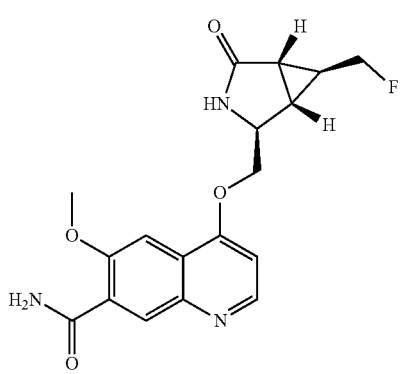 [SMILES: COc1cc2c(OC[C@H]3NC(=O)[C@@H]4[C@@H](CF)[C@@H]43)ccnc2cc1C(N)=O] Chiral | P16 | L79 | | 3, 7 | 360 | $^1$H NMR (400 MHz, dmso-d$_6$) δ 8.64 (d, 1 H), 8.20 (s, 1 H), 7.84 (br. s., 1 H), 7.76 (s, 1 H), 7.68 (br. s., 1 H), 7.54 (s, 1 H), 7.03 (d, 1 H), 4.29-4.52 (m, 2 H), 4.22-4.29 (m, 2 H), 4.00 (s, 3 H), 3.95-3.99 (m, 1 H), 2.05- 2.11 (m, 1 H), 1.94-2.03 (m, 1 H), 1.47-1.56 (m, 1 H) |
| 334 | 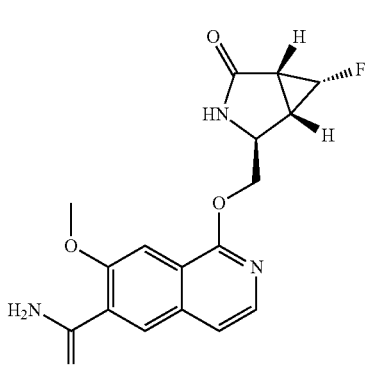 Chiral | P1 | L87 | | 3, 7 | 346 | $^1$H NMR (600 MHz, dmso-d$_6$) δ 8.17 (s, 1 H), 8.04 (s, 1 H), 7.90 (d, 1 H), 7.80 (br. s., 1 H), 7.63 (br. s., 2 H), 7.42 (d, 1 H), 5.15 (ddd, 1 H), 4.59 (dd, 1 H), 4.47 (dd, 1 H), 4.00-4.03 (m, 1 H), 3.96-4.00 (m, 3 H), 2.49 (dt, 2 H), 2.19-2.26 (m, 2 H) |

| Ex. | Structure | Reactant A | Reactant B | Source | Methods | MH+ | Characterization |
|---|---|---|---|---|---|---|---|
| 335 | 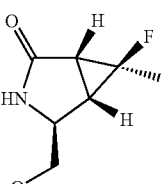 Chiral | P1 | L88 | | 3, 7 | 360 | $^1$H NMR (600 MHz, dmso-d$_6$) δ 8.17 (s, 1 H), 7.96 (d, 1 H), 7.90 (d, 1 H), 7.80 (br. s., 1 H), 7.60-7.66 (m, 2 H), 7.43 (d, 1 H), 4.54 (dd, 1 H), 4.41 (dd, 1 H), 3.99 (s, 3 H), 3.91 (t, 1 H), 2.39 (dd, 1 H), 2.33 (dd, 1 H), 1.61 (d, 3 H) |
| 336 | 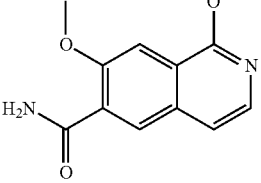 Chiral | P1 | L89 | | 3, 7 | 360 | $^1$H NMR (600 MHz, dmso-d$_6$) δ 8.21 (s, 1 H), 8.14 (s, 1 H), 7.88 (d, 1 H), 7.83 (br. s., 1 H), 7.61 (br. s., 1 H), 7.59 (s, 1 H), 7.41 (d, 1 H), 4.70 (s, 1 H), 4.64 (dd, 1 H), 4.51 (dd, 1 H), 4.44 (dd, 1 H), 3.99-4.02 (m, 1 H), 3.96 (s, 3 H), 3.22-3.31 (m, 1 H), 2.62 (dd, 1 H), 2.30 (dd, 1 H) |
| 337 | 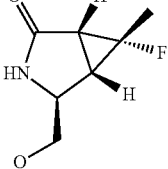 Chiral | P1 | L55 | | 3, 7 | 362 | $^1$H NMR (400 MHz, dmso-d$_6$) δ 8.65 (br. s, 1 H), 8.17 (s, 1 H), 7.91 (d, 1 H), 7.84 (br. s., 1 H), 7.71 (br. s., 1 H), 7.48 (s, 1 H), 7.45 (d, 1 H), 5.13 (dd, 1 H), 4.38-4.47 (m, 2 H), 4.01-4.09 (m, 1 H), 3.97 (s, 3 H), 2.52-2.64 (m, 1 H), 1.49-1.69 (m, 2 H), 1.01 (t, 3 H) |

TABLE 1-continued

| Ex. | Structure | Reactant A | Reactant B | Source | Methods | MH+ | Characterization |
|---|---|---|---|---|---|---|---|
| 338 | Chiral | P9 | L54 | | 3, 7 | 365 | ¹H NMR (400 MHz, dmso-d₆) δ 8.15 (s, 1 H), 7.89 (d, 1 H), 7.83 (br. s, 1 H), 7.73 (s, 1 H), 7.68 (br. s, 1 H), 7.42 (d, 1 H), 4.89 (dd, 1 H), 4.55 (dd, 1 H), 4.23-4.26 (m, 1 H), 4.06-4.09 (m, 1 H), 1.57-1.63 (m, 2 H), 1.02 (t, 3 H) |
| 339 | Chiral | P10 | L54 | | 3, 7 | 406 | ¹H NMR (400 MHz, dmso-d₆) δ 8.87 (br. s, 1 H), 8.27 (s, 1 H), 7.91 (d, 1 H), 7.83 (br. s., 1 H), 7.77 (s, 2 H), 7.45 (d, 1 H), 4.90 (dd, 1 H), 4.55 (dd, 1 H), 4.35-4.43 (m, 1 H), 4.30 (s, 1 H), 4.23 (dd, 1 H), 4.04-4.14 (m, 1 H), 3.80 (t, 2 H), 3.36 (s, 3 H), 2.61-2.69 (m, 1 H), 1.53-1.66 (m, 2 H), 1.02 (t, 3 H) |
| 340 | Chiral | P1 | L60 | | 3, 7 | 360 | ¹H NMR (400 MHz, dmso-d₆) δ 8.17 (s, 1 H), 8.11 (s, 1 H), 7.92 (d, 1 H), 7.85 (br. s., 1 H), 7.71 (br. s., 1 H), 7.58 (s, 1 H), 7.44 (d, 1 H), 4.39-4.54 (m, 2 H), 4.00-4.08 (m, 1 H), 3.98 (s, 3 H), 3.41- 3.56 (m, 2 H), 3.24 (s, 3 H), 2.84-2.98 (m, 1 H), 2.23 (m, 2 H) |

TABLE 1-continued
| Ex. | Structure | Reactant A | Reactant B | Source | Methods | MH+ | Characterization |
|---|---|---|---|---|---|---|---|
| 341 | 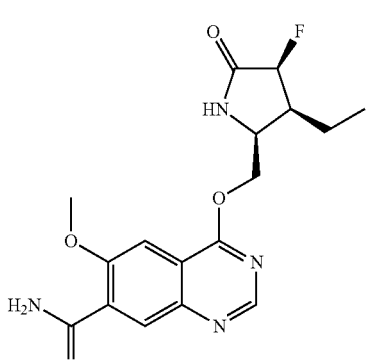<br>Chiral | P3 | L54 | | 3, 7 | 363 | ¹H NMR (400 MHz, dmso-d₆) δ 8.90 (s, 1 H), 8.71 (s, 1 H), 8.03 (s, 1 H), 7.89 (br. s., 1 H), 7.74 (br. s., 1 H), 7.68 (s, 1 H), 4.90 (dd, 1 H), 4.66 (dd, 1 H), 4.32 (dd, 1 H), 4.04-4.19 (m, 1 H), 3.97 (s, 3 H), 2.53-2.72 (m, 1 H), 1.50-1.68 (m, 2 H), 1.02 (t, 3 H) |
| 342 | 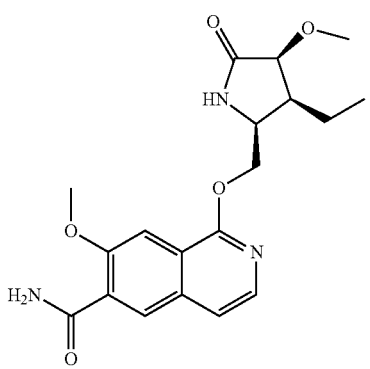 [SMILES: CC[C@@H]1[C@H](OC)C(=O)N[C@@H]1COc1nccc2cc(C(N)=O)c(OC)cc12]<br>Chiral | P1 | L66 | | 3, 7 | 374 | ¹H NMR (400 MHz, CD₃OD) δ 8.31 (s, 1 H), 7.88 (d, 1 H), 7.82 (s, 1 H), 7.34 (d, 1 H), 4.68 (dd, 1 H), 4.35-4.48 (m, 1 H), 4.12-4.19 (m, 1 H), 4.10 (s, 3 H), 3.66 (d, 1 H), 3.57 (s, 3 H), 2.45-2.59 (m, 1 H), 1.70-1.82 (m, 1 H), 1.53-1.70 (m, 1 H), 1.06 (t, 3 H) |
| 343 | 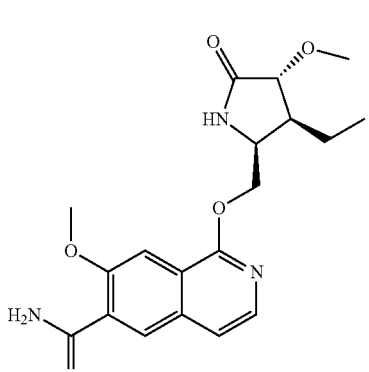<br>Chiral | P1 | L67 | | 3, 7 | 374 | ¹H NMR (400 MHz, dmso-d₆) δ 8.23 (s, 1 H), 8.18 (s, 1 H), 7.91 (d, 1 H), 7.84 (br. s., 1 H), 7.70 (br. s., 1 H), 7.51 (s, 1 H), 7.45 (d, 1 H), 4.32-4.52 (m, 2 H), 3.99 (s, 3 H), 3.95 (br. s., 1 H), 3.86 (d, 1 H), 3.55 (s, 3 H), 2.22-2.37 (m, 1 H), 1.47-1.65 (m, 2 H), 0.98 (t, 3 H) |

TABLE 1-continued
| Ex. | Structure | Reactant A | Reactant B | Source | Methods | MH+ | Characterization |
|---|---|---|---|---|---|---|---|
| 344 | 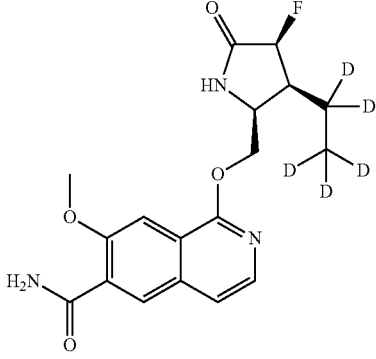 [SMILES: [2H]C([2H])([2H])C([2H])([2H])[C@@H]1[C@H](F)C(=O)N[C@@H]1COc1nccc2cc(C(N)=O)c(OC)cc12] Chiral | P1 | L56 | | 3, 7 | 367 | ¹H NMR (400 MHz, dmso-d₆) δ 8.85 (s, 1 H), 8.15 (s, 1 H), 7.90 (d, 1 H), 7.83 (br. s., 1 H), 7.73 (s, 1 H), 7.69 (br. s., 1 H), 7.43 (d, 1 H), 4.90 (dd, 1 H), 4.54 (dd, 1 H), 4.25 (dd, 1 H), 4.04-4.13 (m, 1 H), 3.97 (s, 3 H), 2.59 (ddd, 1 H) |
| 345 | 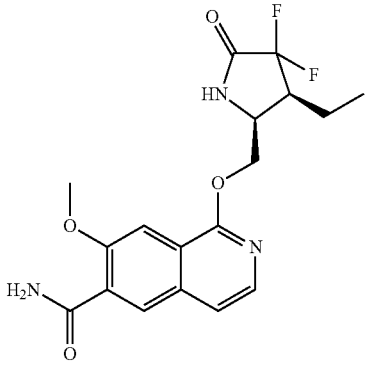 [SMILES: CC[C@H]1[C@@H](COc2nccc3cc(C(N)=O)c(OC)cc23)NC(=O)C1(F)F] Chiral | P1 | L40 | | 3, 7 | 380 | ¹H NMR (400 MHz, dmso-d₆) δ 9.33 (br. s., 1 H), 8.16 (s, 1 H), 7.91 (d, 1 H), 7.84 (br. s., 1 H), 7.70 (br. s., 1 H), 7.60 (s, 1 H), 7.45 (d, 1 H), 4.53 (d, 1 H), 4.33 (d, 1 H), 4.09-4.26 (m, 1 H), 3.94 (s, 3 H), 2.74-2.98 (m, 1 H), 1.53-1.79 (m, 2 H), 1.04 (t, 3 H) |
| 346 | 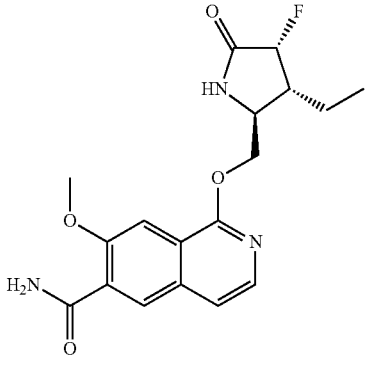 Chiral | P1 | L57 | | 3, 7 | 362 | ¹H NMR (400 MHz, dmso-d₆) δ 8.78 (br. s, 1 H), 8.17 (s, 1 H), 7.90 (d, 1 H), 7.84 (br. s., 1 H), 7.69 (br. s., 1 H), 7.63 (s, 1 H), 7.44 (d, 1 H), 5.17 (dd, 1 H), 4.57 (dd, 1 H), 4.34 (dd, 1 H), 3.99 (s, 3 H), 3.75-3.84 (m, 1 H), 1.59-1.71 (m, 2 H), 1.46-1.59 (m, 1 H), 1.00 (t, 3 H) |

TABLE 1-continued
| Ex. | Structure | Reactant A | Reactant B | Source | Methods | MH+ | Characterization |
|---|---|---|---|---|---|---|---|
| 347 | 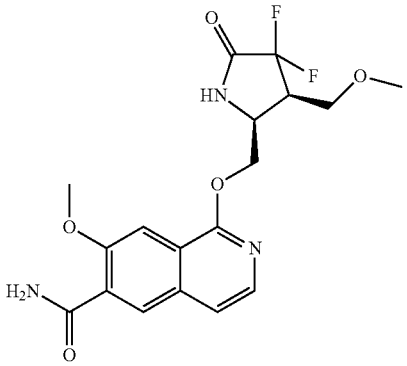 [SMILES: COC[C@H]1[C@@H](COc2nccc3cc(C(N)=O)c(OC)cc23)NC(=O)C1(F)F] Chiral | P1 | L63 | | 3, 7 | 396 | $^1$H NMR (400 MHz, dmso-d$_6$) δ 9.33 (br. s., 1 H), 8.17 (s, 1 H), 7.92 (d, 1 H), 7.83 (br. s., 1 H), 7.70 (br. s., 1 H), 7.59 (s, 1 H), 7.46 (d, 1 H), 4.51-4.59 (m, 1 H), 4.31-4.40 (m, 1 H), 4.19-4.29 (m, 1 H), 3.94 (s, 3 H), 3.71-3.80 (m, 1 H), 3.59-3.71 (m, 1 H), 3.28 (s, 3 H), 3.17-3.26 (m, 1 H) |
| 348 | 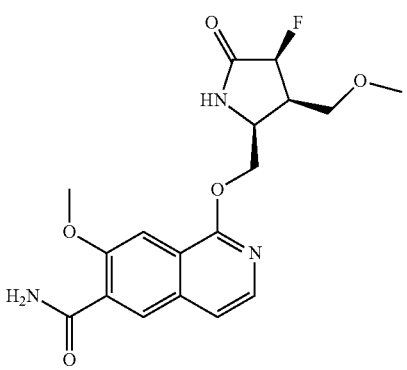 [SMILES: COC[C@@H]1[C@H](F)C(=O)N[C@@H]1COc1nccc2cc(C(N)=O)c(OC)cc12] Chiral | P1 | L61 | | 3, 7 | 378 | $^1$H NMR (400 MHz, dmso-d$_6$) δ 8.86 (s, 1 H), 8.16 (s, 1 H), 7.91 (d, 1 H), 7.84 (br. s., 1 H), 7.72 (s, 1 H), 7.70 (br. s., 1 H), 7.44 (d, 1 H), 4.95 (dd, 1 H), 4.55 (dd, 1 H), 4.25-4.35 (m, 1 H), 4.07-4.18 (m, 1 H), 3.96 (s, 3 H), 3.62-3.73 (m, 1 H), 3.51-3.62 (m, 1 H), 3.27 (s, 3 H), 3.00-3.14 (m, 1 H) |
| 349 | 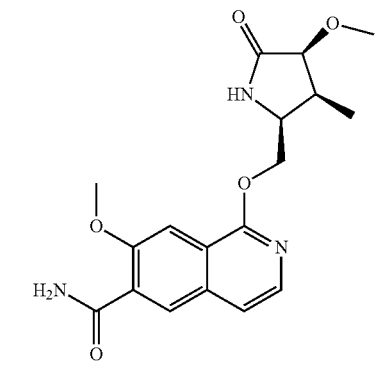 [SMILES: COc1cc2c(OC[C@H]3NC(=O)[C@@H](OC)[C@H]3C)nccc2cc1C(N)=O] Chiral | P1 | L64 | | 3, 7 | 360 | $^1$H NMR (400 MHz, dmso-d$_6$) δ 8.47 (s, 1 H), 8.16 (s, 1 H), 7.90 (d, 1 H), 7.85 (br. s., 1 H), 7.70 (s, 2 H), 7.43 (d, 1 H), 4.56 (dd, 1 H), 4.21-4.32 (m, 1 H), 4.00 (s, 3 H), 3.88-3.98 (m, 1 H), 3.70 (d, 1 H), 3.45 (s, 3 H), 2.69-2.81 (m, 1 H), 0.98 (d, 3 H) |

TABLE 1-continued
| Ex. | Structure | Reactant A | Reactant B | Source | Methods | MH+ | Characterization |
|---|---|---|---|---|---|---|---|
| 350 | 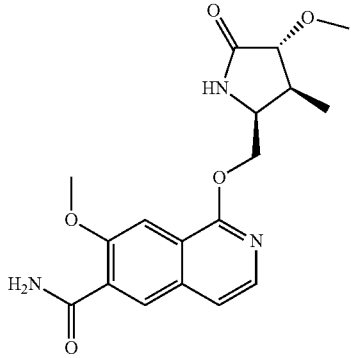 [SMILES: COc1cc2c(OC[C@H]3NC(=O)[C@H](OC)[C@H]3C)nccc2cc1C(N)=O] Chiral | P1 | L65 | | 3, 7 | 360 | ¹H NMR (400 MHz, dmso-d₆) δ 8.23 (s, 1 H), 8.17 (s, 1 H), 7.92 (d, 1 H), 7.84 (br. s., 1 H), 7.70 (br. s., 1 H), 7.52 (s, 1 H), 7.45 (d, 1 H), 4.39-4.50 (m, 2 H), 3.99 (s, 3 H), 3.85-3.91 (m, 1 H), 3.83 (d, 1 H), 3.55 (s, 3 H), 2.55-2.64 (m, 1 H), 1.15 (d, 3 H) |
| 351 | 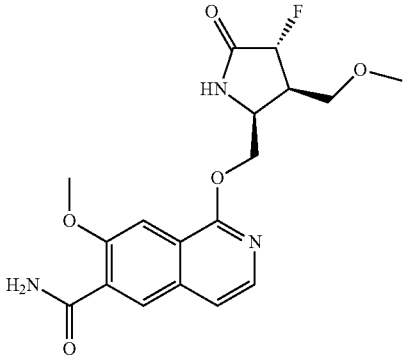 [SMILES: COC[C@H]1[C@@H](COc2nccc3cc(C(N)=O)c(OC)cc23)NC(=O)[C@@H]1F] Chiral | P1 | L61 | | 3, 7 | 378 | ¹H NMR (400 MHz, dmso-d₆) δ 8.74 (s, 1 H), 8.18 (s, 1 H), 7.92 (d, 1 H), 7.84 (br. s., 1 H), 7.71 (br. s., 1 H), 7.51 (s, 1 H), 7.46 (d, 1 H), 5.19 (dd, 1 H), 4.39-4.50 (m, 2 H), 4.05-4.15 (m, 1 H), 3.98 (s, 3 H), 3.57-3.67 (m, 2 H), 3.27 (s, 3 H), 2.86-3.07 (m, 1 H) |
| 352 | 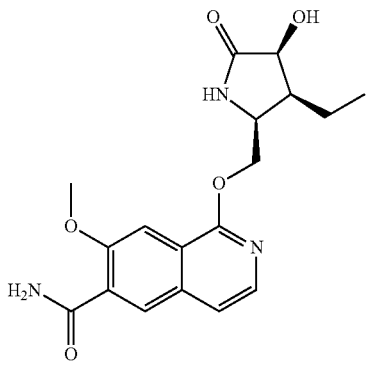 [SMILES: CC[C@@H]1[C@H](O)C(=O)N[C@@H]1COc1nccc2cc(C(N)=O)c(OC)cc12] Chiral | P1 | L68 | | 3, 7, 9, 9 | 360 | ¹H NMR (400 MHz, dmso-d₆) δ 8.47 (s, 1 H), 8.14 (s, 1 H), 7.89 (d, 1 H), 7.84 (br. s., 1 H), 7.80 (s, 1 H), 7.68 (br. s., 1 H), 7.41 (d, 1 H), 5.71 (d, 1 H), 4.55 (dd, 1 H), 4.23-4.36 (m, 1 H), 4.00 (s, 3 H), 3.91-3.99 (m, 1 H), 3.87 (t, 1 H), 1.56-1.69 (m, 1 H), 1.40-1.55 (m, 1 H), 0.97 (t, 3 H) |

TABLE 1-continued
| Ex. | Structure | Reactant A | Reactant B | Source | Methods | MH+ | Characterization |
|---|---|---|---|---|---|---|---|
| 353 | 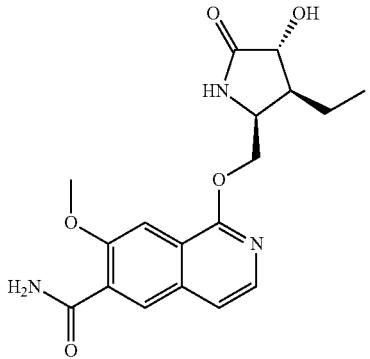 [SMILES: CC[C@H]1[C@@H](COc2nccc3cc(C(N)=O)c(OC)cc23)NC(=O)[C@@H]1O]<br>Chiral | P1 | L68 | | 3, 7, 9, 9 | 360 | ¹H NMR (400 MHz, dmso-d₆) δ 8.16 (br. s., 2 H), 7.91 (d, 1 H), 7.84 (br. s., 1 H), 7.70 (br. s., 1 H), 7.52 (s, 1 H), 7.43 (d, 1 H), 5.48 (d, 1 H), 4.34-4.51 (m, 2 H), 4.00-4.09 (m, 1 H), 3.97 (s, 3 H), 3.86-3.94 (m, 1 H), 2.09-2.23 (m, 1 H), 1.56-1.68 (m, 1 H), 1.43-1.56 (m, 1 H), 1.01 (t, 3 H) |
| 354 | 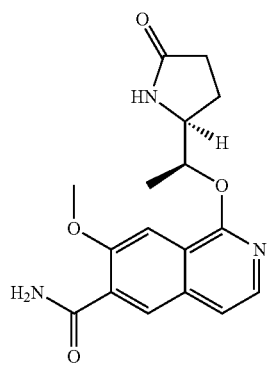 [SMILES: COc1cc2c(O[C@@H](C)[C@@H]3CCC(=O)N3)nccc2cc1C(N)=O]<br>Chiral | P1 | L115 | | 3, 7 | 330 | ¹H NMR (400 MHz, dmso-d₆) δ 8.16 (s, 1 H), 8.14 (s, 1 H), 7.89 (d, 1 H), 7.83 (br. s., 1 H), 7.70 (br. s., 1 H), 7.54 (s, 1 H), 7.40 (d, 1 H), 5.27 (quin, 1 H), 3.96 (s, 3 H), 3.79-3.88 (m, 1 H), 2.09-2.27 (m, 3 H), 1.76-1.88 (m, 1 H), 1.35 (d, 3 H) |
| 355 | 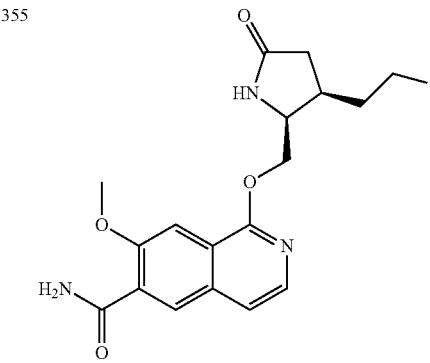<br>Chiral | P1 | L116 | | 3, 7 | 362 | ¹H NMR (400 MHz, dmso-d₆) δ 8.17 (s, 1 H), 8.02 (s, 1 H), 7.91 (d, 1 H), 7.83 (br. s., 1 H), 7.69 (br. s., 1 H), 7.55 (s, 1 H), 7.44 (d, 1 H), 4.53-4.65 (m, 1 H), 4.42-4.53 (m, 3 H), 3.97-4.04 (m, 1 H), 3.97 (s, 3 H), 2.68-2.81 (m, 1 H), 2.20-2.36 (m, 2 H), 1.95-2.12 (m, 1 H), 1.66-1.84 (m, 1 H) |

US 10,793,579 B2
TABLE 1-continued
| Ex. | Structure | Reactant A | Reactant B | Source | Methods | MH+ | Characterization |
|---|---|---|---|---|---|---|---|
| 356 | 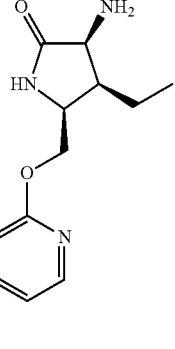 Chiral | P1 | L70 | | 3, 7, 10 | 359 | $^1$H NMR (400 MHz, dmso-d$_6$) δ 8.99 (br. s, 1 H), 8.48 (br. s., 3 H), 8.18 (s, 1 H), 7.93 (d, 1 H), 7.85 (br. s., 1 H), 7.72 (br. s., 1 H), 7.69 (s, 1 H), 7.46 (d, 1 H), 4.68-4.76 (m, 1 H), 4.42-4.51 (m, 1 H), 4.16-4.24 (m, 1 H), 4.00 (s, 3 H), 2.71-2.80 (m, 1 H), 1.47-1.58 (m, 2 H), 1.01 (t, 3 H) |
| 357 | 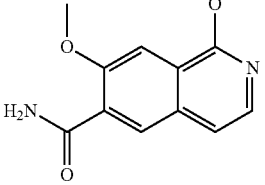 Chiral | P1 | L71 | | 3, 7, 10 | 359 | $^1$H NMR (400 MHz, dmso-d$_6$) δ 8.93 (s, 1 H), 8.45 (br. s., 2 H), 8.19 (s, 1 H), 7.92 (d, 1 H), 7.85 (br. s., 1 H), 7.73 (br. s., 1 H), 7.49 (s, 1 H), 7.47 (d, 1 H), 4.46-4.58 (m, 2 H), 4.11-4.22 (m, 1 H), 3.99 (s, 3 H), 3.86-3.95 (m, 1 H), 2.38-2.47 (m, 1 H), 1.80-1.95 (m, 1 H), 1.40-1.54 (m, 1 H), 1.02 (t, 3 H) |
| 358 | 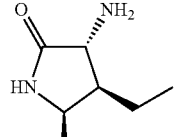 Chiral | P2 | L54 | | 3, 7 | 390 | $^1$H NMR (400 MHz, dmso-d$_6$) δ 8.79 (s, 1 H), 8.17 (s, 1 H), 7.88 (d, 1 H), 7.74 (s, 1 H), 7.72 (br. s., 1 H), 7.70 (br. s., 1 H), 7.41 (d, 1 H), 4.88 (dt, 1 H), 4.90 (dd, 1 H), 4.52 (dd, 1 H), 4.27 (dd, 1 H), 4.01-4.11 (m, 1 H), 2.53-2.69 (m, 1 H), 1.51-1.68 (m, 2 H), 1.38 (t, 6 H), 1.01 (t, 3 H) |

TABLE 1-continued

| Ex. | Structure | Reactant A | Reactant B | Source | Methods | MH+ | Characterization |
|---|---|---|---|---|---|---|---|
| 359 | (Chiral structure) | P7 | L54 | | 3, 7 | 376 | $^1$H NMR (400 MHz, dmso-d$_6$) δ 8.85 (s, 1 H), 8.16 (s, 1 H), 7.89 (d, 1 H), 7.77 (br. s., 1 H), 7.72 (s, 1 H), 7.70 (br. s., 1 H), 7.42 (d, 1 H), 4.90 (dd, 1 H), 4.54 (dd, 1 H), 4.15-4.33 (m, 3 H), 4.02-4.13 (m, 1 H), 2.54-2.71 (m, 1 H), 1.52-1.68 (m, 2 H), 1.44 (t, 3 H), 1.02 (t, 3 H) |
| 360 | (Chiral structure) | P1 | L54 | | 3, 7, 12, HPLC | 380 | $^1$H NMR (400 MHz, dmso-d$_6$) δ 8.86 (s, 1 H), 8.20 (s, 1 H), 7.92 (br. s., 1 H), 7.90 (d, 1 H), 7.80 (br. s., 1 H), 7.78 (d, 1 H), 4.92 (dd, 1 H), 4.54 (dd, 1 H), 4.25 (dd, 1 H), 4.15 (dd, 1 H), 4.01 (s, 3 H), 2.54-2.72 (m, 1 H), 1.54-1.69 (m, 2 H), 1.03 (t, 3 H) |
| 361 | (Chiral structure) | P1 | L54 | | 3, 7, 12, HPLC | 380 | $^1$H NMR (400 MHz, dmso-d$_6$) δ 8.65 (s, 1 H), 7.98 (d, 1 H), 7.93 (br. s., 1 H), 7.89 (s, 1 H), 7.76 (br. s., 1 H), 7.47 (dd, 1 H), 4.85 (dd, 1 H), 4.53 (dd, 1 H), 4.42 (dd, 1 H), 4.03-4.12 (m, 1 H), 3.97 (s, 3 H), 2.54-2.68 (m, 1 H), 1.53-1.68 (m, 2 H), 1.00 (t, 3 H) |

TABLE 1-continued
| Ex. | Structure | Reactant A | Reactant B | Source | Methods | MH+ | Characterization |
|---|---|---|---|---|---|---|---|
| 362 | 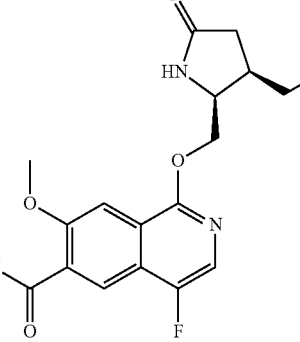<br>Chiral | P1 | L47 | | 3, 7, 12, HPLC | 362 | ¹H NMR (400 MHz, dmso-d$_6$) δ 8.19 (s, 1 H), 8.05 (br. s, 1 H), 7.90 (m, 2 H), 7.80 (br. s, 1 H), 7.60 (s, 1 H), 4.38-4.45 (m, 2 H), 4.00 (s, 3 H), 3.94-3.96 (m, 1 H), 2.43-2.45 (m, 1 H), 2.24-2.33 (m 1 H), 2.09-2.16 (m 1 H), 1.55-1.60 (m, 1 H), 1.33-1.41 (m, 1 H), 0.93 (t, 3 H). |
| 363 | 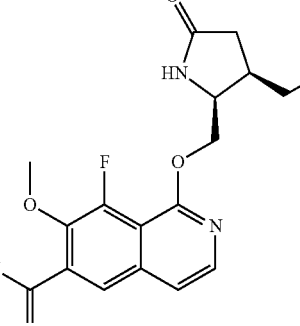<br>Chiral | P1 | L47 | | 3, 7, 12, HPLC | 362 | ¹H NMR (400 MHz, dmso-d$_6$) δ 7.98 (d, 1 H), 7.94 (br. s, 1 H), 7.89 (s, 1 H), 7.77 (br. s, 1 H), 7.70 (s, 1 H), 7.46 (d, 1 H), 4.51-4.55 (dd, 1 H), 4.41-4.45 (dd, 1 H), 3.94 (s, 3 H), 3.89-3.92 (m, 1 H), 2.43-2.45 (m 1 H), 2.17-2.21 (m 2 H), 1.59-1.64 (m 1 H), 1.38-1.44 (m, 1 H), 0.91 (t, 3 H). |
| 364 | 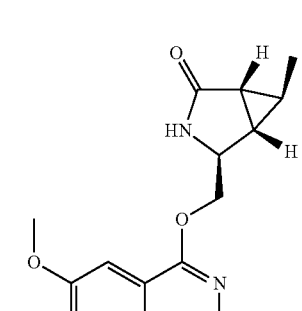<br>Chiral | P1 | L74 | | 3, 7, 12, HPLC | 360 | ¹H NMR (400 MHz, CD$_3$OD) δ 8.47 (s, 1 H), 7.76 (d, 1 H), 7.71 (d, 1 H), 4.43-4.58 (m, 2 H), 4.11 (s, 3 H), 4.04 (t, 1 H), 1.87 (dd, 1 H), 1.71 (d, 1 H), 1.17 (d, 3 H), 1.07-1.15 (m, 1 H) |

385 386
TABLE 1-continued
| Ex. | Structure | Reactant A | Reactant B | Source | Methods | MH+ | Characterization |
|---|---|---|---|---|---|---|---|
| 365 | 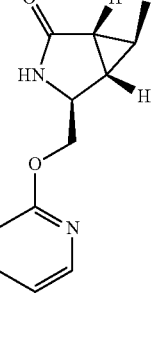 Chiral | P1 | L74 | | 3, 7, 12, HPLC | 360 | $^1$H NMR (400 MHz, CD$_3$OD) δ 8.02 (s, 1 H), 7.95 (d, 1 H), 7.36 (dd, 1 H), 4.45-4.57 (m, 2 H), 4.09 (s, 3 H), 4.02 (t, 1 H), 1.91 (dd, 1 H), 1.68-1.76 (m, 1 H), 1.18 (d, 3 H), 1.08-1.16 (m, 1 H) |
| 366 | 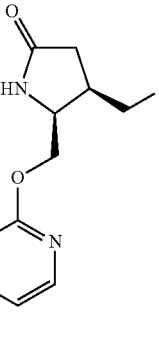 Chiral | P1 | L117 | | 3, 7 | 348 | $^1$H NMR (400 MHz, dmso-d$_6$) δ 8.17 (s, 2 H), 7.91 (d, 1 H), 7.83 (br. s., 1 H), 7.69 (br. s., 1 H), 7.60 (s, 1 H), 7.44 (d, 1 H), 4.70 (d, 1 H), 4.50-4.61 (m, 2 H), 4.41-4.49 (m, 1 H), 4.04-4.15 (m, 1 H), 3.98 (s, 3 H), 2.97-3.13 (m, 1 H), 2.20-2.36 (m, 2 H) |
| 367 | 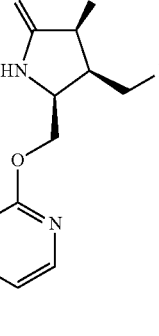 Chiral | P1 | L118 | | 3, 7 | 366 | $^1$H NMR (400 MHz, dmso-d$_6$) δ 8.85 (s, 1 H), 8.16 (s, 1 H), 7.91 (d, 1 H), 7.83 (br. s., 1 H), 7.70 (s, 1 H), 7.68 (br. s., 1 H), 7.45 (d, 1 H), 5.09 (dd, 1 H), 4.81-4.93 (m, 1 H), 4.68-4.81 (m, 1 H), 4.59 (dd, 1 H), 4.36 (dd, 1 H), 4.16-4.25 (m, 1 H), 3.96 (s, 3 H), 3.16-3.28 (m, 1 H) |

TABLE 1-continued

| Ex. | Structure | Reactant A | Reactant B | Source | Methods | MH+ | Characterization |
|---|---|---|---|---|---|---|---|
| 368 | Chiral | P1 | L119 | | 3, 7 | 374 | ¹H NMR (400 MHz, dmso-d₆) δ 8.81 (s, 1 H), 8.16 (s, 1 H), 7.91 (d, 1 H), 7.83 (br. s., 1 H), 7.76 (s, 1 H), 7.68 (br. s., 1 H), 7.42 (d, 1 H), 4.90 (dd, 1 H), 4.71 (dd, 1 H), 4.43 (dd, 1 H), 4.04-4.14 (m, 1 H), 3.98 (s, 3 H), 1.89-2.09 (m, 1 H), 0.80-0.93 (m, 1 H), 0.49-0.59 (m, 2 H), 0.24-0.37 (m, 2 H) |
| 369 | Chiral | P1 | L120 | | 3, 7 | 374 | ¹H NMR (400 MHz, dmso-d₆) δ 8.66 (s, 1 H), 8.18 (s, 1 H), 7.92 (d, 1 H), 7.83 (br. s., 1 H), 7.70 (br. s., 1 H), 7.52 (s, 1 H), 7.45 (d, 1 H), 5.23 (dd, 1 H), 4.51-4.66 (m, 2 H), 4.06 (dt, 1 H), 3.98 (s, 3 H), 1.96-2.14 (m, 1 H), 0.81-0.95 (m, 1 H), 0.46-0.57 (m, 2 H), 0.21-0.34 (m, 2 H) |
| 370 | Chiral | P1 | L121 | | 3, 7 | 380 | ¹H NMR (400 MHz, dmso-d₆) δ 8.85 (br. s., 1 H), 8.16 (s, 1 H), 7.90 (d, 1 H), 7.83 (br. s., 1 H), 7.73 (s, 1 H), 7.68 (br. s., 1 H), 7.43 (d, 1 H), 4.92 (dd, 1 H), 4.62-4.71 (m, 1 H), 4.49-4.60 (m, 2 H), 4.32 (dd, 1 H), 4.09-4.18 (m, 1 H), 3.96 (s, 3 H), 2.77-2.96 (m, 1 H), 1.92-2.08 (m, 2 H). |

TABLE 1-continued

| Ex. | Structure | Reactant A | Reactant B | Source | Methods | MH+ | Characterization |
|---|---|---|---|---|---|---|---|
| 371 | Chiral | P23 | 17342-08-4 | commercial | 3, 22, 16 (Ref. 37) | 424 | ¹H NMR (400 MHz, CD₃OD) δ 8.78 (s, 1 H), 8.00 (s, 1 H), 7.79 (s, 1 H), 7.77 (s, 1 H), 7.39 (s, 1 H), 4.99 (dt, 1 H), 4.59 (dd, 1 H), 4.52 (dd, 1 H), 4.19-4.27 (m, 1 H), 3.85 (s, 3 H), 2.36-2.58 (m, 3 H), 2.06-2.17 (m, 1 H), 1.50 (t, 6 H) |
| 372 | Chiral | P23 | 17342-08-4 | commercial | 3, 22, 16 (Ref. 38) | 438 | ¹H NMR (400 MHz, CD₃OD) δ 8.76 (s, 1 H), 7.98 (s, 1 H), 7.77 (s, 1 H), 7.28 (s, 1 H), 4.99 (dt, 1 H), 4.59 (dd, 1 H), 4.52 (dd, 1 H), 4.19-4.27 (m, 1 H), 3.73 (s, 3 H), 2.47 (s, 3 H), 2.37-2.58 (m, 3 H), 2.07-2.18 (m, 2 H), 1.50 (t, 6 H). |
| 373 | Chiral | P23 | 17342-08-4 | commercial | 3, 22, 16 (Ref. 39) | 424 | ¹H NMR (400 MHz, CD₃OD) δ 8.70 (s, 1 H), 7.99 (s, 1 H), 7.78 (s, 1 H), 7.27 (s, 1 H), 5.00 (dt, 1 H), 4.61 (m, 1 H), 4.52 (dd, 1 H), 4.18-4.28 (m, 1 H), 2.51 (s, 3 H), 2.36-2.60 (m, 3 H), 2.06-2.17 (m, 1 H), 1.50 (t, 6 H) |

TABLE 1-continued
| Ex. | Structure | Reactant A | Reactant B | Source | Methods | MH+ | Characterization |
|---|---|---|---|---|---|---|---|
| 374 | 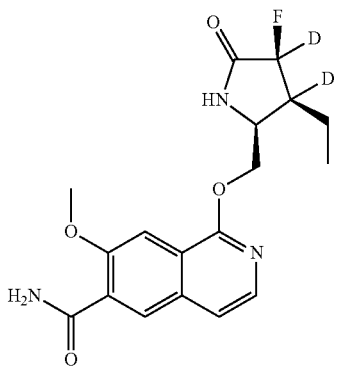 [SMILES: [2H][C@]1(CC)[C@@H](COc2nccc3cc(C(N)=O)c(OC)cc23)NC(=O)[C@@]1([2H])F] Chiral | P1 | L123 | | 3, 7 | 364 | ¹H NMR (600 MHz, dmso-d₆) δ 8.79 (br. s., 1 H), 8.16 (s, 1 H), 7.90 (d, 1 H), 7.80 (br. s., 1 H), 7.74 (s, 1 H), 7.63 (br. s., 1 H), 7.42 (d, 1 H), 4.55 (dd, 1 H), 4.27 (dd, 1 H), 4.04-4.12 (m, 1 H), 3.97 (s, 3 H), 1.54-1.66 (m, 2 H), 1.02 (t, 3 H) |
| 375 | 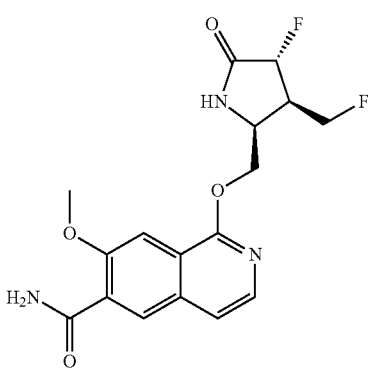 [SMILES: COc1cc2c(OC[C@H]3NC(=O)[C@H](F)[C@H]3CF)nccc2cc1C(N)=O] Chiral | P1 | L124 | | 3, 7 | 366 | ¹H NMR (400 MHz, dmso-d₆) δ 8.81 (s, 1 H), 8.65 (d, 1 H), 8.20 (s, 1 H), 7.83 (br. s., 1 H), 7.68 (br. s., 1 H), 7.46 (s, 1 H), 7.05 (d, 1 H), 5.33 (dd, 1 H) 4.86 (dd, 1 H), 4.74 (dd, 1 H), 4.39-4.27 (m, 1 H), 4.24 (d, 2 H), 3.99 (s, 3 H), 3.26-3.06 (m, 1 H) |
| 376 | 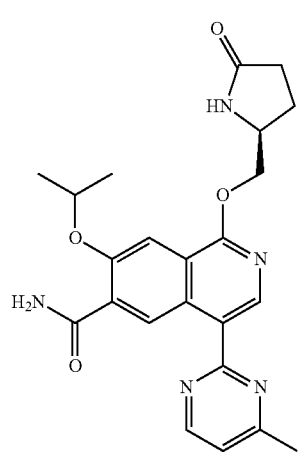 [SMILES: Cc1ccnc(-c2cnc(OC[C@@H]3CCC(=O)N3)c3cc(OC(C)C)c(C(N)=O)cc23)n1] Chiral | P23 | 17342-08-4 | commercial | 3, 22, 16 (Ref 40) | | ¹H NMR (400 MHz, CD₃OD) δ 9.27 (s, 1 H), 8.79 (d, 1 H), 8.49 (s, 1 H), 7.80 (s, 1 H), 7.38 (d, 1 H), 5.00 (dt, 1 H), 4.62-4.69 (m, 1 H), 4.53-4.62 (m, 1 H), 4.20-4.31 (m, 1 H), 2.65 (s, 3 H), 2.38-2.58 (m, 3 H), 2.07-2.19 (m, 1 H), 1.51 (t, 6 H) |

TABLE 1-continued
| Ex. | Structure | Reactant A | Reactant B | Source | Methods | MH+ | Characterization |
|---|---|---|---|---|---|---|---|
| 377 | 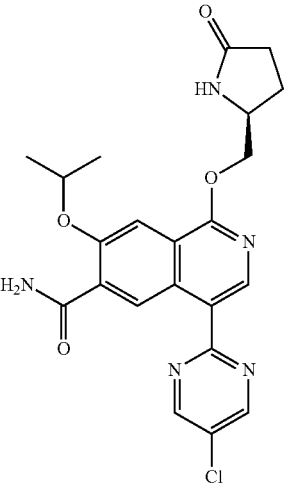 [SMILES: CC(C)Oc1cc2c(OC[C@@H]3CCC(=O)N3)ncc(-c3ncc(Cl)cn3)c2cc1C(N)=O] Chiral | P23 | 17342-08-4 | commercial | 3, 22, 16 (Ref 41) | | ¹H NMR (400 MHz, CD₃OD) δ 9.46 (s, 1 H), 8.97 (s, 2 H), 8.67 (s, 1 H), 7.81 (s, 1 H), 5.00 (dt, 1 H), 4.62-4.72 (m, 1 H), 4.51-4.62 (m, 1 H), 4.18-4.32 (m, 1 H), 2.36-2.62 (m, 3 H), 2.04-2.21 (m, 1 H), 1.51 (t, 6 H) |
| 378 | 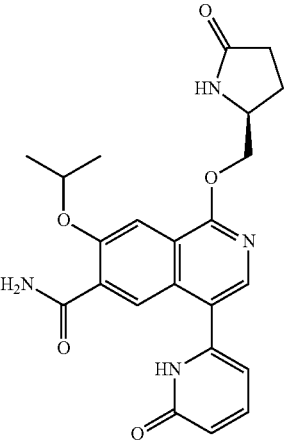 [SMILES: CC(C)Oc1cc2c(OC[C@@H]3CCC(=O)N3)ncc(-c3cccc(=O)[nH]3)c2cc1C(N)=O] Chiral | P23 | 17342-08-4 | commercial | 3, 22, 16 Ref. 42) | | ¹H NMR (400 MHz, CD₃OD) δ 8.36 (s, 1 H), 7.99 (s, 1 H), 7.82 (s, 1 H), 7.72 (dd, 1 H), 6.62 (d, 1 H), 6.53 (d, 1 H), 5.01 (dt, 1 H), 4.61-4.70 (m, 1 H), 4.50-4.60 (m, 1 H), 4.18-4.30 (m, 1 H), 2.36-2.59 (m, 3 H), 2.06-2.20 (m, 1 H), 1.50 (t, 6 H) |
| 379 | 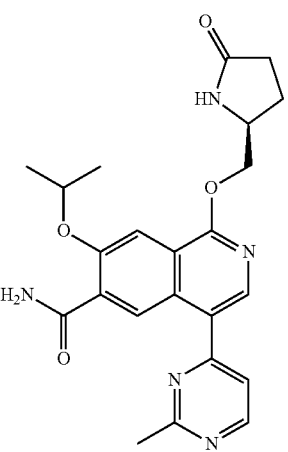 [SMILES: Cc1nccc(-c2cnc(OC[C@@H]3CCC(=O)N3)c3cc(OC(C)C)c(C(N)=O)cc23)n1] Chiral | P23 | 17342-08-4 | commercial | 3, 22, 16 (Ref 43) | | ¹H NMR (400 MHz, CD₃OD) δ 8.85 (s, 1 H), 8.79 (d, 1 H), 8.17 (s, 1 H), 7.83 (s, 1 H), 7.63 (d, 1 H), 5.02 (dt, 1 H), 4.62-4.71 (m, 1 H), 4.53-4.62 (m, 1 H), 4.21-4.31 (m, 1 H), 2.80 (s, 3 H), 2.37-2.59 (m, 3 H), 2.05-2.18 (m, 1 H), 1.51 (t, 6 H) |

TABLE 1 REFERENCES AND NOTES

1. Organic Process Research and Development, 2011, 15, 1052-1062.
2. European Journal of Organic Chemistry 2005, 1354-1366.
3. Prepared as described in US patent application US 2012/95040 A1.
4. Organic & Biomolecular Chemistry, 2005, 3, 603-611.
5. Prepared as described in WPO patent application WO 2007125405 A2
6. Prepared as described in US patent application US 2013/79324 A1.
7. Korean Journal of Medicinal Chemistry, 1994, 4, 119-125.
8. Organic Process Research and Development, 2011, 15, 1052-1062.
9. Journal of Organic Chemistry, 1987, 52, 5247-5254.
10. Prepared as described in US patent application US 2007/0265272 A1.
11. Tetrahedron: Asymmetry 1995, 6, 1181-1190.
12. Bioorganic and Medicinal Chemistry Letters 2010, 20, 4749-4752.
13. Prepared as described in US patent application US 2012/95040 A1.
14. Bioorganic and Medicinal Chemistry Letters 2011, 21, 3290-3296.
15. Tetrahedron 2012, 68, 1286-1298.
16. Prepared as described in World patent application WO 2013/042006 A1.
17. Tetrahedron: Asymmetry 2004, 15, 1659-1665.
18. Tetrahedron: Asymmetry, 2002, 13, 647-658.
19. Prepared as described in World patent application WO 2008/128919 A2.
20. Journal of Medicinal Chemistry 1987, 30, 992-998.
21. Journal of the Chemical Society, Perkin Transactions 1, 2002, 1076-1082.
22. Prepared as described in US patent application US 2010/197654 A1.
23. Journal of the American Chemical Society 2010, 132, 1188-1189.
24. Prostaglandins 1979, 17, 223-226.
25. Organic Letters, 1999, 1, 2105-2107.
26. Tetrahedron, 2007, 63, 10587-10595.
27. Tetrahedron Letters, 1998, 39, 857-860.
28. Prepared as described in European patent application EP 438311 A2.
29. Journal of the American Chemical Society 1999, 121, 10478-10486.
30. Journal of Medicinal Chemistry 1991, 34, 887-900.
31. Journal of the Chemical Society, Perkin Transactions 1: Organic and Bio-Organic Chemistry 1997, 2111-2122.
32. Tetrahedron Letters 1989, 30, 6637-6640.
33. Archiv der Pharmazie 1964, 297, 632-638.
34. Canadian Journal of Chemistry 1956, 34, 815-820.
35. Journal of Organic Chemistry, 1997, 62, 4770-4779.
36. $^1$H NMR (500 MHz, dmso-d$_6$) δ 8.28 (s, 1H, diastereomer 1), 8.18-8.22 (m, 1H, both diastereomers), 8.16 (s, 1H, diastereomer 2), 7.87-7.91 (d, 1H, both diastereomers), 7.74 (br. s., 1H, both diastereomers), 7.71 (s, 1H, both diastereomers), 7.62 (br. s, 1H, both diastereomers), 7.42 (d, 1H, both diastereomers), 4.92-5.01 (m, 1H, diastereomer 1), 4.86-4.93 (m, 1H, diastereomer 2), 4.56 (dd, 1H, diastereomer 1), 4.44-4.51 (m, 1H, diastereomer 2), 4.31-4.38 (m, 1H, diastereomer 1), 4.22 (dd, 1H, diastereomer 2), 3.93-4.05 (m, 1H, both diastereomers), 3.48-3.54 (m, 2H, both diastereomers), 3.27 (s, 3H, diastereomer 1), 3.26 (s, 3H, diastereomer 2), 2.69-2.80 (m, 1H, diastereomer 1), 2.61-2.68 (m, 1H, diastereomer 2), 2.33-2.43 (m, 1H, diastereomer 1), 2.21 (dt, 1H, diastereomer 2), 2.06-2.15 (m, 1H, diastereomer 1), 1.76 (dt, 1H, diastereomer 2), 1.35-1.45 (m, 6H, both diastereomers)
37. 4-Bromo-1-methyl-1H-imidazole was used as the Suzuki coupling partner in the step of Method 16.
38. 4-Bromo-1,2-dimethyl-1H-imidazole was used as the Suzuki coupling partner in the step of Method 16.
39. Tert-butyl 4-bromo-2-methyl-1H-imidazole-1-carboxylate was used as the Suzuki coupling partner in the step of Method 16.
40. 2-Bromo-4-methylpyrimidine was used as the Suzuki coupling partner in the step of Method 16.
41. 2-Bromo-5-chloropyrimidine was used as the Suzuki coupling partner in the step of Method 16.
42. 6-Bromopyridin-2(1H)-one was used as the Suzuki coupling partner in the step of Method 16.
43. 4-Bromo-2-methylpyrimidine was used as the Suzuki coupling partner in the step of Method 16.

Table 2 names some of the specific intermediates unique to this work. As described in Scheme 1, compounds such as P1, P16 or P3, P5, or P25, which may be prepared, respectively, from C5, C29 and C17, C25 and C179 may undergo nucleophilic aromatic substitution reactions with alcohols to afford products of the general structure Ia (See Scheme 1). As described in Scheme 2, compounds such as P5 or P25, which may be prepared, respectively, from C25 and C179, may undergo reactions such as alkylation or Mitsunobu reaction to afford products of the general structure Ia (See Scheme 2). As described in Scheme 10, α,β-unsaturated lactams such as (S)-3,3-dimethyl-1,7a-dihydropyrrolo[1,2-c]oxazol-5(3H)-one (P20) may be treated with an organometallic reagent such as an alkyllithium or alkyl Grignard reagent in the presence of chlorotrimethylsilane and a copper compound. Some examples in the literature include reaction of benzylidene-protected lactams with alkyl or vinyl cuprate reagents to afford addition of an alkyl or vinyl group anti to the existing stereocenter. For example, see: N. Okamoto et al., *Tetrahedron Asymmetry* 2001, 12(9), 1353-1358; S. Hara et al., *Tetrahedron* 2004, 60(37), 8031-8035; A. Endo and S. Danishefsky, *J. Am. Chem. Soc.* 2005, 127 (23), 8298-8299. In the chemistry described herein using the acetonide derivative P20, conjugate addition generally occurs in an unprecedented manner to afford a product with the new substituent syn to the existing stereocenter. Representative conjugate addition products include C53, C54, C55, and C56. Such lactams may undergo further elaboration, for example, to provide fluoro derivatives such as C53, C59, C61, and C62, or oxygenated derivatives such as C54.

TABLE 2

| Intermediate | Structure | Name |
|---|---|---|
| C5 | 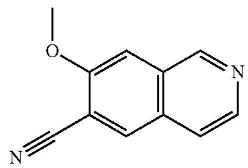 | 7-methoxy-isoquinoline-6-carbonitrile |
| C28 | 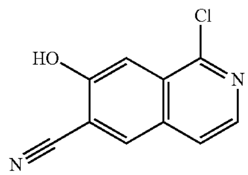 [SMILES: N#Cc1cc2ccnc(Cl)c2cc1O] | 1-chloro-7-hydroxyisoquinoline-6-carbonitrile |
| P1 | 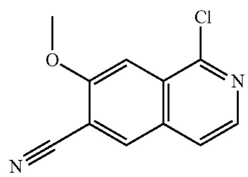 | 1-chloro-7-methoxyisoquinoline-6-carbonitrile |
| C29 | 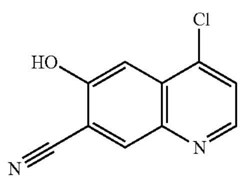 [SMILES: N#Cc1cc2nccc(Cl)c2cc1O] | 4-chloro-6-hydroxyquinoline-7-carbonitrile |
| P16 | 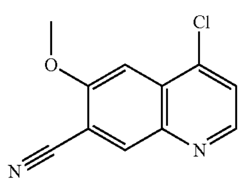 | 4-chloro-6-methoxyquinoline-7-carbonitrile |
| C17 | 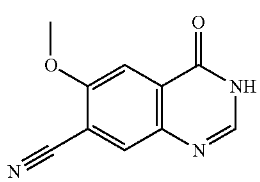 | 6-methoxy-4-oxo-3,4-dihydroquinazoline-7-carbonitrile |
| P3 | 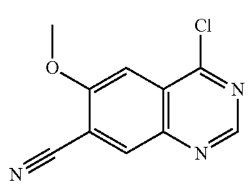 | 4-chloro-6-methoxyquinazoline-7-carbonitrile |
| C25 | 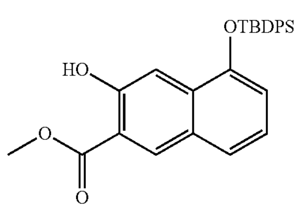 | methyl 5-((tert-butyldiphenylsilyl)oxy)-3-hydroxy-2-naphthoate |

TABLE 2-continued

| Intermediate | Structure | Name |
|---|---|---|
| P5 | 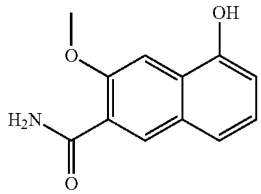 [SMILES: COc1cc2c(O)cccc2cc1C(N)=O] | 5-hydroxy-3-methoxy-2-naphthamide |
| C179 | 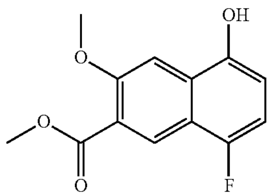 [SMILES: COC(=O)c1cc2c(F)ccc(O)c2cc1OC] | methyl 8-fluoro-5-hydroxy-3-methoxy-2-naphthoate |
| P25 | 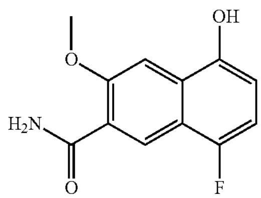 [SMILES: COc1cc2c(O)ccc(F)c2cc1C(N)=O] | 8-fluoro-5-hydroxy-3-methoxy-2-naphthamide |
| C53 | 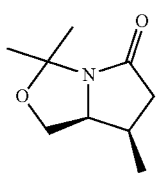 | (7R,7aS)-3,3,7-trimethyltetrahydropyrrolo[1,2-c]oxazol-5(3H)-one |
| C54 | 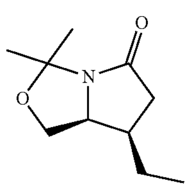 | (7R,7aS)-7-ethyl-3,3-dimethyltetrahydropyrrolo[1,2-c]oxazol-5(3H)-one |
| C55 | 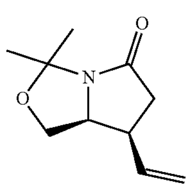 | (7S,7aS)-3,3-dimethyl-7-vinyltetrahydropyrrolo[1,2-c]oxazol-5(3H)-one |
| C56 | 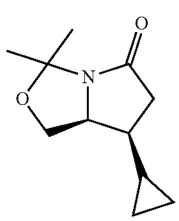 | (7S,7aS)-7-cyclopropyl-3,3-dimethyltetrahydropyrrolo[1,2-c]oxazol-5(3H)-one |
| C58 | 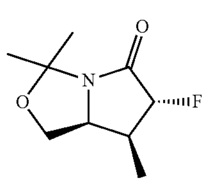 | (6R,7S,7aS)-6-fluoro-3,3,7-trimethyltetrahydropyrrolo[1,2-c]oxazol-5(3H)-one |

TABLE 2-continued

| Intermediate | Structure | Name |
|---|---|---|
| C59 | 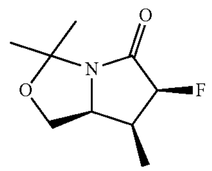 | (6S,7S,7aS)-6-fluoro-3,3,7-trimethyltetrahydropyrrolo[1,2-c]oxazol-5(3H)-one |
| C61 | 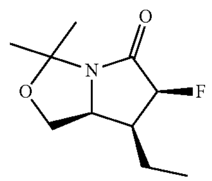 | (6S,7S,7aS)-7-ethyl-6-fluoro-3,3-dimethyltetrahydropyrrolo[1,2-c]oxazol-5(3H)-one |
| C62 | 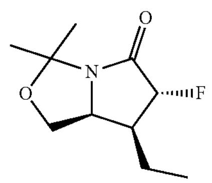 | (6R,7S,7aS)-7-ethyl-6-fluoro-3,3-dimethyltetrahydropyrrolo[1,2-c]oxazol-5(3H)-one |
| C54 | 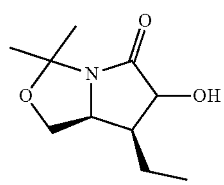 | (7S,7aS)-7-ethyl-6-hydroxy-3,3-dimethyltetrahydropyrrolo[1,2-c]oxazol-5(3H)-one |
| L38 | 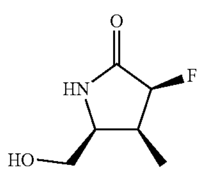 | (3S,4S,5S)-3-fluoro-5-(hydroxymethyl)-4-methylpyrrolidin-2-one |
| L47 | 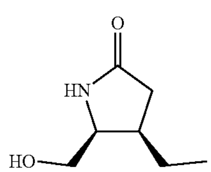 | (4R,5S)-4-ethyl-5-(hydroxymethyl)pyrrolidin-2-one |
| L74 | 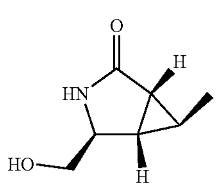 | (1R,4S,5S,6S)-4-(hydroxymethyl)-6-methyl-3-azabicyclo[3.1.0]hexan-2-one |
| L54 | 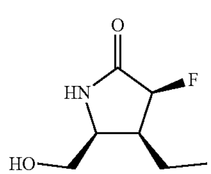 | (3S,4S,5S)-4-ethyl-3-fluoro-5-(hydroxymethyl)pyrrolidin-2-one |

TABLE 2-continued

| Intermediate | Structure | Name |
|---|---|---|
| L61 | 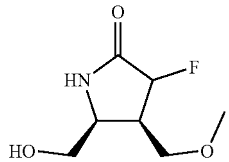 | (4R,5S)-3-fluoro-5-(hydroxymethyl)-4-(methoxymethyl)pyrrolidin-2-one |
| L68 | 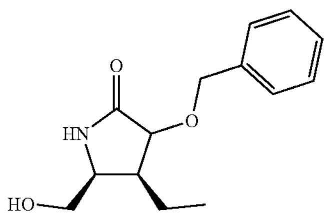 [SMILES: CC[C@@H]1C(OCc2ccccc2)C(=O)N[C@@H]1CO] | (4S,5S)-3-(benzyloxy)-4-ethyl-5-(hydroxymethyl)pyrrolidin-2-one |
| L116 | 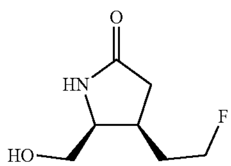 [SMILES: O=C1C[C@@H](CCF)[C@@H](CO)N1] | (4S,5S)-4-(2-fluoroethyl)-5-(hydroxymethyl)pyrrolidin-2-one |
| L118 | 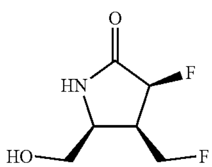 [SMILES: O=C1N[C@H](CO)[C@H](CF)[C@@H]1F] | (3S,4R,5S)-3-fluoro-4-(fluoromethyl)-5-(hydroxymethyl)pyrrolidin-2-one |
| L121 | 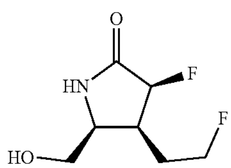 [SMILES: O=C1N[C@H](CO)[C@H](CCF)[C@@H]1F] | (3S,4S,5S)-3-fluoro-4-(2-fluoroethyl)-5-(hydroxymethyl)pyrrolidin-2-one |
| L124 | 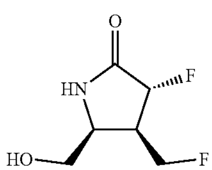 [SMILES: O=C1N[C@H](CO)[C@H](CF)[C@H]1F] | (3R,4R,5S)-3-fluoro-4-(fluoromethyl)-5-(hydroxymethyl)pyrrolidin-2-one |

Biological Activity:
IRAK4 Enzymatic DELFIA Assay, Protocol A.

This is an in vitro assay to measure IRAK4 enzymatic activity utilizing the DELFIA (Dissociation-Enhanced Lanthanide Fluorescent Immunoassay, Perkin-Elmer) platform, with the human IRAK4 FL (Full Length) construct to characterize IRAK4 inhibitor and control compounds at 0.6 mM ATP ($K_M$). The final amount of enzyme in the assay is 0.1 nM IRAK4 FL, final concentration of substrate is 50 nM, and final concentration of DMSO is 2.5%.

The test compound was solubilized in DMSO to a stock concentration of 30 mM. The dose response plates were prepared with a 4 mM primary compound concentration, and then diluted in DMSO in a four-fold series for a total of 11 data points. Compounds were prepared as a 40-fold multiple of the final in-assay concentration.

To begin the assay, 19 µL of reaction mixture containing 20 mM HEPES pH=7.5, 5 mM $MgCl_2$, 0.0025% Brij-35, 600 µM ATP, 0.21 nM Full-length phosphorylated recombinant human IRAK4 (GenBank ID AF445802) were aliquoted into Ultra-Clear Polypropylene, 384-well, U-Bottom Plates (Corning Life Sciences). 1 µL of test compound from the dose-response plate was added to the reaction mixture and incubated for 20 minutes at room temperature. Then 20 µL of 20 mM HEPES pH=7.5, 5 mM $MgCl_2$, 0.0025% Brij-35, 600 µM ATP, and 100 nM ERM-biotinylated peptide (AGAGRDKYKTLRQIR) was added to start the reaction. The reaction was incubated for 60 minutes at room temperature and stopped by the addition of 20 µL 0.3M EDTA.

50 µL of the reaction mixture was transferred to a streptavidin coated detection plate (DELFIA streptavidin coated plates, 384-well, white plates, Perkin-Elmer Life Sciences) and incubated for 30 minutes at room temperature. The plates were washed 4× with 75 µL per well of PBS containing 0.05% Tween-20. Plates were then incubated with 50 µL per well of antibody cocktail of Anti-pERM antibody at 0.125 µg/mL (Cell Signaling Technology), plus Anti-Rabbit IgG EuN1 at 0.25 ug/ml (Perkin-Elmer Life Sciences) in a solution of 10 mM MOPS pH=7.5, 150 mM NaCl, 0.05% Tween-20, 0.02% NaN$_3$, 1% BSA, 0.1% Gelatin for 45 minutes. The plates were washed 4× with 50 μL per well of PBS containing 0.05% Tween-20. Then 50 μL per well of DELFIA Enhancement Solution (Perkin-Elmer Life Sciences) were added to the plate and then read on an EnVision Model 2103 using a 340 nm excitation wavelength and a 665 nm emission wavelength for detection.

IRAK4 Enzymatic DELFIA Assay, Protocol B.

This is an in vitro assay to measure IRAK4 enzymatic activity utilizing the DELFIA (Dissociation-Enhanced Lanthanide Fluorescent Immunoassay, Perkin-Elmer) platform, with the human IRAK4 kinase domain (aa 154-460) construct to characterize IRAK4 inhibitor and control compounds at 0.6 mM ATP ($K_M$). The final amount of enzyme in the assay is 114 μM IRAK4 kinase domain, final concentration of substrate is 200 nM, and final concentration of DMSO is 5%.

The test compound was solubilized in DMSO to a stock concentration of 30 mM. The dose response plates were prepared with a 2 mM primary compound concentration, and then diluted in DMSO in a four-fold series for a total of 10 data points. Compounds were prepared as a 20-fold multiple of the final in-assay concentration To begin the assay, 45 μL of reaction mixture containing 20 mM HEPES pH=7.5, 5 mM MgCl$_2$, 0.0025% Brij-35, 600 μM ATP, 228 μM phosphorylated recombinant human IRAK4 kinase domain (aa 154-460; GenBank ID AF445802) were aliquoted into Ultra-Clear Polypropylene, 96-well, U-Bottom Plates (Corning Life Sciences). 5 μL of test compound from the dose-response plate was added to the reaction mixture and incubated for 15 minutes at room temperature. Then 50 μL of 20 mM HEPES pH=7.5, 5 mM MgCl$_2$, 0.0025% Brij-35, 600 μM ATP, and 400 nM ERM-biotinylated peptide (AGAGRDKYKTLRQIR) were added to start the reaction. The reaction was incubated for 90 minutes at room temperature and stopped by the addition of 25 μL 0.5M EDTA.

100 μL of the reaction mixture was transferred to a streptavidin coated detection plate (EvenCoat Streptavidin Coated Plates, 96-Well, R&D Systems) and incubated for 30 minutes at room temperature. The plates were washed 4 times with 100 μL per well of PBS containing 0.05% Tween-20. Plates were then incubated with 50 μL per well of antibody cocktail of Anti-pERM antibody (Cell Signaling Technology) diluted 1:5000, plus Anti-Rabbit IgG EuN1 at 0.242 μg/ml (Perkin-Elmer Life Sciences) in a solution of 10 mM MOPS pH=7.5, 150 mM NaCl, 0.05% Tween-20, 0.02% NaN$_3$, 1% BSA, 0.1% Gelatin for 45 minutes. The plates were washed 4× with 100 μL per well of PBS containing 0.05% Tween-20. Then 100 μL per well of DELFIA Enhancement Solution were added to the plate and then read on an EnVision Model 2103 using a 340 nm excitation wavelength and a 665 nm emission detection.

R848 Induced TNFα in Human PBMC Assay.

This protocol is for R848-induced TNFα production by human peripheral blood mononuclear cells (PBMCs). R848 is a synthetic agonist for the endosomal Toll-like receptors TLR7 and TLR8, which signal through interleukin-1 receptor-associated kinase 4 (IRAK4). The assay is used to assess cell-based potency of small molecule inhibitors of IRAK4 in the absence of serum.

Peripheral blood mononuclear cells (PBMC) were purified from fresh human blood by separation on a Histopaque-1077 cushion using ACCUSPIN-System-Histopaque—1077 system (Sigma Aldrich). Briefly, 30 mL of human blood were added to an ACCUSPIN tube containing 15 mL of Histopaque-1077 and spun for 20 minutes at 1200×g at room temperature in an Eppendorf 5804R swinging-bucket centrifuge with low brake. The PBMCs in the interphase layer were collected and washed with PBS via centrifugation multiple times until the supernatant is clear. The purified PBMCs were re-suspended in RPMI (Roswell Park Memorial Institute) media (Sigma-Aldrich).

For the assay, a compound dilution plate containing a top concentration of 4 mM compound in DMSO was serially diluted 4-fold for 11 times. 250 nL of the compound dilution plate was spotted into a 384-well, flat bottom with IId, TC-treated, black with clear bottom, sterile, polystyrene plate (Corning Life Sciences). 100,000 PBMCs in 50 μL of RPMI containing 5.5 μM R848 are added to each well of the 384 well plate and allowed to incubate for 3 hours at 37° C.

Plates were briefly spun at 1200×g Eppendorf 5804R swinging-bucket centrifuge for 5 minutes and 15 μL of the supernatant from each well is transferred to the corresponding well of a Human TNFα 384-Well Tissue Culture MSD Kit (Mesoscale Discovery). 10 μL of anti-TNFα antibody labeled with MSD SULFO-TAG at 50 μg/mL was added to each well and allowed to incubate overnight at 4° C. The plates were then washed with 1×PBS containing 0.05% Tween 20 after which 35 μL of MSD read buffer T (Mesoscale Discovery) was added to each well. The plates were then imaged on an MSD Sector Imager 6000.

TABLE 3

| | | | Biological Activity | |
|---|---|---|---|---|
| Ex. # | IRAK4 DELFIA Protocol A IC50 (nM) | IRAK4 DELFIA Protocol B IC50 (nM) | R848-induced TNFa PBMC IC50 (nM) | IUPAC NAME |
| 1 | | 2913 | | 4-(azetidin-3-ylmethoxy)-6-(propan-2-yloxy)quinoline-7-carboxamide |
| 2 | | 4497 | | 4-[(3S)-piperidin-3-ylmethoxy]-6-(propan-2-yloxy)quinoline-7-carboxamide |
| 3 | | 2239 | | 4-[(3R)-piperidin-3-ylmethoxy]-6-(propan-2-yloxy)quinoline-7-carboxamide |
| 4 | | 913 | | 4-(piperidin-4-ylmethoxy)-6-(propan-2-yloxy)quinoline-7-carboxamide |
| 5 | | 323 | | 4-[(1R,5S,6r)-3-azabicyclo[3.1.0]hex-6-ylmethoxy]-6-(propan-2-yloxy)quinoline-7-carboxamide |
| 6 | | 618 | | 4-(oxetan-3-ylmethoxy)-6-(propan-2-yloxy)quinoline-7-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 7 | | 170 | | 4-(cyclopentylmethoxy)-6-(propan-2-yloxy)quinoline-7-carboxamide |
| 8 | | 834 | | 4-(1-cyclobutylethoxy)-6-(propan-2-yloxy)quinoline-7-carboxamide |
| 9 | | 598 | | 4-(cyclobutylmethoxy)-6-(propan-2-yloxy)quinoline-7-carboxamide |
| 10 | | 752 | | 6-(propan-2-yloxy)-4-(tetrahydrofuran-3-ylmethoxy)quinoline-7-carboxamide |
| 11 | | 3234 | | 6-(propan-2-yloxy)-4-(tetrahydrofuran-2-ylmethoxy)quinoline-7-carboxamide |
| 12 | | 1042 | | 4-[(3-methyloxetan-3-yl)methoxy]-6-(propan-2-yloxy)quinoline-7-carboxamide |
| 13 | | 383 | | 4-[(1-methylcyclobutyl)methoxy]-6-(propan-2-yloxy)quinoline-7-carboxamide |
| 14 | | 231 | | 4-[(2R)-bicyclo[2.2.1]hept-2-yloxy]-6-(propan-2-yloxy)quinoline-7-carboxamide |
| 15 | | 2969 | | 6-(propan-2-yloxy)-4-[(2R)-tetrahydrofuran-2-ylmethoxy]quinoline-7-carboxamide |
| 16 | | 386 | | 4-(bicyclo[2.2.1]hept-2-yloxy)-6-(propan-2-yloxy)quinoline-7-carboxamide |
| 17 | | 476 | | 6-(propan-2-yloxy)-4-(tricyclo[2.2.1.0~2,6~]hept-3-yloxy)quinoline-7-carboxamide |
| 18 | | 507 | | 4-(1,3-dioxolan-4-ylmethoxy)-6-(propan-2-yloxy)quinoline-7-carboxamide |
| 19 | | 354 | | 4-[(1S,2R)-bicyclo[2.2.1]hept-2-yloxy]-6-(propan-2-yloxy)quinoline-7-carboxamide |
| 20 | | 102 | | 1-[(3aR,6aS)-octahydrocyclopenta[c]pyrrol-4-yloxy]-7-(propan-2-yloxy)isoquinoline-6-carboxamide |
| 21 | | 83 | | 4-[(3aR,6aS)-octahydrocyclopenta[c]pyrrol-4-yloxy]-6-(propan-2-yloxy)quinoline-7-carboxamide |
| 22 | | 45 | | 4-{[(3S)-1-(cyanoacetyl)pyrrolidin-3-yl]methoxy}-6-(propan-2-yloxy)quinoline-7-carboxamide |
| 23 | 656 | | | 4-{[(3R)-1-(cyanoacetyl)pyrrolidin-3-yl]methoxy}-6-(propan-2-yloxy)quinoline-7-carboxamide |
| 24 | | 492 | | 7-(propan-2-yloxy)-1-(tetrahydrofuran-3-ylmethoxy)isoquinoline-6-carboxamide |
| 25 | | 1130 | | 7-(propan-2-yloxy)-1-(tetrahydro-2H-pyran-2-ylmethoxy)isoquinoline-6-carboxamide |
| 26 | 4.6 | | 133 | 1-{[(2S)-5-oxopyrrolidin-2-yl]methoxy}-7-(propan-2-yloxy)isoquinoline-6-carboxamide |
| 27 | | 2483 | | 1-[(1,1-dioxido-1,2-thiazinan-3-yl)methoxy]-7-(propan-2-yloxy)isoquinoline-6-carboxamide |
| 28 | | 1320 | | 1-[(3S)-piperidin-3-ylmethoxy]-7-(propan-2-yloxy)isoquinoline-6-carboxamide |
| 29 | | 76 | | 1-[(3-methyl-2-oxo-1,3-oxazolidin-4-yl)methoxy]-7-(propan-2-yloxy)isoquinoline-6-carboxamide |
| 30 | | 2445 | | 7-(propan-2-yloxy)-1-[(2R)-tetrahydrofuran-2-ylmethoxy]isoquinoline-6-carboxamide |
| 31 | | 2616 | | 1-{[(2S)-1-methylpyrrolidin-2-yl]methoxy}-7-(propan-2-yloxy)isoquinoline-6-carboxamide |
| 32 | 840 | | | 1-{[(2R)-5-oxopyrrolidin-2-yl]methoxy}-7-(propan-2-yloxy)isoquinoline-6-carboxamide |
| 33 | | 2862 | | 1-[(1-acetylpiperidin-4-yl)methoxy]-7-(propan-2-yloxy)isoquinoline-6-carboxamide |
| 34 | | 483 | | 1-{[(3R,4R)-4-methoxypyrrolidin-3-yl]methoxy}-7-(propan-2-yloxy)isoquinoline-6-carboxamide |
| 35 | | 16 | | 1-[(2-oxo-1,3-oxazolidin-5-yl)methoxy]-7-(propan-2-yloxy)isoquinoline-6-carboxamide |
| 36 | | 735 | | 7-(propan-2-yloxy)-1-(tetrahydro-2H-pyran-4-ylmethoxy)isoquinoline-6-carboxamide |
| 37 | | 3516 | | 1-[(2S)-morpholin-2-ylmethoxy]-7-(propan-2-yloxy)isoquinoline-6-carboxamide |
| 38 | | 4640 | | 1-[(4-fluoropiperidin-4-yl)methoxy]-7-(propan-2-yloxy)isoquinoline-6-carboxamide |
| 39 | | 386 | | 1-(morpholin-2-ylmethoxy)-7-(propan-2-yloxy)isoquinoline-6-carboxamide |
| 40 | | 109 | | 1-[(1S,5S)-3-azabicyclo[3.1.0]hex-1-ylmethoxy]-7-(propan-2-yloxy)isoquinoline-6-carboxamide |
| 41 | | 2351 | | 7-(propan-2-yloxy)-1-[(2R)-pyrrolidin-2-ylmethoxy]isoquinoline-6-carboxamide |
| 42 | | 219 | | 1-[(1R,5S,6r)-3-azabicyclo[3.1.0]hex-6-ylmethoxy]-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 43 | | 3323 | | 1-(piperidin-2-ylmethoxy)-7-(propan-2-yloxy)isoquinoline-6-carboxamide |
| 44 | | 4265 | | 1-[(4-methylmorpholin-2-yl)methoxy]-7-(propan-2-yloxy)isoquinoline-6-carboxamide |
| 45 | | 1922 | | 1-[(1-methylpiperidin-3-yl)methoxy]-7-(propan-2-yloxy)isoquinoline-6-carboxamide |
| 46 | | 237 | | 7-(propan-2-yloxy)-1-{[(3R,4R)-4-(trifluoromethyl)pyrrolidin-3-yl]methoxy}isoquinoline-6-carboxamide |
| 47 | | 2786 | | 1-[(2R)-morpholin-2-ylmethoxy]-7-(propan-2-yloxy)isoquinoline-6-carboxamide |
| 48 | | 366 | | 1-[(3R)-piperidin-3-ylmethoxy]-7-(propan-2-yloxy)isoquinoline-6-carboxamide |
| 49 | | 451 | | 7-(propan-2-yloxy)-1-[(3S)-pyrrolidin-3-ylmethoxy]isoquinoline-6-carboxamide |
| 50 | | 701 | | 6-(propan-2-yloxy)-4-[(3S)-pyrrolidin-3-ylmethoxy]quinoline-7-carboxamide |
| 51 | | 2412 | | 4-[(2S)-morpholin-2-ylmethoxy]-6-(propan-2-yloxy)quinoline-7-carboxamide |
| 52 | | 4236 | | 4-(7-azaspiro[3.5]non-1-yloxy)-6-(propan-2-yloxy)quinoline-7-carboxamide |
| 53 | | 2380 | | 4-[(2R)-morpholin-2-ylmethoxy]-6-(propan-2-yloxy)quinoline-7-carboxamide |
| 54 | | 2435 | | 4-[(4-fluoropiperidin-4-yl)methoxy]-6-(propan-2-yloxy)quinoline-7-carboxamide |
| 55 | | 264 | | 4-{[(3R,4R)-3,4-dimethylpyrrolidin-3-yl]methoxy}-6-(propan-2-yloxy)quinoline-7-carboxamide |
| 56 | | 1489 | | 4-[(4-methylpiperidin-4-yl)methoxy]-6-(propan-2-yloxy)quinoline-7-carboxamide |
| 57 | | 5.8 | | 4-{[(5R)-2-oxo-1,3-oxazolidin-5-yl]methoxy}-6-(propan-2-yloxy)quinoline-7-carboxamide |
| 58 | | 144 | | 4-[(3-methylpiperidin-3-yl)methoxy]-6-(propan-2-yloxy)quinoline-7-carboxamide |
| 59 | | 243 | | 4-(piperidin-3-ylmethoxy)-6-(propan-2-yloxy)quinoline-7-carboxamide |
| 60 | 8.9 | | | 4-{[1-(cyanoacetyl)azetidin-3-yl]methoxy}-6-(propan-2-yloxy)quinoline-7-carboxamide |
| 61 | | 249 | | 1-{[(2R)-1-(cyanoacetyl)pyrrolidin-2-yl]methoxy}-7-(propan-2-yloxy)isoquinoline-6-carboxamide |
| 62 | | 1286 | | 1-{[1-(cyanoacetyl)piperidin-4-yl]methoxy}-7-(propan-2-yloxy)isoquinoline-6-carboxamide |
| 63 | | 252 | | 1-{[(2S)-1-(cyanoacetyl)pyrrolidin-2-yl]methoxy}-7-(propan-2-yloxy)isoquinoline-6-carboxamide |
| 64 | | 641 | | 1-{[(3R)-4-(cyanoacetyl)morpholin-3-yl]methoxy}-7-(propan-2-yloxy)isoquinoline-6-carboxamide |
| 65 | | 563 | | 1-({1-[(cyanoacetyl)amino]cyclopentyl}methoxy)-7-(propan-2-yloxy)isoquinoline-6-carboxamide |
| 66 | | 255 | | 1-{[(3S)-1-(cyanoacetyl)pyrrolidin-3-yl]methoxy}-7-(propan-2-yloxy)isoquinoline-6-carboxamide |
| 67 | | 1730 | | 1-{[(3R)-1-(cyanoacetyl)piperidin-3-yl]methoxy}-7-(propan-2-yloxy)isoquinoline-6-carboxamide |
| 68 | | 320 | | 1-{[(1R,5R,6R)-3-(cyanoacetyl)-3-azabicyclo[3.2.1]oct-6-yl]oxy}-7-(propan-2-yloxy)isoquinoline-6-carboxamide |
| 69 | 29 | | | 1-{[1-(cyanoacetyl)azetidin-3-yl]methoxy}-7-(propan-2-yloxy)isoquinoline-6-carboxamide |
| 70 | | 423 | | 1-{[(3R)-1-(cyanoacetyl)pyrrolidin-3-yl]methoxy}-7-(propan-2-yloxy)isoquinoline-6-carboxamide |
| 71 | | 153 | | 4-{[(3aR,6aS)-2-(cyanoacetyl)octahydrocyclopenta[c]pyrrol-4-yl]oxy}-6-(propan-2-yloxy)quinoline-7-carboxamide |
| 72 | | 2625 | | 1-[(1S,4R)-2-azabicyclo[2.2.1]hept-6-yloxy]-7-(propan-2-yloxy)isoquinoline-6-carboxamide |
| 73 | | 1161 | | 1-{[(2S)-1-(cyanoacetyl)azetidin-2-yl]methoxy}-7-(propan-2-yloxy)isoquinoline-6-carboxamide |
| 74 | | 43 | | 1-{[(1S,4S,5S)-2-(cyanoacetyl)-2-azabicyclo[2.2.1]hept-5-yl]oxy}-7-(propan-2-yloxy)isoquinoline-6-carboxamide |
| 75 | | 4039 | | 1-{[(2S)-4-(cyanoacetyl)morpholin-2-yl]methoxy}-7-(propan-2-yloxy)isoquinoline-6-carboxamide |
| 76 | | 1721 | | 1-{[1-(cyanoacetyl)-4-fluoropiperidin-4-yl]methoxy}-7-(propan-2-yloxy)isoquinoline-6-carboxamide |
| 77 | | 468 | | 1-{[(1S,5S)-3-(cyanoacetyl)-3-azabicyclo[3.1.0]hex-1-yl]methoxy}-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 78 | | 4743 | | 1-{[(2R)-4-(cyanoacetyl)morpholin-2-yl]methoxy}-7-(propan-2-yloxy)isoquinoline-6-carboxamide |
| 79 | | 457 | | 1-{[(3aR,4S,6aS)-2-(cyanoacetyl)octahydrocyclopenta[c]pyrrol-4-yl]oxy}-7-(propan-2-yloxy)isoquinoline-6-carboxamide |
| 80 | | 333 | | 1-{[(3R,4R)-1-(cyanoacetyl)-4-ethylpyrrolidin-3-yl]methoxy}-7-(propan-2-yloxy)isoquinoline-6-carboxamide |
| 81 | | 479 | | 1-{[(1S,5S,6S)-3-(cyanoacetyl)-3-azabicyclo[3.2.1]oct-6-yl]oxy}-7-(propan-2-yloxy)isoquinoline-6-carboxamide |
| 82 | | 969 | | 1-{[1-(cyanoacetyl)-3-methylpyrrolidin-3-yl]methoxy}-7-(propan-2-yloxy)isoquinoline-6-carboxamide |
| 83 | | 175 | | 1-{[(3S)-4-(cyanoacetyl)morpholin-3-yl]methoxy}-7-(propan-2-yloxy)isoquinoline-6-carboxamide |
| 84 | | 534 | | 1-{[(3R,4R)-1-(cyanoacetyl)-4-methoxypyrrolidin-3-yl]methoxy}-7-(propan-2-yloxy)isoquinoline-6-carboxamide |
| 85 | | 610 | | 1-{[(3R,4R)-1-(cyanoacetyl)-4-methylpyrrolidin-3-yl]methoxy}-7-(propan-2-yloxy)isoquinoline-6-carboxamide |
| 86 | | 216 | | 1-{[1-(cyanoacetyl)-4-methylpiperidin-4-yl]methoxy}-7-(propan-2-yloxy)isoquinoline-6-carboxamide |
| 87 | | 2621 | | 4-{[(1R,5S,6r)-3-(cyanoacetyl)-3-azabicyclo[3.1.0]hex-6-yl]methoxy}-6-(propan-2-yloxy)quinoline-7-carboxamide |
| 88 | | 292 | | 4-{[(3R,4R)-1-(cyanoacetyl)-4-methylpyrrolidin-3-yl]methoxy}-6-(propan-2-yloxy)quinoline-7-carboxamide |
| 89 | | 395 | | 4-{[(1R,5R,6R)-3-(cyanoacetyl)-3-azabicyclo[3.2.1]oct-6-yl]oxy}-6-(propan-2-yloxy)quinoline-7-carboxamide |
| 90 | | 438 | | 4-{[(1S,5S)-3-(cyanoacetyl)-3-azabicyclo[3.1.0]hex-1-yl]methoxy}-6-(propan-2-yloxy)quinoline-7-carboxamide |
| 91 | | 489 | | 4-{[1-(cyanoacetyl)-4-methylpiperidin-4-yl]methoxy}-6-(propan-2-yloxy)quinoline-7-carboxamide |
| 92 | | 473 | | 4-{[(1S,5S,6S)-3-(cyanoacetyl)-3-azabicyclo[3.2.1]oct-6-yl]oxy}-6-(propan-2-yloxy)quinoline-7-carboxamide |
| 93 | | 1520 | | 4-{[(3S)-1-(cyanoacetyl)piperidin-3-yl]methoxy}-6-(propan-2-yloxy)quinoline-7-carboxamide |
| 94 | | 526 | | 4-{[(1S,5S)-3-(cyanoacetyl)-3-azabicyclo[3.1.0]hex-1-yl]methoxy}-6-(propan-2-yloxy)quinoline-7-carboxamide |
| 95 | | 3167 | | 4-{[1-(cyanoacetyl)-4-fluoropiperidin-4-yl]methoxy}-6-(propan-2-yloxy)quinoline-7-carboxamide |
| 96 | | 301 | | 4-{[(3R,4R)-1-(cyanoacetyl)-4-methoxypyrrolidin-3-yl]methoxy}-6-(propan-2-yloxy)quinoline-7-carboxamide |
| 97 | | 2741 | | 4-{[(3R)-1-(cyanoacetyl)piperidin-3-yl]methoxy}-6-(propan-2-yloxy)quinoline-7-carboxamide |
| 98 | | 575 | | 4-{[(2S)-4-(cyanoacetyl)morpholin-2-yl]methoxy}-6-(propan-2-yloxy)quinoline-7-carboxamide |
| 99 | | 524 | | 4-{[1-(cyanoacetyl)piperidin-2-yl]methoxy}-6-(propan-2-yloxy)quinoline-7-carboxamide |
| 100 | | 482 | | 4-{[1-(cyanoacetyl)piperidin-4-yl]methoxy}-6-(propan-2-yloxy)quinoline-7-carboxamide |
| 101 | | 1177 | | 1-[(1S,4S,5S)-2-azabicyclo[2.2.1]hept-5-yloxy]-7-(propan-2-yloxy)isoquinoline-6-carboxamide |
| 02 | | 217 | | 1-[(1R,4R,5R)-2-azabicyclo[2.2.1]hept-5-yloxy]-7-(propan-2-yloxy)isoquinoline-6-carboxamide |
| 03 | 575 | | 2741 | 1-{[(2S)-5-oxopyrrolidin-2-yl]methoxy}-7-(propan-2-yloxy)isoquinoline-6-carbonitrile |
| 04 | 6.6 | | 1796 | 1-{[(4R)-2-oxo-1,3-oxazolidin-4-yl]methoxy}-7-(propan-2-yloxy)isoquinoline-6-carboxamide |
| 05 | 84 | | | 4-methyl-1-{[(2S)-5-oxopyrrolidin-2-yl]methoxy}-7-(propan-2-yloxy)isoquinoline-6-carboxamide |
| 06 | 51 | | 472 | 1-{[(2S)-6-oxopiperidin-2-yl]methoxy}-7-(propan-2-yloxy)isoquinoline-6-carboxamide |
| 107 | | 16 | | 1-{[(2S)-4-methyl-5-oxopyrrolidin-2-yl]methoxy}-7-(propan-2-yloxy)isoquinoline-6-carboxamide |
| 108 | | 1867 | | 1-[(1S,4R,6R)-2-azabicyclo[2.2.1]hept-6-yloxy]-7-(propan-2-yloxy)isoquinoline-6-carboxamide |
| 109 | | 1909 | | 1-[(1S,4R,6S)-2-azabicyclo[2.2.1]hept-6-yloxy]-7-(propan-2-yloxy)isoquinoline-6-carboxamide |
| 110 | 418 | | 1167 | 1-{[(2S)-4,4-dimethyl-5-oxopyrrolidin-2-yl]methoxy}-7-(propan-2-yloxy)isoquinoline-6-carboxamide |
| 111 | | 196 | | 1-[(5-oxopyrrolidin-3-yl)methoxy]-7-(propan-2-yloxy)isoquinoline-6-carboxamide |
| 112 | 1 | | 50 | 1-{[(2S)-4-fluoro-5-oxopyrrolidin-2-yl]methoxy}-7-(propan-2-yloxy)isoquinoline-6-carboxamide |
| 113 | | 53 | | 1-{[(2S)-4-ethyl-5-oxopyrrolidin-2-yl]methoxy}-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 114 | 0.7 | | 33 | 5-{[(2S)-5-oxopyrrolidin-2-yl]methoxy}-3-(propan-2-yloxy)naphthalene-2-carboxamide |
| 115 | | 61 | | 3-(propan-2-yloxy)-5-[(3R)-pyrrolidin-3-ylmethoxy]naphthalene-2-carboxamide |
| 116 | 146 | | | 1-[(5-oxomorpholin-3-yl)methoxy]-7-(propan-2-yloxy)isoquinoline-6-carboxamide |
| 117 | | 136 | | 7-(propan-2-yloxy)-1-[(3R)-pyrrolidin-3-ylmethoxy]isoquinoline-6-carboxamide |
| 118 | 162 | | | 1-[(3-oxooctahydro-1H-isoindol-1-yl)methoxy]-7-(propan-2-yloxy)isoquinoline-6-carboxamide |
| 119 | | 1429 | | 1-[(2S)-azetidin-2-ylmethoxy]-7-(propan-2-yloxy)isoquinoline-6-carboxamide |
| 120 | 1141 | | | 7-(cyclobutyloxy)-1-{[(2S)-5-oxopyrrolidin-2-yl]methoxy}isoquinoline-6-carboxamide |
| 121 | 7.6 | | 347 | 7-methoxy-1-{[(2S)-5-oxopyrrolidin-2-yl]methoxy}isoquinoline-6-carboxamide |
| 122 | 24 | | 672 | 7-ethoxy-1-{[(2S)-5-oxopyrrolidin-2-yl]methoxy}isoquinoline-6-carboxamide |
| 123 | 747 | | | 1-[(3aR,6aR)-hexahydrocyclopenta[c]pyrrol-3a(1H)-ylmethoxy]-7-(propan-2-yloxy)isoquinoline-6-carboxamide |
| 124 | 7.8 | | 175 | 1-{[(2S,4R)-4-methyl-5-oxopyrrolidin-2-yl]methoxy}-7-(propan-2-yloxy)isoquinoline-6-carboxamide |
| 125 | 40 | | 685 | 1-{[(2S,4S)-4-methyl-5-oxopyrrolidin-2-yl]methoxy}-7-(propan-2-yloxy)isoquinoline-6-carboxamide |
| 126 | 42 | | | 1-{[(2S)-2-methyl-5-oxopyrrolidin-2-yl]methoxy}-7-(propan-2-yloxy)isoquinoline-6-carboxamide |
| 127 | 65 | | 682 | 1-{[(2S)-4-(methoxymethyl)-5-oxopyrrolidin-2-yl]methoxy}-7-(propan-2-yloxy)isoquinoline-6-carboxamide |
| 128 | 0.3 | | 27 | 1-{[(2S)-4,4-difluoro-5-oxopyrrolidin-2-yl]methoxy}-7-(propan-2-yloxy)isoquinoline-6-carboxamide |
| 129 | 231 | | | 7-(difluoromethoxy)-1-{[(2S)-5-oxopyrrolidin-2-yl]methoxy}isoquinoline-6-carboxamide |
| 130 | | 417 | | 1-{[(3aS,6R,6aR)-2-oxooctahydrocyclopenta[b]pyrrol-6-yl]oxy}-7-(propan-2-yloxy)isoquinoline-6-carboxamide |
| 131 | 0.6 | | 29 | 1-{[(2S,4S)-4-ethyl-4-fluoro-5-oxopyrrolidin-2-yl]methoxy}-7-(propan-2-yloxy)isoquinoline-6-carboxamide |
| 132 | 188 | | 1180 | 1-{[(2S,4R)-4-ethyl-4-fluoro-5-oxopyrrolidin-2-yl]methoxy}-7-(propan-2-yloxy)isoquinoline-6-carboxamide |
| 133 | 175 | | | 1-{[(2S,4R)-4-fluoro-4-methyl-5-oxopyrrolidin-2-yl]methoxy}-7-(propan-2-yloxy)isoquinoline-6-carboxamide |
| 134 | 1 | | 36 | 1-{[(2S,4S)-4-fluoro-4-methyl-5-oxopyrrolidin-2-yl]methoxy}-7-(propan-2-yloxy)isoquinoline-6-carboxamide |
| 135 | 1.2 | | 32 | 1-{[(2S,4S)-4-ethyl-5-oxopyrrolidin-2-yl]methoxy}-7-(propan-2-yloxy)isoquinoline-6-carboxamide |
| 136 | 7.8 | | 184 | 1-{[(2S,4R)-4-ethyl-5-oxopyrrolidin-2-yl]methoxy}-7-(propan-2-yloxy)isoquinoline-6-carboxamide |
| 137 | 98 | | | 1-{[(2S,4R)-4-(2-hydroxypropan-2-yl)-5-oxopyrrolidin-2-yl]methoxy}-7-(propan-2-yloxy)isoquinoline-6-carboxamide |
| 138 | | 1037 | | 1-[(2-oxopiperidin-4-yl)methoxy]-7-(propan-2-yloxy)isoquinoline-6-carboxamide |
| 139 | | 256 | | 1-[(1S,5S)-3-azabicyclo[3.1.0]hex-1-ylmethoxy]-7-(propan-2-yloxy)isoquinoline-6-carboxamide |
| 140 | | 84 | | 1-[(1R,5R)-3-azabicyclo[3.1.0]hex-1-ylmethoxy]-7-(propan-2-yloxy)isoquinoline-6-carboxamide |
| 141 | 70 | | 294 | 1-{[(2S,3S)-3-methyl-5-oxopyrrolidin-2-yl]methoxy}-7-(propan-2-yloxy)isoquinoline-6-carboxamide |
| 142 | 1222 | | | 1-[(6-oxopiperidin-3-yl)methoxy]-7-(propan-2-yloxy)isoquinoline-6-carboxamide |
| 143 | 2542 | | | 1-[(1,1-dioxido-1,2-thiazolidin-3-yl)methoxy]-7-(propan-2-yloxy)isoquinoline-6-carboxamide |
| 144 | 1.4 | | 141 | 1-{[(2S,4R)-4-fluoro-5-oxopyrrolidin-2-yl]methoxy}-7-(propan-2-yloxy)isoquinoline-6-carboxamide |
| 145 | 0.4 | | 41 | 1-{[(2S,4S)-4-fluoro-5-oxopyrrolidin-2-yl]methoxy}-7-(propan-2-yloxy)isoquinoline-6-carboxamide |
| 146 | 0.2 | | 15 | 1-{[(2S)-4,4-difluoro-5-oxopyrrolidin-2-yl]methoxy}-7-methoxyisoquinoline-6-carboxamide |
| 147 | 59 | | 1161 | 1-{[2-(hydroxymethyl)-5-oxopyrrolidin-2-yl]methoxy}-7-(propan-2-yloxy)isoquinoline-6-carboxamide |
| 148 | | 24 | | 1-{[(2S)-4-(hydroxymethyl)-5-oxopyrrolidin-2-yl]methoxy}-7-(propan-2-yloxy)isoquinoline-6-carboxamide |
| 149 | 105 | | | 1-{[(2S,3S)-3-amino-5-oxopyrrolidin-2-yl]methoxy}-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 150 | 41 | | 864 | 1-{[(2S,4S)-4-hydroxy-5-oxopyrrolidin-2-yl]methoxy}-7-(propan-2-yloxy)isoquinoline-6-carboxamide |
| 151 | 1.2 | | 25 | 1-{[(2S,4S)-5-oxo-4-(2,2,2-trifluoroethyl)pyrrolidin-2-yl]methoxy}-7-(propan-2-yloxy)isoquinoline-6-carboxamide |
| 152 | 6.7 | | 139 | 1-{[(2S,4R)-5-oxo-4-(2,2,2-trifluoroethyl)pyrrolidin-2-yl]methoxy}-7-(propan-2-yloxy)isoquinoline-6-carboxamide |
| 153 | 1480 | | | 1-{[(2S)-2-(hydroxymethyl)-5-oxopyrrolidin-2-yl]methoxy}-7-(propan-2-yloxy)isoquinoline-6-carboxamide |
| 154 | 17 | | | 1-{[(2R)-2-(hydroxymethyl)-5-oxopyrrolidin-2-yl]methoxy}-7-(propan-2-yloxy)isoquinoline-6-carboxamide |
| 155 | 267 | | | 1-{[(2S,3S)-5-oxo-3-(trifluoromethyl)pyrrolidin-2-yl]methoxy}-7-(propan-2-yloxy)isoquinoline-6-carboxamide |
| 156 | 4097 | | | 1-{(1R)-1-[(2S)-5-oxopyrrolidin-2-yl]ethoxy}-7-(propan-2-yloxy)isoquinoline-6-carboxamide |
| 157 | 152 | | | 1-{(1S)-1-[(2S)-5-oxopyrrolidin-2-yl]ethoxy}-7-(propan-2-yloxy)isoquinoline-6-carboxamide |
| 158 | | 1443 | | 1-[(3R)-morpholin-3-ylmethoxy]-7-(propan-2-yloxy)isoquinoline-6-carboxamide |
| 159 | | 3377 | | 7-(propan-2-yloxy)-1-(pyrrolidin-2-ylmethoxy)isoquinoline-6-carboxamide |
| 160 | | 151 | | 1-[(3S)-morpholin-3-ylmethoxy]-7-(propan-2-yloxy)isoquinoline-6-carboxamide |
| 161 | | 88 | | 1-[(1R,6S)-3-azabicyclo[4.1.0]hept-1-ylmethoxy]-7-(propan-2-yloxy)isoquinoline-6-carboxamide |
| 162 | | 35 | | 1-[(1S,6R)-3-azabicyclo[4.1.0]hept-1-ylmethoxy]-7-(propan-2-yloxy)isoquinoline-6-carboxamide |
| 163 | 1396 | | 7449 | 1-{[(2S,4S)-4-fluoro-4-(hydroxymethyl)-5-oxopyrrolidin-2-yl]methoxy}-7-(propan-2-yloxy)isoquinoline-6-carboxamide |
| 164 | 1.7 | | 116 | 1-{[(2S,4R)-4-fluoro-4-(hydroxymethyl)-5-oxopyrrolidin-2-yl]methoxy}-7-(propan-2-yloxy)isoquinoline-6-carboxamide |
| 165 | 541 | | | 1-{[(2S,4R)-4-(hydroxymethyl)-5-oxopyrrolidin-2-yl]methoxy}-7-(propan-2-yloxy)isoquinoline-6-carboxamide |
| 166 | 4.3 | | 389 | 1-{[(2S,4S)-4-(hydroxymethyl)-5-oxopyrrolidin-2-yl]methoxy}-7-(propan-2-yloxy)isoquinoline-6-carboxamide |
| 167 | | 19 | | 1-{[(3aR,4R,6aR)-2,2-dimethyl-6-oxotetrahydro-3aH-[1,3]dioxolo[4,5-c]pyrrol-4-yl]methoxy}-7-(propan-2-yloxy)isoquinoline-6-carboxamide |
| 168 | 6.6 | | 1456 | 4-fluoro-1-{[(2S)-5-oxopyrrolidin-2-yl]methoxy}-7-(propan-2-yloxy)isoquinoline-6-carboxamide |
| 169 | 890 | | | 1-{[(2S)-5-oxopyrrolidin-2-yl]methoxy}-7-(propan-2-yloxy)isoquinoline-6-carboxylic acid |
| 170 | 0.8 | | 41 | 1-{[(2S,3S,4R)-4-fluoro-3-methyl-5-oxopyrrolidin-2-yl]methoxy}-7-(propan-2-yloxy)isoquinoline-6-carboxamide |
| 171 | 101 | | | 1-{[(2S,4R)-4-fluoro-4-(2-hydroxypropan-2-yl)-5-oxopyrrolidin-2-yl]methoxy}-7-(propan-2-yloxy)isoquinoline-6-carboxamide |
| 173 | 1.3 | | 37 | 3-methoxy-5-{[(2S)-5-oxopyrrolidin-2-yl]methoxy}naphthalene-2-carboxamide |
| 174 | 3.1 | | 126 | 1-{[(1S,2S,5R)-4-oxo-3-azabicyclo[3.1.0]hex-2-yl]methoxy}-7-(propan-2-yloxy)isoquinoline-6-carboxamide |
| 175 | | 101 | | 1-{[(1S,5S)-4-oxo-3-azabicyclo[3.1.0]hex-1-yl]methoxy}-7-(propan-2-yloxy)isoquinoline-6-carboxamide |
| 176 | 695 | | | 8-fluoro-1-{[(2S)-5-oxopyrrolidin-2-yl]methoxy}-7-(propan-2-yloxy)isoquinoline-6-carboxamide |
| 177 | 3.8 | | 43 | 1-{[(2S,4S)-4-fluoro-4-methyl-5-oxopyrrolidin-2-yl]methoxy}-7-methoxyisoquinoline-6-carboxamide |
| 178 | 1689 | | | 1-{[(2S)-5-oxopyrrolidin-2-yl]methoxy}-7-(trifluoromethoxy)isoquinoline-6-carboxamide |
| 179 | 1.2 | | 199 | 1-{[(2S,4R)-4-hydroxy-5-oxopyrrolidin-2-yl]methoxy}-7-(propan-2-yloxy)isoquinoline-6-carboxamide |
| 180 | 1786 | | 2555 | 1-{[(2S)-1-methyl-5-oxopyrrolidin-2-yl]methoxy}-7-(propan-2-yloxy)isoquinoline-6-carboxamide |
| 181 | 5.7 | | 503 | 1-{[(2S)-4-(4-hydroxytetrahydro-2H-pyran-4-yl)-5-oxopyrrolidin-2-yl]methoxy}-7-(propan-2-yloxy)isoquinoline-6-carboxamide |
| 182 | 1048 | | | 1-{[(2S,4R)-4-hydroxy-5-oxo-4-(2,2,2-trifluoroethyl)pyrrolidin-2-yl]methoxy}-7-(propan-2-yloxy)isoquinoline-6-carboxamide |
| 183 | 0.2 | | 10 | 1-{[(2S,3S)-4,4-difluoro-3-methyl-5-oxopyrrolidin-2-yl]methoxy}-7-(propan-2-yloxy)isoquinoline-6-carboxamide |
| 184 | | 60 | | 1-{[(2S,4S)-4-hydroxy-5-oxo-4-(2,2,2-trifluoroethyl)pyrrolidin-2-yl]methoxy}-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 185 | 116 | | | 1-{[(4S)-1-methyl-2-oxoimidazolidin-4-yl]methoxy}-7-(propan-2-yloxy)isoquinoline-6-carboxamide |
| 186 | 303 | | | 1-{[(5S,6R)-2-oxo-1-azaspiro[4.4]non-6-yl]oxy}-7-(propan-2-yloxy)isoquinoline-6-carboxamide |
| 187 | 1.1 | | 40 | 1-{[(2S,3S,4S)-4-fluoro-3-methyl-5-oxopyrrolidin-2-yl]methoxy}-7-(propan-2-yloxy)isoquinoline-6-carboxamide |
| 188 | 1.9 | | 30 | 1-{[(2S,3S,4R)-4-fluoro-3-methyl-5-oxopyrrolidin-2-yl]methoxy}-7-methoxyisoquinoline-6-carboxamide |
| 189 | 0.3 | | 12 | 1-{[(2S,3S,4S)-4-fluoro-3-methyl-5-oxopyrrolidin-2-yl]methoxy}-7-methoxyisoquinoline-6-carboxamide |
| 190 | 294 | | | 4-cyano-1-{[(2S)-5-oxopyrrolidin-2-yl]methoxy}-7-(propan-2-yloxy)isoquinoline-6-carboxamide |
| 191 | | 252 | | 7-(propan-2-yloxy)-1-(pyrrolidin-3-ylmethoxy)isoquinoline-6-carboxamide |
| 192 | 284 | | | 1-{[(2S,4R)-4-(3-hydroxyoxetan-3-yl)-5-oxopyrrolidin-2-yl]methoxy}-7-(propan-2-yloxy)isoquinoline-6-carboxamide |
| 193 | 238 | | | 1-{[(2S,4S)-4-(3-hydroxyoxetan-3-yl)-5-oxopyrrolidin-2-yl]methoxy}-7-(propan-2-yloxy)isoquinoline-6-carboxamide |
| 194 | 1 | | 5.2 | 5-{[(2S,4S)-4-fluoro-4-methyl-5-oxopyrrolidin-2-yl]methoxy}-3-methoxynaphthalene-2-carboxamide |
| 195 | 3402 | | | 4-(aminomethyl)-1-{[(2S)-5-oxopyrrolidin-2-yl]methoxy}-7-(propan-2-yloxy)isoquinoline-6-carboxamide |
| 196 | | | 11 | 1-{[(2R,3R,4S)-3-ethyl-4-fluoro-3-hydroxy-5-oxopyrrolidin-2-yl]methoxy}-7-methoxyisoquinoline-6-carboxamide |
| 197 | | | 71 | 1-{[(3S,4S)-3-ethyl-4-fluoro-2-hydroxy-5-oxopyrrolidin-2-yl]methoxy}-7-methoxyisoquinoline-6-carboxamide |
| 198 | | | 715 | 1-{[(2S,3R,4S)-4-fluoro-3-(1-hydroxyethyl)-5-oxopyrrolidin-2-yl]methoxy}-7-methoxyisoquinoline-6-carboxamide |
| 199 | 2904 | | | 7-(oxetan-3-yloxy)-1-{[(2S)-5-oxopyrrolidin-2-yl]methoxy}isoquinoline-6-carboxamide |
| 200 | 697 | | | 7-tert-butoxy-1-{[(2S)-5-oxopyrrolidin-2-yl]methoxy}isoquinoline-6-carboxamide |
| 201 | 0.4 | | 1 | 1-{[(2S,3S)-3-ethyl-4,4-difluoro-5-oxopyrrolidin-2-yl]methoxy}-7-(propan-2-yloxy)isoquinoline-6-carboxamide |
| 202 | 85 | | 922 | 1-{[(4S)-2-oxoimidazolidin-4-yl]methoxy}-7-(propan-2-yloxy)isoquinoline-6-carboxamide |
| 203 | 3.5 | | 47 | 1-{[(2S,3R,4S)-4-fluoro-3-methyl-5-oxopyrrolidin-2-yl]methoxy}-7-methoxyisoquinoline-6-carboxamide |
| 204 | 2064 | | | 7-(cyclopropylmethoxy)-1-{[(2S)-5-oxopyrrolidin-2-yl]methoxy}isoquinoline-6-carboxamide |
| 205 | 3.6 | | 380 | 1-{[(2S,4R)-4-fluoro-4-(hydroxymethyl)-5-oxopyrrolidin-2-yl]methoxy}-7-methoxyisoquinoline-6-carboxamide |
| 206 | 216 | | 4570 | 6-methoxy-4-{[(2S)-5-oxopyrrolidin-2-yl]methoxy}isoquinoline-7-carboxamide |
| 207 | | | 41 | 5-{[(2S,4R)-4-fluoro-4-(hydroxymethyl)-5-oxopyrrolidin-2-yl]methoxy}-3-methoxynaphthalene-2-carboxamide |
| 208 | 1.1 | | 87 | 1-{[(2S,3S,4R)-4-fluoro-4-(hydroxymethyl)-3-methyl-5-oxopyrrolidin-2-yl]methoxy}-7-methoxyisoquinoline-6-carboxamide |
| 209 | 251 | | 9309 | 6-methoxy-4-{[(2S)-5-oxopyrrolidin-2-yl]methoxy}quinazoline-7-carboxamide |
| 210 | 3467 | | | 1-{[(2S,3S,4S)-4-fluoro-4-(hydroxymethyl)-3-methyl-5-oxopyrrolidin-2-yl]methoxy}-7-methoxyisoquinoline-6-carboxamide |
| 211 | 2.7 | | 52 | 7-methoxy-1-{[(2S,3R)-3-methyl-5-oxopyrrolidin-2-yl]methoxy}isoquinoline-6-carboxamide |
| 212 | 150 | | | 1-{[(2S,3S)-3-(hydroxymethyl)-5-oxopyrrolidin-2-yl]methoxy}-7-(propan-2-yloxy)isoquinoline-6-carboxamide |
| 213 | 1416 | | | 1-{[(1S,3aS,6aR)-5-methyl-3-oxooctahydropyrrolo[3,4-c]pyrrol-1-yl]methoxy}-7-(propan-2-yloxy)isoquinoline-6-carboxamide |
| 214 | 215 | | | 1-{[(2S,3S)-3-(hydroxymethyl)-5-oxopyrrolidin-2-yl]methoxy}-7-methoxyisoquinoline-6-carboxamide |
| 215 | 1.7 | | 35 | 1-{[(2S,4S)-4-fluoro-4-(fluoromethyl)-5-oxopyrrolidin-2-yl]methoxy}-7-methoxyisoquinoline-6-carboxamide |
| 216 | 0.4 | | 27 | 3-methoxy-5-{[(2S,3R)-3-methyl-5-oxopyrrolidin-2-yl]methoxy}naphthalene-2-carboxamide |
| 218 | 0.3 | | 11 | 5-{[(2S,3S,4S)-4-fluoro-3-methyl-5-oxopyrrolidin-2-yl]methoxy}-3-methoxynaphthalene-2-carboxamide |
| 219 | 1.7 | | 65 | 1-{[(2S,3R)-3-methyl-5-oxopyrrolidin-2-yl]methoxy}-7-(propan-2-yloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 220 | 0.9 | | 14 | 8-fluoro-5-{[(2S,3S,4S)-4-fluoro-3-methyl-5-oxopyrrolidin-2-yl]methoxy}-3-methoxynaphthalene-2-carboxamide |
| 221 | 54 | | | 1-{[(2S)-3,3-dimethyl-5-oxopyrrolidin-2-yl]methoxy}-7-methoxyisoquinoline-6-carboxamide |
| 222 | | 1870 | | 1-{[(2R)-3,3-dimethyl-5-oxopyrrolidin-2-yl]methoxy}-7-methoxyisoquinoline-6-carboxamide |
| 223 | | 15 | | 1-{[(2R)-3,3-dimethyl-5-oxopyrrolidin-2-yl]methoxy}-7-(propan-2-yloxy)isoquinoline-6-carboxamide |
| 224 | 1173 | | | 1-{[(2S,4R)-4-(cyanomethyl)-5-oxopyrrolidin-2-yl]methoxy}-7-methoxyisoquinoline-6-carboxamide |
| 225 | 3.4 | | 155 | 1-{[(2S,4S)-4-(cyanomethyl)-5-oxopyrrolidin-2-yl]methoxy}-7-methoxyisoquinoline-6-carboxamide |
| 226 | 222 | | | 1-{[(1S,3aS,6aR)-3-oxooctahydropyrrolo[3,4-c]pyrrol-1-yl]methoxy}-7-(propan-2-yloxy)isoquinoline-6-carboxamide |
| 227 | 19 | | 749 | 7-methoxy-1-{[(4R,5R)-5-methyl-2-oxo-1,3-oxazolidin-4-yl]methoxy}isoquinoline-6-carboxamide |
| 228 | 4.2 | | 118 | 3-methoxy-5-{[(4R,5R)-5-methyl-2-oxo-1,3-oxazolidin-4-yl]methoxy}naphthalene-2-carboxamide |
| 229 | 3514 | | 6298 | 7-methoxy-1-{[(4S)-2-oxo-1,3-oxazolidin-4-yl]methoxy}isoquinoline-6-carboxamide |
| 230 | 7 | | 199 | 7-methoxy-1-{[(4R)-2-oxo-1,3-oxazolidin-4-yl]methoxy}isoquinoline-6-carboxamide |
| 231 | 67 | | 509 | 3-methoxy-5-{[(2S,4S)-4-methoxy-5-oxopyrrolidin-2-yl]methoxy}naphthalene-2-carboxamide |
| 232 | 20 | | 261 | 3-methoxy-5-{[(2S,4R)-4-methoxy-5-oxopyrrolidin-2-yl]methoxy}naphthalene-2-carboxamide |
| 233 | 0.3 | | 47 | 3-methoxy-5-{[(4R)-2-oxo-1,3-oxazolidin-4-yl]methoxy}naphthalene-2-carboxamide |
| 234 | 1.9 | | 45 | 3-methoxy-5-{[(4R,5S)-5-methyl-2-oxo-1,3-oxazolidin-4-yl]methoxy}naphthalene-2-carboxamide |
| 235 | 97 | | 1092 | 7-methoxy-1-{[(5R)-2-oxo-1,3-oxazolidin-5-yl]methoxy}isoquinoline-6-carboxamide |
| 236 | 8.4 | | 125 | 7-methoxy-1-{[(4R,5S)-5-methyl-2-oxo-1,3-oxazolidin-4-yl]methoxy}isoquinoline-6-carboxamide |
| 237 | 295 | | 1076 | 1-{[(2S,3S,4R)-4-fluoro-3,4-dimethyl-5-oxopyrrolidin-2-yl]methoxy}-7-methoxyisoquinoline-6-carboxamide |
| 238 | 3.7 | | 45 | 1-{[(2S,3S,4S)-4-fluoro-3,4-dimethyl-5-oxopyrrolidin-2-yl]methoxy}-7-methoxyisoquinoline-6-carboxamide |
| 239 | 1182 | | | 7-methoxy-1-{[(5R)-3-methyl-2-oxo-1,3-oxazolidin-5-yl]methoxy}isoquinoline-6-carboxamide |
| 240 | 2.3 | | 24 | 5-{[(2S,4R)-4-fluoro-5-oxo-4-(2,2,2-trifluoroethyl)pyrrolidin-2-yl]methoxy}-3-methoxynaphthalene-2-carboxamide |
| 241 | 161 | | 5765 | 5-{[(2S,4S)-4-fluoro-5-oxo-4-(2,2,2-trifluoroethyl)pyrrolidin-2-yl]methoxy}-3-methoxynaphthalene-2-carboxamide |
| 242 | 263 | | 7248 | 7-methoxy-1-{[(2S,4S)-4-methyl-5-oxopyrrolidin-2-yl]methoxy}isoquinoline-6-carboxamide |
| 243 | 205 | | 713 | 7-methoxy-1-{[(2S,4R)-4-methyl-5-oxopyrrolidin-2-yl]methoxy}isoquinoline-6-carboxamide |
| 244 | 4.7 | | 64 | 1-{[(2S,3S)-3-ethyl-5-oxopyrrolidin-2-yl]methoxy}-7-methoxyisoquinoline-6-carboxamide |
| 245 | 29 | | 529 | 7-methoxy-1-{[(6S)-4-oxo-5-azaspiro[2.4]hept-6-yl]methoxy}isoquinoline-6-carboxamide |
| 246 | 0.5 | | 9 | 1-{[(2S,3R)-3-ethyl-5-oxopyrrolidin-2-yl]methoxy}-7-methoxyisoquinoline-6-carboxamide |
| 247 | 29 | | 2836 | 1-{[(2S,3R,4S)-3,4-dimethyl-5-oxopyrrolidin-2-yl]methoxy}-7-methoxyisoquinoline-6-carboxamide |
| 248 | 3.7 | | 87 | 1-{[(2S,3R,4R)-3,4-dimethyl-5-oxopyrrolidin-2-yl]methoxy}-7-methoxyisoquinoline-6-carboxamide |
| 249 | 20 | | 764 | 1-{[(2S,3S)-3-(fluoromethyl)-5-oxopyrrolidin-2-yl]methoxy}-7-methoxyisoquinoline-6-carboxamide |
| 250 | 0.6 | | 144 | 4-{[(2S,3S,4S)-4-fluoro-3-methyl-5-oxopyrrolidin-2-yl]methoxy}-6-methoxyquinoline-7-carboxamide |
| 251 | 3.4 | | 72 | 1-{[(2S,3S)-3-ethenyl-5-oxopyrrolidin-2-yl]methoxy}-7-methoxyisoquinoline-6-carboxamide |
| 252 | 0.9 | | 40 | 1-{[(2S,4S)-4-fluoro-5-oxopyrrolidin-2-yl]methoxy}-7-methoxyisoquinoline-6-carboxamide |
| 253 | 2.6 | | 122 | 1-{[(2S,4R)-4-fluoro-5-oxopyrrolidin-2-yl]methoxy}-7-methoxyisoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 254 | 2951 | | | 1-{[(2S,3S,4S)-3-(fluoromethyl)-4-methyl-5-oxopyrrolidin-2-yl]methoxy}-7-methoxyisoquinoline-6-carboxamide |
| 255 | 1683 | | 11527 | 7-methoxy-1-{[(2R)-5-oxopyrrolidin-2-yl]methoxy}isoquinoline-6-carboxamide |
| 256 | 2000 | | 5617 | 1-{[(2S,4R)-4-ethyl-4-fluoro-5-oxopyrrolidin-2-yl]methoxy}-7-methoxyisoquinoline-6-carboxamide |
| 257 | 6.8 | | 60 | 1-{[(2S,4S)-4-ethyl-4-fluoro-5-oxopyrrolidin-2-yl]methoxy}-7-methoxyisoquinoline-6-carboxamide |
| 258 | 141 | | 2933 | 1-{[(2S)-4-benzyl-5-oxopyrrolidin-2-yl]methoxy}-7-methoxyisoquinoline-6-carboxamide |
| 259 | 3.1 | | 120 | 4-{[(2S,4S)-4-ethyl-4-fluoro-5-oxopyrrolidin-2-yl]methoxy}-6-methoxyquinoline-7-carboxamide |
| 260 | 202 | | 6275 | 4-{[(2S,4R)-4-ethyl-4-fluoro-5-oxopyrrolidin-2-yl]methoxy}-6-methoxyquinoline-7-carboxamide |
| 261 | 671 | | | 1-{[(2S,4R)-4-fluoro-4-(fluoromethyl)-5-oxopyrrolidin-2-yl]methoxy}-7-methoxyisoquinoline-6-carboxamide |
| 262 | 4.7 | | 1604 | 6-methoxy-4-{[(2S)-5-oxopyrrolidin-2-yl]methoxy}quinoline-7-carboxamide |
| 263 | 80 | | 496 | 1-{[(1R,2S,5S)-6,6-dimethyl-4-oxo-3-azabicyclo[3.1.0]hex-2-yl]methoxy}-7-methoxyisoquinoline-6-carboxamide |
| 264 | 4.8 | | 115 | 7-methoxy-1-{[(1S,2S,5R)-4-oxo-3-azabicyclo[3.1.0]hex-2-yl]methoxy}isoquinoline-6-carboxamide |
| 265 | 1539 | | | 7-methoxy-1-[(3-methyl-5-oxomorpholin-3-yl)methoxy]isoquinoline-6-carboxamide |
| 266 | 74 | | 394 | 7-methoxy-1-[(4-methyl-2-oxo-1,3-oxazolidin-4-yl)methoxy]isoquinoline-6-carboxamide |
| 267 | 15 | | 158 | 7-methoxy-1-{[(2S,4S)-5-oxo-4-(2,2,2-trifluoroethyl)pyrrolidin-2-yl]methoxy}isoquinoline-6-carboxamide |
| 268 | 1.4 | | 175 | 4-{[(2S,4S)-4-fluoro-4-methyl-5-oxopyrrolidin-2-yl]methoxy}-6-methoxyquinoline-7-carboxamide |
| 269 | 0.6 | | 104 | 4-{[(2S,4S)-4-fluoro-4-methyl-5-oxopyrrolidin-2-yl]methoxy}-6-(propan-2-yloxy)quinoline-7-carboxamide |
| 270 | 290 | | | 7-methoxy-1-{[(2S,4R)-5-oxo-4-(2,2,2-trifluoroethyl)pyrrolidin-2-yl]methoxy}isoquinoline-6-carboxamide |
| 271 | 2.4 | | 52 | 7-methoxy-1-{[(1S,2S,5R)-6-methyl-4-oxo-3-azabicyclo[3.1.0]hex-2-yl]methoxy}isoquinoline-6-carboxamide |
| 272 | 432 | | 2470 | 1-{[(2S,3S,4S)-4-fluoro-3-methyl-5-oxopyrrolidin-2-yl]methoxy}-7-methoxyisoquinoline-6-carbonitrile |
| 73 | 4365 | | 1586 | 1-(cyclopentylmethoxy)-7-methoxyisoquinoline-6-carboxamide |
| 274 | 2.2 | | 748 | 4-{[(2S,4R)-4-fluoro-4-(2-fluoroethyl)-5-oxopyrrolidin-2-yl]methoxy}-6-methoxyquinoline-7-carboxamide |
| 275 | 119 | | 5137 | 1-{[(2R,4R)-4-fluoro-5-oxopyrrolidin-2-yl]methoxy}-7-methoxyisoquinoline-6-carboxamide |
| 276 | 4.1 | | 107 | 1-{[(2S,4R)-4-fluoro-4-(2-fluoroethyl)-5-oxopyrrolidin-2-yl]methoxy}-7-methoxyisoquinoline-6-carboxamide |
| 277 | 289 | | 4420 | 7-methoxy-1-{[(2R,3S)-3-methyl-5-oxopyrrolidin-2-yl]methoxy}isoquinoline-6-carboxamide |
| 278 | 8.5 | | 299 | 7-ethoxy-1-{[(2S,4S)-4-fluoro-4-methyl-5-oxopyrrolidin-2-yl]methoxy}isoquinoline-6-carboxamide |
| 279 | 1.2 | | 212 | 6-ethoxy-4-{[(2S,3S,4S)-4-fluoro-3-methyl-5-oxopyrrolidin-2-yl]methoxy}quinoline-7-carboxamide |
| 280 | 3789 | | | 6-ethoxy-4-{[(1S,2S,5R)-4-oxo-3-azabicyclo[3.1.0]hex-2-yl]methoxy}quinoline-7-carboxamide |
| 281 | 11 | | 127 | 7-(cyclopropyloxy)-1-{[(2S,3S,4S)-4-fluoro-3-methyl-5-oxopyrrolidin-2-yl]methoxy}isoquinoline-6-carboxamide |
| 282 | 11 | | 191 | 7-ethoxy-1-{[(1S,2S,5R)-4-oxo-3-azabicyclo[3.1.0]hex-2-yl]methoxy}isoquinoline-6-carboxamide |
| 283 | 1 | | 27 | 7-ethoxy-1-{[(2S,3S,4S)-4-fluoro-3-methyl-5-oxopyrrolidin-2-yl]methoxy}isoquinoline-6-carboxamide |
| 284 | 18 | | 320 | 1-{[(2S,4R)-4-fluoro-5-oxo-4-(tetrahydro-2H-pyran-4-yl)pyrrolidin-2-yl]methoxy}-7-methoxyisoquinoline-6-carboxamide |
| 285 | 153 | | 1056 | 7-methoxy-1-(((1R,2S,5R,6R)-6-methyl-4-oxo-3-azabicyclo[3.1.0]hexan-2-yl)methoxy)isoquinoline-6-carboxamide |
| 286 | 137 | | 7025 | 7-methoxy-1-{[(2S,4S)-5-oxo-4-(tetrahydro-2H-pyran-4-yl)pyrrolidin-2-yl]methoxy}isoquinoline-6-carboxamide |
| 287 | 7.7 | | 2302 | 6-ethoxy-4-{[(2S,4S)-4-fluoro-4-methyl-5-oxopyrrolidin-2-yl]methoxy}quinoline-7-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 288 | 34 | | 1809 | 1-{[(2R,3R,4R)-4-fluoro-3-methyl-5-oxopyrrolidin-2-yl]methoxy}-7-methoxyisoquinoline-6-carboxamide |
| 289 | 562 | | 6271 | 1-{[(2S,4S)-4-(4-hydroxytetrahydro-2H-pyran-4-yl)-5-oxopyrrolidin-2-yl]methoxy}-7-methoxyisoquinoline-6-carboxamide |
| 290 | 1200 | | | 7-methoxy-1-{[(2S)-4-(oxetan-3-ylidene)-5-oxopyrrolidin-2-yl]methoxy}isoquinoline-6-carboxamide |
| 291 | 32 | | | 6-ethoxy-4-{[(2S)-5-oxopyrrolidin-2-yl]methoxy}quinoline-7-carboxamide |
| 292 | 78 | | 3136 | 1-{[(2S,4R)-4-fluoro-4-(methoxymethyl)-5-oxopyrrolidin-2-yl]methoxy}-7-methoxyisoquinoline-6-carboxamide |
| 293 | 1.1 | | 462 | 6-ethoxy-4-{[(2S,4S)-4-fluoro-4-(fluoromethyl)-5-oxopyrrolidin-2-yl]methoxy}quinoline-7-carboxamide |
| 294 | 3.3 | | 24 | 7-ethoxy-1-{[(2S,4S)-4-fluoro-4-(fluoromethyl)-5-oxopyrrolidin-2-yl]methoxy}isoquinoline-6-carboxamide |
| 295 | 7.3 | | 67 | 7-methoxy-1-{[(1S,2S,5R)-1-methyl-4-oxo-3-azabicyclo[3.1.0]hex-2-yl]methoxy}isoquinoline-6-carboxamide |
| 296 | 0.2 | | 2.4 | 1-{[(2S,3S,4S)-3-ethyl-4-fluoro-5-oxopyrrolidin-2-yl]methoxy}-7-methoxyisoquinoline-6-carboxamide |
| 297 | 365 | | 7125 | 7-methoxy-1-{[(1S,2S,5R)-5-methyl-4-oxo-3-azabicyclo[3.1.0]hex-2-yl]methoxy}isoquinoline-6-carboxamide |
| 298 | 1243 | | | 7-methoxy-1-{[(2S,4S)-4-(oxetan-3-yl)-5-oxopyrrolidin-2-yl]methoxy}isoquinoline-6-carboxamide |
| 299 | 4.3 | | 49 | 1-{[(1S,2S,5R)-1-ethyl-4-oxo-3-azabicyclo[3.1.0]hex-2-yl]methoxy}-7-methoxyisoquinoline-6-carboxamide |
| 300 | 75 | | 931 | 1-{[(1S,2S,5R)-6-ethyl-4-oxo-3-azabicyclo[3.1.0]hex-2-yl]methoxy}-7-methoxyisoquinoline-6-carboxamide |
| 301 | 338 | | 4047 | 1-(((1R,2S,5R,6R)-6-ethyl-4-oxo-3-azabicyclo[3.1.0]hexan-2-yl)methoxy)-7-methoxyisoquinoline-6-carboxamide |
| 302 | 28 | | 1275 | 7-methoxy-1-{[(2S)-6-oxopiperidin-2-yl]methoxy}isoquinoline-6-carboxamide |
| 303 | 127 | | 6047 | 1-(((1S,2S,5S,6R)-6-(fluoromethyl)-4-oxo-3-azabicyclo[3.1.0]hexan-2-yl)methoxy)-7-methoxyisoquinoline-6-carboxamide |
| 304 | 1.3 | | 35 | 1-{[(1R,2S,5S)-6-(fluoromethyl)-4-oxo-3-azabicyclo[3.1.0]hex-2-yl]methoxy}-7-methoxyisoquinoline-6-carboxamide |
| 305 | 2 | | 57 | 1-{[(2S,3S)-3-cyclopropyl-5-oxopyrrolidin-2-yl]methoxy}-7-methoxyisoquinoline-6-carboxamide |
| 306 | 155 | | 4058 | 1-(((1R,2S,5R,6R)-6-(2-fluoroethyl)-4-oxo-3-azabicyclo[3.1.0]hexan-2-yl)methoxy)-7-methoxyisoquinoline-6-carboxamide |
| 307 | 2060 | | | 7-methoxy-1-{[(1R,2S,5S)-4-oxo-3-azabicyclo[3.1.0]hex-2-yl]methoxy}isoquinoline-6-carboxamide |
| 308 | 9.8 | | 134 | 7-methoxy-1-{[(1S,2S,5R)-4-oxo-3-azabicyclo[3.2.0]hept-2-yl]methoxy}isoquinoline-6-carboxamide |
| 309 | 0.6 | | 17 | 1-{[(1R,2S,5S)-5-fluoro-6-methyl-4-oxo-3-azabicyclo[3.1.0]hex-2-yl]methoxy}-7-methoxyisoquinoline-6-carboxamide |
| 310 | 10 | | 380 | 1-(((1S,2S,5S,6R)-5-fluoro-6-methyl-4-oxo-3-azabicyclo[3.1.0]hexan-2-yl)methoxy)-7-methoxyisoquinoline-6-carboxamide |
| 311 | 229 | | 1083 | 1-{[(1S,2S,5R)-6,6-dichloro-4-oxo-3-azabicyclo[3.1.0]hex-2-yl]methoxy}-7-methoxyisoquinoline-6-carboxamide |
| 312 | 1.3 | | 26 | 7-methoxy-1-{[(2S,3R)-5-oxo-3-propylpyrrolidin-2-yl]methoxy}isoquinoline-6-carboxamide |
| 313 | 210 | | 1593 | 7-methoxy-1-{[(1S,2S,5S)-6-(methoxymethyl)-4-oxo-3-azabicyclo[3.1.0]hex-2-yl]methoxy}isoquinoline-6-carboxamide |
| 314 | 1980 | | 8356 | 7-methoxy-1-{[(1S,2S,5S)-6-(methoxymethyl)-4-oxo-3-azabicyclo[3.1.0]hex-2-yl]methoxy}isoquinoline-6-carboxamide |
| 315 | 1.5 | | 45 | 1-{[(1S,2S,5R)-6-fluoro-4-oxo-3-azabicyclo[3.1.0]hex-2-yl]methoxy}-7-methoxyisoquinoline-6-carboxamide |
| 316 | 129 | | 464 | 4-{[(2S,3S,4S)-3-ethyl-4-fluoro-5-oxopyrrolidin-2-yl]methoxy}-6-methoxyquinoline-7-carboxamide |
| 317 | 0.6 | | 22 | 1-{[(1R,2S,5S)-5-fluoro-4-oxo-3-azabicyclo[3.1.0]hex-2-yl]methoxy}-7-methoxyisoquinoline-6-carboxamide |
| 318 | 1938 | | 17188 | 1-{[(2S)-5-oxopyrrolidin-2-yl]methoxy}-7-(prop-2-yn-1-yloxy)isoquinoline-6-carboxamide |
| 319 | 1948 | | 10990 | 1-{[(2S)-5-oxopyrrolidin-2-yl]methoxy}-7-(propadienyloxy)isoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 320 | 0.8 | | 11 | 1-{[(1R,2S,5S)-6-(difluoromethyl)-4-oxo-3-azabicyclo[3.1.0]hex-2-yl]methoxy}-7-methoxyisoquinoline-6-carboxamide |
| 321 | 4188 | | | 3-chloro-6-methoxy-4-{[(1S,2S,5R)-6-methyl-4-oxo-3-azabicyclo[3.1.0]hex-2-yl]methoxy}quinoline-7-carboxamide |
| 322 | 6.1 | | 26 | 1-{[(1R,2S,5S)-5-fluoro-4-oxo-3-azabicyclo[3.2.0]hept-2-yl]methoxy}-7-methoxyisoquinoline-6-carboxamide |
| 323 | 0.2 | | 30 | 4-{[(1R,2S,5S)-5-fluoro-6-methyl-4-oxo-3-azabicyclo[3.1.0]hex-2-yl]methoxy}-6-methoxyquinoline-7-carboxamide |
| 324 | 0.6 | | 277 | 4-{[(1S,2S,5R)-6-fluoro-4-oxo-3-azabicyclo[3.1.0]hex-2-yl]methoxy}-6-methoxyquinoline-7-carboxamide |
| 325 | 0.4 | | 87 | 4-{[(1R,2S,5S)-5-fluoro-4-oxo-3-azabicyclo[3.1.0]hex-2-yl]methoxy}-6-methoxyquinoline-7-carboxamide |
| 326 | 1.2 | | 1196 | 6-methoxy-4-{[(1S,2S,5R)-4-oxo-3-azabicyclo[3.1.0]hex-2-yl]methoxy}quinoline-7-carboxamide |
| 327 | 20 | | 3307 | 1-{[(1S,2S,5S)-6-(hydroxymethyl)-4-oxo-3-azabicyclo[3.1.0]hex-2-yl]methoxy}-7-methoxyisoquinoline-6-carboxamide |
| 328 | 93 | | | 1-{[(1S,2S,5S)-6-(hydroxymethyl)-4-oxo-3-azabicyclo[3.1.0]hex-2-yl]methoxy}-7-methoxyisoquinoline-6-carboxamide |
| 329 | 13 | | 252 | 1-{[(2S,3R)-3-ethenyl-5-oxopyrrolidin-2-yl]methoxy}-7-methoxyisoquinoline-6-carboxamide |
| 330 | 14 | | 134 | 7-methoxy-1-{[(4S)-6-oxo-5-azaspiro[2.4]hept-4-yl]methoxy}isoquinoline-6-carboxamide |
| 333 | 0.3 | | 182 | 4-{[(1R,2S,5S)-6-(fluoromethyl)-4-oxo-3-azabicyclo[3.1.0]hex-2-yl]methoxy}-6-methoxyquinoline-7-carboxamide |
| 334 | 4.2 | | 1771 | 1-(((1R,2S,5R,6R)-6-fluoro-4-oxo-3-azabicyclo[3.1.0]hexan-2-yl)methoxy)-7-methoxyisoquinoline-6-carboxamide |
| 335 | 4 | | 746 | 1-{[(1S,2S,5R)-6-fluoro-6-methyl-4-oxo-3-azabicyclo[3.1.0]hex-2-yl]methoxy}-7-methoxyisoquinoline-6-carboxamide |
| 336 | 0.3 | | 674 | 1-{[(1S,2S,5R)-6-fluoro-6-methyl-4-oxo-3-azabicyclo[3.1.0]hex-2-yl]methoxy}-7-methoxyisoquinoline-6-carboxamide |
| 337 | 0.1 | | 6.5 | 1-{[(2S,3S,4R)-3-ethyl-4-fluoro-5-oxopyrrolidin-2-yl]methoxy}-7-methoxyisoquinoline-6-carboxamide |
| 338 | 0.2 | | 3 | 1-{[(2S,3S,4S)-3-ethyl-4-fluoro-5-oxopyrrolidin-2-yl]methoxy}-7-[(trideutero)methyloxy]isoquinoline-6-carboxamide |
| 339 | 90 | | 269 | 1-{[(2S,3S,4S)-3-ethyl-4-fluoro-5-oxopyrrolidin-2-yl]methoxy}-7-(2-methoxyethoxy)isoquinoline-6-carboxamide |
| 340 | 12 | | 456 | 7-methoxy-1-{[(2S,3R)-3-(methoxymethyl)-5-oxopyrrolidin-2-yl]methoxy}isoquinoline-6-carboxamide |
| 341 | 0.3 | | 16 | 4-{[(2S,3S,4S)-3-ethyl-4-fluoro-5-oxopyrrolidin-2-yl]methoxy}-6-methoxyquinazoline-7-carboxamide |
| 342 | 1003 | | 2382 | 1-{[(2S,3S,4S)-3-ethyl-4-methoxy-5-oxopyrrolidin-2-yl]methoxy}-7-methoxyisoquinoline-6-carboxamide |
| 343 | 41 | | 408 | 1-{[(2S,3S,4R)-3-ethyl-4-methoxy-5-oxopyrrolidin-2-yl]methoxy}-7-methoxyisoquinoline-6-carboxamide |
| 344 | 0.2 | | 0.5 | 1-{[(2S,3S,4S)-3-(pentadeutero)ethyl-4-fluoro-5-oxopyrrolidin-2-yl]methoxy}-7-methoxyisoquinoline-6-carboxamide |
| 345 | 0.2 | | 1.6 | 1-{[(2S,3S)-3-ethyl-4,4-difluoro-5-oxopyrrolidin-2-yl]methoxy}-7-methoxyisoquinoline-6-carboxamide |
| 346 | 6.1 | | 150 | 1-{[(2S,3R,4R)-3-ethyl-4-fluoro-5-oxopyrrolidin-2-yl]methoxy}-7-methoxyisoquinoline-6-carboxamide |
| 347 | 0.6 | | 27 | 1-{[(2S,3R)-4,4-difluoro-3-(methoxymethyl)-5-oxopyrrolidin-2-yl]methoxy}-7-methoxyisoquinoline-6-carboxamide |
| 348 | 0.7 | | 42 | 1-{[(2S,3R,4S)-4-fluoro-3-(methoxymethyl)-5-oxopyrrolidin-2-yl]methoxy}-7-methoxyisoquinoline-6-carboxamide |
| 349 | 2962 | | 9461 | 7-methoxy-1-{[(2S,3S,4S)-4-methoxy-3-methyl-5-oxopyrrolidin-2-yl]methoxy}isoquinoline-6-carboxamide |
| 350 | 58 | | 568 | 7-methoxy-1-{[(2S,3S,4R)-4-methoxy-3-methyl-5-oxopyrrolidin-2-yl]methoxy}isoquinoline-6-carboxamide |
| 351 | 6.3 | | 213 | 1-{[(2S,3R,4R)-4-fluoro-3-(methoxymethyl)-5-oxopyrrolidin-2-yl]methoxy}-7-methoxyisoquinoline-6-carboxamide |

TABLE 3-continued

Biological Activity

| Ex. # | IRAK4 DELFIA Protocol A IC50 (nM) | IRAK4 DELFIA Protocol B IC50 (nM) | R848-induced TNFa PBMC IC50 (nM) | IUPAC NAME |
|---|---|---|---|---|
| 352 | 3.3 | | 557 | 1-{[(2S,3S,4S)-3-ethyl-4-hydroxy-5-oxopyrrolidin-2-yl]methoxy}-7-methoxyisoquinoline-6-carboxamide |
| 353 | 0.5 | | 20 | 1-{[(2S,3S,4R)-3-ethyl-4-hydroxy-5-oxopyrrolidin-2-yl]methoxy}-7-methoxyisoquinoline-6-carboxamide |
| 354 | 2887 | | | 7-methoxy-1-{(1S)-1-[(2S)-5-oxopyrrolidin-2-yl]ethoxy}isoquinoline-6-carboxamide |
| 355 | 1.7 | | 33 | 1-{[(2S,3S)-3-(2-fluoroethyl)-5-oxopyrrolidin-2-yl]methoxy}-7-methoxyisoquinoline-6-carboxamide |
| 356 | 115 | | 594 | 1-{[(2S,3R,4S)-4-amino-3-ethyl-5-oxopyrrolidin-2-yl]methoxy}-7-methoxyisoquinoline-6-carboxamide |
| 357 | 30 | | 588 | 1-{[(2S,3R,4R)-4-amino-3-ethyl-5-oxopyrrolidin-2-yl]methoxy}-7-methoxyisoquinoline-6-carboxamide |
| 358 | 0.4 | | 1.3 | 1-{[(2S,3S,4S)-3-ethyl-4-fluoro-5-oxopyrrolidin-2-yl]methoxy}-7-(propan-2-yloxy)isoquinoline-6-carboxamide |
| 359 | 0.4 | | 3.9 | 7-ethoxy-1-{[(2S,3S,4S)-3-ethyl-4-fluoro-5-oxopyrrolidin-2-yl]methoxy}isoquinoline-6-carboxamide |
| 360 | 0.1 | | 3.9 | 1-{[(2S,3S,4S)-3-ethyl-4-fluoro-5-oxopyrrolidin-2-yl]methoxy}-4-fluoro-7-methoxyisoquinoline-6-carboxamide |
| 361 | 4.8 | | 27 | 1-{[(2S,3S,4S)-3-ethyl-4-fluoro-5-oxopyrrolidin-2-yl]methoxy}-8-fluoro-7-methoxyisoquinoline-6-carboxamide |
| 362 | 1.1 | | 28 | 1-{[(2S,3R)-3-ethyl-5-oxopyrrolidin-2-yl]methoxy}-4-fluoro-7-methoxyisoquinoline-6-carboxamide |
| 363 | 11 | | 110 | 1-{[(2S,3R)-3-ethyl-5-oxopyrrolidin-2-yl]methoxy}-8-fluoro-7-methoxyisoquinoline-6-carboxamide |
| 364 | 16 | | 145 | 4-fluoro-7-methoxy-1-{[(1S,2S,5R)-6-methyl-4-oxo-3-azabicyclo[3.1.0]hex-2-yl]methoxy}isoquinoline-6-carboxamide |
| 365 | 187 | | 724 | 8-fluoro-7-methoxy-1-{[(1S,2S,5R)-6-methyl-4-oxo-3-azabicyclo[3.1.0]hex-2-yl]methoxy}isoquinoline-6-carboxamide |
| 366 | 6.1 | | 91 | 1-{[(2S,3R)-3-(fluoromethyl)-5-oxopyrrolidin-2-yl]methoxy}-7-methoxyisoquinoline-6-carboxamide |
| 367 | 0.4 | | 14 | 1-{[(2S,3R,4S)-4-fluoro-3-(fluoromethyl)-5-oxopyrrolidin-2-yl]methoxy}-7-methoxyisoquinoline-6-carboxamide |
| 368 | 0.3 | | 10 | 1-{[(2S,3S,4S)-3-cyclopropyl-4-fluoro-5-oxopyrrolidin-2-yl]methoxy}-7-methoxyisoquinoline-6-carboxamide |
| 369 | 3.7 | | 45 | 1-{[(2S,3S,4R)-3-cyclopropyl-4-fluoro-5-oxopyrrolidin-2-yl]methoxy}-7-methoxyisoquinoline-6-carboxamide |
| 370 | 0.1 | | 3.7 | 1-{[(2S,3S,4S)-4-fluoro-3-(2-fluoroethyl)-5-oxopyrrolidin-2-yl]methoxy}-7-methoxyisoquinoline-6-carboxamide |
| 371 | 7 | | 604 | 4-(1-methyl-1H-imidazol-4-yl)-1-{[(2S)-5-oxopyrrolidin-2-yl]methoxy}-7-(propan-2-yloxy)isoquinoline-6-carboxamide |
| 372 | 11 | | 649 | 4-(1,2-dimethyl-1H-imidazol-4-yl)-1-{[(2S)-5-oxopyrrolidin-2-yl]methoxy}-7-(propan-2-yloxy)isoquinoline-6-carboxamide |
| 373 | 35 | | 6162 | 4-(2-methyl-1H-imidazol-4-yl)-1-{[(2S)-5-oxopyrrolidin-2-yl]methoxy}-7-(propan-2-yloxy)isoquinoline-6-carboxamide |
| 374 | 0.1 | | 1.2 | 1-{[(2S,3S,4S)-3-ethyl-4-fluoro-5-oxo(3,4-bisdeutero)pyrrolidin-2-yl]methoxy}-7-methoxyisoquinoline-6-carboxamide |
| 375 | 0.3 | | | 1-{[(2S,3R,4R)-4-fluoro-3-(fluoromethyl)-5-oxopyrrolidin-2-yl]methoxy}-7-methoxyisoquinoline-6-carboxamide |
| 376 | 740 | | | 4-(4-methylpyrimidin-2-yl)-1-{[(2S)-5-oxopyrrolidin-2-yl]methoxy}-7-(propan-2-yloxy)isoquinoline-6-carboxamide |
| 377 | 72 | | | 4-(5-chloropyrimidin-2-yl)-1-{[(2S)-5-oxopyrrolidin-2-yl]methoxy}-7-(propan-2-yloxy)isoquinoline-6-carboxamide |
| 378 | 59 | | | 4-(6-oxo-1,6-dihydropyridin-2-yl)-1-{[(2S)-5-oxopyrrolidin-2-yl]methoxy}-7-(propan-2-yloxy)isoquinoline-6-carboxamide |
| 379 | 503 | | | 4-(2-methylpyrimidin-4-yl)-1-{[(2S)-5-oxopyrrolidin-2-yl]methoxy}-7-(propan-2-yloxy)isoquinoline-6-carboxamide |

In Vivo Mouse LPS/D-Gal Challenge Model.

Efficacy of IRAK4 compounds of the present invention was also evaluated in an in vivo mouse model of endotoxin induced (Lipopolysaccharide (LPS)) inflammation. See: S. Copeland, H. W. Warren, S. F. Lowry, S. E. Calvano, and D. Remick, *Clin. Diagn. Lab. Immnol.* 2005, 12(1), 60-67. An exemplary protocol for this in vivo model follows.

Female C57/BL6 mice, 8 to 10 weeks old, are orally administered either vehicle or formulated IRAK-4 compound 1 hour prior to the challenge. Vehicle or IRAK4 compound is administered by oral gavage at a volume of 10 mL/kg. One hour post oral delivery of vehicle or compound, the animals are challenged with an intraperitoneal injection (IP) of a solution containing 1 μg/mL LPS and 80 mg/mL D-gal. Each mouse is injected with 200 μL of the solution, for a final challenge dose of 100 ng LPS and 8 mg D-gal. Ninety minutes post LPS/D-gal challenge, animals are euthanized and blood collected. Blood is allowed to clot at room temperature and serum is separated by centrifugation and stored at −80° C. for analysis. Serum TNF and IL-6 are measured by Meso Scale Discovery (MSD) multiplex platform.

The groups consisted of N=10 animals/group. Naïve animals and vehicle control groups were run with each study. Mean cytokine data was plotted and students T-test was performed to calculate significance (t-test, p<0.05 vs. vehicle) of IRAK4 treated group vs. vehicle treated group. Percent inhibition of cytokine induction was calculated for IRAK4 treated group vs. vehicle treated group.

Table 4 contains data from multiple studies with columns for Compound, Dose in mg/kg (mpk) and % inhibition of serum TNF. In cases where doses of certain compounds were repeated in multiple experiments, the average percent inhibition of TNF and standard deviation is shown in the table.

TABLE 4

% Inhibition of TNF in mouse LPS model with various IRAK4 inhibitors.

| Compound | Dose (mpk) | % inhib TNF |
|---|---|---|
| Example 26 | 100 | 78 (±23) |
|  | 30 | 41 (±17) |
|  | 10 | 27 (±19) |
| Example 173 | 100 | 98 |
|  | 30 | 55 |
| Example 189 | 30 | 40 |
| Example 194 | 30 | 76 |

Imiquimod Induced Mouse Model of Skin Inflammation.

Efficacy of IRAK4 inhibitors of the present invention was also evaluated in an in vivo mouse model imiquimod induced skin inflammation (L. van der Fits, S. Mourits, J. S. A. Voerman, M. Kant, L. Boon, J. D. Laman, F. Cornelissen, A.-M. Mus, E. Florencia, E. P. Prens, and E. Luberts, *J. Immunol.* 2009, 182, 5836-5845). An exemplary protocol for this in vivo model follows.

Female Balb/C mice, 12-14 weeks old, received a daily topical dose of commercially available imiquimod cream (5%) on the shaved back and the left ear for 3 consecutive days. This translated into a daily dose of 1.56 mg of the active compound. This dosing regimen was optimized to achieve robust skin inflammation in mice as measured by increased ear thickness. Vehicle or IRAK4 compounds are administered by oral gavage, twice daily (AM and PM) for 5 consecutive days. Ear thickness were measured daily, 1 hour post AM oral administration of compound or vehicle and prior to application of imiquimod. An exemplary protocol for this in vivo model follows.

On Day 1, mice were pre-treated with vehicle or IRAK4 inhibitor by oral gavage at a volume of 10 mL/kg. Oral dosing of compound or vehicle continued twice daily (BID) for 5 consecutive days.

One hour post vehicle or compound delivery, baseline ear thickness was measured in triplicate using a micrometer (Mitutoyo) prior to the application of imiquimod. Ear thickness was measured each day in this manner and then the imiquimod cream was applied to back skin and left ear on Days 1, 2 and 3.

On Day 5 of the study, mice were given the AM dose of vehicle or IRAK4 inhibitor. One hour after oral delivery, ears were measured and animals were euthanized. The left ear was collected; snap frozen and stored at −80° C. for analysis.

Data were presented as mean change in ear thickness (microns) from baseline measurement.

Positive control compound for the model was two IP injections of anti-P40 antibody at a dose of 400 μg/mouse given on Days 1 and 4.

In Vivo Rat Collagen-Induced Arthritis Model.

Efficacy of IRAK4 compounds of the present invention was also evaluated in a rat in vivo model of rheumatoid arthritis (M. Hegen, J. C. Keith, Jr, M. Collins, C. L. Nickerson-Nutter, *Ann. Rheum. Dis.* 2008, 67, 1505-1515). An exemplary protocol for this in vivo model follows.

Female Lewis rats, approximately 7 weeks old, were immunized with an emulsion of type II collagen (CII) and incomplete Freund's adjuvant (IFA) on day 0 and received a boost of CII/IFA on day 7. Hind paw volume increase was taken by plethysmograph. Animals were randomly enrolled into treatment groups based on the development of disease. Beginning on day 11 post immunization, rats were enrolled into random treatment groups based on an increase in a single hind paw volume compared to day 7 post immunization baseline measurements.

The groups consisted of: (1) a naive control group, (2) a vehicle control group, (3) a group dosed orally with a p38 inhibitor, (4) a positive control, at 30 mg/kg once a day, (5) a group dosed orally with Example 26 at 100 mg/kg twice a day, (6) a group dosed orally with Example 26 at 30 mg/kg twice a day, and (7) a group dosed orally with Example 26 at 10 mg/kg twice a day.

Ten rats were enrolled per treatment group with the exception of the naive control group, which contained two rats. Day 0 was designated as the first treatment day, and paw measurements are taken daily by plethysmograph. The rats were weighed on a daily basis.

Figure 2:
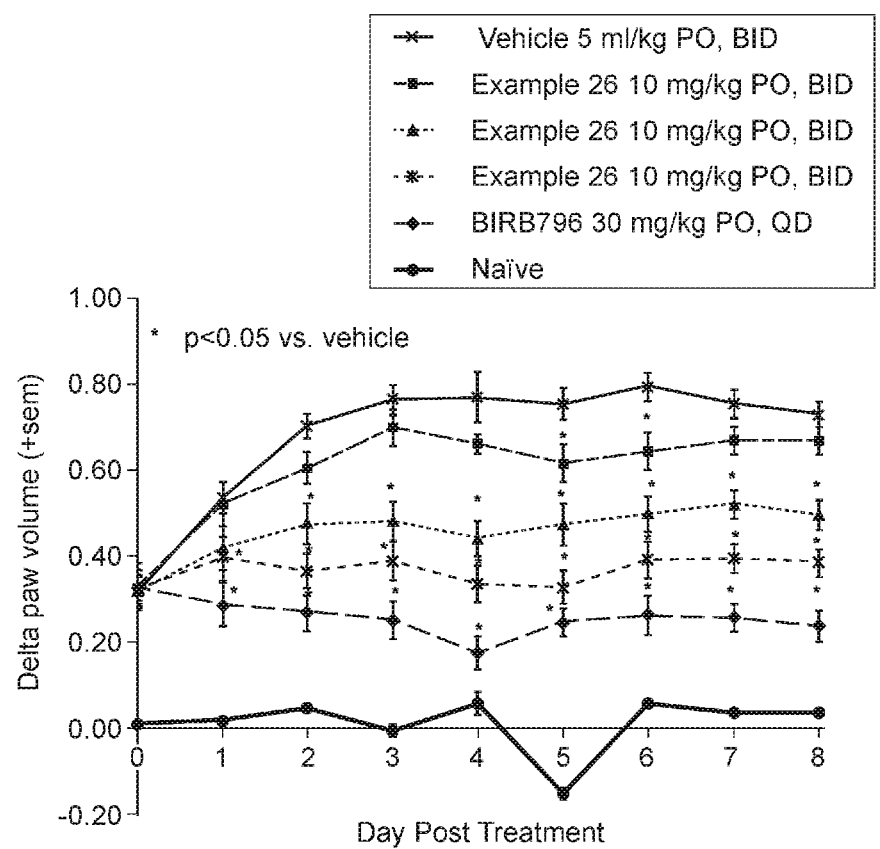
FIG. 2.

IRAK4 inhibitors are efficacious in the Lewis rat model of collagen-induced arthritis. Results of the study are presented in FIG. 2 which demonstrates the average paw volume increase of the groups dosed orally. In particular, therapeutic treatment BID daily with Example 26 for 8 days reduced the hind paw swelling in CIA rats significantly (t-test, p<0.05 vs. vehicle) in the following groups:

| Example 26 | 100 mg/kg PO, BID | Day 1-Day 8 (end) |
| Example 26 | 30 mg/kg PO, BID | Day 2-Day 8 |
| BIRB796 | 30 mg/kg PO, QD | Day 1-Day 8 |

Animals treated with Example 26 at 10 mg/kg PO, BID showed a transiently significant reduction in hind paw swelling only on Day 5 and Day 6 post treatment.

We claim:

1. A pharmaceutical combination comprising 1-(((2S,3S,4S)-3-ethyl-4-fluoro-5-oxopyrrolidin-2-yl)methoxy)-7-methoxyisoquinoline-6-carboxamide, or a pharmaceutically acceptable salt thereof, and tofacitinib, or a pharmaceutically acceptable salt thereof.

2. A pharmaceutical combination comprising 1-(((2S,3S,4S)-3-ethyl-4-fluoro-5-oxopyrrolidin-2-yl)methoxy)-7-methoxyisoquinoline-6-carboxamide, or a pharmaceutically acceptable salt thereof, tofacitinib, or a pharmaceutically acceptable salt thereof, and at least one pharmaceutically acceptable carrier, vehicle, or diluent, or a combination thereof.

3. A method of treating rheumatoid arthritis in a human comprising administering to the human in need of rheumatoid arthritis treatment a therapeutically effective amount of a pharmaceutical combination according to claim 1.

4. A method of treating rheumatoid arthritis in a human comprising administering to the human in need of rheumatoid arthritis treatment a therapeutically effective amount of a pharmaceutical combination according to claim 2.

5. A pharmaceutical combination comprising 1-(((2S,3S,4S)-3-ethyl-4-fluoro-5-oxopyrrolidin-2-yl)methoxy)-7-methoxyisoquinoline-6-carboxamide, or a pharmaceutically acceptable salt thereof, and a JAK3 inhibitor, or a pharmaceutically acceptable salt thereof.

6. A pharmaceutical combination comprising 1-(((2S,3S,4S)-3-ethyl-4-fluoro-5-oxopyrrolidin-2-yl)methoxy)-7-methoxyisoquinoline-6-carboxamide, or a pharmaceutically acceptable salt thereof, a JAK3 inhibitor, or a pharmaceutically acceptable salt thereof, and at least one pharmaceutically acceptable carrier, vehicle, or diluent, or a combination thereof.

7. A method of treating rheumatoid arthritis in a human comprising administering to the human in need of rheumatoid arthritis treatment a therapeutically effective amount of the pharmaceutical combination according to claim 5.

8. A method of treating rheumatoid arthritis in a human comprising administering to the human in need of rheumatoid arthritis treatment a therapeutically effective amount of the pharmaceutical combination according to claim 6.

* * * * *